US012774290B2

(12) United States Patent
Campbell et al.

(10) Patent No.: US 12,774,290 B2
(45) Date of Patent: Oct. 27, 2026

(54) INHIBITORS OF MICROBIALLY INDUCED AMYLOID

(71) Applicant: Vertero Therapeutics, Inc., Woburn, MA (US)

(72) Inventors: Anthony Stewart Campbell, Framingham, MA (US); Christopher J. Oalmann, Watertown, MA (US); Dennis S. Yamashita, Cambridge, MA (US); Alessandra Bartolozzi, Norwalk, CT (US)

(73) Assignee: Vertero Therapeutics, Inc., Woburn, MA (US)

( * ) Notice: Subject to any disclaimer, the term of this patent is extended or adjusted under 35 U.S.C. 154(b) by 972 days.

(21) Appl. No.: 17/791,760

(22) PCT Filed: Jan. 8, 2021

(86) PCT No.: PCT/US2021/012792

§ 371 (c)(1),
(2) Date: Jul. 8, 2022

(87) PCT Pub. No.: WO2021/142333

PCT Pub. Date: Jul. 15, 2021

(65) Prior Publication Data

US 2023/0131899 A1 Apr. 27, 2023

Related U.S. Application Data

(60) Provisional application No. 62/959,385, filed on Jan. 10, 2020.

(51) Int. Cl.

| | |
|---|---|
| ***C07D 513/04*** | (2006.01) |
| ***A61P 25/28*** | (2006.01) |
| ***C07D 471/04*** | (2006.01) |
| ***C07D 519/00*** | (2006.01) |

(52) U.S. Cl.

CPC ............ *C07D 513/04* (2013.01); *A61P 25/28* (2018.01); *C07D 471/04* (2013.01); *C07D 519/00* (2013.01)

(58) Field of Classification Search

CPC .. C07D 471/04; C07D 513/04; C07D 519/00; A61P 25/28

See application file for complete search history.

(56) References Cited

U.S. PATENT DOCUMENTS

2017/0233409 A1 8/2017 Hadjifrangiskou et al.

FOREIGN PATENT DOCUMENTS

| | | | |
|---|---|---|---|
| JP | 2009-025682 A | 2/2009 |
| WO | WO 2005/102330 A2 | 11/2005 |
| WO | WO 2008/054290 A1 | 5/2008 |
| WO | WO 2008/054291 A1 | 5/2008 |
| WO | WO 2012/175514 A1 | 12/2012 |
| WO | WO 2018/213204 A1 | 11/2018 |
| WO | WO 2018/229141 A1 | 12/2018 |
| WO | WO 2019/028456 A1 | 2/2019 |
| WO | WO 2020/006357 A1 | 1/2020 |

OTHER PUBLICATIONS

STN Registry Entry for CAS RN 12664481-29-9; Entered STN Feb. 25, 2011; Accessed Jun. 28, 2025.*

Li et al. J. Org. Chem., May 6, 2011, 76 (9): 3054-63.*

STN Registry Entry for CAS RN 916418-15-0; Entered STN Dec. 28, 2006; Accessed Jan. 21, 2026.*

Invitation to Pay Additional Fees mailed Apr. 14, 2021 for International Application No. PCT/US2021/012792.

International Search Report and Written Opinion mailed Jun. 28, 2021 for International Application No. PCT/US2021/012792.

International Preliminary Report on Patentability mailed Jul. 21, 2022 for International Application No. PCT/US2021/012792.

Pemberton et al., Synthesis and evaluation of dihydroimidazolo and dihydrooxazolo ring-fused 2-pyridones—targeting pilus biogenesis in uropathogenic bacteria. Tetrahedron. Sep. 29, 2008; 64(40):9368-9376. doi: 10.1016/j.tet.2008.07.015.

Percherla et al., Recent Developments in the Synthesis of Imidazo[1,2-a]pyridines. Synthesis. 2015; 47:A-Z. doi: 10.1055/s-0034-1380182.

Li et al., Chemistry of heterocyclic ketene aminals: construction of imidazo(pyrido)[1,2-a]pyridines and imidazo(pyrido)[3,2,1-ij][1,8]naphthyridines via DABCO-catalyzed tandem annulations. J Org Chem. May 6, 2011;76(9):3054-63. doi: 10.1021/jo102167g. Epub Apr. 14, 2011.

Singh et al., Synthesis of Multiring Fused 2-Pyridones via a Nitrene Insertion Reaction: Fluorescent Modulators of α-Synuclein Amyloid Formation. Org Lett. Dec. 18, 2015;17(24):6194-7. doi: 10.1021/acs.orglett.5b03190. Epub Dec. 9, 2015.

Wen et al., Application of 2-(2-chloroaroyl)methyleneimidazolidines in domino and multicomponent reaction: new entries to imidazo[1,2-a]pyridines and benzo[b]imidazo[1,2,3-ij][1,8]naphthyridines. Tetrahedron. 2011;67(2):293-302.

Extended European Search Report for EP App. No. 21738066.6 mailed Nov. 2, 2023.

Aberg et al., Microwave-assisted decarboxylation of bicyclic 2-pyridone scaffolds and identification of Abeta-peptide aggregation inhibitors. Org Biomol Chem. Aug. 7, 2005;3(15):2817-23. doi: 10.1039/b503294f. Epub Jun. 29, 2005.

Horvath et al., Mechanisms of Protein Oligomerization: Inhibitor of Functional Amyloids Templates α-Synuclein Fibrillation.J. Am. Chem. Soc. 2012;134(7):3439-44. Epub Jan. 19, 2012.

Horvath et al., Modulation of α-synuclein fibrillization by ring-fused 2-pyridones: Templation and inhibition involve oligomers with different structure. Archives of Biochemistry and Biophysics. Apr. 15, 2013;532(2):84-90.

(Continued)

*Primary Examiner* — Alicia L Otton

(74) *Attorney, Agent, or Firm* — Wolf, Greenfield & Sacks, P.C.

(57) ABSTRACT

The present disclosure provides compounds useful for the prevention of amyloid formation and the treatment of amyloid related disorders, including synucleopathies such as Parkinson's Disease.

14 Claims, 17 Drawing Sheets

Specification includes a Sequence Listing.

(56) References Cited

OTHER PUBLICATIONS

Sellstedt et al., A novel heterocyclic scaffold formed by ring expansion of a cyclic sulfone to sulfonamides. Org Lett. Dec. 3, 2009;11(23):5470-2. doi: 10.1021/019023024. Supporting information included, 35 pages.
[No Author Listed] STN Registry Entry for CAS RN 1242981-50-5, STN Entry Date: Sep. 27, 2010.
[No Author Listed] STN Registry Entry for CAS RN 1242981-51-6, STN Entry Date: Sep. 27, 2010.
[No Author Listed] STN Registry Entry for CAS RN 1242981-52-7, STN Entry Date: Sep. 27, 2010.
[No Author Listed] STN Registry Entry for CAS RN 1242981-53-8, STN Entry Date: Sep. 27, 2010.
Fan et al., Efficient and regioselective synthesis of bicyclic pyrrolidones or bicyclic pyridones by cyclocondensation of heterocyclic ketene aminals with nitro-phenylpropiolate. RSC advances. Jun. 23, 2014;4(55):28852-28855.
Zou et al., A novel and facile synthesis of 2-oxo-1, 2-dihydropyridine-fused 1, 3-diazaheterocycles via heterocyclic ketene aminals and Konevenagel adducts formed by phthalic anhydride and ethyl cyanacetate. Chinese Chemical Letters. Sep. 2014. 28;25(12):1515-1519.

* cited by examiner

INHIBITORS OF MICROBIALLY INDUCED AMYLOID

CROSS REFERENCE TO RELATED APPLICATIONS

This application is a National Stage filing under 35 U.S.C. § 371 of International PCT Application No. PCT/US2021/012792, filed Jan. 8, 2021 which claims priority under 35 U.S.C. § 119 (e) to U.S. provisional patent application, U.S. Ser. No. 62/959,385, filed Jan. 10, 2020, the entire contents of each of which is incorporated herein by reference.

TECHNICAL FIELD

The present disclosure relates to inhibitors of amyloid formation, and particularly inhibitors of microbially-induced amyloid formation, as well as methods of using such inhibitors to treat or inhibit neurological disorders and other disorders associated with amyloid accumulation. Methods of identifying compositions that inhibit or promote amyloid formation are also provided.

BACKGROUND

Many neurodegenerative diseases are associated with atypical aggregation of proteins in the brain, which leads to cell death and a resulting manifestation of many neuropathies. It is believed that disease specificity is a consequence of (i) the specific proteins involved in aggregation, (ii) the specific regions of the brain affected, and (iii) the specific neuronal cell types affected. In the case of the natural human protein α-synuclein, aberrant aggregation of this protein leads to any of over 50 "α-synucleinopathies," of which Parkinson's Disease is the most common and most widely studied. In Parkinson's Disease, α-synuclein aggregation leads to the accumulation of large precipitated aggregates, called Lewy bodies, within certain neuronal cell types, most typically those that produce the neurotransmitter dopamine. When enough α-synuclein aggregate is present, neuronal death occurs and dopamine production declines. Dopamine is required for proper control of movement, and once dopaminergic neurons are killed they are not replaced. Over time the dopamine pool declines irreversibly to a point where motor symptoms progress and become debilitating.

The most pathogenic form of α-synuclein is still unclear, e.g., whether full intact Lewy bodies or smaller oligomeric α-synuclein fibrils are most relevant to disease progression and pathology. Traditional pharmaceutical and biotech approaches to inhibiting α-synuclein aggregation have focused on attacking the aggregation process in the neurons and brain regions most associated with disease symptoms. Small molecule approaches, antibody approaches and a vaccine approach all have been attempted and continue to be evaluated as interventions for Parkinson's Disease and other α-synucleinopathies. Importantly, all of these strategies presently rely on the therapeutic entity crossing the blood-brain barrier and reaching the target neuronal tissue. Traversing the blood-brain barrier remains one of the most significant pharmacokinetic challenges that hinders drug development for neurodegenerative diseases. Accordingly, there is a need for inhibitors of amyloid formation, and especially α-synuclein aggregation inhibitors, that have the potential for providing therapeutic effects without having to cross the blood-brain barrier.

SUMMARY

In one aspect, provided herein is a compound for Formula (I):

(I)

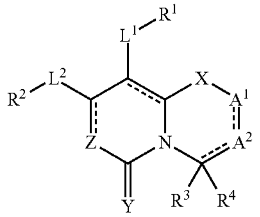

or a pharmaceutically acceptable salt thereof, wherein $R^1$, $R^2$, $R^3$, $R^4$, $L^1$, $L^2$, $A^1$, $A^2$, X, Y and Z are as defined herein.

In some embodiments, the compound of Formula (I) may have a structure selected from Formulae (II), (III), (IV), (V), (VI), (VII), (VIII), (IX), and (X):

(II)

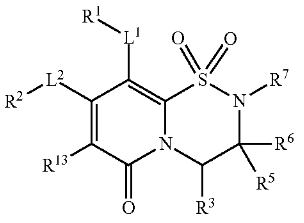

(III)

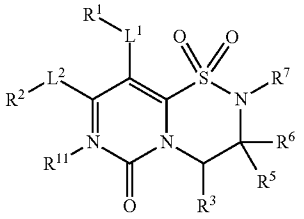

(IV)

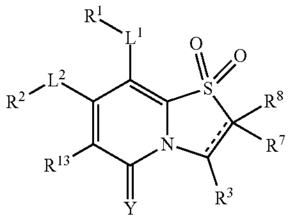

(V)

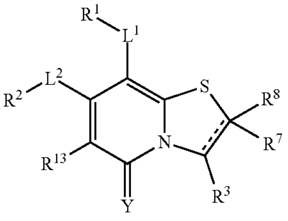

-continued (VI)

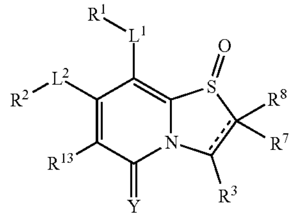

(VII)

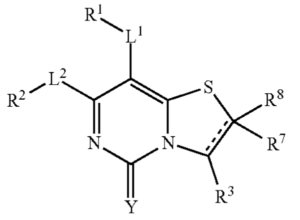

(VIII)

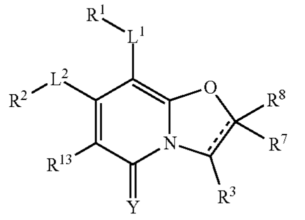

(IX)

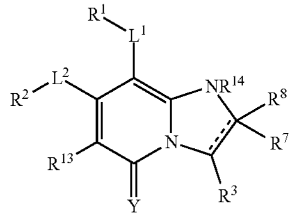

(X)

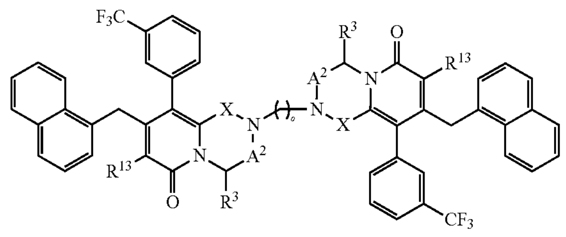

The compounds disclosed herein may be used in the form of a composition that is formulated for delivery outside of the systemic circulation of a subject. Said composition may be formulated for enteric or intranasal delivery, for example, and/or said compositions may further be formulated for controlled release within the lower intestine or colon. In some embodiments, the composition may be formulated for oral administration, injection (e.g., intravenous, subcutaneous, intramuscular, intraperitoneal, intraspinal or intracranial), topical delivery, mucosal delivery, or for delivery to the central nervous system or systemic circulation of a subject. The aforementioned compositions may comprise an enteric-coated capsule, tablet, soft-gel, spray dried powder, polymer matrix, hydrogel, enteric-coated solid, crystalline solid, amorphous solid, glassy solid, coated micronized particle, liquid, nebulized liquid, aerosol, or microcapsule.

The present disclosure further provides a method of disrupting the formation of amyloid aggregates, comprising contacting an amyloid or a precursor of an amyloid with a compound described herein, or a composition thereof.

The present disclosure further provides a method of disrupting the formation of amyloid aggregates in a subject, comprising administering to said subject a compound as described herein, or a composition thereof. Optionally, said subject is additionally selected or identified as one that would receive the benefit of a molecule that disrupts the formation of amyloid aggregates prior to administration of said composition. Such selection or identification can be made by clinical or diagnostic evaluation, prior to administering said composition. Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof. Optionally, prior to, during or after administration of the composition, the disruption or inhibition of the formation of amyloid aggregates in said subject is measured or evaluated.

The present disclosure further provides a method of inhibiting, ameliorating, reducing the likelihood of, delaying the onset of, treating, or preventing an amyloid disorder in a subject in need thereof, comprising administering to the subject a compound as described herein, or a composition thereof. Optionally, the subject is additionally selected or identified as one that would receive the benefit of a compound that inhibits or disrupts the formation of amyloid aggregates prior to administration of said composition, for example by detecting a presence or level of a bacterial protein (such as CsgA), or a presence or level of a microbial organism that makes the bacterial protein in an intestinal sample of the subject. Such selection or identification can be made by clinical or diagnostic evaluation, prior to administering said compound or composition. Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof. Optionally, prior to, during or after administration of the compound or composition, the disruption or inhibition of the formation of amyloid aggregates in said subject is measured or evaluated.

In some embodiments, said amyloid aggregates may comprise one or more mammalian amyloid or mammalian amyloid precursors such as proteins, and/or one or more bacterial or fungal proteins (e.g., a composition comprising CsgA). In some embodiments, said amyloid proteins may comprise one or more mammalian amyloid or mammalian amyloid precursors such as proteins, and/or one or more bacterial or fungal proteins (e.g., a composition comprising CsgA). In some embodiments, said amyloid aggregates may be present within the gastrointestinal tract, the enteric nervous tissue, cranial sinus, oral cavity, or nasal cavity (e.g., the olfactory bulb). In some embodiments, said amyloid proteins may be present within the gastrointestinal tract, the enteric nervous tissue, cranial sinus, oral cavity, or nasal cavity (e.g., the olfactory bulb).

In some embodiments, the methods of the present disclosure further comprise measuring or evaluating a change in the subject's nervous system, such as a neurological symptom, motor behavior, or other behavior of the subject, which may comprise, e.g., one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and/or visual, auditory, olfactory, and/or tactile hallucinations, vertigo, cognitive dysfunction, altered dopamine levels, altered serotonin levels, altered kynurenine levels, or any combination thereof.

In some embodiments, the methods of the present disclosure further comprise measuring or evaluating a change in the gastrointestinal system, such as a gastrointestinal symptom or behavior of the subject, which may comprise, e.g., one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, leaky gut, intestinal dysbiosis, hypersalivation (sialorrhea), anorectal dysfunction, dyssynergic defecation, or any combinations thereof. Such hyperpermeability may result from inflammation of the intestinal lining and/or failure of the tight junctions between cells of the intestinal epithelium, which allows the passage of substances from the lumen into the surrounding tissues where some may enter the peritoneal cavity and/or systemic circulation. Because of this leakage of substances from the gut or intestinal lumen, intestinal hyperpermeability may be referred to as "leaky gut" or "leaky gut syndrome."

In some embodiments, the compounds and compositions of the present disclosure may be administered to a subject prior to, or following, the appearance of a neurological symptom or condition. In some embodiments, the compositions of the present disclosure may be administered to a subject prior to, or following, the appearance of a gastrointestinal symptom or condition associated with an amyloid disorder. In some embodiments, said subject is selected as one that has been identified as being at risk for developing or already having Lewy Body Dementia, incidental Lewy body disease, Lewy body variant of Alzheimer's disease, multiple system atrophy, pure autonomic failure, or any combination thereof, such as by clinical or diagnostic evaluation. In some embodiments, said subject is under the age of 18, 18-30, 30-50, 50-60, 60-70, or over the age of 70. In some embodiments, said subject is one that has been identified or selected as being at risk for developing or already having Parkinson's disease, such as by clinical or diagnostic evaluation or family history analysis.

In some embodiments, a compound or composition as described herein may be co-administered with caffeine, nicotine, theophylline, theobromine, xanthine, methylxanthine, or derivatives thereof. In some embodiments, the methods as disclosed herein further comprise administering to said subject an inhibitor of α-synuclein aggregation. In some embodiments, the methods as disclosed herein further comprise administering to said subject L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like, or any combination thereof. In some embodiments, the methods as disclosed herein comprise administering to said subject an inhibitor of α-synuclein aggregation, and further comprise administering to said subject L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like, or any combination thereof. In some embodiments, the inhibitor of α-synuclein aggregation and the L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like are administered in the same composition. In some embodiments, the inhibitor of α-synuclein aggregation and the L-DOPA, carbodopa, levodopa, Droxidopa, rasagiline, apomorphine hydrochloride, Bromocriptine, Rotigotine, Pramipexole, Ropinirole, Benzotropine, Trihexyphenidyl, Selegiline, Entacapone, Tolcapone, Amantadine, Pimavanersin, Rivastigmine or the like are administered in separate compositions. In some embodiments, the separate compositions are administered at the same time. In some embodiments, the separate compositions are administered at the different times.

In some embodiments, a compound or composition as described herein is for medical use. In some embodiments, the composition described herein is for use in treating an amyloid disorder as described herein (such as an amyloid disorder of Table 2). In some embodiments, the amyloid disorder is selected from the group consisting of Parkinson's Disease, Lewy Body Dementia, incidental Lewy body disease, Lewy body variant of Alzheimer's disease, multiple system atrophy, or pure autonomic failure, or any combination of two or more of these. In some embodiments, a compound or composition described herein is for use in preparing a medicament for the treatment for an amyloid disorder as described herein (such as an amyloid disorder of Table 2). In some embodiments, the amyloid disorder is selected from the group consisting of Parkinson's Disease, Lewy Body Dementia, incidental Lewy body disease, Lewy body variant of Alzheimer's disease, multiple system atrophy, or pure autonomic failure, or any combination of two or more of these. In some embodiments, the composition comprises one or more compounds of the invention, as described herein. In some embodiments, the composition is formulated for delivery to the gastrointestinal tract, for example via oral or rectal delivery, or formulated with an enteric coating. In some embodiments, the composition is formulated for delivery to the central nervous system, for example via intraspinal or intracranial delivery, or formulated to cross the blood brain barrier. In some embodiments, the composition is formulated to bypass the blood brain barrier. Such formulations may be administered, for example, intranasally. Such formulations may also be administered via the olfactory route.

The present disclosure provides methods of identifying compounds or compositions that affect the formation of microbially-induced amyloid. In some approaches, the methods comprise contacting a plurality of concentrations of a microbial amyloid or a microbial amyloid precursor with a plurality of concentrations of α-synuclein and/or other mammalian amyloid or mammalian amyloid precursor in the presence of a compound or composition as described herein, analyzing or measuring the formation of amyloid after the reaction set forth above; and comparing said analysis or measurement to an analysis or measurement of a control, wherein said control comprises analyzing or measuring the formation of amyloid after the reaction set forth above in the absence of said composition. In some methods and compositions disclosed herein, said microbial amyloid or microbial amyloid precursor comprises CsgA. In some embodiments, the methods according to the present disclosure also comprise agitation during the contacting step and/or prior to measurement.

In certain embodiments, said contacting of a plurality of concentrations of a microbial amyloid or a microbial amyloid precursor (e.g., a composition comprising CsgA) with a plurality of concentrations of α-synuclein and/or other mammalian amyloid or mammalian amyloid precursor is conducted in the presence of an indicator of amyloid formation. In some further embodiments, said indicator is a fluorescent indicator, a spin-labeled indicator, an enzyme, an antibody, or a colorimetric indicator. In some further embodiments, said indicator is Thioflavin T (ThT). Where said indicator of amyloid formation is an antibody, the methods of the present disclosure provide that said antibody may have specificity for aggregated α-synuclein and/or another mammalian amyloid or mammalian amyloid precursor, and optionally may be conjugated to a fluorescent label, an enzyme, a colorimetric label, a spin label, a metal ion binding moiety, an electrochemiluminescence label, a nucleic acid, a polysaccharide, or a polypeptide. In some embodiments according to the methods of the present disclosure, CsgA and said α-synuclein and/or other such bacterial amyloid precursor and/or mammalian amyloid/mammalian amyloid precursor are each separately labeled.

In some embodiments according to the methods of the present disclosure, said contacting a plurality of concentrations of a microbial amyloid or a microbial amyloid precursor (e.g., a composition comprising CsgA) with a plurality of concentrations of α-Synuclein and/or other mammalian amyloid or mammalian amyloid precursor in the presence of a compound or composition as described herein, analyzing or measuring the formation of amyloid after the reaction set forth above; and comparing said analysis or measurement to an analysis or measurement of a control, further comprises identifying or selecting a compound or composition that alters or modulates or is suspected of altering or modulating amyloid formation. In some embodiments, the methods described herein further comprise identifying or selecting a compound or compositions that reduces or enhance amyloid formation. In some embodiments, the methods described herein further comprise identifying or selecting a compound or compositions that reduces or enhances amyloid formation that also do not cross the blood brain barrier. The compounds or compositions identified by these methods, can be administered to subjects identified or selected as a population that would benefit from receiving a compound that alters amyloid formation (e.g., a compound that reduces amyloid formation, preferably without crossing the blood brain barrier). Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof.

The methods according to the present disclosure further contemplate a method of making microbially-induced amyloid, comprising contacting a plurality of concentrations of a microbial amyloid or a microbial amyloid precursor with a plurality of concentrations of α-Synuclein and/or other mammalian amyloid or mammalian amyloid precursor in the presence or absence of a compound or composition as described herein; generating microbially-induced amyloid; and analyzing or quantifying the microbially-induced amyloid. In some further embodiments, said microbial amyloid or microbial amyloid precursor comprises CsgA. In some further embodiments, the methods according to the present disclosure further comprise agitation during said contacting or prior to measurement. In some further embodiments, said method is conducted in the presence of an indicator of amyloid formation. In some further embodiments, said indicator of amyloid formation may comprise a fluorescent indicator, a spin-labeled indicator, or a colorimetric indicator. In some embodiments, said indicator said indicator is Thioflavin T (ThT). In some embodiments, CsgA and α-Synuclein, or other such bacterial amyloid/bacterial amyloid precursor and mammalian amyloid/mammalian amyloid precursor are each separately labeled. In some embodiments, said amyloid formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.

In some embodiments according to the methods of the present disclosure, said composition to be present during said contacting of a plurality of concentrations of a microbial amyloid or a microbial amyloid precursor (e.g., a composition comprising CsgA) with a plurality of concentrations of α-Synuclein and/or other mammalian amyloid or mammalian amyloid precursor comprises a mixture of compounds. The composition may comprise tissue, bodily fluid or an extract thereof. In some embodiments, said composition comprises feces, urine, blood, spinal fluid, or saliva, or a component thereof. In some embodiments, the composition comprises an extract from a natural product. In some further embodiments, the natural product is an herb, a botanical substance, or foodstuff. In some embodiments, said natural product is a fungal tissue, legume, seed, berry, leaf, fruit, flower, plant root, plant stem, or plant bark. In some embodiments, the composition may comprise one or more bacteria, bacterial extracts, lysates, conditioned culture media, lyophilized bacteria, lyophilized lysates, lyophilized culture media, or any combination thereof. In some embodiments, the composition may comprise one or more microbes, microbial extracts, lysates, conditioned culture media, lyophilized microbes, lyophized lysates, lyophilized culture media, or any combination thereof. In some embodiments, the methods above further comprise identifying or selecting compositions that increase or reduce amyloid formation, preferably compounds that also do not cross the blood brain barrier. The compounds identified by these methods, can be administered to subjects identified or selected as a population that would benefit from receiving a compound that alters amyloid formation (e.g., a compound that reduces amyloid formation, preferably without crossing the blood brain barrier). Such selected subjects may have been diagnosed or evaluated for Parkinson's Disease, Lewy Body Dementia, incidental Lewy body disease, Lewy body variant of Alzheimer's disease, multiple system atrophy, or pure autonomic failure, or any combination thereof.

In some embodiments, the inhibitors of amyloid formation may be intended for administration systemically or locally to the enteric or central nervous system.

The present disclosure also contemplates a kit comprising a microbial amyloid or a microbial amyloid precursor and α-Synuclein and/or other mammalian amyloid or mammalian amyloid precursor, being present in one or more containers within said kit whereby the methods of the present disclosure may be practiced. In some embodiments, said microbial amyloid or microbial amyloid precursor comprises CsgA.

The present disclosure provides a method of inhibiting amyloid formation in a subject in need thereof, comprising administering to the subject a compound as described herein, or a pharmaceutically acceptable salt thereof, or a pharmaceutical composition thereof.

The present disclosure provides a method of preventing or treating a disorder associated with amyloid formation in a subject in need thereof, comprising administering to the subject a compound as described herein, or a pharmaceutically acceptable salt thereof, or a pharmaceutical composition thereof.

The present disclosure provides a method of preventing or treating an amyloid disorder in a subject in need thereof, comprising administering to the subject a compound as described herein, or a pharmaceutically acceptable salt thereof, or a pharmaceutical composition thereof.

In the methods of the present disclosure, the amyloid disorder or the disorder associated with amyloid formation may be a neurological disorder. The disorder may be Parkinson's disease (PD), Lewy body dementia, multiple system atrophy, multiple sclerosis (MS), frontotemporal dementia (FTD), REM sleep behavior disorders (RBD), α-synucleinopathy, PD-associated constipation, PD-associated hyposmia, Huntington's Disease, Alexander's Disease, amyotrophic lateral sclerosis (ALS), or Alzheimer's Disease. The disorder may be intestinal dysbiosis, intestinal hyperpermeability, irritable bowel syndrome (IBS), inflammatory bowel disease (IBD), ulcerative colitis, or Crohn's disease.

The subject may suffer from gastrointestinal symptoms including one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, hypersalivation (sialorrhea), anorectal dysfunction, dyssynergic defacation, and nausea. The gastrointestinal symptoms may be associated with an alpha-synucleinopathy, Parkinson's Disease, or Parkinsonism.

In certain embodiments, the amyloid disorder can be diagnosed by detecting the presence or level of intestinal bacterial amyloid aggregates. In some embodiments, the amyloid disorder can be diagnosed by detecting the presence or level of intestinal bacterial amyloid proteins. In certain embodiments, the aggregates may comprise a bacterial CsgA protein. In some embodiments, the proteins may comprise a bacterial CsgA protein. In certain embodiments, the disorder can be diagnosed by detecting the presence or level of intestinal bacterial genes and gene transcripts.

The methods of the present disclosure may further comprise detecting the presence or level of a bacterial protein, such as CsgA, or a microorganism that produces the bacterial protein, in an intestinal sample of the subject. In certain embodiments, the subject is selected as in need of said prevention or treatment if the presence of the bacterial protein, a transcript mRNA of the bacterial protein, or the microorganism that produces the bacterial protein is detected in the intestinal sample, or if the level of the bacterial protein or the microorganism that produces the bacterial protein in the intestinal sample is greater than a predetermined level or control.

The methods of the present disclosure may further comprise determining a decrease or absence of the intestinal amyloid aggregates following the administration of the compound of composition, or identifying the subject as displaying a gastrointestinal symptom. The methods of the present disclosure may further comprise determining a decrease or absence of the intestinal amyloid proteins following the administration, or identifying the subject as displaying a gastrointestinal symptom.

In some embodiments, the methods of the present disclosure further comprise measuring or evaluating enteric amyloid levels and/or amyloid aggregation during the course of administration. In some embodiments, the methods of the present disclosure further comprise measuring or evaluating enteric amyloid levels and/or amyloid proteins during the course of administration.

The methods of the present disclosure further provide a method of treating or inhibiting an amyloid disorder (e.g., a neurological disorder such as Parkinson's Disease, Lewy Body Dementia, incidental Lewy body disease, Lewy body variant of Alzheimer's disease, multiple system atrophy, or pure autonomic failure, or any combination thereof) in a tested subject comprising contacting a plurality of concentrations of a microbial amyloid or a microbial amyloid precursor with a plurality of concentrations of α-Synuclein and/or other mammalian amyloid or mammalian amyloid precursor, which may be obtained from a biological sample from said tested subject, in the presence or absence of a compound or composition as described herein; analyzing or measuring the formation of amyloid; and comparing the analysis or measurement made with an analysis or measurement of a control, wherein said control may comprise analyzing or measuring the formation of amyloid in the absence of said composition or comparison to a standard such as the amount or rate or formation of amyloid from a healthy subject or a subject having amyloidosis (e.g., a subject suffering from Parkinson's Disease, Lewy Body Dementia, incidental Lewy body disease, Lewy body variant of Alzheimer's disease, multiple system atrophy, or pure autonomic failure, or any combination thereof); and if the formation of amyloid in the presence of said composition is increased relative to the formation of amyloid in the absence of said composition or if the amount or rate or formation of amyloid is the same or greater in the sample from the tested subject, for example, than the amount, rate, or formation of amyloid from the healthy subject control or the control subject having amyloidosis, administering to said tested subject an effective amount of a pharmaceutical composition suitable for inhibiting or treating said amyloid disorder. In some further embodiments of these methods, said microbial amyloid or microbial amyloid precursor comprises, consists essentially of, or consists of CsgA.

In some embodiments, the methods as described herein further comprise identifying or selecting said tested subject as one that would benefit from a treatment or inhibition of an amyloid disorder, and may further comprise identifying or selecting said subject as one at risk of or showing symptoms of one or more of Parkinson's Disease, Lewy Body Dementia, incidental Lewy body disease, Lewy body variant of Alzheimer's disease, multiple system atrophy, pure autonomic failure, or any combination thereof.

BRIEF DESCRIPTION OF THE DRAWINGS

FIG. 2A is a graph showing total αSyn in whole brain lysates quantified by ELISA. FIG. 2B is a graph showing quantification of insoluble αSyn fibrils in the striatum by dot blot assay. FIGS. 2C-D show quantification of TNFα (FIG. 2C) and IL-6 (FIG. 2D) by ELISA from the striatum. FIGS. 2E-G show the results of staining thin sections of brains derived from ASO mice. Sections were stained for Iba1 (microglia), 3D cellular reconstructions generated, and morphological characteristics quantified of microglia resident in the striatum. n=3 (FIGS. 2A-B), n=6-7 (FIG. 2C, 2D), n=4 (FIGS. 2E-G) (averaged from 20-40 cells for diameters, or 5-7 cells for branching). Points represent individuals, bars represent the mean and standard error. Data analyzed by one-way ANOVA with Tukey post-hoc test for FIGS. 2A-D, or two-tailed t-test for FIGS. 2E and 2F. *p≤0.05; p≤0.01; *p≤0.001; ****p≤0.0001.

FIG. 3G is a graph depicting principal component analysis of compiled motor scores of FIGS. 3A-F. FIGS. 3H-I depict quantification of insoluble αSyn fibrils in the striatum (FIG. 3H) and ventral midbrain (FIG. 31) by dot blot assay. n=8 (FIGS. 3A-G), n=4 (FIG. 3H). Points represent individuals, bars represent the mean and standard error. Time courses analyzed by two-way ANOVA, with Sidak post-hoc test for between group comparisons indicated above individual time points, and brackets indicating significance between treatments. Data in (FIG. 3H) analyzed by two-tailed Mann-Whitney test. For FIGS. 3A-I, *p<0.05; p<0.01; *p<0.001; ****p<0.0001.

FIG. 5 demonstrated an overall increase in number of fecal pellets when mice were treated with compound 004a compared to MC4100-control chow group (a qualitative trend was observed; statistical difference was not reached). Points represent individual animals; bars represent the mean and standard error. Data analyzed by one-way ANOVA with Dunnett's multiple comparisons test.

FIG. 6 demonstrated a significant reduction in % of water content in MC4100-control chow group suggesting disease phenotype. Treatment with compound 004a restored a constipation phenotype induced by the curli operon. Points represent individual animals; bars represent the mean and standard error. Data analyzed by one-way ANOVA with Dunnett's post-hoc test for between group comparison indicated above each treatment group, and brackets indicating significance between treatments; *p<0.05; **p<0.01.

FIG. 7 demonstrated increased time to descend in the MC-4100 control chow group (p=0.0741) compared to KO CsgA group suggesting disease motor phenotype. Compound 004a treatment demonstrated a trend towards improvement of the phenotype. Points represent individual animals; bars represent the mean and standard error. Data analyzed by one-way ANOVA with Dunnett's post-hoc test.

FIG. 8A illustrates csgA expression relative to expression of housekeeping gene recA at 12-14 weeks of age. FIG. 8B illustrates csgA expression relative to expression of housekeeping gene cysG at 12-14 weeks of age. FIG. 8C illustrates csgA expression relative to expression of the housekeeping gene recA at 14-16 weeks of age. FIG. 8D illustrates csgA expression relative to expression of housekeeping gene cysG at 14-16 weeks of age. Points represent individual animals; bars represent the mean and standard error. Data analyzed by one-way ANOVA with Dunnett's post-hoc test for between group comparison indicated above each treatment group, and brackets indicating significance between treatments; *p≤0.05; **p≤0.01.

DETAILED DESCRIPTION

Figure 1A:
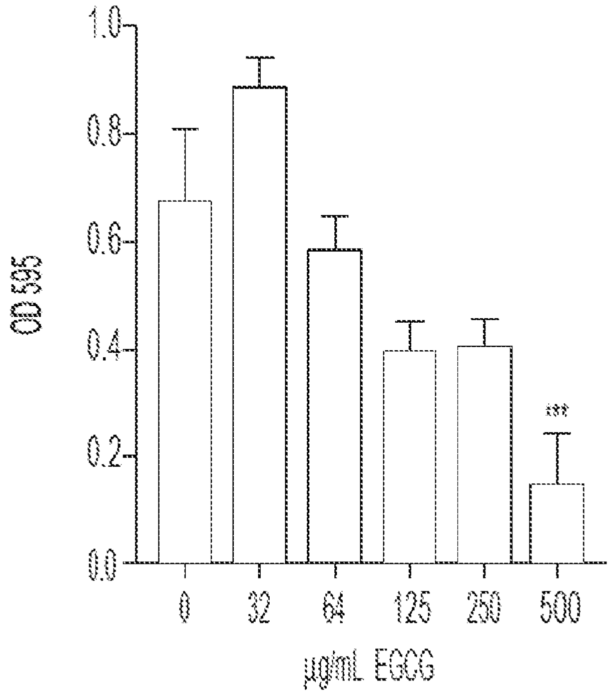
FIG. 1A is a graph showing Crystal violet staining of biofilm growth by wild-type *E. coli* following 4 days in static culture, with indicated concentrations of epigallocatechin gallate (EGCG); data assessed by optical density (OD).

The majority of cases of neurodegenerative diseases are idiopathic, which, conventionally, has made it difficult to identify the etiology of most such diseases. An emerging theory is that many neurodegenerative diseases start not in the brain or central nervous system (CNS), but in the periphery and gradually migrate to the brain over the course of many years in a slow, progressive process. Still, the molecular etiology in the periphery has been the subject of study. In the case of Parkinson's Disease, it is known that constipation and hyposmia occur in many patients often decades before the emergence of the stereotypical motor symptoms that currently define Parkinson's Disease. Without being limited by theory, it is therefore contemplated that α-synuclein aggregation begins in the gastrointestinal (GI) tract and in the olfactory bulb, and that aggregated α-synuclein gradually progresses to the brain in a prion-like propagative process. In this scenario, known more generally as Braak's Hypothesis, it is contemplated that analysis of the molecular mechanisms involved in these peripheral tissues can lead to non-intuitive, non-conventional approaches for preventing and/or treating amyloid disorders, such as α-synucleinopathies, such as Parkinson's Disease.

Without being limited by theory, one molecular mechanism contemplated herein implicates bacterial amyloid as the seeding factor that nucleates or otherwise leads to α-synuclein aggregation thereby initiating the pathological process that leads ultimately to Lewy body deposition and clinical manifestation of Parkinson's Disease and other α-synucleinopathies. Bacterial amyloids are aggregated forms of secreted bacterial proteins and are thought to play a role in both bacterial adhesion to host cells and biofilm formation. In the right environment and in the presence of host proteins prone to aggregation, it is believed, without being limited by theory, that bacterial amyloids themselves serve as a direct structural template for host protein aggregation in a prion-like fashion. The bacterial chaperone machinery responsible for driving bacterial amyloid aggregation may also use the host protein as a substrate and thereby facilitate host protein aggregation into amyloid structures. Once aggregated, the host protein aggregation is perpetuated in a prion-like fashion through the enteric nervous system over the course of many years. Ultimately, these aggregates spread into brain tissue and result in the stereotypical clinical symptoms of Parkinson's Disease. This effect may also result in the development of other amyloid-driven diseases such as Alzheimer's disease, in which aggregation of the host proteins A-beta and/or tau are implicated. Consistent with this, analysis of current publicly-available human microbiome datasets reveals increased representation of the curli-associated csgA gene from *E. coli* in persons with Parkinson's Disease, and transplantation of fecal microbes from PD patients into germ-free (GF) wild-type or ASO mice results in greater csgA abundance compared to microbiomes from healthy controls, based on PICRUSt imputed analysis of 16s rRNA sequences (See, e.g., WO2019/028456, and references cited therein, all of which are hereby incorporated by reference in their entirety). Intestinal amyloid aggregates can lead to symptoms associated with Parkinson's Disease and other amyloid disorders, and treating these animals with compounds that inhibit and/or disrupt amyloid aggregates can ameliorate these symptoms associated with Parkinson's Disease and other amyloid disorders.

The present disclosure relates to compounds, compositions, and methods for the treatment, amelioration, or prevention of amyloid disorders. Compounds disclosed herein alter the ability of bacterial amyloid to promote aggregation and amyloid formation of the eukaryotic protein α-synuclein. Said alterations may include alterations in the extent, rate of formation, stability, and/or rate of disaggregation of microbially induced amyloid, or any combination thereof. Further disclosed herein are compounds, compositions, and methods useful for the treatment or inhibition of neurodegenerative diseases, as well as, compounds, compositions, and methods useful for the prevention or amelioration of the progression of neurodegenerative diseases. Further disclosed herein are compounds, compositions, and methods useful for the treatment or inhibition of gastrointestinal dysfunction related to neurodegenerative diseases. Additionally disclosed herein are methods for studying the molecular etiology of mammalian amyloid diseases and the molecular link between bacterial amyloid production and mammalian amyloid production. In some embodiments, the composition comprises, consists essentially of, or consists of a compound as described herein. The present disclosure further relates to methods that facilitate the evaluation of aggregation and dis-aggregation of both host and bacterial amyloid proteins. Methods of the present disclosure are also useful for identifying drug candidates that affect these processes.

It is contemplated that in some embodiments, a composition comprising, consisting essentially of, or consisting of a compound as described herein is useful in preventing α-synuclein aggregation, the seeding of α-synuclein aggregation by CsgA or other microbial amyloids, or the formation of microbial amyloids that may seed α-synuclein aggregation in vivo, or that such compounds and compositions are useful in preventing or treating Parkinson's Disease and/or other α-synucleinopathies (See, e.g., Example 26 and Tables 3 and 4).

It is contemplated that in some embodiments, a composition comprising, consisting essentially of, or consisting of a compound as described herein may be useful in preventing α-synuclein aggregation with or without seeding by microbial amyloids and thereby may have benefit in preventing or treating α-synucleinopathies independent of microbial amyloids (See, e.g., Example 26 and Tables 3 and 4).

It is contemplated that in some embodiments, a composition comprising, consisting essentially of, or consisting of a compound as described herein may be useful in preventing α-synuclein aggregation seeded by microbial amyloids and thereby have therapeutic benefit, for example if dosed at sites where microbial amyloids may be abundant, such as the gastrointestinal tract.

It is contemplated that in some embodiments, a composition comprising, consisting essentially of, or consisting of a compound as described herein may have therapeutic benefit in Parkinson's Disease and other α-synucleinopathies. Without being limited by theory, this benefit may be due to these compounds' inhibition of aggregation of α-synuclein and/or microbial amyloids. It is further contemplated that for compounds in which more than one type of aggregation is inhibited, these inhibitory effects may be additive or synergistic. (See, e.g., Example 26 and Table 2).

Accordingly, provided herein are compounds that are useful in inhibiting, ameliorating, reducing the likelihood, delaying the onset of, treating, and/or preventing an amyloid disorder, for example, any of the amyloid disorders of Table 2 (infra), such as an α-synucleinopathy, Parkinson's Disease, Lewy Body Dementia, incidental Lewy body disease, Lewy body variant of Alzheimer's disease, multiple system atrophy, pure autonomic failure, or a combination of two or more of the listed items.

Compounds of the Invention

In one aspect, provided herein is a compound for Formula (I):

(I)

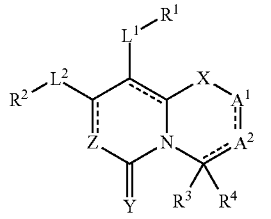

or a pharmaceutically acceptable salt thereof, wherein:

$A^1$ is —C($R^7$)($R^8$), or —CO—; or $A^1$ is —N($R^7$)— when X is —$SO_2$—, CO or —C($R^9$)($R^{10}$);

$A^2$ is absent, or —C($R^5$)($R^6$);

$L^1$ is a bond, (—$CH_2$-)$_m$, —$CF_2$—, —(C=O)—, or —C($R^9$)($R^{10}$)—;

$L^2$ is a bond, (—$CH_2$-)$_m$, —$CF_2$—, —(C=O)—, or —C($R^9$)($R^{10}$)—;

X is —N($R^{11}$)—, —N($R^{14}$)—, —O—, —CO—, —S—, —S(=O)—, —$SO_2$—, —$CF_2$—, —C($R^9$)($R^{10}$)—;

Y is O or S;

Z is =C($R^{13}$)—, =N—, or —N($R^{11}$)—;

$R^1$ is substituted or unsubstituted phenyl, substituted or unsubstituted heterocyclyl;

$R^2$ is substituted or unsubstituted naphthyl, substituted or unsubstituted phenyl, substituted or unsubstituted quinolinyl, substituted or unsubstituted isoquinolinyl, or substituted or unsubstituted heterocyclyl;

$R^3$ and $R^4$ are independently absent, as permitted by valence, or are selected from —H, substituted or unsubstituted $C_1$-$C_{10}$ alkyl, acyl, —$CO_2R^7$, —$CON(R^7)(R^8)$, —$P{=}O(OH)_2$ or —$SO_2(OH)$;

$R^5$ and $R^6$ are independently absent, as permitted by valence, or are selected from —H, and $C_1$-$C_{10}$ alkyl, or together form a spirocarbocyclic or spiro(hetero)carbocyclic ring;

$R^7$ and $R^8$ are independently absent as permitted by valence, or are selected from —H, substituted or unsubstituted $C_1$-$C_{10}$ alkyl, —$(CH_2)_m$-aryl, —$(CH_2)_m$-heteroaryl, —$(CH_2)_m$ substituted or unsubstituted cycloalkyl, —$R^{14}$; or together form a spiropentanyl ring;

$R^9$ and $R^{10}$ are independently, for each occurrence, —H, —Cl, —Br, —F, —$CF_3$, $C_1$-$C_{10}$ alkyl;

$R^{11}$ and $R^{12}$ are independently, for each occurrence, —H, acyl, sulfonyl, substituted or unsubstituted $C_1$-$C_{10}$ alkyl, $C_3$-$C_6$ cycloalkyl, $C_{3-6}$ heterocyclyl, substituted or unsubstituted benzyl, —$(CH_2)_o$-(substituted or unsubstituted aryl), or —$(CH_2)_o$-(substituted or unsubstituted heteroaryl);

$R^{13}$ is selected from —H, —OH, —$OR^{11}$, —Cl, —Br, —F, —CN, —$CF_3$, —$CH_2F$, —$CHF_2$, substituted or unsubstituted $C_1$-$C_{10}$ alkyl, $C_1$-$C_{10}$ alkenyl, $C_3$-$C_6$ cycloalkyl, substituted or unsubstituted $C_3$-$C_6$ heterocycloalkyl, acyl, —$CO_2R^7$, —$(CH_2)_mCO_2N(R^{11})(R^{12})$, —$CON(R^7)(R^8)$, —$(CH_2)_mOH$, —$(CH_2)_mCO_2H$, —$(CH_2)_mNH_2$, —$(CH_2)_mN(R^{11})(R^{12})$, —$N(R^{11})(R^{12})$, —$NR^{11}(C{=}O)(CH_2)_mCH_3$, —$NR^{11}(C{=}O)R^{12}$, and $NR^{12}(SO_2)(CH_2)_mCH_3$;

$R^{14}$ is —H, $C_1$-$C_{10}$ alkyl, $C_1$-$C_{10}$ alkenyl, $C_1$-$C_{10}$ (mono or poly)hydroxylated alkyl, —$(CH_2)_o$—$R^{15}$, —$(CH_2CH_2O)_o$—$R^{15}$, —$(CH_2)_m$—$CO_2H$, —$(CH_2)_m$—$NH_2$, —$(CH_2)_m$—$(CO)NR^{16}R^{17}$, or a protecting group;

$R^{15}$ is —$CON(R^{11})(R^{12})$, —$N(R^{11})(R^{12})$, acyl, —$CO_2R^7$, substituted or unsubstituted aryl, substituted or unsubstituted heteroaryl, substituted or unsubstituted cycloalkyl, substituted or unsubstituted heterocycloalkyl;

$R^{16}$ and $R^{17}$ independently are —H or —$CH_3$;

m is, independently for each occurrence, 0-10;

n is, independently for each occurrence, 1-5;

is independently, for each occurrence, 1-20; and

--- represents a single bond or a double bond;

provided that the compound of Formula (I) is not:

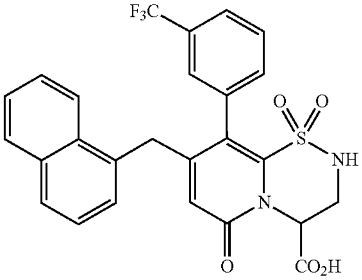

-continued

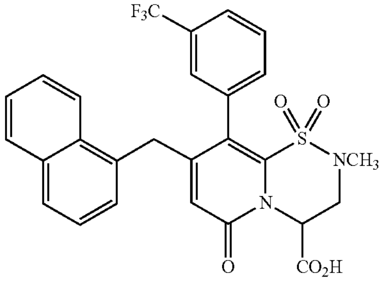

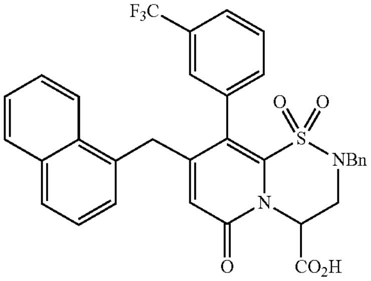

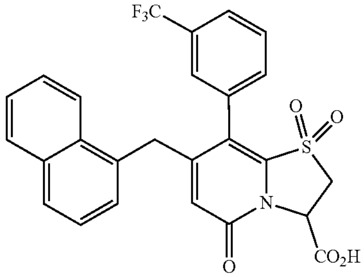

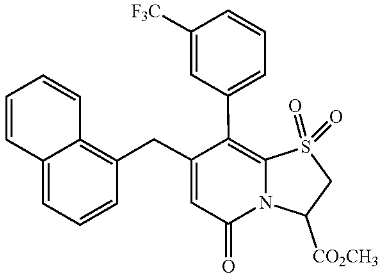

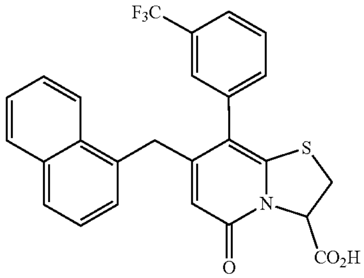

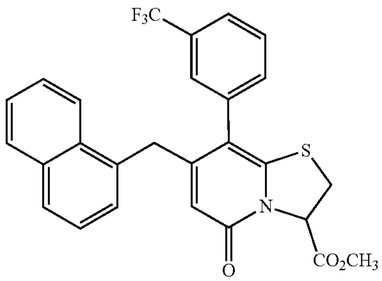

-continued

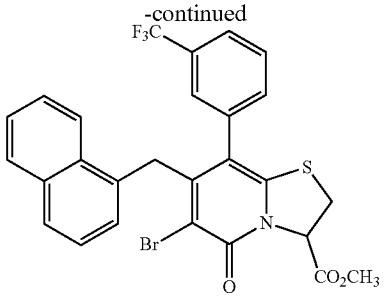

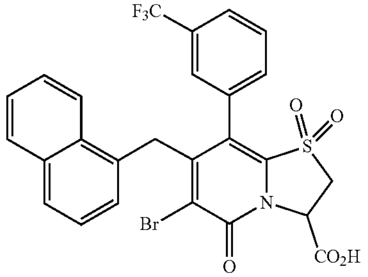

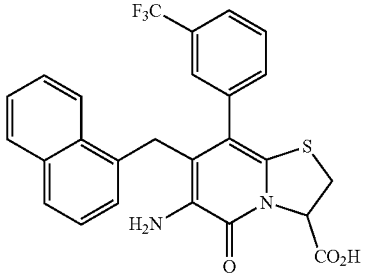

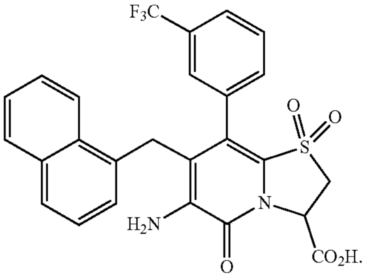

or

In some embodiments, a compound of Formula (I) is of Formula (Ia):

(Ia)

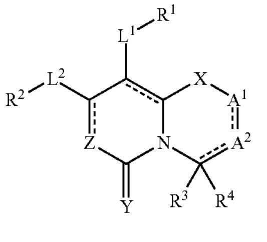

or a pharmaceutically acceptable salt thereof, wherein:

$A^1$ is —$C(R^7)(R^8)$, or —CO—; or $A^1$ is —$N(R^{14})$— when X is —$SO_2$—, CO or —$C(R^9)(R^{10})$;

$A^2$ is absent, or —$C(R^5)(R^6)$;

$L^1$ is a bond, (—$CH_2$-)$_m$, —$CF_2$—, —(C═O)—, or —$C(R^9)(R^{10})$—;

$L^2$ is a bond, (—$CH_2$-)$_m$, —$CF_2$—, —(C═O)—, or —$C(R^9)(R^{10})$—;

X is —$N(R^{11})$—, —O—, —CO—, —S—, —S(═O)—, —$SO_2$—, —$CF_2$—, —$C(R^9)(R^{10})$—;

Y is O or S;

Z is ═$C(R^{13})$—, ═N—, or —$N(R^{11})$—;

$R^1$ is substituted or unsubstituted phenyl, substituted or unsubstituted heterocyclyl;

$R^2$ is substituted or unsubstituted naphthyl, or substituted or unsubstituted heterocyclyl;

$R^3$ and $R^4$ are independently absent, as permitted by valence, or are selected from —H, substituted or unsubstituted $C_1$-$C_{10}$ alkyl, acyl, —$CO_2R^7$, —$CON(R^7)(R^8)$, —P═$O(OH)_2$ or —$SO_2(OH)$;

$R^5$ and $R^6$ are independently absent, as permitted by valence, or are selected from —H, and $C_1$-$C_{10}$ alkyl, or together form a spirocarbocyclic or spiro(hetero)carbocyclic ring;

$R^7$ and $R^8$ are independently absent as permitted by valence, or are selected from —H, substituted or unsubstituted $C_1$-$C_{10}$ alkyl, —$(CH_2)_m$-aryl, —$(CH_2)_m$-heteroaryl, —$(CH_2)_m$ substituted or unsubstituted cycloalkyl, —$R^{14}$; or together form a spiropentanyl ring;

$R^9$ and $R^{10}$ are independently, for each occurrence, —H, —Cl, —Br, —F, —$CF_3$, $C_1$-$C_{10}$ alkyl;

$R^{11}$ and $R^{12}$ are independently, for each occurrence, —H, acyl, sulfonyl, substituted or unsubstituted $C_1$-$C_{10}$ alkyl, $C_3$-$C_6$ cycloalkyl, substituted or unsubstituted benzyl, —$(CH_2)_o$-(substituted or unsubstituted aryl), or —$(CH_2)_o$-(substituted or unsubstituted heteroaryl);

$R^{13}$ is selected from —H, —OH, —$OR^{11}$, —Cl, —Br, —F, —CN, —$CF_3$, —$CH_2F$, —$CHF_2$, substituted or unsubstituted $C_1$-$C_{10}$ alkyl, $C_1$-$C_{10}$ alkenyl, $C_3$-$C_6$ cycloalkyl, substituted or unsubstituted $C_3$-$C_6$ heterocycloalkyl, acyl, —$CO_2R^7$, —$(CH_2)_mCO_2N(R^{11})(R^{12})$—$CON(R^7)(R^8)$, —$(CH_2)_mOH$, —$(CH_2)_mCO_2H$, —$(CH_2)_mNH_2$, —$(CH_2)_mN(R^{11})(R^{12})$, —$N(R^{11})(R^{12})$, —$NR^{11}(C$═$O)(CH_2)_mCH_3$, —$NR^{11}(C$═$O)R^{12}$, and $NR^{12}(SO_2)(CH_2)_mCH_3$;

$R^{14}$ is —H, $C_1$-$C_{10}$ alkyl, $C_1$-$C_{10}$ alkenyl, $C_1$-$C_{10}$ (mono or poly)hydroxylated alkyl, —$(CH_2)$—$R^{15}$, —$(CH_2CH_2O)$—$R^{15}$, —$(CH_2)_m$—$CO_2H$, —$(CH_2)_m$—$NH_2$, —$(CH_2)_m$—$(CO)NR^{16}R^{17}$, or a protecting group;

$R^{15}$ is —$CON(R^{11})(R^{12})$, —$N(R^{11})(R^{12})$, acyl, —$CO_2R^7$, substituted or unsubstituted aryl, substituted or unsubstituted heteroaryl, substituted or unsubstituted cycloalkyl, substituted or unsubstituted heterocycloalkyl;

$R^{16}$ and $R^{17}$ independently are —H or —$CH_3$;

m is, independently for each occurrence, 0-10;

n is, independently for each occurrence, 1-5;

is independently, for each occurrence, 1-20; and

═ represents a single bond or a double bond;

provided that the compound of Formula (Ia) is not:

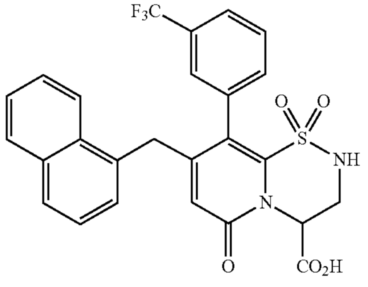

-continued

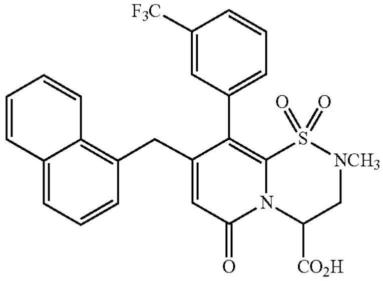

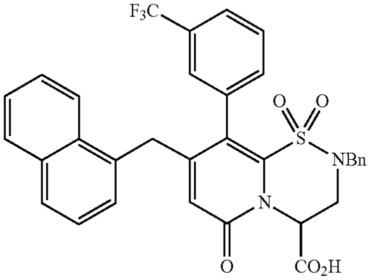

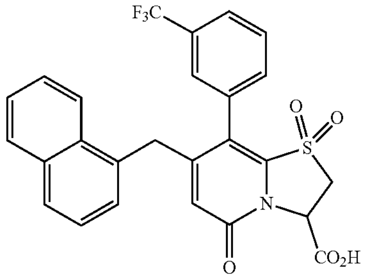

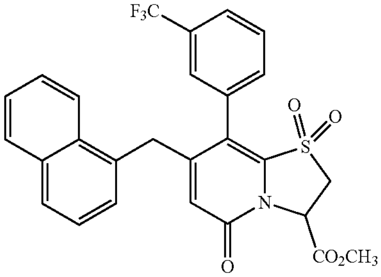

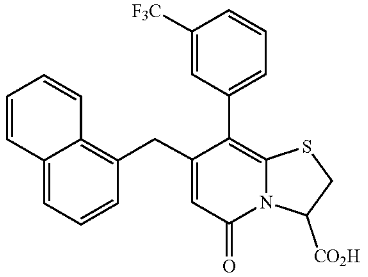

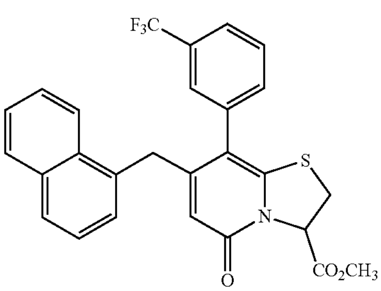

-continued

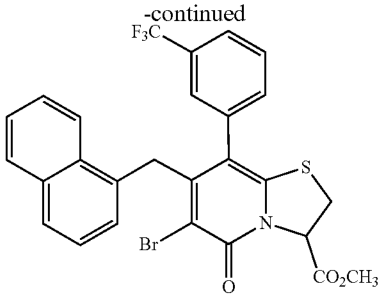

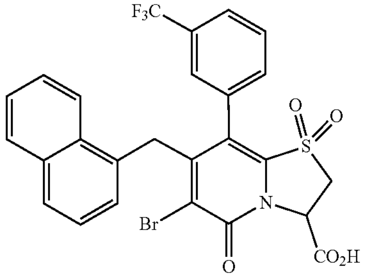

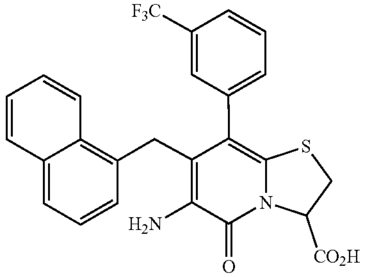

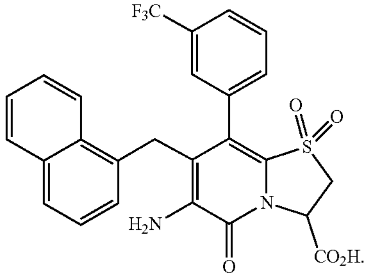

or

In some embodiments, X is —$SO_2$—. In some embodiments, X is —$NR^{14}$—. In some embodiments, X is —S—.

In some embodiments, $A^1$ is —$C(R^7)(R^8)$. In some embodiments, $A^1$ is —CO—. In some embodiments, $A^1$ is —$N(R^7)$— or —$N(R^{14})$— when X is —$SO_2$—, CO or —$C(R^9)(R^{10})$. In certain particular embodiments, $A^1$ is —$N(R^7)$— or —$N(R^{14})$— and X is —$SO_2$—. In certain particular embodiments, $A^1$ is —$N(R^7)$— and X is —$SO_2$—. In certain particular embodiments, $A^1$ is —$N(R^{14})$— and X is —$SO_2$—.

In some embodiments, $A^2$ is absent. In some embodiments, $A^2$ is —$C(R^5)(R^6)$—.

In some embodiments, $L^1$ is —$(CH_2)$-$_m$. In some embodiments, $L^1$ is —$(CH_2)$—. In some embodiments, $L^1$ is —$CF_2$—. In some embodiments, $L^1$ is —(C═O)—. In some embodiments, $L^1$ is —$C(R^9)(R^{10})$—. In some embodiments, $L^1$ is a bond.

In some embodiments, $L^2$ is —$(CH_2)$-$_m$. In some embodiments, $L^2$ is —$(CH_2)$—. In some embodiments, $L^2$ is —$CF_2$—. In some embodiments, $L^2$ is —(C═O)—. In some embodiments, $L^2$ is —$C(R^9)(R^{10})$—. In some embodiments, $L^2$ is a bond.

In some embodiments, X is —$N(R^{11})$—. In some embodiments, X is —O—. In some embodiments, X is —CO—. In some embodiments, X is —S—. In some embodiments, X is —S(═O)—. In some embodiments, X is —$SO_2$—. In some embodiments, X is —$CF_2$—. In some embodiments, X is $C(R^9)(R^{10})$—. In some embodiments, X is —$N(R^{14})$—.

In some embodiments, Y is O. In some embodiments, Y is S.

In some embodiments, Z is ═$C(R^{13})$—. In some embodiments, Z is ═N—, or —$N(R^{11})$—. In some embodiments, Z is —$N(R^{11})$—.

In some embodiments, $R^1$ is unsubstituted phenyl. In some embodiments, $R^1$ is substituted phenyl. In some particular embodiments, $R^1$ is trifluoromethylphenyl. In some embodiments, $R^1$ is unsubstituted heterocyclyl. In some embodiments, $R^1$ is substituted heterocyclyl.

In some embodiments, $R^2$ is unsubstituted naphthyl (e.g., 1-naphthyl or 2-naphthyl). In some embodiments, $R^2$ is substituted naphthyl (e.g., 1-naphthyl or 2-naphthyl). In some embodiments, $R^2$ is unsubstituted heterocyclyl. In some embodiments, $R^2$ is substituted heterocyclyl. In some embodiments, $R^2$ is unsubstituted phenyl. In some embodiments, $R^2$ is substituted phenyl (e.g., tert-butyl-substituted phenyl, or biphenyl). In some embodiments, $R^2$ is unsubstituted quinolinyl (e.g., 4-quinolinyl, 5-quinolinyl, or 8-quinolinyl). In some embodiments, $R^2$ is substituted quinolinyl (e.g., 4-quinolinyl, 5-quinolinyl, or 8-quinolinyl). In some embodiments, $R^2$ is unsubstituted isoquinolinyl (e.g., 4-isoquinolinyl, 5-isoquinolinyl, or 8-isoquinolinyl). In some embodiments, $R^2$ is substituted isoquinolinyl (e.g., 4-isoquinolinyl, 5-isoquinolinyl, or 8-isoquinolinyl).

In some embodiments, $R^3$ is —H. In some embodiments, $R^3$ is unsubstituted $C_1$-$C_{10}$ alkyl. In some embodiments, $R^3$ is substituted $C_1$-$C_{10}$ alkyl. In some embodiments, $R^3$ is acyl. In some embodiments, $R^3$ is —$CO_2R^7$ (e.g., —$CO_2H$). In some embodiments, $R^3$ is —$CON(R^7)(R^8)$. In some embodiments, $R^3$ is —P═$O(OH)_2$. In some embodiments, $R^3$ is —$SO_2(OH)$. In some embodiments, $R^3$ is —$CO_2H$.

In some embodiments, $R^4$ is absent. In some embodiments, $R^4$ is —H. In some embodiments, $R^4$ is unsubstituted $C_1$-$C_{10}$ alkyl. In some embodiments, $R^4$ is substituted $C_1$-$C_{10}$ alkyl. In some embodiments, $R^4$ is acyl. In some embodiments, $R^4$ is —$CO_2R^7$ (e.g., —$CO_2H$). In some embodiments, $R^4$ is —$CON(R^7)(R^8)$. In some embodiments, $R^4$ is —P═$O(OH)_2$. In some embodiments, $R^4$ is —$SO_2$ (OH).

In some embodiments, $R^3$ is —H and $R^4$ is selected from substituted or unsubstituted $C_1$-$C_{10}$ alkyl, acyl, —$CO_2R^7$, —$CON(R^7)(R^8)$, —P═$O(OH)_2$ or —$SO_2(OH)$. In some particular embodiments, $R^3$ is —H and $R^4$ is —$CO_2R^7$ (e.g., —$CO_2H$).

In some embodiments, $R^4$ is —H and $R^3$ is selected from substituted or unsubstituted $C_1$-$C_{10}$ alkyl, acyl, —$CO_2R^7$, —$CON(R^7)(R^8)$, —P═$O(OH)_2$ or —$SO_2(OH)$. In some particular embodiments, $R^4$ is —H and $R^3$ is —$CO_2R^7$ (e.g., —$CO_2H$).

In some particular embodiments, $R^4$ is -Me and $R^3$ is —$CO_2R^7$ (e.g., —$CO_2H$).

In some embodiments, $R^5$ and $R^6$ are absent when $A^2$ is absent. In some embodiments, $R^5$ and $R^6$ are both —H. In some embodiments, $R^5$ and $R^6$ are both $C_1$-$C_{10}$ alkyl. In some embodiments, $R^5$ is absent, and $R^6$ is selected from —H, and $C_1$-$C_{10}$ alkyl. In some embodiments, $R^5$ and $R^6$ together form a spirocarbocyclic or spiro(hetero)carbocyclic ring.

In some embodiments, $R^7$ is absent. In some embodiments, $R^7$ is selected from —H, substituted or unsubstituted $C_1$-$C_{10}$ alkyl, —$(CH_2)_m$-aryl, —$(CH_2)_m$-heteroaryl, —$(CH_2)_m$-substituted or unsubstituted cycloalkyl, —$R^{14}$. In some embodiments, $R^7$ is substituted or unsubstituted $C_1$-$C_{10}$ alkyl. In some embodiments, $R^7$ is —$(CH_2)_m$ substituted or unsubstituted cycloalkyl. In some embodiments, $R^7$ is —$(CH_2)_m$-aryl. In some embodiments, $R^7$ is —H. In some embodiments, $R^7$ is substituted or unsubstituted $C_{1-5}$ alkyl. In some embodiments, $R^7$ is -Me. In some embodiments, $R^7$ is substituted or unsubstituted $C_3$ alkyl.

In some embodiments, $R^8$ is absent. In some embodiments, $R^8$ is selected from —H, substituted or unsubstituted $C_1$-$C_{10}$ alkyl, —$(CH_2)_m$-aryl, —$(CH_2)_m$-heteroaryl, —$(CH_2)_m$ substituted or unsubstituted cycloalkyl, —$R^{14}$.

In some embodiments, $R^7$ and $R^8$ together form a spiropentanyl ring.

In some embodiments, $R^9$ is selected from —H, —Cl, —Br, —F, —$CF_3$, and $C_1$-$C_{10}$ alkyl. In some embodiments, $R^9$ is selected from —H and —F.

In some embodiments, $R^{10}$ is selected from —H, —Cl, —Br, —F, —$CF_3$, and $C_1$-$C_{10}$ alkyl. In some embodiments, $R^{10}$ is selected from —H and —F.

In some embodiments, $R^{11}$ is selected from —H, acyl, sulfonyl, substituted or unsubstituted $C_1$-$C_{10}$ alkyl, $C_3$-$C_6$ cycloalkyl, and $C_{3-6}$ heterocyclyl.

In some embodiments, $R^{12}$ is selected from —H, acyl, sulfonyl, substituted or unsubstituted $C_1$-$C_{10}$ alkyl, $C_3$-$C_6$ cycloalkyl, and $C_{3-6}$ heterocyclyl.

In some embodiments, $R^{13}$ is —H. In some embodiments, $R^{13}$ is substituted $C_1$-$C_{10}$ alkyl (e.g., —$(CH_2)_mCO_2N(R^{11})(R^{12})$, —$CON(R^7)(R^8)$, —$(CH_2)_mOH$, —$(CH_2)_mCO_2H$, —$(CH_2)_mNH_2$, or —$(CH_2)_mN(R^{11})(R^{12})$). In some embodiments, $R^{13}$ is unsubstituted $C_1$-$C_{10}$ alkyl. In some embodiments, $R^{13}$ is —$N(R^{11})(R^{12})$. In some embodiments, $R^{13}$ is —$NR^{11}(C{=}O)(CH_2)_mCH_3$, —$NR^{11}(C{=}O)R^{12}$, or $NR^{12}(SO_2)(CH_2)_mCH_3$. In some embodiments, $R^{13}$ is —Br or —Cl.

In some embodiments, $R^{14}$ is —H. In some embodiments, $R^{14}$ is $C_1$-$C_{10}$ alkyl or $C_1$-$C_{10}$ alkenyl. In some embodiments, $R^{14}$ is $C_1$-$C_{10}$ (mono or poly)hydroxylated alkyl. In some embodiments, $R^{14}$ is —$(CH_2)_o$—$R^{15}$. In some embodiments, $R^{14}$ is —$(CH_2CH_2O)_o$—$R^{15}$. In some embodiments, $R^{14}$ is —$(CH_2)_m$—$CO_2H$. In some embodiments, $R^{14}$ is —$(CH_2)_m$—$NH_2$. In some embodiments, $R^{14}$ is —$(CH_2)_m$—$(CO)NR^{16}R^{17}$. In some embodiments, $R^{14}$ is a protecting group.

In some embodiments, $R^{15}$ is —$CON(R^{11})(R^{12})$. In some embodiments, $R^{15}$ is —$N(R^{11})(R^{12})$ In some embodiments, $R^{15}$ is acyl. In some embodiments, $R^{15}$ is —$CO_2R^7$. In some embodiments, $R^{15}$ is substituted aryl. In some embodiments, $R^{15}$ is unsubstituted aryl. In some embodiments, $R^{15}$ is substituted heteroaryl. In some embodiments, $R^{15}$ is unsubstituted heteroaryl. In some embodiments, $R^{15}$ is substituted cycloalkyl. In some embodiments, $R^{15}$ is unsubstituted cycloalkyl. In some embodiments, $R^{15}$ is substituted heterocycloalkyl. In some embodiments, $R^{15}$ is unsubstituted heterocycloalkyl.

In some embodiments, $R^{16}$ is —H. In some embodiments, $R^{16}$ is —$CH_3$.

In some embodiments, $R^{17}$ is —H. In some embodiments, $R^{17}$ is —$CH_3$.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10.

In some embodiments, n is 1. In some embodiments, n is 2. In some embodiments, n is 3. In some embodiments, n is 4. In some embodiments, n is 5.

In some embodiments, o is 1. In some embodiments, o is 2. In some embodiments, o is 3. In some embodiments, o is 4. In some embodiments, o is 5. In some embodiments, o is 6. In some embodiments, o is 7. In some embodiments, o is 8. In some embodiments, o is 9. In some embodiments, o is 10. In some embodiments, o is 11. In some embodiments, o is 12. In some embodiments, o is 13. In some embodiments, o is 14. In some embodiments, o is 15. In some embodiments, o is 16. In some embodiments, o is 17. In some embodiments, o is 18. In some embodiments, o is 19. In some embodiments, o is 20.

In any of the preceding embodiments, Formula (I) may have a structure selected from Formulae (II), (III), (IV), (V), (VI), (VII), (VIII), (IX), and (X), as defined below.

In some embodiments, Formula (I) has the structure of Formula (II):

(II)

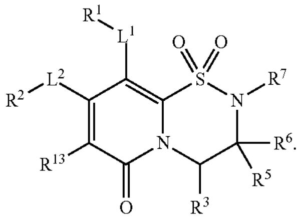

In some embodiments, Formula (I) has the structure of Formula (III):

(III)

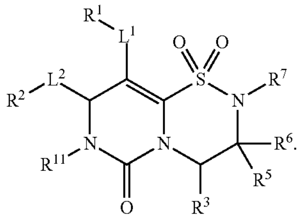

In some embodiments, Formula (I) has the structure of Formula (IV):

(IV)

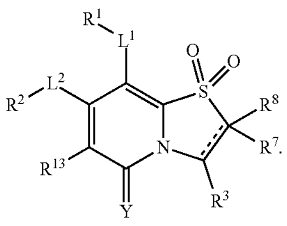

In some embodiments, Formula (I) has the structure of Formula (V):

(V)

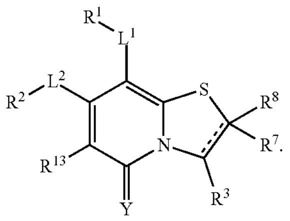

In some embodiments, Formula (I) has the structure of Formula (VI):

(VI)

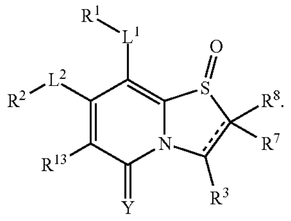

In some embodiments, Formula (I) has the structure of Formula (VII):

(VII)

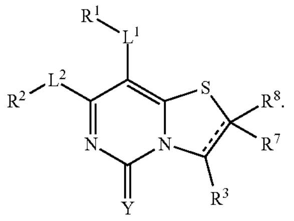

In some embodiments, Formula (I) has the structure of Formula (VIII):

(VIII)

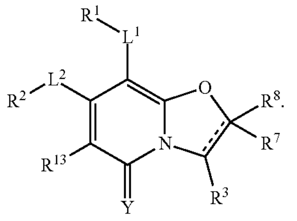

In some embodiments, Formula (I) has the structure of Formula (IX):

(IX)

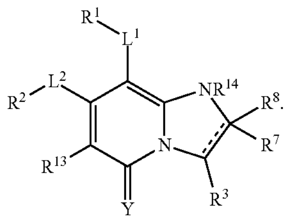

In some embodiments, Formula (I) has the structure of Formula of Formula (X):

(X)

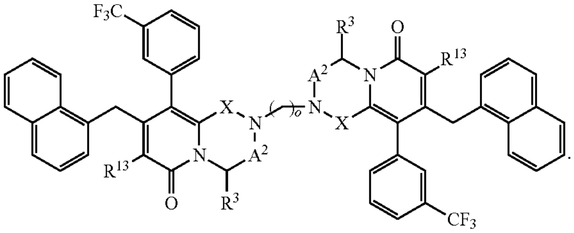

In some embodiments, Formula (II) has the structure of Formula (IIa) or Formula (IIb):

(IIa)

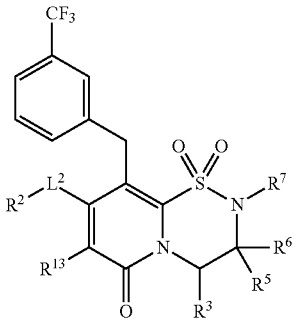

(IIb)

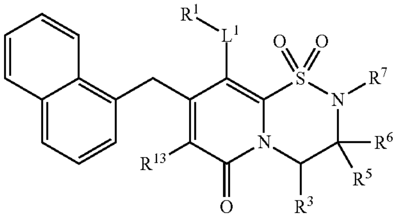

wherein:

$L^1$ is a bond, $(—CH_2-)_m$, $—CF_2—$, or $—(C{=}O)—$;

$L^2$ is a bond, $(—CH_2-)_m$, $—CF_2—$, or $—(C{=}O)—$;

m is, independently for each occurrence, 0-10;

$R^1$ is substituted or unsubstituted phenyl, substituted or unsubstituted heterocyclyl;

$R^2$ is substituted or unsubstituted naphthyl, or substituted or unsubstituted heterocyclyl;

$R^3$ is $—CO_2H$,

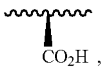 , or 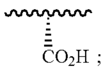 ;

$R^5$ and $R^6$ are each H;

$R^7$ is substituted or unsubstituted $C_1$-$C_{10}$ alkyl, or substituted or unsubstituted cycloalkyl; and $R^{13}$ is selected from —H, —Cl, —Br, —F, —CN, $—CF_3$, $—CH_2F$, $—CHF_2$, substituted or unsubstituted $C_1$-$C_{10}$ alkyl, $—NH_2$, $—CONH_2$, $—(CH_2)—N(CH_3)_2$, —NH (cyclopentyl), —NH(benzyl), —NH(tetrahydropyran), $—NH—(CH_2)$(cyclopentyl), and $—O—(CH_2)_2$-phenyl.

In some embodiments, Formula (II) has the structure of Formula (IIc):

wherein:

(IIc)

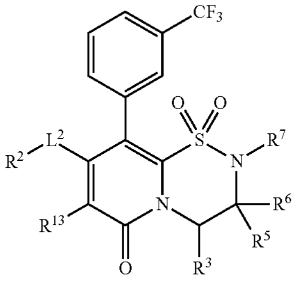

$L^2$ is a bond, $(—CH_2-)_m$, $—CF_2—$, or $—(C{=}O)—$;

m is, independently for each occurrence, 0-10;

$R^2$ is substituted or unsubstituted naphthyl, or substituted or unsubstituted heterocyclyl;

$R^3$ is $—CO_2H$,

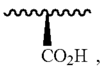 , or 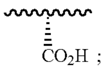 ;

$R^5$ and $R^6$ are each H;

$R^7$ is substituted or unsubstituted $C_1$-$C_{10}$ alkyl, or substituted or unsubstituted cycloalkyl;

and $R^{13}$ is selected from —H, —Cl, —Br, —F, —CN, $—CF_3$, $—CH_2F$, $—CHF_2$, substituted or unsubstituted $C_1$-$C_{10}$ alkyl, $—NH_2$, $—CONH_2$, $—(CH_2)—N(CH_3)_2$, —NH (cyclopentyl), —NH(benzyl), —NH(tetrahydropyran), $—NH—(CH_2)$(cyclopentyl), and $—O—(CH_2)_2$-phenyl.

In some embodiments, Formula (IX) has the structure of Formula (IXa) or Formula (IXb):

(IXa)

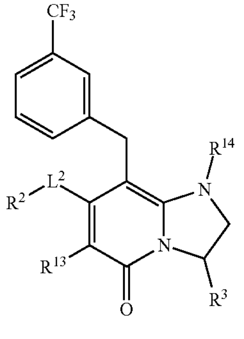

(IXb)

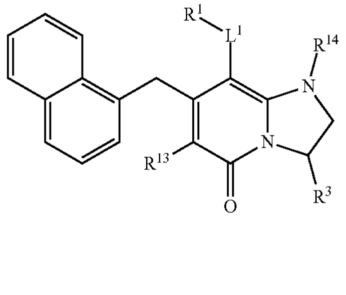

wherein:

$L^1$ is a bond, $(\text{—}CH_2\text{-})_m$, $\text{—}CF_2\text{—}$, or —(C═O)—;

$L^2$ is a bond, $(\text{—}CH_2\text{-})_m$, $\text{—}CF_2\text{—}$, or —(C═O)—;

m is, independently for each occurrence, 0-10;

is, independently for each occurrence, 1-20;

$R^1$ is substituted or unsubstituted phenyl, substituted or unsubstituted heterocyclyl;

$R^2$ is substituted or unsubstituted naphthyl, substituted or unsubstituted quinolinyl, substituted or unsubstituted isoquinolinyl, substituted phenyl, or substituted or unsubstituted heterocyclyl;

$R^3$ is $\text{—}CO_2H$,

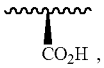 , or 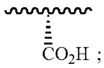 ;

$R^{13}$ is selected from —H, —Cl, —Br, —F, —CN, $\text{—}CF_3$, $\text{—}CH_2F$, $\text{—}CHF_2$, $\text{—}(CH_2)_m\text{—}NMe_2$, — $CONH_2$, $\text{—}CO_2H$, and substituted or unsubstituted $C_1$-$C_{10}$ alkyl; and $R^{14}$ is $C_1$-$C_{10}$ alkyl, $\text{—}(CH_2)_o$-(unsubstituted cycloalkyl), $\text{—}(CH_2)_o$-(substituted or unsubstituted phenyl), $\text{—}(CH_2)_o$-naphthyl, or $\text{—}(CH_2)_o$-biaryl.

In some embodiments, Formula (IX) has the structure of Formula (IXc):

(IXc)

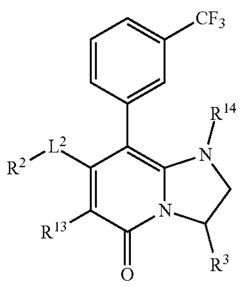

wherein:

$L^2$ is a bond, $(\text{—}CH_2\text{-})_m$, $\text{—}CF_2\text{—}$, or —(C═O)—;

m is, independently for each occurrence, 0-10;

is, independently for each occurrence, 1-20;

$R^2$ is substituted or unsubstituted naphthyl, substituted or unsubstituted quinolinyl, substituted or unsubstituted isoquinolinyl, or substituted or unsubstituted heterocyclyl;

$R^3$ is $\text{—}CO_2H$,

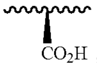 , or 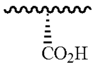 ;

$R^{13}$ is selected from —H, —Cl, —Br, —F, —CN, $\text{—}CF_3$, $\text{—}CH_2F$, $\text{—}CHF_2$, $\text{—}(CH_2)_m\text{—}NMe_2$, $\text{—}CONH_2$, $\text{—}CO_2H$, and substituted or unsubstituted $C_1$-$C_{10}$ alkyl; and $R^{14}$ is $C_1$-$C_{10}$ alkyl, $\text{—}(CH_2)_o$-(unsubstituted cycloalkyl), $\text{—}(CH_2)_o$-(substituted or unsubstituted phenyl), $\text{—}(CH_2)_o$-naphthyl, or $\text{—}(CH_2)_o$-biaryl.

In certain embodiments, the compound of Formula (II) is selected from compounds 015a, 016b, 024, 042, 052, 068, 070, 071, 072, 074, 108, 109, 116, 120, 121, 122, 123, 126, 127, 128, 138, 172, 175, 176, 177, 183, and 184.

In certain embodiments, the compound of Formula (V) is selected from compounds 051, 057, and 062.

In certain embodiments, the compound of Formula (VII) is selected from compounds 022 and 053.

In certain embodiments, the compound of Formula (IX) is selected from compounds 003, 004, 004a, 004b, 140, 161, 162, 163, 164, 167, 178, 179, 180, 181, 198, 200, 202, 207, 208, or 216.

In certain embodiments, the compound of Formula (X) is selected from compounds 188 and 193.

In certain embodiments, the compound of Formula (I) is selected from the compounds of Table 1, and pharmaceutically acceptable salts thereof.

TABLE 1

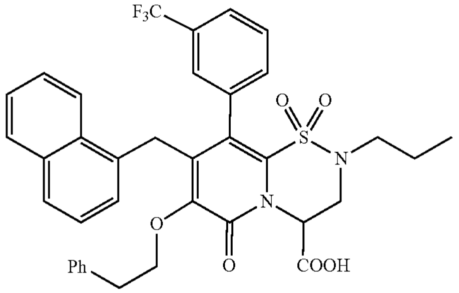 [SMILES: CCCN1CC(C(=O)O)n2c(c(-c3cccc(C(F)(F)F)c3)c(Cc3cccc4ccccc34)c(OCCc3ccccc3)c2=O)S1(=O)=O]

001

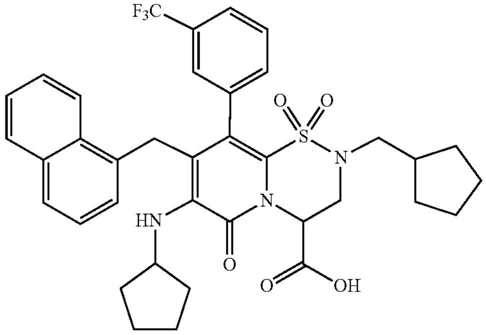 [SMILES: O=C(O)C1CN(CC2CCCC2)S(=O)(=O)c2c(-c3cccc(C(F)(F)F)c3)c(Cc3cccc4ccccc34)c(NC3CCCC3)c(=O)n21]

002

TABLE 1-continued
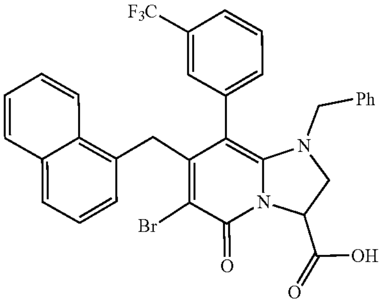 [SMILES: O=C(O)C1CN(Cc2ccccc2)c2c(-c3cccc(C(F)(F)F)c3)c(Cc3cccc4ccccc34)c(Br)c(=O)n21]
003
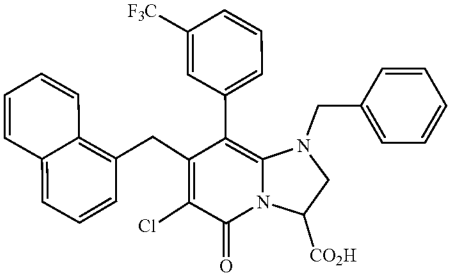 [SMILES: O=C(O)C1CN(Cc2ccccc2)c2c(-c3cccc(C(F)(F)F)c3)c(Cc3cccc4ccccc34)c(Cl)c(=O)n21]
004
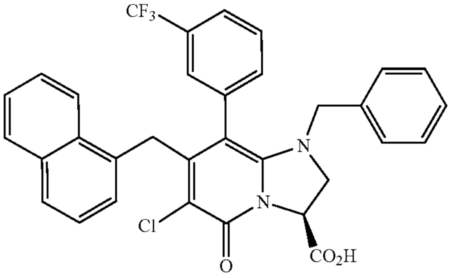 [SMILES: O=C(O)[C@@H]1CN(Cc2ccccc2)c2c(-c3cccc(C(F)(F)F)c3)c(Cc3cccc4ccccc34)c(Cl)c(=O)n21]
004a
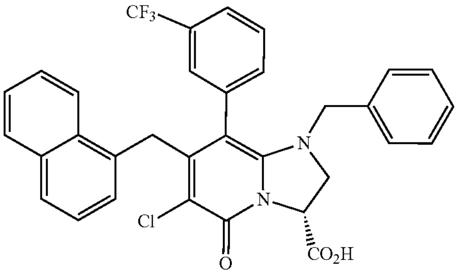 [SMILES: O=C(O)[C@H]1CN(Cc2ccccc2)c2c(-c3cccc(C(F)(F)F)c3)c(Cc3cccc4ccccc34)c(Cl)c(=O)n21]
004b
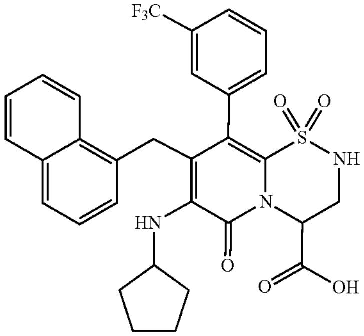 [SMILES: O=C(O)C1CNS(=O)(=O)c2c(-c3cccc(C(F)(F)F)c3)c(Cc3cccc4ccccc34)c(NC3CCCC3)c(=O)n21]
005

TABLE 1-continued
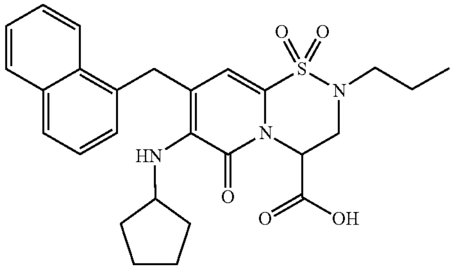 [SMILES: CCCN1CC(C(=O)O)n2c(cc(Cc3cccc4ccccc34)c(NC3CCCC3)c2=O)S1(=O)=O]
006
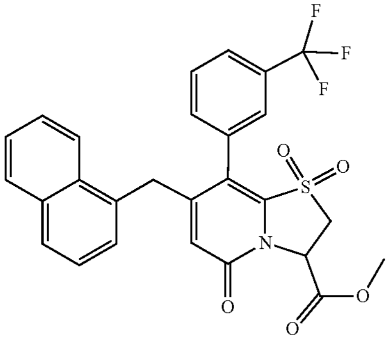 [SMILES: COC(=O)C1CS(=O)(=O)c2c(-c3cccc(C(F)(F)F)c3)c(Cc3cccc4ccccc34)cc(=O)n21]
007
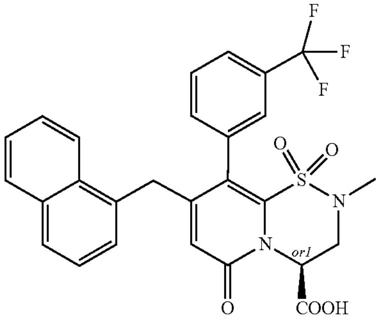 [SMILES: CN1C[C@@H](C(=O)O)n2c(c(-c3cccc(C(F)(F)F)c3)c(Cc3cccc4ccccc34)cc2=O)S1(=O)=O]
008a
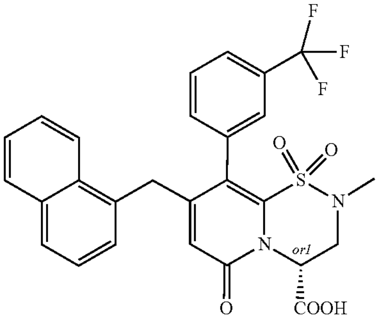 [SMILES: CN1C[C@H](C(=O)O)n2c(c(-c3cccc(C(F)(F)F)c3)c(Cc3cccc4ccccc34)cc2=O)S1(=O)=O]
008b
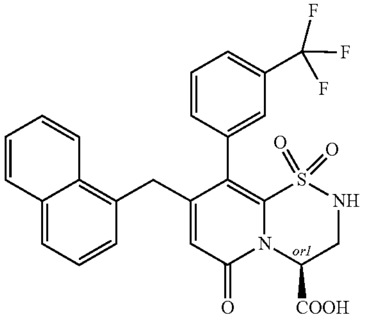 [SMILES: O=C(O)[C@@H]1CNS(=O)(=O)c2c(-c3cccc(C(F)(F)F)c3)c(Cc3cccc4ccccc34)cc(=O)n21]
009a TABLE 1-continued
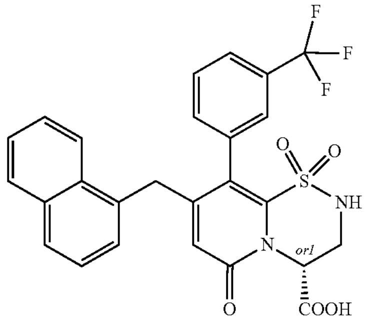 [SMILES: O=C(O)[C@H]1CNS(=O)(=O)c2c(-c3cccc(C(F)(F)F)c3)c(Cc3cccc4ccccc34)cc(=O)n21]
009b
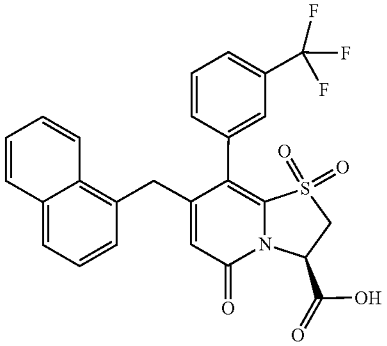
010a
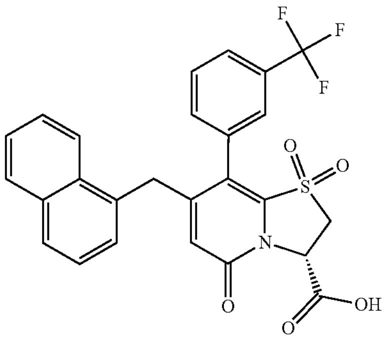 [SMILES: O=C(O)[C@H]1CS(=O)(=O)c2c(-c3cccc(C(F)(F)F)c3)c(Cc3cccc4ccccc34)cc(=O)n21]
010b
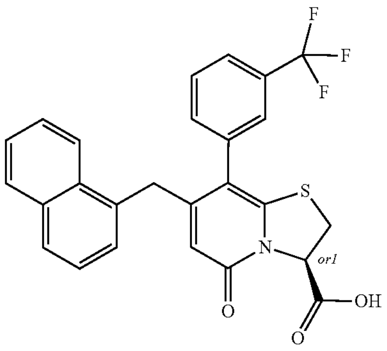 [SMILES: O=C(O)[C@@H]1CSc2c(-c3cccc(C(F)(F)F)c3)c(Cc3cccc4ccccc34)cc(=O)n21]
011a TABLE 1-continued
011b
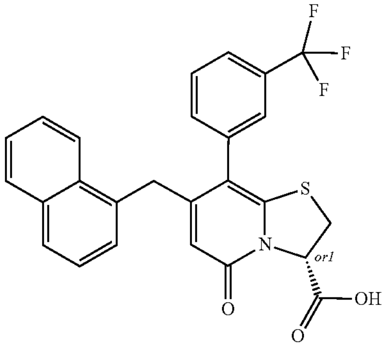 [SMILES: O=C(O)[C@H]1CSc2c(-c3cccc(C(F)(F)F)c3)c(Cc3cccc4ccccc34)cc(=O)n21]
012
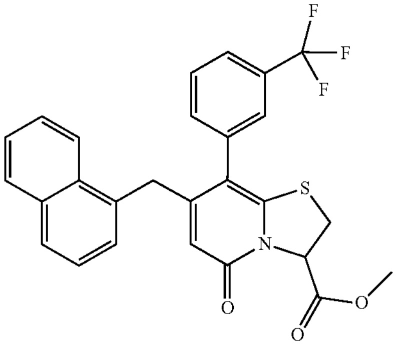 [SMILES: COC(=O)C1CSc2c(-c3cccc(C(F)(F)F)c3)c(Cc3cccc4ccccc34)cc(=O)n21]
013
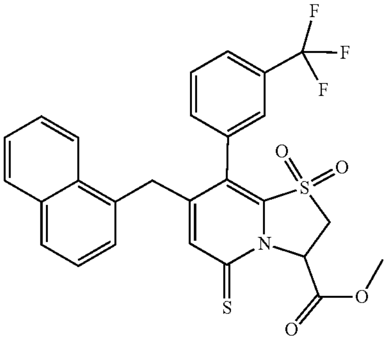 [SMILES: COC(=O)C1CS(=O)(=O)c2c(-c3cccc(C(F)(F)F)c3)c(Cc3cccc4ccccc34)cc(=S)n21]
014
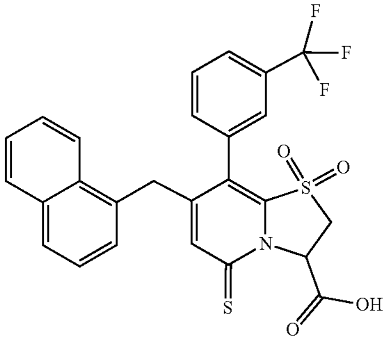 [SMILES: O=C(O)C1CS(=O)(=O)c2c(-c3cccc(C(F)(F)F)c3)c(Cc3cccc4ccccc34)cc(=S)n21]

TABLE 1-continued
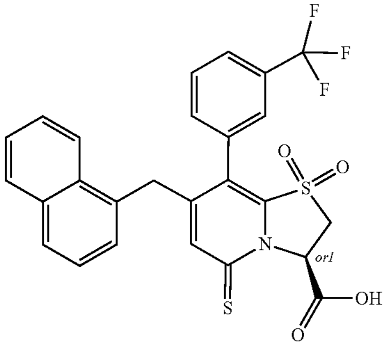 [SMILES: O=C(O)[C@@H]1CS(=O)(=O)c2c(-c3cccc(C(F)(F)F)c3)c(Cc3cccc4ccccc34)cc(=S)n21]
014a
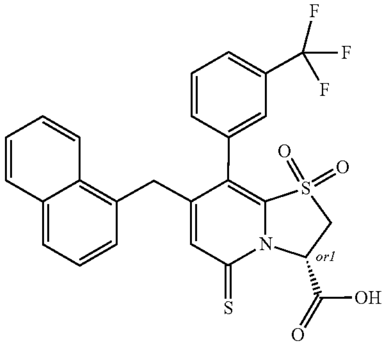 [SMILES: O=C(O)[C@H]1CS(=O)(=O)c2c(-c3cccc(C(F)(F)F)c3)c(Cc3cccc4ccccc34)cc(=S)n21]
014b
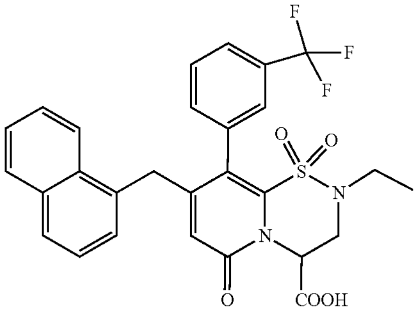 [SMILES: CCN1CC(C(=O)O)n2c(c(-c3cccc(C(F)(F)F)c3)c(Cc3cccc4ccccc34)cc2=O)S1(=O)=O]
015
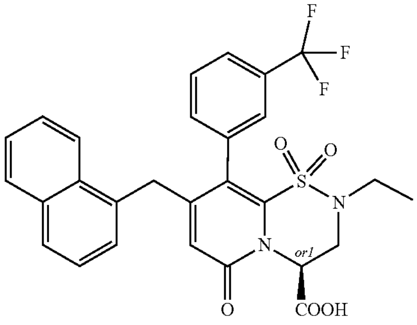 [SMILES: CCN1C[C@@H](C(=O)O)n2c(c(-c3cccc(C(F)(F)F)c3)c(Cc3cccc4ccccc34)cc2=O)S1(=O)=O]
015a TABLE 1-continued
015b
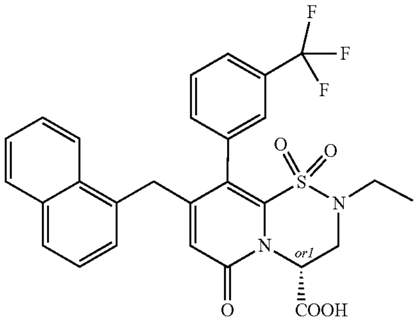 [SMILES: CCN1C[C@H](C(=O)O)n2c(c(-c3cccc(C(F)(F)F)c3)c(Cc3cccc4ccccc34)cc2=O)S1(=O)=O]
016
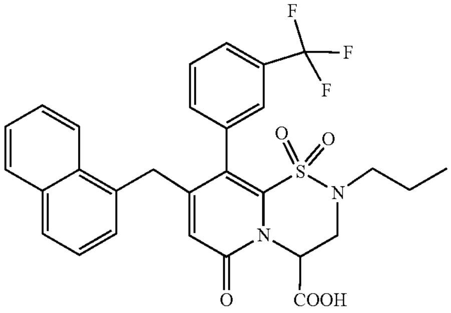 [SMILES: CCCN1CC(C(=O)O)n2c(c(-c3cccc(C(F)(F)F)c3)c(Cc3cccc4ccccc34)cc2=O)S1(=O)=O]
016a
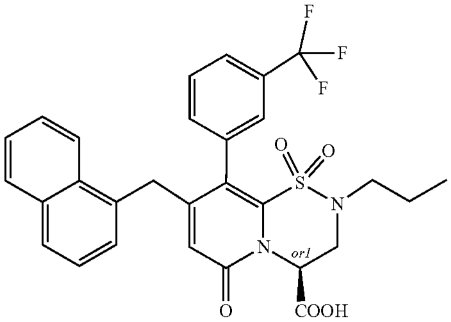 [SMILES: CCCN1C[C@@H](C(=O)O)n2c(c(-c3cccc(C(F)(F)F)c3)c(Cc3cccc4ccccc34)cc2=O)S1(=O)=O]
016b
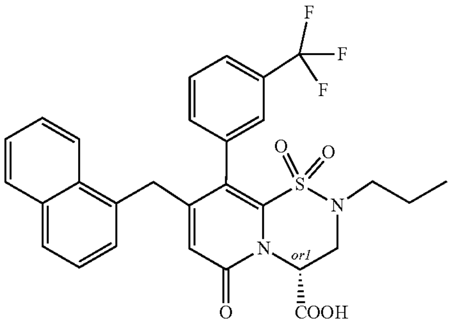 [SMILES: CCCN1C[C@H](C(=O)O)n2c(c(-c3cccc(C(F)(F)F)c3)c(Cc3cccc4ccccc34)cc2=O)S1(=O)=O]
017
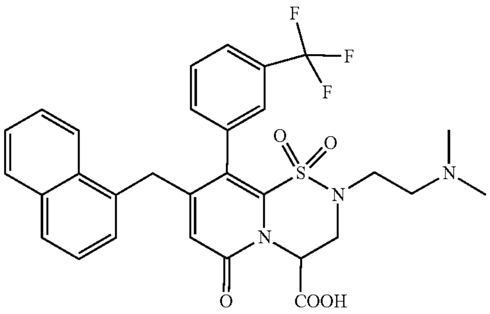 [SMILES: CN(C)CCN1CC(C(=O)O)n2c(c(-c3cccc(C(F)(F)F)c3)c(Cc3cccc4ccccc34)cc2=O)S1(=O)=O]

TABLE 1-continued
018
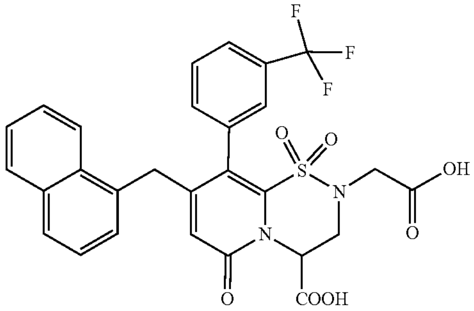 [SMILES: O=C(O)CN1CC(C(=O)O)n2c(c(-c3cccc(C(F)(F)F)c3)c(Cc3cccc4ccccc34)cc2=O)S1(=O)=O]
019
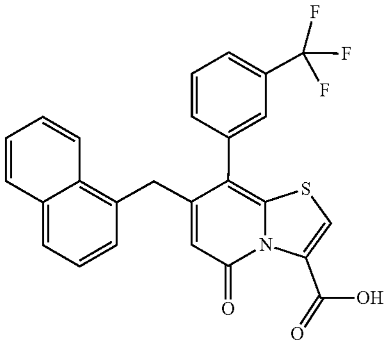 [SMILES: O=C(O)c1csc2c(-c3cccc(C(F)(F)F)c3)c(Cc3cccc4ccccc34)cc(=O)n12]
021
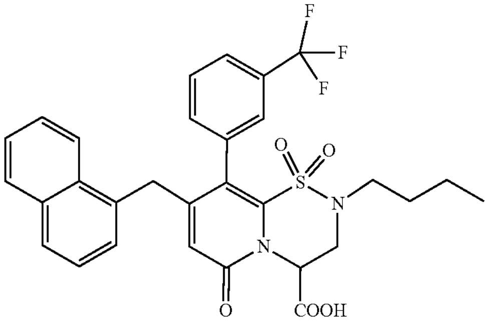 [SMILES: CCCCN1CC(C(=O)O)n2c(c(-c3cccc(C(F)(F)F)c3)c(Cc3cccc4ccccc34)cc2=O)S1(=O)=O]
021a
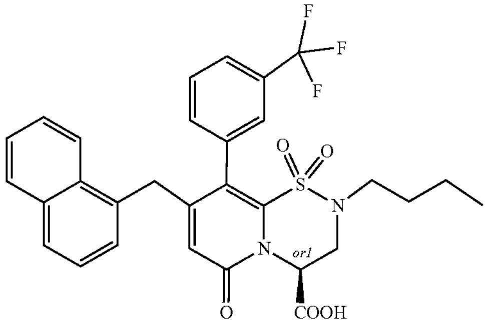 [SMILES: CCCCN1C[C@@H](C(=O)O)n2c(c(-c3cccc(C(F)(F)F)c3)c(Cc3cccc4ccccc34)cc2=O)S1(=O)=O]
021b
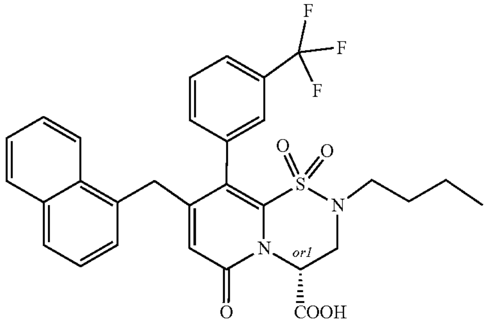 [SMILES: CCCCN1C[C@H](C(=O)O)n2c(c(-c3cccc(C(F)(F)F)c3)c(Cc3cccc4ccccc34)cc2=O)S1(=O)=O]

TABLE 1-continued
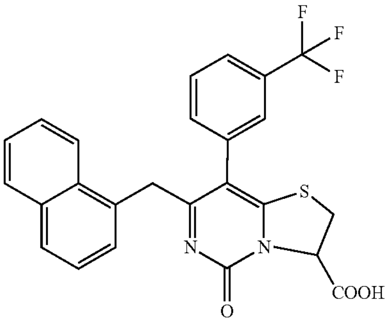 [SMILES: O=C(O)C1CSc2c(-c3cccc(C(F)(F)F)c3)c(Cc3cccc4ccccc34)nc(=O)n21]
022
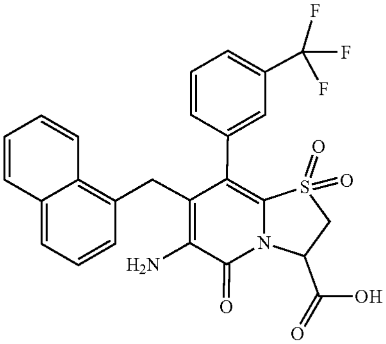 [SMILES: Nc1c(Cc2cccc3ccccc23)c(-c2cccc(C(F)(F)F)c2)c2n(c1=O)C(C(=O)O)CS2(=O)=O]
023
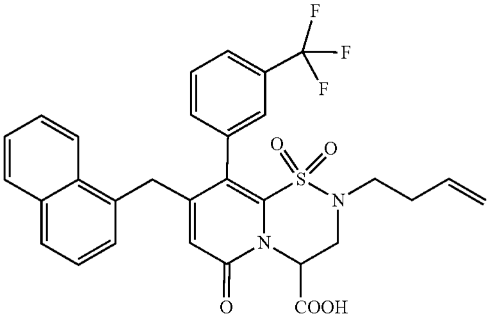 [SMILES: C=CCCN1CC(C(=O)O)n2c(c(-c3cccc(C(F)(F)F)c3)c(Cc3cccc4ccccc34)cc2=O)S1(=O)=O]
024
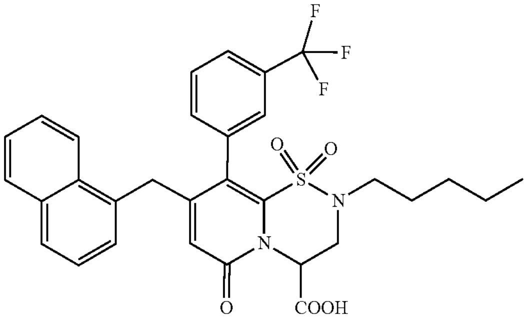 [SMILES: CCCCCN1CC(C(=O)O)n2c(c(-c3cccc(C(F)(F)F)c3)c(Cc3cccc4ccccc34)cc2=O)S1(=O)=O]
25

TABLE 1-continued
025a
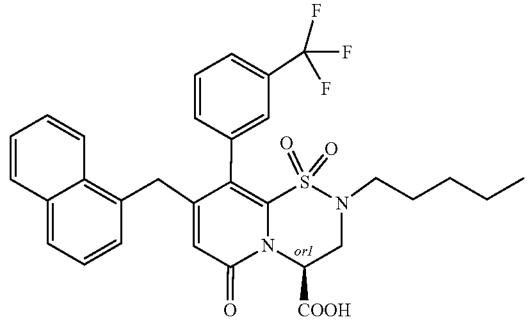 [SMILES: CCCCCN1C[C@@H](C(=O)O)n2c(c(-c3cccc(C(F)(F)F)c3)c(Cc3cccc4ccccc34)cc2=O)S1(=O)=O]
025b
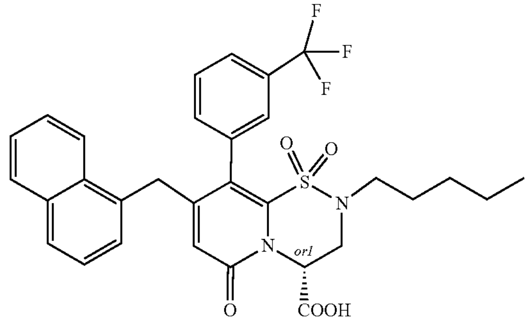 [SMILES: CCCCCN1C[C@H](C(=O)O)n2c(c(-c3cccc(C(F)(F)F)c3)c(Cc3cccc4ccccc34)cc2=O)S1(=O)=O]
026a
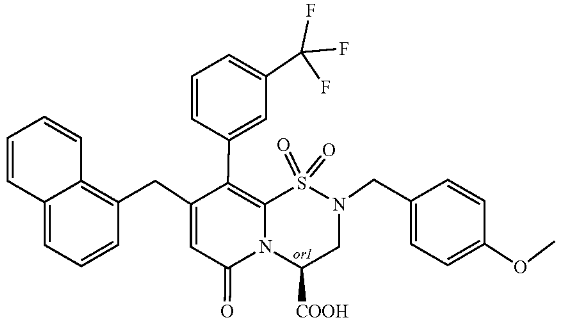 [SMILES: COc1ccc(CN2C[C@@H](C(=O)O)n3c(c(-c4cccc(C(F)(F)F)c4)c(Cc4cccc5ccccc45)cc3=O)S2(=O)=O)cc1]
026b
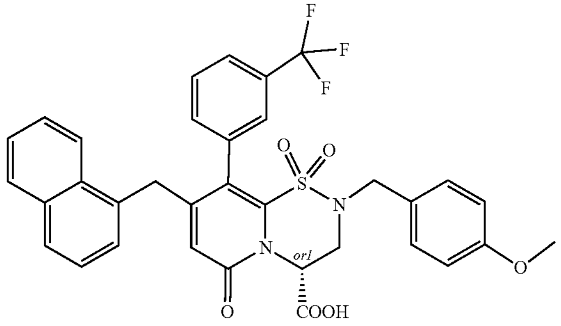 [SMILES: COc1ccc(CN2C[C@H](C(=O)O)n3c(c(-c4cccc(C(F)(F)F)c4)c(Cc4cccc5ccccc45)cc3=O)S2(=O)=O)cc1]
027a
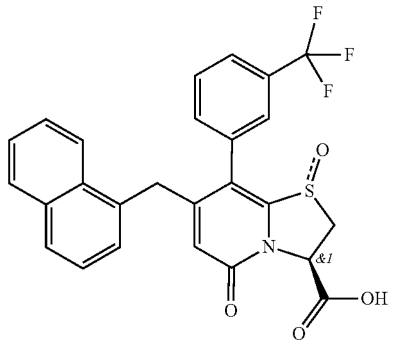

TABLE 1-continued
027b
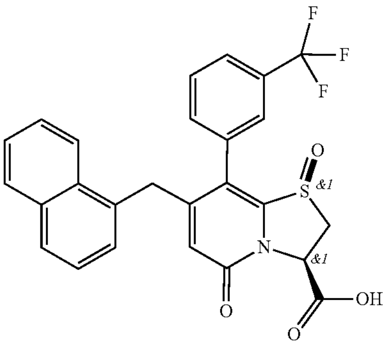 [SMILES: O=C(O)[C@@H]1CS(=O)c2c(-c3cccc(C(F)(F)F)c3)c(Cc3cccc4ccccc34)cc(=O)n21]
028
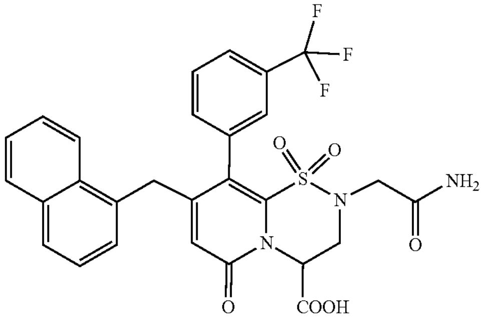 [SMILES: NC(=O)CN1CC(C(=O)O)n2c(c(-c3cccc(C(F)(F)F)c3)c(Cc3cccc4ccccc34)cc2=O)S1(=O)=O]
029
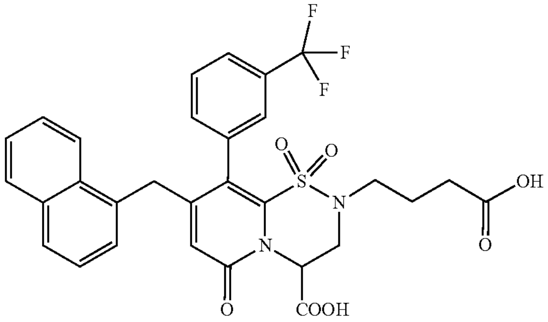 [SMILES: O=C(O)CCCN1CC(C(=O)O)n2c(c(-c3cccc(C(F)(F)F)c3)c(Cc3cccc4ccccc34)cc2=O)S1(=O)=O]
030
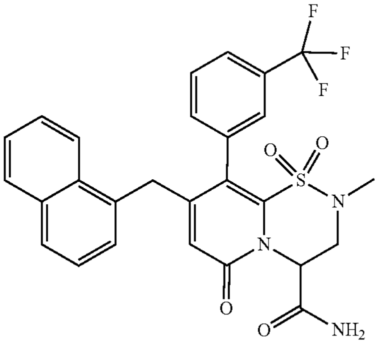 [SMILES: CN1CC(C(N)=O)n2c(c(-c3cccc(C(F)(F)F)c3)c(Cc3cccc4ccccc34)cc2=O)S1(=O)=O]

TABLE 1-continued
031
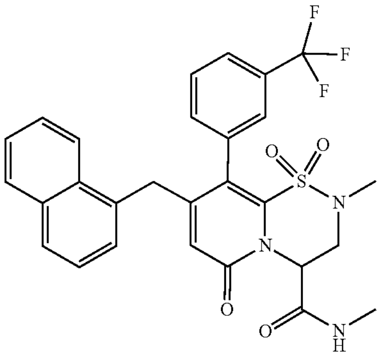 [SMILES: CNC(=O)C1CN(C)S(=O)(=O)c2c(-c3cccc(C(F)(F)F)c3)c(Cc3cccc4ccccc34)cc(=O)n21]
032
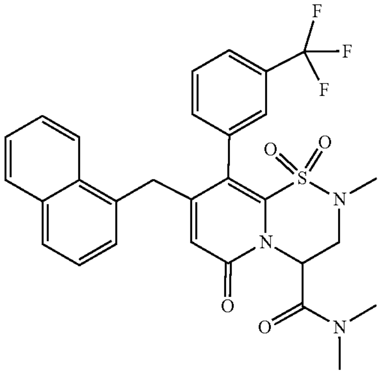 [SMILES: CN(C)C(=O)C1CN(C)S(=O)(=O)c2c(-c3cccc(C(F)(F)F)c3)c(Cc3cccc4ccccc34)cc(=O)n21]
033
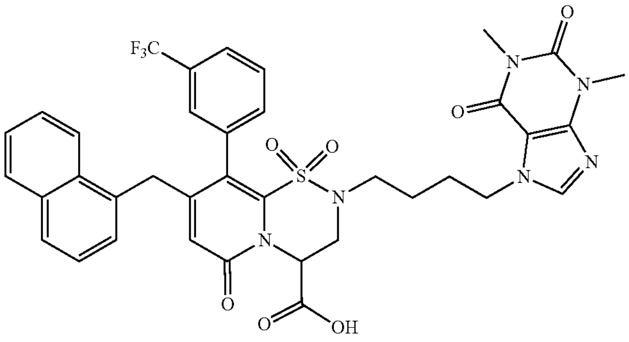 [SMILES: Cn1c(=O)c2c(ncn2CCCCN2CC(C(=O)O)n3c(c(-c4cccc(C(F)(F)F)c4)c(Cc4cccc5ccccc45)cc3=O)S2(=O)=O)n(C)c1=O]
034
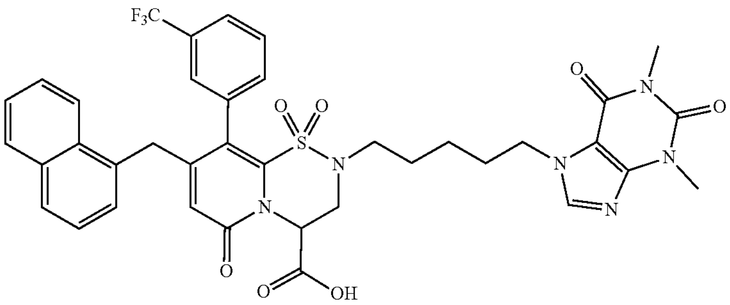 [SMILES: Cn1c(=O)c2c(ncn2CCCCCN2CC(C(=O)O)n3c(c(-c4cccc(C(F)(F)F)c4)c(Cc4cccc5ccccc45)cc3=O)S2(=O)=O)n(C)c1=O]

TABLE 1-continued
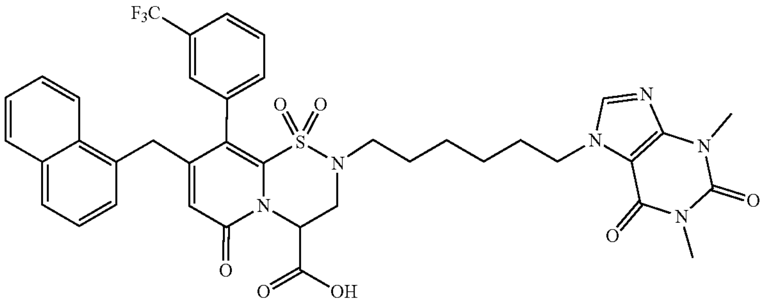 [SMILES: Cn1c(=O)c2c(ncn2CCCCCCN2CC(C(=O)O)n3c(c(-c4cccc(C(F)(F)F)c4)c(Cc4cccc5ccccc45)cc3=O)S2(=O)=O)n(C)c1=O]
035
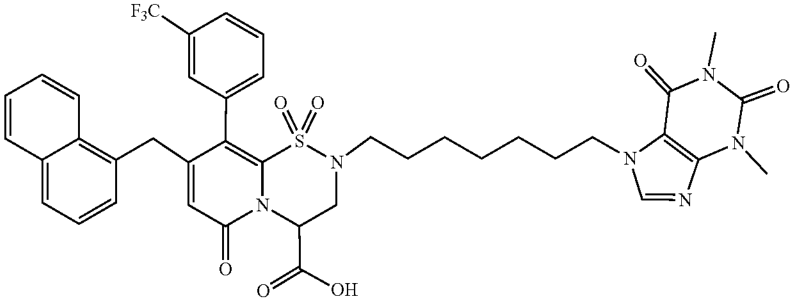 [SMILES: Cn1c(=O)c2c(ncn2CCCCCCCN2CC(C(=O)O)n3c(c(-c4cccc(C(F)(F)F)c4)c(Cc4cccc5ccccc45)cc3=O)S2(=O)=O)n(C)c1=O]
036
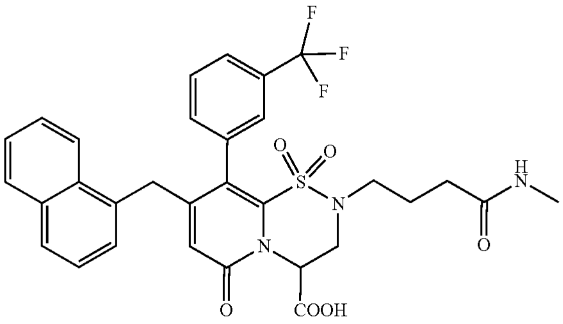 [SMILES: CNC(=O)CCCN1CC(C(=O)O)n2c(c(-c3cccc(C(F)(F)F)c3)c(Cc3cccc4ccccc34)cc2=O)S1(=O)=O]
037
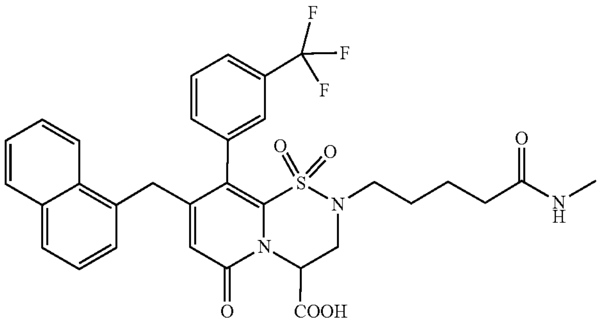 [SMILES: CNC(=O)CCCCN1CC(C(=O)O)n2c(c(-c3cccc(C(F)(F)F)c3)c(Cc3cccc4ccccc34)cc2=O)S1(=O)=O]
038
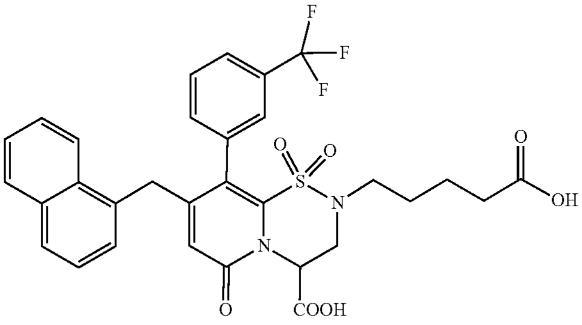 [SMILES: O=C(O)CCCCN1CC(C(=O)O)n2c(c(-c3cccc(C(F)(F)F)c3)c(Cc3cccc4ccccc34)cc2=O)S1(=O)=O]
039

TABLE 1-continued
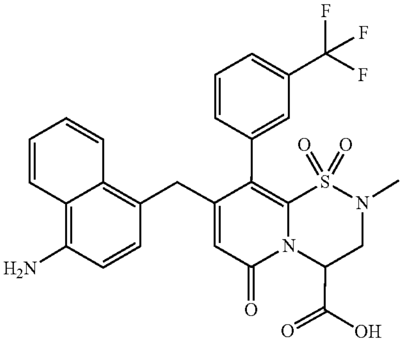 [SMILES: CN1CC(C(=O)O)n2c(c(-c3cccc(C(F)(F)F)c3)c(Cc3ccc(N)c4ccccc34)cc2=O)S1(=O)=O]
040
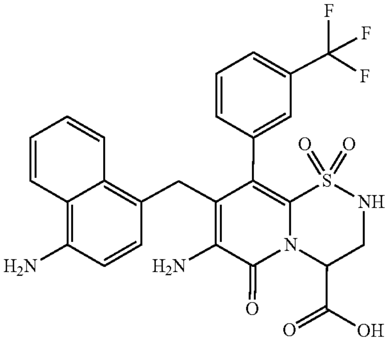 [SMILES: Nc1c(Cc2ccc(N)c3ccccc23)c(-c2cccc(C(F)(F)F)c2)c2n(c1=O)C(C(=O)O)CNS2(=O)=O]
041
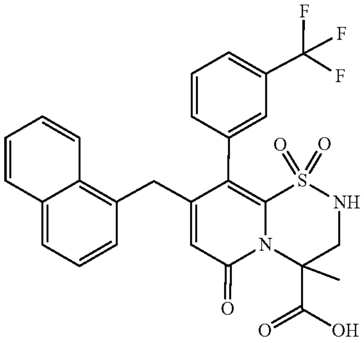 [SMILES: CC1(C(=O)O)CNS(=O)(=O)c2c(-c3cccc(C(F)(F)F)c3)c(Cc3cccc4ccccc34)cc(=O)n21]
042
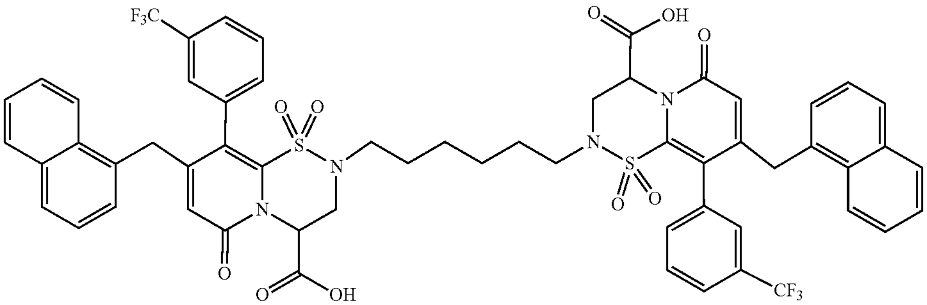 [SMILES: O=C(O)C1CN(CCCCCCN2CC(C(=O)O)n3c(c(-c4cccc(C(F)(F)F)c4)c(Cc4cccc5ccccc45)cc3=O)S2(=O)=O)S(=O)(=O)c2c(-c3cccc(C(F)(F)F)c3)c(Cc3cccc4ccccc34)cc(=O)n21]
043
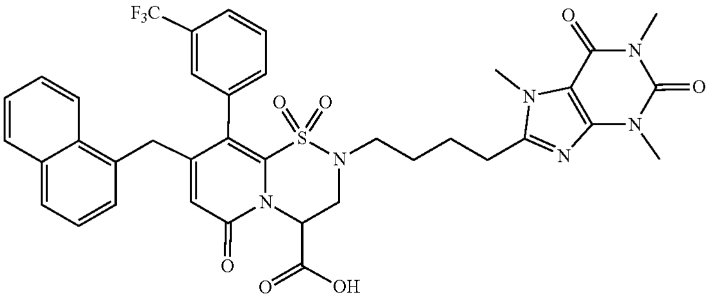 [SMILES: Cn1c(=O)c2c(nc(CCCCN3CC(C(=O)O)n4c(c(-c5cccc(C(F)(F)F)c5)c(Cc5cccc6ccccc56)cc4=O)S3(=O)=O)n2C)n(C)c1=O]
044

TABLE 1-continued
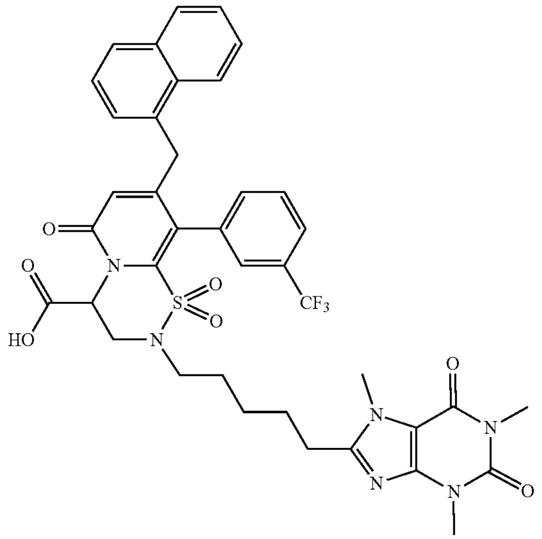 [SMILES: Cn1c(=O)c2c(nc(CCCCCN3CC(C(=O)O)n4c(c(-c5cccc(C(F)(F)F)c5)c(Cc5cccc6ccccc56)cc4=O)S3(=O)=O)n2C)n(C)c1=O]
045
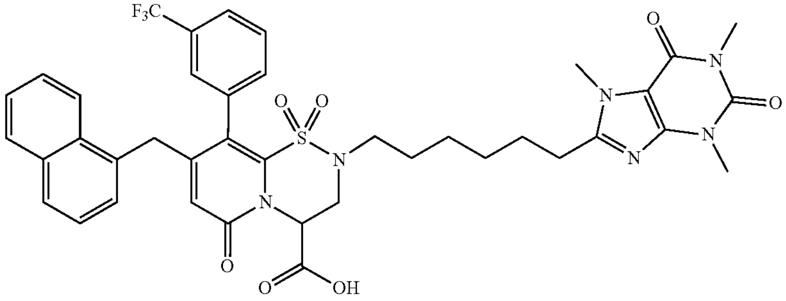 [SMILES: Cn1c(=O)c2c(nc(CCCCCCN3CC(C(=O)O)n4c(c(-c5cccc(C(F)(F)F)c5)c(Cc5cccc6ccccc56)cc4=O)S3(=O)=O)n2C)n(C)c1=O]
046
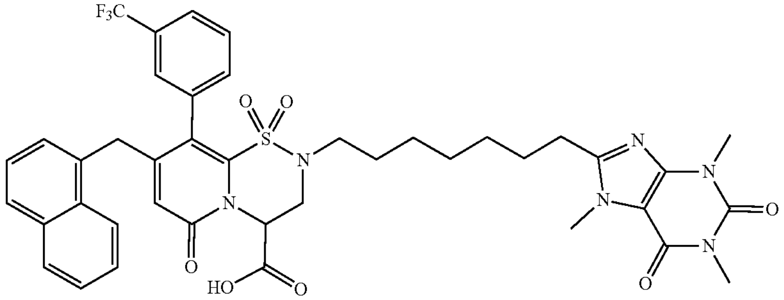 [SMILES: Cn1c(=O)c2c(nc(CCCCCCCN3CC(C(=O)O)n4c(c(-c5cccc(C(F)(F)F)c5)c(Cc5cccc6ccccc56)cc4=O)S3(=O)=O)n2C)n(C)c1=O]
047
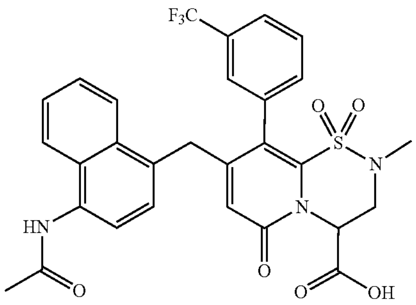 [SMILES: CC(=O)Nc1ccc(Cc2cc(=O)n3c(c2-c2cccc(C(F)(F)F)c2)S(=O)(=O)N(C)CC3C(=O)O)c2ccccc12]
048

TABLE 1-continued
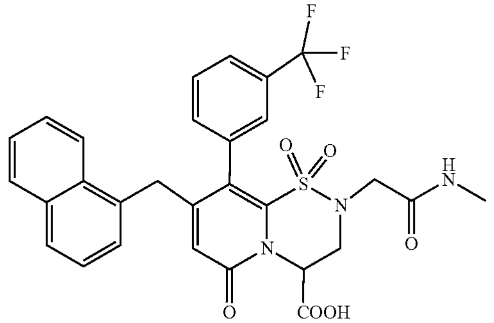 [SMILES: CNC(=O)CN1CC(C(=O)O)n2c(c(-c3cccc(C(F)(F)F)c3)c(Cc3cccc4ccccc34)cc2=O)S1(=O)=O]
049
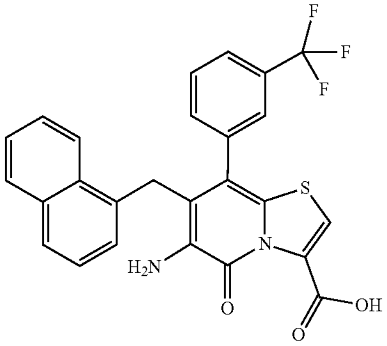 [SMILES: Nc1c(Cc2cccc3ccccc23)c(-c2cccc(C(F)(F)F)c2)c2scc(C(=O)O)n2c1=O]
050
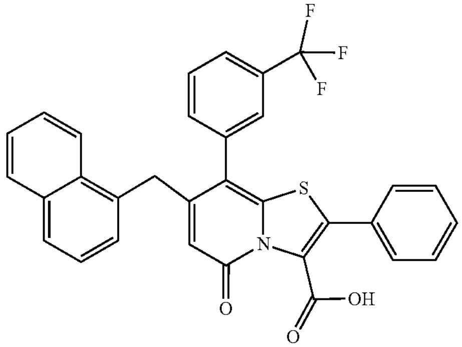 [SMILES: O=C(O)c1c(-c2ccccc2)sc2c(-c3cccc(C(F)(F)F)c3)c(Cc3cccc4ccccc34)cc(=O)n12]
051
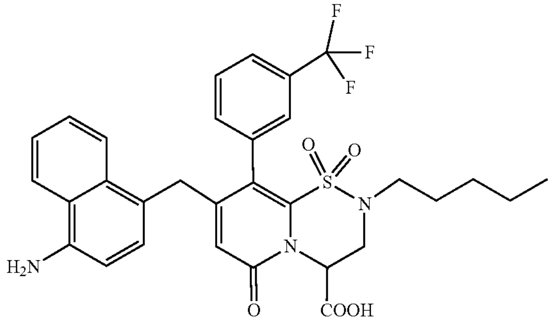 [SMILES: CCCCCN1CC(C(=O)O)n2c(c(-c3cccc(C(F)(F)F)c3)c(Cc3ccc(N)c4ccccc34)cc2=O)S1(=O)=O]
052

TABLE 1-continued
053
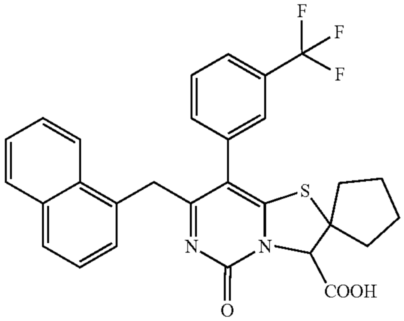 [SMILES: O=C(O)C1n2c(c(-c3cccc(C(F)(F)F)c3)c(Cc3cccc4ccccc34)nc2=O)SC12CCCC2]
054
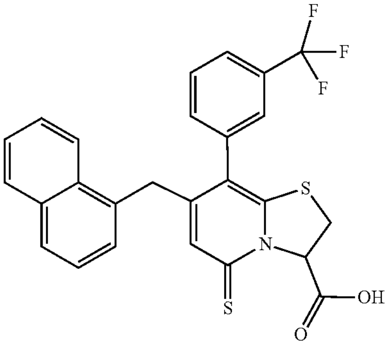 [SMILES: O=C(O)C1CSc2c(-c3cccc(C(F)(F)F)c3)c(Cc3cccc4ccccc34)cc(=S)n21]
055
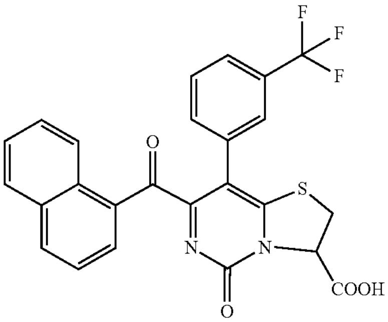 [SMILES: O=C(c1nc(=O)n2c(c1-c1cccc(C(F)(F)F)c1)SCC2C(=O)O)c1cccc2ccccc12]
056
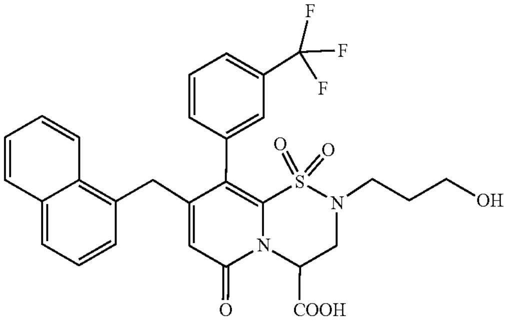 [SMILES: O=C(O)C1CN(CCCO)S(=O)(=O)c2c(-c3cccc(C(F)(F)F)c3)c(Cc3cccc4ccccc34)cc(=O)n21]

TABLE 1-continued
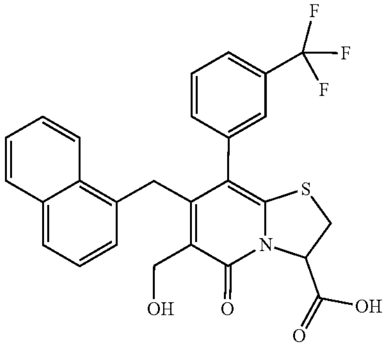 [SMILES: O=C(O)C1CSc2c(-c3cccc(C(F)(F)F)c3)c(Cc3cccc4ccccc34)c(CO)c(=O)n21]
057
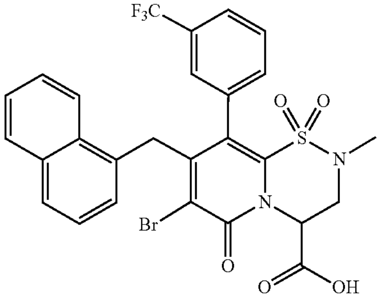 [SMILES: CN1CC(C(=O)O)n2c(c(-c3cccc(C(F)(F)F)c3)c(Cc3cccc4ccccc34)c(Br)c2=O)S1(=O)=O]
058
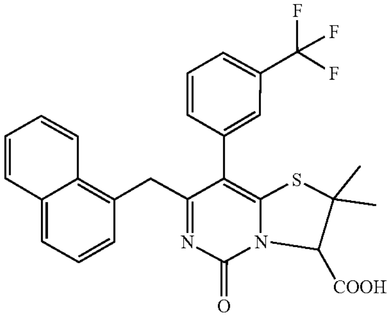 [SMILES: CC1(C)Sc2c(-c3cccc(C(F)(F)F)c3)c(Cc3cccc4ccccc34)nc(=O)n2C1C(=O)O]
059
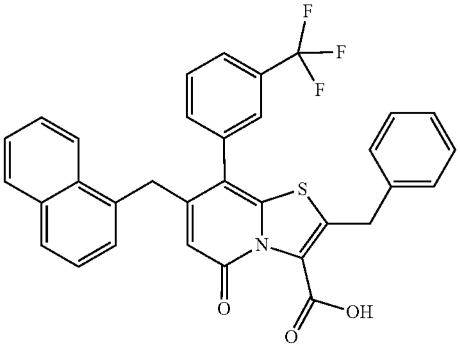 [SMILES: O=C(O)c1c(Cc2ccccc2)sc2c(-c3cccc(C(F)(F)F)c3)c(Cc3cccc4ccccc34)cc(=O)n12]
060

TABLE 1-continued
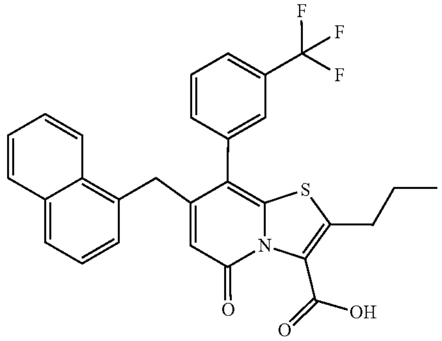 [SMILES: CCCc1sc2c(-c3cccc(C(F)(F)F)c3)c(Cc3cccc4ccccc34)cc(=O)n2c1C(=O)O]
061
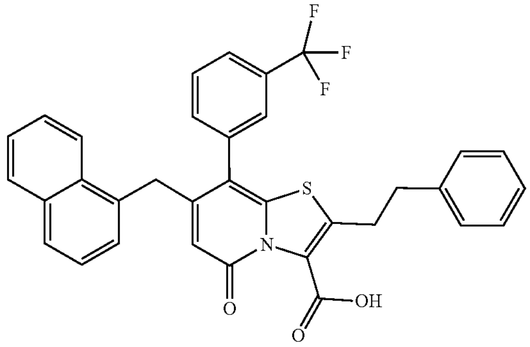 [SMILES: O=C(O)c1c(CCc2ccccc2)sc2c(-c3cccc(C(F)(F)F)c3)c(Cc3cccc4ccccc34)cc(=O)n12]
062
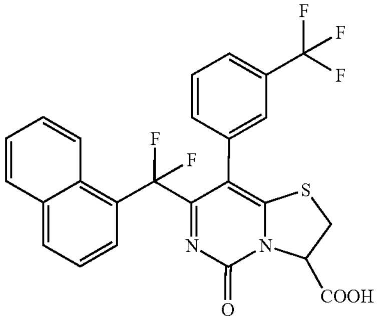 [SMILES: O=C(O)C1CSc2c(-c3cccc(C(F)(F)F)c3)c(C(F)(F)c3cccc4ccccc34)nc(=O)n21]
063
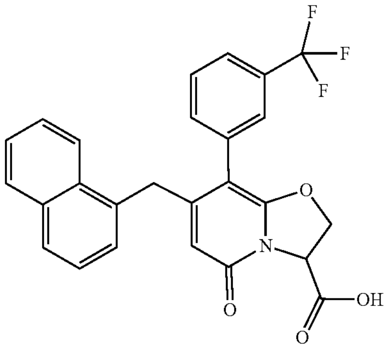 [SMILES: O=C(O)C1COc2c(-c3cccc(C(F)(F)F)c3)c(Cc3cccc4ccccc34)cc(=O)n21]
064

TABLE 1-continued
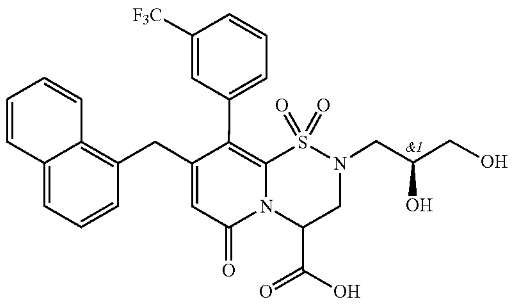 [SMILES: O=C(O)C1CN(C[C@H](O)CO)S(=O)(=O)c2c(-c3cccc(C(F)(F)F)c3)c(Cc3cccc4ccccc34)cc(=O)n21]
065a
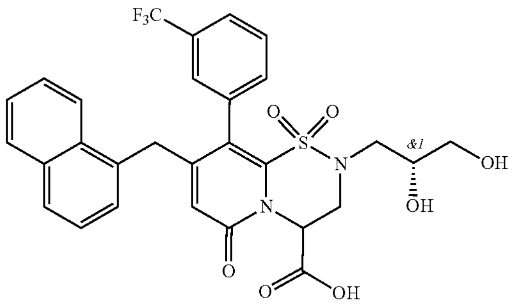 [SMILES: O=C(O)C1CN(C[C@@H](O)CO)S(=O)(=O)c2c(-c3cccc(C(F)(F)F)c3)c(Cc3cccc4ccccc34)cc(=O)n21]
065b
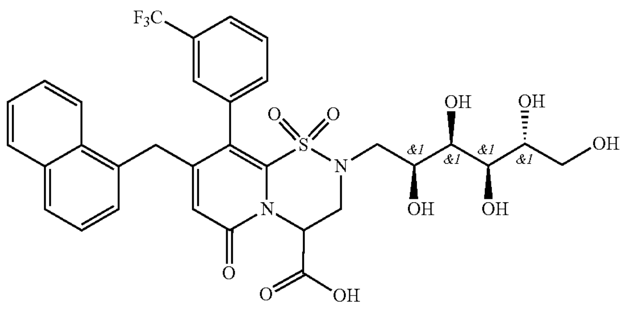 [SMILES: O=C(O)C1CN(C[C@H](O)[C@@H](O)[C@H](O)[C@H](O)CO)S(=O)(=O)c2c(-c3cccc(C(F)(F)F)c3)c(Cc3cccc4ccccc34)cc(=O)n21]
066
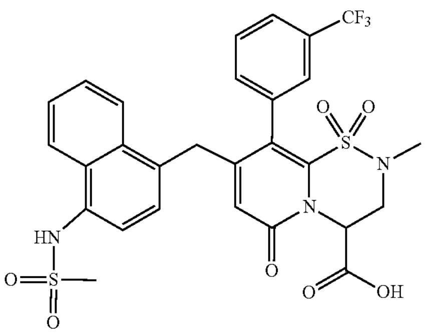 [SMILES: CN1CC(C(=O)O)n2c(c(-c3cccc(C(F)(F)F)c3)c(Cc3ccc(NS(C)(=O)=O)c4ccccc34)cc2=O)S1(=O)=O]
067
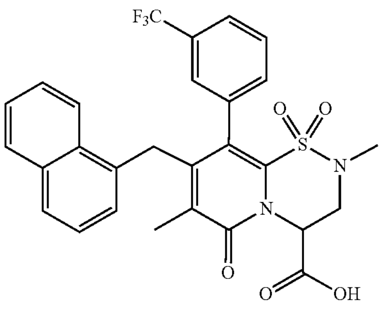 [SMILES: Cc1c(Cc2cccc3ccccc23)c(-c2cccc(C(F)(F)F)c2)c2n(c1=O)C(C(=O)O)CN(C)S2(=O)=O]
068

TABLE 1-continued
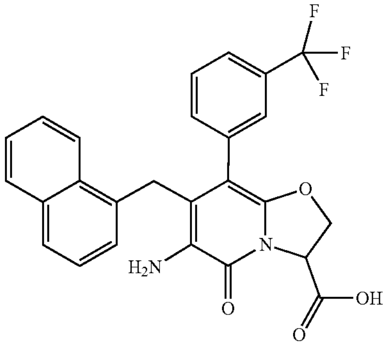 [SMILES: Nc1c(Cc2cccc3ccccc23)c(-c2cccc(C(F)(F)F)c2)c2n(c1=O)C(C(=O)O)CO2]
069
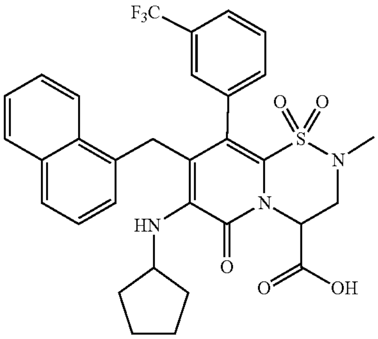 [SMILES: CN1CC(C(=O)O)n2c(c(-c3cccc(C(F)(F)F)c3)c(Cc3cccc4ccccc34)c(NC3CCCC3)c2=O)S1(=O)=O]
070
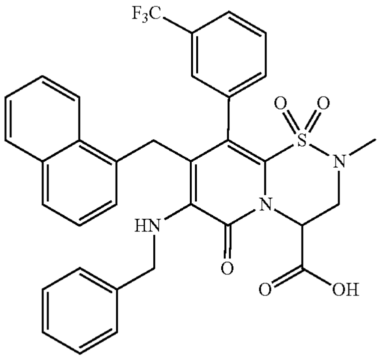 [SMILES: CN1CC(C(=O)O)n2c(c(-c3cccc(C(F)(F)F)c3)c(Cc3cccc4ccccc34)c(NCc3ccccc3)c2=O)S1(=O)=O]
071
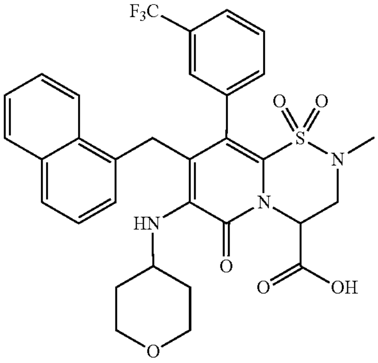 [SMILES: CN1CC(C(=O)O)n2c(c(-c3cccc(C(F)(F)F)c3)c(Cc3cccc4ccccc34)c(NC3CCOCC3)c2=O)S1(=O)=O]
072

TABLE 1-continued
073
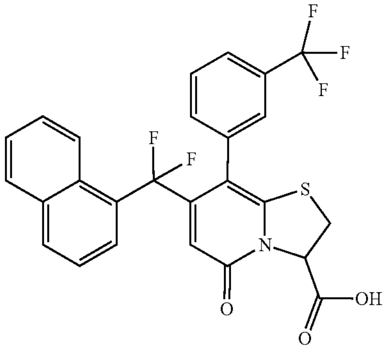 [SMILES: O=C(O)C1CSc2c(-c3cccc(C(F)(F)F)c3)c(C(F)(F)c3cccc4ccccc34)cc(=O)n21]
074
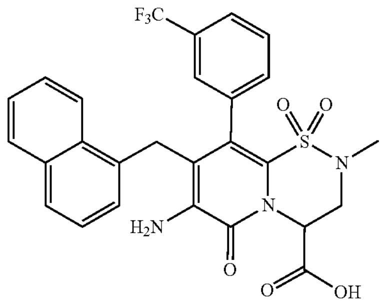 [SMILES: CN1CC(C(=O)O)n2c(c(-c3cccc(C(F)(F)F)c3)c(Cc3cccc4ccccc34)c(N)c2=O)S1(=O)=O]
075
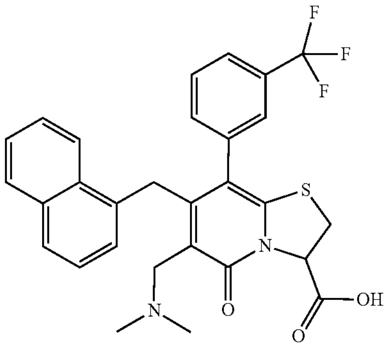 [SMILES: CN(C)Cc1c(Cc2cccc3ccccc23)c(-c2cccc(C(F)(F)F)c2)c2n(c1=O)C(C(=O)O)CS2]
076
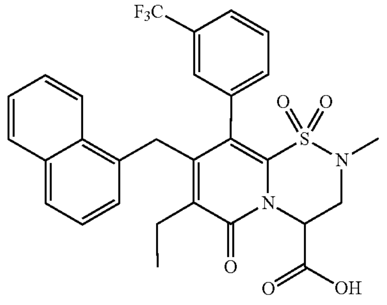 [SMILES: CCc1c(Cc2cccc3ccccc23)c(-c2cccc(C(F)(F)F)c2)c2n(c1=O)C(C(=O)O)CN(C)S2(=O)=O]
077
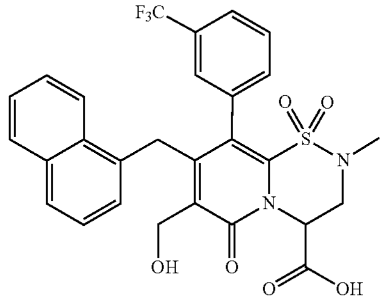 [SMILES: CN1CC(C(=O)O)n2c(c(-c3cccc(C(F)(F)F)c3)c(Cc3cccc4ccccc34)c(CO)c2=O)S1(=O)=O]

TABLE 1-continued
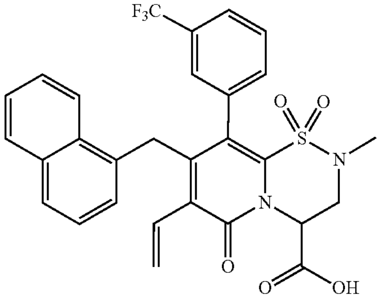 [SMILES: C=Cc1c(Cc2cccc3ccccc23)c(-c2cccc(C(F)(F)F)c2)c2n(c1=O)C(C(=O)O)CN(C)S2(=O)=O]
078
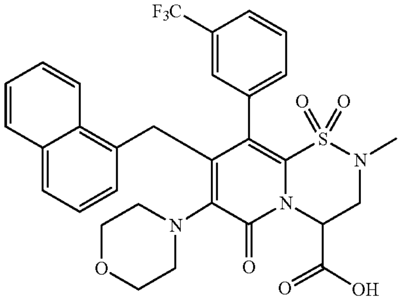 [SMILES: CN1CC(C(=O)O)n2c(c(-c3cccc(C(F)(F)F)c3)c(Cc3cccc4ccccc34)c(N3CCOCC3)c2=O)S1(=O)=O]
079
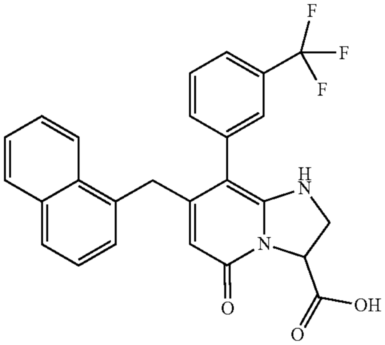 [SMILES: O=C(O)C1CNc2c(-c3cccc(C(F)(F)F)c3)c(Cc3cccc4ccccc34)cc(=O)n21]
080
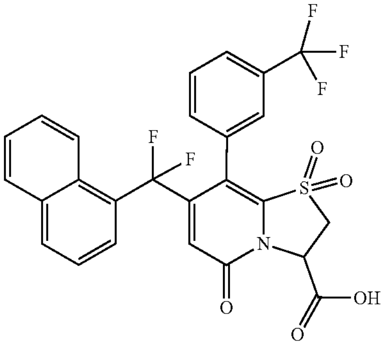 [SMILES: O=C(O)C1CS(=O)(=O)c2c(-c3cccc(C(F)(F)F)c3)c(C(F)(F)c3cccc4ccccc34)cc(=O)n21]
081
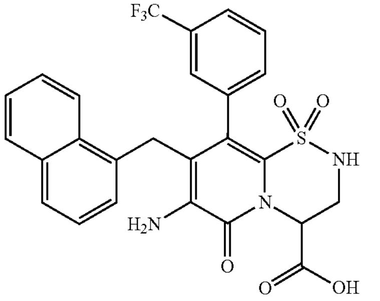 [SMILES: Nc1c(Cc2cccc3ccccc23)c(-c2cccc(C(F)(F)F)c2)c2n(c1=O)C(C(=O)O)CNS2(=O)=O]
082

TABLE 1-continued
083
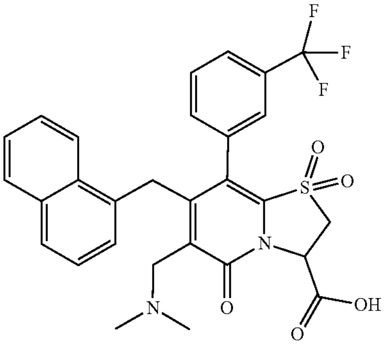 [SMILES: CN(C)Cc1c(Cc2cccc3ccccc23)c(-c2cccc(C(F)(F)F)c2)c2n(c1=O)C(C(=O)O)CS2(=O)=O]
084
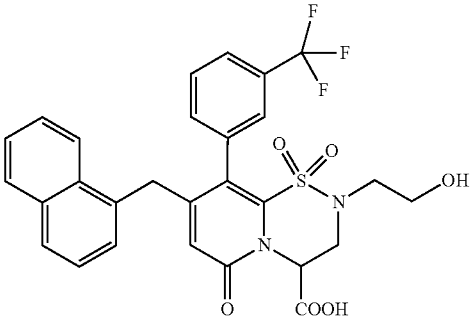 [SMILES: O=C(O)C1CN(CCO)S(=O)(=O)c2c(-c3cccc(C(F)(F)F)c3)c(Cc3cccc4ccccc34)cc(=O)n21]
085
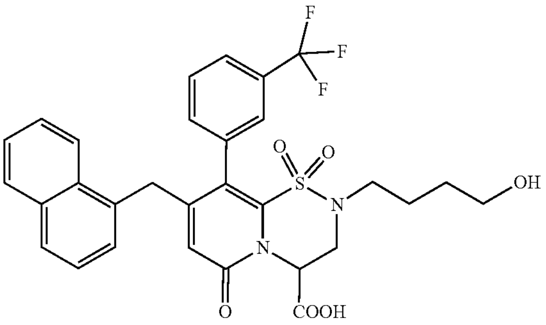 [SMILES: O=C(O)C1CN(CCCCO)S(=O)(=O)c2c(-c3cccc(C(F)(F)F)c3)c(Cc3cccc4ccccc34)cc(=O)n21]
086
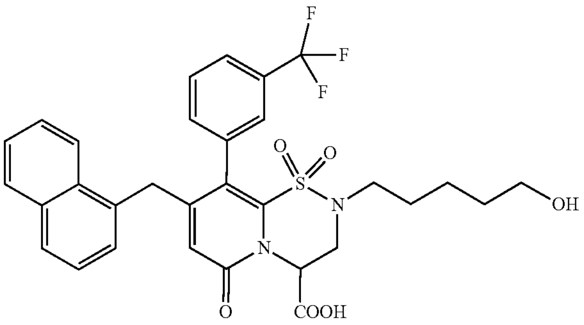 [SMILES: O=C(O)C1CN(CCCCCO)S(=O)(=O)c2c(-c3cccc(C(F)(F)F)c3)c(Cc3cccc4ccccc34)cc(=O)n21]
087
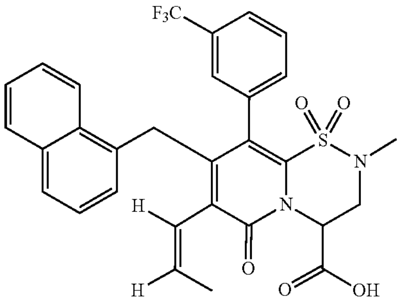 [SMILES: C/C=C\c1c(Cc2cccc3ccccc23)c(-c2cccc(C(F)(F)F)c2)c2n(c1=O)C(C(=O)O)CN(C)S2(=O)=O]

TABLE 1-continued
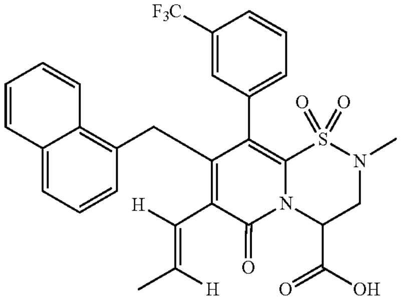 [SMILES: C/C=C/c1c(Cc2cccc3ccccc23)c(-c2cccc(C(F)(F)F)c2)c2n(c1=O)C(C(=O)O)CN(C)S2(=O)=O]
088
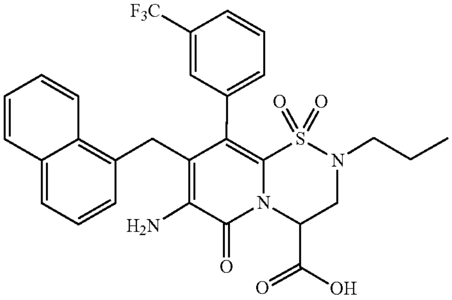 [SMILES: CCCN1CC(C(=O)O)n2c(c(-c3cccc(C(F)(F)F)c3)c(Cc3cccc4ccccc34)c(N)c2=O)S1(=O)=O]
089
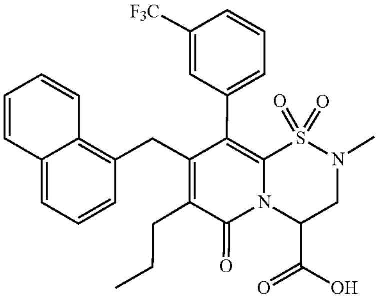 [SMILES: CCCc1c(Cc2cccc3ccccc23)c(-c2cccc(C(F)(F)F)c2)c2n(c1=O)C(C(=O)O)CN(C)S2(=O)=O]
090
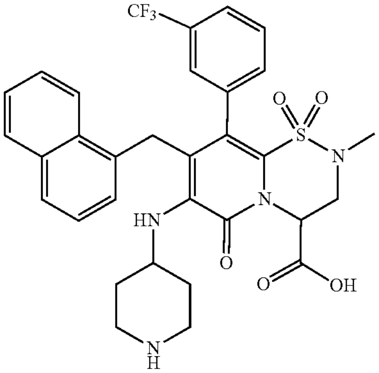 [SMILES: CN1CC(C(=O)O)n2c(c(-c3cccc(C(F)(F)F)c3)c(Cc3cccc4ccccc34)c(NC3CCNCC3)c2=O)S1(=O)=O]
091
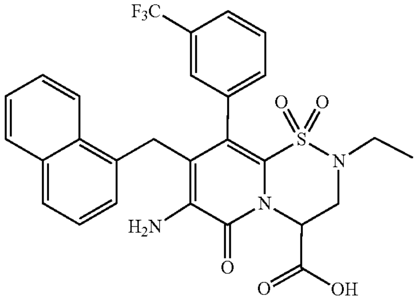 [SMILES: CCN1CC(C(=O)O)n2c(c(-c3cccc(C(F)(F)F)c3)c(Cc3cccc4ccccc34)c(N)c2=O)S1(=O)=O]
092

TABLE 1-continued
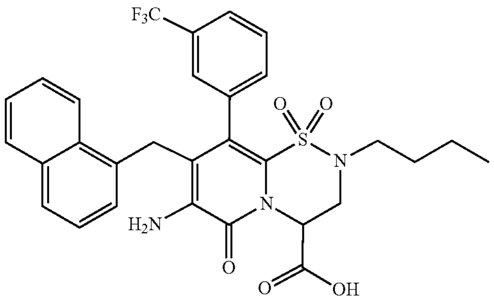 [SMILES: CCCCN1CC(C(=O)O)n2c(c(-c3cccc(C(F)(F)F)c3)c(Cc3cccc4ccccc34)c(N)c2=O)S1(=O)=O]
093
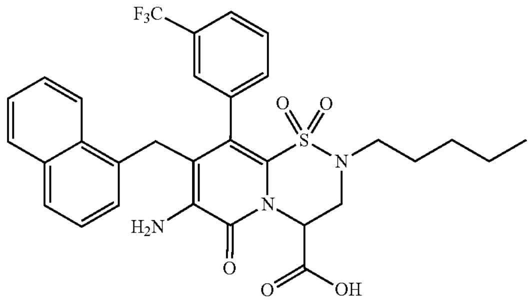 [SMILES: CCCCCN1CC(C(=O)O)n2c(c(-c3cccc(C(F)(F)F)c3)c(Cc3cccc4ccccc34)c(N)c2=O)S1(=O)=O]
094
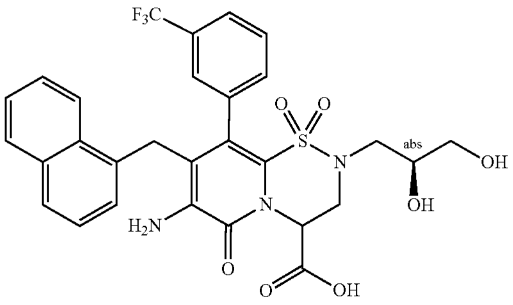 [SMILES: Nc1c(Cc2cccc3ccccc23)c(-c2cccc(C(F)(F)F)c2)c2n(c1=O)C(C(=O)O)CN(C[C@H](O)CO)S2(=O)=O]
095
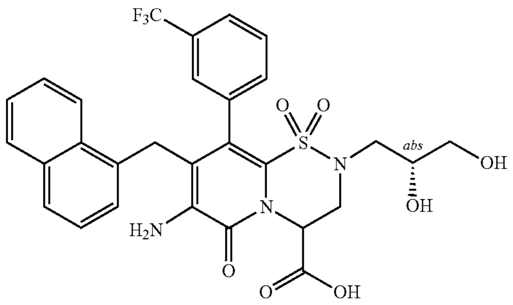 [SMILES: Nc1c(Cc2cccc3ccccc23)c(-c2cccc(C(F)(F)F)c2)c2n(c1=O)C(C(=O)O)CN(C[C@@H](O)CO)S2(=O)=O]
096
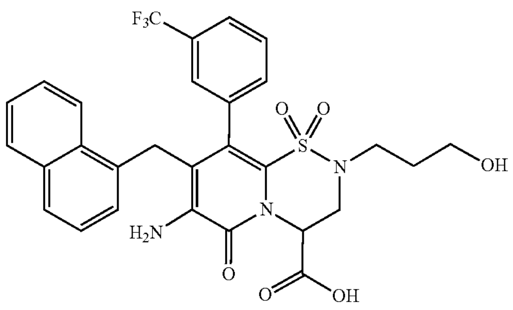 [SMILES: Nc1c(Cc2cccc3ccccc23)c(-c2cccc(C(F)(F)F)c2)c2n(c1=O)C(C(=O)O)CN(CCCO)S2(=O)=O]
097

TABLE 1-continued
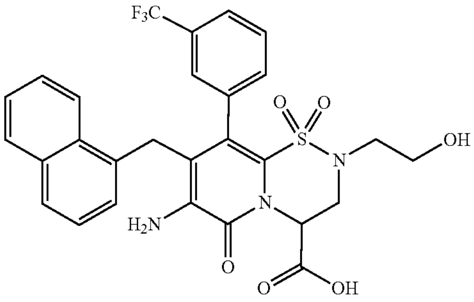 [SMILES: Nc1c(Cc2cccc3ccccc23)c(-c2cccc(C(F)(F)F)c2)c2n(c1=O)C(C(=O)O)CN(CCO)S2(=O)=O]
098
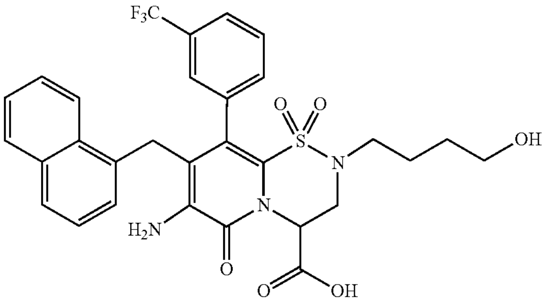 [SMILES: Nc1c(Cc2cccc3ccccc23)c(-c2cccc(C(F)(F)F)c2)c2n(c1=O)C(C(=O)O)CN(CCCCO)S2(=O)=O]
099
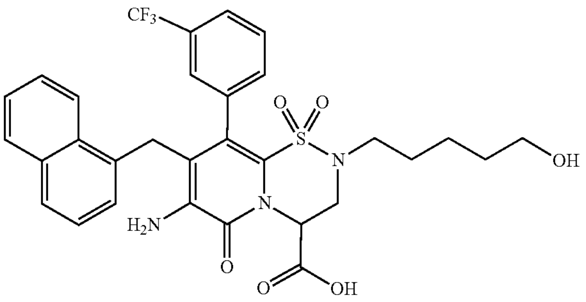 [SMILES: Nc1c(Cc2cccc3ccccc23)c(-c2cccc(C(F)(F)F)c2)c2n(c1=O)C(C(=O)O)CN(CCCCCO)S2(=O)=O]
100
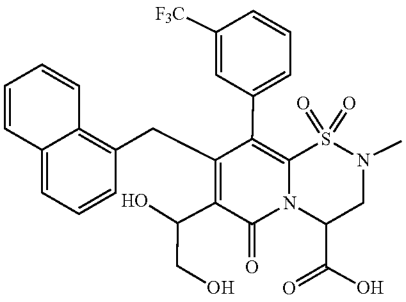 [SMILES: CN1CC(C(=O)O)n2c(c(-c3cccc(C(F)(F)F)c3)c(Cc3cccc4ccccc34)c(C(O)CO)c2=O)S1(=O)=O]
101
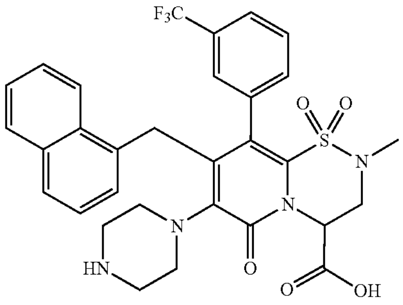 [SMILES: CN1CC(C(=O)O)n2c(c(-c3cccc(C(F)(F)F)c3)c(Cc3cccc4ccccc34)c(N3CCNCC3)c2=O)S1(=O)=O]
102

TABLE 1-continued
103
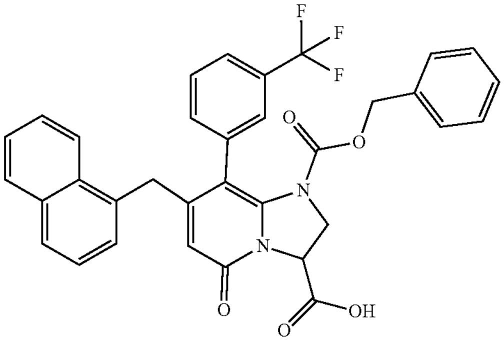 [SMILES: O=C(O)C1CN(C(=O)OCc2ccccc2)c2c(-c3cccc(C(F)(F)F)c3)c(Cc3cccc4ccccc34)cc(=O)n21]
104
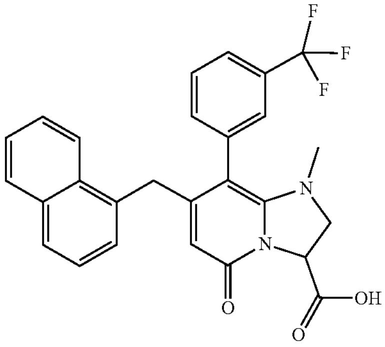 [SMILES: CN1CC(C(=O)O)n2c1c(-c1cccc(C(F)(F)F)c1)c(Cc1cccc3ccccc13)cc2=O]
105
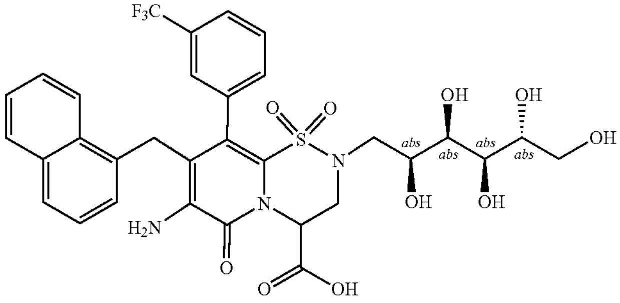 [SMILES: Nc1c(Cc2cccc3ccccc23)c(-c2cccc(C(F)(F)F)c2)c2n(c1=O)C(C(=O)O)CN(C[C@H](O)[C@@H](O)[C@H](O)[C@H](O)CO)S2(=O)=O]
106
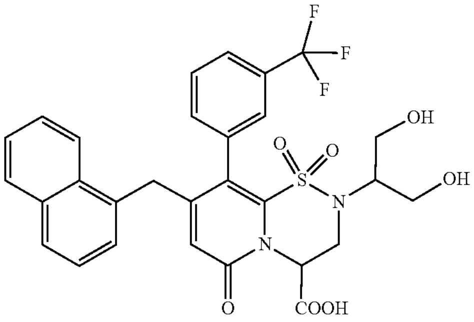 [SMILES: O=C(O)C1CN(C(CO)CO)S(=O)(=O)c2c(-c3cccc(C(F)(F)F)c3)c(Cc3cccc4ccccc34)cc(=O)n21]
107
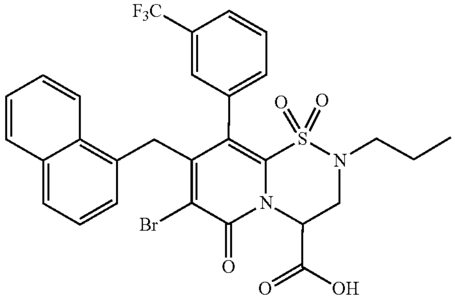 [SMILES: CCCN1CC(C(=O)O)n2c(c(-c3cccc(C(F)(F)F)c3)c(Cc3cccc4ccccc34)c(Br)c2=O)S1(=O)=O]

TABLE 1-continued
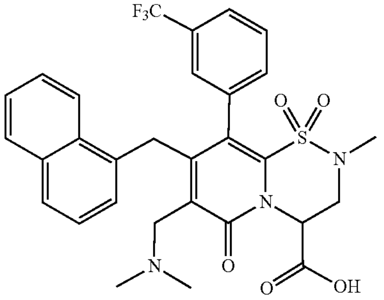 [SMILES: CN(C)Cc1c(Cc2cccc3ccccc23)c(-c2cccc(C(F)(F)F)c2)c2n(c1=O)C(C(=O)O)CN(C)S2(=O)=O]
108
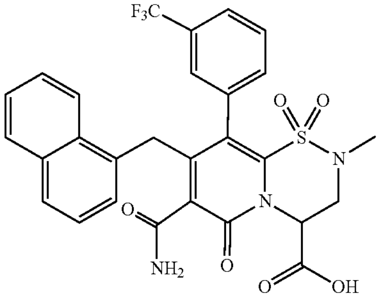 [SMILES: CN1CC(C(=O)O)n2c(c(-c3cccc(C(F)(F)F)c3)c(Cc3cccc4ccccc34)c(C(N)=O)c2=O)S1(=O)=O]
109
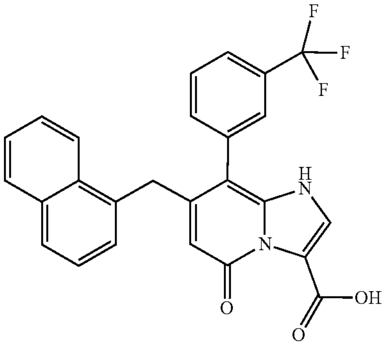 [SMILES: O=C(O)c1c[nH]c2c(-c3cccc(C(F)(F)F)c3)c(Cc3cccc4ccccc34)cc(=O)n12]
110
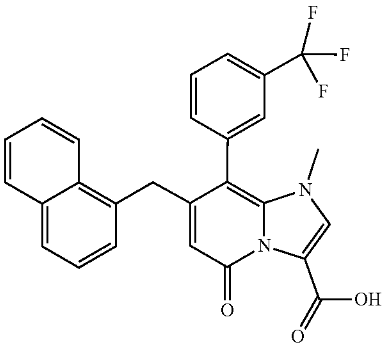 [SMILES: Cn1cc(C(=O)O)n2c(=O)cc(Cc3cccc4ccccc34)c(-c3cccc(C(F)(F)F)c3)c12]
111
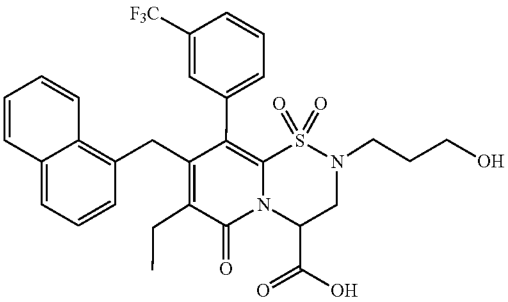 [SMILES: CCc1c(Cc2cccc3ccccc23)c(-c2cccc(C(F)(F)F)c2)c2n(c1=O)C(C(=O)O)CN(CCCO)S2(=O)=O]
112

TABLE 1-continued
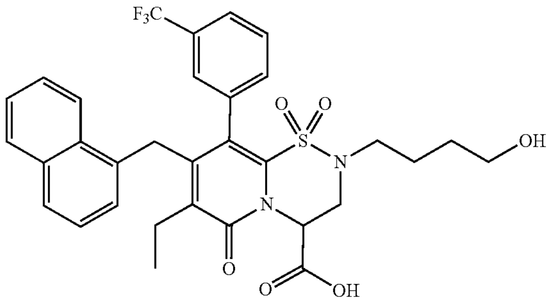 [SMILES: CCc1c(Cc2cccc3ccccc23)c(-c2cccc(C(F)(F)F)c2)c2n(c1=O)C(C(=O)O)CN(CCCCO)S2(=O)=O]
113
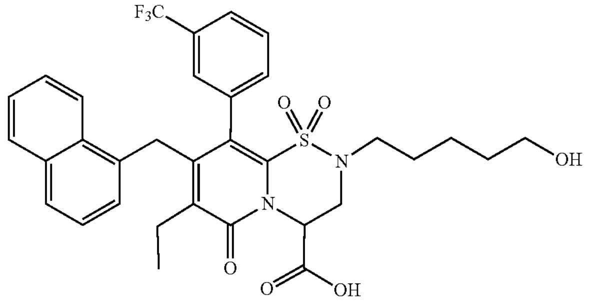 [SMILES: CCc1c(Cc2cccc3ccccc23)c(-c2cccc(C(F)(F)F)c2)c2n(c1=O)C(C(=O)O)CN(CCCCCO)S2(=O)=O]
114
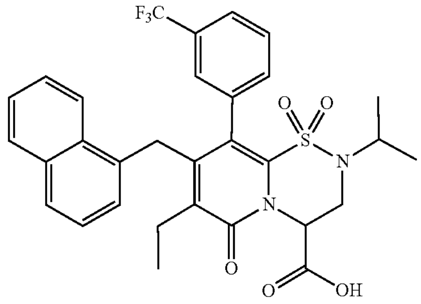 [SMILES: CCc1c(Cc2cccc3ccccc23)c(-c2cccc(C(F)(F)F)c2)c2n(c1=O)C(C(=O)O)CN(C(C)C)S2(=O)=O]
115
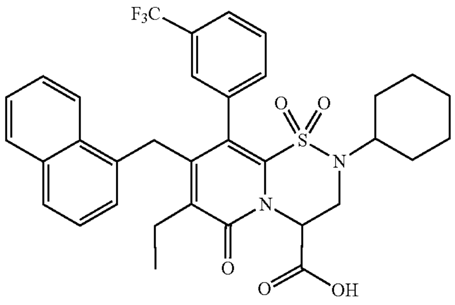 [SMILES: CCc1c(Cc2cccc3ccccc23)c(-c2cccc(C(F)(F)F)c2)c2n(c1=O)C(C(=O)O)CN(C1CCCCC1)S2(=O)=O]
116
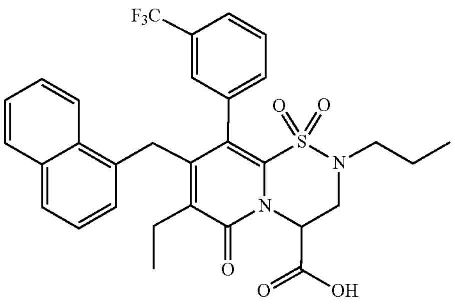 [SMILES: CCCN1CC(C(=O)O)n2c(c(-c3cccc(C(F)(F)F)c3)c(Cc3cccc4ccccc34)c(CC)c2=O)S1(=O)=O]
117

TABLE 1-continued
118
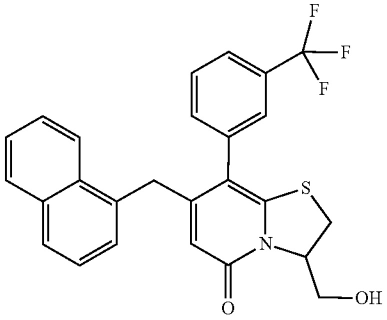 [SMILES: O=c1cc(Cc2cccc3ccccc23)c(-c2cccc(C(F)(F)F)c2)c2n1C(CO)CS2]
119
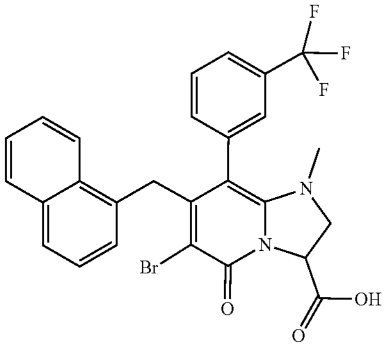 [SMILES: CN1CC(C(=O)O)n2c1c(-c1cccc(C(F)(F)F)c1)c(Cc1cccc3ccccc13)c(Br)c2=O]
120
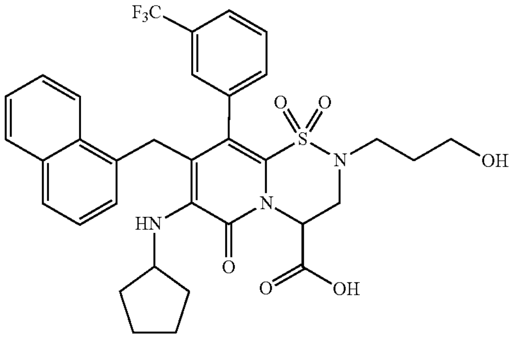 [SMILES: O=C(O)C1CN(CCCO)S(=O)(=O)c2c(-c3cccc(C(F)(F)F)c3)c(Cc3cccc4ccccc34)c(NC3CCCC3)c(=O)n21]
121
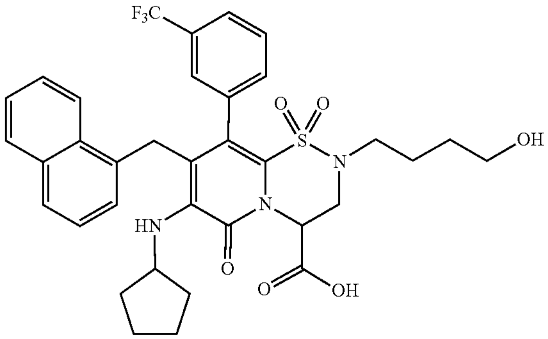 [SMILES: O=C(O)C1CN(CCCCO)S(=O)(=O)c2c(-c3cccc(C(F)(F)F)c3)c(Cc3cccc4ccccc34)c(NC3CCCC3)c(=O)n21]

TABLE 1-continued
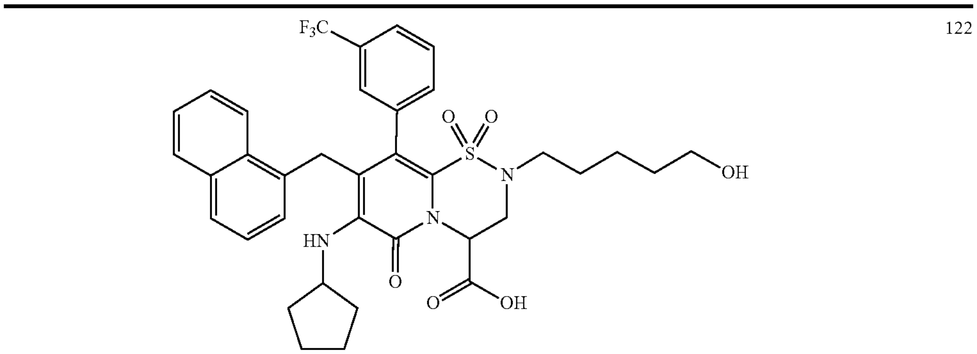
122
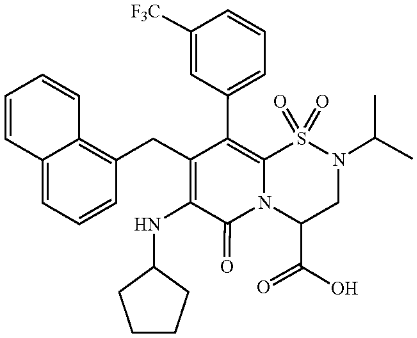 [SMILES: CC(C)N1CC(C(=O)O)n2c(c(-c3cccc(C(F)(F)F)c3)c(Cc3cccc4ccccc34)c(NC3CCCC3)c2=O)S1(=O)=O]
123
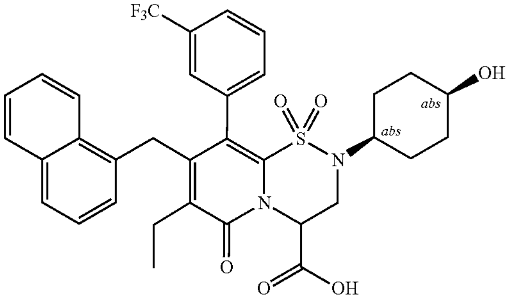 [SMILES: CCc1c(Cc2cccc3ccccc23)c(-c2cccc(C(F)(F)F)c2)c2n(c1=O)C(C(=O)O)CN([C@H]1CC[C@@H](O)CC1)S2(=O)=O]
124
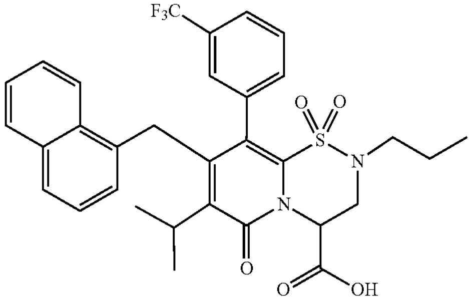 [SMILES: CCCN1CC(C(=O)O)n2c(c(-c3cccc(C(F)(F)F)c3)c(Cc3cccc4ccccc34)c(C(C)C)c2=O)S1(=O)=O]
125
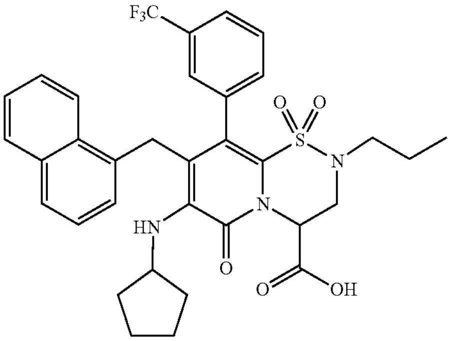 [SMILES: CCCN1CC(C(=O)O)n2c(c(-c3cccc(C(F)(F)F)c3)c(Cc3cccc4ccccc34)c(NC3CCCC3)c2=O)S1(=O)=O]
126

TABLE 1-continued
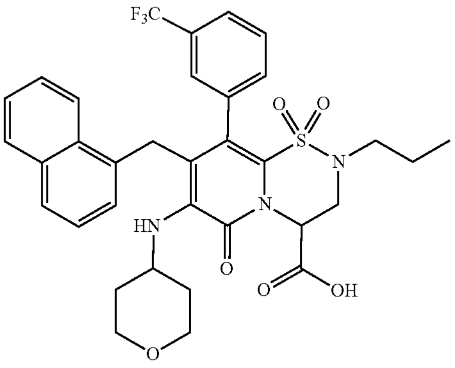 [SMILES: CCCN1CC(C(=O)O)n2c(c(-c3cccc(C(F)(F)F)c3)c(Cc3cccc4ccccc34)c(NC3CCOCC3)c2=O)S1(=O)=O]
127
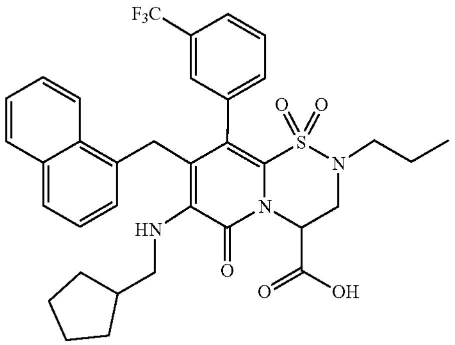 [SMILES: CCCN1CC(C(=O)O)n2c(c(-c3cccc(C(F)(F)F)c3)c(Cc3cccc4ccccc34)c(NCC3CCCC3)c2=O)S1(=O)=O]
128
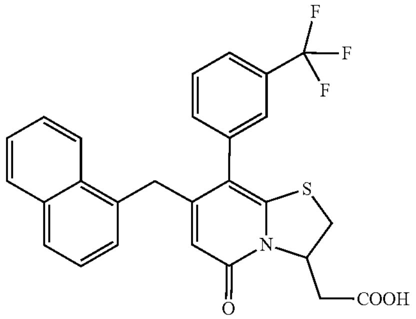 [SMILES: O=C(O)CC1CSc2c(-c3cccc(C(F)(F)F)c3)c(Cc3cccc4ccccc34)cc(=O)n21]
129
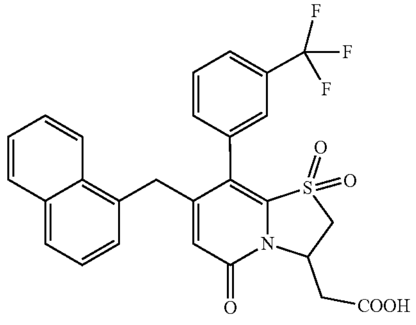 [SMILES: O=C(O)CC1CS(=O)(=O)c2c(-c3cccc(C(F)(F)F)c3)c(Cc3cccc4ccccc34)cc(=O)n21]
130

TABLE 1-continued
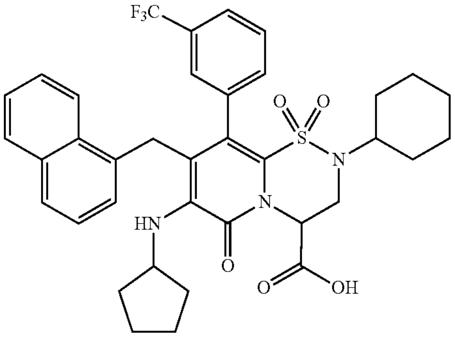 [SMILES: O=C(O)C1CN(C2CCCCC2)S(=O)(=O)c2c(-c3cccc(C(F)(F)F)c3)c(Cc3cccc4ccccc34)c(NC3CCCC3)c(=O)n21]
131
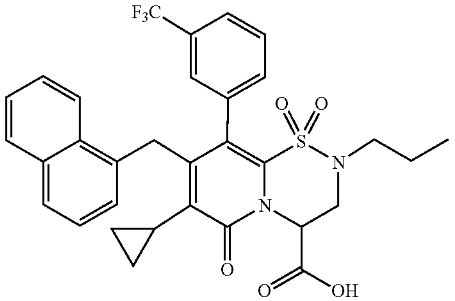 [SMILES: CCCN1CC(C(=O)O)n2c(c(-c3cccc(C(F)(F)F)c3)c(Cc3cccc4ccccc34)c(C3CC3)c2=O)S1(=O)=O]
132
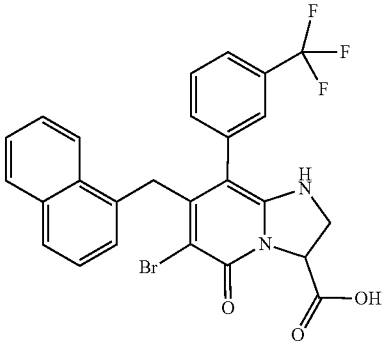 [SMILES: O=C(O)C1CNc2c(-c3cccc(C(F)(F)F)c3)c(Cc3cccc4ccccc34)c(Br)c(=O)n21]
133
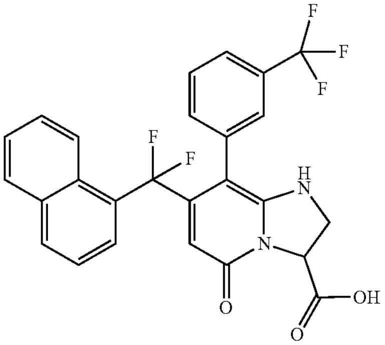 [SMILES: O=C(O)C1CNc2c(-c3cccc(C(F)(F)F)c3)c(C(F)(F)c3cccc4ccccc34)cc(=O)n21]
134

TABLE 1-continued
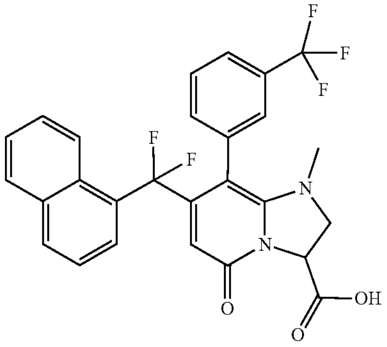 [SMILES: CN1CC(C(=O)O)n2c1c(-c1cccc(C(F)(F)F)c1)c(C(F)(F)c1cccc3ccccc13)cc2=O]
135
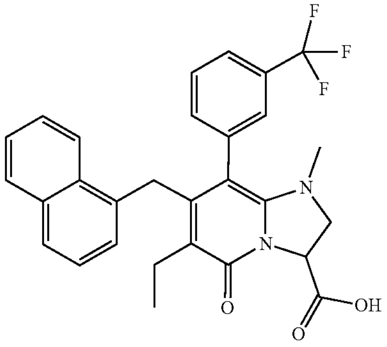 [SMILES: CCc1c(Cc2cccc3ccccc23)c(-c2cccc(C(F)(F)F)c2)c2n(c1=O)C(C(=O)O)CN2C]
136
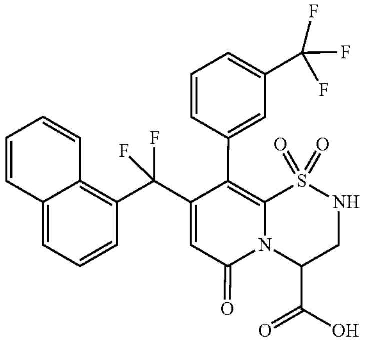 [SMILES: O=C(O)C1CNS(=O)(=O)c2c(-c3cccc(C(F)(F)F)c3)c(C(F)(F)c3cccc4ccccc34)cc(=O)n21]
137
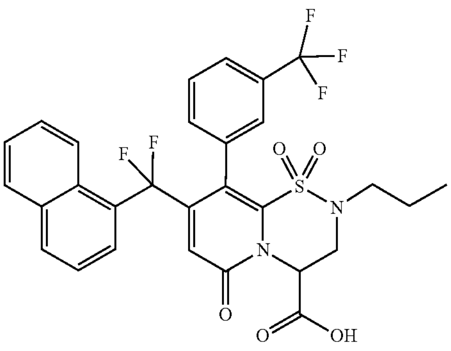 [SMILES: CCCN1CC(C(=O)O)n2c(c(-c3cccc(C(F)(F)F)c3)c(C(F)(F)c3cccc4ccccc34)cc2=O)S1(=O)=O]
138

TABLE 1-continued
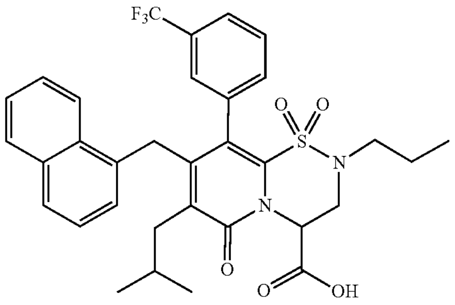 [SMILES: CCCN1CC(C(=O)O)n2c(c(-c3cccc(C(F)(F)F)c3)c(Cc3cccc4ccccc34)c(CC(C)C)c2=O)S1(=O)=O]
139
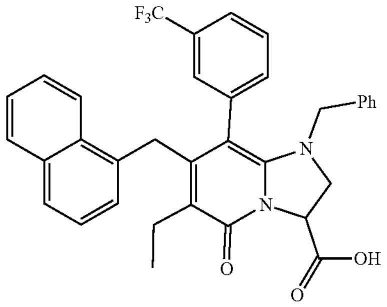 [SMILES: CCc1c(Cc2cccc3ccccc23)c(-c2cccc(C(F)(F)F)c2)c2n(c1=O)C(C(=O)O)CN2Cc1ccccc1]
140
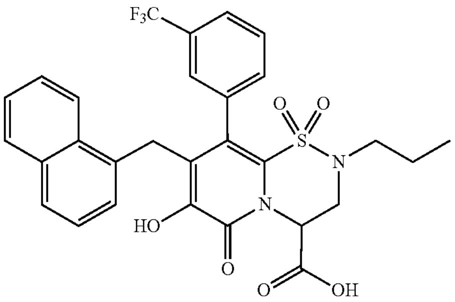 [SMILES: CCCN1CC(C(=O)O)n2c(c(-c3cccc(C(F)(F)F)c3)c(Cc3cccc4ccccc34)c(O)c2=O)S1(=O)=O]
141
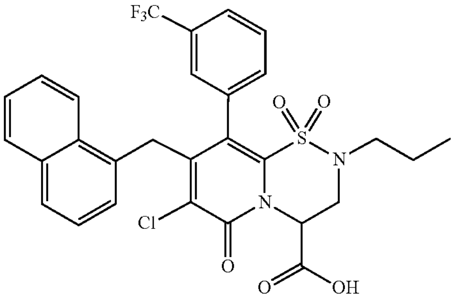 [SMILES: CCCN1CC(C(=O)O)n2c(c(-c3cccc(C(F)(F)F)c3)c(Cc3cccc4ccccc34)c(Cl)c2=O)S1(=O)=O]
142
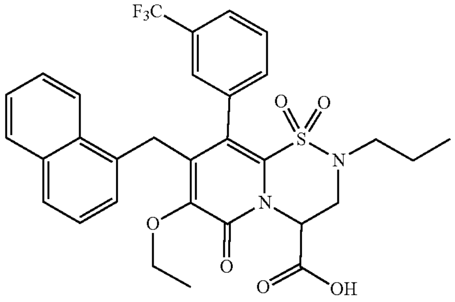 [SMILES: CCCN1CC(C(=O)O)n2c(c(-c3cccc(C(F)(F)F)c3)c(Cc3cccc4ccccc34)c(OCC)c2=O)S1(=O)=O]
143

TABLE 1-continued
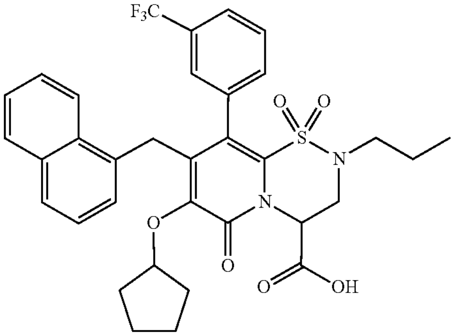 [SMILES: CCCN1CC(C(=O)O)n2c(c(-c3cccc(C(F)(F)F)c3)c(Cc3cccc4ccccc34)c(OC3CCCC3)c2=O)S1(=O)=O]
144
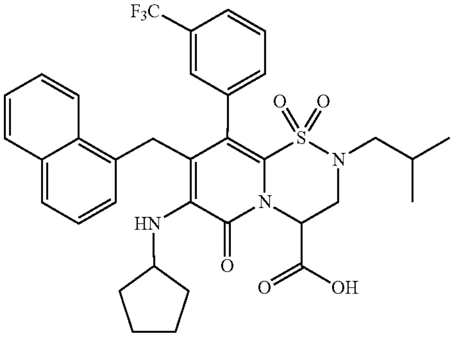 [SMILES: CC(C)CN1CC(C(=O)O)n2c(c(-c3cccc(C(F)(F)F)c3)c(Cc3cccc4ccccc34)c(NC3CCCC3)c2=O)S1(=O)=O]
145
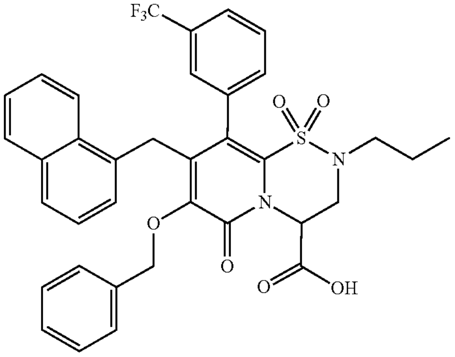 [SMILES: CCCN1CC(C(=O)O)n2c(c(-c3cccc(C(F)(F)F)c3)c(Cc3cccc4ccccc34)c(OCc3ccccc3)c2=O)S1(=O)=O]
146
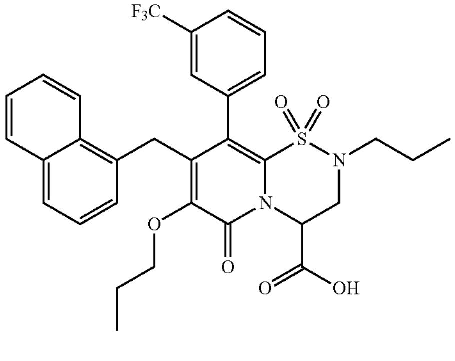 [SMILES: CCCOc1c(Cc2cccc3ccccc23)c(-c2cccc(C(F)(F)F)c2)c2n(c1=O)C(C(=O)O)CN(CCC)S2(=O)=O]
147

TABLE 1-continued
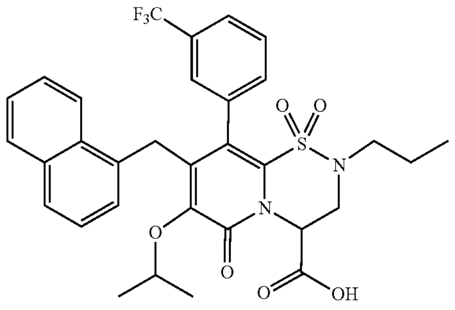 [SMILES: CCCN1CC(C(=O)O)n2c(c(-c3cccc(C(F)(F)F)c3)c(Cc3cccc4ccccc34)c(OC(C)C)c2=O)S1(=O)=O]
148
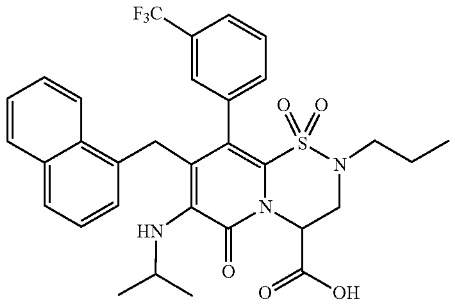 [SMILES: CCCN1CC(C(=O)O)n2c(c(-c3cccc(C(F)(F)F)c3)c(Cc3cccc4ccccc34)c(NC(C)C)c2=O)S1(=O)=O]
149
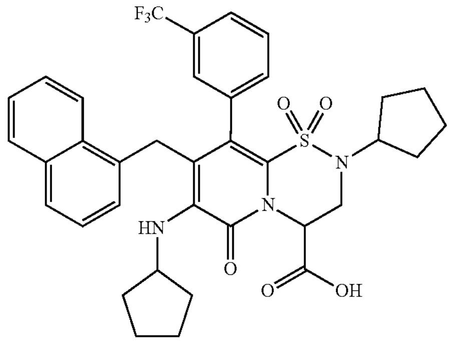 [SMILES: O=C(O)C1CN(C2CCCC2)S(=O)(=O)c2c(-c3cccc(C(F)(F)F)c3)c(Cc3cccc4ccccc34)c(NC3CCCC3)c(=O)n21]
150
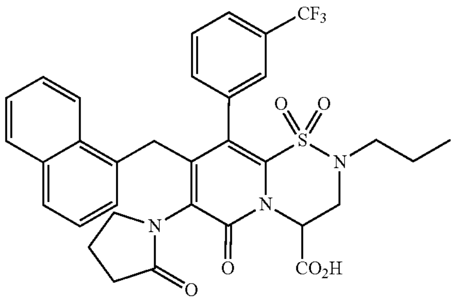 [SMILES: CCCN1CC(C(=O)O)n2c(c(-c3cccc(C(F)(F)F)c3)c(Cc3cccc4ccccc34)c(N3CCCC3=O)c2=O)S1(=O)=O]
151
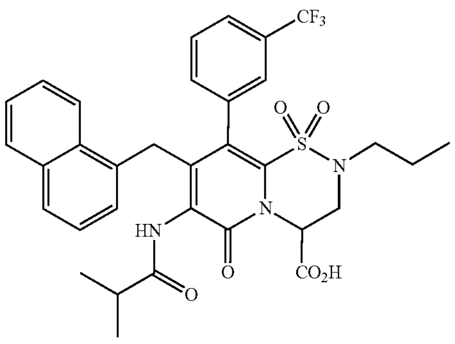 [SMILES: CCCN1CC(C(=O)O)n2c(c(-c3cccc(C(F)(F)F)c3)c(Cc3cccc4ccccc34)c(NC(=O)C(C)C)c2=O)S1(=O)=O]
152

TABLE 1-continued
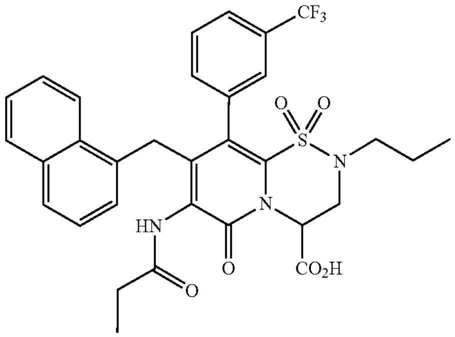 [SMILES: CCCN1CC(C(=O)O)n2c(c(-c3cccc(C(F)(F)F)c3)c(Cc3cccc4ccccc34)c(NC(=O)CC)c2=O)S1(=O)=O]
153
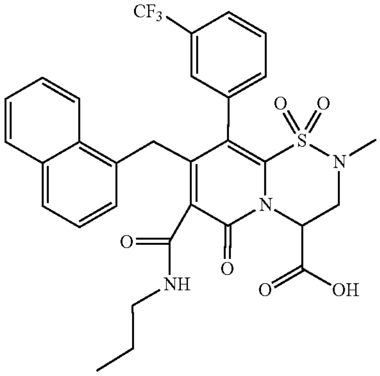 [SMILES: CCCNC(=O)c1c(Cc2cccc3ccccc23)c(-c2cccc(C(F)(F)F)c2)c2n(c1=O)C(C(=O)O)CN(C)S2(=O)=O]
154
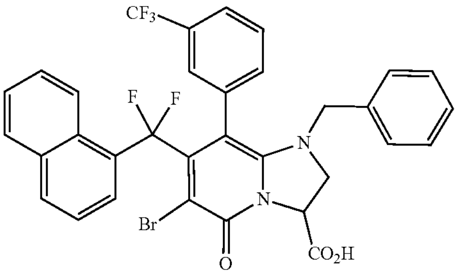 [SMILES: O=C(O)C1CN(Cc2ccccc2)c2c(-c3cccc(C(F)(F)F)c3)c(C(F)(F)c3cccc4ccccc34)c(Br)c(=O)n21]
155
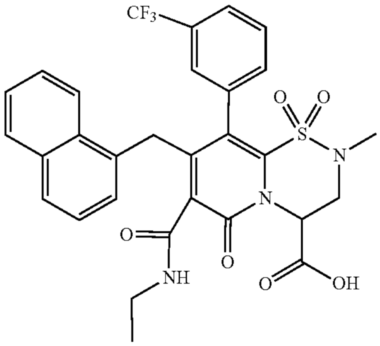 [SMILES: CCNC(=O)c1c(Cc2cccc3ccccc23)c(-c2cccc(C(F)(F)F)c2)c2n(c1=O)C(C(=O)O)CN(C)S2(=O)=O]
156

TABLE 1-continued
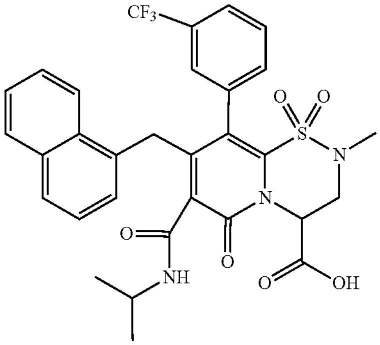 [SMILES: CC(C)NC(=O)c1c(Cc2cccc3ccccc23)c(-c2cccc(C(F)(F)F)c2)c2n(c1=O)C(C(=O)O)CN(C)S2(=O)=O]
157
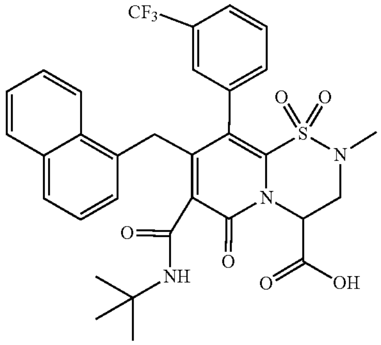 [SMILES: CN1CC(C(=O)O)n2c(c(-c3cccc(C(F)(F)F)c3)c(Cc3cccc4ccccc34)c(C(=O)NC(C)(C)C)c2=O)S1(=O)=O]
158
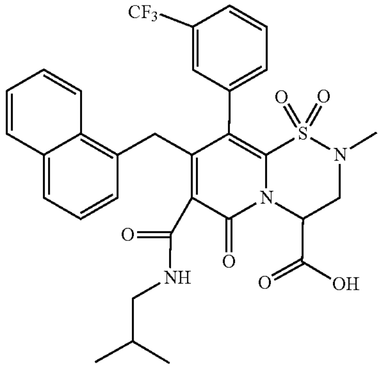 [SMILES: CC(C)CNC(=O)c1c(Cc2cccc3ccccc23)c(-c2cccc(C(F)(F)F)c2)c2n(c1=O)C(C(=O)O)CN(C)S2(=O)=O]
159
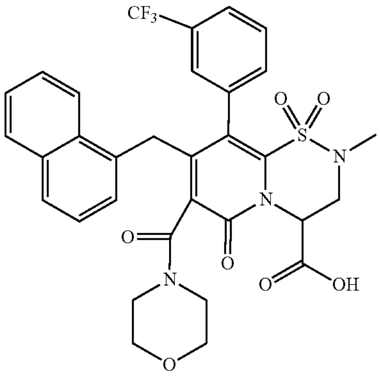 [SMILES: CN1CC(C(=O)O)n2c(c(-c3cccc(C(F)(F)F)c3)c(Cc3cccc4ccccc34)c(C(=O)N3CCOCC3)c2=O)S1(=O)=O]
160

TABLE 1-continued
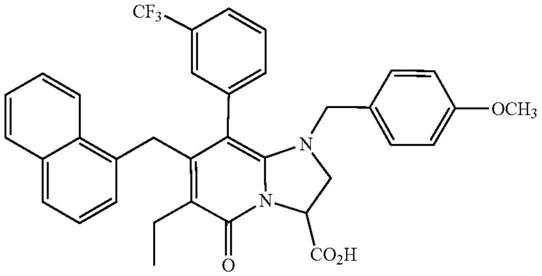 [SMILES: CCc1c(Cc2cccc3ccccc23)c(-c2cccc(C(F)(F)F)c2)c2n(c1=O)C(C(=O)O)CN2Cc1ccc(OC)cc1]
161
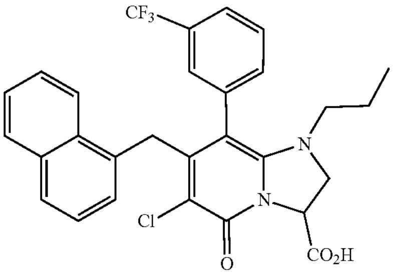 [SMILES: CCCN1CC(C(=O)O)n2c1c(-c1cccc(C(F)(F)F)c1)c(Cc1cccc3ccccc13)c(Cl)c2=O]
162
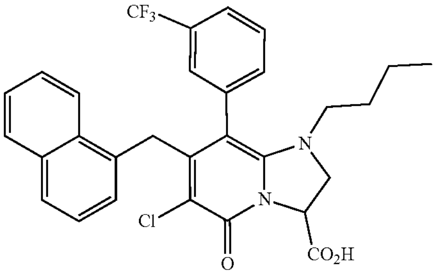 [SMILES: CCCCN1CC(C(=O)O)n2c1c(-c1cccc(C(F)(F)F)c1)c(Cc1cccc3ccccc13)c(Cl)c2=O]
163
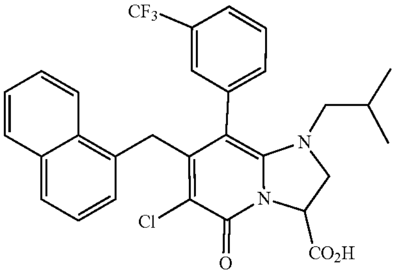 [SMILES: CC(C)CN1CC(C(=O)O)n2c1c(-c1cccc(C(F)(F)F)c1)c(Cc1cccc3ccccc13)c(Cl)c2=O]
164
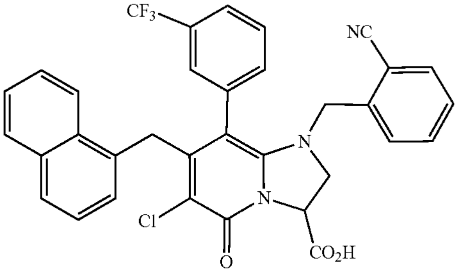 [SMILES: N#Cc1ccccc1CN1CC(C(=O)O)n2c1c(-c1cccc(C(F)(F)F)c1)c(Cc1cccc3ccccc13)c(Cl)c2=O]
165

TABLE 1-continued
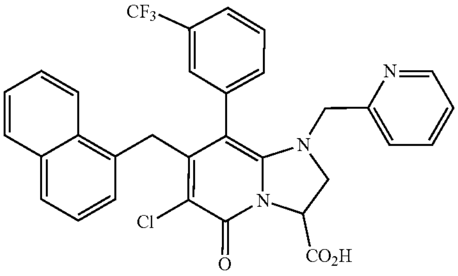 [SMILES: O=C(O)C1CN(Cc2ccccn2)c2c(-c3cccc(C(F)(F)F)c3)c(Cc3cccc4ccccc34)c(Cl)c(=O)n21]
166
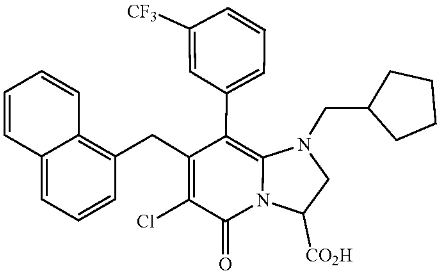 [SMILES: O=C(O)C1CN(CC2CCCC2)c2c(-c3cccc(C(F)(F)F)c3)c(Cc3cccc4ccccc34)c(Cl)c(=O)n21]
167
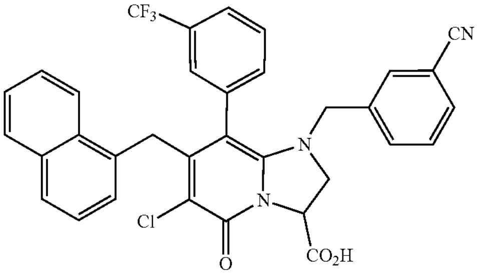 [SMILES: N#Cc1cccc(CN2CC(C(=O)O)n3c2c(-c2cccc(C(F)(F)F)c2)c(Cc2cccc4ccccc24)c(Cl)c3=O)c1]
168
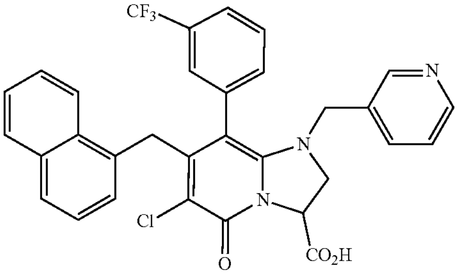 [SMILES: O=C(O)C1CN(Cc2cccnc2)c2c(-c3cccc(C(F)(F)F)c3)c(Cc3cccc4ccccc34)c(Cl)c(=O)n21]
169
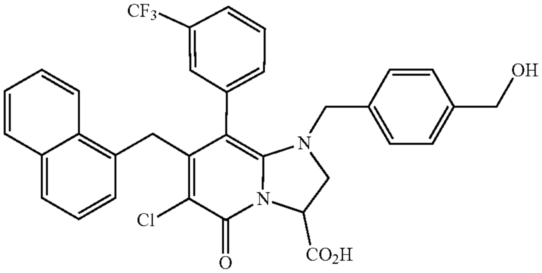 [SMILES: O=C(O)C1CN(Cc2ccc(CO)cc2)c2c(-c3cccc(C(F)(F)F)c3)c(Cc3cccc4ccccc34)c(Cl)c(=O)n21]
170

TABLE 1-continued
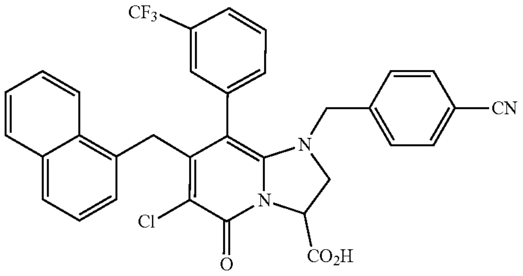 [SMILES: N#Cc1ccc(CN2CC(C(=O)O)n3c2c(-c2cccc(C(F)(F)F)c2)c(Cc2cccc4ccccc24)c(Cl)c3=O)cc1]
171
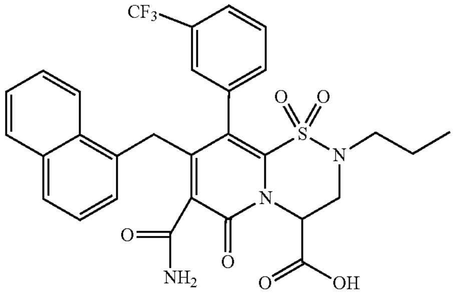 [SMILES: CCCN1CC(C(=O)O)n2c(c(-c3cccc(C(F)(F)F)c3)c(Cc3cccc4ccccc34)c(C(N)=O)c2=O)S1(=O)=O]
172
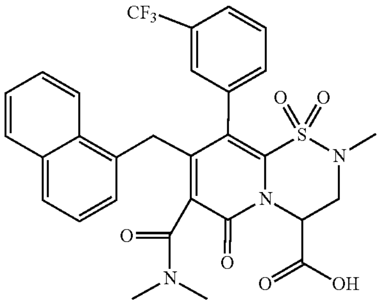 [SMILES: CN(C)C(=O)c1c(Cc2cccc3ccccc23)c(-c2cccc(C(F)(F)F)c2)c2n(c1=O)C(C(=O)O)CN(C)S2(=O)=O]
173
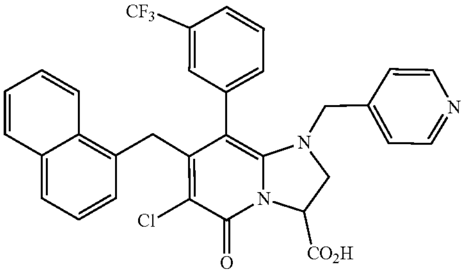 [SMILES: O=C(O)C1CN(Cc2ccncc2)c2c(-c3cccc(C(F)(F)F)c3)c(Cc3cccc4ccccc34)c(Cl)c(=O)n21]
174
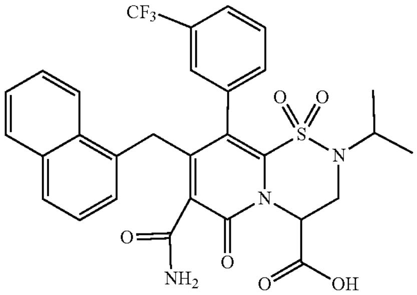 [SMILES: CC(C)N1CC(C(=O)O)n2c(c(-c3cccc(C(F)(F)F)c3)c(Cc3cccc4ccccc34)c(C(N)=O)c2=O)S1(=O)=O]
175

TABLE 1-continued
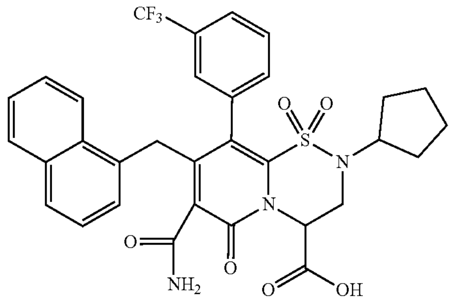 [SMILES: NC(=O)c1c(Cc2cccc3ccccc23)c(-c2cccc(C(F)(F)F)c2)c2n(c1=O)C(C(=O)O)CN(C1CCCC1)S2(=O)=O]
176
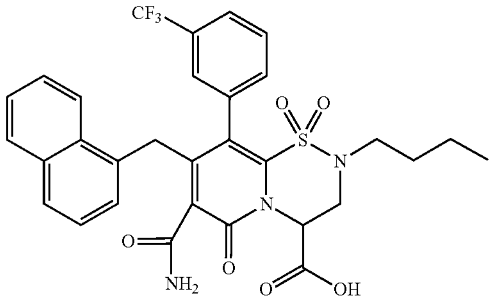 [SMILES: CCCCN1CC(C(=O)O)n2c(c(-c3cccc(C(F)(F)F)c3)c(Cc3cccc4ccccc34)c(C(N)=O)c2=O)S1(=O)=O]
177
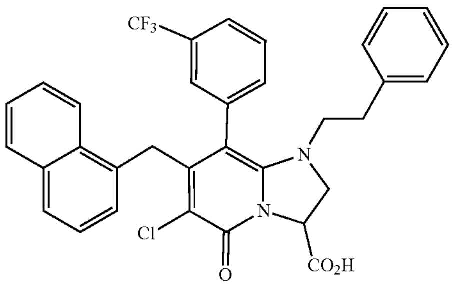 [SMILES: O=C(O)C1CN(CCc2ccccc2)c2c(-c3cccc(C(F)(F)F)c3)c(Cc3cccc4ccccc34)c(Cl)c(=O)n21]
178
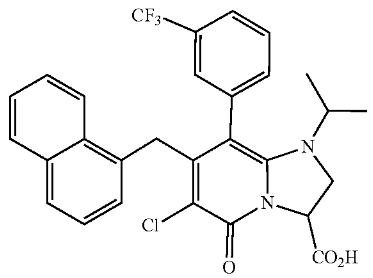 [SMILES: CC(C)N1CC(C(=O)O)n2c1c(-c1cccc(C(F)(F)F)c1)c(Cc1cccc3ccccc13)c(Cl)c2=O]
179
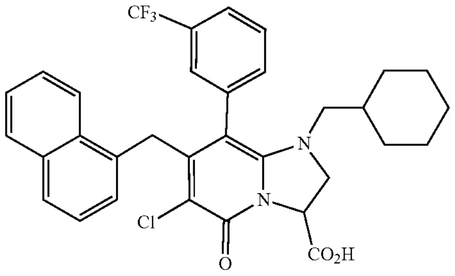 [SMILES: O=C(O)C1CN(CC2CCCCC2)c2c(-c3cccc(C(F)(F)F)c3)c(Cc3cccc4ccccc34)c(Cl)c(=O)n21]
180

TABLE 1-continued
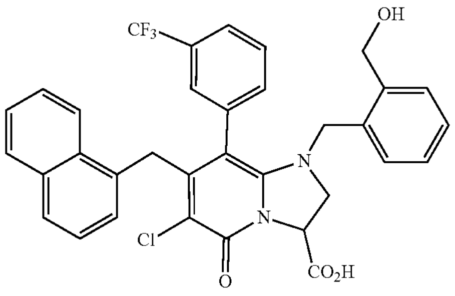 [SMILES: O=C(O)C1CN(Cc2ccccc2CO)c2c(-c3cccc(C(F)(F)F)c3)c(Cc3cccc4ccccc34)c(Cl)c(=O)n21]
181
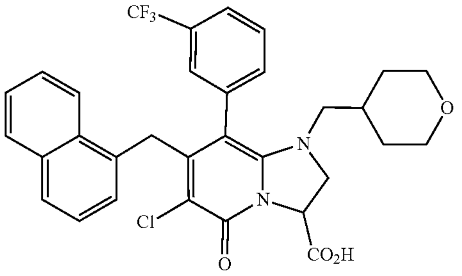 [SMILES: O=C(O)C1CN(CC2CCOCC2)c2c(-c3cccc(C(F)(F)F)c3)c(Cc3cccc4ccccc34)c(Cl)c(=O)n21]
182
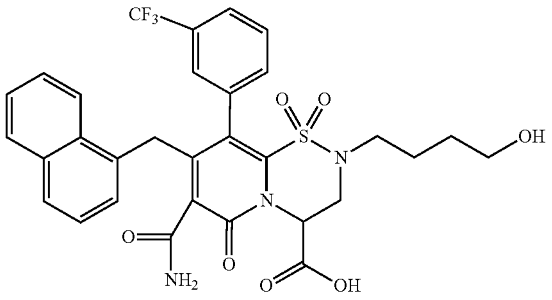 [SMILES: NC(=O)c1c(Cc2cccc3ccccc23)c(-c2cccc(C(F)(F)F)c2)c2n(c1=O)C(C(=O)O)CN(CCCCO)S2(=O)=O]
183
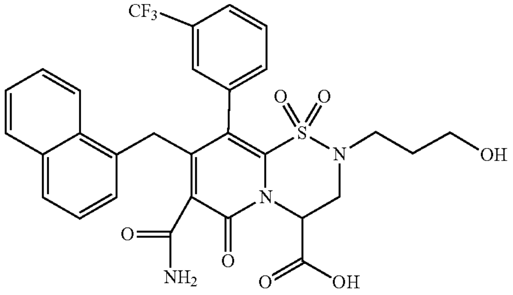 [SMILES: NC(=O)c1c(Cc2cccc3ccccc23)c(-c2cccc(C(F)(F)F)c2)c2n(c1=O)C(C(=O)O)CN(CCCO)S2(=O)=O]
184
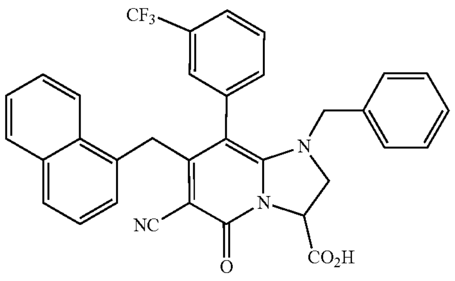
185

TABLE 1-continued
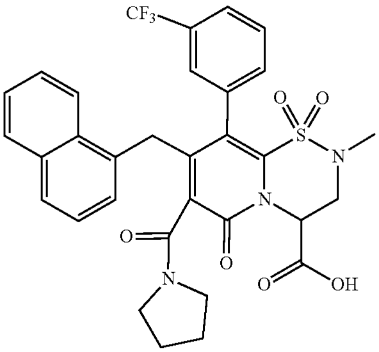 [SMILES: CN1CC(C(=O)O)n2c(c(-c3cccc(C(F)(F)F)c3)c(Cc3cccc4ccccc34)c(C(=O)N3CCCC3)c2=O)S1(=O)=O]
186
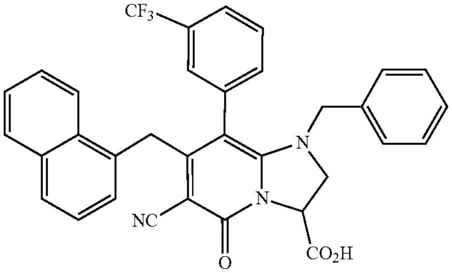 [SMILES: N#Cc1c(Cc2cccc3ccccc23)c(-c2cccc(C(F)(F)F)c2)c2n(c1=O)C(C(=O)O)CN2Cc1ccccc1]
187
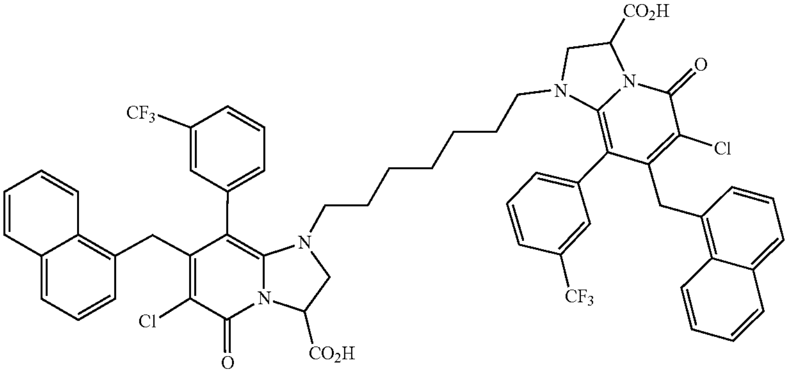 [SMILES: O=C(O)C1CN(CCCCCCCN2CC(C(=O)O)n3c2c(-c2cccc(C(F)(F)F)c2)c(Cc2cccc4ccccc24)c(Cl)c3=O)c2c(-c3cccc(C(F)(F)F)c3)c(Cc3cccc4ccccc34)c(Cl)c(=O)n21]
188
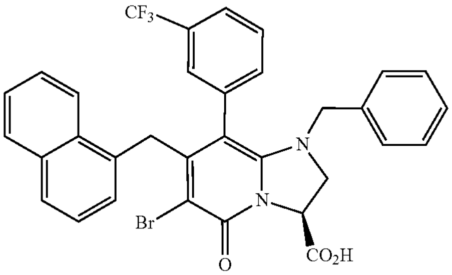 [SMILES: O=C(O)[C@@H]1CN(Cc2ccccc2)c2c(-c3cccc(C(F)(F)F)c3)c(Cc3cccc4ccccc34)c(Br)c(=O)n21]
189
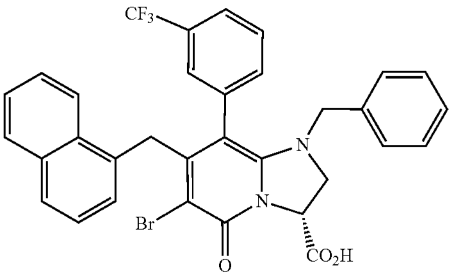 [SMILES: O=C(O)[C@H]1CN(Cc2ccccc2)c2c(-c3cccc(C(F)(F)F)c3)c(Cc3cccc4ccccc34)c(Br)c(=O)n21]
190

TABLE 1-continued
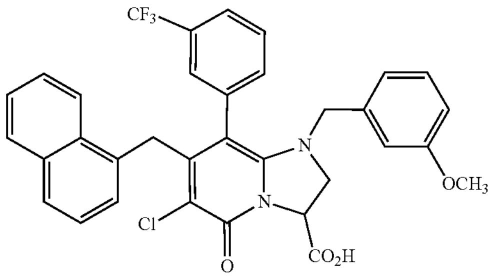 [SMILES: COc1cccc(CN2CC(C(=O)O)n3c2c(-c2cccc(C(F)(F)F)c2)c(Cc2cccc4ccccc24)c(Cl)c3=O)c1]
191
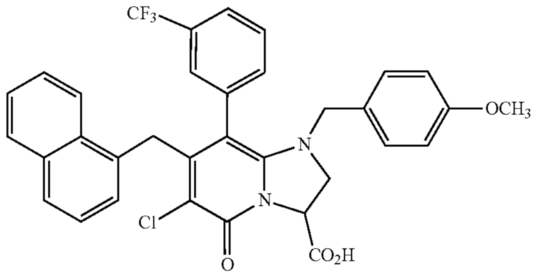 [SMILES: COc1ccc(CN2CC(C(=O)O)n3c2c(-c2cccc(C(F)(F)F)c2)c(Cc2cccc4ccccc24)c(Cl)c3=O)cc1]
192
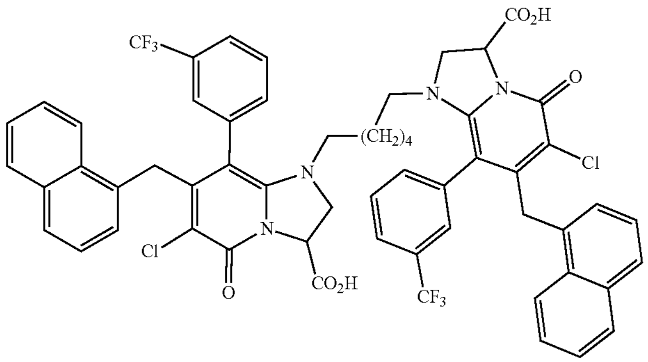
193
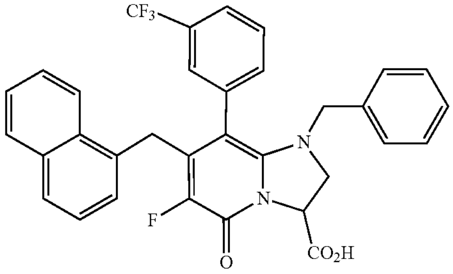 [SMILES: O=C(O)C1CN(Cc2ccccc2)c2c(-c3cccc(C(F)(F)F)c3)c(Cc3cccc4ccccc34)c(F)c(=O)n21]
194
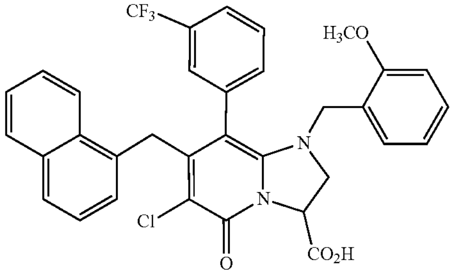 [SMILES: COc1ccccc1CN1CC(C(=O)O)n2c1c(-c1cccc(C(F)(F)F)c1)c(Cc1cccc3ccccc13)c(Cl)c2=O]
195

TABLE 1-continued
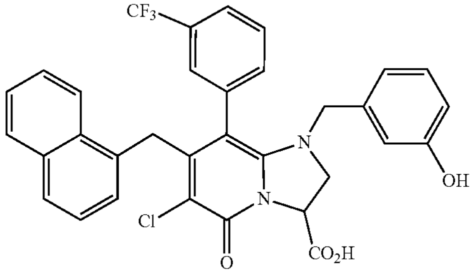 [SMILES: O=C(O)C1CN(Cc2cccc(O)c2)c2c(-c3cccc(C(F)(F)F)c3)c(Cc3cccc4ccccc34)c(Cl)c(=O)n21]
196
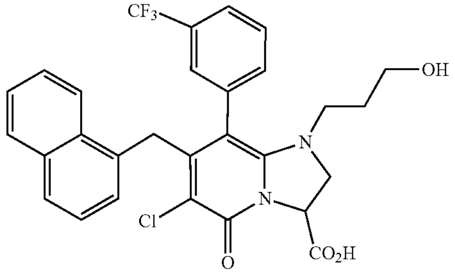 [SMILES: O=C(O)C1CN(CCCO)c2c(-c3cccc(C(F)(F)F)c3)c(Cc3cccc4ccccc34)c(Cl)c(=O)n21]
197
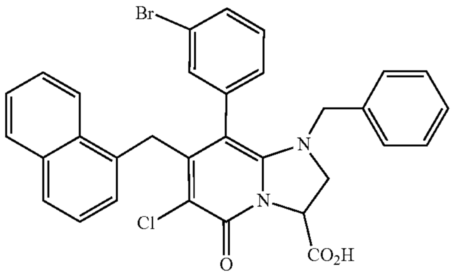 [SMILES: O=C(O)C1CN(Cc2ccccc2)c2c(-c3cccc(Br)c3)c(Cc3cccc4ccccc34)c(Cl)c(=O)n21]
198
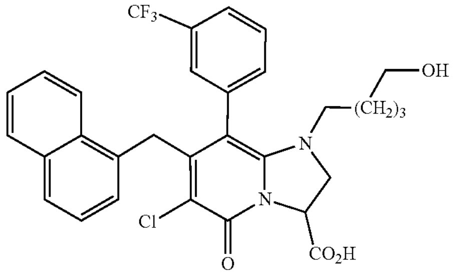
199
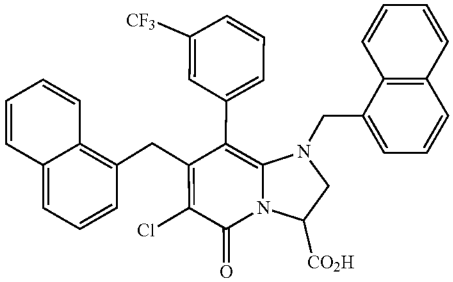 [SMILES: O=C(O)C1CN(Cc2cccc3ccccc23)c2c(-c3cccc(C(F)(F)F)c3)c(Cc3cccc4ccccc34)c(Cl)c(=O)n21]
200

TABLE 1-continued
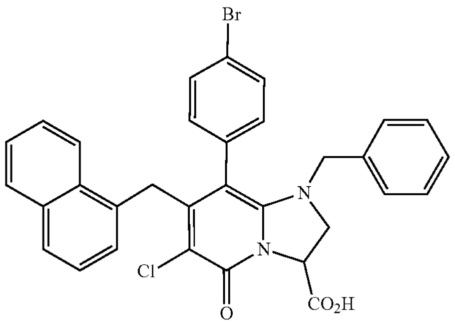 [SMILES: O=C(O)C1CN(Cc2ccccc2)c2c(-c3ccc(Br)cc3)c(Cc3cccc4ccccc34)c(Cl)c(=O)n21]
201
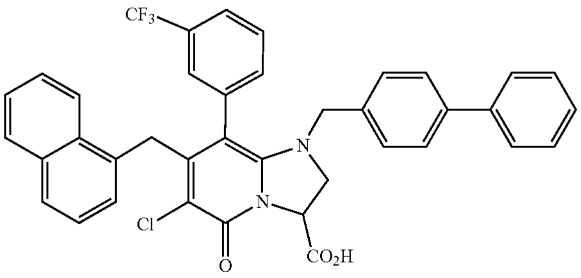 [SMILES: O=C(O)C1CN(Cc2ccc(-c3ccccc3)cc2)c2c(-c3cccc(C(F)(F)F)c3)c(Cc3cccc4ccccc34)c(Cl)c(=O)n21]
202
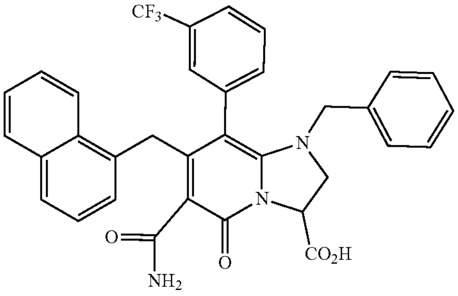 [SMILES: NC(=O)c1c(Cc2cccc3ccccc23)c(-c2cccc(C(F)(F)F)c2)c2n(c1=O)C(C(=O)O)CN2Cc1ccccc1]
203
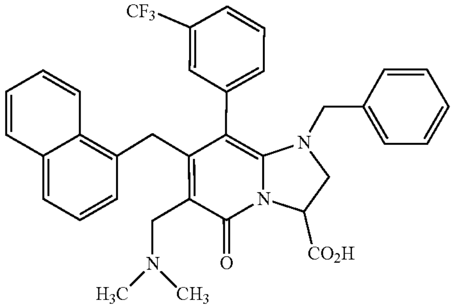 [SMILES: CN(C)Cc1c(Cc2cccc3ccccc23)c(-c2cccc(C(F)(F)F)c2)c2n(c1=O)C(C(=O)O)CN2Cc1ccccc1]
204
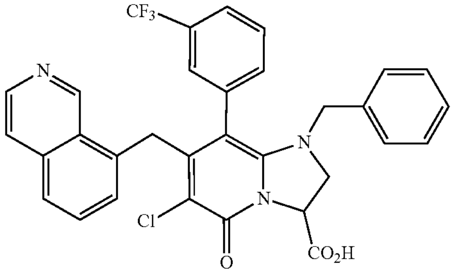 [SMILES: O=C(O)C1CN(Cc2ccccc2)c2c(-c3cccc(C(F)(F)F)c3)c(Cc3cccc4ccncc34)c(Cl)c(=O)n21]
205

TABLE 1-continued
206
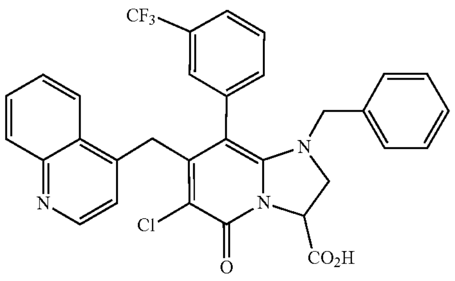 [SMILES: O=C(O)C1CN(Cc2ccccc2)c2c(-c3cccc(C(F)(F)F)c3)c(Cc3ccnc4ccccc34)c(Cl)c(=O)n21]
207
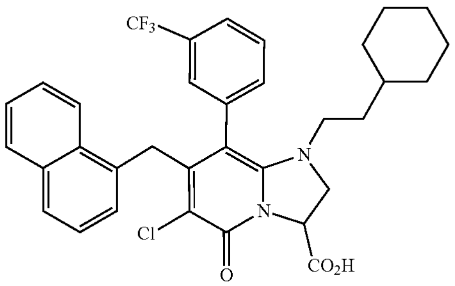 [SMILES: O=C(O)C1CN(CCC2CCCCC2)c2c(-c3cccc(C(F)(F)F)c3)c(Cc3cccc4ccccc34)c(Cl)c(=O)n21]
208
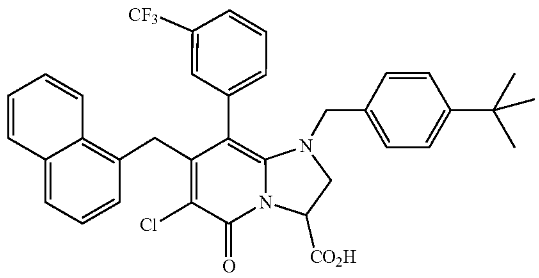 [SMILES: CC(C)(C)c1ccc(CN2CC(C(=O)O)n3c2c(-c2cccc(C(F)(F)F)c2)c(Cc2cccc4ccccc24)c(Cl)c3=O)cc1]
209
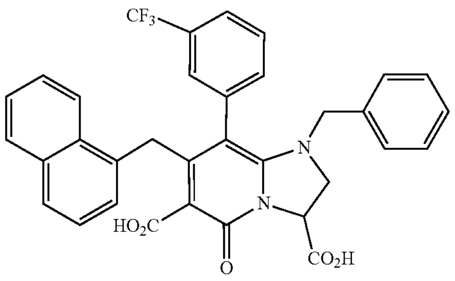 [SMILES: O=C(O)c1c(Cc2cccc3ccccc23)c(-c2cccc(C(F)(F)F)c2)c2n(c1=O)C(C(=O)O)CN2Cc1ccccc1]
210
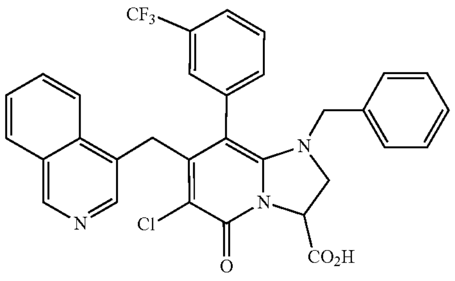 [SMILES: O=C(O)C1CN(Cc2ccccc2)c2c(-c3cccc(C(F)(F)F)c3)c(Cc3cncc4ccccc34)c(Cl)c(=O)n21]

TABLE 1-continued
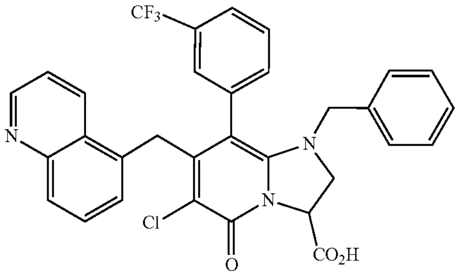 [SMILES: O=C(O)C1CN(Cc2ccccc2)c2c(-c3cccc(C(F)(F)F)c3)c(Cc3cccc4ncccc34)c(Cl)c(=O)n21]
211
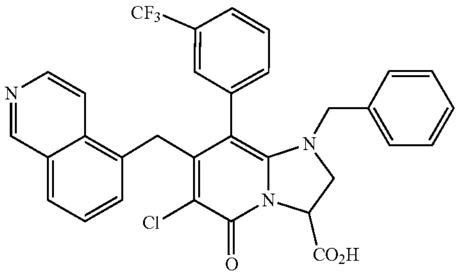 [SMILES: O=C(O)C1CN(Cc2ccccc2)c2c(-c3cccc(C(F)(F)F)c3)c(Cc3cccc4cnccc34)c(Cl)c(=O)n21]
212
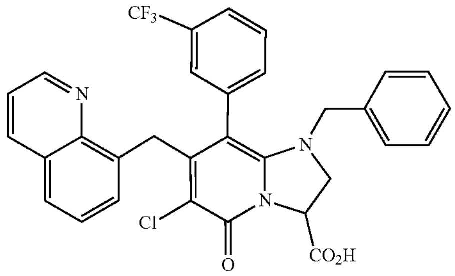 [SMILES: O=C(O)C1CN(Cc2ccccc2)c2c(-c3cccc(C(F)(F)F)c3)c(Cc3cccc4cccnc34)c(Cl)c(=O)n21]
213
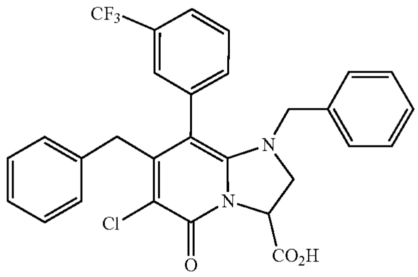 [SMILES: O=C(O)C1CN(Cc2ccccc2)c2c(-c3cccc(C(F)(F)F)c3)c(Cc3ccccc3)c(Cl)c(=O)n21]
214
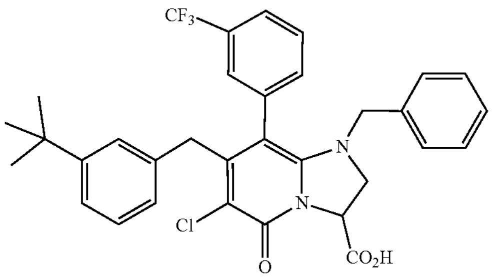 [SMILES: CC(C)(C)c1cccc(Cc2c(-c3cccc(C(F)(F)F)c3)c3n(c(=O)c2Cl)C(C(=O)O)CN3Cc2ccccc2)c1]
215

TABLE 1-continued
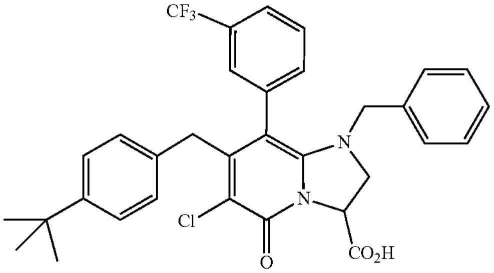 [SMILES: CC(C)(C)c1ccc(Cc2c(-c3cccc(C(F)(F)F)c3)c3n(c(=O)c2Cl)C(C(=O)O)CN3Cc2ccccc2)cc1]
216
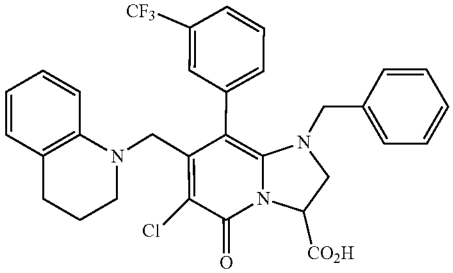 [SMILES: O=C(O)C1CN(Cc2ccccc2)c2c(-c3cccc(C(F)(F)F)c3)c(CN3CCCc4ccccc43)c(Cl)c(=O)n21]
217
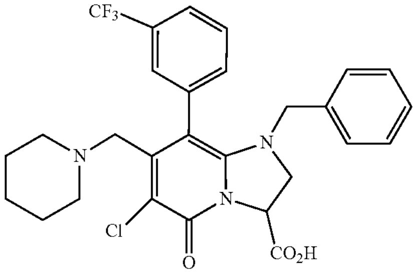 [SMILES: O=C(O)C1CN(Cc2ccccc2)c2c(-c3cccc(C(F)(F)F)c3)c(CN3CCCCC3)c(Cl)c(=O)n21]
218
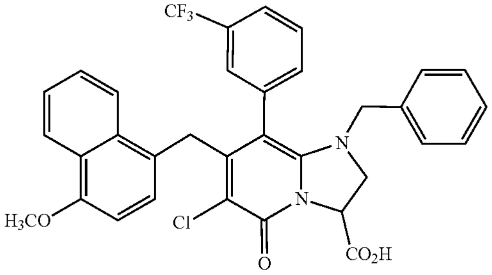 [SMILES: COc1ccc(Cc2c(-c3cccc(C(F)(F)F)c3)c3n(c(=O)c2Cl)C(C(=O)O)CN3Cc2ccccc2)c2ccccc12]
219
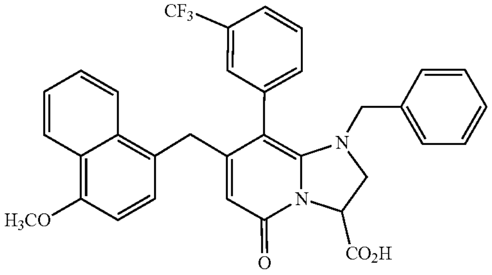 [SMILES: COc1ccc(Cc2cc(=O)n3c(c2-c2cccc(C(F)(F)F)c2)N(Cc2ccccc2)CC3C(=O)O)c2ccccc12]
220

TABLE 1-continued
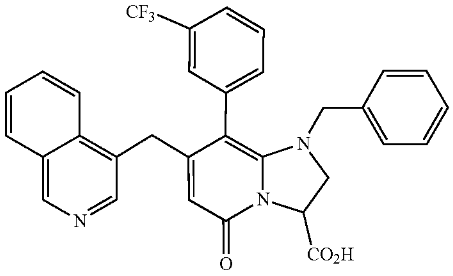 [SMILES: O=C(O)C1CN(Cc2ccccc2)c2c(-c3cccc(C(F)(F)F)c3)c(Cc3cncc4ccccc34)cc(=O)n21]
221
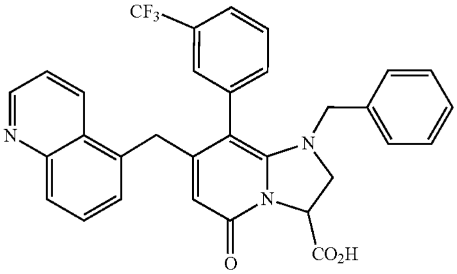 [SMILES: O=C(O)C1CN(Cc2ccccc2)c2c(-c3cccc(C(F)(F)F)c3)c(Cc3cccc4ncccc34)cc(=O)n21]
222
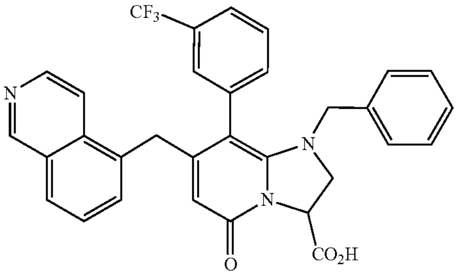 [SMILES: O=C(O)C1CN(Cc2ccccc2)c2c(-c3cccc(C(F)(F)F)c3)c(Cc3cccc4cnccc34)cc(=O)n21]
223
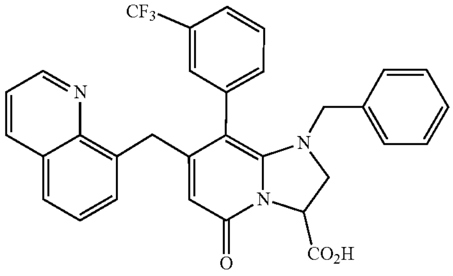 [SMILES: O=C(O)C1CN(Cc2ccccc2)c2c(-c3cccc(C(F)(F)F)c3)c(Cc3cccc4cccnc34)cc(=O)n21]
224
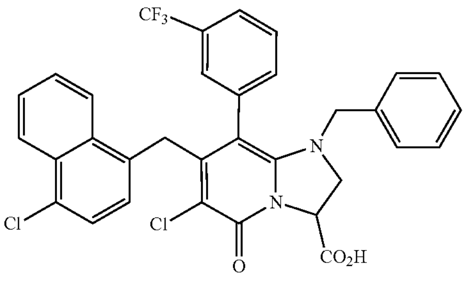 [SMILES: O=C(O)C1CN(Cc2ccccc2)c2c(-c3cccc(C(F)(F)F)c3)c(Cc3ccc(Cl)c4ccccc34)c(Cl)c(=O)n21]
225

TABLE 1-continued
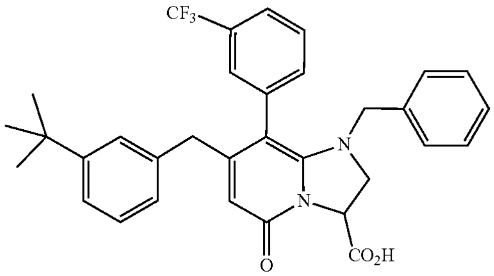 [SMILES: CC(C)(C)c1cccc(Cc2cc(=O)n3c(c2-c2cccc(C(F)(F)F)c2)N(Cc2ccccc2)CC3C(=O)O)c1]
226
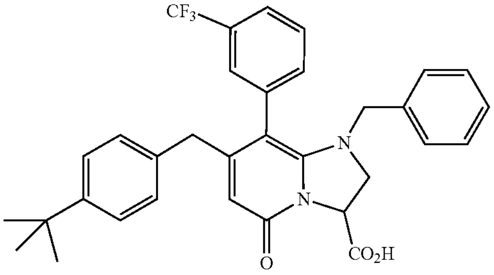 [SMILES: CC(C)(C)c1ccc(Cc2cc(=O)n3c(c2-c2cccc(C(F)(F)F)c2)N(Cc2ccccc2)CC3C(=O)O)cc1]
227
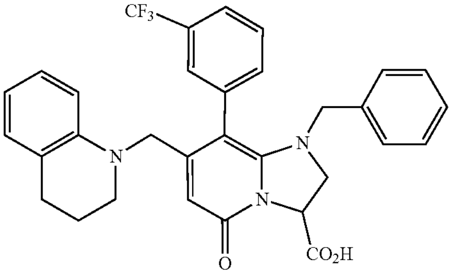 [SMILES: O=C(O)C1CN(Cc2ccccc2)c2c(-c3cccc(C(F)(F)F)c3)c(CN3CCCc4ccccc43)cc(=O)n21]
228
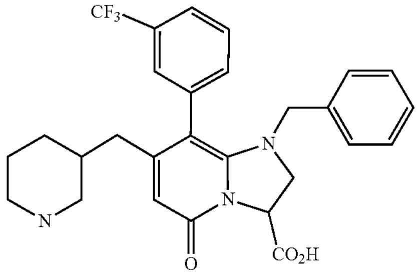 [SMILES: O=C(O)C1CN(Cc2ccccc2)c2c(-c3cccc(C(F)(F)F)c3)c(CC3CCCNC3)cc(=O)n21]
229
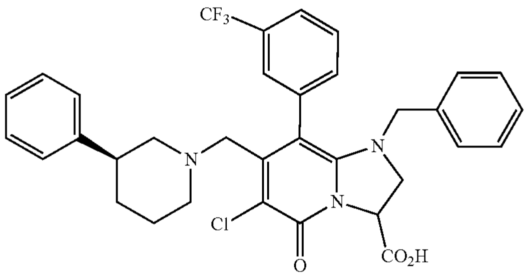 [SMILES: O=C(O)C1CN(Cc2ccccc2)c2c(-c3cccc(C(F)(F)F)c3)c(CN3CCC[C@@H](c4ccccc4)C3)c(Cl)c(=O)n21]
230

TABLE 1-continued
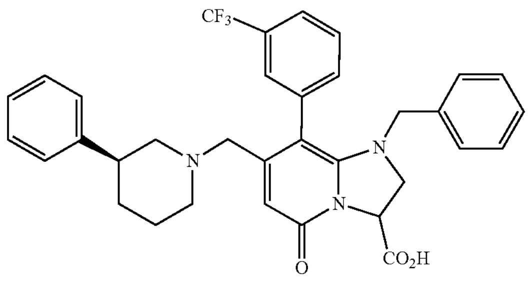 [SMILES: O=C(O)C1CN(Cc2ccccc2)c2c(-c3cccc(C(F)(F)F)c3)c(CN3CCC[C@@H](c4ccccc4)C3)cc(=O)n21]
231
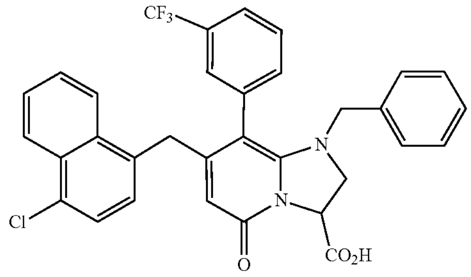 [SMILES: O=C(O)C1CN(Cc2ccccc2)c2c(-c3cccc(C(F)(F)F)c3)c(Cc3ccc(Cl)c4ccccc34)cc(=O)n21]
232
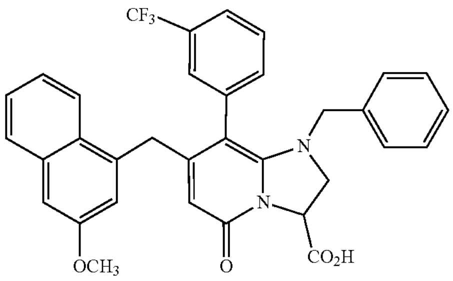 [SMILES: COc1cc(Cc2cc(=O)n3c(c2-c2cccc(C(F)(F)F)c2)N(Cc2ccccc2)CC3C(=O)O)c2ccccc2c1]
233
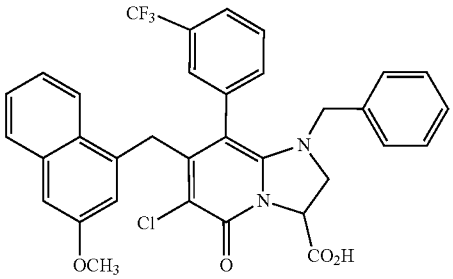
234
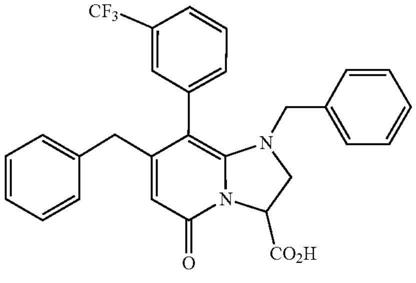 [SMILES: O=C(O)C1CN(Cc2ccccc2)c2c(-c3cccc(C(F)(F)F)c3)c(Cc3ccccc3)cc(=O)n21]
235

TABLE 1-continued
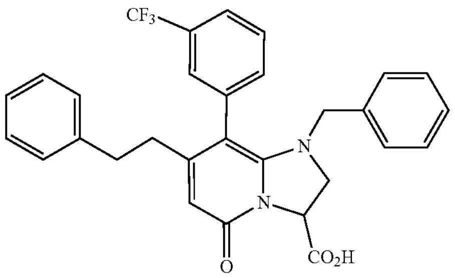 [SMILES: O=C(O)C1CN(Cc2ccccc2)c2c(-c3cccc(C(F)(F)F)c3)c(CCc3ccccc3)cc(=O)n21]
236
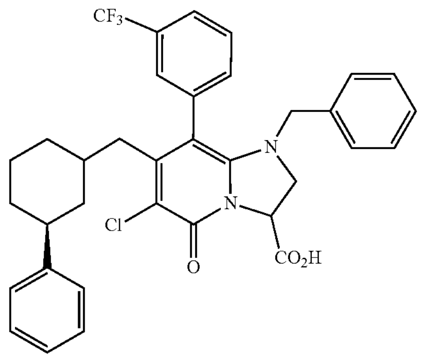 [SMILES: O=C(O)C1CN(Cc2ccccc2)c2c(-c3cccc(C(F)(F)F)c3)c(CC3CCC[C@H](c4ccccc4)C3)c(Cl)c(=O)n21]
237
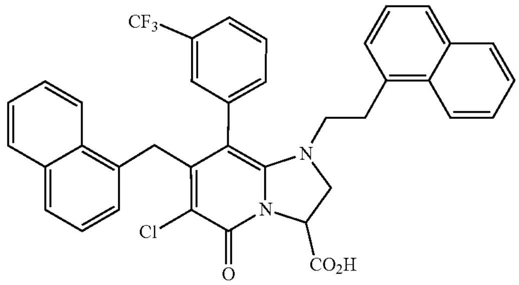 [SMILES: O=C(O)C1CN(CCc2cccc3ccccc23)c2c(-c3cccc(C(F)(F)F)c3)c(Cc3cccc4ccccc34)c(Cl)c(=O)n21]
238
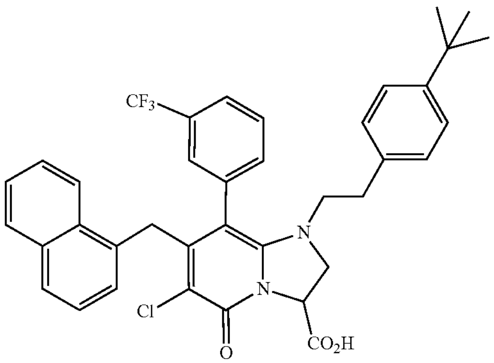 [SMILES: CC(C)(C)c1ccc(CCN2CC(C(=O)O)n3c2c(-c2cccc(C(F)(F)F)c2)c(Cc2cccc4ccccc24)c(Cl)c3=O)cc1]
239
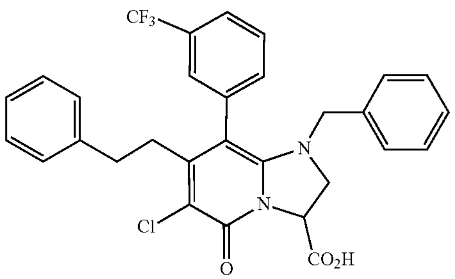 [SMILES: O=C(O)C1CN(Cc2ccccc2)c2c(-c3cccc(C(F)(F)F)c3)c(CCc3ccccc3)c(Cl)c(=O)n21]
240

In a particular embodiment, the compound of Formula (I) is selected from compounds 001, 003, 004, 004a, 004b, 070, 094, 108, 109, 116, 122, 140, and pharmaceutically acceptable salts thereof.

The compounds described above, and pharmaceutically acceptable salts thereof, may be referred to collectively as compounds of the invention.

The following compounds are referenced herein:

008

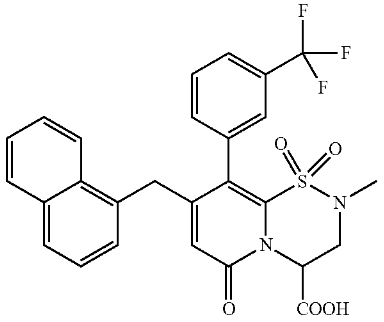

009

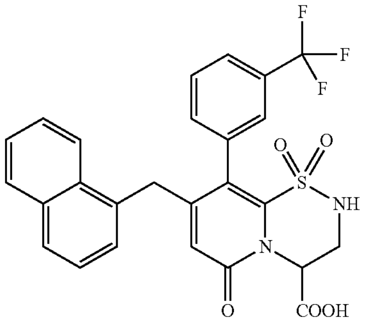

010

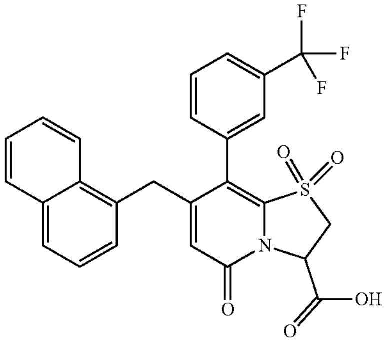

011

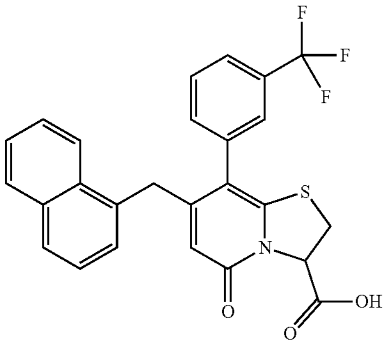

-continued

020

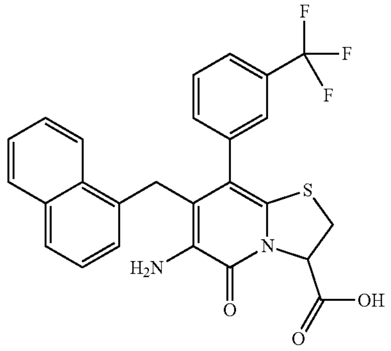

020a

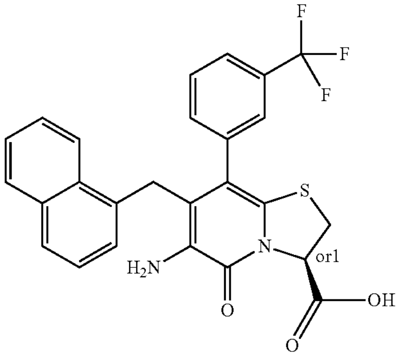

020b

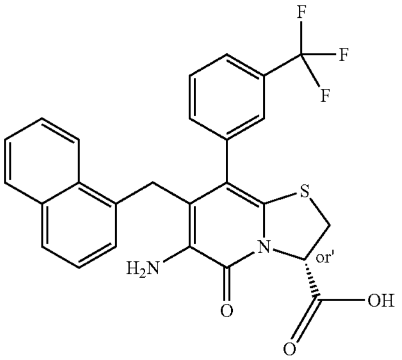

The term "alkyl" refers to a radical of a straight-chain or branched saturated hydrocarbon group having from 1 to 20 carbon atoms ("$C_{1-20}$ alkyl") In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu or s-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$ or benzyl (Bn)). An alkyl group may be branched or unbranched.

The term "alkenyl" refers to a radical of a straight-chain or branched hydrocarbon group having from 1 to 20 carbon atoms and one or more carbon-carbon double bonds (e.g., 1, 2, 3, or 4 double bonds). In some embodiments, an alkenyl group has 1 to 20 carbon atoms ("$C_{1-20}$ alkenyl"). In some embodiments, an alkenyl group has 1 to 12 carbon atoms ("$C_{1-12}$ alkenyl"). In some embodiments, an alkenyl group has 1 to 11 carbon atoms ("$C_{1-11}$ alkenyl"). In some embodiments, an alkenyl group has 1 to 10 carbon atoms ("$C_{1-10}$ alkenyl"). In some embodiments, an alkenyl group has 1 to 9 carbon atoms ("$C_{1-9}$ alkenyl"). In some embodiments, an alkenyl group has 1 to 8 carbon atoms ("$C_{1-8}$ alkenyl"). In some embodiments, an alkenyl group has 1 to 7 carbon atoms ("$C_{1-7}$ alkenyl"). In some embodiments, an alkenyl group has 1 to 6 carbon atoms ("$C_{1-6}$ alkenyl"). In some embodiments, an alkenyl group has 1 to 5 carbon atoms ("$C_{1-5}$ alkenyl"). In some embodiments, an alkenyl group has 1 to 4 carbon atoms ("$C_{1-4}$ alkenyl"). In some embodiments, an alkenyl group has 1 to 3 carbon atoms ("$C_{1-3}$ alkenyl"). In some embodiments, an alkenyl group has 1 to 2 carbon atoms ("$C_{1-2}$ alkenyl"). In some embodiments, an alkenyl group has 1 carbon atom ("$C_1$ alkenyl"). The one or more carbon-carbon double bonds can be internal (such as in 2-butenyl) or terminal (such as in 1-butenyl). Examples of $C_{1-4}$ alkenyl groups include methylidenyl ($C_1$), ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{1-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{1-20}$ alkenyl. In certain embodiments, the alkenyl group is a substituted $C_{1-20}$ alkenyl. In an alkenyl group, a C═C double bond for which the stereochemistry is not specified (e.g., —CH═$CHCH_3$ or

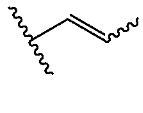
)

may be in the (E)- or (Z)-configuration.

The term "cycloalkyl" refers to cyclic alkyl radical having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_5$_cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_5$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

The term "acyl" refers to a group having the general formula —C(═O)$R^{X1}$, —C(═O)O$R^{X1}$, —C(═O)—O—C(═O)$R^{X1}$, —C(═O)S$R^{X1}$, —C(═O)N($R^{X1}$)$_2$, —C(═S)$R^{X1}$, —C(═S)N($R^{X1}$)$_2$, and —C(═S)S($R^{X1}$), —C(═N$R^{X1}$)$R^{X1}$, —C(═N$R^{X1}$)O$R^{X1}$, —C(═N$R^{X1}$)S$R^{X1}$, and —C(═N$R^{X1}$)N($R^{X1}$)$_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "sulfonyl" refers to a group selected from —$SO_2N(R^{bb})_2$, —$SO_2R^{aa}$, and —$SO_2OR^{aa}$, wherein $R^{aa}$ and $R^{bb}$ are as defined herein.

The term "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents (e.g., —F, —OH or —O($C_{1-6}$ alkyl). In certain embodiments, the aryl group is an unsubstituted $C_{6-14}$ aryl. In certain embodiments, the aryl group is a substituted $C_{6-14}$ aryl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl. In certain embodiments, the heterocyclyl is substituted or unsubstituted, 3- to 7-membered, monocyclic heterocyclyl, wherein 1, 2, or 3 atoms in the heterocyclic ring system are independently oxygen, nitrogen, or sulfur, as valency permits.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include azirdinyl, oxiranyl, and thiiranyl. Exemplary 4-membered heterocyclyl groups containing 1 heteroatom include azetidinyl, oxetanyl, and thietanyl. Exemplary 5-membered heterocyclyl groups containing 1 heteroatom include tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include dioxolanyl, oxathiolanyl and dithiolanyl. Exemplary 5-membered heterocyclyl groups containing 3 heteroatoms include triazolinyl, oxadiazolinyl, and thiadiazolinyl. Exemplary 6-membered heterocyclyl groups containing 1 heteroatom include piperidinyl, tetrahydropyranyl, dihydropyridinyl, and thianyl. Exemplary 6-membered heterocyclyl groups containing 2 heteroatoms include piperazinyl, morpholinyl, dithianyl, and dioxanyl. Exemplary 6-membered heterocyclyl groups containing 3 heteroatoms include triazinyl. Exemplary 7-membered heterocyclyl groups containing 1 heteroatom include azepanyl, oxepanyl and thiepanyl. Exemplary 8-membered heterocyclyl groups containing 1 heteroatom include azocanyl, oxecanyl and thiocanyl. Exemplary bicyclic heterocyclyl groups include indolinyl, isoindolinyl, dihydrobenzofuranyl, dihydrobenzothienyl, tetrahydro-benzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetra-hydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydro-thieno[3,2-b]pyridinyl, 1,2,3,4-tetrahydro-1,6-naphthyridinyl, and the like.

The term "heteroaryl" refers to a radical of a 5-14 membered monocyclic or polycyclic (e.g., bicyclic, tricyclic) 4n+2 aromatic ring system (e.g., having 6, 10, or 14 $\pi$ electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, e.g., either the ring bearing a heteroatom (e.g., 2-indolyl) or the ring that does not contain a heteroatom (e.g., 5-indolyl). In certain embodiments, the heteroaryl is substituted or unsubstituted, 5- or 6-membered, monocyclic heteroaryl, wherein 1, 2, 3, or 4 atoms in the heteroaryl ring system are independently oxygen, nitrogen, or sulfur. In certain embodiments, the heteroaryl is substituted or unsubstituted, 9- or 10-membered, bicyclic heteroaryl, wherein 1, 2, 3, or 4 atoms in the heteroaryl ring system are independently oxygen, nitrogen, or sulfur.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include pyrrolyl, furanyl, and thiophenyl. Exemplary 5-membered heteroaryl groups containing 2 heteroatoms include imidazolyl, pyrazolyl, oxazolyl, isoxazolyl, thiazolyl, and isothiazolyl. Exemplary 5-membered heteroaryl groups containing 3 heteroatoms include triazolyl, oxadiazolyl, and thiadiazolyl. Exemplary 5-membered heteroaryl groups containing 4 heteroatoms include tetrazolyl. Exemplary 6-membered heteroaryl groups containing 1 heteroatom include pyridinyl. Exemplary 6-membered heteroaryl groups containing 2 heteroatoms include pyridazinyl, pyrimidinyl, and pyrazinyl. Exemplary 6-membered heteroaryl groups containing 3 or 4 heteroatoms include triazinyl and tetrazinyl, respectively. Exemplary 7-membered heteroaryl groups containing 1 heteroatom include azepinyl, oxepinyl, and thiepinyl. Exemplary 5,6-bicyclic heteroaryl groups include indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include naphthyridinyl, pteridinyl, quinolinyl, isoquinolinyl, cinnolinyl, quinoxalinyl, phthalazinyl, and quinazolinyl. Exemplary tricyclic heteroaryl groups include phenanthridinyl, dibenzofuranyl, carbazolyl, acridinyl, phenothiazinyl, phenoxazinyl, and phenazinyl.

As used herein in reference to the stereochemistry, term "arbitrary" indicates that the relative or absolute stereochemistry of a compound was not determined.

The terms "decrease", "reduced", "reduction", "inhibit" or "disrupt" are all used herein to mean a decrease by a statistically significant amount. In some embodiments, "reduce," "reduction", "decrease", "inhibit" or "disrupt" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

Therapeutic Methods

Amyloids are produced in the gastrointestinal tract by members of the gastrointestinal microbiota, such as *E. coli* and some other Proteobacteria. These microbial amyloids may interact with cells with which they are in contact in the gastrointestinal tract and affect α-synuclein expression and/or α-synuclein aggregation. The STC-1 cell line was derived from tumors of the mouse small intestine and possesses many features of native gastrointestinal enteroendocrine cells (McCarthy et al. (2015), STC-1 Cells. In: Verhoeckx K. et al. (eds) The Impact of Food Bioactives on Health. Springer, Cham.). In an in vitro assay wherein α-synuclein expression by STC-1 cells was determined by Western blot, exposure to an *E. coli* strain expressing wild-type CsgA resulted in a notable increase in α-synuclein expression, while exposure to an isogenic mutant in which csgA was deleted had little effect on α-synuclein levels (See, e.g., WO2019/028456, and references cited therein). Thus, while the exact mechanisms by which CsgA affected α-synuclein expression are unclear, CsgA can interact with enteroendocrine-like cells of the gastrointestinal tract and cause α-synuclein over-expression in vitro, suggesting that similar effects may take place in vivo when pathogenic microbial amyloids contact enteroendocrine cells or other cells in the gastrointestinal tract. While mouse α-synuclein is generally not observed to aggregate, over-expression of human α-synuclein may lead to aggregation that in turn impairs cell function, propagates in a prion-like fashion to adjacent cells in the gastrointestinal tract and enteric nervous system, and has detrimental effects on gastrointestinal function. These negative effects can include one or more of intestinal dysbiosis, intestinal hyperpermeability, irritable bowel syndrome (IBS), inflammatory bowel disease (IBD), ulcerative colitis and/or Crohn's disease. These disorders can be associated with one or more symptoms, including dysphagia, reduced gut motility, gastroparesis, constipation (including chronic constipation and chronic idiopathic constipation), small intestinal bacterial overgrowth (SIBO), diarrhea (including chronic diarrhea), abdominal pain and/or cramping, bloating, flatulence, and nausea. In some cases, neurological and gastrointestinal symptoms of amyloid disorders can be linked. For example, in Parkinson's Disease and Parkinsonism (a clinical syndrome characterized by tremor, bradykinesia, rigidity, and postural instability) decreased levels of dopamine can lead to the neurological symptom of dyskinesia and the gastrointestinal symptom of chronic idiopathic constipation. Thus, treatments which improve gut motility, including the methods of the invention, can improve dopamine absorption in the gut and, thereby, reduce dyskinesia. Therefore, treatments that manage constipation (or, more generally, intestinal dysbiosis or intestinal hyperpermeability) can slow the progression of motor symptoms of Parkinson's Disease as well as increasing "on-time" periods of adequate control of Parkinson's Disease symptoms.

Consistent with the ability of STC-1 cells to respond to *E. coli* CsgA in vitro, gastrointestinal cells have been observed to sense and respond to microbial amyloids. For example, *Salmonella enterica* CsgA has been shown to modulate gastrointestinal permeability in mice via activation of the $TLR^2$/PI3K pathway. Additionally, U.S. Pat. No. 9,814,756 discloses a method for modulating gastrointestinal permeability via administration of variants of CsgA and/or CsgB. U.S. Pat. No. 9,814,756 discloses the decreasing permeability of epithelium of the small intestine or large intestine by administering a composition comprising, inter alia, an isolated curli fibril having epithelium permeability-reducing activity such as (i) a CsgA polypeptide variant which differs from a naturally occurring CsgA polypeptide in that from 1 to 5 amino acids have been substituted, deleted or added; (ii) a CsgB polypeptide variant which differs from a naturally occurring CsgB polypeptide in that from 1 to 5 amino acids have been substituted, deleted or added; or (iii) a combination of said CsgA polypeptide variant and said CsgB polypeptide variant. Thus, while there may be additional mechanisms by which microbial amyloids interact with gastrointestinal cells, at least one such mechanism is contemplated herein.

In one aspect, provided herein is a method of inhibiting amyloid formation in a subject in need thereof, comprising administering to the subject a compound as described herein, or a pharmaceutically acceptable salt thereof, or a pharmaceutical composition thereof.

In another aspect, provided herein is a method of inhibiting, ameliorating, reducing the likelihood, delaying the onset of, treating, and/or preventing an amyloid disorder in a subject in need thereof, comprising administering to the subject a compound as described herein (e.g., a compound of Formula (I), or a compound of Table 1) or a pharmaceutically acceptable salt thereof. Such amyloid disorders include neurological disorders, as well as Parkinson's disease (PD), Lewy body dementia, multiple system atrophy, multiple sclerosis (MS), frontotemporal dementia (FTD), REM sleep behavior disorders (RBD), α-synucleinopathy, PD-associated constipation, PD-associated hyposmia, Huntington's Disease, Alexander's Disease, amyotrophic lateral sclerosis (ALS), or Alzheimer's Disease and/or other diseases in which amyloids are implicated. In some embodiments, the amyloid disorder is intestinal dysbiosis, intestinal hyperpermeability, irritable bowel syndrome (IBS), inflammatory bowel disease (IBD), ulcerative colitis or Crohn's disease.

In another aspect, provided herein is a method for preventing or treating an inflammatory disorder in a subject in need thereof, comprising administering to the subject a compound as described herein, or a pharmaceutically acceptable salt thereof, or a pharmaceutical composition thereof. In some embodiments, the inflammatory disorder is selected from bacterial sepsis, autoimmune disease, lupus erythematosus, ischemia-reperfusion injury, stroke, metabolic disease, obesity-related metabolic inflammation, gout, and cancer. In some embodiments, the inflammatory disorder is lupus erythematosus.

For persons having lupus erythematosus, e.g., systemic lupus erythematosus (SLE), infection is a common environmental trigger for flares (20-55%) and is associated with increased morbidity/mortality. Recombinant curli-DNA complexes from *Salmonella typhimurium* act as powerful immune stimulators by activating innate/adaptive immunity and triggering autoantibody formation and activate dendritic cells in vitro and also in vivo in lupus prone mice. For example, i.p. administration of recombinant curli-DNA complex (50 ug 1× or 3× per week) in lupus prone mice results in formation of dsDNA and chromatin antibodies, indicators of SLE initiation. Infection with curli-producing bacteria (*E. coli* or *S. typhimurium*) also accelerates autoimmunity in lupus prone mice in vivo. See, e.g., Gallo, P. M., et al. Immunity, 2015, 42, 1171-1184. These observations suggest that inhibitors of bacterial curli formation should prevent or inhibit the activation of auto-immunity, and as such represent a treatment modality for SLE.

For persons having multiple sclerosis (MS), focal lymphocytic infiltration has been found to lead to damage of myelin and axons, and is associated with gut microbiome dysbiosis. For example, levels of Akkermansia muciniphila and *Acinetobacter calcoaceticus* are elevated, and levels of Parabacteroides *distasonis* are reduced in persons having MS. See, e.g., Cekanaviciute, E. et al. Proc. Nat. Acad. Sci., 114, 10713-10718. Moreover, levels of *Pseudomonas, Mycoplana, Haemophilus, Blautia*, and *Dorea* are elevated, and levels of Parabacteroides, Adlercreutzia and *Prevotella* genera are reduced in persons having MS. See, e.g., Chen, J. et al. Nature Sci. Rep., 2016, 6:28484. See also, Liu, J. Q. et al. J Exp Neuropath. Exp. Neurol. 2009, 68, 179; and Papadopoulos D. et al. Mol. Cell Neurosci. 2006, 31, 597.

Synucleinopathy has been observed in brains of deceased MS patients, as well as in Experimental Autoimmune Encephalomyelitis (EAE) rat models. Transplantation of patient-derived microbiota (vs healthy controls) in EAE models was found to drive disease severity. These observations suggest that inhibitors of bacterial curli formation represent a treatment modality for MS.

In some embodiments, the subject is selected as in need of the composition by detecting a presence and/or level of aggregates in an intestinal sample of the subject, such as a fecal sample. A presence or level of intestinal aggregates greater than a negative control (for example, fecal sample of a healthy control subject, or control subject known not to have an amyloid disorder) can indicate that the subject is in need of the composition. In some embodiments, the subject is selected as in need of the composition by detecting a presence and/or level of aggregates in an intestinal sample of the subject in combination with other factors, such as genetic susceptibility.

In some embodiments, detecting the presence and/or level of intestinal aggregates in a sample of the subject comprises detecting a presence and/or level of a bacterial protein in the sample, for example a curli-associated protein, such as CsgA. In some embodiments, detecting the presence and/or level of intestinal aggregates in a sample of the subject comprises detecting a level of a bacteria that produces an amyloid in the sample, for example a curli-associated protein, such as CsgA. For example, a bacterial amyloid can be detected directly, or a nucleic acid encoding the amyloid can be detected in the sample, thus indicating a presence of amyloid-producing bacteria in the subject's gastrointestinal tract. Examples of amyloid-producing bacteria can include CsgA-producing Enterobacteraceae such as *E. coli.*

Compounds of Formula (I), and pharmaceutically acceptable salts thereof, may be administered in the form of a composition. In some embodiments, the composition comprises or consists essentially of one or more compounds selected from the group consisting of the compounds identified by a compound activity range of "++++" in any column of Table 3 or Table 4 (infra). In some embodiments, the composition comprises or consists essentially of one or more compounds selected from the group consisting of the compounds identified by a compound activity range of "+++" in any column of Table 3 or Table 4. In some embodiments, the composition comprises or consists essentially of one or more compounds selected from the group consisting of the compounds identified by a compound activity range of "+++" or "++++" in any column of Table 3 or Table 4. In some embodiments, the composition comprises or consists essentially of one or more compounds selected from the group consisting of the compounds identified by a compound activity range of "++" or "+++" in any column of Table 3 or Table 4. In some embodiments, the composition comprises or consists essentially of one or more compounds selected from the group consisting of the set of compounds identified by a compound activity range of "++", "+++", or "++++" in any column of Table 3 or Table 4. In some embodiments, the composition comprises or consists essentially of one or more compounds selected from the group consisting of the set of compounds identified by a compound activity range of "+", "++," "+++" or "++++" in any column of Table 3 or Table 4. In some embodiments, the composition comprises or consists essentially of one or more compounds selected from the group consisting of the compounds identified by a compound activity range of "+++" in the "αSyn ThT Assay" column of Table 3 or Table 4. In some embodiments, the composition comprises or consists essentially of one or more compounds selected from the group consisting of the set of compounds identified by a compound activity range of "++" or "+++" in the "αSyn ThT Assay" column of Table 4. In some embodiments, the composition comprises or consists essentially of one or more compounds selected from the group consisting of the set of compounds identified by a compound activity range of "+", "++," or "+++" in the "αSyn ThT Assay" column of Table 3 or Table 4. In some embodiments, the composition comprises or consists essentially of one or more compounds selected from the group consisting of the compounds identified by a compound activity range of "++++" in the "CsgA ThT Assay" column of Table 3 or Table 4. In some embodiments, the composition comprises or consists essentially of one or more compounds selected from the group consisting of the compounds identified by a compound activity range of "+++" in the "CsgA ThT Assay" column of Table 3 or Table 4. In some embodiments, the composition comprises or consists essentially of one or more compounds selected from the group consisting of the set of compounds identified by a compound activity range of "+++" or "++++" in the "CsgA ThT Assay" column of Table 3 or Table 4. In some embodiments, the composition comprises or consists essentially of one or more compounds selected from the group consisting of the set of compounds identified by a compound activity range of "++", "+++" or "++++" in the "CsgA ThT Assay" column of Table 3 or Table 4. In some embodiments, the composition comprises or consists essentially of one or more compounds selected from the group consisting of the set of compounds identified by a compound activity range of "+", "++", "+++" or "++++" in the "CsgA ThT Assay" column of Table 3 or Table 4.

Compounds of Formula (I), and pharmaceutically acceptable salts thereof, may be administered in the form of a composition. In some embodiments, the composition comprises or consists essentially of one or more compounds selected from the group consisting of the compounds identified by a compound activity range of "**" in any column of Table 3 or Table 4 (infra). In some embodiments, the composition comprises or consists essentially of one or more compounds selected from the group consisting of the compounds identified by a compound activity range of "*" in any column of Table 3 or Table 4. In some embodiments, the composition comprises or consists essentially of one or more compounds selected from the group consisting of the compounds identified by a compound activity range of "*" or "" in any column of Table 3 or Table 4. In some embodiments, the composition comprises or consists essentially of one or more compounds selected from the group consisting of the compounds identified by a compound activity range of "" or "*" in any column of Table 3 or Table 4. In some embodiments, the composition comprises or consists essentially of one or more compounds selected from the group consisting of the set of compounds identified by a compound activity range of "", "*", or "**" in any column of Table 3 or Table 4. In some embodiments, the composition comprises or consists essentially of one or more compounds selected from the group consisting of the set of compounds identified by a compound activity range of "*", "", "*" or "**" in any column of Table 3 or Table 4. In some embodiments, the composition comprises or consists essentially of one or more compounds selected from the group consisting of the compounds identified by a compound activity range of "" in the "Reporter Assay" column of Table 3 or Table 4. In some embodiments, the composition comprises or consists essentially of one or more compounds selected from the group consisting of the compounds identified by a compound activity range of "*" in the "Reporter Assay" column of Table 3 or Table 4. In some embodiments, the composition comprises or consists essentially of one or more compounds selected from the group consisting of the set of compounds identified by a compound activity range of "*" or "*" in the "Reporter Assay" column of Table 3 or Table 4. In some embodiments, the composition comprises or consists essentially of one or more compounds selected from the group consisting of the set of compounds identified by a compound activity range of "", "*" or "****" in the "Reporter Assay" column of Table 3 or Table 4. In some embodiments, the composition comprises or consists essentially of one or more compounds selected from the group consisting of the set of compounds identified by a compound activity range of "*", "", "*" or "****" in the "Reporter Assay" column of Table 3 or Table 4. In some embodiments, the subject is selected as in need of the composition by detecting a presence and/or level of aggregates in an intestinal sample of the subject, such as a fecal sample. A presence or level of intestinal aggregates greater than a negative control (for example, fecal sample of a healthy control subject, or control subject known not to have an amyloid disorder) can indicate that the subject is in need of the composition.

In some embodiments, the composition comprises or consists essentially of one or more compounds of Formula (I) having an $IC_{50}$ of less than 150 μM. In some embodiments, the composition comprises or consists essentially of one or more compounds of Formula (I) having an $IC_{50}$ of less than 80 μM. In some embodiments, the composition comprises or consists essentially of one or more compounds of Formula (I) having an $IC_{50}$ of less than 35 μM. In some embodiments, the composition comprises or consists essentially of one or more compounds of Formula (I) having an $IC_{50}$ of less than 20 μM. In some embodiments, the composition comprises or consists essentially of one or more compounds of Formula (I) having an $IC_{50}$ of less than 10 μM. In some embodiments, the composition comprises or consists essentially of one or more compounds of Formula (I) having an $IC_{50}$ of less than 4.6 μM. In some embodiments, the composition comprises or consists essentially of one or more compounds of Formula (I) having an $IC_{50}$ of less than 1.3 μM. In some embodiments, the composition comprises or consists essentially of one or more compounds of Formula (I) having an $IC_{50}$ of 1.3-4.5 μM. In some embodiments, the composition comprises or consists essentially of one or more compounds of Formula (I) having an $IC_{50}$ of less than 4.6-10 μM. In some embodiments, the composition comprises or consists essentially of one or more compounds of Formula (I) having an $IC_{50}$ of greater than 10 μM.

In some embodiments, the composition comprises or consists essentially of one or more compounds of Formula (I) having a % control $B_{max}$ of less than or equal to 125% in the ThT assay of CsgA aggregation. In some embodiments, the composition comprises or consists essentially of one or more compounds of Formula (I) having a % control $B_{max}$ of less than or equal to 100%. In some embodiments, the composition comprises or consists essentially of one or more compounds of Formula (I) having a % control $B_{max}$ of less than or equal to 90%. In some embodiments, the composition comprises or consists essentially of one or more compounds of Formula (I) having a % control $B_{max}$ of less than or equal to 80%. In some embodiments, the composition comprises or consists essentially of one or more compounds of Formula (I) having a % control $B_{max}$ of less than or equal to 70%. In some embodiments, the composition comprises or consists essentially of one or more compounds of Formula (I) having a % control $B_{max}$ of less than or equal to 60%. In some embodiments, the composition comprises or consists essentially of one or more compounds of Formula (I) having a % control $B_{max}$ of less than or equal to 50%. In some embodiments, the composition comprises or consists essentially of one or more compounds of Formula (I) having a % control $B_{max}$ of less than or equal to 40%. In some embodiments, the composition comprises or consists essentially of one or more compounds of Formula (I) having a % control $B_{max}$ of less than or equal to 30%. In some embodiments, the composition comprises or consists essentially of one or more compounds of Formula (I) having a % control $B_{max}$ of less than or equal to 20%. In some embodiments, the composition comprises or consists essentially of one or more compounds of Formula (I) having a % control $B_{max}$ of less than or equal to 10%. In some embodiments, the composition comprises or consists essentially of one or more compounds of Formula (I) having a % control $B_{max}$ of greater than 60%. In some embodiments, the composition comprises or consists essentially of one or more compounds of Formula (I) having a % control $B_{max}$ of 31 to 60%. In some embodiments, the composition comprises or consists essentially of one or more compounds of Formula (I) having a % control $B_{max}$ of 11 to 31%. In some embodiments, the % control $B_{max}$ is determined relative to a vehicle control comprising all the components of the assay except one or more compounds of Formula (I). In some embodiments, the % control $B_{max}$ is determined relative to a vehicle control comprising solvent and the reporter strain. In some embodiments the solvent is DMSO. The assay and controls (for the CsgA ThT assay) are described in Example 26, and % control $B_{max}$ is described in paragraph [000336].

In some embodiments, the composition comprises or consists essentially of one or more compounds of Formula (I) having a % control $B_{max}$ of less than or equal to 125% in the ThT assay of CsgA aggregation. In some embodiments, the composition comprises or consists essentially of one or more compounds of Formula (I) having a % control $B_{max}$ of less than or equal to 100%. In some embodiments, the composition comprises or consists essentially of one or more compounds of Formula (I) having a % control $B_{max}$ of less than or equal to 90%. In some embodiments, the composition comprises or consists essentially of one or more compounds of Formula (I) having a % control $B_{max}$ of less than or equal to 80%. In some embodiments, the composition comprises or consists essentially of one or more compounds of Formula (I) having a % control $B_{max}$ of less than or equal to 70%. In some embodiments, the composition comprises or consists essentially of one or more compounds of Formula (I) having a % control $B_{max}$ of less than or equal to 60%. In some embodiments, the composition comprises or consists essentially of one or more compounds of Formula (I) having a % control $B_{max}$ of less than or equal to 50%. In some embodiments, the composition comprises or consists essentially of one or more compounds of Formula (I) having a % control $B_{max}$ of less than or equal to 40%. In some embodiments, the composition comprises or consists essentially of one or more compounds of Formula (I) having a % control $B_{max}$ of less than or equal to 30%. In some embodiments, the composition comprises or consists essentially of one or more compounds of Formula (I) having a % control $B_{max}$ of less than or equal to 20%. In some embodiments, the composition comprises or consists essentially of one or more compounds of Formula (I) having a % control $B_{max}$ of less than or equal to 10%. In some embodiments, the composition comprises or consists essentially of one or more compounds of Formula (I) having a % control $B_{max}$ of greater than 60%. In some embodiments, the composition comprises or consists essentially of one or more compounds of Formula (I) having a % control $B_{max}$ of 31 to 60%. In some embodiments, the composition comprises or consists essentially of one or more compounds of Formula (I) having a % control $B_{max}$ of 11 to 31%. In some embodiments, the % control $B_{max}$ is determined relative to a vehicle control comprising all the components of the assay except one or more compounds of Formula (I). In some embodiments, the % control $B_{max}$ is determined relative to a vehicle control comprising solvent and the reporter strain. In some embodiments the solvent is DMSO. The assay and controls (for the CsgA ThT assay) are described in Example 26, and % control $B_max$ is described in Example 26.

In some embodiments, the composition comprises or consists essentially of one or more compounds of Formula (I) having a % control AUC of less than 125% in the ThT fluorescence assay of CsgA aggregation. In some embodiments, the composition comprises or consists essentially of one or more compounds of Formula (I) having a % control AUC of less than or equal to 100%. In some embodiments, the composition comprises or consists essentially of one or more compounds of Formula (I) having a % control AUC of less than or equal to 90%. In some embodiments, the composition comprises or consists essentially of one or more compounds of Formula (I) having a % control AUC of less than or equal to 80%. In some embodiments, the composition comprises or consists essentially of one or more compounds of Formula (I) having a % control AUC of less than or equal to 70%. In some embodiments, the composition comprises or consists essentially of one or more compounds of Formula (I) having a % control AUC of less than or equal to 60%. In some embodiments, the composition comprises or consists essentially of one or more compounds of Formula (I) having a % control AUC of less than or equal to 50%. In some embodiments, the composition comprises or consists essentially of one or more compounds of Formula (I) having a % control AUC of less than or equal to 40%. In some embodiments, the composition comprises or consists essentially of one or more compounds of Formula (I) having a % control AUC of less than or equal to 30%. In some embodiments, the composition comprises or consists essentially of one or more compounds of Formula (I) having a % control AUC of less than or equal to 20%. In some embodiments, the composition comprises or consists essentially of one or more compounds of Formula (I) having a % control AUC of less than or equal to 10%. In some embodiments, the composition comprises or consists essentially of one or more compounds of Formula (I) having a % control AUC of greater than 60%. In some embodiments, the composition comprises or consists essentially of one or more compounds of Formula (I) having a % control AUC of 31 to 60%. In some embodiments, the composition comprises or consists essentially of one or more compounds of Formula (I) having a % control AUC of 11 to 31%. In some embodiments, the % control AUC is determined relative to a vehicle control comprising all the components of the assay except one or more compounds of Formula (I). In some embodiments, the % control AUC is determined relative to a vehicle control comprising solvent and the reporter strain. In some embodiments the solvent is DMSO. The assay and controls are described in Example 26, and the AUC calculation is described in Example 26.

In some embodiments, the composition comprises or consists essentially of one or more compounds of Formula (I) producing at least 10% inhibition. In some embodiments, the composition comprises or consists essentially of one or more compounds of Formula (I) producing at least 20% inhibition. In some embodiments, the composition comprises or consists essentially of one or more compounds of Formula (I) producing at least 30% inhibition. In some embodiments, the composition comprises or consists essentially of one or more compounds of Formula (I) producing at least 40% inhibition. In some embodiments, the composition comprises or consists essentially of one or more compounds of Formula (I) producing at least 50% inhibition. In some embodiments, the composition comprises or consists essentially of one or more compounds of Formula (I) producing at least 60% inhibition. In some embodiments, the composition comprises or consists essentially of one or more compounds of Formula (I) producing at least 70% inhibition. In some embodiments, the composition comprises or consists essentially of one or more compounds of Formula (I) producing at least 80% inhibition. In some embodiments, the composition comprises or consists essentially of one or more compounds of Formula (I) producing at least 90% inhibition. In some embodiments, the composition comprises or consists essentially of one or more compounds of Formula (I) producing less than −10% inhibition. In some embodiments, the composition comprises or consists essentially of one or more compounds of Formula (I) producing −10 to 10% inhibition. In some embodiments, the composition comprises or consists essentially of one or more compounds of Formula (I) producing 11 to 30% inhibition. In some embodiments, the composition comprises or consists essentially of one or more compounds of Formula (I) producing 31 to 60% inhibition. In some embodiments, the composition comprises or consists essentially of one or more compounds of Formula (I) producing greater than 60% inhibition.

In some embodiments, the subject is selected as in need of the composition by detecting a presence and/or level of aggregates in an intestinal sample of the subject, such as a fecal sample. A presence or level of intestinal aggregates greater than a negative control (for example, fecal sample of a healthy control subject, or control subject known not to have an amyloid disorder) can indicate that the subject is in need of the composition.

Pharmaceutical Compositions, Formulation, Administration and Dosing

In another aspect, provided herein is a pharmaceutical composition comprising a compound described herein and a pharmaceutically acceptable carrier. Pharmaceutical compositions described herein are useful for inhibiting amyloid formation.

In certain embodiments, the pharmaceutical composition is formulated for delivery outside of the systemic circulation of a subject. In certain embodiments, the pharmaceutical composition is formulated for delivery to the central nervous system of a subject. Said composition may be formulated for enteric delivery, and/or said compositions may further be formulated for controlled release within the lower intestine or colon, and/or formulated for topical, oral, or mucosal delivery. The aforementioned compositions may comprise an enteric-coated capsule, tablet, soft-gel, spray dried powder, polymer matrix, hydrogel, enteric-coated solid, crystalline solid, amorphous solid, glassy solid, coated micronized particle, liquid, nebulized liquid, aerosol, or microcapsule.

In certain embodiments, the pharmaceutical composition is formulated for oral administration. In certain embodiments, the pharmaceutical composition is formulated for administration by injection. The injection may be intravenous, subcutaneous, intramuscular, intraperitoneal, intraspinal or intracranial.

Standard pharmaceutical and/or dietary supplement formulation techniques may be used, such as those disclosed in Remington's The Science and Practice of Pharmacy, 21st Ed., Lippincott Williams & Wilkins (2005), incorporated herein by reference in its entirety. Accordingly, some embodiments include pharmaceutical and/or dietary supplement compositions comprising: (a) a safe and therapeutically effective amount of one or more compounds described herein, or pharmaceutically acceptable salts thereof; and (b) a pharmaceutically acceptable carrier, diluent, excipient or combination thereof.

The pharmaceutical composition comprises an effective amount of one or more compounds of the invention. The effective amount is sufficient to achieve one or more desired biological and/or pharmacological effects, e.g., the disruption or inhibition of the formation of amyloid aggregates, the treatment or prevention of a neurological disorder, or symptoms of a neurological disorder, or the treatment or prevention of a gastrointestinal disorders, or symptoms of a gastrointestinal disorder. An "effective amount" or "effective dose" of a compound (e.g., a compound described herein) or composition containing such compound, refers to the amount sufficient to achieve a desired biological and/or pharmacological effect, e.g., when delivered to a cell or organism according to a selected administration form, route, and/or schedule. The phrases "effective amount" and "therapeutically effective amount" may be used interchangeably. As will be appreciated by those of ordinary skill in this art, the absolute amount of a particular compound or composition that is effective may vary depending on such factors as the desired biological or pharmacological endpoint, the agent to be delivered, the target tissue, etc. Those of ordinary skill in the art will further understand that an "effective amount" may be administered to a subject in a single dose, or through use of multiple doses, in various embodiments.

"Administering" has its customary and ordinary meaning as understood by one of skill in the art in view of this disclosure. It refers to providing a pharmaceutical agent, dietary supplement, or composition to a subject, and includes, but is not limited to, administering by a medical professional and self-administration. Administration of the compounds disclosed herein or the pharmaceutically acceptable salts thereof can be via any of the accepted modes of administration for agents that serve similar utilities including, but not limited to, orally, intraperitoneally, or rectally. Oral administrations are customary in administering the compositions that are the subject of the preferred embodiments. However, in some embodiments, the compositions to be administered according to the methods of the present disclosure are administered rectally, such as by enema or suppository. In some embodiments, administration of the compounds may occur outside the body, for example, by apheresis or dialysis.

The term "agent" has its customary and ordinary meaning as understood by one of skill in the art in view of this disclosure. It includes any substance, molecule, element, compound, entity, or a combination thereof. It includes, but is not limited to, e.g., protein, polypeptide, peptide or mimetic, small organic molecule, polysaccharide, polynucleotide, polymer, resin, organic or inorganic microparticle, organic or inorganic nanoparticle, and the like. It can be a natural product, a synthetic compound, or a chemical compound, or a combination of two or more substances.

The term "pharmaceutically acceptable carrier" or "pharmaceutically acceptable excipient" has its customary and ordinary meaning as understood by one of skill in the art in view of this disclosure. It includes any and all solvents, diluents, emulsifiers, binders, buffers, dispersion media, coatings, antibacterial and antifungal agents, isotonic and absorption delaying agents and the like, or any other such compound as is known by those of skill in the art to be useful in preparing pharmaceutical formulations. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, NJ Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

Some examples of substances, which can serve as pharmaceutically-acceptable carriers or components thereof in accordance with methods and compositions of some embodiments herein, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such as sodium lauryl sulfate; coloring agents; flavoring agents; tableting agents, stabilizers; antioxidants; preservatives; pyrogen-free water; isotonic saline; and/or phosphate buffer solutions, or any combination thereof.

The choice of a pharmaceutically-acceptable carrier to be used in conjunction with the one or more compounds for administration as described herein can be determined by the way the compound is to be administered.

In addition, the present disclosure includes compositions comprising various salts, esters, hydrates, prodrugs, fluorinated analogs, or isotopically substituted analogs, including deuterated forms, of the compounds described herein.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and N+(C1-4 alkyl)4-salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

"Solvate" has its customary and ordinary meaning as understood by one of skill in the art in view of this disclosure. It refers to the compound formed by the interaction of a solvent and an active pharmaceutical ingredient (or API), a metabolite, or salt thereof. Suitable solvates are pharmaceutically acceptable solvates including hydrates.

As used herein, "systemic circulation" has its customary and ordinary meaning as understood by one of skill in the art in view of this disclosure. It refers to circulation within the blood or circulatory system of a subject.

As used herein, "enteric coating" has its customary and ordinary meaning as understood by one of skill in the art in view of this disclosure. It refers to a pharmaceutical excipient coating or placed around a particle which, by control of its solubility or timing of dissolution, increases the likelihood that said particle will be protected from solvent until its arrival in a desired portion of the gastrointestinal tract, for example, by conferring resistance to stomach acid or by having higher solubility at neutral or basic pH. Representative enteric coatings include, for example, those described in Remington's The Science and Practice of Pharmacy, 21st Ed., Lippincott Williams & Wilkins (2005). Exemplary enteric coatings include but are not limited to, shellac, sodium alginate, zein, cellulose acetate trimellitate, methyl methacrylate-methacrylic acid copolymer, polyvinyl acetate phthalate, polylactic acid, polylactic-co-glycolic acid, hypromellose acetate, hypromellose acetate succinate, Hydroxypropyl methyl cellulose phthalate, Cellulose acetate succinate, Cellulose acetate phthalate, Methyl acrylate-methacrylic acid copolymer, polyvinyl acetate phthalate, Opadry®, and others as are known in the art of drug delivery and formulation. In accordance with method and compositions of some embodiments, the composition comprising a compound as described herein further comprises an enteric coating.

The term "gut selective" as used herein has its customary and ordinary meaning as understood by one of skill in the art in view of this disclosure. It refers to a composition or formulation that is released in the gut of a subject, and preferably is not absorbed, or if absorption occurs, does not enter the systemic circulation.

The term "intrinsically enteric" as used herein has its customary and ordinary meaning as understood by one of skill in the art in view of this disclosure. With reference to a pharmaceutical formulation refers to a composition which innately has the ability to prevent disintegration or release in the gastric environment.

A composition for administration to a subject as described herein is preferably provided in a unit dosage form. As used herein, a "unit dosage form" has its customary and ordinary meaning as understood by one of skill in the art in view of this disclosure. It refers to a composition containing an amount of a compound that is suitable for administration to a subject, in a single dose, according to good medical practice. The preparation of a single or unit dosage form however, does not imply that the dosage form is administered once per day or once per course of therapy. A unit dosage form may comprise a single daily dose or a fractional sub-dose wherein several unit dosage forms are to be administered over the course of a day in order to complete a daily dose. According to the present disclosure, a unit dosage form may be given more or less often that once daily, and may be administered more than once during a course of therapy. Such dosage forms may be administered in any manner consistent with their formulation, including orally, rectally, nasally, and/or parenterally. While single administrations are specifically contemplated, the compositions administered according to the methods described herein may also be administered as a continuous infusion or via an implantable infusion pump.

The methods as described herein may utilize any of a variety of suitable forms for a variety of routes for administration, for example, for oral, nasal, rectal, or parenteral routes of administration. Depending upon the particular route of administration desired, a variety of pharmaceutically-acceptable carriers well-known in the art may be used. Pharmaceutically-acceptable carriers include, for example, solid or liquid fillers, diluents, hydrotropes, surface-active agents, and encapsulating substances. Optional pharmaceutically-active materials may be included, which do not substantially interfere with the activity of the one or more compounds in the formulation. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004).

Various oral dosage forms can be used, including such solid forms as tablets, capsules, granules and/or bulk powders. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and/or melting agents. Further solid dosage forms may comprise milled powders, spray-dried powders, crystalline forms, amorphous forms, and glassy forms, which may be administered as tablets or may be administered as aerosols or airborne particles, for example for nasal or pulmonary delivery. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and/or flavoring agents, or any combination thereof. Further liquid dosage forms may comprise forms for intranasal or pulmonary delivery. Such dosage forms may comprise liquids for intranasal injection, nasal lavage, pulmonary lavage, nebulization or aerosol delivery.

The pharmaceutically-acceptable carriers suitable for the preparation of unit dosage forms for peroral administration in accordance with methods and compositions of some embodiments herein are well-known in the art. Tablets typically comprise conventional pharmaceutically-compatible adjuvants as inert diluents, such as calcium carbonate, sodium carbonate, mannitol, lactose and/or cellulose; binders such as starch, gelatin and/or sucrose; disintegrants such as starch, alginic acid and/or croscarmelose; lubricants such as magnesium stearate, stearic acid, microcrystalline cellulose, carboxymethyl cellulose, and/or talc. Tablets may also comprise solubilizers or emulsifiers, such as poloxamers, cremophor/Kolliphor®/Lutrol®, or methylcellulose, hydroxypropylmethylcellulose, or others as are known in the art, or any combination thereof. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and/or fruit flavors, or any combination thereof, are useful adjuvants for chewable tablets. Capsules typically comprise one or more solid diluents disclosed above. The selection of carrier components depends on secondary considerations like taste, cost, and shelf stability, which can be readily made by a person skilled in the art.

Peroral (PO) compositions in accordance with methods and compositions of some embodiments herein also include liquid solutions, emulsions, or suspensions. The pharmaceutically-acceptable carriers suitable for preparation of such compositions are well known in the art. Typical components of carriers for syrups, elixirs, emulsions and/or suspensions include ethanol, glycerol, propylene glycol, polyethylene glycol, liquid sucrose, sorbitol and/or water. For a suspension, typical suspending agents include methyl cellulose, sodium carboxymethyl cellulose, AVICEL RC-591, tragacanth and/or sodium alginate; typical wetting agents include lecithin and/or polysorbate 80; and typical preservatives include methyl paraben and/or sodium benzoate, or any combination thereof. Peroral liquid compositions may also contain one or more components such as sweeteners, flavoring agents and/or colorants, as disclosed above.

Such compositions may also be coated by conventional methods, typically with pH or time-dependent coatings, such that the subject one or more compounds are released in the gastrointestinal tract in the vicinity of the desired application, or at various times to extend the desired action. Exemplary dosage forms for release in the gastrointestinal tract may incorporate one or more of cellulose acetate phthalate, polyvinyl acetate phthalate, hydroxypropyl methyl cellulose phthalate, ethyl cellulose, Eudragit coatings, waxes, alginate and/or shellac, or other excipients known to those of skill in the art, or any combination thereof. According to some embodiments, the compositions to be administered according to the methods described herein are formulated for release in the gastrointestinal tract. According to some embodiments, the compositions to be administered according to the methods described herein are formulated for release in the lower gastrointestinal tract. In some embodiments, the compositions are provided as enteric coated capsules, tablets, soft gels; or intrinsically enteric capsules.

The actual unit dose of the compositions in accordance with methods and compositions of some embodiments herein depends on the one or more compounds in the formulation. In some embodiments, dose in milligrams per kilogram of subject body weight in the formulation may be from 0.01 mg/kg to 0.05 mg/kg per day, from 0.04 mg/kg to 0.1 mg/kg per day, from 0.09 mg/kg to 0.15 mg/kg per day, from 0.14 mg/kg to 0.2 mg/kg per day, from 0.2 mg/kg to 0.5 mg/kg of per day, from 0.4 mg/kg to 1 mg/kg per day, from 1 mg/kg to 6 mg/kg per day, 5 mg/kg to 500 mg/kg or more per day, from 10 mg/kg or less to 70 mg/kg, from 50 mg/kg to 80 mg/kg per day, from 70 mg/kg to 120 mg/kg per day, from 100 mg/kg to 300 mg/kg per day, or from 250 mg/kg to 500 mg/kg per day. In some embodiments, the dose may be less than 100 mg/kg, 500 mg/kg, 300 mg/kg, 200 mg/kg, 150 mg/kg, 100 mg/kg, 50 mg/kg, 40 mg/kg, 30 mg/kg, 25 mg/kg, 20 mg/kg, 10 mg/kg, 7.5 mg/kg, 6 mg/kg, 5 mg/kg, 4 mg/kg, 3 mg/kg, 2.5 mg/kg, or 1 mg/kg per day or an amount that is within a range defined by any two of the aforementioned amounts. In some embodiments, the actual unit dose is 5, 10, 25, 50, 75, 100, 150, or 200 mg/kg per day or an amount that is within a range defined by any two of the aforementioned amounts. Thus, for administration to a 70 kg person, for example, the dosage range is from 0.1 mg to 1 mg, 0.9 mg to 2 mg, from 1.5 mg to 5 mg, from 4 mg to 10 mg, from 9 mg to 20 mg, from 15 mg to 50 mg, from 40 mg to 75 mg, from 50 mg to 100 mg, from 75 mg to 200 mg, from 100 mg to 300 mg, from 200 mg to 400 mg, 350 mg to 750 mg, from 500 mg to 1 g, from 750 mg to 2 g, from 1 g to 5 g, from 2.5 g to 6 g, from 4 g to 10 g, from 8 g to 20 g, from 15 g to 35 g, or from 1 g or less to 35 g or more, or an amount that is within a range defined by any two of the aforementioned amounts. In some embodiments, the actual unit dose is 6 g. In some embodiments, the actual unit dose is 10 g. In some embodiments, the actual unit dose is 35 g. In some embodiments, the actual unit dose is 1 g or less but not zero. In some embodiments, the actual unit dose is 10 g or less but not zero. In some embodiments, the actual unit dose is 35 mg or less but not zero.

"Loading dose," as used herein refers to an initial dose of a compound which is higher than subsequent doses.

"Maintenance dose," as used herein refers to a subsequent dose that follows a loading dose, and occurs later in time than a loading dose. One of ordinary skill in the art will be aware that the dosage form or mode of administration of a maintenance dose may be different from that used for the loading dose. In any of the embodiments disclosed herein, a maintenance dose may comprise administration of the unit dosage form on any dosing schedule contemplated herein, including but not limited to, monthly or multiple times per month, biweekly or multiple times each two weeks, weekly or multiple times per week, daily or multiple times per day. It is contemplated within the present disclosure that dosing holidays may be incorporated into the dosing period of the maintenance dose. Such dosing holidays may occur immediately after the administration of the loading dose or at any time during the period of administration of the maintenance dose. As used herein, the period of administration of the maintenance dose may be referred to as the "maintenance phase" of the treatment period.

"Mode of administration" as used herein refers to the avenue by which one or more compounds are administered to a subject. As used herein, "mode of administration" comprises the dosage form (for example, a tablet, powder, dissolved liquid, suspension, emulsion, etc.) and mechanism by which the dosage form is applied to the subject (for example, by injection, topically, such as by cream, lotion, or patch; orally, such as by a pill, dissolved liquid, oral suspension, buccal film, or mouth rinse). As used herein, "mode of administration" also comprises the dose, dose amount, and dosing schedule by which a compound is administered to a subject.

In some embodiments, the compositions to be administered according to the methods of the present disclosure are provided with, or mixed into, a foodstuff, beverage, or other ingestible item. In some embodiments, said beverage, foodstuff, or other ingestible item may comprise one or more of a candy, an applesauce, a yogurt, a soft pudding, a gelatin foodstuff, a juice, milk, a soy or nut beverage, a thickened beverage, or a cheese, or any combination thereof. One of ordinary skill will readily recognize that the combination of the compositions to be administered according to the methods of the disclosure can be combined with any suitable food or beverage to facilitate ingestion of the compositions.

In some embodiments in accordance with methods and compositions of some embodiments herein, the mode of administration comprises administering a loading dose followed by a maintenance dose. In some embodiments, the loading dose is 20 g or less but not zero; 15 g or less but not zero; 10 g or less but not zero, 6 g or less but not zero, 4 g or less but not zero, 2 g or less but not zero, or 1 g or less but not zero or an amount that is within a range defined by any two of the aforementioned amounts. In some embodiments, the maintenance dose is 20 g or less but not zero; 10 g or less but not zero, 6 g or less but not zero, 4 g or less but not zero, 2 g or less but not zero, 1 g or less but not zero, 500 mg or less but not zero, or 250 mg or less but not zero or an amount that is within a range defined by any two of the aforementioned amounts.

In some embodiments in accordance with methods and compositions of some embodiments herein, the loading dose is administered over a period of one day or 24-hour period. In some embodiments the loading dose is administered in a single administration. In some embodiments, the loading dose is administered in multiple administrations. In some embodiments, the loading dose is administered in multiple administrations during a single day or 24-hour period. In some embodiments the loading dose is administered over a period of 2 days. In some embodiments the loading dose is administered over a period of 3 days. In some embodiments the loading dose is administered over a period of 4 days. In some embodiments the loading dose is administered over a period of 5, 6 or 7 days. In some embodiments, the loading dose is administered over a period of 8-14 days or fewer. In some embodiments, the loading dose is administered over a period of 14 days.

The methods according to the present disclosure contemplate varying or controlling the timing of administration of a composition described herein, in order to enhance the effectiveness of any treatment that is administered. In some embodiments, a composition to be administered according to the methods of the present disclosure may be administered with food, such as concurrently with a meal or other ingestion of a foodstuff. In some further embodiments, a composition to be administered according to the methods of the present disclosure may be administered immediately before or immediately after a meal or other ingestion of a foodstuff. In some further embodiments, a composition to be administered according to the methods of the present disclosure may be administered within 1-5 minutes, within 3-10 minutes, within 6-15 minutes, within 10-20 minutes, within 15-30 minutes, within 20-45 minutes, or within one hour before or after a meal or other ingestion of a foodstuff. In some embodiments, a composition to be administered according to the methods of the present disclosure may be administered without food, such as between 1-3 hours, between 2-5 hours, between 4-8 hours, between 6-12 hours, between 9-18 hours, between 12-24 hours, or more than 24 hours before or after a meal or other ingestion of a foodstuff.

As used herein, "duration of the treatment" refers to the time commencing with administration of the first dose and concluding with the administration of the final dose, such length of time being determined by one of ordinary skill in the art of treating neurological disorders or disorders implicating intestinal hyperpermeability or "leaky gut," with reference to the symptoms and health of the subject being treated therefor. Such duration may be determined with reference to periodic, sporadic, or ongoing monitoring of the levels of amyloid as disclosed herein or as known to one of skill in the art of treating neurological disorders.

As used herein, "dosing holiday" refers to a period of 24 hours or more during which either no dose is administered to the subject, or a reduced dose is administered to the subject. As used herein, "reduced dose" refers to a dose that is less than the total daily dose to be administered to a subject.

According to the present disclosure, the dosing schedule may be varied so as to attain the desired therapeutic effect. In each of the embodiments as disclosed herein, variations in dosing schedule may be repeated throughout the duration of the therapeutic protocol being administered. In each of the embodiments as disclosed herein, the first dosage may be higher, lower, or the same as the dosages following the first dosage. In each of the embodiments disclosed herein, a loading dose may precede the disclosed dosing regimen, and a dosing holiday may or may not follow the administration of the loading dose.

In some embodiments the methods of the present disclosure comprise administration of one or more compositions as provided herein daily or less frequently than daily, such as every second day, every third day, every fourth day, every fifth day, every sixth day, or every seventh day or for a time period that is within a range defined by any two of the aforementioned times. In some embodiments, the compositions as described herein are formulated for such administration.

According to the methods disclosed herein, a treatment or inhibition of a disorder implicating amyloid formation may be achieved by modulating the dosing schedule for the administration of a composition such that subjects experience periodic partial or full reductions in dosing for fixed amounts of time, followed by a resumption of dosing. In some embodiments, dosages are administered daily for between one and thirty days, followed by a dosing holiday lasting for between one and thirty days. In some embodiments, during the dosing holiday, no dose is administered. In some further embodiments, the composition of the present disclosure is allowed to clear completely from the subject's body prior to administration of the next dose. In some other embodiments, during the dosing holiday, a dose less than the usual daily dose is administered. In some further embodiments, an amount of the administered composition less than the therapeutically effective amount is allowed to remain within the subject during the dosing holiday. In some further embodiments, an amount of the administered composition sufficient to maintain therapeutic levels in the affected tissues is allowed to remain within the subject. In some embodiments, a composition is administered at any time following the onset of one or more of the aforementioned symptoms of a neurological disorder associated with amyloid formation. In some embodiments, a composition according to the methods described herein is administered prior to the onset of symptoms of said disorder or disorders. In some embodiments, a composition according to the methods described herein is administered concurrently with or after the onset of symptoms of said disorder or disorders.

Methods of Use

The present disclosure provides methods for inhibiting, ameliorating, reducing the likelihood, delaying the onset of, treating, and/or preventing the amyloid disorder, including methods that inhibit or disrupt one or more of the following: (1) bacterial amyloid aggregation on the bacterial surface or in the proximal extracellular space; (2) the interaction between bacterial amyloid and α-synuclein in the GI tract or olfactory system (including enteroendocrine cells and enteric neuronal cells); and/or (3) aggregation of α-synuclein in the GI tract (including enteroendocrine cells and enteric neuronal cells).

According to the methods of the present disclosure, α-synuclein should be viewed as a representative amyloid protein of the wider range of known host amyloid proteins, including one or more of Beta amyloid from Amyloid precursor protein, Medin, tau, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, superoxide dismutase 1 (SOD1) and/or Immunoglobulin light chain AL, and the compositions and methods as disclosed herein may be adapted by one of skill in the art to disrupt the aggregation of any amyloid protein in which one amyloid protein (bacterial or human) prompts aggregation of another amyloid protein.

Without being limited by theory, representative disorders that present amyloid formation and the proteins involved in these disorders, which may be inhibited or disrupted using the methods of the present disclosure, include but are not limited to those disclosed in Table 2.

TABLE 2

| Amyloid Disorders | | |
|---|---|---|
| Disease | Protein featured | Abbreviation |
| Alzheimer's disease (AD) | Beta amyloid from Amyloid precursor protein | Aβ, APP |
| Aortic medial amyloid | Medin | AMed |
| Atherosclerosis | Apolipoprotein A1 | AApoA1 |
| Cardiac arrhythmias, isolated atrial amyloidosis | Atrial natriuretic factor | AANF |
| Cerebral amyloid angiopathy | Beta amyloid | Aβ |
| Cerebral amyloid angiopathy (Icelandic type) | Cystatin | ACys |
| Diabetes mellitus type 2 | IAPP (Amylin) | AIAPP |
| Dialysis related amyloidosis | Beta-2 microglobulin | Aβ2M |
| Familial amyloid polyneuropathy | Transthyretin | ATTR |
| Fatal familial insomnia | PrP | APrP |
| Finnish amyloidosis | Gelsolin | AGel |
| Hereditary non-neuropathic systemic amyloidosis | Lysozyme | ALys |
| Huntington's disease (HD) | Huntingtin | HTT |
| Lattice corneal dystrophy | Keratoepithelin | AKer |
| Medullary carcinoma of the thyroid | Calcitonin | ACal |
| Parkinson's disease (PD) | α-synuclein | α-Syn |
| Prolactinomas | Prolactin | APro |
| Rheumatoid arthritis (RA) | Serum amyloid A | AA |
| Sporadic Inclusion body myositis (S-IBM) | various, including beta-amyloid | |
| Systemic AL amyloidosis | Immunoglobulin light chain AL | AL |
| Transmissible spongiform encephalopathy (e.g., bovine spongiform encephalopathy) | PrP | APrP |

The methods of the compositions and methods of the invention can also be used to treat amyloid-mediated disorders of the gastrointestinal tract including intestinal dysbiosis, intestinal hyperpermeability, irritable bowel syndrome (IBS), inflammatory bowel disease (IBD), ulcerative colitis and/or Crohn's disease. These disorders can be associated with one or more symptoms, including dysphagia, reduced gut motility, gastroparesis, constipation (including chronic constipation and chronic idiopathic constipation), small intestinal bacterial overgrowth (SIBO), diarrhea (including chronic diarrhea), abdominal pain and/or cramping, bloating, flatulence, and nausea.

As used herein, the term "intestinal dysbiosis" has its customary and ordinary meaning as understood by one of skill in the art in view of this disclosure and refers to an imbalance and/or maladaptation of the flora or microbiota within the gut or intestines, and particularly the small intestine. Such dysbiosis is characterized by a change in the composition of the intestinal or gut microbiome, in terms of the species/strains which are present and/or the relative abundance or proportion of the species/strains which are present, in which the change has a deleterious effect on the host organism. The deleterious effect on the host organism can result from microbiome-mediated changes in electrolyte balance, biofilm formation, integrity of the barrier formed by the intestinal epithelial lining, or the release from the microbiome of metabolites which are directly (e.g., as toxicity or effectors) or indirectly (e.g., as pre-cursors to toxins or effector) injurious to the health of the host.

As used herein, the term "intestinal hyperpermeability" has its customary and ordinary meaning as understood by one of skill in the art in view of this disclosure. It refers to abnormal increased permeability of the barrier formed by the intestinal epithelial lining between the intestinal lumen and the surrounding issues. Such hyperpermeability may result from inflammation of the intestinal lining and/or failure of the tight junctions between cells of the intestinal epithelium, which allows the passage of substances from the lumen into the surrounding tissues where some may enter the peritoneal cavity and/or systemic circulation. Because of this leakage of substances from the gut or intestinal lumen, intestinal hyperpermeability may be referred to as "leaky gut" or "leaky gut syndrome."

As used herein, the term "amyloid disorders," including variations of this root term, includes, but is not limited to any or all of the disorders of Table 2 as well as amyloid-mediated disorders of the gastrointestinal tract.

As used herein, the term "mammalian amyloid or mammalian amyloid precursor" includes, but is not limited to, one or more of tau, Beta amyloid from Amyloid precursor protein, Medin, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, and/or Immunoglobulin light chain AL. In certain methods and compositions disclosed herein, said microbial amyloid or microbial amyloid precursor comprises CsgA.

The terms "amyloid aggregate" and "aggregates of amyloid proteins" are used interchangeably.

Some embodiments include a method of inhibiting, ameliorating, reducing the likelihood, delaying the onset of, treating, or preventing an amyloid disorder, the method comprising administering a composition as described herein to a subject in need thereof. The amyloid disorder can be selected from the group consisting of: α-synucleinopathy, Parkinson's Disease, Lewy Body Dementia, incidental Lewy body disease, Lewy body variant of Alzheimer's disease, multiple system atrophy, and pure autonomic failure, or any combination of any of these. The amyloid disorder can also be selected from the group consisting of: intestinal dysbiosis, intestinal hyperpermeability, irritable bowel syndrome (IBS), inflammatory bowel disease (IBD), ulcerative colitis and/or Crohn's disease. In some embodiments, the composition administered in the method comprises, consists essentially of, or consists of any of the compounds of Table 1. In some embodiments, the composition administered in the method comprises, consists essentially of, or consists of a compound as described herein. In some embodiments of the method, the amyloid disorder comprises intestinal amyloid aggregates. For example, the aggregates can comprise a bacterial protein, for example a curli-associated protein such as CsgA. Accordingly, in some embodiments, the method further comprises detecting a presence or level of such a bacterial protein in an intestinal sample of the subject, a presence or level of nucleic acids encoding the microbial (e.g., bacterial) protein, or a presence of level of a microbial organism that produces the bacterial protein (e.g., a curli-associated protein such as CsgA) in the intestinal sample of the subject, for example a fecal sample. For example, the protein can be detected by an immunoassay such as an ELISA, Western Blot, lateral flow assay, no-wash assay or the like. For example, the microbial organism that produces the microbial protein can be detected by nucleic acid analysis (such as qualitative or quantitative PCR, microarray analysis, or sequencing). For example, the nucleic acid that encodes the microbial protein can be detected by qualitative or quantitative PCR, microarray analysis, sequencing or branched DNA analysis. An intestinal presence of the bacterial protein or microbial organism that produces the protein, or a level of the bacterial protein (or microbial organism that produces the protein) greater than a control can identify the subject as being in need of the composition. By way of example, suitable controls can include subjects that are negative for the bacterial protein (or microbial organisms that make the bacterial protein), for example healthy individuals, or an individual identified as not having the bacterial protein (or microbial organisms that make the bacterial protein) in their intestines. In some embodiments, the method comprises detecting a presence or level of intestinal curli (or a curli-associated protein such as CsgA), or an intestinal level of a microorganism that produces intestinal curli-associated protein (such as CsgA) in a sample of the subject. In some embodiments, the subject is identified as a member of a subpopulation of subject having the amyloid disorder, and in need of the composition. In some embodiments, the method further comprises determining a decrease or absence of the intestinal amyloid aggregates following the administration. In some embodiments, the method further comprises determining a decrease or absence of the intestinal amyloid proteins following the administration.

The compositions of the present disclosure may, in some embodiments, inhibit the formation of α-synuclein aggregates (e.g., fibrils, Lewy bodies, or other aggregates) or other host amyloid at its point of initiation in the gut, thus depriving microbially induced amyloid aggregation thought to serve as a template or seed for α-synuclein or other host amyloid aggregation and doing so without having to cross the blood brain barrier. Targeting α-synuclein or other host amyloid aggregation in the gut obviates the need for the drug to cross the blood-brain barrier, providing efficacy at a lower dose, with fewer side-effects due to reduction in systemic exposure. Further, targeting α-synuclein or other host amyloid aggregation at its point of initiation allows intervention at an earlier stage in the pathogenic process, preventing or inhibiting disease progression before motor symptoms or other neurodegenerative symptoms develop. Targeting α-synuclein aggregation in the gut may also address gastrointestinal dysfunction and/or ameliorate gastrointestinal symptoms or behaviors of the subject, which may comprise, e.g., one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD, e.g., ulcerative colitis and Crohn's disease), intestinal hyperpermeability, hypersalivation (sialorrhea), anorectal dysfunction, dyssynergic defecation, or any combinations thereof, for example in accordance with compositions and methods of some embodiments herein.

In addition to targeting host amyloid aggregation in the brain as an approach to treating or inhibiting neurodegenerative diseases, targeting bacterial amyloid aggregation provides new therapies for infectious diseases, such as urinary tract infections (UTIs). In both cases, the compounds described herein have been identified as having the ability to inhibit amyloid aggregation process in tissues of interest, such as in the brain for α-synuclein and the urinary mucosae for UTIs.

In some embodiments, the compositions and methods of the present disclosure contemplate the use of compounds described herein as inhibitors of the interaction between a host amyloid, such as α-synuclein and a bacterial amyloid, such as curli or adhesive pili. In some embodiments, the compositions and methods of the present disclosure, contemplate the use of the compounds described herein as inhibitors of host amyloid aggregation and/or promoters of amyloid dis-aggregation in peripheral tissue, such as the gut or nasopharynx, rather than in the brain. The compositions and methods of the present disclosure further contemplate modified derivatives of the compounds as described herein that act locally in the gut and are essentially not absorbed into peripheral tissues, such as, for example, non-orally bioavailable derivatives that retain amyloid inhibiting activity, but do not traverse the gut epithelium or enter the primary circulation.

In some embodiments, the compositions and methods of the present disclosure contemplate formulations that enable delivery of said compositions to the site of action in the lower small intestine, the large intestine, and/or the colon. Said formulations may comprise enteric coated tablets, capsules, liquid-gels or powders, and the like, such that the formulation inhibits the release of the drug in the stomach or upper GI tract. Alternatively, said compositions may comprise intrinsically enteric capsules or similar solid dosage forms wherein the capsule composition comprises a polymer or material that dissolves at or near the site of action, such as, for example, EnTrinsic® intrinsically enteric capsules, preferably in the lower GI tract, and more especially the lower small intestine, the large intestine, or the colon. In some embodiments, said compositions are not absorbed and remain in the GI tract.

The compositions and methods of the present disclosure contemplate gut-restricted small molecule inhibitors that target one or more elements of amyloid formation. Exemplary compounds of the invention include polyphenol moieties, many of which are orally bioavailable. The compositions and methods of the present disclosure also contemplate gut-selective or gut-restricted, non-orally absorbed derivatives of non-polyphenol classes that are known to have the ability to inhibit amyloid formation. The compositions and methods according to the present disclosure further contemplate non-orally absorbed, gut-selective derivatives or formulations of said polyphenol or non-polyphenol compounds.

"Subject" as used herein, has its customary and ordinary meaning as understood by one of skill in the art in view of this disclosure. It refers to a human or a non-human mammal including but not limited to a dog, cat, horse, donkey, mule, cow, domestic buffalo, camel, llama, alpaca, bison, yak, goat, sheep, pig, elk, deer, domestic antelope, or a non-human primate selected or identified for a diagnosis, treatment, inhibition, amelioration of a neurological disease or neurological disorder associated with microbially induced amyloid, such as Parkinson's Disease, Lewy Body Dementia, incidental Lewy body disease, Lewy body variant of Alzheimer's disease, multiple system atrophy, pure autonomic failure, intestinal dysbiosis, intestinal hyperpermeability, irritable bowel syndrome (IBS), inflammatory bowel disease (IBD), ulcerative colitis, Crohn's disease, or any combination thereof.

"Diagnosing" has its customary and ordinary meaning as understood by one of skill in the art in view of this disclosure. It can refer to the act or process of determining whether a subject exhibits any symptom or indicator of a neurological disease or neurological disorder associated with microbially induced amyloid such as Parkinson's Disease, Lewy Body Dementia, incidental Lewy body disease, Lewy body variant of Alzheimer's disease, multiple system atrophy, pure autonomic failure, or any combination thereof. It can also refer to the act or process of determining whether a subject exhibits any symptom or indicator of a gastrointestinal disorder associated with microbially induced amyloid such as intestinal dysbiosis, intestinal hyperpermeability, irritable bowel syndrome (IBS), inflammatory bowel disease (IBD), ulcerative colitis and/or Crohn's disease. Diagnosing may further comprise the determination of whether the body of a subject or any tissue, fluid, component, organ, or compartment thereof contains microbially induced amyloid. Diagnosing may further comprise the determination of whether the body of a subject or any tissue, fluid, component, organ, or compartment thereof contains any factor capable of affecting the rate of aggregation or disaggregation of microbially induced amyloid.

"Subject suspected of having" has its customary and ordinary meaning as understood by one of skill in the art in view of this disclosure. It refers to a subject exhibiting one or more clinical indicators of a disease or condition. In certain embodiments, the disease or condition may comprise one or more of Parkinson's Disease, Lewy Body Dementia, incidental Lewy body disease, Lewy body variant of Alzheimer's disease, multiple system atrophy, pure autonomic failure, or any combination thereof. In some embodiments, the disorder can be selected from the group consisting of: intestinal dysbiosis, intestinal hyperpermeability, irritable bowel syndrome (IBS), inflammatory bowel disease (IBD), ulcerative colitis and/or Crohn's disease.

"Subject in need thereof" has its customary and ordinary meaning as understood by one of skill in the art in view of this disclosure. It refers to a subject selected or identified as one being in need of diagnosis of a disorder implicating amyloid formation, or one in need of a treatment, inhibition, amelioration of a neurological disease or neurological disorder associated with microbially induced amyloid such as Parkinson's Disease, Lewy Body Dementia, incidental Lewy body disease, Lewy body variant of Alzheimer's disease, multiple system atrophy, pure autonomic failure, or any combination thereof. In other embodiments, the disorder can be selected from the group consisting of: intestinal dysbiosis, intestinal hyperpermeability, irritable bowel syndrome (IBS), inflammatory bowel disease (IBD), ulcerative colitis and/or Crohn's disease.

"Bacteria" and "microbe" (and related terms "bacterial" and "microbial") are art recognized terms which as used herein encompass bacteria, fungi, viruses, protists, archae, and the like.

"Microbially induced amyloid" as used herein has its customary and ordinary meaning as understood by one of skill in the art in view of this disclosure. It refers to amyloid fibrils or aggregates that are produced through the contact of a mammalian or microbial protein with one or more microbial proteins. Said microbial protein may comprise one or more proteins of bacterial or fungal origin, although the present disclosure contemplates amyloid produced by the interaction of proteins, whatever their origin, with proteins originating from bacteriophages, viruses, bacteria, archaea, fungi, and other eukaryotes.

A "therapeutic effect" has its customary and ordinary meaning as understood by one of skill in the art in view of this disclosure. It relieves, to some extent, one or more of the symptoms of a disease or disorder, and includes curing the disease or disorder. "Curing" means that the symptoms of active disease are eliminated. However, certain long-term or permanent effects of the disease may exist even after a cure is obtained (such as tissue damage).

"Amelioration" has its customary and ordinary meaning as understood by one of skill in the art in view of this disclosure. It refers to a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"Modulation" has its customary and ordinary meaning as understood by one of skill in the art in view of this disclosure. It refers to an alteration in the presence, absolute level, relative level, function or activity of any factor within the body of a subject or any tissue, fluid, component, organ, or compartment thereof. In certain embodiments, modulation refers to an increase in gene expression. In certain embodiments, modulation refers to a decrease in gene expression. In certain embodiments, modulation refers to an increase or decrease in total serum levels of a specific protein. In certain embodiments, modulation refers to an increase or decrease in free serum levels of a specific protein. In certain embodiments, modulation refers to an increase or decrease in the aggregation state of a protein. In certain embodiments, modulation refers to increasing or decreasing the stability of amyloid fibrils. In certain embodiments modulation refers to increasing or decreasing the length, width, spacing, or density of amyloid fibrils. In certain embodiments, modulation refers to an increase or decrease in total serum levels of a specific non-protein factor, e.g., a metabolite. In certain embodiments, modulation refers to an increase or decrease in free serum levels of a specific non-protein factor. In certain embodiments, modulation refers to an increase or decrease in total bioavailability of a specific protein. In certain embodiments, modulation refers to an increase or decrease in total bioavailability of a specific non-protein factor. In certain embodiments, modulation refers to alterations in the aggregation state of a protein. In certain embodiments modulation refers to alterations in the rate or extent of aggregation or disaggregation of microbially induced amyloid.

In some compositions and methods of some embodiments in accordance with the present disclosure, a subject is selected or identified to receive the administration of the compositions described herein. In some embodiments, said subject is selected or identified as one having elevated levels of curli in the gut. Such a selection can be made by clinical or diagnostic evaluation. In some embodiments, said subject is selected or identified as one having elevated levels of microbially induced amyloid in the gut. Such a selection can also be made by clinical or diagnostic evaluation. In some embodiments, said subject is selected or identified as one having elevated levels of α-synuclein in the gut. Again, such a selection can be made by clinical or diagnostic evaluation. In some further embodiments, said subject is one showing one or more symptoms of a neurodegenerative disorder, such as a demonstration of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, and/or altered kynurenine levels, gastroparesis, anorectal dysfunction, dyssnergic defecation, or any combination thereof. In some embodiments, said subject has been diagnosed according to methods known in the art of diagnosis of neurological and amyloid disorders, as having an amyloid disorder. In some further embodiments, said subject has been diagnosed as having or as being at risk of having Lewy Body Dementia, incidental Lewy body disease, Lewy body variant of Alzheimer's disease, multiple system atrophy, pure autonomic failure, or any combination thereof. In some embodiments, said subject further displays gastrointestinal symptoms. In some further embodiments, said gastrointestinal symptoms may comprise one or more of constipation, diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof.

In some embodiments, the compound or pharmaceutical composition is administered prior to the appearance of a neurological symptom or condition, such as a demonstration of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, altered kynurenine levels, and/or any combination thereof.

In compositions and methods according to some embodiments of the present disclosure, a subject selected for treatment may be under the age of 18 years. In some embodiments, a subject selected for treatment may be between 17 and 30 years of age. In some embodiments, a subject selected for treatment may be between 29 and 50 years of age. In some embodiments, a subject selected for treatment may be between 49 and 60 years of age. In some embodiments, a subject selected for treatment may be between 59 and 70 years of age. In some embodiments, a subject selected for treatment according to the compositions and methods described herein may be greater than 69 years of age.

In compositions and methods according to some embodiments of the present disclosure, administration of one or more of the compositions as described herein provides the effect of preventing the formation of, or promoting the disaggregation of, amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of inhibiting the further aggregation of amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of causing or enhancing the disaggregation of amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of causing or enhancing the disaggregation of preexisting amyloid or microbially induced amyloid in the gut, nasal cavity, olfactory bulb, or enteric nervous tissue, e.g., without having to pass the blood brain barrier. In some embodiments, administration of one or more of the compositions as described herein provides the effect of preventing the development of one or more symptoms of one or more neurological or neurodegenerative disorders. In some embodiments, administration of one or more of the compositions as described herein provides the effect of ameliorating one or more symptoms of one or more neurological or neurodegenerative disorders. In some embodiments, administration of one or more of the compositions as described herein provides the effect of reversing one or more symptoms of one or more neurological or neurodegenerative disorders. In some embodiments, said one or more symptoms of one or more neurological disorders may comprise one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, and/or altered kynurenine levels, gastroparesis, anorectal dysfunction, dyssnergic defecation, or any combination thereof. In some embodiments, said one or more neurological disorders may comprise an amyloid disorder. In some further embodiments, said one or more neurological disorders may comprise one or more of Lewy Body Dementia, incidental Lewy body disease, Lewy body variant of Alzheimer's disease, multiple system atrophy, and/or pure autonomic failure, or any combination thereof.

In other embodiments, the inhibitors of amyloid formation may be intended for administration systemically or locally to the enteric of central nervous system. For example, inhibitors which are effective against mammalian amyloid or mammalian amyloid precursor protein aggregation may be useful in treatment of one or more of the amyloid disorders described herein (Table 2). Therefore, for such embodiments, the compositions comprising the inhibitors of amyloid formation may be formulated for parenteral administration, including systemic administration (e.g., intravenous, subcutaneous, intramuscular, intraperitoneal) or local administration (e.g., local injection near the vagus nerve, intraspinal injection, or intracranial injection). For delivery into the CNS, it is necessary for the inhibitors to pass through the blood brain barrier. Therefore, in such embodiments, the inhibitors are preferably lipid soluble molecules, or may be modified to increase lipid solubility, or may be co-administered with compounds that enhance passage through the blood brain barrier (see, e.g., WO2014-076655A1, WO2012159052A2, WO1992018529A1).

In compositions and methods according to some embodiments of the present disclosure, levels of amyloid and/or microbially induced amyloid in the tissues, fluids, or feces of the subject are monitored or evaluated during the course of therapy. In some further embodiments, levels of amyloid and/or microbially induced amyloid are monitored before and/or after the course of therapy. In some embodiments, levels of α-synuclein in the tissues, fluids, or feces of the subject are monitored during the course of therapy. In some embodiments, levels of α-synuclein are monitored before and/or after the course of therapy. In some embodiments, measurement of amyloid, microbially induced amyloid, and/or α-synuclein are measured in a fecal sample from the subject. In some embodiments, measurement of amyloid, microbially induced amyloid, and/or α-synuclein are measured in a tissue sample from the subject. In some embodiments, said tissue sample comprises gut epithelium, peritoneum, enteric nervous tissue, olfactory tissue, nasal endothelium, sinus endothelium, brain, and/or nervous tissue. In some embodiments, said tissue sample comprises cerebrospinal fluid or synovial fluid. In some embodiments, said tissue sample comprises blood, lymph, or plasma.

Methods to Identify Compounds

Disclosed herein are methods to identify compounds, which alter the ability of bacterial amyloid to promote aggregation and amyloid formation of the eukaryotic protein α-synuclein. Further disclosed herein are methods of screening for entities useful for the treatment or inhibition of neurodegenerative diseases and screening for entities useful for the prevention or amelioration of the progression of neurodegenerative diseases. Further disclosed herein are methods of screening for entities useful for the treatment or inhibition of gastrointestinal dysfunction related to neurodegenerative diseases. Additionally disclosed herein are methods for studying the molecular etiology of mammalian amyloid diseases and the molecular link between bacterial amyloid production and mammalian amyloid production. According to the methods of the present disclosure, said neurodegenerative diseases and/or mammalian amyloid diseases may comprise one or more of Parkinson's disease (PD), Lewy body dementia, multiple system atrophy, multiple sclerosis (MS), frontotemporal dementia (FTD), REM sleep behavior disorders (RBD), α-synucleinopathy, PD-associated constipation, PD-associated hyposmia, Huntington's Disease, Alexander's Disease, amyotrophic lateral sclerosis (ALS), or Alzheimer's Disease and other diseases in which amyloids are implicated.

The methods as disclosed herein comprise a suite of in vitro assays that measure one or more of the following (1) bacterial amyloid aggregation on the bacterial surface or in the proximal extracellular space; (2) the interaction between bacterial amyloid and α-synuclein in the GI tract or olfactory system (including enteroendocrine cells and enteric neuronal cells); or (3) aggregation of α-synuclein in the GI tract (including enteroendocrine cells and enteric neuronal cells). According to the methods of the present disclosure, α-synuclein should be viewed as a representative amyloid protein of the wider range of known mammalian amyloid or mammalian amyloid precursor proteins, and the methods as disclosed herein may be adapted by one of skill in the art to evaluate the aggregation of any amyloid protein in which a one amyloid protein (bacterial or human) prompts aggregation of another amyloid protein. Representative disorders that present amyloid formation and the proteins involved in these disorders, which may be evaluated using the methods of the present disclosure, include but are not limited to those disclosed in Table 2. Accordingly, in some embodiments, the methods comprise contacting a plurality of concentrations of a microbial amyloid or a microbial amyloid precursor with a plurality of concentrations of α-Synuclein and/or other mammalian amyloid or mammalian amyloid precursor in the presence of a composition, analyzing or measuring the formation or disaggregation of amyloid after the reaction set forth above; and comparing said analysis or measurement to an analysis or measurement of a control, wherein said control comprises analyzing or measuring the formation of amyloid after the reaction set forth above in the absence of said composition. In certain methods and compositions disclosed herein, said microbial amyloid or microbial amyloid precursor comprises CsgA.

In some embodiments, the methods according to the present disclosure contemplate contacting a microbial amyloid or a microbial amyloid precursor (e.g., a composition comprising CsgA) with varying concentrations of a mammalian amyloid or mammalian amyloid precursor in the presence of a composition, said composition comprising a compound or mixture to be tested for its ability to inhibit amyloid formation or enhance amyloid disaggregation. In some further embodiments, said combination of microbial amyloid or microbial amyloid precursor, mammalian amyloid or mammalian amyloid precursor, and test composition are analyzed or measured for changes in the amount of amyloid present. In some further embodiments, the rate and/or extent of amyloid formation within said combination of microbial amyloid or microbial amyloid precursor, mammalian amyloid or mammalian amyloid precursor, and test composition is compared to the rate of amyloid formation within a control sample lacking said composition. In some embodiments, the rate of formation of amyloid is measured. In some further embodiments, the total amount of amyloid formation is measured. In some further embodiments, the temperature of the assay is varied, whereby the stability of the newly-formed amyloid fibrils is measured relative to those formed under native conditions. In some embodiments, the methods are carried out by placing said composition within the wells of a multi-well assay plate. In some further embodiments, the methods according to the present disclosure are carried out in the presence of a physical agitator. In some further embodiments, said physical agitator comprises glass, teflon, or polymer beads. In some further embodiments, said polymer beads may comprise polystyrene, polylactic acid, poly lactic-co-glycolic acid, polycarbonate, or polytetrafluoroethylene (Teflon®) beads. In some embodiments, the beads or objects used for agitation will be from 10-1000 μm in their longest dimension. In some embodiments, the beads or objects used for agitation are from 10-100 μm, from 80-200, from 180-300 μm, from 280-400 μm, from 380-500 μm, from 480-600 μm, from 580-700 μm, from 680-800 μm, from 780-900 μm, or from 880-1000 μm in their longest dimension. In some embodiments, the beads or objects used for agitation will be greater than 1 mm in their longest dimension. In some embodiments, the beads or objects used for agitation will be less than 10 mm in their longest dimension. In certain embodiments, the beads or objects are 1-3 mm, 1-5 mm, 2-5 mm, 3-5 mm, 4-5 mm, 5-6 mm, 5-7 mm, 5-8 mm, 5-9 mm, 5-10 mm, 2-10 mm, 4-10 mm, 6-10 mm, or 8-10 mm. In certain particular embodiments, the beads or objects are 1 mm, 2 mm, 3 mm, 4 mm, 5 mm, 6 mm, 7 mm, 8 mm, 9 mm, or 10 mm in their longest dimension.

In some embodiments, the microbial amyloid or microbial amyloid precursor comprises CsgA, the major protein constituent of curli, also known as adhesive pili, or any analogue or homologue thereof. In some embodiments, the microbial amyloid or microbial amyloid precursor comprises CsgB, which nucleates the conversion of CsgA to its amyloid form, or polypeptides derived therefrom. In some embodiments, said mammalian amyloid or mammalian amyloid precursor comprises α-synuclein.

In some embodiments, contacting microbial amyloid or a microbial amyloid precursor (e.g., a composition comprising CsgA) with varying concentrations of mammalian amyloid or mammalian amyloid precursor with a composition occurs in the presence of an indicator of amyloid formation. In some further embodiments, said indicator may comprise a fluorescent indicator, in which the fluorescence intensity of the indicator varies in a manner correlated with the amount of amyloid present in the sample. Said variation may occur due to changes in fluorescence related to changes in the molecular environment associated with interposition of the label into the assembling amyloid fibril. In some further embodiments, said indicator may comprise thioflavin T (ThT). In some embodiments, labels that are bound to amyloid precursor molecules may show changes in intensity or wavelength of emission due to intermolecular fluorescence quenching or fluorescence resonance energy transfer that is correlated with the formation of amyloid fibrils.

Exemplary fluorescent labels are disclosed in The Molecular Probes Handbook (Invitrogen, Inc., 2010), which is hereby incorporated by reference for its teachings regarding FRET pairs, fluorescence quenching, and fluorescent probes conjugatable to proteins. Other exemplary fluorescent labels may comprise fluorescence proteins, including but not limited to the Green fluorescent protein (GFP), the Yellow Fluorescent Protein (YFP), AmCyan1, AsREd2, mBanana, mCherry, Dendra2, DsRed2, DsRed-express, DsRed-monomer, DsRed, E2-Crimson, GFP-UV, the Blue Fluorescent Protein (BFP), HcRed1, mOrange, PAmCherry, mPlum, mRaspberry, mStrawberry, tdTomato, ZsGreen1, ZsYellow1, or AcGFP1, or their derivatives, or others fluorescent proteins as are known in the art. In some further embodiments, the label attached to the mammalian amyloid precursor is different from the label that is attached to the bacterial amyloid or bacterial amyloid precursor. In some embodiments, the bacterial amyloid or bacterial amyloid precursor is unlabeled. In some embodiments, the mammalian amyloid, mammalian amyloid precursor, bacterial amyloid precursor, or bacterial amyloid contain more than one label. In some further embodiments, said indicator may comprise a colorimetric indicator, a spin label (such as, for example, 3H, 15N or 13C), a metal ion binding compound (such as, for example, a porphyrin, chelator, polyhistidine, or other metal binding polypeptide), an enzyme, or an amyloid-specific antibody. In some embodiments, the development of amyloid fibrils is observed directly by optical microscopy. In some embodiments, amyloid formation is observed by direct light transmission, or by reflectivity. In some embodiments, amyloid formation is observed by total internal reflection FTIR. In some embodiments, amyloid formation is observed by NMR, FTIR, SPIR, or SPR spectroscopy. In some embodiments, amyloid formation is observed and/or confirmed by optical birefringence. In some embodiments, samples are stained with congo red dye prior to visualization. In some embodiments, amyloid formation is observed by Raman scattering. In some embodiments, amyloid formation is observed by monitoring changes in the internal fluorescence of the sample, such as that due to internal tryptophan, tyrosine, phenylalanine, histidine, and arginine residues. In some embodiments, amyloid formation is observed by monitoring the binding of an amyloid-specific antibody, by means as are known in the art such as by conjugation of said antibody to a fluorescent label, a colorimetric label, a spin label, a radioisotope, and enzyme, a fluorescent protein, a metal binding domain or other methods known to those of ordinary skill in the art for the detection or visualization of antibodies. According to the methods as described herein, said antibody may comprise an antibody with binding activity that is selective for either amyloid, or amyloid precursor.

In some embodiments, the methods of the present disclosure may be carried out by monitoring the kinetics of fluorescence intensity of an amyloid specific dye in the presence of a mammalian amyloid precursor, and one or more bacterial amyloid precursors or aggregates. In some embodiments, said mammalian amyloid precursor is α-synuclein. In some embodiments, said bacterial amyloid precursor or aggregate is CsgA. In some embodiments, said amyloid specific dye is Thioflavin T.

In some embodiments, the present disclosure contemplates a kit for the practice of the methods described herein. In some embodiments, said kit comprises at least a mammalian amyloid or mammalian amyloid precursor, a bacterial amyloid or bacterial amyloid precursor, an indicator of amyloid formation as described herein, wherein such indicator may or may not be conjugated to said mammalian amyloid or mammalian amyloid precursor, a bacterial amyloid or bacterial amyloid precursor, and one or more reaction vessels. Said kit may comprise a multi-well plate. Said kit may further comprise instructions for the carrying out of the methods described herein.

The methods of the present disclosure provide methods of screening candidate compounds in order to identify compounds that modulate the aggregation and/or disaggregation of amyloid, especially microbially induced amyloid. In some embodiments, the methods of the present disclosure comprise the screening of a library of candidate compounds. In some further embodiments, the compositions contacted with mammalian amyloid or mammalian amyloid precursor, and bacterial amyloid precursor or bacterial amyloid, according to the methods disclosed herein, comprise one or more compounds, or combinations thereof, suspected in the art to inhibit amyloid formation or to destabilize or disaggregate existing amyloid. In certain embodiments the compositions contacted with mammalian amyloid or mammalian amyloid precursor, and bacterial amyloid precursor or bacterial amyloid, according to the methods disclosed herein, comprise a natural product or an extract from a natural product. In some embodiments the compositions contacted with mammalian amyloid or mammalian amyloid precursor, and bacterial amyloid precursor or bacterial amyloid, according to the methods disclosed herein, comprise an herb, herbal extract, or botanical substance. In some embodiments, said compositions may comprise tissue or fluid from an animal, plant, or fungus. In some further embodiments, said compositions may comprise tissue, fluid, or extracts of tissue or fluid, from a seed, fruit, flower, leaf, stem, cambium, or root of a plant, or combinations thereof. In some further embodiments, said compositions may comprise tissue, fluid, or extracts of a tissue or fluid, from the feces, urine, blood, lymphatic fluid, synovial fluid, cerebrospinal fluid, saliva, or any internal organ of an animal. In some embodiments, said composition may comprise one or more bacteria, or lysates, extracts, conditioned culture media, lyophilized bacteria, lyophilized lysates, lyophilized culture media thereof, or any combination thereof. In some embodiments said bacteria comprise one or more of *Bacteroides, Prevotella, Parabacteroides, Faecalibacterium, Eubacterium, Roseburia, Blautia, Coprococcus*, and *Bifidobacterium*, or any combination thereof.

In some embodiments, the methods of the present disclosure can be used to diagnose or assess the risk for developing an amyloid disorder in a subject. The methods of the present disclosure may be used in the treatment, prevention, and/or amelioration of one or more neurological disorders including Parkinson's Disease, Lewy Body Dementia, incidental Lewy body disease, Lewy body variant of Alzheimer's disease, multiple system atrophy, pure autonomic failure, or any combination thereof. The disorders may include behavioral symptoms as are known in the art of clinical diagnosis and treatment of neurological disorders such as communicative symptoms, stereotyped behaviors, sensorimotor issues, and/or anxiety-like behaviors in addition to physical symptoms as are known in the art of diagnosis and treatment of neurological disorders such as tremors, paralysis, dyskinesia, and/or gastrointestinal symptoms such one or more of constipation, diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof. Accordingly, such clinical and/or diagnostic evaluations and determinations can be used to identify and/or select one or more subjects for receiving one or more compounds described herein in accordance with the one or more methods provided in this disclosure. The methods of the present disclosure may, in some embodiments, include monitoring of the behavioral, physical, and/or gastrointestinal symptoms as are known in the art of diagnosis and treatment of neurological disorders. In some embodiments, the methods according to the present disclosure incorporate monitoring changes in the behavior of a subject. In some further embodiments, the methods according to the present disclosure incorporate monitoring the subject for behavioral symptoms as are known to be related to Parkinson's Disease, Lewy Body Dementia, incidental Lewy body disease, Lewy body variant of Alzheimer's disease, multiple system atrophy, pure autonomic failure, or any combination thereof. In some further embodiments, the methods according to the present disclosure incorporate monitoring the subject for bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, or any combination thereof or any other symptom known to those in the art of neurological diagnosis or treatment to be useful in the diagnosis of amyloid disorders, and especially α-synucleinopathies. In some further embodiments, the methods according to the present disclosure incorporate monitoring the subject for gut motility, including gastroparesis, colonic motility, anorectal dysfunction and dyssynergic defecation. Again, such clinical and/or diagnostic evaluations and determinations can be used to identify and/or select one or more subjects for diagnosis and/or treatment according to the methods described herein. In some embodiments, the methods of the present disclosure may include monitoring of levels of bacterial, host-derived, and microbially-induced amyloid as disclosed herein in addition to the aforementioned clinical monitoring. According to the methods of the present disclosure, said amyloid may be monitored in the gut, feces, urine, blood, saliva, cerebrospinal fluid, and/or synovial fluid of a subject. The methods of the present disclosure contemplate the monitoring of said amyloid in any tissue or fluid obtainable from a subject during the course of treatment, and thereby identifying whether said sample contains factors which enhance or inhibit amyloid formation. In some embodiments, a subject from whom a tissue, fluid, or other sample is derived, for which sample the assays described herein indicate the presence of factors, which enhance or accelerate amyloid formation, may be considered to be at elevated risk of developing an amyloid disorder. In some embodiments, said subject may be administered a drug or treatment to ameliorate or prevent said amyloid disorder. Again, such clinical and/or diagnostic evaluations and determinations can be used to identify and/or select one or more subjects for receiving one or more compounds described herein in accordance with the one or more methods provided in this disclosure.

According to the methods disclosed herein, a treatment or inhibition of a disorder implicating amyloid formation may be achieved by modulating the dosing schedule for the administration of a composition such that subjects experience periodic partial or full reductions in dosing for fixed amounts of time, followed by a resumption of dosing. In some embodiments, dosages are administered daily for between one and thirty days, followed by a dosing holiday lasting for between one and thirty days. In some embodiments, during the dosing holiday, no dose is administered. In some further embodiments, the composition of the present disclosure is allowed to clear completely from the subject's body prior to administration of the next dose. In some other embodiments, during the dosing holiday, a dose less than the usual daily dose is administered. In some further embodiments, an amount of the administered composition less than the therapeutically effective amount is allowed to remain within the subject during the dosing holiday. In some further embodiments, an amount of the administered composition sufficient to maintain therapeutic levels in the affected tissues is allowed to remain within the subject. In some embodiments, a composition is administered at any time following the onset of one or more of the aforementioned symptoms of a neurological disorder associated with amyloid formation. In some embodiments, a composition according to the methods described herein is administered prior to the onset of symptoms of said disorder or disorders. In some embodiments, a composition according to the methods described herein is administered concurrently with or after the onset of symptoms of said disorder or disorders.

The following items are set forth in accordance with some embodiments herein.

1. A method of disrupting and/or inhibiting the formation of aggregates of amyloid proteins comprising contacting amyloid or a precursor of amyloid with a composition comprising a compound described herein.
2. A method of inhibiting the formation of aggregates of amyloid proteins comprising contacting amyloid or a precursor of amyloid with a composition comprising a compound described herein.
3. A method of disrupting the formation of aggregates of amyloid proteins in a subject comprising:
   administering to said subject a composition comprising a compound described herein; and
   optionally, selecting said subject to receive the benefit of a molecule that disrupts the formation of amyloid aggregates, such as by clinical or diagnostic evaluation, prior to administering said composition; and/or
   optionally, measuring a disruption or inhibition of the formation of amyloid aggregates in said subject after administration of said composition.
4. A method of disrupting the formation of aggregates of amyloid proteins comprising contacting amyloid or a precursor of amyloid with a composition comprising a compound described herein.
5. A method of inhibiting, ameliorating, reducing the likelihood, delaying the onset of, treating, or preventing an amyloid disorder, the method comprising administering to a subject in need thereof a compound described herein, or a pharmaceutical composition thereof.
6. The method of Item 5, wherein the amyloid disorder is selected from the group consisting of: α-synucleinopathy, Parkinson's Disease, Lewy Body Dementia, incidental Lewy body disease, Lewy body variant of Alzheimer's disease, multiple system atrophy, or pure autonomic failure, or any combination thereof.
7. The method of any one of Items 5-6, wherein the amyloid disorder comprises intestinal amyloid proteins or aggregates, for example proteins or aggregates that comprise a bacterial protein such as CsgA.
8. The method of any one of Items 5-7, wherein the amyloid disorder is intestinal dysbiosis, intestinal hyperpermeability, irritable bowel syndrome (IBS), inflammatory bowel disease (IBD), ulcerative colitis and Crohn's disease.

9. The method of any one of Items 5-8, further comprising detecting a presence or level of a bacterial protein, such as CsgA, nucleic acids encoding the microbial protein, or a microorganism that produces the bacterial protein in an intestinal sample of the subject.
10. The method of Item 9, wherein the subject is selected as in need of the composition if a presence of the bacterial protein or the microorganism that produces the bacterial protein is detected in the intestinal sample, or if a level of the bacterial protein or the microorganism that produces the bacterial protein in the intestinal sample is greater than a predetermined level or control.
11. The method of any one of Items 7-10, further comprising determining a decrease or absence of the intestinal amyloid proteins following the administration.
12. The method of any one of Items 7-11, further comprising identifying the subject as displaying a gastrointestinal symptom.
14. The method of any one of Items 5-12, wherein the subject suffers from gastrointestinal symptoms comprising one or more of dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, hypersalivation (sialorrhea), anorectal dysfunction, dyssynergic defecation, and nausea.
16. The method of any of Items 1-14, wherein said composition is formulated for enteric, oral, or intranasal delivery.
17. The method of any of Items 1-16, wherein said composition is formulated for controlled release within the lower intestine or colon.
18. The method of any of Items 1-17, wherein said composition is an enteric-coated capsule, tablet, softgel, spray dried powder, polymer matrix, hydrogel, enteric-coated solid, crystalline solid, amorphous solid, glassy solid, coated micronized particle, liquid, nebulized liquid, aerosol, or microcapsule.
19. The method of any of Items 1-18, wherein said amyloid proteins comprise one or more mammalian proteins such as, any one or more of α-synuclein, tau, Beta amyloid from Amyloid precursor protein, Medin, Apolipoprotein AI, Atrial natriuretic factor, Beta amyloid, Cystatin, IAPP (Amylin), Beta-2 microglobulin, Transthyretin, PrP, Gelsolin, Lysozyme, Huntingtin, Keratoepithelin, Calcitonin, Prolactin, Serum amyloid A, SOD1, and/or Immunoglobulin light chain AL.
20. The method of any of Items 1-19, wherein said amyloid proteins comprise one or more bacterial or fungal proteins, such as CsgA.
21. The method of any of Items 1-20, wherein said amyloid proteins comprise a bacterial protein, such as CsgA.
22. The method of any of Items 1-21, wherein said amyloid proteins are present within the gastrointestinal tract, cranial sinus, oral cavity, or nasal cavity.
23. The method of any of Items 1-22, wherein said amyloid proteins are present within enteric nervous tissue or the olfactory bulb.
24. The method of any of Items 1-23, wherein the composition is administered daily.
25. The method of any of Items 1-24, wherein the composition is administered multiple times per day.
26. The method of any of Items 1-25, wherein the composition is administered less frequently than daily.
27. The method of any of Items 1-24 or 26, wherein the composition is administered every second day, every third day, every fourth day, every fifth day, every sixth day, or every seventh day.
28. The method of any of Items 1-27, further comprising measuring or evaluating enteric amyloid levels and/or amyloid proteins during the course of administration.
29. The method of any of Items 1-28, further comprising measuring or evaluating enteric amyloid levels and/or amyloid proteins following the course of administration.
30. The method of any of Items 1-29, further comprising measuring or evaluating a change in the nervous system, such as a neurological symptom or behavior of the subject.
31. The method of any of Items 1-30, wherein said subject is under the age of 18, 18-30, 30-50, 50-60, 60-70, or over the age of 70.
32. The method of any of Items 1-31, further comprising measuring or evaluating a change in the gastrointestinal system, such as a gastrointestinal symptom or behavior of the subject.
33. The method of Item 32, wherein said gastrointestinal symptom comprises constipation.
34. The method of any of Items 1-33, wherein said subject suffers from gastrointestinal symptoms comprising one or more of constipation, diarrhea, abdominal pain and/or cramping, bloating, flatulence, nausea, or any other symptoms of irritable bowel syndrome (IBS), inflammatory bowel disease (IBD), such as ulcerative colitis and Crohn disease), intestinal hyperpermeability, or any combinations thereof.
35. The method of any of Items 1-34, wherein the composition is administered following the appearance of a neurological symptom or condition.
36. The method of Item 35, wherein said neurological symptom or condition comprises one or more of anosmia, hyposmia, bradykinesia, ataxia, tremor, muscle rigidity, impaired posture and balance, loss of automatic movements, dysarthria or other speech changes, handwriting changes, orthostatic hypotension, memory deficit, dysphagia, incontinence, sleep disruption, cardiac arrhythmia, visual disturbance, psychiatric problems including depression and visual, auditory, olfactory, or tactile hallucinations, vertigo, cognitive dysfunction, altered dopamine levels, altered serotonin levels, altered kynurenine levels, and/or any combination thereof.
37. The method of any of Items 1-36, wherein the composition is administered prior to the appearance of a neurological symptom or condition.
38. The method of any of Items 1-37, wherein the method is repeated.
39. The method of any of Items 1-38, wherein, for a given administration, the composition is different from a composition previously administered.
40. The method of any of Items 1-39, wherein, for a given administration, the dose administered is different from a dosage previously administered.
41. The method of any of Items 1-40, wherein the composition is co-administered with a caffeine, nicotine, theophylline, theobromine, xanthine, methylxanthine, or derivatives thereof.

42. The method of any of Items 1-41, further comprising administering to said subject an inhibitor of α-synuclein aggregation.
43. The method of any of Items 1-42, wherein said subject is one that has been identified or selected as being at risk for developing or already having Parkinson's disease, such as by clinical or diagnostic evaluation.
44. The method of any of Items 1-43, wherein said subject is one that has been identified or selected as being at risk for developing or already having Lewy Body Dementia, incidental Lewy body disease, Lewy body variant of Alzheimer's disease, multiple system atrophy, pure autonomic failure, or any combination thereof, such as by clinical or diagnostic evaluation.
45. The method of item 14, wherein the gastrointestinal symptoms are associated with Parkinson's Disease or Parkinsonism.
46. The method of any one of items 1-44, wherein the amyloid disorder can be diagnosed by detecting the presence or level of intestinal bacterial amyloid proteins.

Additional Options

The following options are set forth in accordance with some embodiments herein.

A method of identifying a composition that affects the formation of microbially-induced amyloid, comprising:
(a) contacting a plurality of concentrations of a microbial amyloid or a microbial amyloid precursor (e.g., CsgA) with a plurality of concentrations of α-Synuclein in the presence of a composition comprising a compound described herein;
(b) analyzing or measuring the formation of amyloid produced by the reaction set forth in (a); and
(c) comparing the analysis or measurement made in (b) with an analysis or measurement of a control, wherein said control comprises analyzing or measuring the formation of amyloid after the reaction set forth in (a) in the absence of said composition.

2. The method of Option 1, wherein said microbial amyloid or microbial amyloid precursor comprises CsgA.
3. The method of Options 1 or 2, further comprising agitation during (a).
4. The method of Options 1-3, wherein the contacting performed in (a) is conducted in the presence of an indicator of amyloid formation.
5. The method of Option 4, wherein said indicator is a fluorescent indicator, a spin-labeled indicator, an enzyme, an antibody, or a colorimetric indicator.
6. The method of Option 4, wherein said indicator is Thioflavin T.
7. The method of Option 4 wherein said antibody has specificity for aggregated α-Synuclein, and wherein said antibody optionally is conjugated to a fluorescent label, an enzyme, a colorimetric label, a spin label, a metal ion binding moiety, a nucleic acid, a polysaccharide, or a polypeptide.
8. The method of any of Options 1-7, wherein said CsgA and said α-Synuclein are each separately labeled.
9. The method of any of Options 1-8, wherein the formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.
10. The method of any of Options 1-9, wherein said composition comprises a mixture of compounds.
11. The method of any of Options 1-10, wherein said composition comprises tissue, bodily fluid or an extract thereof.
12. The method of any of Options 1-11, wherein said composition comprises feces, urine, blood, spinal fluid, or saliva, or a component thereof.
16. The method of any of Options 1-10 wherein said composition comprises one or more bacteria, bacterial extracts, lysates, conditioned culture media, lyophilized bacteria, lyophilized lysates, lyophilized culture media, or any combination thereof.
17. The method of any of Options 1-16, further comprising identifying or selecting compositions that alter amyloid formation.
18. The method of any of Options 1-17, further comprising identifying or selecting compositions that reduce amyloid formation.
19. The method of any of Options 1-18, wherein the rate of formation of amyloid is analyzed or measured in (b).
20. A method of making microbially-induced amyloid, comprising:
(a) contacting a plurality of concentrations of a microbial amyloid or a microbial amyloid precursor (e.g., CsgA) with a plurality of concentrations of α-Synuclein in the presence of a composition comprising a compound described herein;
(b) providing conditions that allow for the formation of new microbially-induced amyloid; and
(c) analyzing or quantifying the microbially-induced amyloid formed in (b).
21. The method of Option 20, wherein said microbial amyloid or microbial amyloid precursor comprises CsgA.
22. The method of Options 20 or 21, further comprising agitation during (a).
23. The method of any of Options 20-22, wherein the contacting performed in (a) is conducted in the presence of an indicator of amyloid formation.
24. The method of Option 23, wherein said indicator is a fluorescent indicator, a spin-labeled indicator, or a colorimetric indicator.
25. The method of Options 23 or 24, wherein said indicator is Thioflavin T.
26. The method of any of Options 20-25, wherein said CsgA and said α-Synuclein are each separately labeled.
27. The method of any of Options 20-26, wherein the formation is analyzed or measured by internal fluorescence, by fluorescence of a dye or label, by fluorescence resonance energy transfer, by fluorescence polarization, by fluorescence polarization transfer, by UV/Vis Spectroscopy, by magnetic resonance, by Raman scattering, by electron paramagnetic spin resonance, by light microscopy, by electron microscopy, by scanning tunneling microscopy, or by atomic force microscopy.
28. The method of any of Options 20-27, wherein said composition comprises a mixture of compounds.
29. The method of any of Options 20-28, wherein said composition comprises tissue, bodily fluid or an extract thereof.

30. The method of any of Options 20-29, wherein said composition comprises feces, urine, blood, spinal fluid, or saliva, or a component thereof.
31. The method of any of Options 28-30 wherein said composition comprises one or more bacteria, bacterial extracts, lysates, conditioned culture media, lyophilized bacteria, lyophilized lysates, lyophilized culture media, or any combination thereof.
35. The method of any of Options 20-34, further comprising identifying or selecting compositions that reduce amyloid formation.
36. The method of any of Options 20-35, wherein the rate of formation of amyloid is analyzed or quantified in (c).
37. A kit comprising a microbial amyloid or a microbial amyloid precursor and α-Synuclein, being present in one or more containers within said kit.
38. The kit of Option 37, wherein said microbial amyloid or microbial amyloid precursor comprises CsgA.
39. A method of treating or inhibiting an amyloid disorder in a subject comprising:
(a) contacting a plurality of concentrations of a microbial amyloid or a microbial amyloid precursor with a plurality of concentrations of α-Synuclein in the presence of a composition;
(b) analyzing or measuring the formation of new amyloid after the reaction set forth in (a);
(c) comparing the analysis or measurement made in (b) with an analysis or measurement of a control, wherein said control comprises analyzing or measuring the formation of amyloid after the reaction set forth in (a) in the absence of said composition; and
(d) if the formation of amyloid in the presence of said composition is increased relative to the formation of amyloid in the absence of said composition, administering to said subject an effective amount of a pharmaceutical composition suitable for inhibiting or treating said amyloid disorder.
40. The method of Option 39, wherein said microbial amyloid or microbial amyloid precursor comprises CsgA.
41. The method of any of Options 39-40, wherein said composition comprises tissue, bodily fluid or an extract thereof.
42. The method of any of Options 39-41, wherein said composition comprises feces, urine, blood, spinal fluid, or saliva, or a component thereof.
43. The method of Options 39-42, wherein said pharmaceutical composition comprises one or more probiotic bacteria.
44. The method of Options 39-43, wherein said pharmaceutical composition comprises one or more bacteria selected from the group consisting of *Bacteroides, Prevotella, Parabacteroides, Faecalibacterium, Eubacterium, Roseburia, Blautia, Coprococcus*, and *Bifidobacterium*, or any combination thereof.
45. The method of Options 39-44, wherein said pharmaceutical composition comprises one or more bacteria selected from the group consisting of *B. fragilis, B. vulgatus*, and *B. thetaiotaomicron*; or any combination thereof.
46. The method of any of Options 39-45, wherein the rate of formation of amyloid is analyzed or quantified in (b).
47. The method of any of Options 39-46, further comprising identifying or selecting said subject as one that would benefit from a treatment or inhibition of an amyloid disorder.

48. The method of any of Options 39-47, further comprising identifying or selecting said subject as one at risk of or showing symptoms of one or more of Parkinson's Disease, Lewy Body Dementia, incidental Lewy body disease, Lewy body variant of Alzheimer's disease, multiple system atrophy, pure autonomic failure, or any combination thereof.

EXAMPLES

Example 1

To a subject, one or more of the compounds described herein (or a composition thereof) is administered orally or rectally on a regular basis, such as daily. Bacterial amyloid formation in the GI tract and/or α-synuclein aggregation levels within the GI tissue are monitored by fecal sampling or by biopsy. Therapy is continued to prevent bacterial amyloid (curli) formation and/or α-synuclein aggregation. Changes in the patient's GI function and motor symptoms are monitored. For subjects in which the administration of said one or more compounds results in reduced formation of microbially-induced amyloid in the gut, improvements in one or more GI symptoms, one or more motor symptoms and/or one or more neurological symptoms are observed.

Example 2

One or more of the compounds described herein are obtained or synthesized and incorporated into an enteric or colon-selective formulations to release material at site of action and by-pass the stomach and most of the small intestine. This provides delivery of the composition at the site of curli production and/or α-synuclein aggregation, and minimizes absorption of the composition into systemic circulation.

Example 3

One or more of the compounds described herein are obtained or synthesized and incorporated into a formulation for controlled release in the lower small intestine or in the colon. This provides for lower and/or less frequent dosing, and side effects are minimized. Controlled release in the lower small intestine or colon may be achieved by any of a variety of approaches known in the art and includes enteric coated capsules, tablets, soft gels, intrinsically enteric capsules, multi-layered formulations, coated micronized forms of the polymeric material, and the like.

Example 4

A subject is administered a combination of more than one of the compounds described herein. Combining a curli inhibitor with an α-synuclein aggregation inhibitor blocks aggregation at two critical points simultaneously. For subjects in which the administration of said one or more compounds results in reduced formation of microbially-induced amyloid in the gut, improvements in one or more GI symptoms, one or more motor symptoms and/or one or more neurological symptoms are observed or measured.

Example 5

Roles of functional amyloid formation in curli-driven pathophysiology were examined in mice using techniques described in international publication number WO/2018/

Figure 1B:
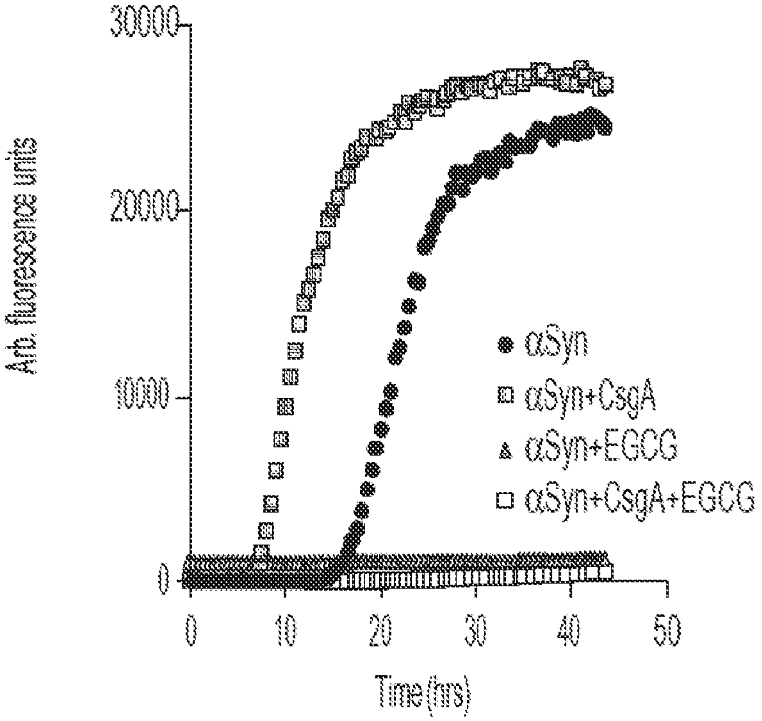
FIG. 1B is a graph showing in vitro αSyn aggregation measured by Thioflavin T fluorescence during αSyn amyloid formation alone or in the presence of CsgA (25:1 molar ratio), with and without EGCG (50 M) treatment.

213204, the entire content of which are herein incorporated by reference. As an initial matter, effects of epigallocatechin gallate (EGCG) on biofilm growth by wild-type *E. coli* were examined, along with effects of EGCG on αSyn amyloid formation in vitro. FIG. 1A is a graph showing Crystal violet staining of biofilm growth by wild-type *E. coli* following 4 days in static culture, with indicated concentrations of EGCG; data assessed by optical density (OD). FIG. 1B is a graph showing in vitro αSyn aggregation measured by Thioflavin T fluorescence during αSyn amyloid formation alone or in the presence of CsgA (25:1 molar ratio), with and without EGCG (50 M) treatment.

Example 6

Figure 2A:
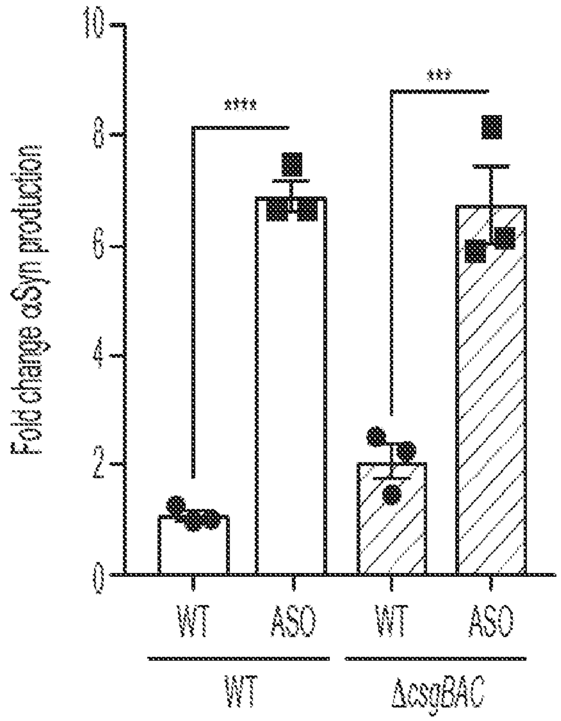
FIGS. 2A-G are a series of graphs and images depicting that mono-colonization with curli-sufficient bacteria induce increased αSyn-dependent pathology and inflammatory responses in the brain. Germ-free (GF) wild-type (WT) or Thy1-αSyn (ASO) animals were mono-colonized with either wild-type, curli-sufficient *E. coli* (WT) or curli-deficient *E. coli* (ΔcsgBAC).
Figure 2B:
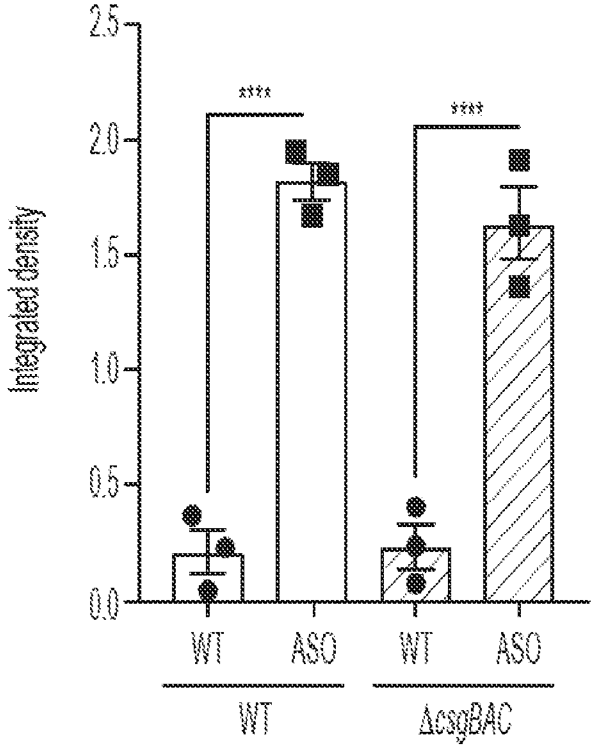
Figure 2C:
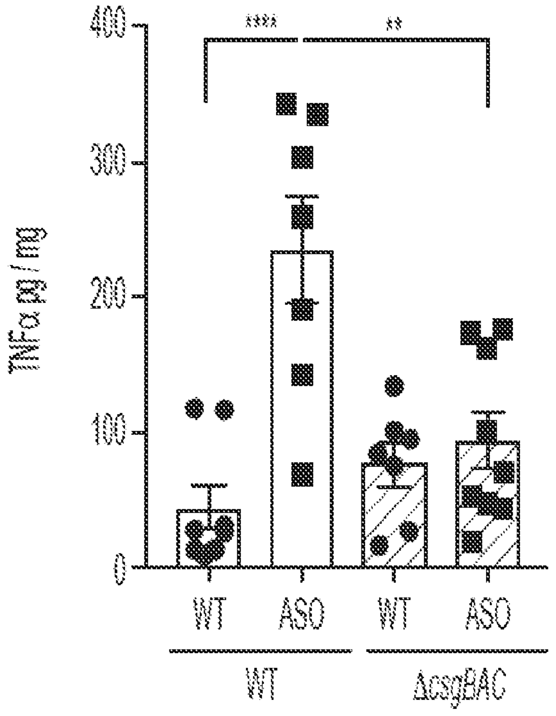
Figure 2D:
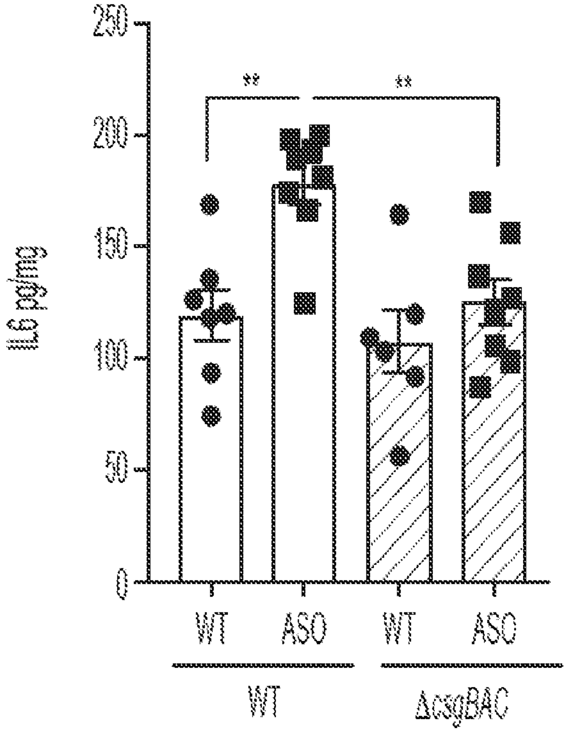
Figure 2E:
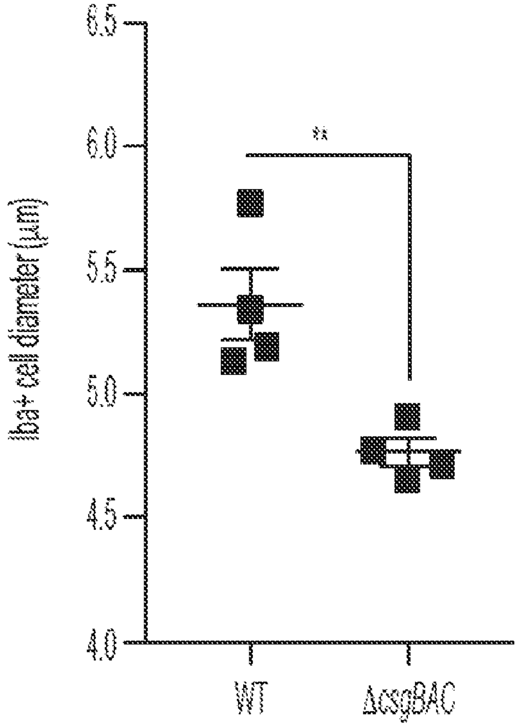
Figure 2F:
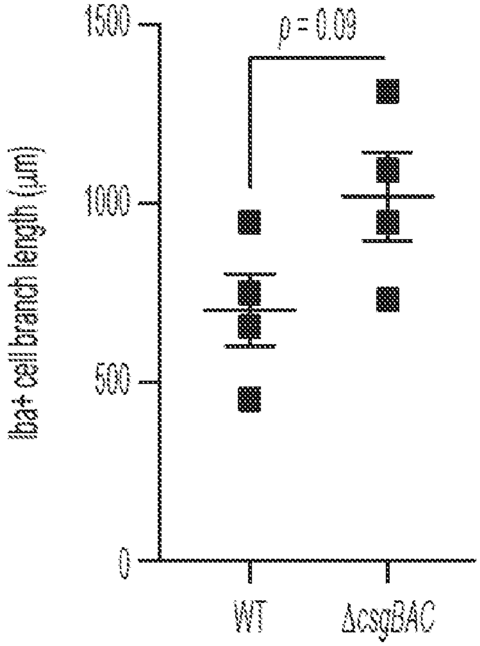
Figure 2G:
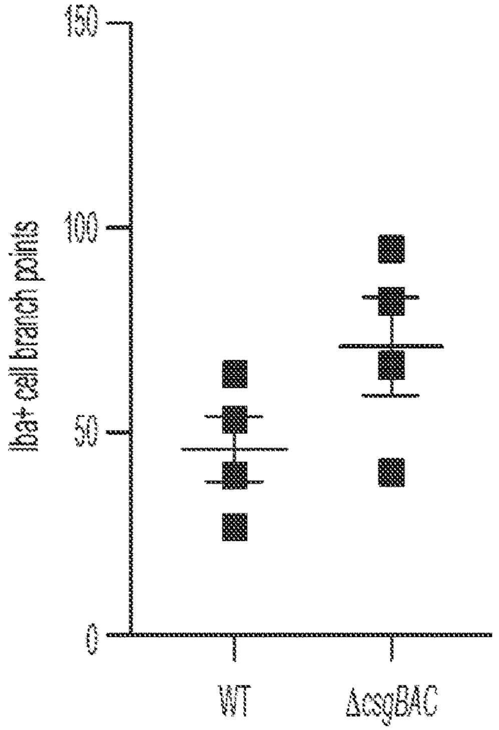
Figure 2H:
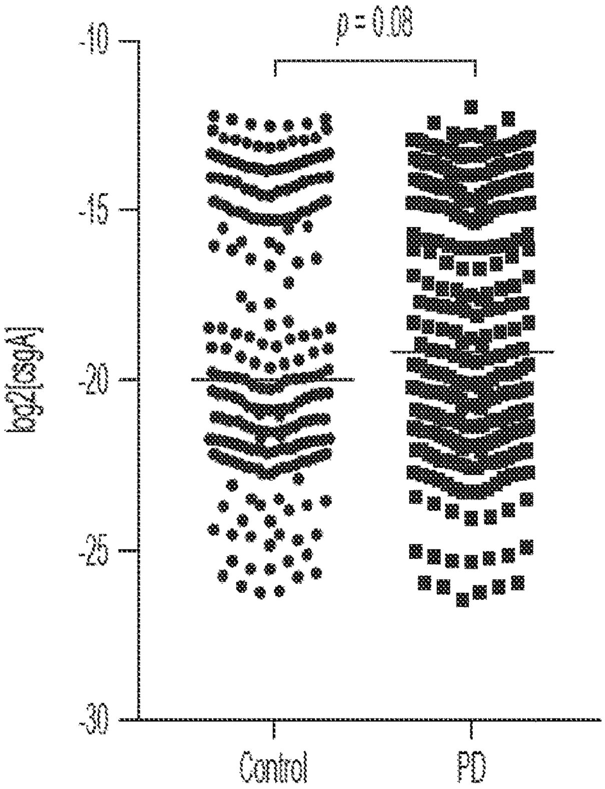
FIGS. 2H-J are a series of graphs showing levels of csgA in human fecal samples (FIG. 2H), in wild-type mice colonized with microbes derived from persons with PD or matched controls (FIG. 2I), or in Thy1-αSyn (ASO) mice colonized with microbes derived from persons with PD or matched controls (FIG. 2J). Consistent with these data, csgA is predicted to be enriched in microbes derived from persons with PD.
Figure 2I:
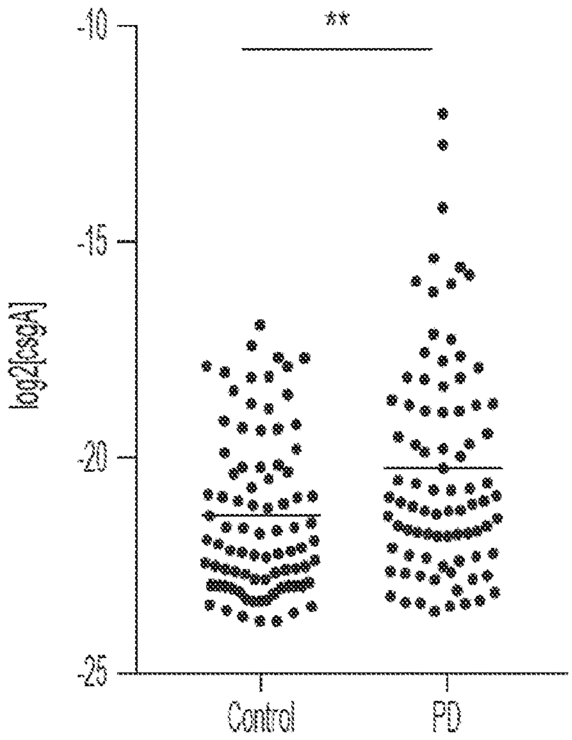
Figure 2J:
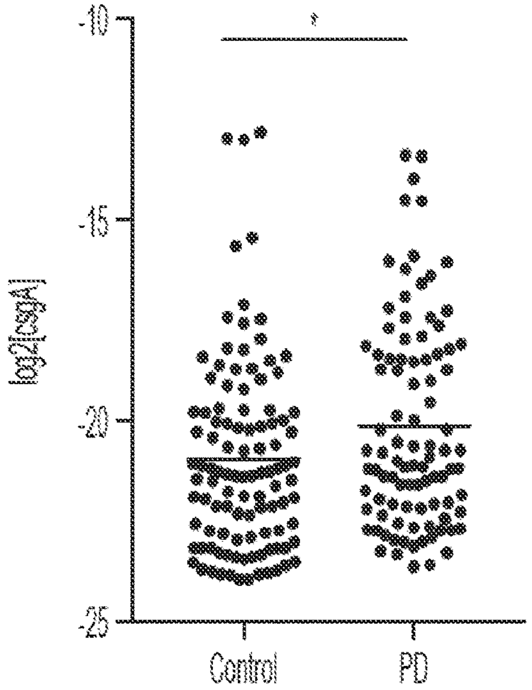

Additional experiments, using techniques described in international publication number WO/2018/213204, the entire content of which are herein incorporated by reference, showed that mono-colonization with curli-sufficient bacteria induce increased αSyn-dependent pathology and inflammatory responses in the brain. Germ-free (GF) wild-type (WT) or Thy1l-αSyn (ASO) mice were mono-colonized with either wild-type, curli-sufficient *E. coli* (WT) or curli-deficient *E. coli* (ΔcsgBAC). FIG. 2A is a graph showing total αSyn in whole brain lysates quantified by ELISA. FIG. 2B is a graph showing quantification of insoluble αSyn fibrils in the striatum by dot blot assay. FIGS. 2C-D show quantification of TNFα (FIG. 2C) and IL-6 (FIG. 2D) by ELISA from the striatum. FIGS. 2E-G show the results of staining thin sections of brains derived from ASO mice were stained for Iba1 (microglia), 3D cellular reconstructions generated, and morphological characteristics quantified of microglia resident in the striatum. n=3 (FIGS. 2A-B), n=6-7 (FIG. 2C, 2D), n=4 (FIGS. 2E-G) (averaged from 20-40 cells for diameters, or 5-7 cells for branching). Points represent individuals, bars represent the mean and standard error. Data analyzed by one-way ANOVA with Tukey post-hoc test for FIGS. 2A-D, or two-tailed t-test for FIGS. 2E and 2F *p≤0.05; p 0.01; *p 0.001; **p≤0.0001. Consistent with this effect of curli-sufficient bacteria on mouse models, it is shown that the relative abundance of csgA is increased in the gut of human Parkinson's Disease (PD) patients. Relative abundance of csgA was determined by PICRUSt analysis of available 16S RNA data from human fecal samples (ENA Accessions: PRJNA268515, PRJEB4927, and PRJEB14674). Based on this analysis, it was observed that relative abundance of csgA was higher in the gut of the PD patients (FIG. 2H). Furthermore, wild-type (FIG. 2I) or Thy1-αSyn (ASO) (FIG. 2J) mice were colonized with microbes derived from persons with PD or matched controls (ENA Accession: PRJEB17694), and PICRUSt imputed analysis of 16s rRNA sequences indicated greater abundance in the PD-transplanted microbiomes compared to healthy controls (FIG. 2K). For FIGS. 2**H-J, points represent individuals, bars represent the mean, data analyzed by two-tailed Mann-Whitney test. *p≤0.05; **p≤0.01. Thus, it is observed that the presence or elevated levels (compared to healthy controls) of bacterial proteins such as csgA in the gut correlates with amyloid disorders, including PD.

Example 7

Figure 3A:
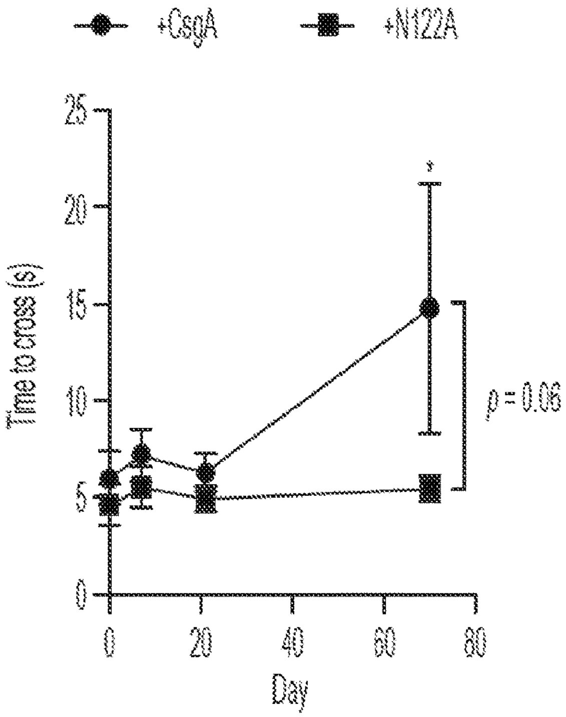
FIGS. 3A-I are a series of graphs depicting that intestinal curli promotes progressive synuclein-dependent pathophysiology. Conventionally-raised Thy1-αSyn (ASO) animals were injected intestinally with 30 g of synthetic CsgA hexamer (CsgA; N-QYGGNN-C) or non-amyloidogenic peptide (N122A; N-QYGGNA-C). For FIGS. 3A-G, motor and GI function tested overtime at 0, 7, 21, and 70 days post-injection in the beam traversal (FIG. 3A), pole descent (FIG. 3B), adhesive removal (FIG. 3C), hindlimb clasping score (FIG. 3D), wirehang (FIG. 3E), and fecal output assessments (at day 70) (FIG. 3F).
Figure 3B:
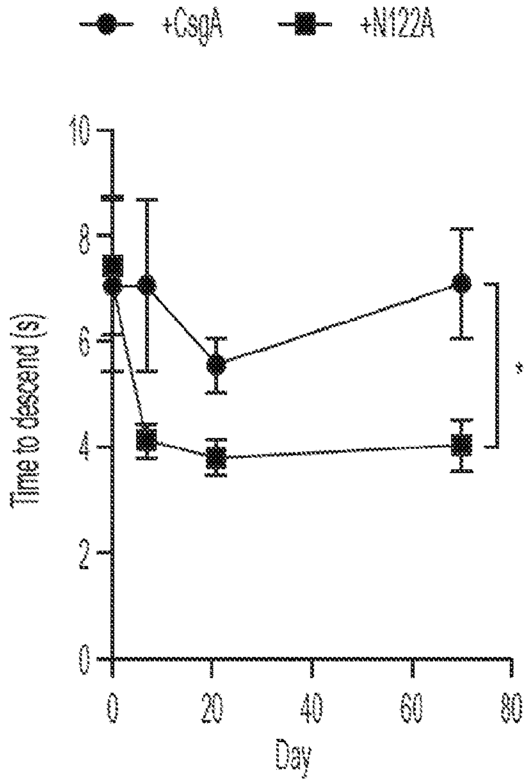
Figure 3C:
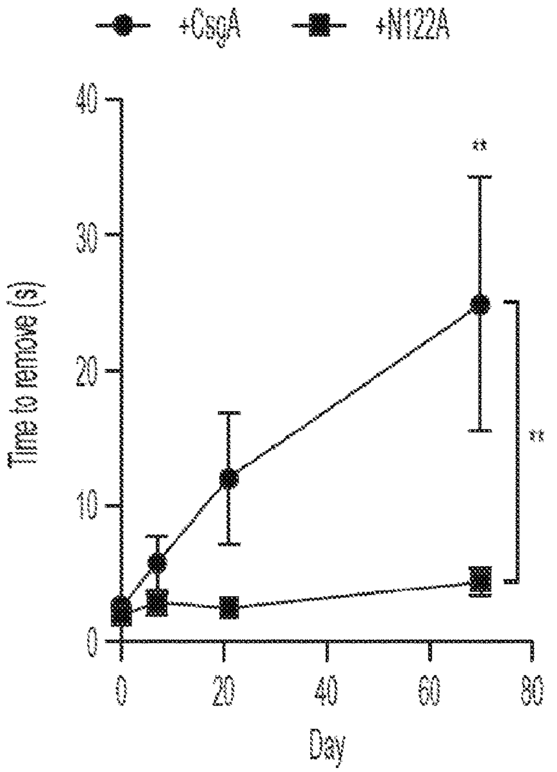
Figure 3D:
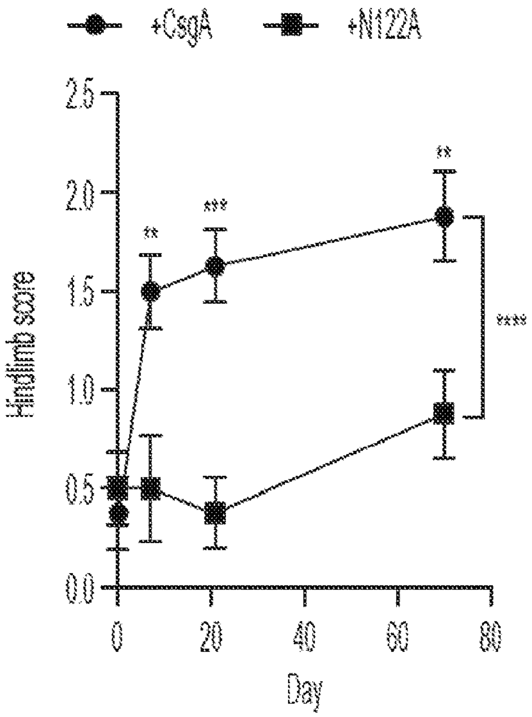
Figure 3E:
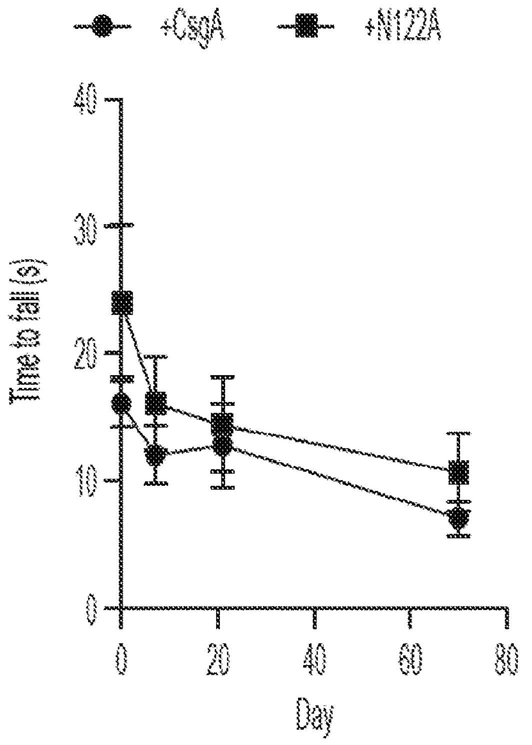
Figure 3F:
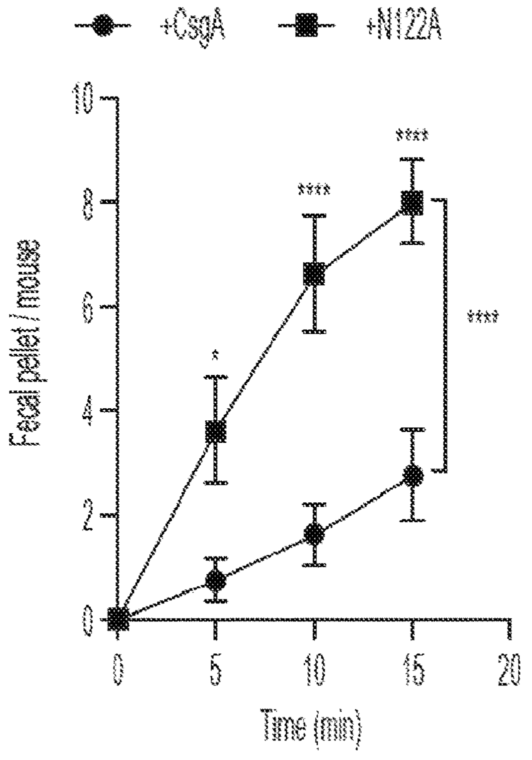
Figure 3G:
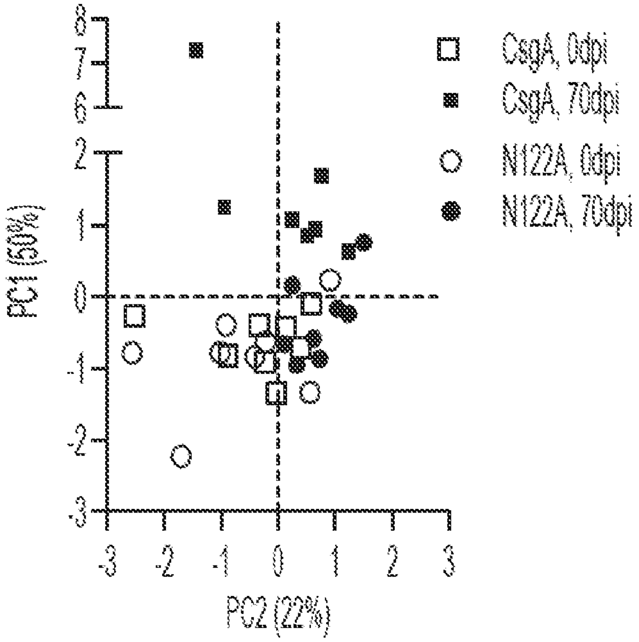
Figure 3H:
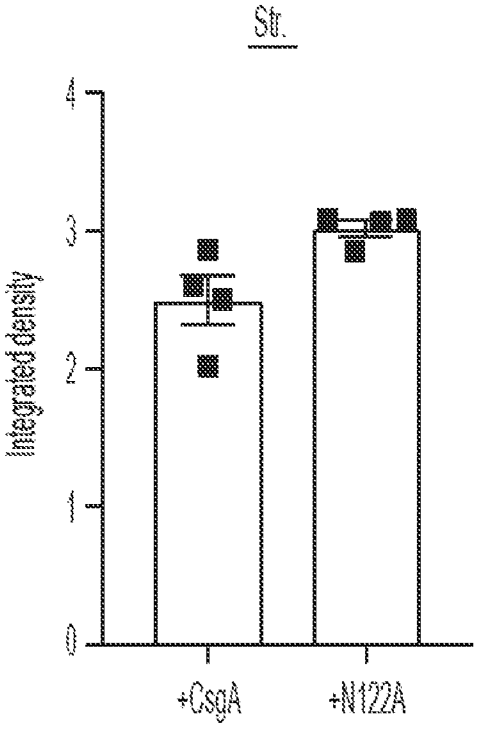
Figure 3I:
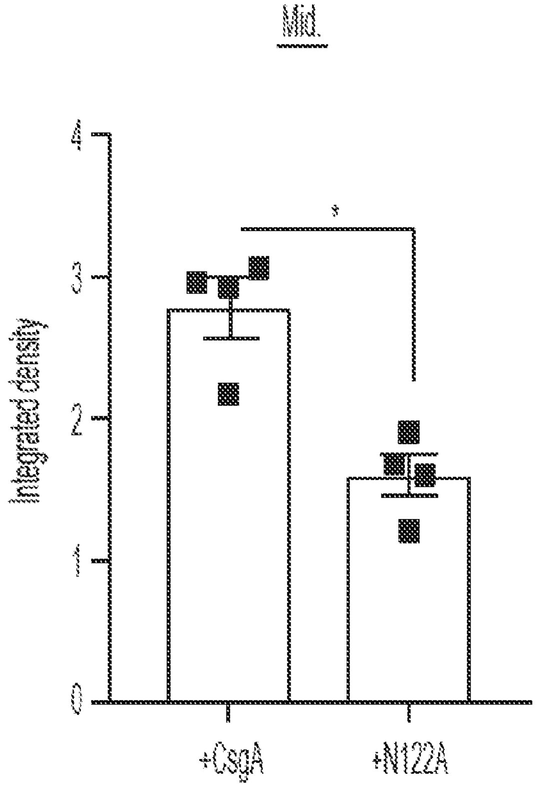
Figure 4A:
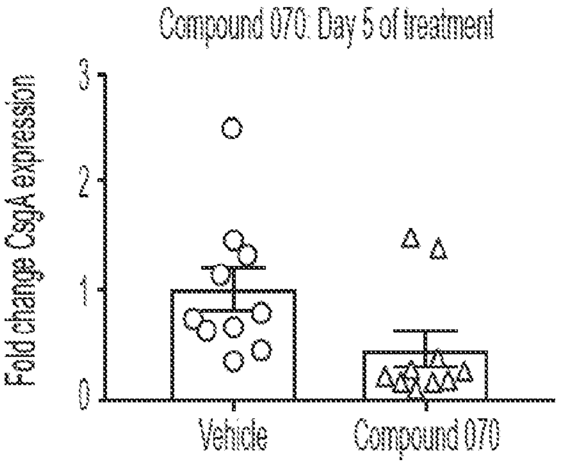
FIGS. 4A-B depict data from an in vivo study utilizing the procedure of Example 27A, indicating reduction of csgA expression in *E. coli* MC4100 monocolonized mice on day five of treatment with 30 mg/kg Compound 070 (A) or 30 mg/kg Compound 016 (B) relative to mice treated with vehicle alone.
Figure 4B:
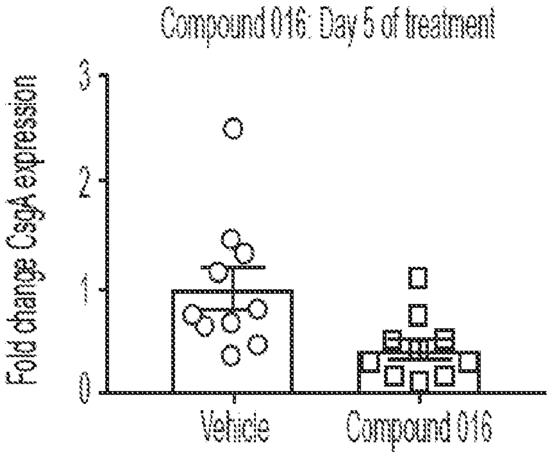
Figure 5:
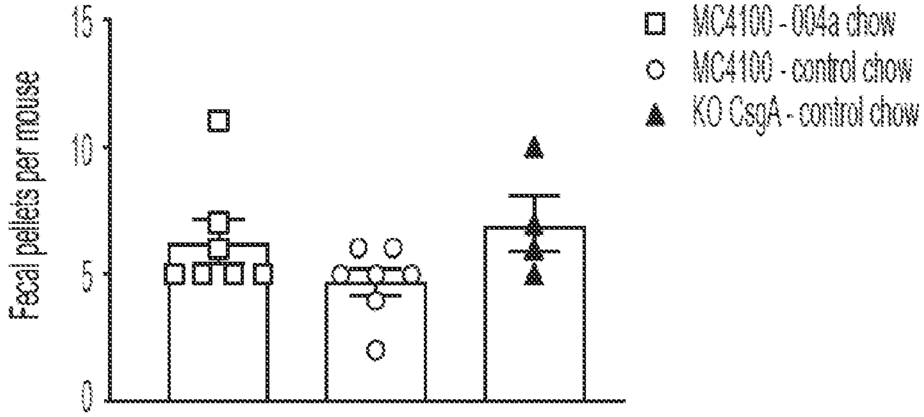
FIG. 5 is a graph showing the number of fecal pellets a mouse produced at 15 min interval when the animals were 12-14 weeks of age.
Figure 6:
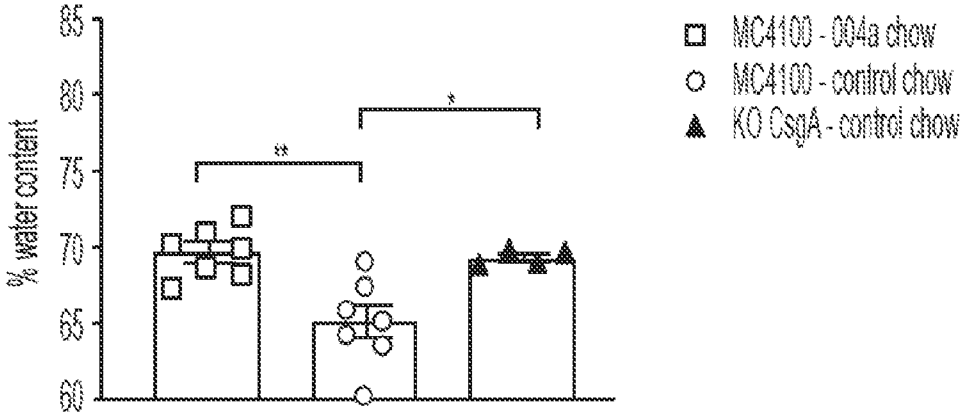
FIG. 6 is a graph showing fecal water content measured when the animals were 12-14 weeks of age.
Figure 7:
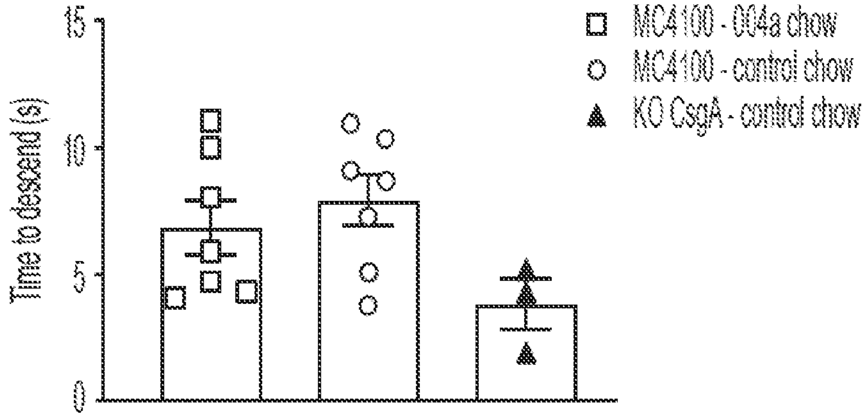
FIG. 7 is a graph showing time to descend from a pole into a home cage at 18-20 weeks of age.
Figure 8A:
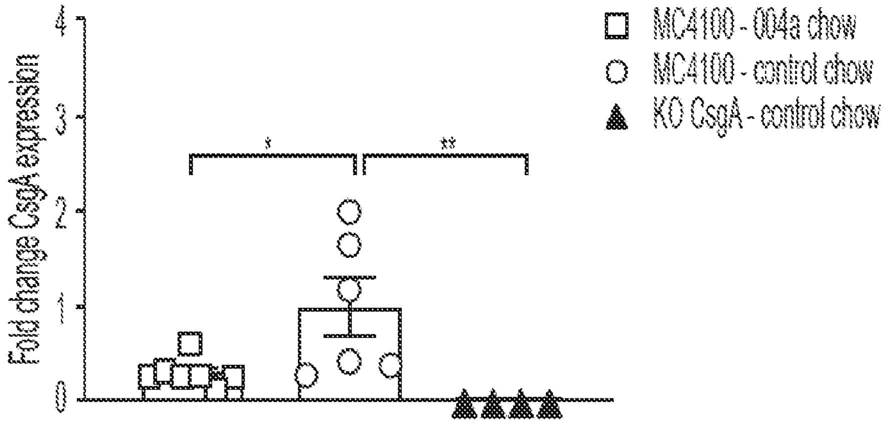
FIGS. 8A-D are a series of graphs depicting reduction of csgA expression in *E. coli* MC4100 monocolonized mice with compound 004a treatment as early as 12-14 weeks of age. This effect was repeated and observed again at 14-16 weeks of age.
Figure 8B:
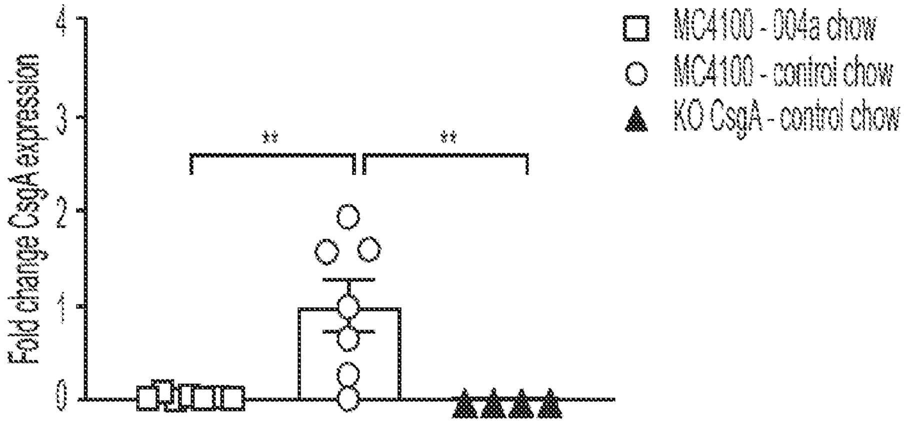
Figure 8C:
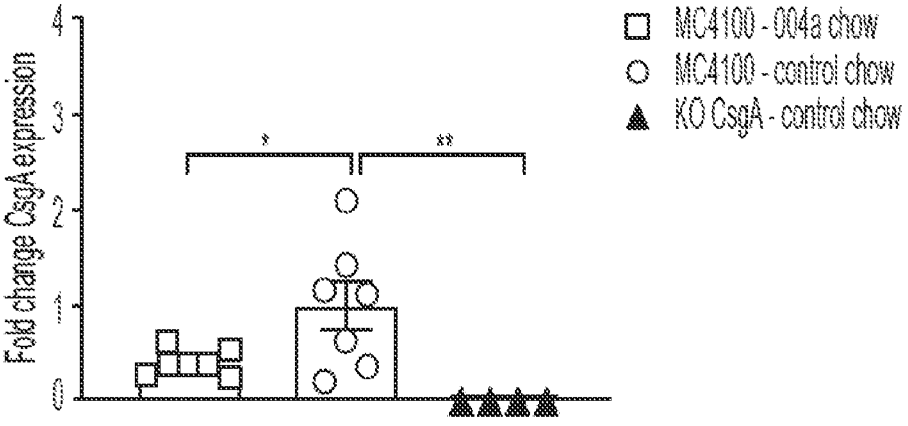
Figure 8D:
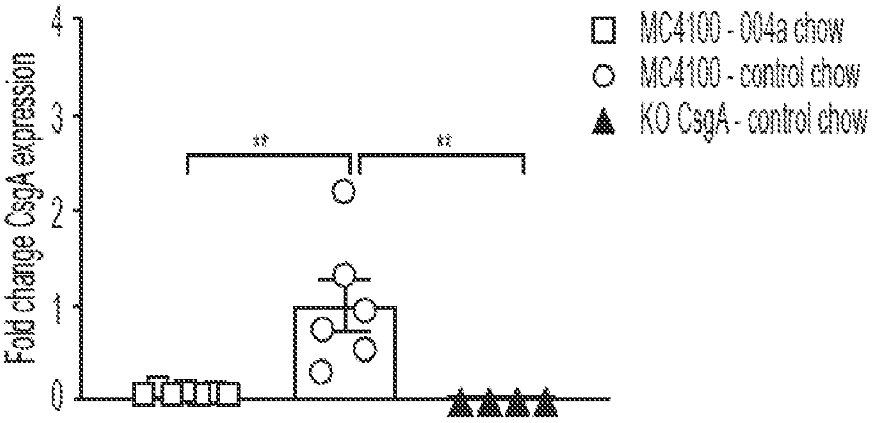

Additional experiments show that that intestinal curli promotes progressive synuclein-dependent pathophysiology. Conventionally-raised Thy1-αSyn (ASO) animals were injected intestinally with 30 g of synthetic CsgA hexamer (CsgA; N-QYGGNN-C) or non-amyloidogenic peptide (N122A; N-QYGGNA-C). Each peptide spanned the aggregation domain of CsgA. Motor and GI function tested over time at 0, 7, 21, and 70 days post-injection in the beam traversal (FIG. 3A), pole descent (FIG. 3B), adhesive removal (FIG. 3C), hindlimb clasping score (FIG. 3D), wire hang (FIG. 3E), fecal output (at day 70) (FIG. 3F). FIG. 3G is a graph depicting principal component analysis of compiled motor scores of FIGS. 3A-F. FIGS. 3H-I depict quantification of insoluble αSyn fibrils in the striatum (FIG. 3H) and ventral midbrain (FIG. 31) by dot blot assay. n=8 (FIGS. 3A-G), n=4 (FIG. 3H). Points represent individuals, bars represent the mean and standard error. Time courses analyzed by two-way ANOVA, with Sidak post-hoc test for between group comparisons indicated above individual time points, and brackets indicating significance between treatments. Data in FIG. 3H were analyzed by two-tailed Mann-Whitney test. For FIGS. 3A-I, *p≤0.05; p≤0.01; *p≤0.001; **p≤0.0001. Compilation of motor performance by PCA indicates a symptomatic shift in mice injected with the CsgA peptide compared to controls, demonstrating that the overall motor function of these animals has been impaired (FIG. 3G). Furthermore, increased αSyn fibrils are detected in the midbrains of amyloidogenic CsgA-injected animals (FIG. 3**H), demonstrating alterations to central nervous system (CNS) pathology following amyloid administration directly to the GI tract. Thus, gut exposure to a CsgA peptide capable of forming amyloids is sufficient to exacerbate long-lasting motor deficits in αSyn over-expressing mice.

Thus, it was shown herein that intestinal curli increased time to cross, time to descend, time to remove, and hindlimb score, and decreased time to fall and fecal pellets per mouse. The increases in time to cross, time to descend, and hindlimb score, and decrease in fecal pellets per mouse were statistically significant at the noted levels (See FIGS. 3B-D and 3F). Accordingly, it is contemplated that intestinal curli can induce symptoms of amyloid disorders in vivo.

Example 8

A library of potential amyloidogenesis inhibitors is obtained. Such libraries may be found in preexisting repositories, or may be generated de novo by, for example, combinatorial synthesis or by solid phase peptide synthesis utilizing such methods as are well known in the art. See, for example, Jensen, K. J. et al., eds, *Peptide Synthesis and Applications,* 2nd Edition, 2913, which is incorporated by reference herein for its teachings of solid phase peptide synthesis, combinatorial peptide synthesis, and the generation of peptide libraries. Natural product libraries may also be utilized. In a multi-well assay plate, a bacterial amyloid initiator, such as *E. coli* CsgA is placed in varying concentrations in one dimension, while a host-derived amyloidogenic protein, such as α-synuclein, is placed in varying amounts in the second dimension, such that each well contains a different ratio of amyloid initiator and amyloid precursor. To each well, a constant amount of an indicator of amyloid formation, such as thioflavin (ThT), is added, as well as a constant amount of an individual test compound. Each tray is agitated to initiate amyloid formation, and thioflavin fluorescence is monitored. Compounds that show deviations in the rate of fluorescence development over time will be identified as candidates that enhance or inhibit amyloid formation.

Example 9

A suspected amyloidogenesis inhibitor is combined with a bacterial amyloid initiator and an amyloid precursor in the presence of Thioflavin T (ThT). Separately, as a control, bacterial amyloid initiator, amyloid precursor, and Thioflavin T are combined in the absence of the suspected amyloidogenesis inhibitor. Thioflavin T fluorescence is monitored over time. A reduction in the rate of increase in Thioflavin T fluorescence, and/or a reduction in the maximum level of Thioflavin T fluorescence in the sample containing the suspected inhibitor, relative to the control sample, confirms that the suspected amyloidogenesis inhibitor is in fact functioning to inhibit amyloid formation.

Example 10

A sample of tissue, fluid, feces, or intestinal contents is collected from a subject. Said sample is combined with a bacterial amyloid initiator, such as *E. coli* CsgA, a host-derived amyloidogenic protein, such as α-synuclein and an indicator of amyloid formation, such as Thioflavin T (ThT). Thioflavin T fluorescence is monitored. An increase in fluorescence consistent with an increase in the rate of formation of amyloid in the presence of said sample, relative to the rate of amyloid formation in the absence of said sample, indicates an increase in the risk of α-synucleinopathy, including Parkinson's disease and/or Lewy body dementia. This increased risk is further correlated with results from conventional neurological examinations in order to calculate a defined risk of commencement and/or progression of an α-synucleinopathy or other neurodegenerative disorder implicating amyloid formation.

Example 11

In non-binding, black plastic, 96-well plates, 50-100 μM α-synuclein is incubated in 0.01M Tris buffer (pH 7.4) or 0.05 M potassium phosphate buffer pH 7.3 in the presence of 12 μM of Thioflavin T (prepared in water). Purified CsgA monomer in 0.05 M potassium phosphate buffer, pH 7.3 is added to each well at a molar ratio of 1:10, 1:25, 1:50, or 1:100. Inhibitory compounds are prepared in appropriate buffered solutions based on solubility, such as 0.05 M potassium phosphate buffer, pH 7.3 or DMSO. Compounds and appropriate buffer controls are added to α-synuclein- and CsgA-containing wells, to a final volume of 150 μL per well. The concentration of each compound is dependent on the type of compound being screened but generally is expected to fall within the range of 1 μM to 200 μM in initial screens. Details regarding the addition of such compounds depend on the types of compounds available in the accessible small molecule libraries. Independent wells containing α-synuclein alone and CsgA alone serve as specificity controls, or in combination in the absence of potential inhibitors. A single, sterilized glass or Teflon bead with a ~1-2 mm diameter is added to each well. The plate is incubated within a fluorescent-capable microplate reader with continuous orbital shaking (~100-250 rpm) at 37° C. Fluorescence is measured every 1-2 hours with an excitation of 440±10 nm and emission of 490±10 nm. Measurements are taken over a 24-72 hour period. As α-synuclein amyloids form, emission spectra hit maximum intensity ~24-72 hours under these conditions following a sigmoidal curve. After this time, emission intensity can decrease as amyloids become insoluble and non-fluorescent.

Amyloid formation appears over 3 phases (See, e.g., FIG. 1B): (1) a lag phase whereby fluorescence intensity is low occurring over the first ~0-24 hrs; (2) A log phase whereby fluorescence intensity increases logarithmically from ~2-48 hrs; and (3) a plateau phase whereby fluorescence intensity hits a maximum and either remains unchanged for the remaining time period or begins to decrease due to insoluble α-synuclein precipitating out of solution. Maximum intensity generally occurs between 24-72 hours.

Aggregation kinetics, as measured by thioflavin fluorescence, in the presence of compounds can be normalized to the kinetics observed with α-synuclein and CsgA alone. Potential inhibitors may act to lengthen the lag phase, decrease the rate of change during the log phase, decrease the maximum intensity reached, or any combination thereof.

Once initial candidates are identified, dose responses over a wide-range of concentrations can be determined, as well as specificity against CsgA:synuclein aggregates, or CsgA and α-synuclein individually. In some variations of this screen, CsgA:synuclein aggregates can be monitored until the log phase, and potential inhibitory compounds introduced at this time. Subsequently, inhibitors which can act once amyloid formation is already in process can be identified (See, e.g., FIG. 1B).

Example 12

The assay is practiced as described in Example 11, in which full concentration curves are generated for each compound. This enables accurate determination of the EC50 for each compound and can expose certain compounds limitations (e.g., expose compounds that do not lead to complete inhibition of aggregation).

Example 13

The assay is practiced as described in Example 11, and is formatted for higher throughput screening in a variety of ways. For example, rather than a full concentration curve for each compound, a three-point concentration curve is used to distinguish compounds with a dose-response effect from those with a non-specific and concentration-independent effect. For even higher throughput screening, the assay is formatted in 96-well, 384-well or 1536-well plates and compounds are tested at a single concentration (e.g., 100 μM) and at a single timepoint (e.g., 24-72 hours). This enables the observer to distinguish potential candidates from compounds with no effect or with no effect at a relevant concentration.

Example 14

The assay is practiced as described in Example 11, in which full time course curves are generated for each compound. Time-course curves show whether a compound inhibits in a linear or sigmoidal fashion over time, and/or whether the complete inhibition can be achieved with a given compound.

Example 15

The assay is practiced as described in Example 11, and is further modified to assess mechanistic processes and compound activity in a more dynamic environment in which both α-synuclein (or other host amyloid protein) and curli (or other bacterial amyloid) are present in the assay. The observer then assesses the ability of compounds to inhibit aggregation of one or the other proteins in the presence of an aggregation template. For example, bacterial amyloid component CsgA is known to promote and/or accelerate α-synuclein aggregation. In an in vivo environment, a candidate compound with α-synuclein aggregation inhibition activity is exposed to an aggregation promoting or templating activity from bacterial amyloid. Thus, formatting the assay by inclusion of both monomeric α-synuclein (or other host amyloid) and aggregated bacterial amyloid allows assessment of drug candidates in a more physiologically relevant in vitro environment.

Example 16

The assay is practiced as described in Example 11, wherein the method further comprises combining a curli (bacterial amyloid) aggregation inhibitor with an α-synuclein aggregation inhibitor. This combination has the added benefit of blocking aggregation at two critical points simultaneously. The assay utilizes the monomeric forms of both α-synuclein and curli (CsgA), and measurements analogous to those shown in FIG. 1B are obtained.

Example 17

The assay is practiced as described in Example 11, wherein the method further comprises combining a curli (bacterial amyloid) dis-aggregation promoter with a promoter of α-synuclein dis-aggregation. This combination has the added advantage of effecting dis-aggregation at two critical points simultaneously. The assay utilizes the fully aggregated forms of both α-synuclein and curli, and measurements analogous to those shown in FIG. 1B are obtained.

Example 18

The assay is practiced as described in Example 11, wherein the method further comprises combining a curli (CsgA, bacterial amyloid) aggregation inhibitor with an α-synuclein dis-aggregation promoter. This combination has the added advantage of inhibiting the nucleation or origination of amyloid while simultaneously effecting dis-aggregation of an already initiated process. The assay utilizes the fully aggregated form of α-synuclein and the monomeric form of curli (CsgA), and measurements analogous to those shown in FIGS. 2A-3I are obtained.

Example 19

The assay is practiced as described in Example 11, wherein the method further comprises combining a curli (bacterial amyloid) dis-aggregation promoter with an α-synuclein aggregation inhibitor. This combination has the added advantage of destroying pathogenic bacterial amyloid while simultaneously inhibiting α-synuclein aggregation. The assay utilizes the monomeric form of α-synuclein and the fully aggregated form of curli, and measurements analogous to those shown in FIGS. 2A-3I are obtained.

Example 20

The assay is practiced as in any of Examples 16-24, except that a CsgA mutant that is incapable of aggregation is included. Compounds that rely on the presence of structured (aggregated) CsgA in these processes will show reduced effectiveness in this version of the assay.

Example 21

Human α-synuclein was expressed in *E. coli* BL21(DE3) from a plasmid derived from pT7 or pET11a into which the full-length gene for untagged human α-synuclein was inserted. Cells were induced at OD600 0.6 with 0.8 mM IPTG for 4 hours, harvested by centrifugation and suspended in a volume of lysis buffer (10 mM Tris, pH 8.0, 1 mM EDTA, and 1 mM PMSF) equivalent to one-tenth the volume of culture, and lysed by boiling for 20 minutes. Cell debris was pelleted by centrifugation, clarified lysate was treated with 10% streptomycin sulfate at 136 μL/mL followed by glacial acetic acid at 228 μL/mL, lysate was centrifuged, supernatant was transferred to a fresh tube and protein was precipitated via addition of an equal volume of saturated (100%) ammonium sulfate and incubated at 4° C. on a rocking shaker for 1 hour. The protein was pelleted via centrifugation and washed with an equal volume of 100 mM ammonium acetate in chilled ethanol, pelleted via centrifugation, washed twice with chilled ethanol, dried overnight, resuspended in 50 mM potassium phosphate buffer pH 7.3 or 10 mM Tris pH 7.4, and passed through a 50 kDa cut-off column. Immediately prior to use, the purified α-synuclein was filtered with a 0.2 μm nylon filter. The α-synuclein concentration was determined using the absorption at 280 nm or BCA assay.

Example 22

Full length, recombinant CsgA monomers can be prepared as described from Zhou et al. (2012). Journal of Biological Chemistry 287 (42). Briefly, csgA is cloned into a pET11d vector containing a C-terminal 6× His tag. Following growth in rich media, CsgA production is induced at an $OD_{600}$ of approximately 0.9 by 0.5 mM IPTG at 37° C. for 1 hour. Bacteria were lysed in 8 M guanidine hydrochloride in 50 mM potassium phosphate buffer, pH 7.3 overnight or for approximately 1-2 hours at room temperature on a rocking platform. After centrifugation at 10,000×g for 20 minutes, the supernatant was sonicated on ice for six 10 second intervals, incubated with nickel-nitrilotriacetic acid resin (Sigma) at room temperature for 1 hour and then loaded onto a disposable polypropylene column (Thermo). The column was washed with 50 mM potassium phosphate buffer, pH 7.3 and 50 mM potassium phosphate buffer pH 7.3 containing 12.5 mM imidazole. Proteins were eluted with 50 mM potassium phosphate buffer, pH 7.3 containing 125 mM imidazole. To get monomeric CsgA, fractions containing the target protein were combined and loaded onto a 30-kDa centrifugal filter unit (Thermo) to remove dimers and other oligomers. Purified CsgA was passed through a pre-chilled desalting column (Zeba) to remove imidazole.

Alternatively, synthetic hexapeptides of CsgA consisting of the sequence: Nterm-QYGGNN-Cterm, are commercially available from Bio-synthesis, Inc.

Example 23

Another alternative is to utilize pre-formed CsgA amyloid seeds, by preparing purified curli extracts from biofilms as described in Collinson et al. (1991). Journal of Bacteriology. 173 (15). Wild-type *Escherichia coli* is grown on YESCA media with or without Congo Red dye added, for 3-7 days at room temperature. The cultures are scraped into 10-30 mLs of 10 mM Tris, pH 8. Cells are lysed by sonication or by freeze-thaw. Cell lysates are treated with 0.1 mg RNase A, 0.1 mg DNase I and MgCl2 added to 1 mM, and incubated for 20-30 min at 37 C. Lysozyme is added to 1 mg/mL and further incubated at 37° C. for 20-40 min. SDS is added to 1% and incubated at 37° C. for 20-40 min. Insoluble material is collected by centrifugation at 12,000×g for 15 min. Samples are re-suspended in 1-10 mL Tris buffer, boiled at 90° C. for 15 min, and the above processes are repeated (Digestion with RNase, DNase, Lysozyme, and SDS treatment). Samples are washed twice with Tris buffer, resuspended in Laemli buffer, boiled, and loaded onto an SDS-PAGE gel (4-20%). Samples are electrophoresed at 20 mA for 5 hrs. The remaining insoluble material in the stacking gel is collected, washed three times with water, washed twice with 95% ethanol, and dried. The sample is resuspended in 0.2M glycine pH 1.5 and boiled for 10-15 min. Insoluble material is collected by centrifuging at 16 k×g for 10 min. The insoluble material is washed five times with water, and resuspended in PBS. Finally, the sample is sonicated by electrode or water bath for 1 hour before protein content determined by BCA or absorbance at 280 nm.

Such alterations may change the kinetics of aggregation, the concentrations of compounds needed to inhibit aggregation, the ratios required to display CsgA-mediated synuclein aggregation, or combinations of the above.

Example 24

In other iterations of the protein purifications used in the assays of Examples 22 and 23, CsgA may be produced without a histidine tag or with an alternate tag, and it may contain a sequence to promote its excretion from the cell. α-synuclein may be engineered to contain a histidine tag or other tag to promote purification by affinity for example to immobilized metals such as nickel. CsgA and α-synuclein may be purified using alternate methods familiar to one skilled in the art, such as ammonium sulfate precipitation with alternate concentrations of ammonium sulfate in a single step or in multiple steps with increasing concentrations of ammonium sulfate; alternately, ammonium sulfate precipitation may be omitted. Alternate resins or materials to separate CsgA or α-synuclein from other proteins based on protein affinity, cation exchange, anion exchange, hydrophobic interactions, multiple modes or mixed modes may be used, as are familiar to one skilled in the art. Protein separation may be performed using batch purification, prepacked columns, gravity flow, low pressure, high pressure, and high pressure liquid chromatography, using methods familiar to one skilled in the art, and the methods may be used individually or in combination. CsgA or α-synuclein may be separated from other proteins on the basis of size using methods familiar to one skilled in the art, such as size exclusion chromatography or high pressure liquid chromatography. CsgA and α-synuclein may be purified under denaturing conditions for all or part of the assay purification process, with alternate concentrations of guanidinium hydrochloride or with alternate denaturants at various concentrations known to one skilled, such as urea. Alternately, CsgA and α-synuclein may be purified under native conditions familiar to one skilled in the art; under native conditions or with steps using non-denaturing buffers, CsgA is generally purified rapidly to avoid aggregation during the purification process. His-tagged CsgA may be eluted from immobilized metal affinity materials such as Ni-NTA using alternate methods known to one skilled in the art, such as decreasing pH or addition of chelators such as ethylenediaminetetraacetic acid. In addition to or instead of immobilized metal affinity chromatography based on the affinity of histidine residues in the protein to immobilized nickel, alternate immobilized metal affinity chromatography or batch purification methods may be used, such as materials with immobilized copper, zinc, cobalt or nickel interacting with histidine or alternate amino acids in the protein, such as cysteine or tryptophan, as known to one skilled in the art. As known to one skilled in the art, alternate buffers may be used with Ni-NTA agarose, such as tris(hydroxymethyl)aminomethane, ("Tris"); 4-(2-hydroxyethyl)-1-piperazine ethanesulfonic acid, ("HEPES"); 3-(N-morpholino)propanesulfonic acid, ("MOPS"), optionally including sodium chloride, potassium chloride or other salts, and various detergents and reducing agents of compositions and concentrations compatible with Ni-NTA agarose chromatography or batch purification.

In the assays, alternate concentrations of dimethyl sulfoxide may be used, and concentrations of dimethyl sulfoxide significantly elevated above or decreased below 1% may affect the aggregation kinetics of CsgA and α-synuclein. Alternate concentrations of Thioflavin T may be used in the assay and may affect the fluorescent signal and sensitivity of the assay. Alternate concentrations of CsgA and α-synuclein may be used and such alterations may affect aggregation kinetics of α-synuclein and CsgA in the assay. Alternate concentrations of compounds may be tested in the assay, and dose-responses may be evaluated. Additional reagents may be added to the assay which may affect aggregation kinetics of α-synuclein and CsgA depending on their concentration, including detergents such as sodium dodecyl sulfate. Shaking may be included at alternate intervals in the assay and may affect CsgA and α-synuclein aggregation kinetics. 2 mm glass beads may be omitted from the assays including α-synuclein or may be included in the assays including CsgA, or other sizes or compositions of beads may be used, and these alterations may affect CsgA and α-synuclein aggregation kinetics. Alternate buffers, such as Tris, HEPES and MOPS, and alternate buffer concentrations may be used in the assay and may affect CsgA and α-synuclein aggregation kinetics. Any plate reader capable of fluorescent reads with excitation at 438 nM and emission at 495 nm with sufficiently narrow bandwidths, such as 10 nm, may be used. Alternate microplates may be used in the assay, such as black microplates with clear bottoms. Plates may be sealed with alternate coverings that do not absorb ThT fluorescence, or the coverings may be removed prior to reads. The fluorescence may be read at a single endpoint or at multiple points over various time intervals, and the time intervals at which the fluorescence is measured may be constant or may vary during the course of the assay. Other metrics may be used to determine the effects of the compounds on α-synuclein and CsgA expression, including examination of Thioflavin T signal over the course of a kinetic read to determine lag phase in Thioflavin T fluorescence, the shape of a curve produced by the fluorescent signal, and the slope of the curve.

Example 25

To assess the effects of compounds on aggregation of α-synuclein, a cell-free assay was performed using purified α-synuclein and Thioflavin T. In the assay, human α-synuclein was expressed in *E. coli* BL21(DE3) from a plasmid derived from pT7 or pET11a into which the full-length gene for untagged human α-synuclein was inserted. Cells were induced at $OD_{600}$ 0.6 with 0.8 mM IPTG for 4 hours, harvested by centrifugation and suspended in a volume of lysis buffer (10 mM Tris, pH 8.0, 1 mM EDTA, and 1 mM PMSF) equivalent to one-tenth the volume of culture and lysed by boiling for 20 minutes. Cell debris was pelleted by centrifugation, clarified lysate was treated with 10% streptomycin sulfate at 136 μL/mL followed by glacial acetic acid at 228 μL/mL, lysate was centrifuged, supernatant was transferred to a fresh tube and protein was precipitated via addition of an equal volume of saturated (100%) ammonium sulfate and incubated at 4° C. on a rocking shaker for 1 hour. The protein was pelleted via centrifugation and washed with an equal volume of 100 mM ammonium acetate in chilled ethanol, pelleted via centrifugation, washed twice with chilled ethanol, dried overnight, resuspended in 50 mM potassium phosphate buffer pH 7.3 or 10 mM Tris pH 7.4, and passed through a 50 kDa cut-off column. Immediately prior to use, the purified α-synuclein was filtered with a 0.2 μm nylon filter. The assay was conducted in 96-well black microplates with a single 1-2 mm glass bead in each well, 20-40 μM ThioflavinT, 1% DMSO, α-synuclein at 50 μM and compounds at 20-100 μM. Plates were sealed with sealing tape (ThermoFisher 232701), incubated at 37° C. in a Tecan Nano F200 plate reader with excitation at 438 nm using a 439 nm filter with a bandwidth of 8 nm, and emission at 495 nm with a 490 nm filter with a bandwidth of 10 nm. During the assay, plates were shaken continuously or were shaken for 999 seconds every 18 minutes. Readings were performed hourly for up to 73 hours. The effect of compounds on α-synuclein aggregation in the assay was determined with data at 36, 47, 48 or 72 hours or from the final timepoint of the assay, prior to or roughly near the time when ThT fluorescence plateaued in the vehicle control wells. The vehicle controls contained all components of the assay except compounds and represented the level of α-synuclein aggregation in the absence of an inhibitor or accelerator. Fluorescence values for each compound with α-synuclein were first adjusted by subtracting the average fluorescence of the compound in the absence of α-synuclein. These adjusted values were normalized by dividing them by the average fluorescence at the same timepoint in the vehicle control wells, and the average normalized fluorescence with the compound was expressed as a percentage of the average fluorescence observed in untreated controls. Percent inhibition of α-synuclein aggregation by a compound was determined by subtracting the percent average fluorescence with the compound relative to the average vehicle control from 100%. A higher positive percent inhibition reflects greater inhibition of α-synuclein aggregation, while a negative percent inhibition reflects potentiation of α-synuclein aggregation.

In some embodiments, with other variations of the protein purification used in the assays, α-synuclein may be purified using alternate methods familiar to the skilled artisan, such as ammonium sulfate precipitation with alternate concentrations of ammonium sulfate in a single step or ammonium sulfate precipitation may be omitted. In some embodiments, alternate resins or materials may be used to separate α-synuclein from other proteins, such as those based on protein affinity, cation exchange, anion exchange, or hydrophobic interactions, and multiple modes or mixed modes may be used, as are familiar to one skilled in the art. In some embodiments, protein separation may be performed using batch purification, pre-packed columns, gravity flow, low pressure, high pressure, and high-pressure liquid chromatography, using methods familiar to the skilled artisan, and the methods may be used individually or in combination. α-Synuclein may be separated from other proteins by size using methods familiar to one of skill in the art, such as size exclusion chromatography or high-pressure liquid chromatography. α-Synuclein may be purified under denaturing conditions for all or part of the assay purification process, with various concentrations of guanidinium hydrochloride or with alternate denaturants at various concentrations known to one skilled, such as urea. Alternately, α-synuclein may be purified utilizing an affinity tag including but not limited to a Histidine tag, BAP tag, or GST tag. As known to one skilled in the art, multiple alternative buffers may be used, such as but not limited to tris(hydroxymethyl)aminomethane, ("Tris"); 4-(2-hydroxyethyl)-1-piperazine ethanesulfonic acid, ("HEPES"); 3-(N-morpholino) propanesulfonic acid, ("MOPS"); or phosphate-buffered saline, optionally including sodium chloride, potassium chloride or other salts, and various detergents and reducing agents of compositions and concentrations compatible with protein purification.

For the assays described herein, alternate concentrations of dimethyl sulfoxide may be used, and concentrations of dimethyl sulfoxide significantly elevated above or decreased below 1 percent may affect the aggregation kinetics of α-synuclein. Alternate concentrations of Thioflavin T may be used in the assay and may affect the fluorescent signal and sensitivity of the assay. Alternate concentrations of α-synuclein may be used and such alterations may affect aggregation kinetics of α-synuclein in the assay. Alternate concentrations of compounds may be tested in the assay, and dose-responses may be evaluated. Additional reagents may be added to the assay which may affect aggregation kinetics of α-synuclein depending on their concentration, including detergents such as sodium dodecyl sulfate, sodium chloride, dithiotreitol, or bovine serum albumin. Shaking may be included at alternate intervals in the assay and may affect α-synuclein aggregation kinetics. Teflon beads of various sizes may be included in the assays or other compositions of beads may be used, and these alterations may affect α-synuclein aggregation kinetics. Alternate buffers, such as Tris, phosphate buffered saline, HEPES and MOPS, and alternate buffer concentrations may be used in the assay and may affect α-synuclein aggregation kinetics. Any plate reader capable of fluorescent reads with excitation at 438 nM and emission at 495 nm with sufficiently narrow bandwidths, such as 10 nm, may be used. Examples include but are not limited to a SpectraMax M5, SpectraMax M2 or SpectraMax® i3X (Molecular Devices, San Jose, CA). Alternate microplates may be used in the assay, such as black microplates with clear bottoms, solid white, or white with clear bottom. Different plate density may also be used such as 384 or 1536 well formats. Plates may also have a variety of treatments to include but not limited to non-binding coating or high binding coating, and they can also be untreated. Plates may be sealed with alternate coverings that do not absorb ThT fluorescence, or the coverings may be removed prior to reads. The fluorescence may be read at a single endpoint or at multiple points over various time intervals, and the time intervals at which the fluorescence is measured may be constant or may vary during the time course of the assay. Results are shown in Tables 3 and 4. A higher positive percent inhibition reflects greater inhibition of α-synuclein aggregation, while a negative percent inhibition reflects potentiation of α-synuclein aggregation.

Example 26

In vitro ThioflavinT assay to determine effects of compounds on CsgA aggregation. To assess the effects of compounds on aggregation of *E. coli* CsgA, a cell-free assay was performed using purified CsgA and Thioflavin T. In the assay, histidine-tagged CsgA was over-expressed in *E. coli* NEB 3016 slyD::kan cells harboring a pET11d vector containing a C-terminal 6× His tag. Following growth in rich media, CsgA production is induced at an $OD_{600}$ of approximately 1.0 by addition of 0.5 mM IPTG (isopropyl beta-D-1-thiogalactopyranoside) followed by incubation at 37° C. for 1-4 hours with shaking at 200-250 rpm. Bacteria were resuspended in 8 M guanidine hydrochloride in 50 mM potassium phosphate buffer, pH 7.3 and lysed by sonication on ice using three 20 second intervals. The resulting lysate was incubated on a platform rocker for 1 hour at room temperature. After centrifugation at 10,000×g for 20 minutes, the supernatant was further sonicated on ice for three 20 second intervals and then incubated with nickel-nitrilotriacetic acid resin (Sigma) at room temperature for 1 hour in a 50 mL conical tube on a platform rocker. The resin was washed and pelleted 5 times with 45 mL 8 M guanidine in 50 mM potassium phosphate buffer pH 7.3. The resin was further washed and pelleted two times with 8 M guanidine hydrochloride in 50 mM potassium phosphate buffer pH 7.3 containing 12.5 mM imidazole. Purified CsgA protein was eluted two times with 5 mL of 6-8 M guanidine hydrochloride in 50 mM potassium phosphate buffer, pH 7.3 containing 250 mM imidazole. The eluted protein was aliquoted with 150 μL per aliquot, snap frozen in liquid nitrogen, and stored at −80 C. In order to obtain monomeric CsgA, the purified CsgA protein was thawed and passed through two pre-chilled desalting columns (Zeba) to remove imidazole and guanidine. The buffer exchanged protein was loaded onto a 30-kDa centrifugal filter unit (Amicon) and spun for 30 minutes at 7500×g to remove dimers and other oligomers. Protein concentration was assessed by the NanoDrop technique (Thermo Scientific), as is familiar to one skilled in the art. The CsgA aggregation assay was conducted in 96-well black non-binding surface or white untreated microplates with 20-40 μM ThioflavinT, 50 mM potassium phosphate buffer pH 7.3, 1% DMSO, CsgA at 2-20 μM, and compounds at 3.125-200 uM. The vehicle control wells contain all components of the assay except test compounds and represent the level of CsgA aggregation in the absence of any inhibitor or accelerator. Plates were incubated at room temperature in a Tecan Nano F200 plate reader with excitation at 438 nm using a 439 nm filter with a bandwidth of 8 nm, and emission at 495 nm with a 490 nm filter with a bandwidth of 10 nm, or in a SpectraMax M5, SpectraMax M2 or SpectraMax® i3X (Molecular Devices, San Jose, CA) spectrophotometer with excitation at 438 nM and emission at 495 nm. During the assay, plates were shaken initially for 5 seconds and subsequently for 3 seconds prior to fluorescent readings. Readings were performed every 15 minutes for up to 1005 minutes. The effect of compounds on CsgA aggregation in the assay was determined with data from 0-17 hours. Fluorescence values for each compound with CsgA were first adjusted by subtracting the average fluorescence of the compound in the absence of CsgA or in the presence of CsgA and compound at time 0 or 15 minutes. The data were analyzed in several ways:

1. The adjusted ThT fluorescence values were normalized by dividing them by the average fluorescence in the vehicle control wells containing CsgA. The median normalized fluorescence from 6-6.5 hours or 8-9 hours with the compound was expressed as a percentage of the median fluorescence observed in vehicle controls over the same time period. Percent inhibition of CsgA aggregation by a compound was determined by subtracting the percent average fluorescence with the compound relative to the vehicle controls from 100%. A higher positive percent inhibition reflects greater inhibition of CsgA aggregation, while a negative percent inhibition reflects potentiation of CsgA aggregation.
2. The adjusted ThT fluorescence values for each compound concentration and vehicle controls over time were plotted as progress curves using GraphPad Prism (GraphPad Software, San Diego, CA). The area under the curve (AUC) for vehicle controls and for each compound at each tested concentration was determined at different time points (105 minutes, 255 minutes, 510 minutes, 750 minutes, and 1005 minutes). The percent control AUC was determined by dividing the average AUC for each compound at each test concentration at a given timepoint by the average AUC for the vehicle controls at the same timepoint. A lower percent control AUC reflects greater inhibition of CsgA aggregation by a compound at a given concentration and timepoint, while a higher percent control AUC reflects lower inhibition of CsgA aggregation by the compound at a given concentration and timepoint.
3. The adjusted ThT florescence values for each compound concentration and vehicle control were plotted as progress curves using GraphPad Prism. The progress curves were fitted with the GraphPad Prism equation for specific binding with Hill slope ($Y=B_{max}*X^h/(T_{1/2}^h+X^h)$). The binding maximum, or $B_{max}$, represents the maximum specific binding for ThT fluorescence. Time to one half binding maximum ($T_{1/2}$) is the time required to achieve a half-maximum $B_{max}$ fluorescence, with a higher $T_{1/2}$ indicating that a compound slows CsgA aggregation in the assay or increases the lag phase of CsgA aggregation in the assay. The Hill slope (h) equals 1.0 when a ThT molecule binds with no cooperativity to one site on CsgA. When the Hill slope is greater than 1.0, CsgA has multiple binding sites for ThT with positive cooperativity. The Hill slope is less than zero when there are multiple binding sites with different affinities for CsgA or when there is negative cooperativity. For each test concentration of a compound, the percent vehicle control $B_{max}$ was determined by dividing the average $B_{max}$ of the compound by the average $B_{max}$ of the vehicle control and multiplying by 100%. A lower percent vehicle control $B_{max}$ reflects greater inhibition of CsgA aggregation by a compound in the assay. The values obtained for each parameter were replotted using the GraphPad Prism equation [Inhibitor] vs. response—Variable slope (four parameters) and the data were reported as an $IC_{50}$.

In other embodiments, the protein purifications used in the assays of CsgA may be produced without a histidine tag or with an alternate tag, and they may contain a sequence to promote its excretion from a cell. CsgA protein induction may be induced in cultures with alternate cell densities and with varying concentrations of IPTG for varying amounts of time and temperatures. CsgA may be purified using alternate methods familiar to the skilled artisan, such as ammonium sulfate precipitation with alternate concentrations of ammonium sulfate in a single step or in multiple steps with increasing concentrations of ammonium sulfate; in some embodiments, ammonium sulfate precipitation may be omitted. In some embodiments, alternate resins or materials to separate CsgA from other proteins based on protein affinity, cation exchange, anion exchange, hydrophobic interactions, multiple modes or mixed modes may be used, and are familiar to the skilled artisan. Protein separation may be performed using batch purification, pre-packed columns, gravity flow, low pressure, high pressure, and high-pressure liquid chromatography, using methods familiar to one skilled in the art, and the methods may be used individually or in combination. CsgA may be separated from other proteins by size using methods familiar to the skilled artisan, such as size exclusion chromatography or high-pressure liquid chromatography. CsgA may be purified under denaturing conditions for all or part of the assay purification process, with alternate concentrations of guanidinium hydrochloride or with alternate denaturants at various concentrations familiar to the skilled artisan, such as urea. In some embodiments, CsgA may be purified under native conditions familiar to the skilled artisan; under native conditions or with steps using non-denaturing buffers, CsgA is generally purified rapidly to avoid aggregation during the purification process. His-tagged CsgA may be eluted from immobilized metal affinity materials such as Ni-NTA using alternate methods known to the skilled artisan, such as decreasing pH or adding chelators such as ethylenediaminetetraacetic acid. In addition to or instead of immobilized metal affinity chromatography based on the affinity of histidine residues in the protein to immobilized nickel, in some embodiments, immobilized metal affinity chromatography or batch purification methods may be utilized, using such as materials as immobilized copper, zinc, cobalt or nickel interacting with histidine or alternate amino acids in the protein, such as cysteine or tryptophan, as known by the skilled artisan. In some embodiments, alternate buffers may be used with Ni-NTA agarose, such as tris(hydroxymethyl) aminomethane, ("Tris"); 4-(2-hydroxyethyl)-1-piperazine ethanesulfonic acid, ("HEPES"); 3-(N-morpholino) propanesulfonic acid, ("MOPS"), optionally including sodium chloride, potassium chloride or other salts, and various detergents and reducing agents of compositions and concentrations compatible with Ni-NTA agarose chromatography or batch purification. In the assays, alternate concentrations of dimethyl sulfoxide may be used, and concentrations of dimethyl sulfoxide significantly elevated above or decreased below 1 percent may affect the aggregation kinetics of CsgA. Alternate concentrations of Thioflavin T may be used in the assay and may affect the fluorescent signal and sensitivity of the assay. Alternate concentrations of CsgA may be used and such alterations may affect aggregation kinetics of CsgA in the assay. Alternate concentrations of compounds may be tested in the assay, and dose-responses may be evaluated. Additional reagents may be added to the assay which may affect aggregation kinetics of CsgA depending on their concentration, including detergents such as sodium dodecyl sulfate, NaCl, dithiotreitol, or bovine serum albumin. Agitation by shaking may be included at alternate intervals in the assay and may affect CsgA aggregation kinetics. 2 mm glass beads or teflon beads may be included in the assays including CsgA, or other sizes or compositions of beads may be used, and these alterations may affect CsgA aggregation kinetics. Alternate buffers, such as Tris, HEPES and MOPS, and alternate buffer concentrations may be used in the assay and may affect CsgA aggregation kinetics. Any plate reader capable of fluorescent reads with excitation at 438 nM and emission at 495 nm with sufficiently narrow bandwidths, such as 10 nm, may be used. Alternate microplates may be used in the assay, such as black microplates with clear bottoms, solid white, or white with clear bottom. Different plate density may also be used such as 384 or 1536 well formats. Plates may also have a variety of treatments to include but not limited to non-binding coating, high binding coating, and they can also be untreated. Plates may be sealed with alternate coverings that do not absorb ThT fluorescence, or the coverings may be removed prior to reads. The fluorescence may be read at a single endpoint or at multiple points over various time intervals, and the time intervals at which the fluorescence is measured may be constant or may vary during the time course of the assay. Results are shown in Tables 3 and 4. A lower percent control $B_{max}$ or a lower percent control AUC reflects greater inhibition of CsgA aggregation, while a higher percent control $B_{max}$ or a higher percent control AUC reflects lower inhibition of CsgA aggregation.

Example 26A

In vitro Thioflavin T assay to determine the effects of compounds on CsgA-seeded α-synuclein aggregation. To assess the effects of compounds on aggregation of α-synuclein seeded by *E. coli* CsgA, a cell-free assay was performed using purified α-synuclein, purified CsgA and Thioflavin T. In the assay, histidine-tagged CsgA was overexpressed in *E. coli* NEB 3016 slyD::kan cells harboring a pET11d vector containing csgA with the sequence for 6 histidine residues added to the C-terminus and without the Sec signal (amino acid 1-22) sequence. To induce overexpression of CsgA, 0.5 mM IPTG was added to cultures with an optical density at 600 nm ($OD_{600}$) of 0.8-1, and induced cells were cultured at 37° C. for 1 hour prior to harvest via centrifugation. Cells were lysed under denaturing conditions with 8 M guanidine hydrochloride in 50 mM potassium phosphate buffer pH 7.3 for 1-2 hours on a rocking platform at room temperature or at 4° C. overnight, and CsgA was purified via immobilized-metal affinity chromatography by batch purification with Nickel-NTA agarose and a combination of low pressure and gravity flow through a disposable polypropylene column, including washes under low pressure applied manually via application of a syringe plunger to the column with 50 mM potassium phosphate buffer pH 7.3 followed by 12.5 mM imidazole in 50 mM potassium phosphate buffer pH 7.3, and elution with 125 mM imidazole in 50 mM potassium phosphate buffer pH 7.3. Buffers with imidazole were freshly prepared prior to the protein purification. Purified CsgA was passed through a 30 kDa molecular weight cut-off filter and through a desalting column. All steps of the CsgA purification in the absence of guanidine hydrochloride were conducted in rapid succession with as little delay as possible. CsgA was quantified using a BCA assay or absorbance at 280 nm with a nanodrop spectrophotometer. Human α-synuclein was expressed in *E. coli* BL21(DE3) from a plasmid derived from pT7 or pET11a into which the full-length gene for untagged human α-synuclein was inserted. Cells were induced at $OD_{600}$ 0.6 with 0.8 mM IPTG for 4 hours. Cells were lysed by boiling for 20 minutes, cell debris was pelleted by centrifugation, clarified lysate was treated with 10% streptomycin sulfate at 136 μL/mL and glacial acetic acid at 228 μL/mL, lysate was centrifuged, supernatant was transferred to a fresh tube and protein was precipitated via addition of an equal volume of saturated (100%) ammonium sulfate. The ammonium sulfate pellet was washed with an equal volume of 100 mM ammonium acetate in ethanol, pelleted via centrifugation, washed twice with ethanol, dried overnight, resuspended in 10 mM Tris pH 7.4, and passed through a 50 kDa cut-off column. Immediately prior to use, the purified α-synuclein was filtered with a 0.2 μm nylon filter. The assay was conducted in 96-well black microplates with a single glass 1-2 mm bead per well, 20-40 μM ThioflavinT, 1% DMSO, 2 μM CsgA, 50-60 μM α-synuclein, 100 mM sodium chloride, 9.3 mM potassium phosphate pH 7.3, and compounds at 50 μM. Compounds were tested in triplicate. Plates were sealed with sealing tape (ThermoFisher 232701), incubated with continuous shaking at 37° C. in a Tecan Nano F200 plate reader, with excitation at 438 nm using a 439 nm filter with a bandwidth of 8 nm, and emission at 495 nm with a 490 nm filter with a bandwidth of 10 nm, or in a SpectraMax M5 or SpectraMax® i3X with excitation at 438 nM and emission at 495 nm., and readings were performed hourly for up to 73 hours. The effect of compounds on CsgA-seeded α-synuclein aggregation in the assay was determined with data from timepoints within 16-52 hours. Fluorescence values for each compound with CsgA and α-synuclein were first adjusted by subtracting the average fluorescence of the compound in the absence of CsgA and α-synuclein. These adjusted values were normalized by dividing them by the average fluorescence at the same timepoint in the vehicle control wells containing all assay components except compounds, and the average or median normalized fluorescence with the compound was expressed as a percentage of the average or median fluorescence observed in vehicle controls at the same timepoints. Percent inhibition of CsgA-seeded α-synuclein aggregation by a compound was determined by subtracting the percent average or median fluorescence with the compound at from 100%. A higher positive percent inhibition reflects greater inhibition of CsgA-seeded α-synuclein aggregation, while a negative percent inhibition reflects potentiation of CsgA-seeded α-synuclein aggregation.

TABLE 3

| | CsgA ThT Assay (2 μM CsgA) | | Reporter | |
|---|---|---|---|---|
| Compound | % Control $B_{max}$ 100 μM | % Control $B_{max}$ 25 μM | Assay Abs $IC_{50}$ (μM) | αSyn ThT Assay % inhibition |
| 002 | 137 (+) | 60 (++) | 4.1 (***) | |
| 003 | 16 (+++) | 54 (++) | 0.8 (****) | 76$^{\dagger}$ (+++) |
| 004 | 26 (+++) | 57 (++) | 0.7 (****) | 55 (++) |
| 004a | 24 (+++) | 64 (+) | 0.2 (****) | 42 (++) |
| 004b | 40 (++) | 54 (++) | 0.5 (****) | 44 (++) |
| 005 | 20 (+++) | 66 (+) | N/A (++) | 48$^{\dagger\dagger}$ (++) |
| 006 | 34 (++) | 66 (+) | 70 (*) | |
| 131 | 94 (+) | 53 (++) | 0.9 (****) | |
| 132 | 122 (+) | 76 (+) | 2.4 (***) | |
| 133 | 36 (++) | 71 (+) | 3.7 (***) | |
| 134 | 66 (+) | 92 (+) | 15.6 (*) | |
| 135 | 67 (+) | 88 (+) | 4 (***) | |
| 136 | 27 (+++) | 77 (+) | 3.5 (***) | |
| 137 | 50 (++) | 81 (+) | 2.2 (***) | |
| 138 | 43 (++) | 73 (+) | 2.5 (***) | 74$^{\dagger}$ (+++) |
| 139 | 35 (++) | 51 (++) | 2.5 (***) | |
| 140 | 19 (+++) | 35 (++) | 1 (****) | 48 (++) |
| 141 | 94 (+) | 80 (+) | 2.7 (***) | 79$^{\dagger}$ (+++) |
| 142 | 121 (+) | 87 (+) | 2.3 (***) | 40 (++) |
| 143 | 88 (+) | 87 (+) | 5.2 (**) | 96 (+++) |
| 144 | | 77 (+) | | 29 (+) |
| 145 | 39 (++) | 76 (+) | 2 (***) | |
| 146 | 63 (+) | 113 (+) | | |
| 147 | 139 (+) | 101 (+) | | |
| 148 | 113 (+) | 79 (+) | | |
| 149 | 115 (+) | 98 (+) | N/A | |

TABLE 3-continued

| | CsgA ThT Assay (2 μM CsgA) | | Reporter | |
|---|---|---|---|---|
| Compound | % Control $B_{max}$ 100 μM | % Control $B_{max}$ 25 μM | Assay Abs $IC_{50}$ (μM) | αSyn ThT Assay % inhibition |
| 150 | 199 (+) | 78 (+) | 4.2 (***) | |
| 151 | 73 (+) | 67 (+) | N/A | 61 (+++) |
| 152 | 107 (+) | 90 (+) | 11.4 (*) | 54 (++) |
| 153 | 83 (+) | 91 (+) | 16.6 (*) | 48 (++) |
| 154 | 63 (+) | 92 (+) | 6.1 (**) | 89$^{\dagger}$ (+++) |
| 155 | 112 (+) | 57 (++) | 3 (***) | 60+ (++) |
| 156 | 90 (+) | 80 (+) | 9.3 (**) | 70$^{\dagger}$ (+++) |
| 157 | 124 (+) | 81 (+) | N/A | 83 (+++) |
| 158 | 72 (+) | 69 (+) | 1.7 (***) | 79 (+++) |
| 159 | 76 (+) | 64 (+) | N/A | 83 (+++) |
| 160 | 116 (+) | 101 (+) | 65.8 (*) | 17 (+) |
| 161 | 29 (+++) | 54 (++) | 2.1 (***) | 44 (++) |
| 162 | 49 (++) | 34 (++) | 1.1 (****) | 67$^{\dagger}$ (+++) |
| 163 | 42 (++) | 33 (++) | 1.2 (****) | 47$^{\dagger}$ (++) |
| 164 | 42 (++) | 52 (++) | 0.9 (****) | 43 (++) |
| 165 | | | 0.8 (****) | 30 (+) |
| 166 | 40 (++) | 72 (+) | 2.5 (***) | |
| 167 | 49 (++) | 65 (+) | 0.6 (****) | 45 (++) |
| 168 | 47 (++) | 76 (+) | 1.3 (***) | 43 (++) |
| 169 | 64 (+) | 77 (+) | 3.8 (***) | 33 (++) |
| 170 | 38 (++) | 62 (+) | 2.2 (***) | 30 (+) |
| 171 | | | 1.1 (****) | 32 (++) |
| 172 | 17 (+++) | 26 (+++) | 4.2 (***) | 98 (+++) |
| 173 | 40 (++) | 73 (+) | 6.7 (**) | 86$^{\dagger}$ (+++) |
| 174 | 60 (++) | 77 (+) | 4.4 (***) | 23 (+) |
| 175 | 24 (+++) | 33 (++) | 1.4 (***) | 98 (+++) |
| 176 | 24 (+++) | 25 (+++) | 1.3 (***) | 98 (+++) |
| 177 | 21 (+++) | 32 (++) | 1.3 (***) | 97 (+++) |
| 178 | 9 (++++) | 57 (++) | 0.8 (****) | 43 (++) |
| 179 | 48 (++) | 65 (+) | 1.4 (***) | 72 (+++) |
| 180 | 21 (+++) | 65 (+) | 0.5 (****) | 63$^{\dagger}$ (+++) |
| 181 | 40 (++) | 57 (++) | 2.0 (***) | 31 (++) |
| 182 | 61 (+) | 68 (+) | 2.5 (***) | 33 (++) |
| 183 | 26 (+++) | 32 (++) | 0.8 (****) | |
| 184 | 22 (+++) | 45 (++) | 2.7 (***) | 75$^{\dagger\dagger}$ (+++) |
| 185 | 91 (+) | 69 (+) | 1.8 (***) | |

TABLE 3-continued

| | CsgA ThT Assay (2 μM CsgA) | | Reporter | |
|---|---|---|---|---|
| Compound | % Control $B_{max}$ 100 μM | % Control $B_{max}$ 25 μM | Assay Abs $IC_{50}$ (μM) | αSyn ThT Assay % inhibition |
| 186 | 72 (+) | 117 (+) | 4.7 (**) | |
| 187 | 74 (+) | 69 (+) | 19 (*) | 45†† (++) |
| 188 | 14 (+++) | 33 (++) | 0.8 (****) | 62 (+++) |
| 189 | 49 (++) | 58 (++) | 1.4 (***) | |
| 190 | 56 (++) | 63 (+) | 1.6 (***) | |
| 191 | 43 (++) | 58 (++) | | 55 (++) |
| 192 | 95 (+) | 87 (+) | 2.5 (***) | 59†† (++) |
| 193 | 10 (++++) | 53 (++) | 0.6 (****) | 69 (+++) |
| 194 | 67 (+) | 100 (+) | 1.4 (***) | 57 (++) |
| 195 | | | 1.8 (***) | 45† (++) |
| 196 | | 67 (+) | 2.8 (***) | 61 (+++) |
| 197 | 64 (+) | 86 (+) | 19.3 (*) | 39 (++) |
| 198 | 39 (++) | 61 (+) | 5.0 (**) | 75 (+++) |
| 199 | 99 (+) | 83 (+) | 6.9 (**) | 29 (+) |
| 200 | 7 (++++) | 52 (++) | 1.3 (***) | 84† (+++) |
| 201 | 35 (++) | 70 (+) | 1.8 (***) | |
| 202 | | 51 (++) | 0.8 (****) | 54 (++) |
| 203 | 64 (+) | 62 (+) | 1.1 (****) | |
| 204 | 71 (+) | | 1.9 (***) | |
| 205 | 44 (++) | 69 (+) | 22.4 (*) | |
| 206 | 54 (++) | 64 (+) | 13.2 (*) | |
| 207 | 20 (+++) | 51 (++) | 0.7 (****) | 71 (+++) |
| 208 | 25 (+++) | 46 (++) | 1.0 (****) | |
| 209 | 64 (+) | 81 (+) | 6.6 (**) | |
| 210 | 61 (+) | 79 (+) | 2.5 (***) | |
| 211 | 65 (+) | 85 (+) | 20.6 (*) | |
| 212 | 56 (++) | 64 (+) | 13 (*) | |
| 213 | 44 (++) | 72 (+) | 9.1 (**) | |
| 214 | 84 (+) | 90 (+) | 1.8 (***) | |
| 215 | 61 (+) | 97 (+) | 1.3 (***) | |
| 216 | 55 (++) | 95 (+) | 0.7 (****) | 46 (++) |
| 217 | | 65 (+) | 1.1 (****) | |
| 218 | 109 (+) | 115 (+) | | |
| 219 | | | 0.8 (****) | |
| 220 | | | 1.2 (****) | |
| 221 | | | 6.7 (**) | |
| 222 | | | 31.8 (*) | |
| 223 | | | 21.7 (*) | |
| 224 | | | 9.7 (**) | |
| 225 | | | 1.6 (***) | |
| 226 | | | 2.7 | |
| 227 | | | 1.8 (***) | |
| 228 | | | 3.9 (***) | |
| 229 | | | | |
| 230 | | | 1.2 (****) | |
| 231 | | | 3.4 (***) | |
| 232 | | | 0.7 (****) | 23 (+) |
| 233 | | | 0.6 (****) | 50† (++) |
| 234 | | | 0.4 (****) | 70†† (+++) |
| 235 | | | 2.7 (***) | |
| 236 | | | 1.7 (***) | |
| 237 | | | 1.3 (***) | |
| 238 | | | 0.7 (****) | 94 (+++) |
| 239 | | | 0.6 (****) | 58†† (++) |
| 240 | | | 1.4 (***) | |

†N = 2

††N = 1

N/A = Not Applicable: maximum expression reduction is <50% of control

Compound effects were determined on CsgA aggregation, CsgA expression, and αSyn aggregation: Mean CsgA maximum aggregation ($B_{max}$) as a percentage of DMSO control in the ThT assay with CsgA at 2 μM in white plates, with compounds at 100 μM and 25 μM; median Abs $IC_{50}$ in the CsgA reporter assay; and mean percent inhibition of αSyn aggregation relative to DMSO control in the ThT assay with αSyn at 50 μM and compounds at 100 μM.

TABLE 4

| | CsgA ThT Assay (10 μM CsgA) % Control AUC at 1005 minutes | | Reporter Assay | αSyn ThT Assay |
|---|---|---|---|---|
| Compound | 100 μM | 25 μM | Abs $IC_{50}$ (μM) | % Inhibition |
| 001 | 35 (++) | 36 (++) | 1.5 (***) | |
| 007 | | | | |
| 008 | | | 4.3 (***) | |
| 008a | 38 (++) | 71 (+) | | 16 (+) |
| 008b | | | | 10 (−) |
| 009 | | | | 28 (+) |
| 009a | 17 (+++) | 46 (++) | N/A | |

TABLE 4-continued

| Compound | CsgA ThT Assay (10 μM CsgA) % Control AUC at 1005 minutes 100 μM | 25 μM | Reporter Assay Abs $IC_{50}$ (μM) | αSyn ThT Assay % Inhibition |
|---|---|---|---|---|
| 009b | 37 (++) | 67 (+) | N/A | |
| 010 | | | | 13 (+) |
| 010a | 37 (++) | 85 (+) | 43.9 (*) | 41 (++) |
| 010b | 45 (++) | 85 (+) | 58.5 (*) | 35 (++) |
| 011 | 62 (+) | 63 (+) | 5.8 (**) | 56 (++) |
| 011a | 41 (++) | 47 (++) | 4.4 (***) | 13 (+) |
| 011b | 53 (++) | 54 (++) | 4.1 (***) | |
| 012 | 107 (+) | 108 (+) | 3.3 (***) | |
| 013 | | | N/A | |
| 014 | | | N/A | 35 (++) |
| 014a | 29 (+++) | 37 (++) | N/A | 68 (+++) |
| 014b | 26 (+++) | 71 (+) | 44 (*) | |
| 015 | 27 (+++) | 28 (+++) | 8 (**) | |
| 015a | 17 (+++) | 25 (+++) | 21.7 (*) | 62 (+++) |
| 015b | 23 (+++) | 29 (+++) | 22.5 (*) | |
| 016 | 33 (++) | 48 (++) | 5 (**) | 68 (+++) |
| 016a | 14 (+++) | 21 (+++) | 8.3 (**) | |
| 016b | 23 (+++) | 33 (++) | 6.6 (**) | 95 (+++) |
| 017 | 70 (+) | 95 (+) | 2.7 (***) | 53 (++) |
| 018 | 60 (++) | 95 (+) | 147.7 (*) | 22 (+) |
| 019 | 104 (+) | 69 (+) | | 41 (++) |
| 020 | 7 (++++) | 18 (+++) | 3.9 (***) | 53 (++) |
| 020a | 20 (+++) | 27 (+++) | 4.4 (***) | |
| 020b | 16 (+++) | 26 (+++) | 5.7 (**) | 25 (+) |
| 021 | | | 2.6 (***) | |
| 021a | 73 (+) | 36 (++) | 3.3 (***) | |
| 021b | 99 (+) | 36 (++) | 2.1 (***) | |
| 022 | 23 (+++) | 70 (+) | 4.1 (***) | 49 (++) |
| 023 | 34 (++) | 73 (+) | 19.6 (*) | 21 (+) |
| 024 | 39 (++) | 35 (++) | 9.9 (**) | 69 (+++) |
| 025 | | 49 (++) | 1.9 (***) | 59 (++) |
| 025a | 143 (+) | 38 (++) | 2 (***) | 50 (++) |
| 025b | 107 (+) | 46 (++) | 2.4 (***) | |
| 026a | | 41 (++) | 2 (***) | 51 (++) |
| 026b | | 47 (++) | 2.8 (***) | |
| 027a | 39 (++) | 99 (+) | 98 (*) | −2 (−) |
| 027b | 74 (+) | 108 (+) | 77.5 (*) | 4 (−) |
| 028 | 27 (+++) | 66 (+) | 18.2 (*) | 33 (++) |
| 029 | 48 (++) | 71 (+) | N/A | −2 (−) |
| 030 | | 82 (+) | 5 (**) | 4 (−) |
| 031 | 99 (+) | 100 (+) | 4.2 (***) | 18 (+) |
| 032 | | 92 (+) | 3.3 (***) | 8 (−) |
| 033 | 79 (+) | 68 (+) | 3.3 (***) | 6 (−) |
| 034 | 95 (+) | 62 (+) | 2.8 (***) | 5 (−) |
| 035 | | 65 (+) | 1.5 (***) | |
| 036 | | 65 (+) | 1.6 (***) | 16 (+) |
| 037 | 53 (++) | 71 (+) | 23.6 (*) | 36 (++) |
| 038 | 25 (+++) | 86 (+) | 24 (*) | 42 (++) |
| 039 | 24 (+++) | 92 (+) | N/A | |
| 040 | 8 (++++) | 78 (+) | N/A | 61 (+++) |
| 041 | 27 (+++) | 75 (+) | 20.2 (*) | 25 (+) |
| 042 | 18 (+++) | 52 (++) | 3.3 (***) | 84 (+++) |
| 043 | | | 0.7 (****) | 72† (+++) |
| 044 | 42 (++) | 55 (++) | 1.5 (***) | 10 (−) |
| 045 | 53 (++) | 59 (++) | 1.3 (***) | 15 (+) |
| 046 | 55 (++) | 55 (++) | 1.6 (***) | 28 (+) |
| 047 | 71 (+) | 55 (++) | 0.9 (****) | 21* (+) |
| 048 | 61 (+) | 90 (+) | N/A | 18 (+) |
| 049 | 35 (++) | 74 (+) | 8.9 (**) | |
| 050 | 22 (+++) | 36 (++) | | 49 (++) |
| 051 | 54 (++) | 81 (+) | 1 (****) | 47 (++) |
| 052 | 20 (+++) | 42 (++) | 1.1 (****) | |
| 053 | 12 (+++) | 39 (++) | 16.3 (*) | 65 (+++) |
| 054 | 50 (++) | 44 (++) | 6.3 (**) | 39 (++) |
| 055 | 17 (+++) | 73 (+) | 11 (*) | |
| 056 | 34 (++) | 38 (++) | 19.8 (*) | 59 (++) |
| 057 | 24 (+++) | 59 (++) | 7.1 (**) | 54 (++) |
| 058 | 22 (+++) | 47 (++) | 19.8 (*) | |
| 059 | 22 (+++) | 63 (+) | 21.1 (*) | 36 (++) |
| 060 | 98 (+) | 91 (+) | 1.4 (***) | |
| 061 | 45 (++) | 44 (++) | 2.1 (***) | |
| 062 | 97 (+) | 77 (+) | 0.9 (****) | 87 (+++) |
| 063 | 21 (+++) | 61 (+) | 11.2 (*) | |

TABLE 4-continued

| Compound | CsgA ThT Assay (10 μM CsgA) % Control AUC at 1005 minutes 100 μM | 25 μM | Reporter Assay Abs $IC_{50}$ (μM) | αSyn ThT Assay % Inhibition |
|---|---|---|---|---|
| 064 | 16 (+++) | 45 (++) | 45.3 (*) | 37 (++) |
| 065a | 18 (+++) | 65 (+) | 24.5 (*) | 32 (++) |
| 065b | 16 (+++) | 66 (+) | 18.1 (*) | 9 (−) |
| 066 | 29 (+++) | 88 (+) | 40.2 (*) | 13 (+) |
| 067 | 16 (+++) | 67 (+) | N/A | 35 (++) |
| 068 | 23 (+++) | 43 (++) | 11.1 (*) | 74 (+++) |
| 069 | 14 (+++) | 58 (++) | 5.7 (**) | |
| 070 | 29 (+++) | 17 (+++) | 2.3 (***) | 53 (++) |
| 071 | 78 (+) | 25 (+++) | 1.6 (***) | 38 (++) |
| 072 | 10 (++++) | 24 (+++) | 6.9 (**) | |
| 073 | 97 (+) | 27 (+++) | 6 (**) | 76 (+++) |
| 074 | 24 (+++) | 28 (+++) | 29.2 (*) | 38 (++) |
| 075 | 117 (+) | 118 (+) | 5.6 (**) | 2 (−) |
| 076 | 14 (+++) | 17 (+++) | | |
| 077 | 87 (+) | 97 (+) | 51.6 (*) | |
| 078 | 12 (+++) | 19 (+++) | 5.1 (**) | |
| 079 | 14 (+++) | 40 (++) | 10.7 (*) | |
| 080 | 72 (+) | 80 (+) | 26.3 (*) | |
| 081 | 24 (+++) | 25 (+++) | 16.5 (*) | |
| 082 | 12 (+++) | 51 (++) | 17.5 (*) | |
| 083 | 80 (+) | 102 (+) | 14.6 (*) | |
| 084 | 19 (+++) | 57 (++) | 27 (*) | |
| 085 | 18 (+++) | 52 (++) | 15.3 (*) | |
| 086 | 20 (+++) | 33 (++) | 9.6 (**) | |
| 087 | 15 (+++) | 30 (+++) | 6 (**) | |
| 088 | 26 (+++) | 36 (++) | 5.2 (**) | |
| 089 | 23 (+++) | 31 (++) | 8 (**) | |
| 090 | 30 (+++) | 54 (++) | 5.9 (**) | |
| 091 | 65 (+) | 90 (+) | 5.6 (**) | |
| 092 | 52 (++) | 64 (+) | 18.8 (*) | |
| 093 | 37 (++) | 49 (++) | 3.6 (***) | |
| 094 | 30 (+++) | 51 (++) | 1.9 (***) | |
| 095 | 70 (+) | 91 (+) | 25.9 (*) | |
| 096 | 71 (+) | 79 (+) | 22.9 (*) | |
| 097 | 41 (++) | 63 (+) | 18.4 (*) | |
| 098 | 33 (++) | 60 (++) | 20.9 (*) | |

TABLE 4-continued

| Compound | CsgA ThT Assay (10 μM CsgA) % Control AUC at 1005 minutes 100 μM | 25 μM | Reporter Assay Abs $IC_{50}$ (μM) | αSyn ThT Assay % Inhibition |
|---|---|---|---|---|
| 099 | 44 (++) | 56 (++) | 17.6 (*) | |
| 100 | 31 (++) | 41 (++) | 14.5 (*) | |
| 101 | 15 (+++) | 61 (+) | 29 (*) | |
| 102 | 57 (++) | 90 (+) | 5.4 (**) | |
| 103 | 102 (+) | 95 (+) | N/A | |
| 104 | 52 (++) | 82 (+) | 6 (**) | |
| 105 | 70 (+) | 102 (+) | 36 (*) | |
| 106 | 38 (++) | 95 (+) | 28.3 (*) | |
| 107 | 38 (++) | 36 (++) | 3.7 (***) | |
| 108 | 25 (+++) | 14 (+++) | 0.6 (****) | |
| 109 | 22 (+++) | 55 (++) | 1.9 (***) | 99 (+++) |
| 110 | | | 13.7 (*) | |
| 111 | 95 (+) | 98 (+) | N/A | |
| 112 | 20 (+++) | 35 (++) | 9 (**) | |
| 113 | 24 (+++) | 41 (++) | 4.6 (**) | |
| 114 | 21 (+++) | 37 (++) | 7 (**) | |
| 115 | 23 (+++) | 35 (++) | 7.2 (**) | |
| 116 | 38 (++) | 30 (+++) | 1.5 (***) | 47 (++) |
| 117 | 22 (+++) | 32 (++) | 5.9 (**) | |
| 118 | 76 (+) | 92 (+) | 3.9 (***) | |
| 119 | 35 (++) | 47 (++) | 2.5 (***) | 41[†] (**) |
| 120 | 12 (+++) | 28 (+++) | 3.1 (***) | 40 (++) |
| 121 | 15 (+++) | 32 (++) | 2 (***) | 27 (+) |
| 122 | 15 (+++) | 32 (++) | 1.9 (***) | 38 (++) |
| 123 | 25 (+++) | 26 (+++) | 3.3 (***) | 76 (+++) |
| 124 | 21 (+++) | 35 (++) | 3.1 (***) | |
| 125 | 44 (++) | 25 (+++) | 2.7 (***) | |
| 126 | 40 (++) | 36 (++) | 1.9 (***) | 32 (++) |
| 127 | 7 (++++) | 26 (+++) | 4.8 (**) | 67[††] (+++) |
| 128 | 28 (+++) | 29 (+++) | 2.2 (***) | |
| 129 | 61 (+) | 28 (+++) | 3.4 (***) | |

TABLE 4-continued

| | CsgA ThT Assay (10 μM CsgA) % Control AUC at 1005 minutes | | Reporter Assay | αSyn ThT Assay |
|---|---|---|---|---|
| Compound | 100 μM | 25 μM | Abs $IC_{50}$ (μM) | % Inhibition |
| 130 | 15 (+++) | 49 (++) | 14.8 (*) | |

†N = 2

††N = 1

N/A = Not Applicable: maximum expression reduction is <50% of control

% Inhibition ranges presented are defined as follows: (−−) represents less than −10; (−) represents −10 to 10; (+) represents 11 to 30; (++) represents 31 to 60; and (+++) represents greater than 60.

% Control $B_{max}$ and % Control AUC ranges presented are defined as follows: (++++) represents ≤10; (+++) represents 11 to 30; (++) represents 31 to 60; and (+) represents greater than 60.

Reporter Assay $IC_{50}$ (μM) ranges presented are defined as follows: (**) represents <1.3; (*) represents 1.3 to 4.5; (**) represents 4.6 to 10; (*) represents >10.

Compound effects were determined on CsgA aggregation, CsgA expression, and αSyn aggregation: Mean AUC as a percentage of DMSO control in the ThT assay with CsgA at 10 μM in black plates, with compounds at 100 μM and 25 μM; median Abs $IC_{50}$ in the CsgA reporter assay; and mean percent inhibition of αSyn aggregation relative to DMSO control in the ThT assay with αSyn at 50 μM and compounds at 100 PM.

Results of Thioflavin T assays of compound effects on aggregation. Compound activity ranges are defined in Table 3 and Table 4. Tested compounds demonstrated a variety of effects in the Thioflavin T assays of aggregation of α-synuclein and CsgA. The compounds demonstrated a range of activities. The inhibition of the various types of aggregation as described in Table 3 and Table 4 suggests that the compounds of the invention (e.g., compounds shown in Table 1) may be useful in preventing α-synuclein aggregation, the seeding of α-synuclein aggregation by CsgA or other microbial amyloids, and the formation of microbial amyloids that may seed α-synuclein aggregation in vivo, and these compounds may thereby be useful in preventing or treating Parkinson's Disease and other α-synucleinopathies. Oral administration of these compounds may allow relatively high concentrations to be achieved in the gut, where microbes producing amyloids may be abundant, and the compounds could inhibit their seeding of α-synuclein aggregation. Inhibition by these compounds of aggregation of α-synuclein on its own could be independently beneficial or may be synergistic with their inhibition of microbial amyloid-seeded α-synuclein aggregation. In keeping with Braak's hypothesis of prion-like propagation of α-synuclein from the enteric nervous system to the central nervous system (see, e.g., Rietdijk et al., "Exploring Braak's Hypothesis of Parkinson's Disease," *Front. Neurol.,* 13 Feb. 2017), these inhibitory effects could be beneficial in preventing propagation of α-synuclein aggregates in both the enteric and central nervous systems; furthermore, if orally administered compounds alleviate a continual seeding of α-synuclein aggregation by microbial amyloids or independent formation of α-synuclein aggregates, the processes by which subjects may clear α-synuclein aggregates may be able to have a greater net effect (i.e., the processed may be able to keep pace with the aggregates formed), and the compounds may thereby be efficacious in preventing or treating Parkinson's Disease and other microbial amyloid-seeded α-synucleinopathies. Without being limited by theory, oral administration may provide particular benefit in the gastrointestinal tract, potentially restoring gastrointestinal function in those patients in whom it is compromised or in preventing or slowing additional loss of gastrointestinal function and/or improving one or more symptoms of, e.g., dysphagia, reduced gut motility, gastroparesis, constipation (including chronic constipation and chronic idiopathic constipation), small intestine bacterial overgrowth (SIBO), diarrhea, abdominal pain and/or cramping, bloating, flatulence, nausea, or any other symptoms of irritable bowel syndrome (IBS), inflammatory bowel disease (IBD), ulcerative colitis, Crohn's disease, intestinal hyperpermeability, or any combinations thereof, in patients with α-synucleinopathies or in subjects at risk for developing α-synucleinopathies.

As shown in Table 3 and Table 4, some compounds demonstrated inhibition of only one or two types of aggregation in the assays, while other compounds appeared inactive or enhanced one or more types of aggregation. Some compounds may also inhibit CsgA-seeded alpha-Syn aggregation.

Example 27

In vitro live cell fluorescent reporter assay to determine effects of compounds on CsgA transcription. To assess the impact of compounds on CsgA gene expression, a live cell assay was performed using an engineered strain of *E. coli* UTI89 with a fluorescent CsgA gene expression reporter driven by the csgBAC promoter. In the reporter strain, a gene encoding Green Fluorescent Protein (GFP) was placed immediately downstream of the full intergenic region between csgDEF and csgBAC, containing the csgBAC promoter and other transcriptional regulatory elements, and inserted in single copy into the *E. coli* UTI89 chromosome, as described in Cegelski et. al., "Small-molecule inhibitors target *Escherichia coli* amyloid biogenesis and biofilm formation," Nat. Chem. Bio., 25 Oct. 2009. With this construct, GFP expression in the reporter strain was under the same regulation as CsgA expression. The reporter strain was struck out on a YESCA agar plate (1 g/L yeast extract, 10 g/L casamino acids, 20 g/L Bacto Agar) and grown at about 27° C. for 2 days, or until single colonies were sufficiently large to pick. A single colony of the reporter strain was used to inoculate 5 mL of YESCA broth (1 g/L yeast extract, 10 g/L casamino acids), which was grown overnight at about 27° C. The inoculum was diluted 1:10 in YESCA broth and the optical density at 600 nm ($OD_{600}$) was measured on a SpectraMax M2 or M5e (Molecular Devices, San Jose, CA) spectrophotometer in cuvettes. The culture was then further diluted to achieve a final $OD_{600}$ of 0.003, which was confirmed by measurement of the $OD_{600}$. Compounds were diluted in dimethyl sulfoxide (DMSO) and plated on black clear-bottomed tissue culture-treated 96-well plates with 1.5 μL/well for final test concentrations from 0.14-100 μM. All assay wells, including vehicle controls and positive controls for inhibition, included 1% DMSO final. Vehicle control wells consisted of DMSO and the reporter strain to assess the expression of the reporter strain in the assay in the absence of any compound. Positive controls for inhibition included wells with compound 020, which had previously been observed via qRT-PCR to inhibit CsgA expression in WT *E. coli*, and wells with 10 g/L salt final, which largely or fully inhibits CsgA expression in vitro. 148.5 μL culture at $OD_{600}$ 0.003 in YESCA broth was added to all wells for 150 μL final volume. Plates were incubated at 27° C. for 20 hours, then GFP fluorescence signal for each well was read on a Spectramax M2 or M5e plate reader with excitation at 485 nm, emission at 525 nm, and a cutoff at 515 nm. $OD_{600}$ for each well was also measured on the Spectramax M2 or M5e plate reader. Background fluorescence was calculated by averaging the values from the wells with bacteria in YESCA with 10 g/L NaCl, as 10 g/L NaCl fully inhibits CsgA expression in these growth conditions. Background fluorescence was subtracted from all wells, then fluorescence signal for each well was normalized to the mean of the vehicle control wells. Normalized dose response curves were plotted for each compound, and compound inhibition of CsgA transcription was determined by assessing the curve-fit $IC_{50}$, bottom, top, span (top-bottom), and Hill slope using GraphPad Prism software version 8.1.1 (GraphPad Software, San Diego, CA). An additional metric used to evaluate compounds was the concentration at which the curve reached 50% of the expression level of the vehicle control. This was written as a custom analysis in GraphPad Prism according to the formula X[50], or the X value at which Y=50, ie, the compound concentration at which fluorescence of the reporter strain was calculated to reach 50% of the vehicle control fluorescence. Separately from the fluorescence data, $OD_{600}$ values were normalized to the mean of the vehicle control wells, and dose response curves were plotted for each compound. $OD_{600}$ reduction of greater than 10% indicated compounds had some toxicity or negative impact on bacterial growth.

In some embodiments, other versions of the live cell reporter assay for CsgA expression may use a plasmid-encoded reporter construct. The same reporter, consisting of the gene for GFP directly behind the *E. coli* intergenic region containing the csgBAC promoter and all transcriptional regulatory elements, may be encoded on a plasmid along with a selectable marker, such as antibiotic resistance driven by a constitutive promoter. The plasmid may be low, mid or high copy number. The plasmid-borne reporter may be transformed into additional microbial strains including other *E. coli* strains, strains of other compatible species, and engineered or selected variants such as a csgB knockout. In some embodiments, other reporters could be used including other fluorophores such as mCherry, chemiluminescent reporters such as Luciferase, and colorimetric reporters such as LacZ. Amyloid-binding dyes could also be used separately or in combination with the reporter to directly quantify curli production. Other modifications to the reporter assay may include altering the assay format to 6-, 12-, 24-, 48-, or 384-well plates, culture tubes, microcentrifuge tubes, or other culture vessels. Spectrophotometric readings may occur in various assay plate types (clear, black, white, solid bottom or clear bottom plates with lids or plate seals) or in cuvettes. In some embodiments, the assay volume may range from about 30 μL to several mL. Growth conditions of both the starter culture and the plated bacteria may be changed, including incubation temperatures of about 20-37° C., growth on solid agar instead of in broth, growth in different media types such as Luria-Bertani medium (LB) from which salt is omitted, dilution of the starter culture to a different initial $OD_{600}$, and growth with shaking. The assay may be extended up to 72 hours. Bacteria may be dosed with compounds about 12-16 hours after being plated to allow growth into the plateau phase before exposure to compounds, or compounds may be washed out after about 12-16 hours to evaluate recovery from compound effect. Final DMSO concentration may be significantly reduced or elevated from 1% to alter the assay window and perhaps the sensitivity. In some embodiments, the assay may also be performed with kinetic reads instead of an endpoint to ascertain effects of compounds on CsgA expression over time. Results are shown in Table 3 and Table 4

Example 27A

Monocolonized Mouse Model. To assess effects of compounds on CsgA expression in vivo, germ-free female C57 BL/6NTac mice were randomized into groups of about 5-10 mice each and housed in isolators with appropriate practices to maintain their gnotobiotic status throughout the study. Mice were mono-colonized at age 5-8 weeks with *E. coli* MC4100. At least 6 days following colonization, mono-colonized mice were treated daily with either vehicle or compound via oral gavage for 9-14 days. Fecal pellets were collected from individual mice, flash-frozen on dry ice within 60 minutes of defecation, and stored at −80° C. Fecal pellets were assessed by culture, qPCR and/or 16S rRNA gene sequencing to confirm germ-free or mono-colonized status and determine colonization levels.

CsgA expression relative to expression of housekeeping genes recA, cysG, hcaT and/or idnT was assessed via qRT-PCR. All reagents and materials employed in RNA isolation, reverse transcription and qPCR were certified RNase-free. Controls included cultures of WT *E. coli* and a CsgA deletion mutant. RNA was isolated from one to three fecal pellets per mouse using the ZymoBIOMICS RNA Miniprep kit, catalog number $R^{2001}$, protocol version 1.1.0 (Zymo Research, Irvine, CA). For each sample, one to three fecal pellets were added to a ZR BashingBead Lysis Tube, 750 μL DNA/RNA Shield was added to the tube, and the tube was secured in a Bead Ruptor Elite bead mill homogenizer (Omni International, Kennesaw, GA). Samples were processed in the bead mill homogenizer at 3.25 m/s, with 4 cycles of 2 minutes on and 2 minutes off, for 16 minutes total processing time. The BashingBead Lysis Tubes were centrifuged for 1 minute at 16,000×g, and 300 μL supernatant was transferred to a new RNase-free tube. Nucleic acid was extracted from the supernatant following the ZymoBIOMICS RNA Miniprep kit, catalog number $R^{2001}$, protocol version 1.1.0, omitting the DNase treatment step specified in the kit protocol. Following nucleic acid isolation, DNA was eliminated from the nucleic acids using the Invitrogen TURBO DNA-Free™ Kit, catalog number AM1907, following the Invitrogen TURBO DNA-Free™ Kit User Guide Publication Number 1907M Revision H (ThermoFisher Scientific Baltics, Vilnius, Lithuania). The RNA concentration and quality were assessed by measuring absorbance at 260, 280 and 230 nm with a NanoDrop 2000 spectrophotometer (Thermo Scientific, Wilmington, DE) and determining $A_{260}/A_{280}$ and $A_{230}/A_{280}$ ratios for each sample.

Reverse transcription was performed in 20 μL reactions including 2.5 ng/μL RNA final, 0.2 ng/μL SuperScript Vilo IV Master Mix final (catalog number 11756500, Life Technologies, Carlsbad, CA) and nuclease-free water. Reactions were incubated at 25° C. for 10 minutes, 50° C. for 10 minutes, and 85° C. for 5 minutes. Reactions were set up and executed in parallel without reverse transcriptase to monitor for contaminating DNA.

qPCR was performed using primers to detect csgA (forward primer: TCT GGC AGG TGT TGT TCC TC, reverse primer: CCG CCG CCA TGC TGG GTA AT) and the housekeeping gene recA (forward primer: CTGTTCGTCTCGACATCCGT, reverse primer TCGCCGTAGAGGATCTGGAA), hcaT (forward primer: TTCTGGCCTGCGTTTGTTTAT, reverse primer AGATCAACAGCATATCGCGTG), cysG (forward primer AACAACGATCAGAAAGCCATT, reverse primer TATCGTCAGAAACCAGACGGT) and/or idnT (forward primer ACTCGCTTTGAGAAAGCACCA, reverse primer GGTTACCGACAAATTCAAAGA). qPCR reactions included 50 nM forward primer final, 50 nM reverse primer final, 10 μL Applied Biosystems PowerUp™ SYBR Green master mix (Thermo Fisher Scientific, Austin, TX), approximately 5 ng cDNA, and RNase/DNase free water in 20 μL final reaction volumes. qPCR reactions were performed in 384-well plates in an Applied Biosystems QuantStudio 5 Real-Time PCR System (Thermo Fisher Scientific, Waltham, MA) at 50° C. for 2 minutes, 95° C. for 10 minutes, and 40 cycles of 95° C. for 15 seconds and 60° C. for 1 minute. All reactions were performed in triplicate, and controls included reactions without template, reactions with the products of reverse transcriptase-negative controls, WT *E. coli* and a CsgA deletion mutant. Melting temperatures were examined to ensure that cycle threshold (CT) values corresponded to the intended target prior to inclusion of the data in subsequent analyses. To determine the effects of different treatments on csgA expression, CT values from reactions with csgA primers were normalized to CT values from reactions with housekeeping gene primers, and the percent change in expression relative to the vehicle control group was determined. See FIGS. 29A and 29B.

In other embodiments of the assay described herein, germ-free mice may be mono-colonized with amyloid-producing bacteria other than *E. coli* MC4100, and mice may be colonized through alternate methods, such as administration of viable bacterial cells on bedding, in food, or in drinking water, or through exposure to mono-colonized mice or to the bedding or feces of mono-colonized mice. Lines of mice other than C57 BL/6NTac and male mice may be used. Compounds and vehicle may be administered through alternate routes, such as in drinking water, in food, or intranasally. Compounds may be administered for less than 9 days or longer than 14 days. Fecal pellets may be added to an RNA protectant such as RNA Later instead of or in addition to being flash frozen.

In other embodiments of the qRT-PCR assays described in Example X to assess compound effects on CsgA expression, alternate primers may be designed and implemented to assess csgA, recA, cysG, hcaT, and idnT expression levels, using methods familiar to one skilled in the art. Alternate housekeeping genes, such as rrsA, fliC, pbpC, uxuB, ugpQ, uxuR, and ispA, may be used to normalize csgA qRT-PCR values. Expression of csgB and/or csgC, which are in the same operon as csgA, may be assessed in lieu of or in addition to csgA, and expression of regulators of csgA expression may be monitored, such as CsgD. Instead of or in addition to assessing csgA mRNA levels in feces, csgA mRNA levels may be assessed in gastrointestinal tract contents, sections of the gastrointestinal tract, or the entire gastrointestinal tract. Alternate methods and materials may be used to isolate RNA from samples and to eliminate DNA from RNA samples. Alternate reverse transcriptase methods, alternate enzymes, alternate oligomers such as target-specific oligomers, higher or lower reverse transcriptase concentrations, higher or lower oligomer concentrations, higher or lower RNA concentrations, and alternate temperature and time cycling parameters may be used to generate cDNA. Alternate chemistries may be used in qPCR, such as Taqman probes or alternate SYBR Green formulations, and alternate qPCR instruments may be used with compatible qPCR reagents. Higher or lower cDNA concentrations, higher or lower primer concentrations, and alternate cycling parameters may be applied in qPCR, as is familiar to one skilled in the art. Single-step qRT-PCR may be performed in lieu of separate reverse transcription and qPCR reactions, and mRNA levels may be measured by methods other than qRT-PCR, such as by fluorescent in-situ hybridization.

In some embodiments, in order to assess a compound's effects on CsgA in mice, in lieu of or in addition to assessing csgA mRNA levels, the actual CsgA protein levels may be assessed. In some embodiments, CsgA protein levels in feces, gastrointestinal tract contents, or sections of the gastrointestinal tract may be monitored by a variety of methods, including Western blots, ELISA, and mass spectrometry methods.

Example 27B 96-well Congo Red Assay. To assess the effects of compounds on production of curli in live bacterial cells, an in vitro assay was performed using *Escherichia coli* MC4100 or UTI89 ΔbcsA and YESCA agar (10 g/L casamino acids, 1 g/L yeast extract, and 20 g/L agar) containing Congo Red, a dye that binds to curli. Inoculum for the assay was prepared by inoculating a single colony of *E. coli* MC4100 or UTI89 ΔbcsA into 5 mL of Luria Broth, incubating with shaking for 18 hours at 37 degrees Celsius, and diluting the overnight culture to $OD_{600}$ 0.05 in YESCA broth (10 g/L casamino acids and 1 g/L yeast extract). The assay was conducted in 96-well clear, polystyrene Denville cell-culture plates, product number T1096, from Thomas Scientific (Swedesboro, NJ). Compounds were tested at two-fold dilutions with a range from 100 μM to 1.25 μM final concentration. Positive controls for curli inhibition included 25 g/L sodium chloride, as salt inhibits the expression of curli. Assay plates were prepared by first spotting 1.5 μl DMSO, DMSO with sodium chloride, or compound in appropriate wells. 150 μl of molten YESCA agar with 5 μg/mL final concentration of Congo Red were added to all wells of the assay plate. The mixture was pipetted up and down five times to ensure appropriate mixing of the compound and the agar. After plates were prepared, 5 μl inoculum was spotted on top of the agar in appropriate wells of the 96-well plate. Three wells were spotted with bacteria-free YESCA media to serve as blank wells for normalizing data. After addition of the media or bacteria, plates were allowed to dry in a biological safety cabinet. The dry assay plates were incubated at 26 degrees Celsius in a water-jacketed, standing incubator for 24-72 hours. The binding of Congo Red to curli on the bacterial surface was measured with a fluorescent reading on a SpectraMax M2 or M5 spectrophotometric plate reader (Molecular Devices, San Jose, CA) with excitation set at 497 nm and emission set at 614 nm. The $OD_{600}$ of each well was measured with a SpectraMax M2 or M5 plate reader to confirm bacterial growth. Both Congo Red fluorescence and $OD_{600}$ reads were performed at 20-25 degrees Celsius. Congo Red fluorescent values for the bacteria in each well were calculated by subtracting the average fluorescence read of blank wells (containing DMSO and Congo Red YESCA agar but no bacteria) from the raw fluorescence values of wells with bacteria. Fluorescent values from wells with compounds were divided by the average fluorescence read of DMSO control wells, which included bacteria and DMSO. The percent of the DMSO control at each compound concentration was calculated, with a lower percent of the DMSO control indicating a more potent compound. Additionally, $IC_{50}$s were calculated using a non-linear regression, inhibitor vs response (four parameters) equation using GraphPad Prism software version 8.0.1 by GraphPad Software Inc (San Diego, CA).

In some embodiments, the 96-well Congo Red assay described above may be performed with a different or alternative amyloid binding dyes such as (E,E)-1-fluoro-2,5-bis(3-hydroxycarbonyl-4-hydroxy) styrylbenzene (FSB) or turmeric, which are thought to bind curli specifically, while Congo Red binds both cellulose and curli (Reichhardt and Cegelski, PLoS One, 2018 and McCrate et al., Chem Communication, 2013). In some embodiments, amyloid-producing microbial strains other than *E. coli* MC4100 or UTI89 AbcsA may be included in the assay, such as strains of *Citrobacter, Salmonella, Enterobacter, Staphylococcus, Bacillus* or *Pseudomonas*. In some embodiments, the DMSO concentration used in the assay could be increased, decreased or eliminated. For *E. coli*, an increase in DMSO has been reported to upregulate the level of curli production until a concentration harmful to the bacteria is reached, while a decrease would reduce the level of curli production (Lim et al., Appl Environ Micorbiol, 2012). Likewise, the concentrations at which compounds are tested may be increased or decreased. In some embodiments, the concentration of Congo Red dye, or an alternate dye used, may be increased or decreased, and the dye concentration may be varied to identify the best signal window between background fluorescence from the dye in the agar itself and the fluorescence of the dye binding to curli. The overnight culture may be incubated in YESCA broth or another salt free medium, and this may affect the amount of time required for assay readout after the bacteria are plated, as salt, which is present in Luria Broth, inhibits the expression of curli. In contrast, another rich medium besides LB may be used for the starter culture to continue to limit production of curli until the bacteria are plated. The number of bacteria at the start of the assay may be increased or decreased, and this increase or decrease in the initial number of cells in the assay may be implemented by altering the volume of the inoculum spotted onto the assay plate or by changing the $OD_{600}$ of the bacteria that are plated. The temperature at which plates are incubated may be increased or decreased in the assay, and this change in temperature may affect the signal window and/or duration of the assay. Depending on the stability of compounds being tested, the assay timing may be varied to allow for prolonged bacterial growth on the plates. Optimal expression of curli proteins appears to occur during stationary phase so extending the incubation may highlight differences between strong production of curli in the DMSO control as compared to the reduced curli expression from a strong, stable inhibitor. In some embodiments, the assay may be performed in liquid media by adding the amyloid-binding dye to liquid cultures in the assay plate after co-incubation of compounds with bacteria under conditions that permit amyloid expression, incubating the dye to allow for binding to the bacterial amyloid, pelleting the bacteria to remove unbound dye, and re-suspending the pellet in fresh media before measuring fluorescence. The specific type of assay plate used to run the assay could be modified to reduce the number of wells and increase the size of the bacterial lawn spotted on agar. In some embodiments, the assay may be performed in a 96, 48, 24, 12, or 6 well assay plate or a petri dish, and the assay volume may be increased or decreased. In some embodiments, the assay may be performed in a polystyrene plate, a polypropylene plate, a white plate, a black plate, a clear-bottomed plate, an untreated plate, a non-binding plate or a high-binding plate. In some embodiments, the amount of amyloid produced and the inhibition of amyloid production by compounds in the assay may be assessed visually, since darker red growth indicates increased binding of CongoRed to amyloid in the assay; this visual assessment may involve development of a color scale, for example from 0 to 5, with 0 being assigned to a light color indicating minimal expression of curli and 5 indicating robust expression of curli denoted by intense binding of the dye.

Example 28

Synthesis of 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide. Compound 008 (Racemic), Compound 008a, and Compound 008b Compound 008

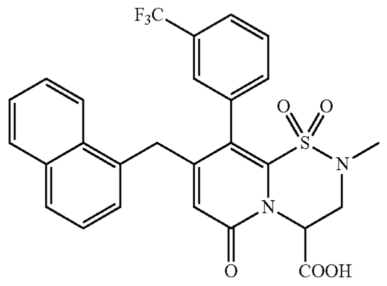

(Racemic)

Step-1: Preparation of ethyl 2-(3-(trifluoromethyl)phenyl)acetimidate 2-(3-(Trifluoromethyl)phenyl)acetonitrile (50.0 g, 270.0 mmol) was dissolved in ethanol (80 mL) and cool to 0° C. HCl gas was purged through the reaction mixture for 4h. The reaction mixture was stirred at room temperature for 16 h. The reaction mixture was then evaporated to give ethyl 2-(3-(trifluoromethyl)phenyl)acetimidate as a white solid (70.0 g) which was used without purification.

Step-2: Preparation of (R)-2-(3-(trifluoromethyl) benzyl)-4,5-dihydrothiazol-4-yl acetate

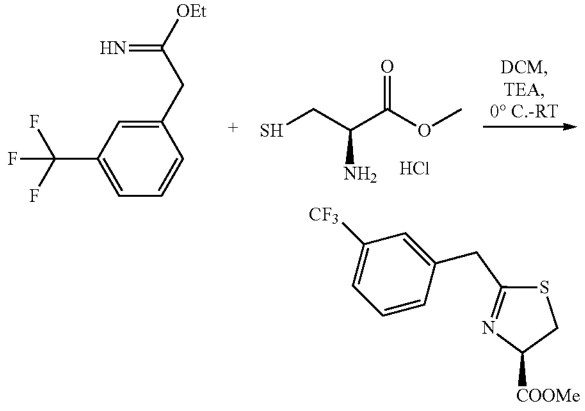

Methyl L-cysteinate hydrochloride (70.0 g, 407.92 mmol) was dissolved in dichloromethane (800 mL) and cooled to 0° C. Triethylamine (56.07 mL, 399.76 mmol) was added. The reaction was allowed to stir at room temperature for 30 min. The reaction mixture was further cooled to 0° C. Ethyl 2-(3-(trifluoromethyl)phenyl)acetimidate (69.79 g, 301.86 mmol) was dissolve in dichloromethane (300 mL) and added dropwise. The reaction mixture was stirred at room temperature for 16 h. The reaction was quenched with saturated aqueous sodium bicarbonate (800 mL) and extracted with Ethyl acetate (3×800 mL). The organic layer was dried over sodium sulphate and concentrated under reduced pressure. The crude residue was purified using column chromatography eluting with 0-25% Ethyl acetate in hexane to give (R)-2-(3-(trifluoromethyl)benzyl)-4,5-dihydrothiazol-4-yl acetate as a colorless liquid (52 g, 63%, over two steps). Liquid Chromatography Mass Spectroscopy (LCMS Method-C3): 99.27% (RT: 1.719, 235.0 nm) (MS: s ESI+ve 304.3 [M+H]). $^{1}H$ NMR: (400 MHz, DMSO) δ ppm: 1.58-3.67 (m, 2H), 3.78-3.81 (d, J=12.8 Hz, 3H), 4.0 (s, 2H), 5.20-5.25 (t, J=17.6 Hz, 1H), 7.53-7.56 (m, 1H), 7.60-7.62 (d, J=7.6 Hz, 2H), 7.66 (s, 1H).

Step 3: Preparation of 5-(1-hydroxy-2-(naphthalen-1-yl)ethylidene)-2,2-dimethyl-1,3-dioxane-4,6-dione

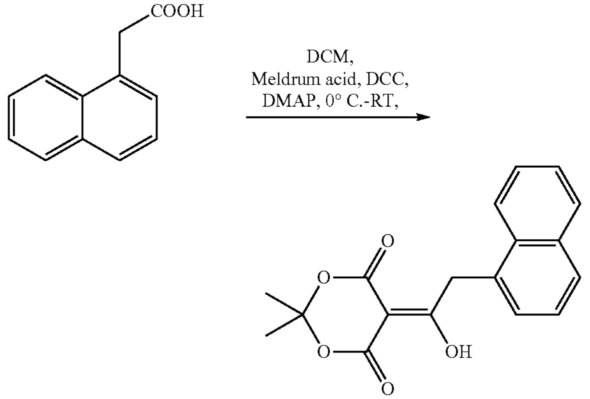

2-(naphthalen-1-yl)acetic acid (100 g, 537 mmol) and Meldrum's acid (78.06 g, 540.0 mmol) was dissolved in DCM (1500 mL) under N2. DMAP (106 g, 865.0 mmol) was added at 0° C. and the mixture was stirred for 1 h. DCC (167 g, 811.0 mmol) dissolved in DCM (300 mL) was then added dropwise at 0° C. and stirred at room temperature for 16 h. The reaction was quenched in 6% aq. $KHSO_4$ solution (4000 mL) and DCM (1000 mL) was added. The solution was filtered. The organic layer was dried over sodium sulphate. The solvent was removed under reduced pressure followed by trituration with MTBE (800 mL) and methanol (400 mL). The solid was collected by filtration to give 5-(1-hydroxy-2-(naphthalen-1-yl) ethylidene)-2, 2-dimethyl-1,3-dioxane-4,6-dione as an off white solid. (70.0 g, 41.73%) LCMS (Method-C3): 95.62% (RT: 2.121, 202.0 nm) (MS: ESI−ve 311.2 [M−H]). 1H NMR: (400 MHz, DMSO) δ ppm: 1.70 (s, 6H), 4.84 (s, 2H), 7.44-7.48 (m, 2H), 7.52-7.54 (m, 2H), 7.84-7.86 (d, J=8.8 Hz, 1H), 7.94-7.95 (d, J=6.8 Hz, 2H).

Step-4: Preparation of methyl 7-(naphthalen-1-ylmethyl)-5-oxo-8-(3-(trifluoromethyl)phenyl)-2,3-dihydro-5H-thiazolo[3,2-a]pyridine-3-carboxylate

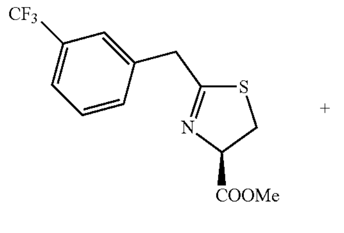

-continued

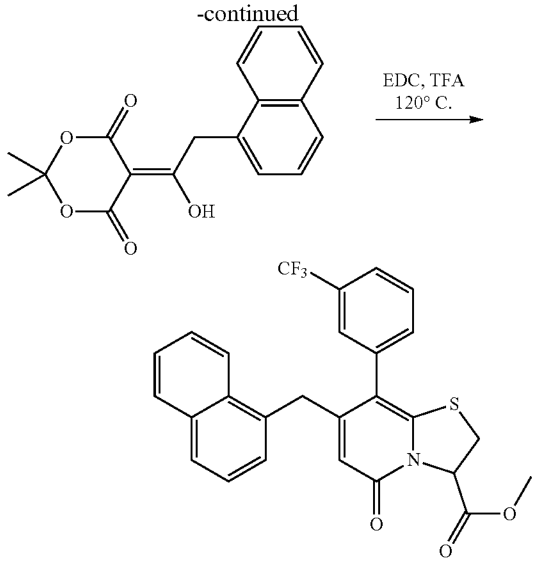

Compound 012

(R)-2-(3-(trifluoromethyl)benzyl)-4,5-dihydrothiazol-4-yl acetate (70.0 g, 230.74 mmol) and (5-(1-hydroxy-2-(naphthalen-1-yl)ethylidene)-2-methyl-4,6-dioxo-1,3-dioxan-2-yl)methylium (180.16 g, 576.8 mmol) was dissolved in 1,2 dichloroethane (800 mL). Trifluoroacetic acid (39.10 mL, 507.64 mmol) was added and the mixture was stirred at 120° C. for 16 h. The reaction was quenched in water (700 mL) and $NaHCO_3$ (500 mL) then extracted with Ethyl acetate (3×700 mL). The organic layer was dried over sodium sulphate and concentrated under reduced pressure to give the crude product which was purified using column chromatography eluting with 0-40% Ethyl acetate/hexane to give methyl 7-(naphthalen-1-ylmethyl)-5-oxo-8-(3-(trifluoromethyl)phenyl)-2,3-dihydro-5H-thiazolo[3,2-a]pyridine-3-carboxylate (60 g, 52.46%) LCMS (Method-C3): 92.46% (RT: 1.949, 225.0 nm) (MS: ESI+ve 496.37 [M+H]) $^{1}H$ NMR: (400 MHz, DMSO) δ ppm: 3.52-3.55 (d, J=12 Hz, 1H), 3.70-3.73 (d, J=10 Hz, 3H), 3.85-3.90 (m, 1H), 4.04 (s, 2H), 5.59-5.86 (m, 2H), 7.24-7.26 (d, J=6.8 Hz, 1H), 7.41-7.51 (m, 3H), 7.59-7.74 (m, 5H), 7.81-7.83 (d, J=8.4 Hz, 1H), 7.90-7.92 (d, J=7.6 Hz, 1H).

Step-5: Preparation of methyl 7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (Compound 007)

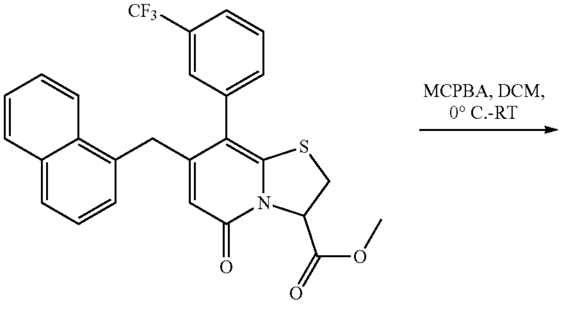

-continued

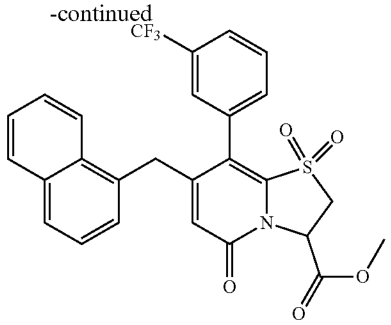

Compound 007

Methyl 7-(naphthalen-1-ylmethyl)-5-oxo-8-(3-(trifluoromethyl)phenyl)-2,3-dihydro-5H-thiazolo[3,2-a]pyridine-3-carboxylate (0.5 g, 1.009 mmol) was dissolved in DCM (10 mL). A solution of MCPBA (55%) (0.435 g, 2.52 mmol) in DCM (50 mL) was added at 0° C. and the mixture was stirred at room temperature for 16 h. The reaction was quenched in water (50 mL) and saturated aqueous $NaHCO_3$ (20 mL). The mixture was extracted with ethyl acetate (3×50 mL) and the organic layer was dried over sodium sulphate and concentrated under reduced pressure to give the crude product which was purified by column chromatography eluting with 0-50% ethyl acetate/hexane to give 0.6 g product which was used in subsequent reactions. LCMS (Method-C3): 91.25% (RT: 1.991, 224.0 nm) (MS: ESI+ve 528.21[M+H]). This material (0.098 g) was further purified using Prep HPLC Method 4 to give methyl 7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (Compound 007), as an off white solid (0.06 g, 57.51%). LCMS (Method-C3): 100.0% (RT: 1.906, 230.0 nm) (MS: ESI+ve 528.36 [M+H]). $^1$H NMR: (400 MHz, $CDCl_3$) δ ppm: 3.76-3.82 (m, 1H), 3.84-3.86 (m, 1H), 3.90 (s, 3H), 3.99-4.058 (m, 1H), 4.10-4.15 (m, 1H), 5.55-5.60 (m, 1H), 6.41-6.43 (d, J=9.6 Hz, 1H), 7.22-7.24 (d, J=6.8 Hz, 1H), 7.42-7.51 (m, 3H), 7.53-7.75 (m, 5H), 7.82-7.84 (d, J=8 Hz, 1H), 7.89-7.90 (d, J=7.6 Hz, 1H).

Step-6: Preparation of methyl 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate1,1-dioxide

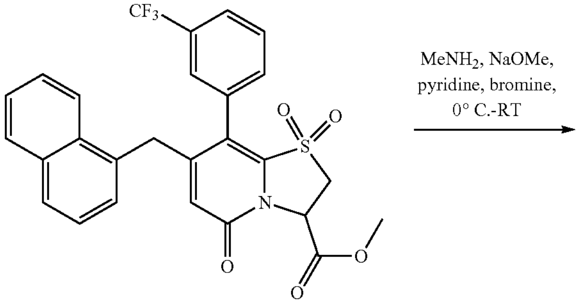

-continued

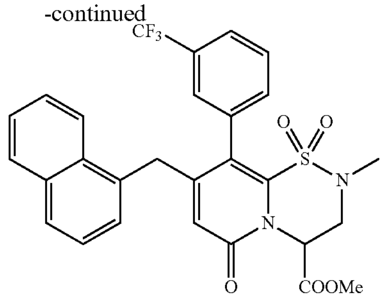

Methyl 7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.85 g, 1.612 mmol) was dissolved in methanol (9.64 mL) and cooled to 0° C. Methylamine in methanol (33%) (0.182 g, 1.935 mmol) was added portion-wise over 5 minutes. Methanolic sodium methoxide (9.64 mL, 0.2 M) was added dropwise at 0° C. and the mixture was stirred for 16 h at room temperature. The mixture was concentrated under reduced pressure and concentrated twice from chloroform. The residue was dissolved in acetonitrile (16.12 mL) and cooled to 0° C. Pyridine (0.128 mL, 1.61 mmol) was added followed by bromine (0.309 g, 1.935 mmol) and the reaction mixture was stirred for 1h. The reaction was quenched in water (50 mL) and extracted with ethyl acetate (3×50 mL). The organic layer was dried over sodium sulphate and concentrated under reduced pressure to give the crude product which was purified by column chromatography eluting with 0-20% ethyl acetate in DCM to give methyl 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.26 g, 28.99%). LCMS (Method-C3): 68.17% (RT: 1.957, 222.0 nm) (MS: ESI+ve 557.42[M+H]).

Step-7: Preparation of 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 008) (Racemic)

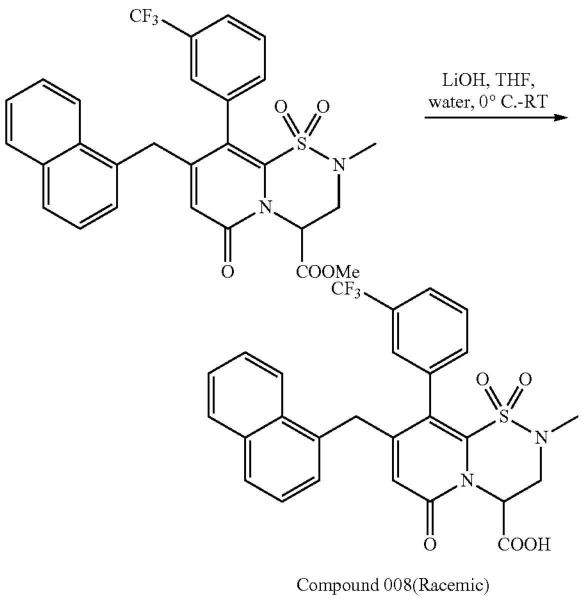

Compound 008(Racemic)

Methyl 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.26 g, 0.467 mmol) was dissolved in THF (3 mL) was cooled to 0° C. A solution of lithium hydroxide (0.058 g, 1.401 mmol) in water (3 mL) was added dropwise and stirred at room temperature for 16 h. The mixture was concentrated under reduced pressure and ice-cold water (10 mL) was added followed by 1N HCl (3-4 mL). The resulting precipitate was collected by filtration and dried under vacuum. The crude product was purified by Prep HPLC Method 1 to give 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 008) (Racemic), as an off white solid (0.040 g, 15.78%). LCMS (Method-C3): 100% (RT 2.357, 254.4 nm) (MS: ESI+ve 543.0 [M+H]). $^1$H NMR: (400 MHz, DMSO) δ ppm: 2.84 (s, 3H), 3.90 (s, 2H), 4.07-4.12 (m, 1H), 4.21-4.26 (m, 1H), 5.08 (s, 1H), 6.07-6.11 (d, J=14.8 Hz, 1H), 7.24-7.25 (d, J=6.8 Hz, 1H), 7.43-7.51 (m, 3H), 7.58-7.72 (m, 5H), 7.83-7.85 (d, J=8 Hz, 1H), 7.91-7.92 (d, J=7.6 Hz, 1H), 13.69 (s, 1H).

SFC separation of 7-(naphthalen-1-ylmethyl)-5-thioxo-8-(3-(trifluoromethyl)phenyl)-2,3-dihydro-5H-thiazolo[3,2-a]pyridine-3-carboxylic acid 1,1-dioxide (Compound 008a and Compound 008b)

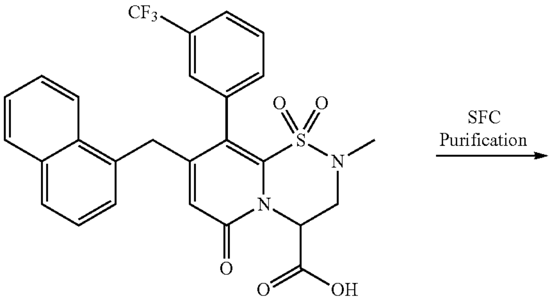

Compound 008(Racemic)

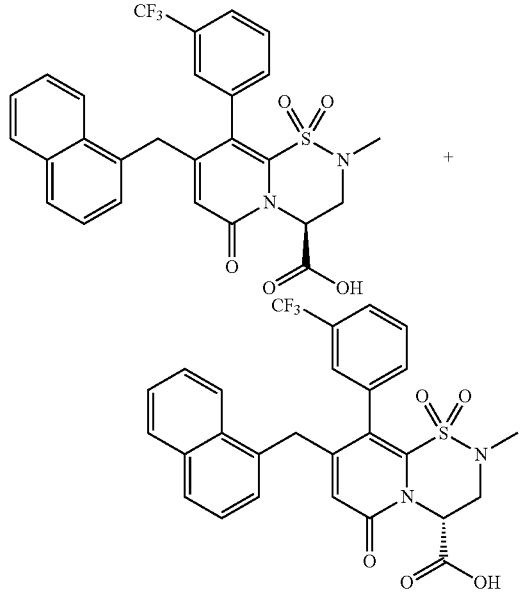

7-(Naphthalen-1-ylmethyl)-5-thioxo-8-(3-(trifluoromethyl)phenyl)-2,3-dihydro-5H-thiazolo[3,2-a]pyridine-3-carboxylic acid 1,1-dioxide (Compound 008) (0.1 g) was separated on a Shimadzu LC-20AP chromatography system with a UV detector. The column used was CHIRALPAK IC (250*21.0) mm, 5 micron, column flow was 18.0 ml/min. Mobile phase (A) 0.2% TEA in n-Hexane (B) 0.2% TEA in Methanol:Ethanol (50:50). Solvent B gradient was 80-20% over 35 min.

Isolated (0.004 g, 4.56%) of fraction 1 (Compound 008a). LCMS (Method-$C_3$): 100% (RT: 1.857, 225.0 nm) (MS: ESI+ve 542.5 [M+H]). $^1$H NMR (FR-1): (400 MHz, $CD_3OD$) δ ppm: 2.97-2.98 (d, J=2.4 Hz, 3H), 3.94 (s, 2H), 4.19-4.24 (m, 1H), 4.30-4.35 (m, 1H), 5.12-5.15 (m, 1H), 6.26-6.28 (d, J=6.8 Hz, 1H), 7.27-7.30 (m, 1H), 7.42-7.55 (m, 3H), 7.59-7.63 (m, 1H), 7.67-7.71 (m, 3H), 7.80 (s, 1H), 7.82 (s, 1H), 7.86-7.88 (m, 1H). Chiral HPLC (Fr-1): 100% (RT: 13.08).

Isolated (0.003 g, 3.78%) of fraction 2 (Compound 008b). LCMS (Method-$C_3$): 100% (RT: 1.829, 202.0 nm) (MS: ESI+ve 543.4 [M+H]). $^1$H NMR (FR-2): (400 MHz, $CD_3OD$) δ ppm: 2.92 (m, 3H), 3.88-3.98 (m, 2H), 4.20-4.23 (d, J=12.4 Hz, 1H), 4.29-4.34 (m, 1H), 5.09 (s, 1H), 6.25-6.27 (d, J=7.2 Hz, 1H), 7.27-7.30 (m, 1H), 7.42-7.54 (m, 3H), 7.59-7.63 (m, 1H), 7.67-7.72 (m, 3H), 7.79-7.818 (d, J=8 Hz, 1H), 7.85-7.87 (d, J=7.2 Hz, 2H). Chiral HPLC (Fr-2): 96.59% (RT: 14.50).

Example 29

Synthesis of 7-(naphthalen-1-ylmethyl)-5-oxo-8-(3-(trifluoromethyl)phenyl)-2,3-dihydro-5H-thiazolo[3,2-a]pyridine-3-carboxylic acid (Compound 011) (Racemic), (Compound 011a) and (Compound 011b)

Compound 011

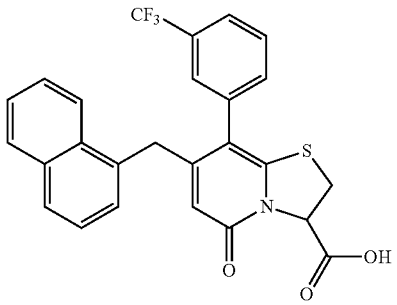

(Racemic)
Compound 011a
Arbitrary stereochemistry
Compound 011b
Arbitrary stereochemistry Step-1: Preparation of 7-(naphthalen-1-ylmethyl)-5-oxo-8-(3-(trifluoromethyl)phenyl)-2,3-dihydro-5H-thiazolo[3,2-a]pyridine-3-carboxylic acid (Compound 011)(Racemic)

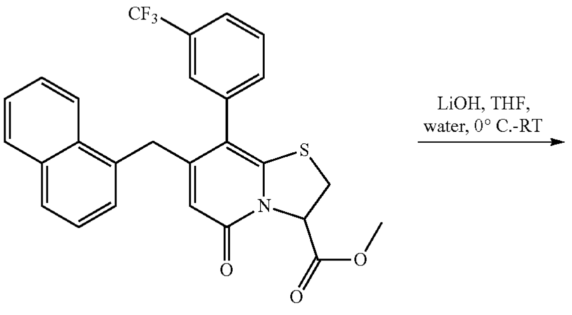

Compound 012

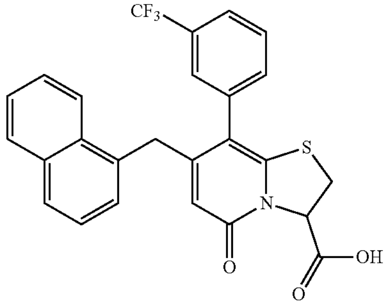

Compound 011(Racemic)

Methyl 7-(naphthalen-1-ylmethyl)-5-oxo-8-(3-(trifluoromethyl)phenyl)-2,3-dihydro-5H-thiazolo[3,2-a]pyridine-3-carboxylate (Compound 012) (0.18 g, 0.3636 mmol) was dissolved in THF (5 mL) and cooled to 0° C. A solution of LiOH (0.0457 g, 1.09 mmol) in water (5 mL) was added and the mixture was stirred at room temperature for 16 h. The mixture was concentrated under reduced pressure and ice-cold water (10 mL) was added followed by 1N HCl (3-4 mL). The resulting precipitate was collected by filtration and dried under vacuum. The crude product was purified by Prep HPLC Method 1 to give 7-(naphthalen-1-ylmethyl)-5-oxo-8-(3-(trifluoromethyl)phenyl)-2,3-dihydro-5H-thiazolo[3,2-a]pyridine-3-carboxylic acid (Compound 011)(Racemic), as an off white solid (0.025 g, 14.29%). LCMS (Method-C3): 100.0% (RT 1.848, 223.0 nm) (MS: ESI+ve 482.47 [M+H]). $^{1}$H NMR: (400 MHz, DMSO) δ ppm: 3.47-3.67 (m, 2H), 4.00 (s, 2H) 5.13-5.15 (d, J=8 Hz, 1H), 5.52 (s, 1H), 7.25-7.27 (d, J=6.8 Hz, 1H), 7.42-7.52 (m, 4H), 7.64-7.66 (d, J=7.2 Hz, 3H), 7.74-7.76 (d, J=7.6 Hz, 1H), 7.81-7.83 (d, J=8 Hz, 1H), 7.91-7.93 (d, J=8.8 Hz, 1H).

SFC separation of 7-(naphthalen-1-ylmethyl)-5-oxo-8-(3-(trifluoromethyl)phenyl)-2,3-dihydro-5H-thiazolo[3,2-a]pyridine-3-carboxylic acid (Compound 011a) and (Compound 011b)

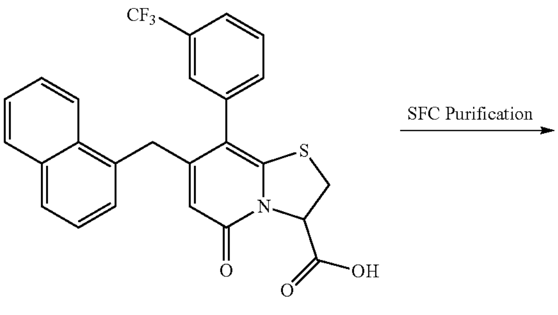

Compound 011 (Racemic)

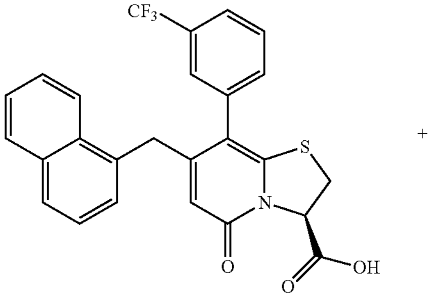

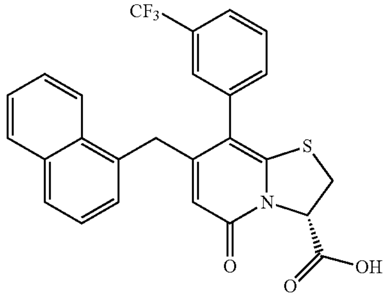

7-(Naphthalen-1-ylmethyl)-5-oxo-8-(3-(trifluoromethyl)phenyl)-2,3-dihydro-5H-thiazolo[3,2-a]pyridine-3-carboxylic acid (0.1 g) was separated on a Waters SFC 200 chromatography system with a UV detector. The column was Chiralpak IG (250*21.0) mm, 5 micron, column flow was 80.0 ml/min and automated back pressure regulator (ABPR) setting was 100 bar. Mobile phase (A) Liquid Carbon dioxide (Liq. CO2) and (B) 0.1% DEA in Methanol. The gradient solvent B was 18-18% over 20 min.

Isolated fraction 1 (Compound 011a) (0.013 g, 13.38%). LCMS (Method-$C_3$): 100.0% (RT 1.856, 223.0 nm) (MS: ESI+ve 482.66 [M+H]). $^{1}$H NMR: (400 MHz, DMSO) δ ppm: 3.49-3.52 (d, J=12 Hz, 1H), 3.83-3.86 (t, 1H), 4.04 (s, 2H), 5.46-5.48 (d, J=8.4 Hz, 1H), 5.60-5.63 (d, J=14.8 Hz, 1H), 7.25-7.27 (d, J=6.8 Hz, 1H), 7.42-7.51 (m, 3H), 7.63-7.75 (m, 5H), 7.82-7.84 (d, J=8.4 Hz, 1H), 7.91-7.93 (d, J=8.8 Hz, 1H) 13.54 (s, 1H). Chiral HPLC (Fr-1): 100% (RT: 10.92)

Isolated fraction 2 and (Compound 011b) (0.01 g, 10.29%). LCMS (Method-$C_3$): 100.0% (RT 1.852, 225.0 nm) (MS: ESI+ve 482.61 [M+H]). $^{1}$H NMR: (400 MHz, DMSO) δ ppm: 3.48-3.51 (d, J=12 Hz, 1H), 3.84 (t, 1H), 4.02 (s, 2H), 5.44-5.47 (d, J=8.4 Hz, 1H), 5.58-5.61 (d, J=13.2 Hz, 1H), 7.23-7.25 (d, J=6.8 Hz, 1H), 7.40-7.50 (m, 3H), 7.57-7.73 (m, 5H), 7.80-7.82 (d, J=8 Hz, 1H), 7.89-7.91 (d, J=7.6 Hz, 1H) 13.56 (s, 1H). Chiral HPLC (Fr-2): 100% (RT: 13.1).

Example 30

Synthesis of 7-(naphthalen-1-ylmethyl)-5-oxo-8-(3-(trifluoromethyl)phenyl)-2,3-dihydro-5H-thiazolo[3,2-a]pyridine-3-carboxylic acid 1-oxide (Compound 027a, Compound 027b)

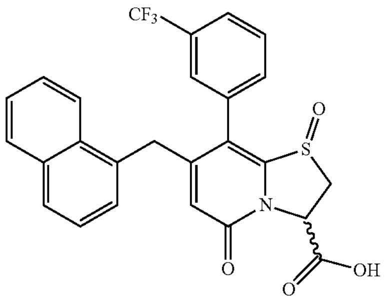

Compound 027a
Arbitrary stereochemistry
Compound 027b
Arbitrary stereochemistry

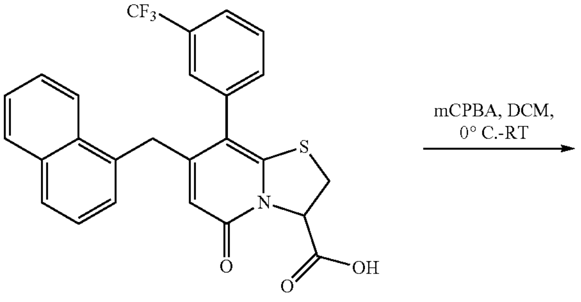

Compound 011

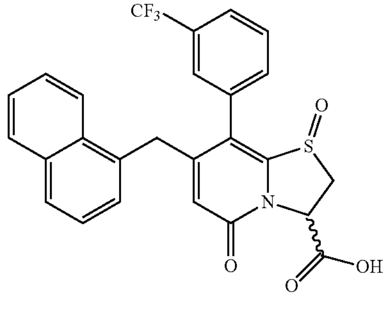

Compound 027a and 027b 7-(Naphthalen-1-ylmethyl)-5-oxo-8-(3-(trifluoromethyl)phenyl)-2,3-dihydro-5H-thiazolo[3,2-a]pyridine-3-carboxylic acid (0.16 g, 0.332 mmol) was dissolved in DCM (5 mL) and cooled to 0° C. A solution of MCPBA (60%) (0.0688 g, 0.399 mmol) dissolved in DCM (2 mL) was added at 0° C. and the mixture was stirred at room temperature for 6 h. The reaction was quenched in water (50 mL) and extracted with DCM (3×50 mL). The organic layer was dried over sodium sulphate and concentrated under reduced pressure. The crude residue (0.17 g) was purified using Prep HPLC Method 3

Isolated fraction 1 (Compound 027a) (0.008 g, 4.71%) LCMS (Method-J): 100% (RT: 4.646, 202.0 nm) (MS: ESI+ve 498.0 [M+H]). $^{1}$H NMR: (400 MHz, DMSO) δ ppm: 3.62-3.73 (m, 2H), 4.11-4.26 (m, 2H), 5.36-5.38 (d, J=7.2 Hz, 1H), 6.11-6.12 (d, J=4.4 Hz, 1H), 7.20-7.25 (m, 1H), 7.40-7.52 (m, 3H), 7.65-7.69 (t, 1H), 7.75-7.77 (m, 2H), 7.83-7.94 (m, 4H).

Isolated fraction 2 (0.020 g, 11.76%) (Compound 027b) LCMS (Method-J): 100% (RT: 5.120, 202.0 nm) (MS: ESI+ve 498.0 [M+H]). $^{1}$H NMR: (400 MHz, DMSO) δ ppm: 3.71-3.76 (m, 2H), 4.10-4.27 (m, 2H), 5.69-5.74 (t, 1H), 6.10-6.14 (d, J=16.8 Hz, 1H), 7.22-7.26 (t, 1H), 7.41-7.51 (m, 3H), 7.68-7.94 (m, 7H).

Example 31

Synthesis of 7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 010) (Racemic) (Compound 010a, Compound 010b)

Compound 010

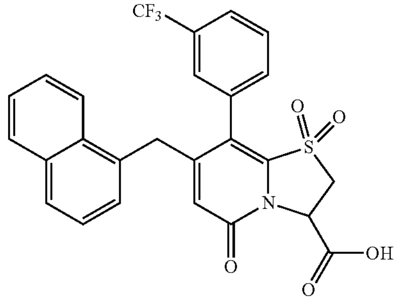

(Racemic)
Compound 010a
Arbitrary Stereochemistry
Compound 010b
Arbitrary Stereochemistry

Step-1: Preparation of 7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 010)(Racemic)

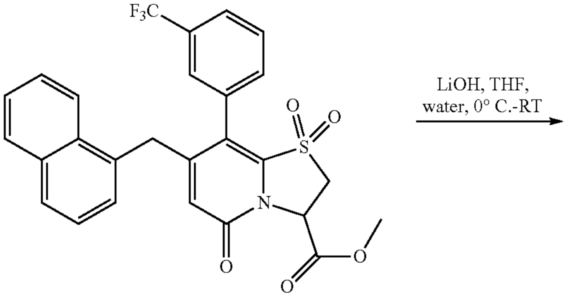

Compound 007

-continued

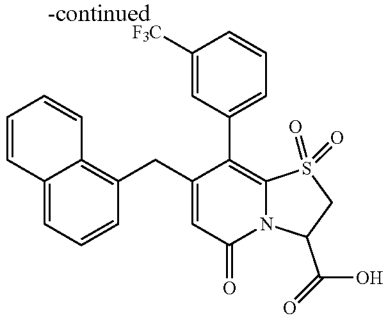

Compound 010 (Racemic)

Methyl 7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.1 g, 0.189 mmol) was dissolved in THF (3 mL). A solution of LiOH (0.0457 g, 1.09 mmol) in water (3 mL) was added at 0° C. and the mixture was stirred at room temperature for 16 h. The mixture was concentrated under reduced pressure and ice-cold water (10 mL) was added followed by 1N HCl (3-4 mL). The resulting precipitate was collected by filtration and dried under vacuum. The crude product was purified using Prep HPLC Method 1 to give 7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 010) (Racemic), as an off white solid (0.02 g 20.55%), LCMS (Method-C3): 96.57% (RT 1.733, 224.0 nm) (MS: ESI+ve 514.0 [M+H]). $^{1}$H NMR: (400 MHz, DMSO) δ ppm: 4.07-4.22 (m, 4H), 5.43-5.44 (d, J=5.6 Hz, 1H), 6.15-6.21 (d, J=30.8 Hz, 1H), 7.24-7.25 (t, 1H), 7.43-7.51 (m, 3H), 7.61-7.80 (m, 5H), 7.84-7.86 (d, J=8 Hz, 1H), 7.92-7.94 (d, J=7.6 Hz, 1H), 13.99 (s, 1H).

SFC separation of 7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 010a, Compound 010b)

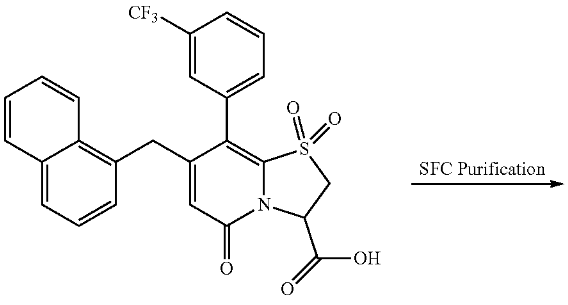

Compound 010 (Racemic)

-continued

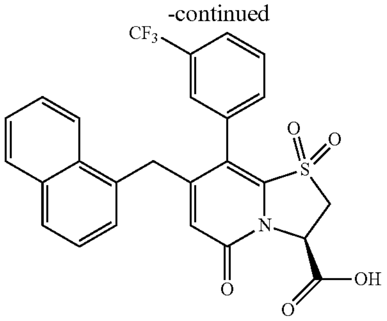

+

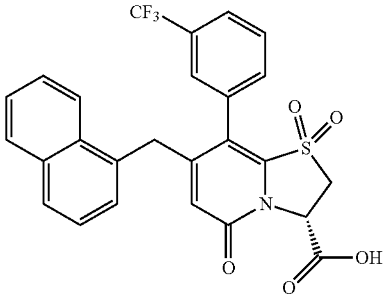

Racemic 7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (0.1 g) was separated on a Waters SFC 200 chromatography system with a UV detector. The column was Chiralpak IC (250*21.0) mm, 5 micron, column flow was 80.0 ml/min and ABPR was 100 bar. Mobile phase (A) Liquid Carbon dioxide (Liq. CO2) and (B) 0.1% DEA in Methanol. The gradient solvent B was 15-15% over 35 min.

Isolated fraction 1 (Compound 010a) (0.024 g, 24.66%). LCMS (Method-$C_3$): 100.0% (RT 1.782, 225.0 nm) (MS: ESI+ve 513.14 [M+H]). $^{1}$H NMR: (400 MHz, DMSO) δ ppm: 4.06-4.20 (m, 4H), 5.41 (s, 1H), 6.14-6.22 (d, J=30.4 Hz, 1H), 7.23-7.25 (d, J=4.8 Hz, 1H), 7.43-7.51 (m, 3H), 7.61-7.80 (m, 5H), 7.84-7.86 (d, J=7.6 Hz, 1H), 7.92-7.94 (d, J=7.6 Hz, 1H). Chiral HPLC (Fr-1): 99.75% (RT: 5.79), Isolated fraction 2 (Compound 010b) (0.026 g, 26.71%). LCMS (Method-$C_3$): 100.0% (RT 1.781, 225.0 nm) (MS: ESI+ve 513.23 [M+H]). $^{1}$H NMR: (400 MHz, DMSO) δ ppm: 4.07-4.21 (m, 4H), 5.41-5.43 (t, 1H), 6.15-6.22 (d, J=30 Hz, 1H), 7.24-7.25 (t, 1H), 7.43-7.51 (m, 3H), 7.61-7.80 (m, 5H), 7.84-7.86 (d, J=8 Hz, 1H), 7.92-7.94 (d, J=8 Hz, 1H). Chiral HPLC (Fr-2): 94.19% (RT: 6.07).

Example 32

Synthesis of 7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 014) (Racemic), Compound 014a, Compound 014b Compound 014

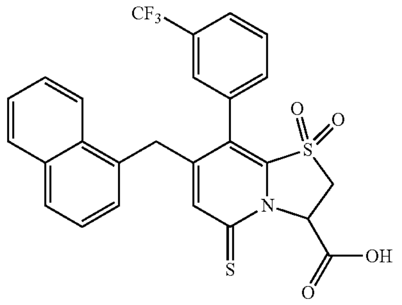

(Racemic)
Compound 014a
Arbitrary stereochemistry
Compound 014b
Arbitrary stereochemistry

Step-1: Preparation of methyl 7-(naphthalen-1-ylmethyl)-5-thioxo-8-(3-(trifluoromethyl)phenyl)-2,3-dihydro-5H-thiazolo[3,2-a]pyridine-3-carboxylate 1,1-dioxide (Compound 013)(Racemic)

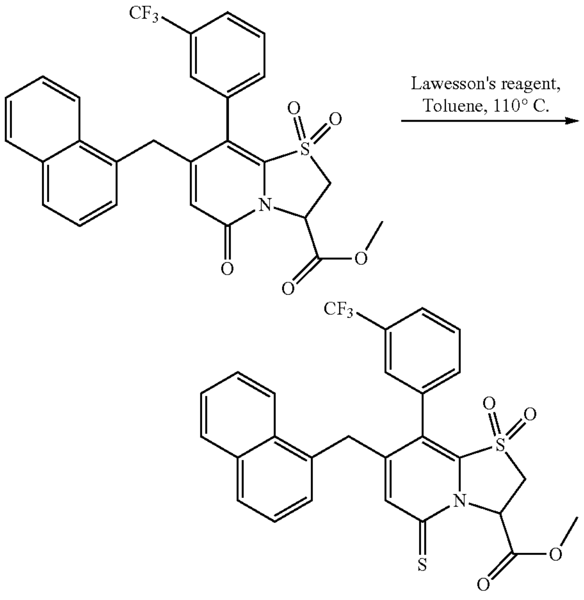

Compound 013 (Racemic)

Methyl 7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.5 g, 0.948 mmol) was dissolved in toluene (10 mL). Lawesson's reagent (0.0457 g, 1.09 mmol) was added, and the mixture was heated in a sealed tube at 110° C. for 16 h. The reaction was quenched with water (50 mL) and extracted with ethyl acetate (3×50 mL). The organic layer was dried over sodium sulphate and concentrated under reduced pressure to give methyl 7-(naphthalen-1-ylmethyl)-5-thioxo-8-(3-(trifluoromethyl)phenyl)-2,3-dihydro-5H-thiazolo[3,2-a]pyridine-3-carboxylate 1,1-dioxide (Compound 013) (Racemic), as a yellow solid (0.2 g, 38.82%), LCMS (Method-C3): 100.0% (RT 2.050, 222.0 nm) (MS: ESI+ve 544.47 [M+H]). $^{1}$H NMR: (400 MHz, $CDCl_3$) δ ppm: 3.85-3.99 (m, 6H), 4.02-4.09 (m, 1H), 4.10-4.14 (t, 1H), 6.27-6.29 (d, J=6.4 Hz, 1H), 7.21-7.23 (d, J=6.8 Hz, 1H), 7.31-7.39 (m, 1H), 7.42-7.63 (m, 6H), 7.65-7.71 (m, 1H), 7.82-7.91 (m, 2H).

Step-2: Preparation of 7-(naphthalen-1-ylmethyl)-5-thioxo-8-(3-(trifluoromethyl)phenyl)-2,3-dihydro-5H-thiazolo[3,2-a]pyridine-3-carboxylic acid 1,1-dioxide (Compound 014)(Racemic)

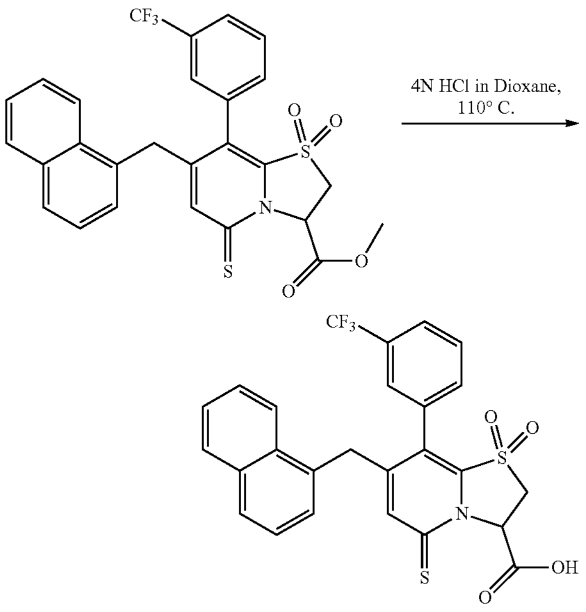

Compound 014 (Racemic)

Methyl 7-(naphthalen-1-ylmethyl)-5-thioxo-8-(3-(trifluoromethyl)phenyl)-2,3-dihydro-5H-thiazolo[3,2-a]pyridine-3-carboxylate 1,1-dioxide (0.03 g, 0.05518 mmol) was dissolved in 1, 4-dioxane (0.3 mL). 4 N HCl in dioxane (0.05 mL) was added and the mixture was heated in a sealed tube at 110° C. for 6 h. The mixture was concentrated under vacuum and the crude product was purified using Prep HPLC Method 1 to give 7-(naphthalen-1-ylmethyl)-5-thioxo-8-(3-(trifluoromethyl)phenyl)-2,3-dihydro-5H-thiazolo[3,2-a]pyridine-3-carboxylic acid 1,1-dioxide (Compound 014)(Racemic), as a yellow solid (0.007 g, 23.95%). LCMS (Method-C3): 100.0% (RT 1.841, 254.0 nm) (MS: ESI+ve 530.56 [M+H]). $^{1}$H NMR: (400 MHz, DMSO) δ ppm: 4.09-4.26 (m, 3H), 4.36-4.40 (d, J=14.4 Hz, 1H), 5.96-5.98 (d, J=8.4 Hz, 1H), 7.08-7.17 (d, J=34.4 Hz, 1H), 7.26-7.29 (t, 1H), 7.45-7.52 (m, 3H), 7.66-7.80 (m, 4H), 7.86-7.96 (m, 3H), 14.07 (s, 1H).

SFC separation of 7-(naphthalen-1-ylmethyl)-5-thioxo-8-(3-(trifluoromethyl)phenyl)-2,3-dihydro-5H-thiazolo[3,2-a]pyridine-3-carboxylic acid 1,1-dioxide (Compound 014a, Compound 014b)

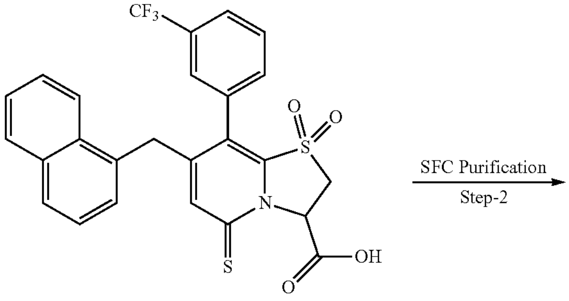

Compound 014 (Racemic)

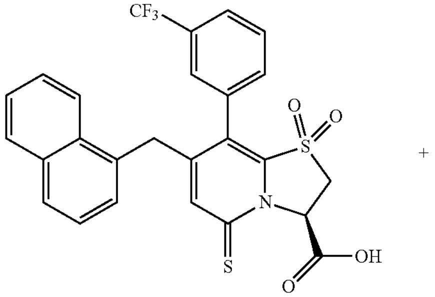

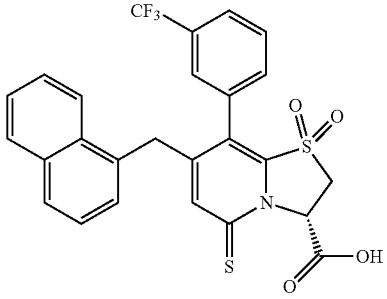

Racemic 7-(naphthalen-1-ylmethyl)-5-thioxo-8-(3-(trifluoromethyl)phenyl)-2,3-dihydro-5H-thiazolo[3,2-a]pyridine-3-carboxylic acid 1,1-dioxide (0.075 g) was separated on a Waters SFC 200 chromatography system with a UV detector. The column was Chiralpak AD-H (250*21.0) mm, 5 micron, column flow was 80.0 ml/min and ABPR was 100 bar. Mobile phase (A) Liquid Carbon dioxide (Liq. CO2) and $(B)_{0.1}$% DEA Methanol. The gradient solvent B was 20-20% over 20 min.

Isolated fraction 1 (Compound 014a) as an off white solid (0.009 g, 12.32%) LCMS (Method-J): 98.46% (RT 4.583, 220.0 nm) (MS: ESI+ve 530.52 [M+H]). 1H NMR: (400 MHz, DMSO) δ ppm: 4.07-4.24 (m, 3H), 4.34-4.37 (d, J=12.4 Hz, 1H), 5.94-5.96 (d, J=8.4 Hz, 1H), 7.06-7.14 (d, J=34 Hz, 1H), 7.24-7.27 (t, 1H), 7.44-7.51 (m, 3H), 7.64-7.78 (m, 5H), 7.84-7.86 (d, J=7.6 Hz, 1H), 7.92-7.94 (d, J=7.2 Hz, 1H), 14.08 (s, 1H). Chiral HPLC (Fr-1): 97.34% (RT: 3.91), Isolated fraction 2 and (Compound 014b), as an off white solid (0.017 g, 23.27%) LCMS (Method-J): 100% (RT 4.577, 224.0 nm) (MS: ESI+ve 530.52 [M+H]). $^{1}H$ NMR: (400 MHz, DMSO) δ ppm: 4.07-4.24 (m, 3H), 4.34-4.38 (d, J=14.4 Hz, 1H), 5.94-5.96 (d, J=8.4 Hz, 1H), 7.06-7.15 (d, J=34.4 Hz, 1H), 7.24-7.27 (t, 1H), 7.44-7.51 (m, 3H), 7.65-7.78 (m, 5H), 7.84-7.86 (d, J=8 Hz, 1H), 7.92-7.94 (d, J=7.6 Hz, 1H), 14.05 (s, 1H). Chiral HPLC (Fr-2): 96.1% (RT: 4.62)

Example 33

Synthesis of 7-(naphthalen-1-ylmethyl)-5-thioxo-8-(3-(trifluoromethyl)phenyl)-2,3-dihydro-5H-thiazolo[3,2-a]pyridine-3-carboxylic acid (Compound 054)

Compound 054

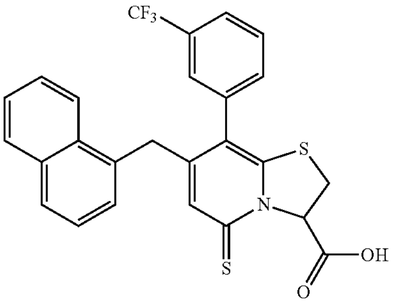

Step 1: Preparation of methyl 7-(naphthalen-1-ylmethyl)-5-thioxo-8-(3-(trifluoromethyl)phenyl)-2,3-dihydro-5H-thiazolo[3,2-a]pyridine-3-carboxylate

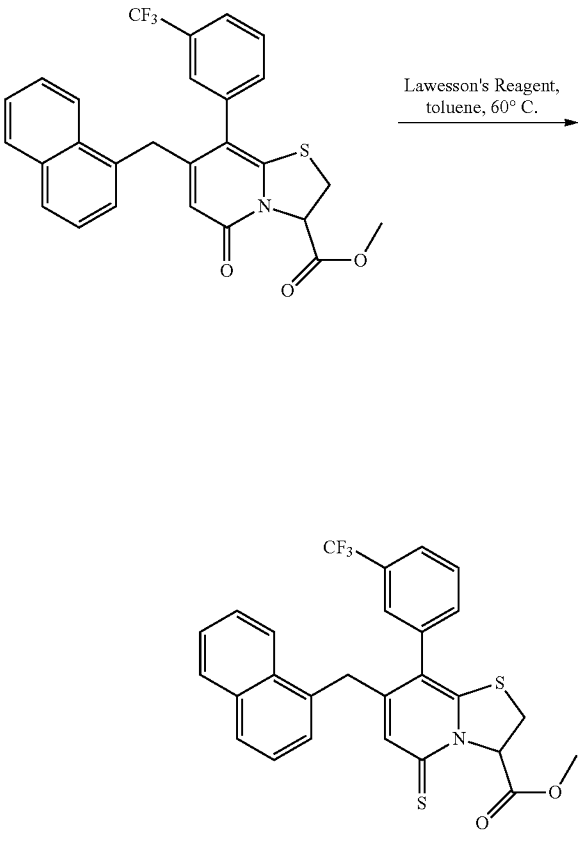

Methyl 7-(naphthalen-1-ylmethyl)-5-oxo-8-(3-(trifluoromethyl)phenyl)-2,3-dihydro-5H-thiazolo[3,2-a]pyridine-3-carboxylate (0.4 g, 0.807 mmol) was dissolved in toluene (5 mL) and Lawesson's reagent (0.32 g, 0.807 mmol) was added. The mixture was stirred at 60° C. for 16 h. then quenched with water (30 mL) and extracted with ethyl acetate (3x30 mL). The organic layer was dried over sodium sulphate and concentrated under reduced pressure. The crude product was purified using column chromatography eluting with 40% ethyl acetate/hexane to give methyl 7-(naphthalen-1-ylmethyl)-5-thioxo-8-(3-(trifluoromethyl)phenyl)-2,3-dihydro-5H-thiazolo[3,2-a]pyridine-3-carboxylate as a pale yellow gum. (0.170 g, 41.17%) LCMS (Method-$C_3$): 98.97% (RT: 2.131, 225 nm) (MS: ESI+ve 512.4 [M+H]).

Step 2: Preparation of 7-(naphthalen-1-ylmethyl)-5-thioxo-8-(3-(trifluoromethyl)phenyl)-2,3-dihydro-5H-thiazolo[3,2-a]pyridine-3-carboxylic acid (Compound 054)

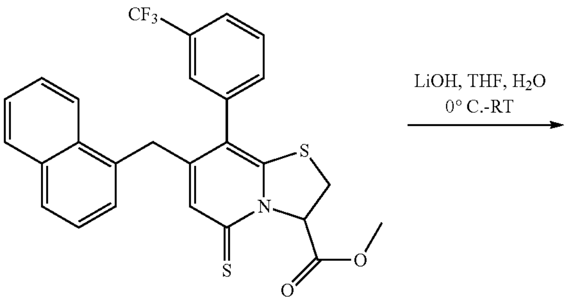

-continued

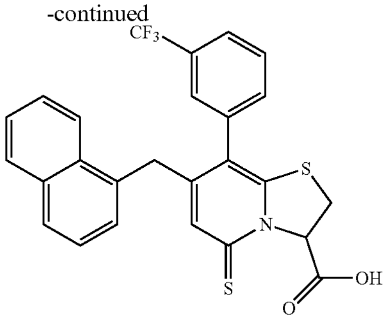

Compound 054

Methyl 7-(naphthalen-1-ylmethyl)-5-thioxo-8-(3-(trifluoromethyl)phenyl)-2,3-dihydro-5H-thiazolo[3,2-a]pyridine-3-carboxylate (0.19 g, 0.371 mmol) was dissolved in THF: $H_2O$ (1:1, 6 mL). LiOH—$H_2O$ (0.093 g 2.228 mmol) was added and the mixture was stirred at room temperature for 4 h. The mixture was concentrated and cold water (10 mL) was added followed by 1N HCl (3-4 mL) and the resulting solid was collected by filtration and dried under vacuum. The crude product was purified using Prep HPLC Method 1 to give 7-(naphthalen-1-ylmethyl)-5-thioxo-8-(3-(trifluoromethyl)phenyl)-2,3-dihydro-5H-thiazolo[3,2-a]pyridine-3-carboxylic acid (Compound 054), as a light yellow solid (0.005 g, 2.77%). LCMS (Method-C3): 95.2% (RT 5.401, 254.4 nm) (MS: ESI+ve 498.0 [M+H]). $^1$H NMR: (400 MHz, DMSO) δ ppm: 3.51-3.54 (d, J=11.2 Hz, 1H), 3.80 (s, 1H), 4.01 (s, 2H), 5.90-5.92 (s, 1H), 6.53-6.56 (d, J=13.2 Hz, 1H), 7.19 (s, 1H), 7.26-7.28 (d, J=6.8 Hz, 1H), 7.42-7.54 (m, 3H), 7.64-7.75 (m, 4H), 7.82-7.84 (d, J=8.4, 1H), 7.90-7.92 (d, J=7.2, 1H).

Example 34

Synthesis of 3-(hydroxymethyl)-7-(naphthalen-1-ylmethyl)-8-(3-(trifluoromethyl)phenyl)-2,3-dihydro-5H-thiazolo[3,2-a]pyridin-5-one (Compound 118)

Compound 118

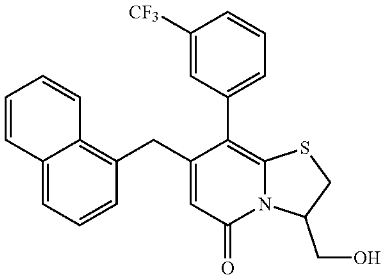

Compound 118

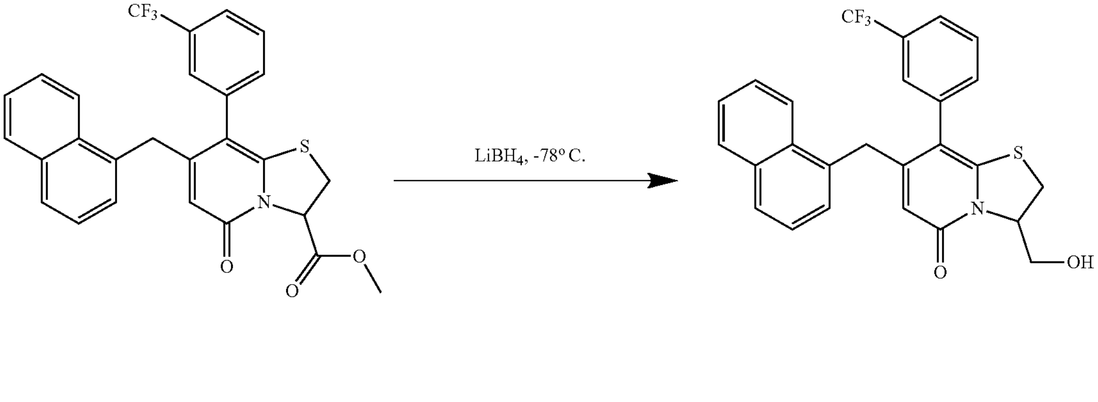

Methyl 7-(naphthalen-1-ylmethyl)-5-oxo-8-(3-(trifluoromethyl)phenyl)-2,3-dihydro-5H-thiazolo[3,2-a]pyridine-3-carboxylate (2.0 g, 4.04 mmol) was dissolved in tetrahydrofuran (10 mL) and cooled to −78° C. 4M lithium borohydride in tetrahydrofuran (1.5 mL, 6.06 mmol) was added at −78° C. dropwise and the mixture was stirred at −78° C. for 2 h, then at room temperature for 30 min. The reaction was quenched in 1 N HCl (15 mL) and extracted with ethyl acetate (2×25 mL). The organic layer was dried over sodium sulphate and evaporated under vacuum. The crude product was triturated with n-pentane to give 3-(hydroxymethyl)-7-(naphthalen-1-ylmethyl)-8-(3-(trifluoromethyl)phenyl)-2,3-dihydro-5H-thiazolo[3,2-a]pyridin-5-one (Compound 118), as a yellowish solid (1.7 g, 89.94% yield). LCMS (Method-C3): 96.39% (RT 2.323) (MS: ESI+ve 468.0 [M+H]). $^1$H NMR: (400 MHz, DMSO) δ ppm: 3.38-3.43 (t, 1H), 3.62 (s, 3H), 3.93-4.04 (t, 2H), 5.01-5.02 (d, J=3.6 Hz, 1H), 5.31 (s, 1H), 5.56-5.59 (d, J=13.6 Hz, 1H), 7.23-7.25 (d, J=6.8 Hz, 1H), 7.41-7.58 (m, 3H), 7.64-7.73 (m, 5H), 7.81-7.83 (d, J=8 Hz, 1H), 7.90-7.92 (d, J=7.6 Hz, 1H).

Example 35

Synthesis of 2-(7-(naphthalen-1-ylmethyl)-5-oxo-8-(3-(trifluoromethyl)phenyl)-2,3-dihydro-5H-thiazolo[3,2-a]pyridin-3-yl)acetic acid (Compound 129)

Compound 129

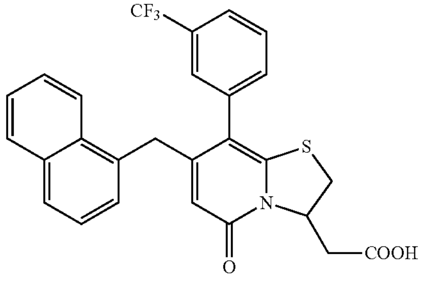

Step-1: Preparation of 3-(iodomethyl)-7-(naphthalen-1-ylmethyl)-8-(3-(trifluoromethyl)phenyl)-2,3-dihydro-5H-thiazolo[3,2-a]pyridin-5-one

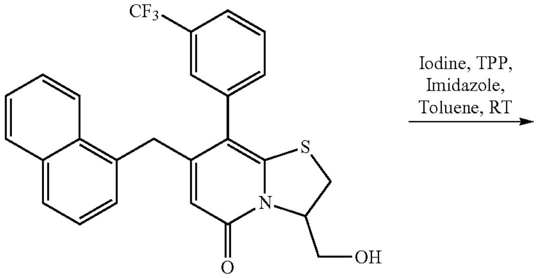

-continued

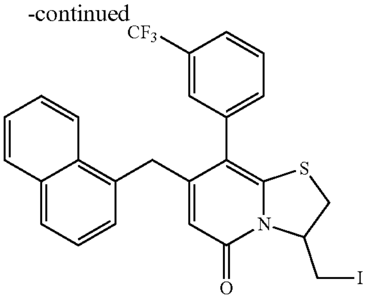

3-(Hydroxymethyl)-7-(naphthalen-1-ylmethyl)-8-(3-(trifluoromethyl)phenyl)-2,3-dihydro-5H-thiazolo[3,2-a]pyridin-5-one (1.8 g, 3.85 mmol) was dissolved in toluene (20 mL), and Iodine (1.95 g, 7.708 mmol), triphenyl phosphine (2.12 g, 8.094 mmol) and imidazole (0.733 g, 10.79 mmol) were added sequentially, and the mixture was stirred at room temperature for 24 h. The reaction was quenched in ice water (150 mL) and extracted with ethyl acetate (3×150 mL). The organic layer was dried over sodium sulphate and concentrated under reduced pressure. The crude product was purified using column chromatography eluting with 0-50% ethyl acetate/hexane to give 3-(iodomethyl)-7-(naphthalen-1-ylmethyl)-8-(3-(trifluoromethyl)phenyl)-2,3-dihydro-5H-thiazolo[3,2-a]pyridin-5-one, as an off white solid (1.4 g, 62.97%). LCMS (Method-C3): 97.07% (RT: 2.599, 202.4 nm) (MS: ESI+ve 578.0 [M+1]). $^1$H NMR: (400 MHz, DMSO) δ ppm: 3.50 (m, 2H), 3.63-3.74 (m, 2H), 3.93-4.05 (m, 2H), 5.17-5.20 (t, 1H), 5.60-5.63 (d, J=14.8 Hz, 1H), 7.22-7.23 (d, J=6.8 Hz, 1H), 7.39-7.49 (m, 3H), 7.59-7.71 (m, 5H), 7.79-7.81 (d, J=8 Hz, 1H), 7.89-7.91 (d, J=7.6 Hz, 1H).

Step 2: Preparation of 2-(7-(naphthalen-1-ylmethyl)-5-oxo-8-(3-(trifluoromethyl)phenyl)-2,3-dihydro-5H-thiazolo[3,2-a]pyridin-3-yl)acetonitrile

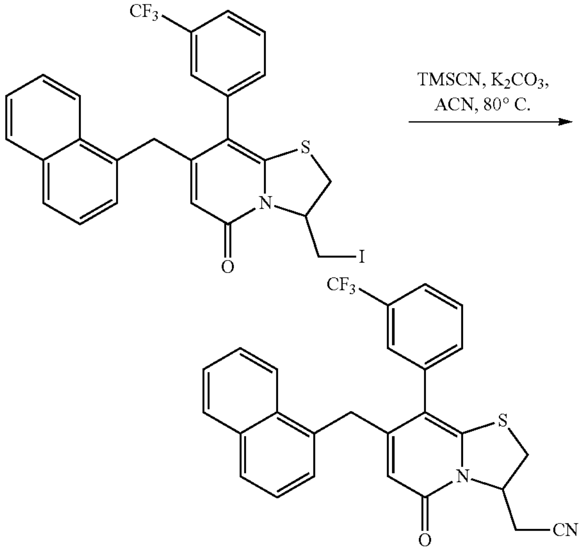

3-(Iodomethyl)-7-(naphthalen-1-ylmethyl)-8-(3-(trifluoromethyl)phenyl)-2,3-dihydro-5H-thiazolo[3,2-a]pyridin-5-one (0.3 g, 0.519 mmol) was dissolved in acetonitrile (6 mL). Potassium carbonate (0.143 g, 1.039 mmol), and TMSCN (0.103 g, 1.55 mmol) were added sequentially and the mixture was stirred at 80° C. for 24 h. in a sealed tube. The reaction was quenched in ice water (50 mL) and extracted with ethyl acetate (3×50 mL). The organic layer was dried over sodium sulphate and concentrated under reduced pressure. The crude product was purified using column chromatography eluting with 0-50% ethyl acetate/hexane to give 2-(7-(naphthalen-1-ylmethyl)-5-oxo-8-(3-(trifluoromethyl)phenyl)-2,3-dihydro-5H-thiazolo[3,2-a]pyridin-3-yl)acetonitrile, as an off white solid (0.22 g, 88.86%). LCMS (Method-C3): 97.61% (RT: 2.418, 202.4 nm) (MS: ESI+ve 477.0 [M+1]). $^{1}$H NMR: (400 MHz, DMSO) δ ppm: 3.05-3.10 (m, 1H), 3.207 (s, 1H), 3.70 (s, 1H), 3.80 (s, 1H), 3.97-4.07 (m, 2H), 5.31-5.31 (d, J=3.2 Hz, 1H), 5.64-5.68 (d, J=15.2 Hz, 1H), 7.23-7.25 (d, J=6.8 Hz, 1H), 7.40-7.51 (m, 3H), 7.61-7.73 (m, 5H), 7.83-7.81 (d, J=8 Hz, 1H), 7.90-7.92 (d, J=7.6 Hz, 1H).

Step-3: Preparation of 2-(7-(naphthalen-1-ylmethyl)-5-oxo-8-(3-(trifluoromethyl)phenyl)-2,3-dihydro-5H-thiazolo[3,2-a]pyridin-3-yl)acetic acid (Compound 129)

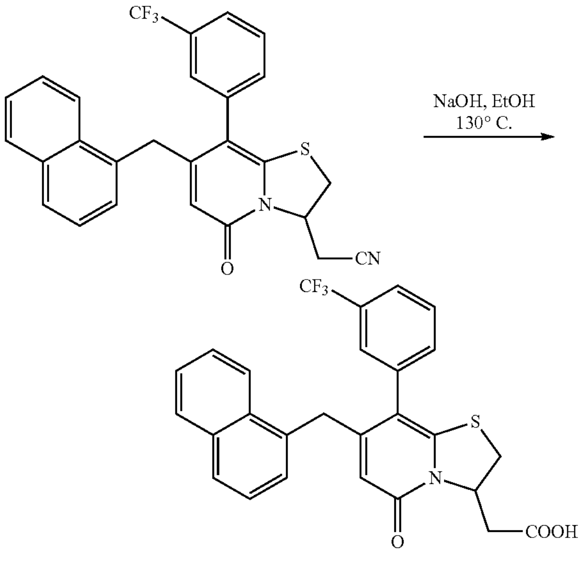

Compound 129

2-(7-(naphthalen-1-ylmethyl)-5-oxo-8-(3-(trifluoromethyl)phenyl)-2,3-dihydro-5H-thiazolo[3,2-a]pyridin-3-yl)acetonitrile (0.2 g, 0.4201 mmol) was dissolved in ethanol (11 mL) and 2 M NaOH (3.33 mL). The mixture was heated in a microwave reactor, under microwave irradiation, at 130° C. for 10 min. The mixture was concentrated then ice-cold water (10 mL) and 1N HCl (10 mL) were added. The mixture was extracted with ethyl acetate (3×50 mL). The organic layer was dried over sodium sulphate and concentrated under reduced pressure. The crude product was purified using Prep HPLC Method 1 to give 2-(7-(naphthalen-1-ylmethyl)-5-oxo-8-(3-(trifluoromethyl)phenyl)-2,3-dihydro-5H-thiazolo[3,2-a]pyridin-3-yl)acetic acid (Compound 129), as an off white solid (0.080 g, 38.47%). LCMS (Method-J): 99.75% (RT 5.281, 202.4 nm) (MS: ESI+ve 496.0 [M+H]). $^{1}$H NMR: (400 MHz, DMSO) δ ppm: 2.59-2.70 (m, 2H), 3.22-3.25 (m, 1H), 3.73 (s, 1H), 3.92-3.97 (d, J=18 Hz, 2H), 5.24 (s, 1H), 5.56-5.60 (d, J=17.2 Hz, 1H), 7.22-7.23 (d, J=6.4 Hz, 1H), 7.39-7.49 (m, 3H), 7.60-7.71 (m, 5H), 7.79-7.81 (d, J=8 Hz, 1H), 7.89-7.90 (d, J=7.2 Hz, 1H). 12.81 (bs, 1H).

Example 36

Synthesis of 2-(7-(naphthalen-1-ylmethyl)-1,1-dioxido-5-oxo-8-(3-(trifluoromethyl)phenyl)-2,3-dihydro-5H-thiazolo[3,2-a]pyridin-3-yl)acetic acid (Compound 130)

Compound 130

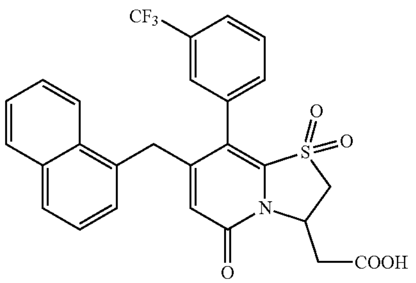

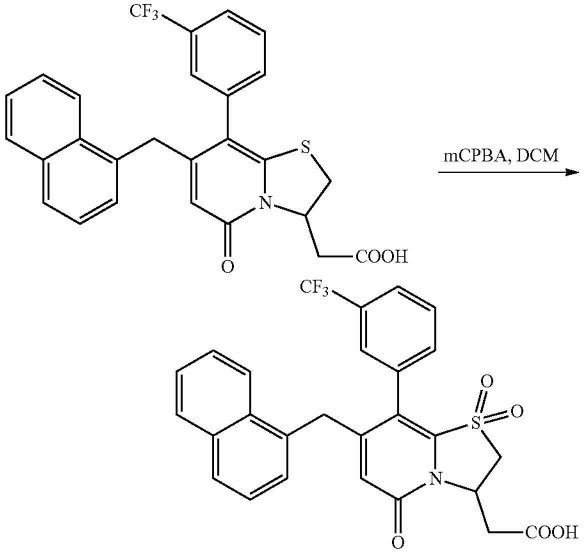

Compound 130

2-(7-(naphthalen-1-ylmethyl)-5-oxo-8-(3-(trifluoromethyl)phenyl)-2,3-dihydro-5H-thiazolo[3,2-a]pyridin-3-yl)acetic acid (0.2 g, 0.4036 mmol) was dissolved in DCM (10 mL) and cooled to 0° C. A solution of MCPBA (55%) (0.348 g, 1.21 mmol) in DCM (2 mL) was added and the mixture was stirred at room temperature for 16 h. The reaction was quenched in water (50 mL), extracted with DCM (3×50 mL) and the combined organic layers were dried over sodium sulphate then concentrated under reduced pressure. The crude product was purified using Prep HPLC Method 1 to give 2-(7-(naphthalen-1-ylmethyl)-1,1-dioxido-5-oxo-8-(3-(trifluoromethyl)phenyl)-2,3-dihydro-5H-thiazolo[3,2-a]pyridin-3-yl)acetic acid (Compound 130), as an off white solid (0.1 g, 46.97%). LCMS (Method-C3): 97.54% (RT: 2.251, 214.4 nm) (MS: ESI−ve 526.0 [M−H]). 1H NMR: (400 MHz, DMSO) δ ppm: 2.62-2.79 (m, 1H), 2.94-2.99 (m, 1H), 3.99-4.19 (m, 4H), 5.18 (s, 1H), 6.14-6.22 (d, J=30 Hz, 1H), 7.22-7.25 (t, 1H), 7.42-7.51 (m, 3H), 7.60-7.78 (m, 5H), 7.83-7.85 (d, J=8.4 Hz, 1H), 7.91-7.93 (d, J=7.6 Hz, 1H), 12.88 (s, 1H).

Example 37

Synthesis of 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 075)

Compound 075

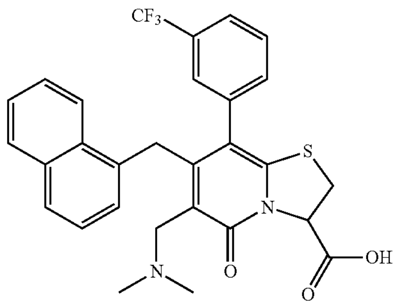

Step 1: preparation of methyl 6-formyl-7-(naphthalen-1-ylmethyl)-5-oxo-8-(3-(trifluoromethyl)phenyl)-2,3-dihydro-5H-thiazolo[3,2-a]pyridine-3-carboxylate

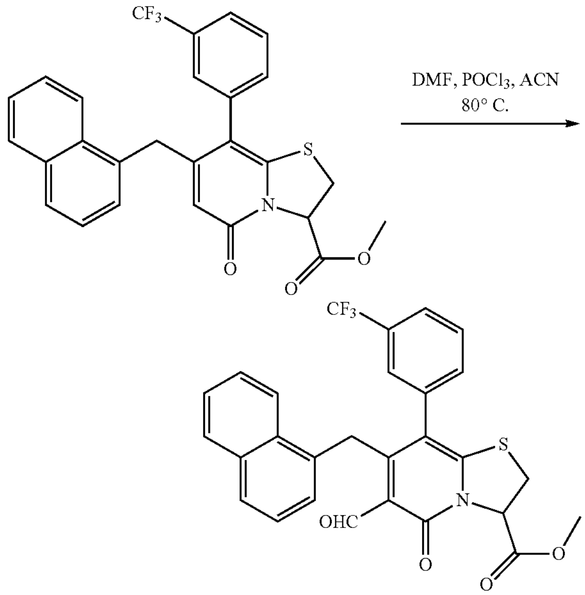

$POCl_3$ (7.41 g, 48 mmol) was added to DMF (3.51 g, 48 mmol) in acetonitrile at 0° C. The mixture was stirred for 1 h at 50° C. A solution of methyl 7-(naphthalen-1-ylmethyl)-5-oxo-8-(3-(trifluoromethyl)phenyl)-2,3-dihydro-5H-thiazolo[3,2-a]pyridine-3-carboxylate (6 g, 12.12 mmol) in ACN (60 mL) was added, and the reaction mixture was stirred for 3 h at 80° C. The reaction was quenched by the addition of sat. aq. $NaHCO_3$ (50 mL) and extracted with ethyl acetate (3×50 mL). The organic layer was dried over sodium sulphate and concentrated under reduced pressure. The crude product was purified using column chromatography eluting with 0-40% ethyl acetate/DCM to give methyl 6-formyl-7-(naphthalen-1-ylmethyl)-5-oxo-8-(3-(trifluoromethyl)phenyl)-2,3-dihydro-5H-thiazolo[3,2-a]pyridine-3-carboxylate (5.19 g, 81.87%). LCMS (Method-C3): 77.35% (RT: 1.964, 225 nm) (MS: ESI+ve 524.2 [M+1]).

Step 2: preparation of methyl 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylate

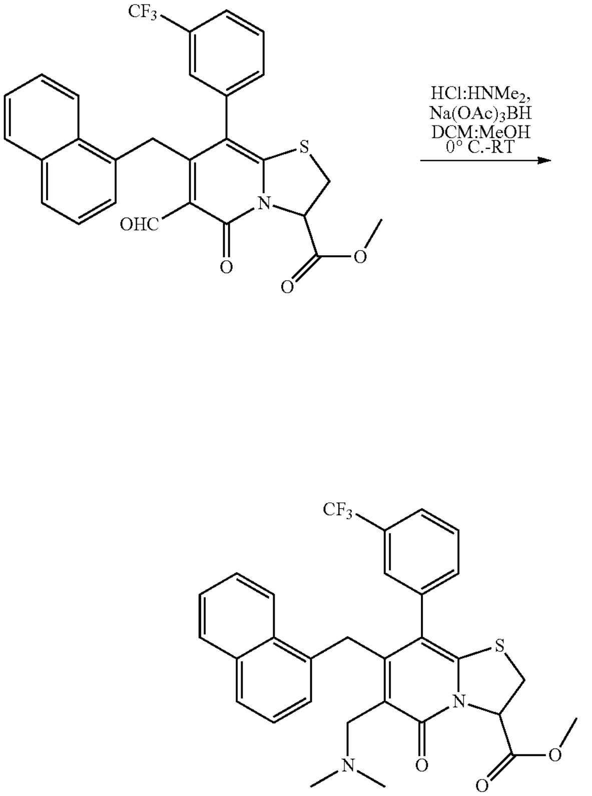

Methyl 6-formyl-7-(naphthalen-1-ylmethyl)-5-oxo-8-(3-(trifluoromethyl)phenyl)-2,3-dihydro-5H-thiazolo[3,2-a]pyridine-3-carboxylate (2 g, 3.82 mmol) was dissolved in MeOH:DCM (1:1, 20 mL). 3A molecular sieves were added followed by dimethylamine hydrochloride (0.325 g, 3.86 mmol). The mixture was stirred at 0° C. for 0.5 h, then sodium triacetoxyborohydride (1.45 g, 6.88 mmol) was added, and stirring was continued at room temperature for 16 h The reaction was quenched with sat. aq. $NaHCO_3$ (10 mL) and extracted with ethyl acetate (3×20 mL). The organic layer was dried over sodium sulphate and concentrated under reduced pressure. The crude product was purified using column chromatography eluting with 0-10% MeOH/DCM to give methyl 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylate as a solid (0.6 g, 28.42%) LCMS (Method-C3): 85.61% (RT: 1.635, 285 nm) (MS: ESI+ve 553.51 [M+1]).

Step 3: preparation of 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 075)

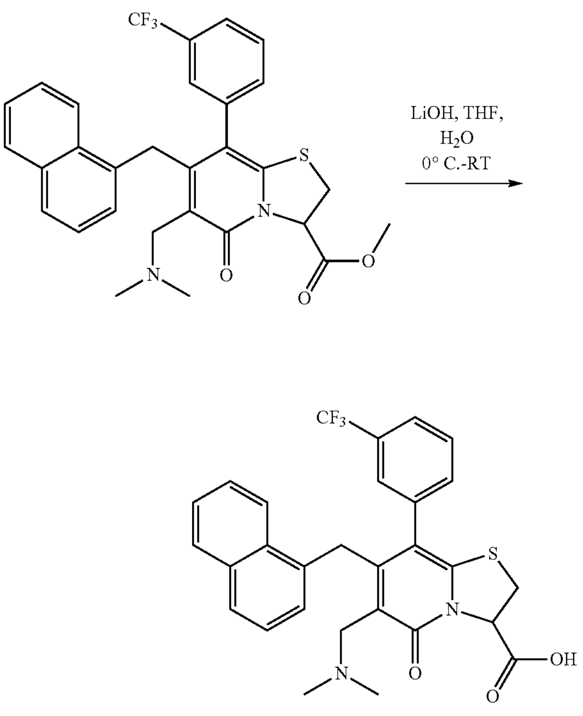

Compound 075

Methyl 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylate (0.15 g, 0.271 mmol) was dissolved in THF:$H_2O$ (1:1, 2 mL). LiOH (0.033 g 0.731 mmol) was added and the mixture was stirred at room temperature for 2 h. The mixture was concentrated then water (1 mL) and 1N HCl (1 mL) were added. The resulting solid was collected by filtration and dried under vacuum. The crude product was purified using Prep HPLC Method 1 to give 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylic acid as a white solid. (Compound 075) (0.06 g, 41.04%). LCMS (Method-C3): 100% (RT 1.560, 225.0 nm) (MS: ESI+ve 539.4 [M+H]). $^1$H NMR: (400 MHz, DMSO-$d_6$) δ ppm: 2.63 (s, 6H), 3.55-3.58 (m, 1H), 3.71 (m, 2H), 4.00 (m, 2H), 4.15-4.27 (m, 2H), 5.41-5.43 (d, J=4 Hz, 1H), 7.14 (m, 1H), 7.47-7.31 (m, 6H), 7.76 (m, 2H), 7.84-7.86 (d, J=8 Hz, 1H).

Example 38

Synthesis of 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 083)

Compound 083

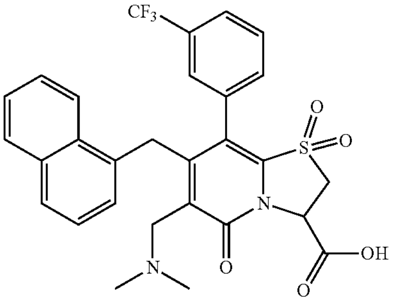

Step 1: Preparation of methyl 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide

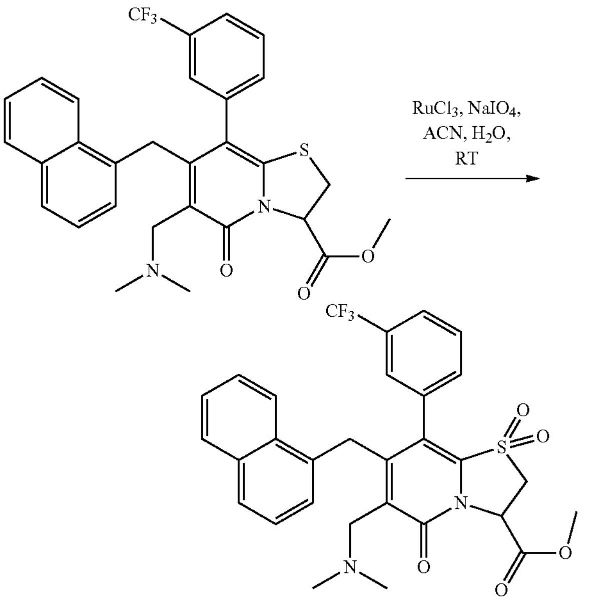

Methyl 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylate (0.70 g, 1.26 mmol) was dissolved in acetonitrile (5 mL) and water (5 mL). Sodium periodate (0.612 g, 2.87 mmol) and ruthenium trichloride (0.026 g, 0.9 mmol) were added and the mixture was stirred for 16 h. The reaction was quenched in ice water (10 mL) and extracted with ethyl acetate (3×10 mL). The organic layer was dried over sodium sulphate and concentrated under reduced pressure to give methyl 6-((dimethylamino)methyl)-7-(naphthalen-1-ylmethyl)-5-oxo-8-(3-(trifluoromethyl)phenyl)-2,3-dihydro-5H-thiazolo[3,2-a]

pyridine-3-carboxylate 1,1-dioxide as a solid (0.5 g, crude). LCMS (Method-C3): 63.85% (RT 1.612, 225.0 nm) (MS: ESI+ve 585.39 [M+H]).

Step 2: preparation of 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 083)

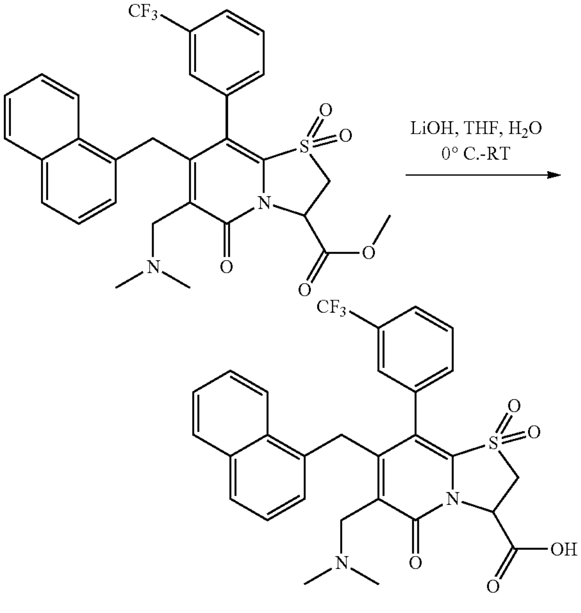

Compound 083

Methyl 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.16 g, 0.274 mmol) was dissolved in THF:$H_2O$ (1:1.2 mL). LiOH (0.033 g 0.804 mmol) was added and the mixture was stirred at room temperature for 4 h. The mixture was concentrated then cold water (1 mL) and 1N HCl (1 mL) were added. The resulting solid was collected by filtration and dried under vacuum. The crude compound was purified using Prep HPLC Method 1 to give 6-((dimethylamino) methyl)-7-(naphthalen-1-ylmethyl)-5-oxo-8-(3-(trifluoromethyl)phenyl)-2,3-dihydro-5H-thiazolo[3,2-a]pyridine-3-carboxylic acid as a white solid (Compound 083) (0.052 g, 33.30%). LCMS (Method-C3): 100% (RT 1.960, 254.0 nm (MS: ESI+ve 571.3 [M+H]), 1H NMR: (400 MHz, DMSO-$d_6$) δ ppm: 2.32 (s, 6H), 3.71 (m, 2H), 4.04 (m, 1H), 4.10 (m, 1H), 4.32-4.47 (m, 2H), 5.47-5.45 (t, J=4 Hz, 1H), 7.20-7.17 (m, 1H), 7.31.7.42 (m, 5H), 7.43 (m, 1H), 7.70-7.72 (d, J=8 Hz, 2H), 7.81-7.83 (d, J=8 Hz, 1H).

Example 39

Synthesis of 6-(hydroxymethyl)-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 057)

Compound 057

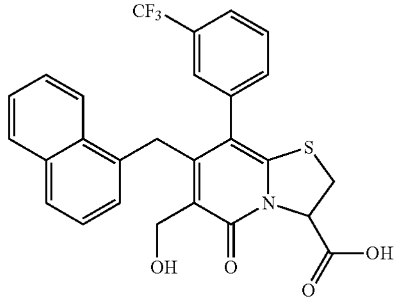

Step 1: preparation of methyl 6-(hydroxymethyl)-7-(naphthalen-1-ylmethyl)-5-oxo-8-(3-(trifluoromethyl)phenyl)-2,3-dihydro-5H-thiazolo[3,2-a]pyridine-3-carboxylate

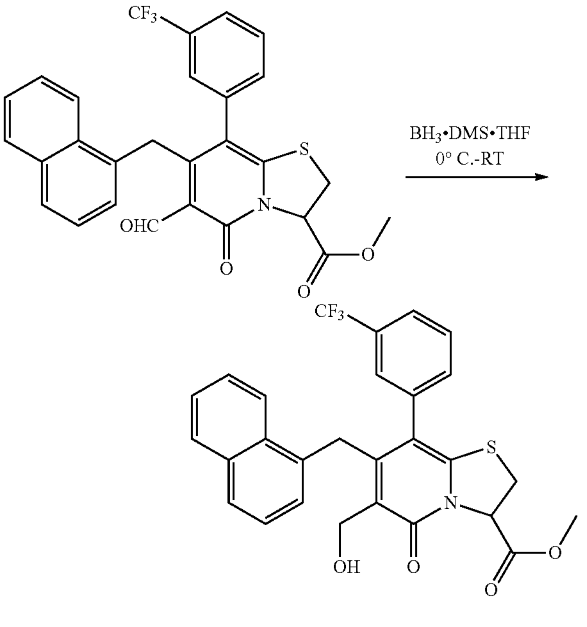

Methyl 6-formyl-7-(naphthalen-1-ylmethyl)-5-oxo-8-(3-(trifluoromethyl)phenyl)-2,3-dihydro-5H-thiazolo[3,2-a] pyridine-3-carboxylate (0.20 g, 0.382 mmol) was dissolved in THF (2 mL) and borane dimethylsulfide complex (0.030 g, 0.420 mmol) in THF was added dropwise over 15 min. The mixture was stirred at room temperature for 1 h. then quenched with methanol and concentrated twice from methanol. The crude residue was purified using column chromatography eluting with $CH_2Cl_2$/10% MeOH to give methyl 6-(hydroxymethyl)-7-(naphthalen-1-ylmethyl)-5-oxo-8-(3-(trifluoromethyl)phenyl)-2,3-dihydro-5H-thiazolo

[3,2-a]pyridine-3-carboxylate (0.20 g, 99.62%). LCMS (Method-C3): 85.84% (RT: 1.864, 225 nm) (MS: ESI+ve 526.4 [M+1]).

Step 2: Preparation of 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 057)

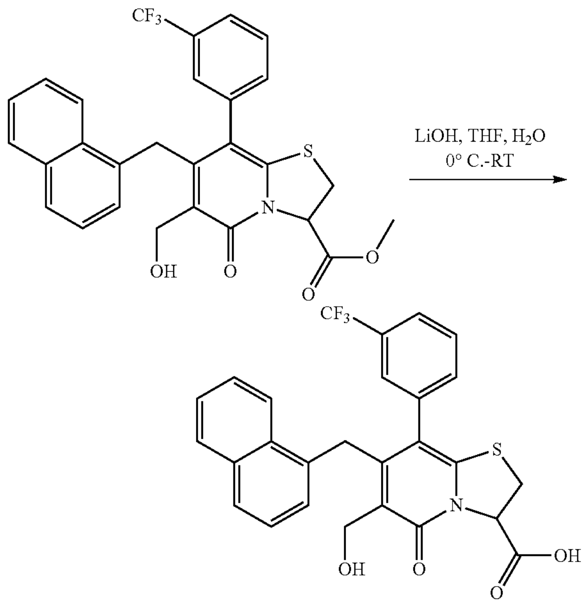

Compound 057

Methyl 6-(hydroxymethyl)-7-(naphthalen-1-ylmethyl)-5-oxo-8-(3-(trifluoromethyl)phenyl)-2,3-dihydro-5H-thiazolo[3,2-a]pyridine-3-carboxylate (0.20 g, 0.380 mmol) was dissolved in THF:$H_2O$, 1:1, 2 mL). LiOH (0.046 g 1.02 mmol) was added and the mixture was stirred at rt for 2 h. The mixture was concentrated, then water (1 mL) and 1N HCl (1 mL) were added. The resulting solid was collected by filtration and dried under vacuum. The crude product was purified using Prep HPLC Method 1 to give 6-((dimethylamino)methyl)-7-(naphthalen-1-ylmethyl)-5-oxo-8-(3-(trifluoromethyl)phenyl)-2,3-dihydro-5H-thiazolo[3,2-a]pyridine-3-carboxylic acid as a white solid (Compound 057) (0.052 g, 20.00%). LCMS (Method-C3): 100% (RT 4.698, 254.0 nm) (MS: ESI+ve 512.2 [M+H]). $^1$H NMR: (400 MHz, DMSO-$d_6$) δ ppm: 3.50-3.53 (m, 1H), 3.85 (m, 1H), 4.23-4.11 (m, 2H), 4.29-4.37 (m, 2H), 4.87 (m, 1H), 5.59-5.61 (d, J=8 Hz, 1H), 7.01-7.03 (m, 1H), 7.08-7.11 (d, J=12 Hz, 1H), 7.33-747. (m, 6H), 7.73-7.78 (m, 2H), 7.85-7.87 (d, J=8 Hz, 1H), 13.66 (s, 1H).

Example 40

Synthesis of 2-((R)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 137)

Compound 137

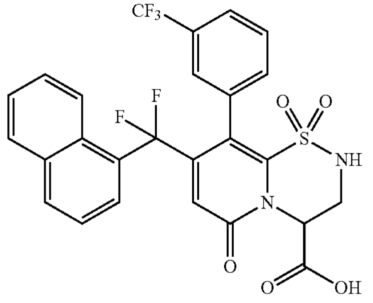

Step 1: Preparation of 5-(2,2-difluoro-1-hydroxy-2-(naphthalen-1-yl)ethylidene)-2,2-dimethyl-1,3-dioxane-4,6-dione

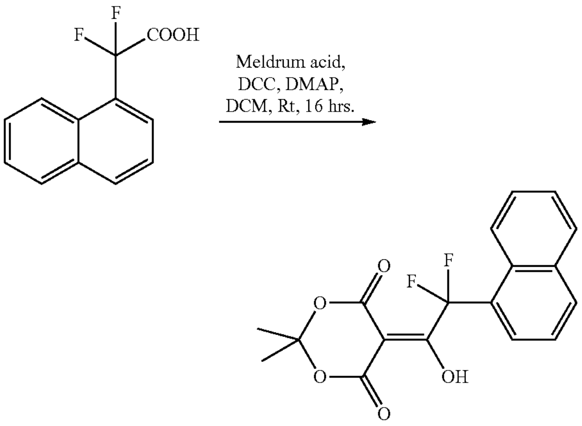

2,2-Difluoro-2-(naphthalen-1-yl)acetic acid (4.7 g, 21.200 mmol) was dissolved in dichloromethane (80 mL). 2,2-Dimethyl-1,3-dioxane-4,6-dione (3.0 g, 21.200 mmol) was added and the mixture was cooled to 0° C. 4-Dimethylaminopyridine (4.1 g, 33.900 mmol) was added in portions over 10 min. The reaction mixture was stirred for 45 min. at 0° C. A solution of N,N-dicyclohexyl carbodiimide (6.5 g, 31.800 mmol) in dichloromethane (10 mL) was added and the mixture was stirred for 16 h. slowly warming to room temperature. Water (100 mL) was added to the reaction mixture and the layers were separated. The organic layer was washed with potassium hydrogen sulphate (2×100 mL) and dried then concentrated to give 5-(2,2-difluoro-1-hydroxy-2-(naphthalen-1-yl)ethylidene)-2,2-dimethyl-1,3-dioxane-4,6-dione. n-Pentane and methyl tertiary butyl ether was added to the crude mass and the mixture was stirred for 15 min. The solid was collected by filtration and dried under vacuum to give 5-(2,2-difluoro-1-hydroxy-2-(naphthalen-1-yl)ethylidene)-2,2-dimethyl-1,3-dioxane-4,6-dione (3.2 g, 43.8%), as a white solid. LCMS: (Method-C)—83.88% (RT: 1.870, 222.0 nm) (MS: ESI−ve 347.0 [M−1]).

Step 2: Preparation of methyl 7-(difluoro(naphthalen-1-yl)methyl)-5-oxo-8-(3-(trifluoromethyl)phenyl)-2,3-dihydro-5H-thiazolo[3,2-a]pyridine-3-carboxylate

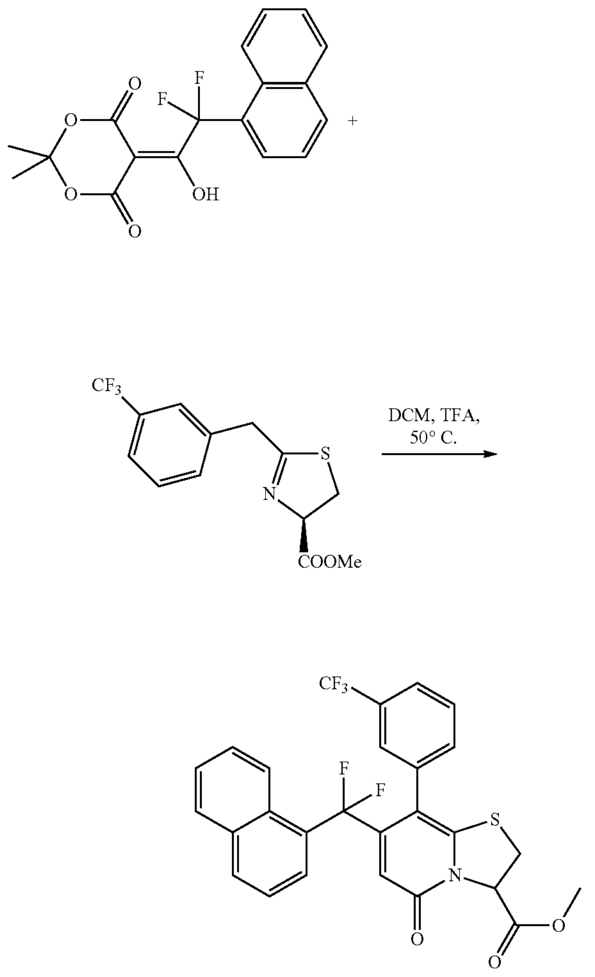

Methyl (R)-2-(3-(trifluoromethyl)benzyl)-4,5-dihydrothiazole-4-carboxylate (1.4 g, 4.600 mmol) was dissolved in dichloromethane (25 mL). 5-(2,2-difluoro-1-hydroxy-2-(naphthalen-1-yl)ethylidene)-2,2-dimethyl-1,3-dioxane-4,6-dione (3.2 g, 9.200 mmol) was added and the mixture was cooled to 0° C. Trifluoroacetic acid (1.1 g, 10.100 mmol) was added and the reaction mixture was heated at 50° C. for 16 h. The reaction was quenched in saturated aqueous sodium bicarbonate solution and extracted with dichloromethane (2×30 mL). The organic layer was dried and concentrated. The crude product was purified using column chromatography eluting with 35-100% ethyl acetate/hexane to give methyl 7-(difluoro(naphthalen-1-yl)methyl)-5-oxo-8-(3-(trifluoromethyl)phenyl)-2,3-dihydro-5H-thiazolo[3,2-a]pyridine-3-carboxylate (1.2 g, 50%). LCMS: (Method-C)—72.06% (RT: 2.033, 220.0 nm) (MS: ESI+ve 532.6 [M+1]).

Step 3: Preparation of methyl 7-(difluoro(naphthalen-1-yl)methyl)-5-oxo-8-(3-(trifluoromethyl)phenyl)-2,3-dihydro-5H-thiazolo[3,2-a]pyridine-3-carboxylate 1,1-dioxide

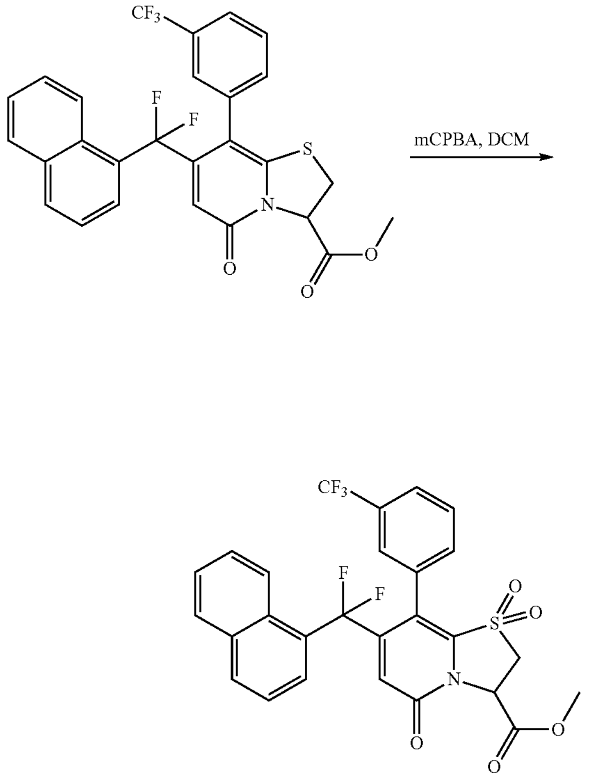

Methyl7-(difluoro(naphthalen-1-yl)methyl)-5-oxo-8-(3-(trifluoromethyl)phenyl)-2,3-dihydro-5H-thiazolo[3,2-a]pyridine-3-carboxylate (0.526 g, 0.9896 mmoles) was dissolved in dichloromethane (10 mL) and cooled to 0° C. A solution of meta-chloroperbenzoic acid (MCPBA) (55% moisture) (0.853 g, 2.689 mmol) in Dichloromethane (10 mL) was added. The reaction mixture was stirred at room temperature for 16 h. The mixture was extracted with saturated aqueous sodium bicarbonate (30 mL) and dichloromethane (3×10 mL). The organic layer was dried over sodium sulphate and concentrated under reduced pressure. The crude product was purified using column chromatography eluting with 0-70% ethyl acetate/hexane to give methyl 7-(difluoro(naphthalen-1-yl)methyl)-5-oxo-8-(3-(trifluoromethyl)phenyl)-2,3-dihydro-5H-thiazolo[3,2-a]pyridine-3-carboxylate 1,1-dioxide (0.240 g, 43% yield). LCMS (Method-C3): 89.33% (RT 2.250 nm) (MS: ESI+ve 564.0 [M+1]).

Step 4: Preparation of methyl 8-(difluoro(naphthalen-1-yl)methyl)-2-(4-methoxybenzyl)-6-oxo-9-(3-(trifluoromethyl)phenyl)-3,4-dihydro-2H,6H-pyrido[1,2-e][1,2,5]thiadiazine-4-carboxylate 1,1-dioxide

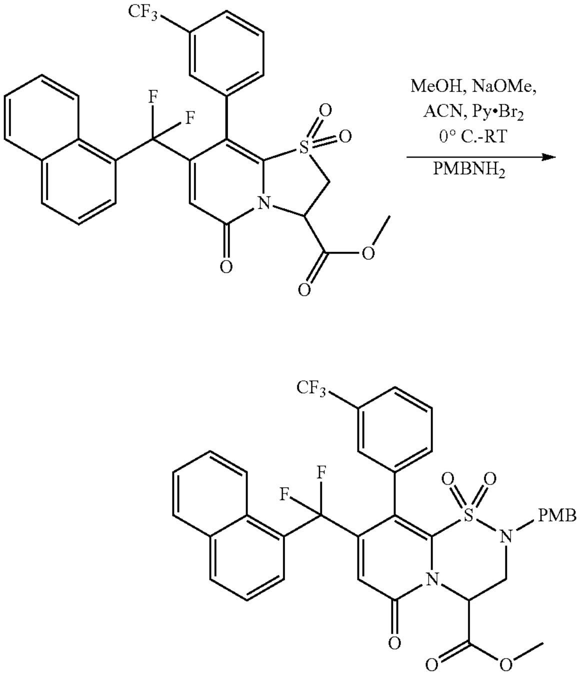

Methyl-7-(difluoro(naphthalen-1-yl)methyl)-5-oxo-8-(3-(trifluoromethyl)phenyl)-2,3-dihydro-5H-thiazolo[3,2-a]pyridine-3-carboxylate 1,1-dioxide (0.240 g, 0.4259 mmol) was dissolved in methanol (2.50 mL) and cooled at 0° C. 4-Methoxybenzylamine (0.070 g, 0.5110 mmol) was added followed by freshly prepared sodium methoxide (0.2M) (2.50 mL). The mixture was stirred at room temperature for 16 h. then concentrated under vacuum at 35° C. The crude residue was concentrated from chloroform (3×10 mL) then dissolved in acetonitrile (4.2 mL) and cooled to 0° C. Pyridine (0.033 g, 0.4259 mmol) and bromine (0.081 g, 0.5110 mmol) were added and the reaction mixture stirred for 10 min, then warmed to room temperature for 1 h. The reaction was quenched in ice-water (7 mL) and extracted with ethyl acetate (3×10 mL). The organic layer was dried over sodium sulphate and concentrated. The crude product was purified using column chromatography eluting with 0-60% hexane/ethyl acetate. (0.079 g, 26.5%) LCMS (Method-C3): 78.39% (RT: 2.462, 222.0 nm) (MS: ESI+ve 699.0 [M+1]).

Step 5: Preparation of methyl 8-(difluoro(naphthalen-1-yl)methyl)-6-oxo-9-(3-(trifluoromethyl)phenyl)-3,4-dihydro-2H,6H-pyrido[1,2-e][1,2,5]thiadiazine-4-carboxylate 1,1-dioxide

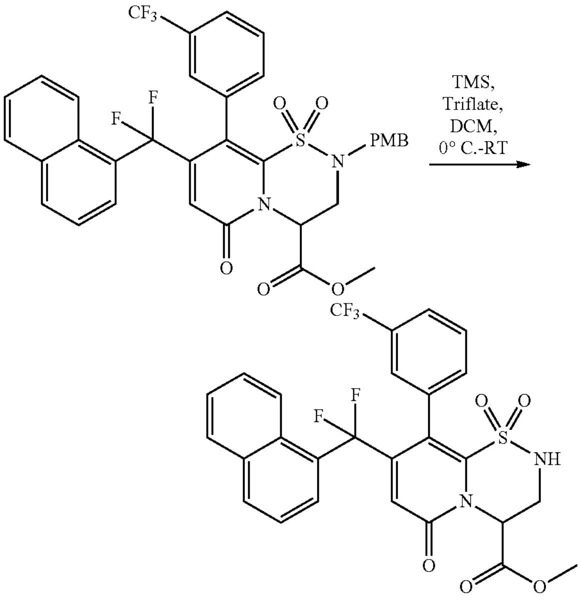

Methyl-8-(difluoro(naphthalen-1-yl)methyl)-2-(4-methoxybenzyl)-6-oxo-9-(3-(trifluoromethyl)phenyl)-3,4-dihydro-2H,6H-pyrido[1,2-e][1,2,5]thiadiazine-4-carboxylate 1,1-dioxide (0.055 g, 0.0787 mmol) was dissolved in dichloromethane (10 mL) and cooled to 0° C. Trimethyl silyl trifluoromethanesulfonate (0.034 g, 0.1574 mmol) was added and the reaction mixture was stirred at room temperature for 16 h. The reaction was quenched in saturated sodium bicarbonate and extracted with dichloromethane (3×10 mL) to give methyl 8-(difluoro(naphthalen-1-yl)methyl)-6-oxo-9-(3 (trifluoromethyl)phenyl)-3,4-dihydro-2H,6H-pyrido[1,2-e][1,2,5]thiadiazine-4-carboxylate 1,1-dioxide (0.044 g, 97.7% yield), as a white solid. LCMS (Method-$C_3$): 81.22% (RT: 2.341, 214.0 nm) (MS: ESI+ve 579.2 [M+1]).

Step 6: Preparation of 8-(difluoro(naphthalen-1-yl)methyl)-6-oxo-9-(3-(trifluoromethyl)phenyl)-3,4-dihydro-2H,6H-pyrido[1,2-e][1,2,5]thiadiazine-4-carboxylic acid 1,1-dioxide. (Compound 137)

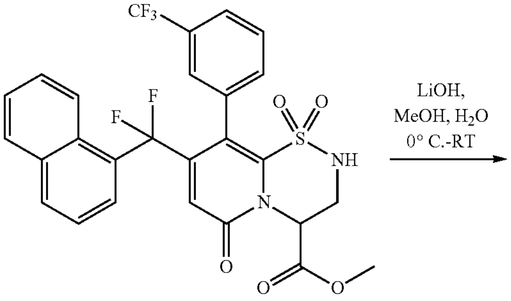

-continued

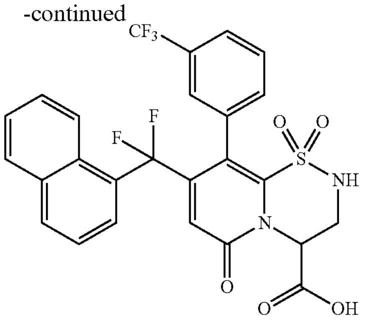

Compound 137

Methyl-8-(difluoro(naphthalen-1-yl)methyl)-6-oxo-9-(3-(trifluoromethyl)phenyl)-3,4-dihydro-2H,6H-pyrido[1,2-e][1,2,5]thiadiazine-4-carboxylate 1,1-dioxide (0.044 g, 0.0760 mmol) was dissolved in methanol (2 mL). A solution of lithium hydroxide (0.079 g, 0.1901 mmol) in water (2 mL) was added and the mixture was stirred at room temperature for 16 h then concentrated under vacuum. After acidifying with 1N HCl (5 mL), the resulting solid was dissolved in dichloromethane (10 mL) and the organic layer was dried and concentrated. The crude product was purified using Prep HPLC Method 1 to give 8-(difluoro(naphthalen-1-yl)methyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 137) (0.034 g, 7.9%), to give a white solid. LCMS (Method-C3): 100% (RT: 2.152, 202.0 nm) (MS: ESI−ve 563.2 [M−1]). $^{1}$H NMR: (400 MHz, DMSO) δ ppm: 3.45-3.44 (m, 4H), 3.66 (s, 1H), 3.90-3.78 (m, 2H), 3.99-3.96 (m, 1H), 4.21-4.18 (d, J=12 Hz, 1H), 4.79 (s, 1H), 5.00 (s, 1H), 6.00-5.99 (d, J=4 Hz, 1H), 7.26-7.24 (d, J=8 Hz, 1H), 7.68-7.44 (m, 8H), 7.85-7.83 (d, J=8 Hz, 1H), 7.93-7.91 (d, J=8 Hz, 1H).

Example 41

Synthesis of 8-(difluoro(naphthalen-1-yl)methyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 138)

Compound 138

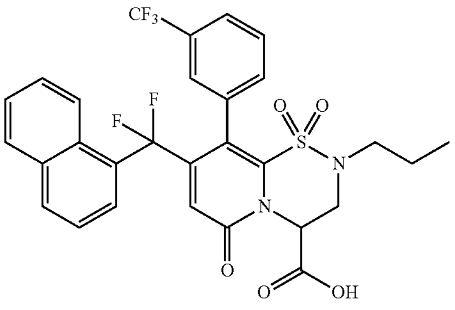

Step 1: Preparation of methyl 8-(difluoro(naphthalen-1-yl)methyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

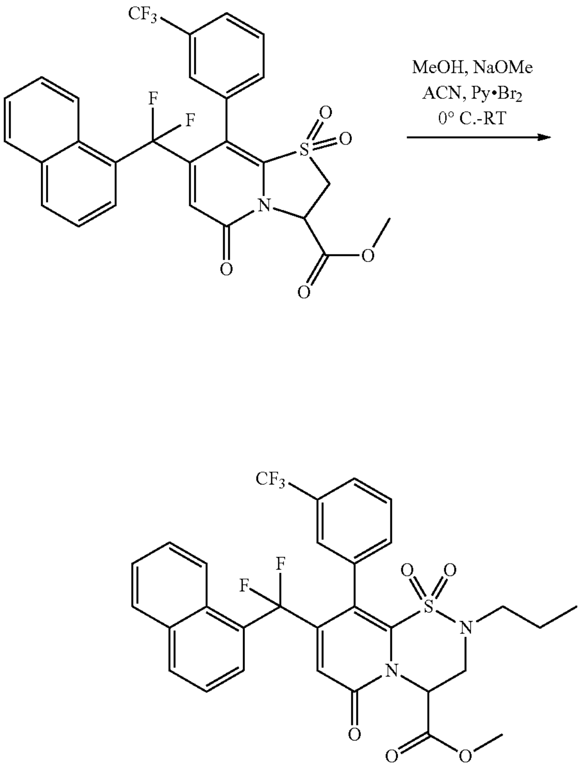 [SMILES: COC(=O)C1CS(=O)(=O)c2c(-c3cccc(C(F)(F)F)c3)c(C(F)(F)c3cccc4ccccc34)cc(=O)n21 ; CCCN1CC(C(=O)OC)n2c(c(-c3cccc(C(F)(F)F)c3)c(C(F)(F)c3cccc4ccccc34)cc2=O)S1(=O)=O]

Methyl-7-(difluoro(naphthalen-1-yl)methyl)-5-oxo-8-(3-(trifluoromethyl)phenyl)-2,3-dihydro-5H-thiazolo[3,2-a]pyridine-3-carboxylate 1,1-dioxide (0.238 g, 0.422 mmol) was dissolved in methanol (2.5 mL) and cooled to 0° C. n-Propylamine (0.299 g, 0.506 mmol) was added followed by sodium methoxide (0.2M) (2.50 mL). The reaction mixture was stirred at room temperature for 16 h then concentrated under vacuum, and concentrated from chloroform (3×10 mL). The crude residue was dissolved in acetonitrile (4.2 mL). Pyridine (0.33 g, 0.422 mmol) and bromine (0.809 g, 0.506 mmol) were added and the reaction mixture was stirred at 0° C. for 10 min, then room temperature for 1 h. The reaction was quenched in ice water (15 mL) and extracted with ethyl acetate (3×15 mL). The organic layer was dried over sodium sulphate and concentrated. The crude product was purified using column chromatography eluting 0-40% ethyl acetate/hexane, to give a white solid (0.050 g, 19%). LCMS (Method-C3): 59.5% (RT: 2.562, 214.0 nm) (MS: ESI−ve 619.2 [M−1]).

Step 2: Preparation of 8-(difluoro(naphthalen-1-yl)methyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide. (Compound 138)

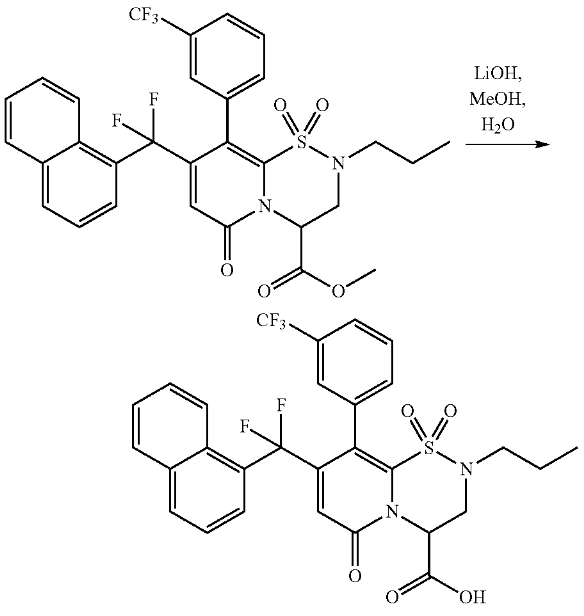

Compound 138

Methyl 8-(difluoro(naphthalen-1-yl)methyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.050 g, 0.0805 mmoles) was dissolved in methanol (2 mL). A solution of lithium hydroxide (0.0084 g, 0.2014 mmoles) in water (2 mL) was added and the mixture was stirred at room temperature for 16 h. The reaction mixture was concentrated then ice and 0.1N HCl were added. The resulting solid was collected by filtration and washed with water. The crude product was purified using Prep HPLC Method 1 to give 8-(difluoro(naphthalen-1-yl)methyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 138) (0.015 g, 10.4%), as a white solid. LCMS (Method-C3): 100% (RT—0.317, 254.0 nm) (MS: ESI+ve 607.2 [M+1]). $^1H$ NMR: (400 MHz, DMSO) δ ppm: 0.727-0.744 (m, 3H), 1.526-1.542 (m, 2H), 3.071-3.103 (t, J=12.8 Hz, 2H), 4.059-4.199 (m, 2H), 5.140-5.214 (d, J=29.6 Hz, 1H), 6.618 (s, 1H), 7.003 (s, 1H), 7.095-7.206 (m, 2H), 7.370-7.406 (m, 2H), 7.522-7.563 (m, 2H), 7.820-7.995 (m, 3H).

Example 42

Synthesis of 7-(difluoro(naphthalen-1-yl)methyl)-5-oxo-8-(3-(trifluoromethyl)phenyl)-2,3-dihydro-5H-thiazolo[3,2-a]pyridine-3-carboxylic acid (Compound 073)

Compound 073

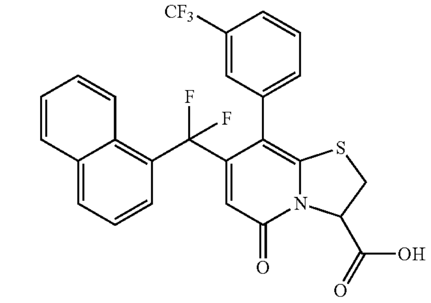

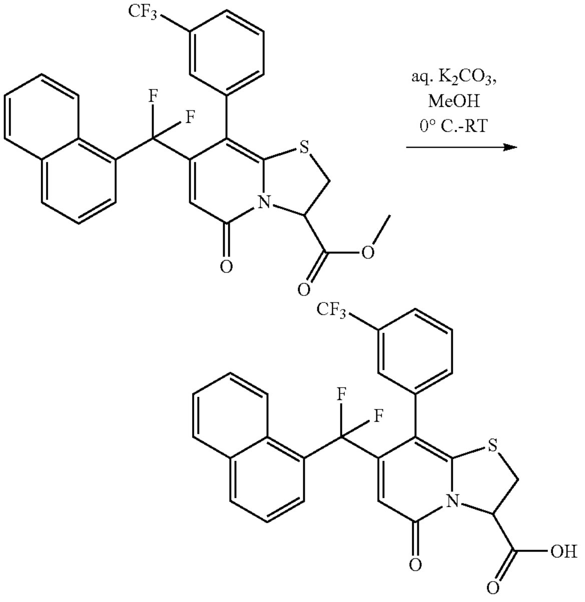

Compound 073

Methyl 7-(difluoro(naphthalen-1-yl)methyl)-5-oxo-8-(3-(trifluoromethyl)phenyl)-2,3-dihydro-5H-thiazolo[3,2-a]pyridine-3-carboxylate (0.150 g, 0.2822 mmol) was dissolved in methanol (3 mL) and a solution of aqueous potassium carbonate (1 M, 3 mL) was added at room temperature and stirred for 2 h. The reaction was quenched with ice and 0.1N HCl (10 mL) and extracted with ethyl acetate (2×20 mL). The organic layer was concentrated under vacuum. The crude product was purified using Prep HPLC Method 1 to give 7-(difluoro (naphthalen-1-yl)methyl)-5-oxo-8-(3-(trifluoromethyl) phenyl)-2,3-dihydro-5H-thiazolo[3,2-a]pyridine-3-carboxylic acid (Compound 073), as a yellow solid (0.005 g, 3.9%). LCMS (Method-C-3): 100% (RT 1.862, 220.0 nm) (MS: ESI+ve 518.6 [M+1]). $^1H$ NMR: (400 MHz, DMSO) δ ppm: 3.50-3.47 (d, J=10.8 Hz, 2H), 3.807 (s, 1H), 5.501 (s, 1H), 6.61-6.58 (d, J=11.6 Hz, 1H), 6.77-6.74 (d, J=12.8 Hz, 1H), 7.16-7.14 (d, J=6.8 Hz, 1H), 7.22-7.21 (d, J=12.8 Hz, 2H), 7.48-7.46 (m, 1H), 7.59 (s, 3H), 8.00-7.93 (m, 3H).

Example 43

Synthesis of 7-(difluoro(naphthalen-1-yl)methyl)-5-oxo-8-(3-(trifluoromethyl)phenyl)-2,3-dihydro-5H-thiazolo[3,2-a]pyridine-3-carboxylic acid 1,1-dioxide (Compound 081)

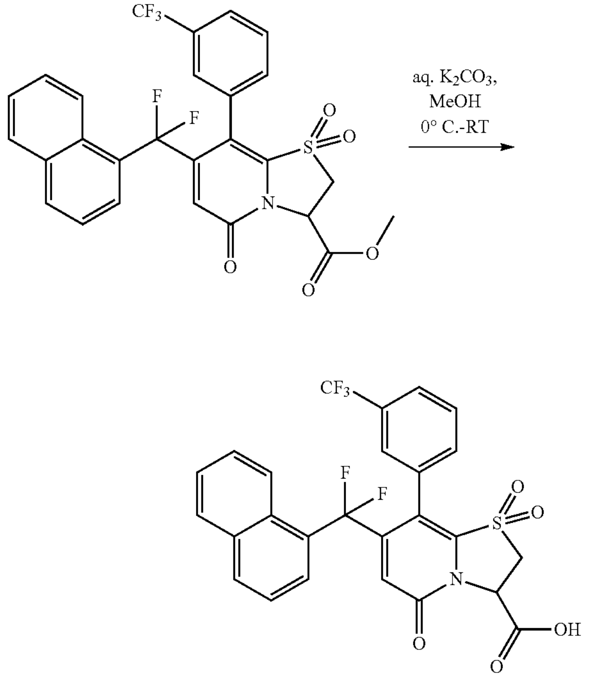

Compound 081

Methyl-7-(difluoro(naphthalen-1-yl)methyl)-5-oxo-8-(3-(trifluoromethyl)phenyl)-2,3-dihydro-5H-thiazolo[3,2-a]pyridine-3-carboxylate 1,1-dioxide (0.190 g, 0.3371 mmol) was dissolved in methanol (4 mL). A solution of aqueous potassium carbonate (1M, 4 mL) was added at room temperature. The reaction mixture was stirred at room temperature for 4 h. The mixture was poured into 0.1 N HCl (10 mL) and ice. The resulting solid was collected by filtration then dissolved in dichloromethane and concentrated. The crude product was purified using Prep HPLC Method 1 to give 7-(difluoro(naphthalen-1-yl)methyl)-5-oxo-8-(3-(trifluoromethyl)phenyl)-2,3-dihydro-5H-thiazolo[3,2-a]pyridine-3-carboxylic acid 1,1-dioxide (Compound 081), as a white solid (0.010 g, 5.7%). LCMS (Method-J): 100% (RT 4.744, 202.0 nm) (MS: ESI+ve 550 [M+1]). $^1$H NMR: (400 MHz, DMSO) δ ppm: 4.07-4.01 (d, J=23.6 Hz, 1H), 4.20-4.17 (d, J=13.6 Hz, 1H), 5.46-5.47 (d, J=8.8 Hz, 1H), 6.66 (s, 1H), 7.11-7.09 (d, J=8 Hz, 1H), 7.30-7.20 (m, 3H), 7.46 (s, 1H), 7.62-7.58 (d, J=14.8 Hz, 3H), 7.89 (s, 1H), 8.00 (s, 2H).

Example 44

Synthesis of 2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 085)

Compound 085

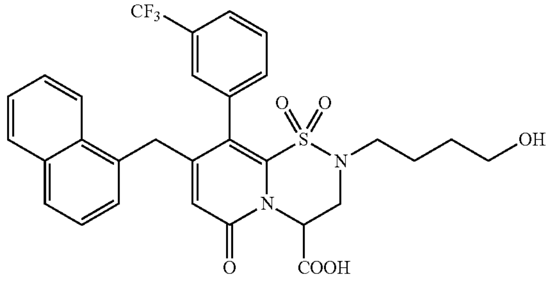

Prepared by a procedure similar to that reported for 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 008) (Racemic) substituting 4-aminobutan-1-ol in step 6. The crude product was purified using Prep HPLC Method 1 to give 2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as an off white solid (0.091 g, 11.25%). (Compound 085). LCMS (Method-C3): 99.48% (RT 2.060, 254.4 nm) (MS: ESI+ve 601.2 [M+H]). $^1$H NMR: (400 MHz, DMSO) δ ppm: 1.32-1.38 (m, 2H), 1.47-1.52 (m, 2H), 3.14-3.16 (d, 2H), 3.85-3.95 (m, 2H), 4.08-4.21 (m, 2H), 5.14-5.15 (d, J=4.0 Hz, 1H), 6.07-6.11 (m, 1H), 7.24-7.25 (d, J=5.6 Hz, 1H), 7.44-7.52 (m, 3H), 7.57-7.73 (m, 5H), 7.84-7.85d, J=5.6 Hz, 1H), 7.91-7.93 (d, J=7.6 Hz, 1H), 13.76 (s, 1H).

Example 45

Synthesis of 2-(2-(dimethylamino)ethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 017)

Compound 017

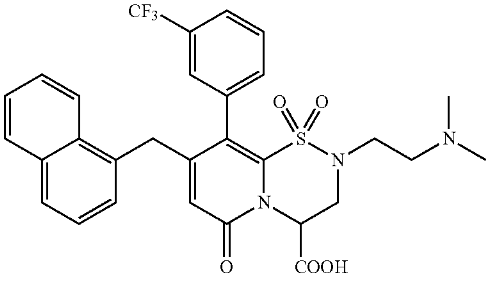

Prepared by a procedure similar to that reported for 2-methyl-8-(naphthalen-1-ylmethyl)-6-oxo-9-(3-(trifluoromethyl)phenyl)-3,4-dihydro-2H,6H-pyrido[1,2-e][1,2,5]

thiadiazine-4-carboxylic acid 1,1-dioxide (Compound 008) (Racemic) substituting $N^1$,$N^1$-dimethylethane-1,2-diamine in step 6. The crude product was purified using Prep HPLC Method 8 to give 2-(2-(dimethylamino)ethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 017), as the formate salt (0.006 g, 15.35%). LCMS (Method-C3): 100% (RT: 1.722, 225.4.0 nm) (MS: ESI+ve 600.4 [M+H]). $^1$H NMR: (400 MHz, DMSO) δ ppm: 2.48 (s, 3H), 2.52 (s, 3H), 2.69-2.86 (m, 4H), 3.81-3.89 (m, 2H), 4.19 (m, 2H), 5.00 (s, 1H) 6.03-6.05 (d, J=10.4 Hz, 1H) 7.25-7.26 (m, 1H) 7.46-7.52 (m, 3H) 7.58-7.65 (m, 4H) 7.83-7.84 (m, 1H) 7.86 (m, 1H) 7.91-7.93 (d, J=7.6 Hz, 1H).

Example 46

Synthesis of 2-((R)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 065b)

Compound 065b

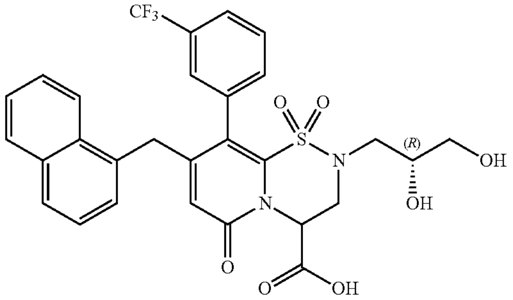

Prepared by a procedure similar to that reported for 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 008) (Racemic) substituting (R)-3-aminopropane-1,2-diol in step 6. The crude product was purified using Prep HPLC Method 1 to give 2-((R)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 065b) as a mixture of diastereomers (0.044 g, 34.66%). LCMS (Method-C3): 100% (RT-1.678, 230.0 nm) (MS: ESI+ve 603.4 [M+1]). $^1$H NMR: (400 MHz, DMSO) δ ppm: 3.35-2.95 (m, 4H), 3.49 (s, 1H), 3.93-3.83 (m, 2H), 4.22-4.18 (d, J=16 Hz, 1H), 4.31-4.27 (m, 1H), 4.64 (s, 1H), 5.07-5.06 (d, J=4 Hz, 1H), 7.24-7.23 (d, J=4 Hz, 1H), 7.50-7.43 (m, 3H), 7.69-7.57 (m, 5H) 7.84-7.82 (d, J=8 Hz, 1H) 7.92-7.90 (d, J=8 Hz, 1H).

Example 47

Synthesis of 2-((S)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 065a)

Compound 065a

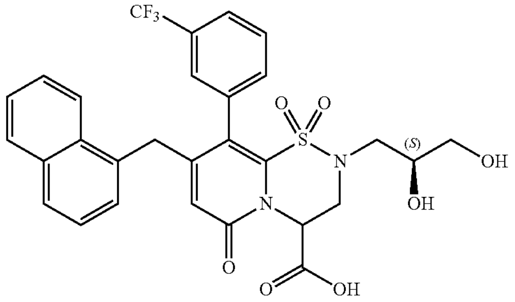

Prepared by a procedure similar to that reported for 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 008) (Racemic) substituting (S)-3-aminopropane-1,2-diol in step 6. The crude product was purified using Prep HPLC Method 1 to give 2-((S)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 065a) as a mixture of diastereomers LCMS (Method-C3): 96.59% (RT: 1.704, 225.0 nm, 222.0 nm) (MS: ESI+ve 603.57 [M+H]). $^1$H NMR: (400 MHz, DMSO) δ ppm: 2.97 (m, H), 3.12 (m, 1H), 3.14-3.09 (m, 1H), 3.24 (m, 2H), 3.49 (m, 2H), 3.89 (s, 2H), 4.32-4.18 (m, 2H), 4.65 (s, 1H), 5.09-4.99 (m, 2H), 6.09-6.05 (m, 1H), 7.23-7.24 (d, J=6.4, 1H), 7.41-7.48 (m, 3H), 7.57 (s, 3H), 7.70 (s, 1H), 7.82-7.84 (d, J=7.6, 1H), 7.90-7.92 (d, J=7.6, 1H).

Example 48

Synthesis of 8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylic acid 1,1-dioxide (Compound 066)

Compound 066

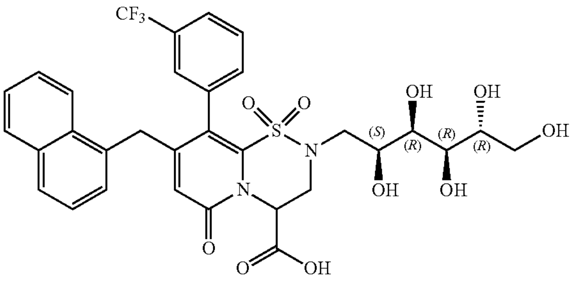

Prepared by a procedure similar to that reported for 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 008) (Racemic) substituting D-Glucamine in step 6. The crude product was purified using Prep HPLC Method 1 to give 8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylic acid 1,1-dioxide (Compound 066) (0.039 g, 17.79%), as a white solid. LCMS (Method-H): 100% (RT-3.112, 221.0 nm) (MS: ESI−ve 691.0 [M−1]). $^1$H NMR: (400 MHz, DMSO) δ ppm: 3.20-3.15 (m, 1H), 3.41 (s, 2H), 3.56-3.53 (d, J=12 Hz, 2H), 3.66 (s, 1H), 3.90 (s, 2H), 4.21-4.17 (d, J=16 Hz, 1H), 4.40-4.29 (d, J=44 Hz, 1H), 5.05-5.00 (d, J=20 Hz, 2H), 6.08-6.05 (d, J=12 Hz, 1H), 7.26-7.24 (d, J=8 Hz, 1H) 7.50-7.46 (t, J=16 Hz, 3H) 7.68-7.59 (m, 5H), 7.85-7.83 (d, J=8 Hz, 1H), 7.93-7.91 (d, J=8 Hz, 1H).

Example 48a

Synthesis of 2-(1,3-dihydroxypropan-2-yl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 106)

Compound 106

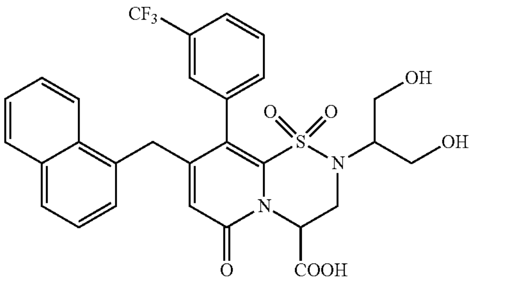

Prepared by a procedure similar to that reported for 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 008) (Racemic) substituting 2-aminopropane-1, 3-diol in step 6. The crude product was purified using Prep HPLC Method 3 to give 2-(1,3-dihydroxypropan-2-yl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 106) (0.026 g, 10%), as a white solid. LCMS (Method-C3): 100% (RT 1.621, 202.0 nm) (MS: ESI+ve 603.3 [M+1]). $^1$H NMR: (400 MHz, DMSO) δ ppm: 3.45-3.44 (m, 4H), 3.66 (s, 1H), 3.90-3.78 (m, 2H), 3.99-3.96 (m, 1H), 4.21-4.18 (d, J=12 Hz, 1H), 4.79 (s, 1H), 5.00 (s, 1H), 6.00-5.99 (d, J=4 Hz, 1H), 7.26-7.24 (d, J=8 Hz, 1H), 7.68-7.44 (m, 8H), 7.85-7.83 (d, J=8 Hz, 1H), 7.93-7.91 (d, J=8 Hz, 1H).

Example 48b

Synthesis of 2-(carboxymethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 018)

Compound 018

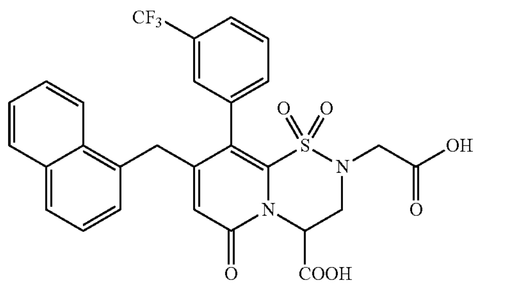

Step-1: Preparation of methyl 2-(2-(tert-butoxy)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

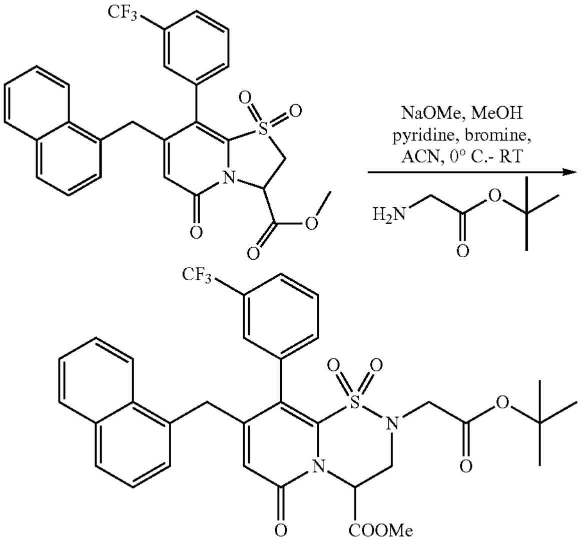

Methyl 7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.2 g, 0.037 mmol) was dissolved in methanol (2.26 mL). After cooling to 0° C., tert-butyl glycinate (0.060 g, 0.045 mmol) was added in portions over 5 min, then 0.2 M sodium methoxide in methanol (2.26 mL) was added dropwise at 0° C. and the reaction mixture was stirred for 16 h at room temperature. The mixture was concentrated under reduced pressure, then concentrated twice from chloroform (10 mL). The residue was dissolved in acetonitrile (8 mL) and cooled to 0° C. Pyridine (0.03 mL, 0.265 mmol) was added followed by bromine (0.071 g, 0.045 mmol) and the reaction mixture stirred for 1 h at room temperature. The mixture was quenched in water (45 mL) and extracted with ethyl acetate (3×30 mL). The organic layer was dried over sodium sulphate and concentrated under reduced pressure to give crude product which was purified by column chromatography, eluting with 0-80% ethyl acetate in/hexane to give methyl 2-(2-(tert-butoxy)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide yellow (0.025 g, 10.33%). LCMS (Method-C3): 100% (RT 2.222, 220.0 nm) (MS: ESI+ve 657.39 [M+H]).

Step-2: Preparation of 2-(4-(methoxycarbonyl)-8-(naphthalen-1-ylmethyl)-1,1-dioxido-6-oxo-9-(3-(trifluoromethyl)phenyl)-3,4-dihydro-2H,6H-pyrido [1,2-e][1,2,5]thiadiazin-2-yl)acetic acid

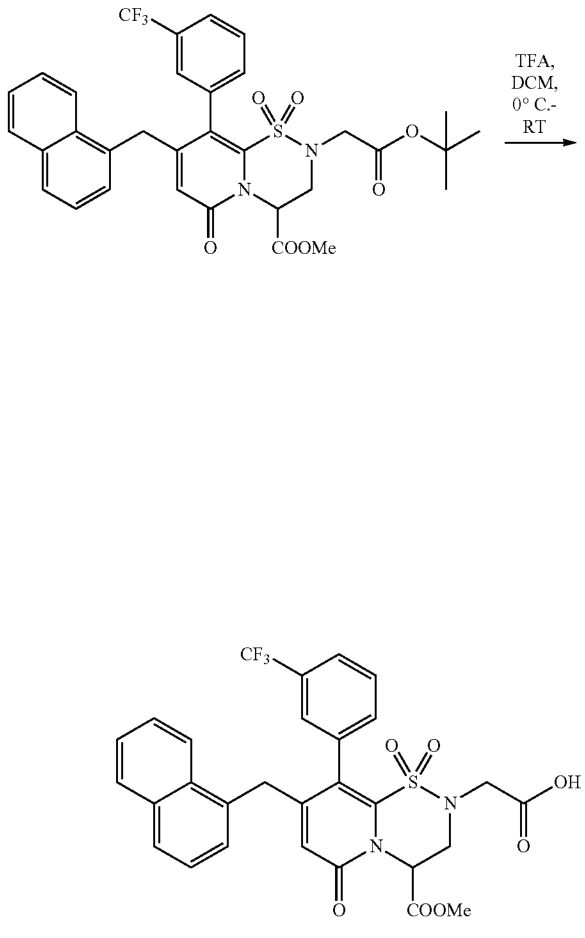

Methyl 2-(2-(tert-butoxy)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.05 g, 0.159 mmol) was dissolved in DCM (2 mL) at room temperature. Trifluoroacetic acid (0.1 g) was added at 0° C. and the mixture was stirred at room temperature for 16 h. The reaction mixture was concentrated to give 2-(4-(methoxycarbonyl)-8-(naphthalen-1-ylmethyl)-1,1-dioxido-6-oxo-9-(3-(trifluoromethyl) phenyl)-3,4-dihydro-2H,6H-pyrido[1,2-e][1,2,5]thiadiazin-2-yl)acetic acid as a yellow solid (0.03 g, 65.61%) LCMS (Method-C3): 91.22% (RT: 1.903, 225.0 nm) (MS: ESI+ve 601.3 [M+H]).

Step-3: Preparation of 2-(carboxymethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 018)

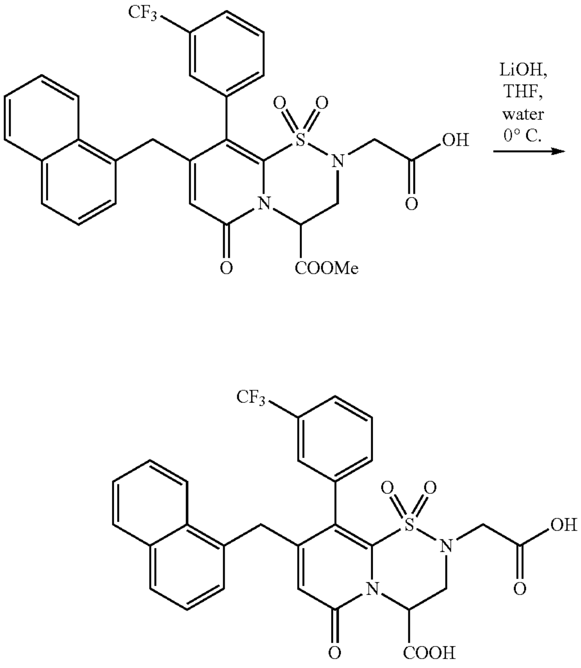

Compound 018

2-(4-(methoxycarbonyl)-8-(naphthalen-1-ylmethyl)-1,1-dioxido-6-oxo-9-(3-(trifluoromethyl)phenyl)-3,4-dihydro-2H,6H-pyrido[1,2-e][1,2,5]thiadiazin-2-yl)acetic acid (0.03 g, 0.40 mmol) was dissolved in THF:$H_2O$ (2 mL, 1:1), and LiOH (0.007 g, 0.167 mmol) was added at 0° C. The reaction mixture was stirred at RT for 5 h then concentrated and diluted with 0.1 N HCl (3 mL). The resulting precipitate was collected by filtration and washed with $H_2O$ (5 mL) then dried under vacuum. The crude product was purified using Prep HPLC Method 1 to give 2-(carboxymethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 018) (0.003 g, 10.24%). LCMS (Method-J): 100% (RT: 4.716, 222.0 nm) (MS: ESI−ve 585.2 μM−H]). $^1H$ NMR: (400 MHz, DMSO) δ ppm: 3.91 (t, J=6.7 Hz, 2H), 4.08-3.92 (m, 2H), 4.15 (dd, J=15.0 Hz, 6.2 Hz, 1H), 4.26 (d, J=14.7 Hz, 1H), 5.36 (s, 1H), 6.13 (d, J=14.7 Hz, 1H), 7.25 (d, J=7.2 Hz, 1H), 7.53-7.42 (m, 3H), 7.71-7.50 (m, 5H), 7.85 (d, J=8.3 Hz, 1H), 7.93 (d, J=8.0 Hz, 1H).

Example 49

Synthesis of 2-(2-(methylamino)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 049)

Compound 049

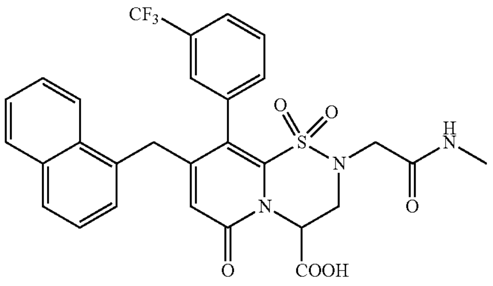

Step 1: Synthesis of methyl 2-(2-(methylamino)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

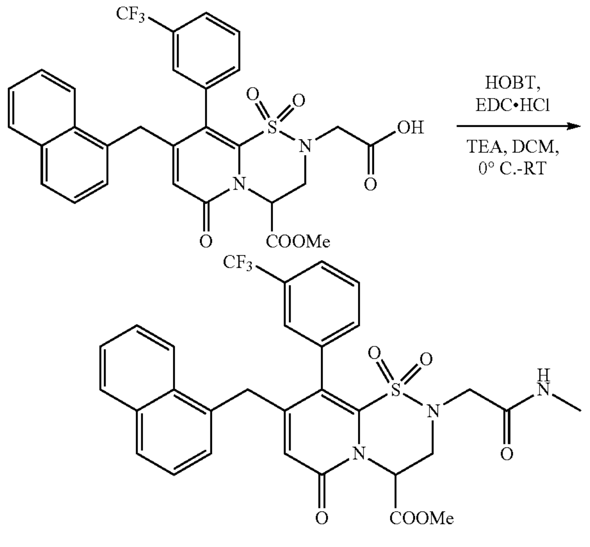

2-(4-(Methoxycarbonyl)-8-(naphthalen-1-ylmethyl)-1,1-dioxido-6-oxo-9-(3-(trifluoromethyl)phenyl)-3,4-dihydro-2H,6H-pyrido[1,2-e][1,2,5]thiadiazin-2-yl)acetic acid (0.350 g, 0.582 mmol) was dissolved in DCM (5 mL) and cooled to 0° C. Methylamine hydrochloride (0.059 g, 0.873 mmol) was added followed by triethylamine (0.235 g, 2.32 mmol), EDC.HCl (0.167 g, 0.873 mmol) and HOBT (0.118 g, 0.873 mmol). The reaction mixture was stirred slowly warming to room temperature for 16 h. The reaction was quenched with $H_2O$ and extracted with DCM (3×20 mL). The organic layer was dried over sodium sulphate and concentrated. The crude product was purified by column chromatography, eluting with 8% methanol/dichloromethane to give methyl 2-(2-(methylamino)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as an off white solid (0.280 g, 78.30%). LCMS (Method $C_3$): 80.90% (RT 1.865, 226.0 nm) (MS: ESI+ve 658.3 [M+H])

Step-4: Preparation of 2-(2-(methylamino)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 049)

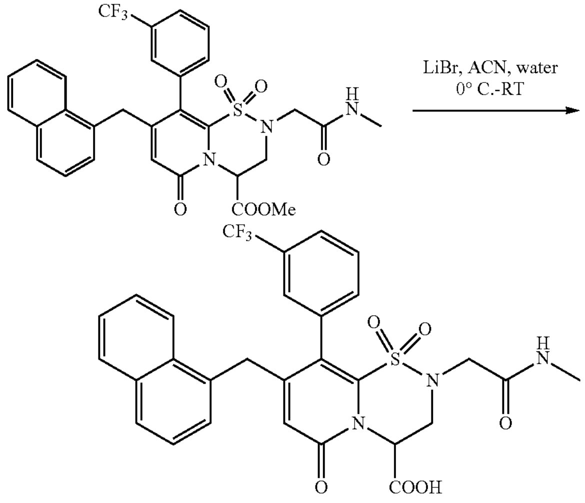

Compound 049

Methyl 2-(2-(methylamino)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.25 g, 0.407 mmol) was dissolved in ACN: $H_2O$ (50:1, 4.89 mL) and cooled to 0° C. LiBr (0.353 g, 4.078 mmol) and TEA (0.17 mL, 1.223 mmol) were added and the mixture was stirred for 45 min then warmed to room temperature and stirred for 5 h. The reaction mixture was diluted with 10% methanol/DCM and washed with 2% aqueous $KHSO_4$ solution. The mixture was concentrated and the crude product was purified Prep HPLC Method 1 to give 2-(2-(methylamino)-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as an off white solid (0.02 g, 8.19%). (Compound 049), LCMS (Method-J): 100% (RT 4.682, 202.4 nm) (MS: ESI+ve 600.2 [M+H]). $^1H$ NMR: (400 MHz, DMSO) δ ppm: 2.68 (s, 3H), 3.77-3.91 (m, 4H), 4.10-4.24 (m, 2H), 5.32-5.41 (d, J=37.2 Hz, 1H), 6.12-6.16 (d, J=16.4 Hz, 1H), 7.27-7.29 (t, 1H), 7.44-7.66 (m, 7H), 7.84-7.86 (d, J=8.4 Hz, 1H), 7.91-7.93 (m, 2H), 13.52 (s, 1H).

Example 50

Synthesis of 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 009)(Racemic)

Compound 009

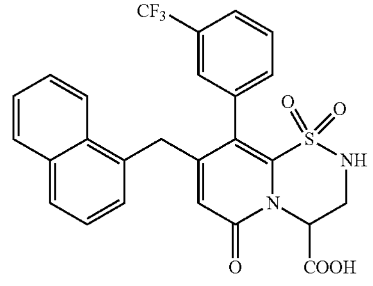

(Racemic)

Step-1: Preparation of methyl 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

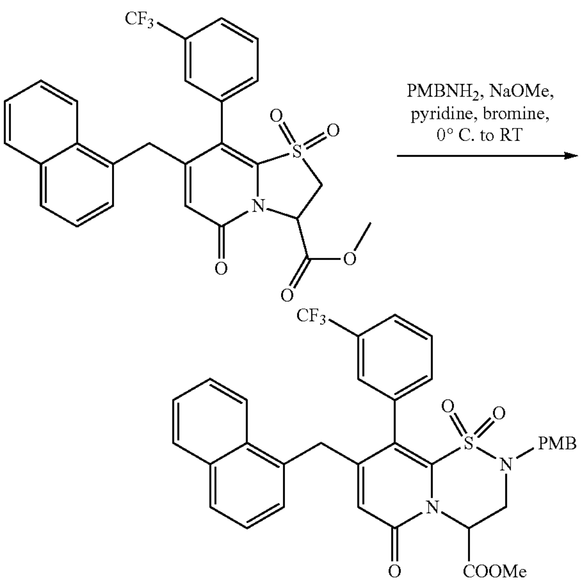

Methyl 7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.8 g, 1.518 mmol) was dissolved in methanol (9.08 mL). After cooling to 0° C., (4-methoxyphenyl)methanamine (0.249 g, 1.821 mmol) was added portion-wise over 5 min. 0.2 M sodium methoxide in methanol (9.08 mL) was added dropwise at 0° C., and the mixture was stirred for 16 h at room temperature. The mixture was concentrated under reduced pressure, and concentrated twice from chloroform. The residue was dissolved in acetonitrile (15.18 mL) and cooled to 0° C. Pyridine (0.12 mL, 1.51 mmol) and bromine (0.291 g, 1.821 mmol) were added and the reaction mixture was stirred for 1 h at room temperature. The reaction was quenched in water (100 mL) and extracted with ethyl acetate (3×100 mL). The organic layer was dried over sodium sulphate and concentrated under reduced pressure to give crude product which was purified by column chromatography, eluting with 0-50% ethyl acetate in/hexane to give methyl 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.31 g, 30.85%). LCMS (Method-C3): 93.95% (RT: 1.982, 230.0 nm) (MS: ESI+ve 663.47[M+H]). $^1H$ NMR: (400 MHz, $CDCl_3$) δ ppm: 3.71 (s, 3H), 3.84 (s, 3H), 3.86-3.89 (m, 2H), 4.00-4.02 (m, 2H), 4.13-4.18 (m, 1H), 4.37-4.42 (m, 1H), 5.26-5.33 (m, 1H), 6.28 (s, 1H), 6.91-6.93 (d, J=8.4 Hz, 2H), 7.19-7.25 (m, 2H), 7.42-7.55 (m, 5H), 7.59-7.61 (m, 2H), 7.67-7.70 (t, 2H), 7.81-7.83 (d, J=8.4 Hz, 1H), 7.87-7.89 (d, J=7.2 Hz, 1H).

Step-2: Preparation of methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

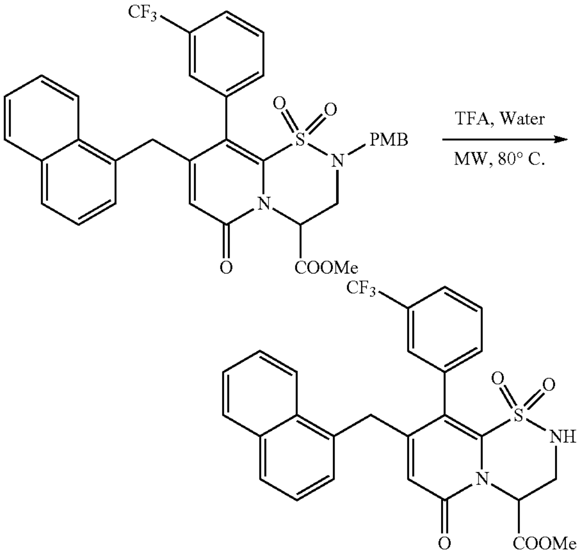

A solution of methyl 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.45 g, 0.679 mmol) in TFA (3.017 mL) and water (0.16 mL) was heated in a microwave reactor, under microwave irradiation, at 80° C. for 10 min. The reaction mixture was poured into ice water (20 mL), quenched with saturated aqueous sodium bicarbonate (20 mL), extracted with ethyl acetate (3×50 mL), dried over sodium sulphate and concentrated under reduced pressure. The crude product was purified using column chromatography, eluting with 0-50% ethyl acetate/hexane to give methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a brown solid (0.31 g, 84.15%), LCMS (Method-H): 97.34% (RT 5.498, 285 nm) (MS: ESI+ve 543.2 [M+H]). $^1H$ NMR: (400 MHz, DMSO) δ ppm: 2.09-2.31 (m, 5H), 4.00-4.32 (m, 2H), 4.93-4.94 (t, 1H), 5.21-5.23 (t, 1H), 6.27 (s, 1H), 7.21-7.23 (t, 1H), 7.41-7.51 (m, 4H), 7.55-7.73 (m, 4H), 7.81-7.83 (d, J=8.4 Hz, 1H), 7.78-7.89 (d, J=8 Hz, 1H).

Step-3: Preparation of 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 009)(Racemic)

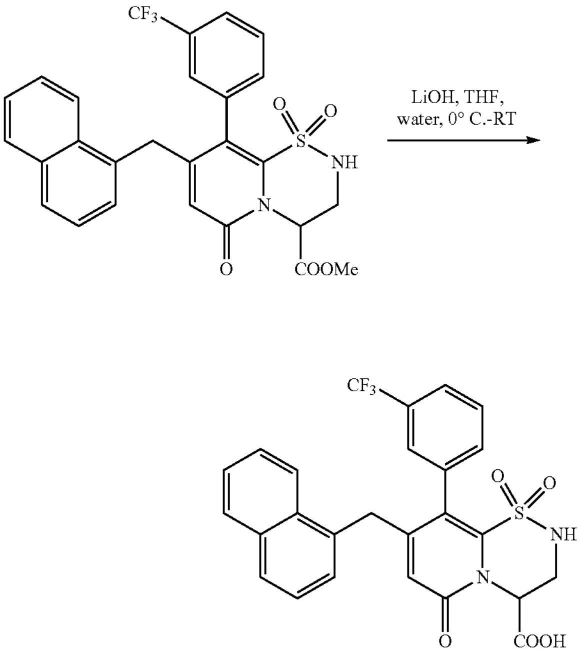

Compound 009 (Racemic)

Methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.1 g, 0.184 mmol) was dissolved in THF (3 mL) and cooled to 0° C. A solution of lithium hydroxide (0.0309 g, 0.737 mmol) in water (3 mL) was added at 0° C. dropwise, stirred at room temperature for 16 h., then concentrated under reduced pressure. Ice water (10 mL) and aq. 1N HCl (3-4 mL) were added, and the resulting precipitate was collected by filtration to give 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 009)(Racemic), as an off white solid (0.07 g, 71.86%) LCMS (Method-$C_3$): 98.31% (RT 1.715, 238.0 nm) (MS: ESI+ve 527.41 [M+H]). $^1$H NMR: (400 MHz, DMSO) δ ppm: 3.84-3.95 (m, 3H), 4.03 (m, 1H), 5.03 (s, 1H), 6.06-6.11 (d, J=21.6 Hz, 1H), 7.23-7.27 (t, 1H), 7.43-7.50 (m, 3H), 7.55-7.73 (m, 5H), 7.83-7.93 (m, 2H), 8.66 (s, 1H), 13.56 (s, 1H).

Example 51

Synthesis of 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 026a, Compound 026b)

Compound 026

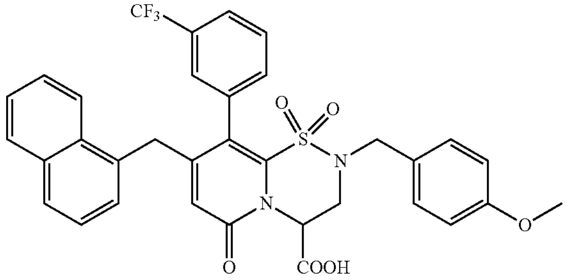

(Racemic)

Step-1: Preparation of 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 026)(Racemic)

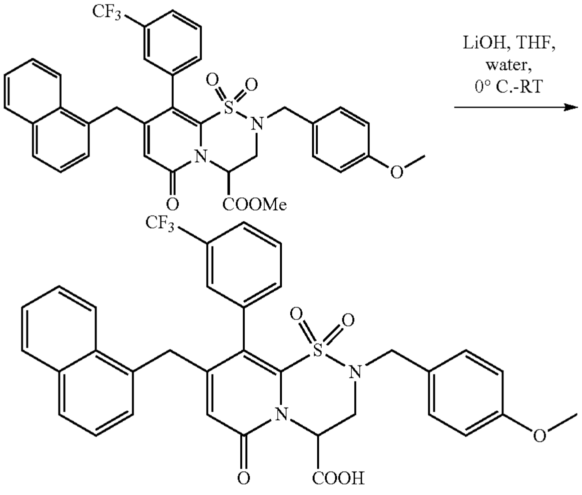

Compound 026 (Racemic)

Methyl 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.25 g, 0.377 mmol) was dissolved in THF (5 mL) and cooled to 0° C. A solution of lithium hydroxide (0.047 g, 1.13 mmol) in water (5 mL) was added dropwise and stirring continued at room temperature for 16 h. The reaction mixture was concentrated under reduced pressure, and ice-cold water (10 mL) was added followed by 1N aqueous HCl (3-4 mL). The resulting precipitate was collected by filtration and dried. Purified by Prep HPLC Method 7 to give 2-(4-methoxybenzyl)-8-(naphthalen-1-ylmethyl)-6-oxo-9-

(3-(trifluoromethyl)phenyl)-3,4-dihydro-2H,6H-pyrido[1,2-e][1,2,5]thiadiazine-4-carboxylic acid 1,1-dioxide (Compound 26)(Racemic), as an off white solid (0.108 g, 36.78%). LCMS (Method-J): 96.09% (RT 5.635, 214.4 nm) (MS: ESI+ve 649.2 [M+H]). $^1$H NMR: (400 MHz, DMSO) δ ppm: 3.71-3.75 (t, 3H), 3.90-3.95 (m, 3H), 4.04-4.08 (m, 1H), 4.22-4.34 (m, 2H), 5.05 (s, 1H), 6.00-6.06 (d, J=22.8 Hz, 2H), 6.88-6.90 (d, J=7.2 Hz, 3H), 7.18-7.28 (m, 3H), 7.43-7.49 (m, 2H), 7.56-7.74 (m, 5H), 7.83-7.85 (d, J=8 Hz, 1H), 7.90-7.92 (d, J=7.6 Hz, 1H).

SFC separation of 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 026a, Compound 026b)

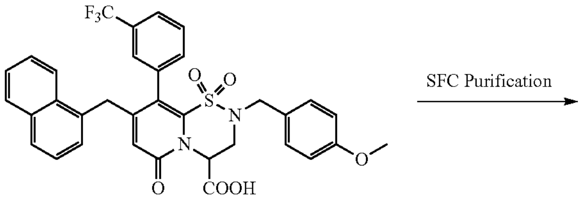

Compound 026 (Racemic)

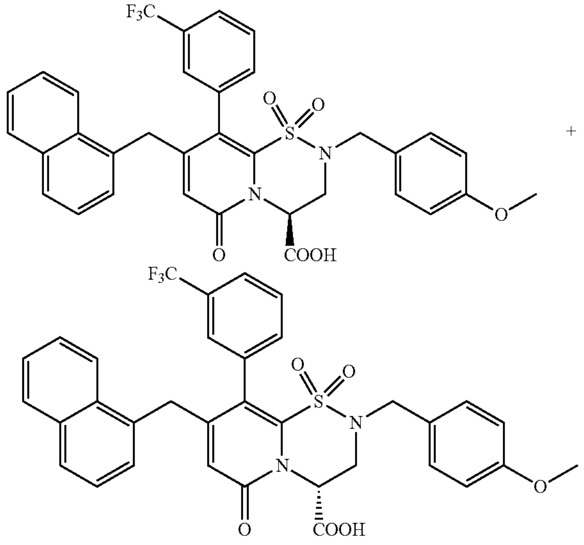

Racemic 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (0.09 g) was separated on a Waters SFC 200 chromatography system with a UV detector. The column was Chiralpak AD-H (250*21.0) mm, 5 micron, column flow was 80.0 ml/min and ABPR was 100 bar. Mobile phase (A) Liquid Carbon dioxide (Liq. CO2) and (B) 0.1% DEA Methanol: Acetonitrile (50:50). The gradient solvent B was 20-20% over 20 min.

Isolated (0.004 g, 4.44%) of fraction 1 (Compound 026a) as an off white solid. LCMS (Method-J): 100% (RT: 5.692, 222.0 nm) (MS: ESI+ve 649.2 [M+H])$^1$H NMR: (400 MHz, DMSO) δ ppm: 3.72-3.72 (d, J=3.2 Hz, 3H), 3.91-3.94 (m, 3H), 4.05 (m, 1H), 4.21-4.33 (m, 2H), 5.11 (s, 1H), 6.02-6.07 (d, J=22.8 Hz, 1H), 6.89-6.91 (d, J=8.8 Hz, 2H), 7.18-7.25 (m, 3H), 7.43-7.47 (m, 3H) 7.60-7.76 (m, 5H), 7.83-7.92 (m, 2H). Chiral HPLC (Fr-1): 98.98% (RT: 4.0), Isolated (0.008 g, 8.89%) of fraction 2 (Compound 026b), LCMS (Method-J): 100% (RT: 7.713, 222.0 nm) (MS: ESI+ve 649.2 [M+H])$^1$H NMR: (400 MHz, DMSO) δ ppm: 3.71-3.72 (d, J=3.2 Hz, 3H), 3.91-3.95 (m, 3H), 4.06 (m, 1H), 4.21-4.33 (m, 2H), 5.11 (s, 1H), 6.02-6.08 (d, J=22.8 Hz, 1H), 6.89-6.91 (d, J=7.6 Hz, 2H), 7.18-7.25 (m, 3H), 7.43-7.49 (m, 3H) 7.60-7.75 (m, 5H) 7.90-7.92 (m, 2H) Chiral HPLC (Fr-2): 95.08% (RT: 4.85).

Example 52

Synthesis of 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 009a)

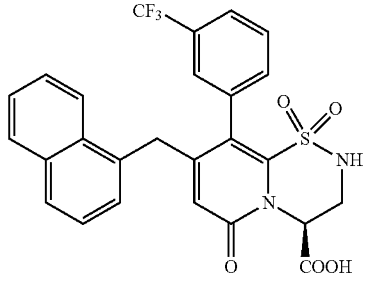

Compound 009a
Single enantiomer
Arbitrary stereochemistry

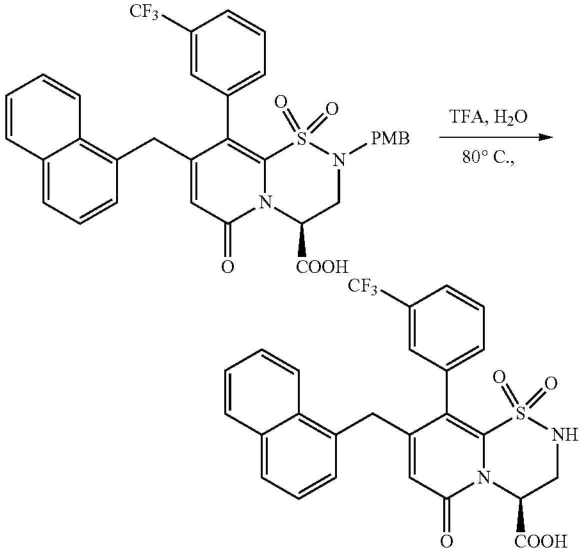

Compound 009a

A mixture of (S)-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 026a) (0.02 g, 0.0308 mmol) in TFA (0.18 mL) and water (0.009 mL) was heated at 80° C. for 15 min. The mixture was poured into ice water (5 mL), then sat. aq. sodium bicarbonate (5 mL) was added. The mixture was extracted with ethyl acetate (3×10 mL) and the organic layer was dried over sodium sulphate then concentrated under reduced pressure. The crude product was purified by Reverse Phase Prep HPLC. Prep HPLC Method 7 to give (S)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 009a), as a white solid (0.004 g, 24.55%). LCMS (Method-J): 100.0% (RT 4.942, 202.4 nm) (MS: ESI+ve 529.2 [M+H]). $^{1}$H NMR: (400 MHz, DMSO) δ ppm: 3.83-4.02 (m, 4H), 5.01 (s, 1H), 6.05-6.10 (d, J=21.2 Hz, 1H), 7.23-7.27 (t, 1H), 7.46-7.73 (m, 8H), 7.83-7.86 (t, 1H), 7.92-7.94 (d, J=6.8 Hz, 1H), 8.61 (s, 1H). Chiral HPLC (Fr-1): 96.52% (RT: 6.75).

Example 52a

Synthesis of 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 009b)

Compound 009b

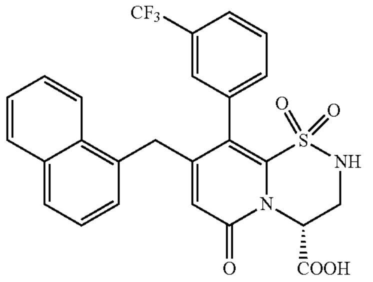

Single enantiomer
Arbitrary stereochemistry

Prepared by a procedure similar to that described for 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 009a) using (R)-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 026b). Purified using Prep HPLC Method 1. to give (R)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 009b), as a white solid (0.006 g, 36.82%). LCMS (Method-J): 100% (RT: 5.410, 202.4 nm) (MS: ESI+ve 527.2 [M+H]). $^{1}$H NMR: (400 MHz, DMSO) δ ppm: 3.89-4.00 (m, 4H), 5.00 (m, 1H), 6.04-6.10 (d, J=21.2 Hz, 1H), 7.26 (m, 1H), 7.48-7.64 (m, 8H), 7.85-7.92 (m, 2H), 8.55 (s, 1H). Chiral HPLC (Fr-2): 98.49% (RT: 6.59).

Example 53

Synthesis of 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015 (Racemic), Compound 015a, Compound 015b)

Compound 015

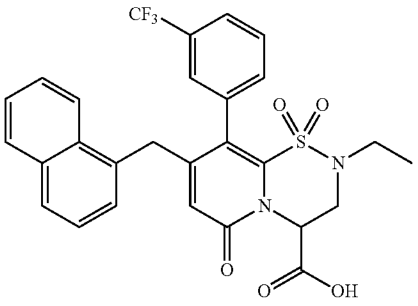

(Racemic)
Compound 015a
Arbitrary stereochemistry
Compound 015b
Arbitrary stereochemistry

Step-1: Preparation of methyl 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

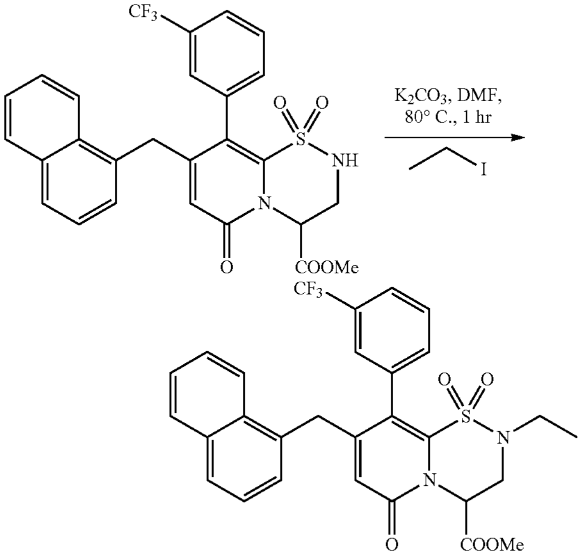

Methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.25 g, 0.4612 mmol) was dissolved in DMF (3 mL). Ethyl iodide (0.05 mL, 0.691 mmol) and potassium carbonate (0.097 g, 0.6912 mmol) were added and the mixture was stirred for 1 h at 80° C. The reaction was quenched in ice water and extracted with ethyl acetate (3×15 mL). The organic layers were combined and dried over sodium sulphate. The solvent was removed under reduced pressure and the crude product was purified by column chromatography eluting with 30-40% ethyl acetate/hexane to give methyl 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.15 g, 57.05%). LCMS (Method-C3): 91.09% (RT 2.032, 226.0 nm) (MS: ESI+ve 570.3 [M+H]).

Step-2: Preparation of 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide. (Compound 015) (Racemic)

Methyl 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.08 g, 0.140 mmol) was dissolved in THF:$H_2O$ (3 mL)(1:1) at room temperature. LiOH (0.017 g, 0.420 mmol) was added at 0° C. and the mixture was stirred at room temperature for 3 h. The mixture was concentrated under reduced pressure and ice water (10 mL) was added followed by 1N HCl (3-4 mL). The resulting precipitate was collected by filtration, dried under vacuum and purified by Prep HPLC Method 1 to give 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide. (Compound 015)(Racemic), as an off white solid (0.021 g, 26.91%). LCMS (Method-C3): 100% (RT 1.889, 230.0 nm) (MS: ESI+ve 557.3 [M+H]). $^1$H NMR: (400 MHz, DMSO) δ ppm: 1.06-1.10 (m, 3H), 3.19-3.21 (d, J=8 Hz, 2H), 3.90 (s, 2H), 4.10-4.17 (m, 2H), 5.14 (s, 1H), 6.08-6.11 (d, J=13.2 Hz, 1H), 7.24-7.26 (d, J=6.4 Hz, 1H) 7.45-7.52 (m, 3H) 7.58-7.72 (m, 5H), 7.84-7.86 (d, J=6.8 Hz, 1H) 7.92-7.94 (d, J=7.6 Hz, 1H).

SFC separation of 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide. (Compound 015a and Compound 015b)

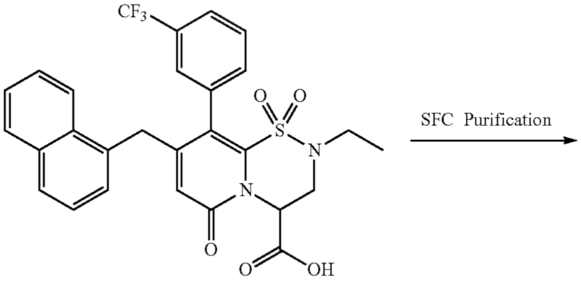

Compound 015 (Racemic)

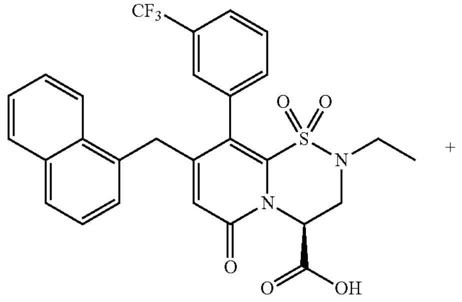

-continued

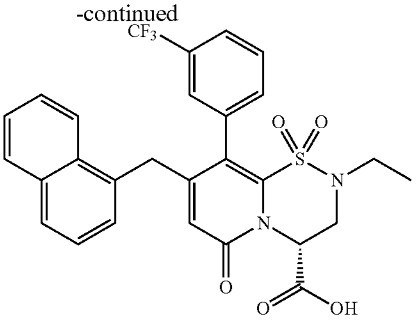

2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015) (0.090 g) was separated on a Waters SFC 200 instrument. The column used was ChiralPAK IC (250*21.0) mm, 5 micron, column flow was 80.0 ml/min and ABPR was 100 bar. Mobile phase (A) Liquid Carbon dioxide (Liq. CO2) and (B) 0.1% DEA IN IPA:Acetonitrile (50:50).

Isolated (0.016 g, 18.23%) of fraction 1 (Compound 015a). LCMS (Method-$C_3$): 100% (RT 2.312, 202.0 nm) (MS: ESI+ve 557.2 [M+H]). $^1$H NMR: (400 MHz, DMSO) δ ppm: 1.04-1.08 (t, J=16 Hz, 3H), 3.16-3.21 (m, 2H), 3.89 (s, 2H), 4.07-4.19 (m, 2H), 5.15 (s, 1H), 6.07-6.10 (d, J=12 Hz, 1H), 7.22-7.24 (d, J=8 Hz, 1H), 7.42-7.50 (m, 3H), 7.56-7.70 (m, 5H), 7.82-7.84 (d, J=8 Hz, 1H), 7.90-7.92 (d, J=8 Hz, 1H). Chiral HPLC (Fr-1): 97.50% (RT: 5.61).

Isolated (0.018 g, 20.50%) of fraction 2 (Compound 015b). LCMS (Method-$C_3$): 100% (RT 2.316, 202.0 nm) (MS: ESI+ve 557.2 [M+H]). $^1$H NMR: (400 MHz, DMSO) δ ppm: 1.04-1.08 (t, J=8 Hz, 3H), 3.16-3.20 (t, J=16 Hz, 2H), 3.89 (s, 2H), 4.08-4.19 (m, 2H), 5.15-5.16 (d, J=4 Hz, 1H), 6.07-6.10 (d, J=12 Hz, 1H), 7.22-7.24 (d, J=8 Hz, 1H), 7.43-7.48 (m, 3H), 7.56-7.70 (m, 5H), 7.82-7.84 (d, J=8 Hz, 1H), 7.90-7.92 (d, J=8 Hz, 1H), 13.65 (s, 1H). Chiral HPLC (Fr-1): 97.87% (RT: 6.36).

Example 54

Synthesis of 8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 016 (Racemic), Compound 016a, Compound 016b)

Compound 016

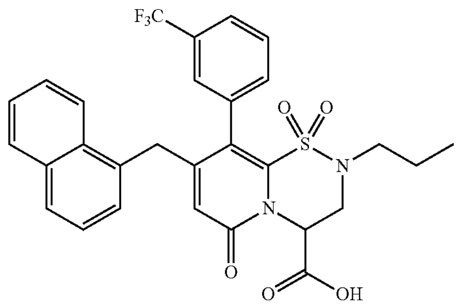

(Racemic)
Compound 016a
Arbitrary stereochemistry
Compound 016b
Arbitrary stereochemistry Prepared by a procedure similar to that described for 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015)(Racemic) using n-propyl iodide in step 1 to give 8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide. The crude product was purified by Prep HPLC Method 1, to give an off white solid (0.022 g, 11.27%) LCMS (Method-J): 100% (RT 4.806, 202.0 nm) (MS: ESI+ve 571.7 [M+H]). $^{1}$H NMR: (400 MHz, DMSO) δ ppm: 0.79 (t, J=7.3 Hz, 3H), 1.48 (m, 2H), 3.10-3.11 (d, J=7.2 Hz, 2H), 3.85-4.21 (m, 4H), 5.13 (s, 1H), 6.07-6.11 (d, J=16 Hz, 1H), 7.24-7.25 (d, J=4 Hz, 1H), 7.46-7.50 (t, J=8 Hz, 3H), 7.56-7.73 (m, 5H), 7.84-7.86 (d, J=8 Hz, 1H), 7.91-7.93 (d, J=8 Hz, 1H).

SFC separation of 8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 016a, Compound 016b)

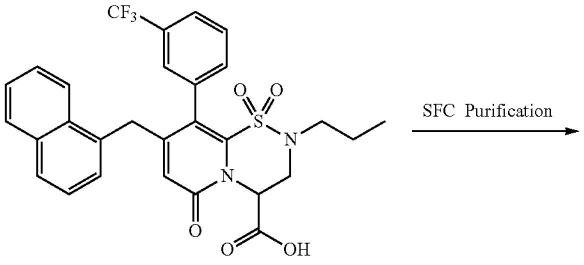

Compound 016
(Racemic)

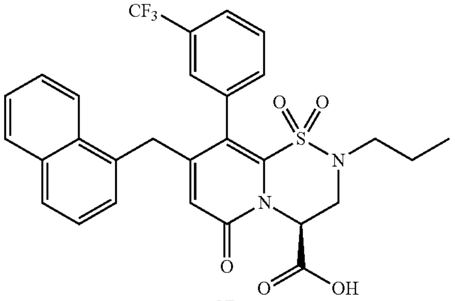

+

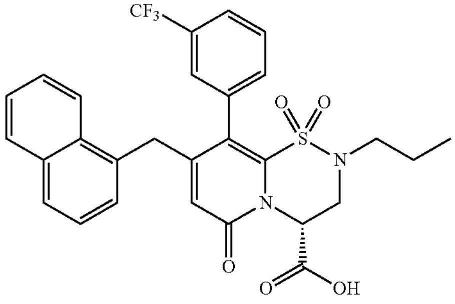

8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 016) (Racemic) (0.095 g) was separated on a Waters SFC 200 chromatography system with a UV detector. The column used was Chiralcel OX-H (250*21.0) mm, 5 micron, column flow was 80.0 ml/min and ABPR was 100 bar. Mobile phase (A) Liquid Carbon dioxide (Liq. CO2) and (B)$_{0.1}$% DEA Methanol:Acetonitrile (50:50)

Isolated (0.025 g, 26.96%) of fraction 1 (Compound 016a) as an off white solid. LCMS (Method-C3): 100% (RT 2.370, 202.0 nm) (MS: ESI+ve 571.2 [M+H]). $^{1}$H NMR: (400 MHz, DMSO) δ ppm: 0.75-0.79 (t, J=16 Hz, 3H), 1.44-1.49 (m, 2H), 3.01-3.11 (m, 2H), 3.84-3.20 (m, 4H), 5.15 (s, 1H), 6.07-6.10 (d, J=12 Hz, 1H), 7.22-7.24 (d, J=8 Hz, 1H), 7.42-7.50 (m, 3H), 7.55-7.72 (m, 5H), 7.82-7.92 (m, 2H). Chiral HPLC (Fr-1): 98.39% (RT: 5.72)

Isolated (0.024 g, 25.88%) of fraction 2 (Compound 016b) as an off white solid LCMS (Method-C3): 100% (RT 2.370, 202.0 nm) (MS: ESI+ve 571.2 [M+H]). $^{1}$H NMR: (400 MHz, DMSO) δ ppm: 0.75-0.79 (t, J=16 Hz, 3H), 1.44-1.49 (m, 2H), 3.01-3.13 (m, 2H), 3.84-3.20 (m, 4H), 5.15-5.17 (d, J=8 Hz, 1H), 6.06-6.10 (d, J=16 Hz, 1H), 7.23-7.24 (d, J=4 Hz, 1H), 7.42-7.50 (m, 3H), 7.55-7.72 (m, 5H), 7.82-7.84 (d, J=8 Hz, 1H), 7.90-7.92 (d, J=8 Hz, 1H). Chiral HPLC (Fr-1): 100% (RT: 8.22).

Example 55

Synthesis of 2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 021 (Racemic), Compound 021a, Compound 021b)

Compound 021

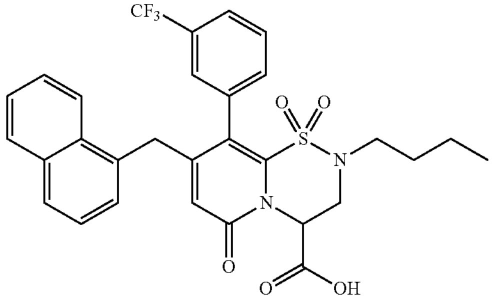

(Racemic)
Compound 021a
Arbitrary stereochemistry
Compound 021b
Arbitrary stereochemistry Prepared by a procedure similar to that described for 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015) (Racemic) using n-butyl bromide in step 1 to give 2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide Compound 021 (Racemic) (0.044, 34.66%). Purified using Prep HPLC Method 6. LCMS (Method-J): 100% (RT 5.699, 202.0 nm) (MS: ESI+ve 585.2 [M+H]). $^{1}$H NMR: (400 MHz, DMSO) δ ppm: 0.79-0.83 (t, J=7.6 Hz, 3H), 1.17-1.22 (m, 2H), 1.39-1.45 (m, 2H), 3.10-3.11 (d, J=6.8 Hz, 2H), 3.885 (s, 2H), 4.05-4.18 (m, 2H), 5.13-5.14 (d, J=4 Hz, 1H), 6.06-6.10 (d, J=16.4, 1H), 7.22-7.24 (d, J=10 Hz, 1H), 7.42-7.72 (m, 8H) 7.83-7.84 (d, J=5.2 Hz, 1H) 7.903-7.922 (d, J=7.6 Hz, 1H), 13.71-13.68 (d, J=12 Hz, 1H).

SFC separation of 2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 021a, Compound 021b)

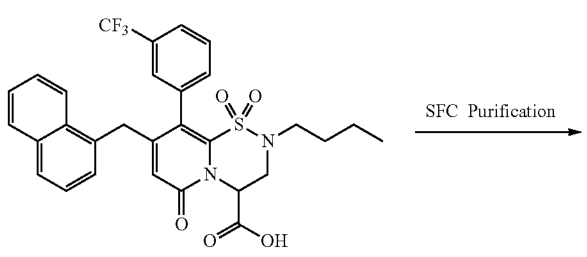

Compound 021 (Racemic)

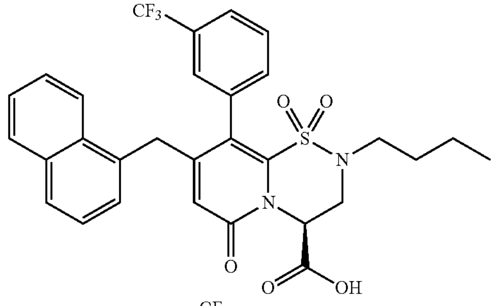

+

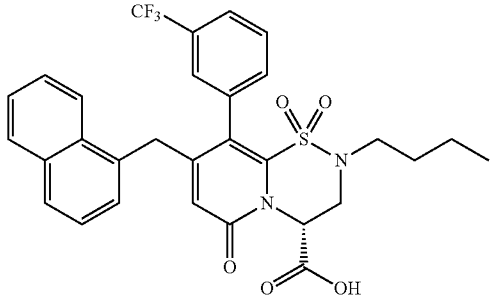

2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 021) (0.095 g) was separated on a Waters SFC 200 chromatography system with a UV detector. The column used was Chiralcel OX-H (250*21.0) mm, 5 micron, column flow was 80.0 ml/min and ABPR was 100 bar. Mobile phase (A) Liquid Carbon dioxide (Liq. $CO_2$) and (B) 0.1% DEA in Propan-2-ol: Methanol (50:50)

Isolated (0.021 g, 22.64%) of fraction 1 (Compound 021a). LCMS (Method-$C_3$): 100% (RT 1.921, 220.0 nm) (MS: ESI+ve 585.3 [M+H]). $^1$H NMR: (400 MHz, DMSO) δ ppm: 0.81-0.84 (t, J=12 Hz, 3H), 1.18-1.24 (m, 3H), 1.41-1.46 (m, 2H), 3.12 (s, 2H), 3.85-3.95 (m, 2H), 4.06-4.20 (m, 2H), 6.83-6.12 (d, J=16 Hz, 1H), 7.24-7.25 (d, J=4 Hz, 1H), 7.44-7.51 (m, 3H), 7.57-7.73 (m, 5H) 7.84-7.85 (d, J=4 Hz, 1H), 7.91-7.93 (d, J=8 Hz, 1H). Chiral HPLC (Fr-1): 100% (RT: 5.52).

Isolated (0.017 g, 18.32%) of fraction 2 (Compound 021b). LCMS (Method-$C_3$): 100% (RT 1.922, 220.0 nm) (MS: ESI+ve 585.35 [M+H]). $^1$H NMR: (400 MHz, DMSO) δ ppm: 0.81-0.84 (t, J=12 Hz, 3H), 1.18-1.24 (m, 2H), 1.40-1.47 (m, 2H), 3.11-3.18 (m, 2H), 3.85-4.20 (m, 4H), 5.13-5.14 (d, J=4 Hz, 1H), 6.07-6.11 (d, J=16 Hz, 1H), 7.24-7.25 (d, J=4 Hz 1H), 7.43-7.51 (m, 3H), 7.55-7.73 (m, 5H), 7.83-7.85 (t, J=4 Hz, 1H). 7.91-7.93 (d, J=8 Hz, 1H). Chiral HPLC (Fr-1): 97.61% (RT: 7.95).

Example 55a

Synthesis of 8-(naphthalen-1-ylmethyl)-6-oxo-2-pentyl-9-(3-(trifluoromethyl)phenyl)-3,4-dihydro-2H,6H-pyrido[1,2-e][1,2,5]thiadiazine-4-carboxylic acid 1,1-dioxide (Compound 025 (Racemic), Compound 025a, Compound 025b)

Compound 025

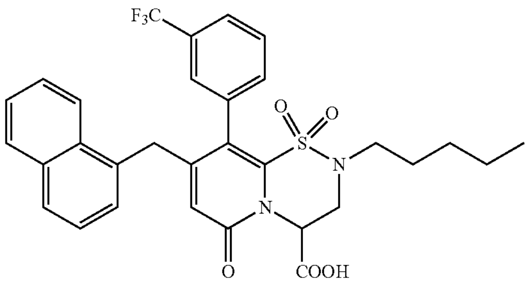

(Racemic)
Compound 025a
Arbitrary stereochemistry
Compound 025b
Arbitrary stereochemistry Prepared by a procedure similar to that described for 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015)(Racemic) using n-pentyl iodide in step 1 to give 8-(naphthalen-1-ylmethyl)-6-oxo-2-pentyl-9-(3-(trifluoromethyl)phenyl)-3,4-dihydro-2H,6H-pyrido[1,2-e][1,2,5]thiadiazine-4-carboxylic acid 1,1-dioxide (0.11 g, 51%) (Compound 025) (Racemic). Purified using Prep HPLC Method 1, LCMS (Method-J): 100% (RT: 5.923, 202.4 nm) (MS: ESI+ve 599.2 [M+H]). $^1$H NMR: (400 MHz, DMSO) δ ppm: 0.82-0.85 (t, J=7.2 Hz, 3H), 1.17-1.25 (m, 4H), 1.45-1.48 (t, J=6.8 Hz, 2H), 3.11-3.13 (d, J=6.8 Hz, 2H), 3.90 (s, 2H), 4.07-4.20 (m, 2H), 5.17 (s, 1H), 6.08-6.12 (d, J=16.8 Hz, 1H), 7.24-7.26 (d, J=6.8 Hz, 1H), 7.43-7.73 (m, 8H), 7.84-7.86 (d, J=8.0 Hz, 1H) 7.91-7.93 (d, J=7.6 Hz, 1H), 13.68 (s, 1H).

SFC separation of 8-(naphthalen-1-ylmethyl)-6-oxo-2-pentyl-9-(3-(trifluoromethyl)phenyl)-3,4-dihydro-2H,6H-pyrido[1,2-e][1,2,5]thiadiazine-4-carboxylic acid 1,1-dioxide (Compound 025a, Compound 025b)

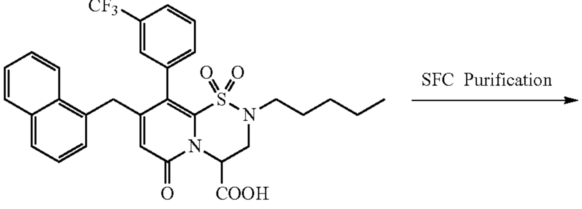

Compound 025 (Racemic)

-continued

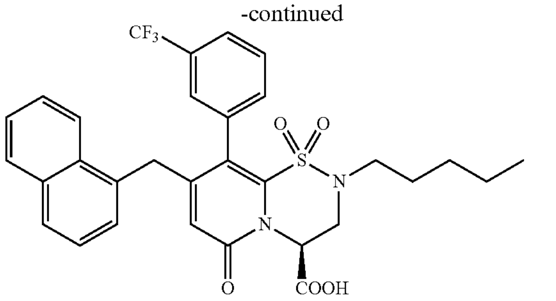

+

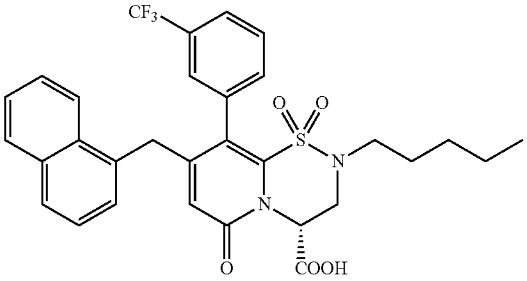

8-(naphthalen-1-ylmethyl)-6-oxo-2-pentyl-9-(3-(trifluoromethyl)phenyl)-3,4-dihydro-2H,6H-pyrido[1,2-e][1,2,5] thiadiazine-4-carboxylic acid 1,1-dioxide (Compound 025) (0.055 g) was separated on a Waters SFC 200 chromatography system with a UV detector. The column was Chiralcel OX-H (250*21.0) mm, 5 micron, column flow was 80.0 ml/min and ABPR was 100 bar. Mobile phase (A) Liquid Carbon dioxide (Liq. CO2) and (B) 0.1% DEA Methanol: Propane-2-ol (50:50). The gradient solvent B was 25-25% over 15 min.

Isolated (0.006 g, 10.91%) of fraction 1 (Compound 025a) (0.006 g, 10.91%) (Compound 025a), LCMS (Method-C3): 100% (RT 2.045, 222.0 nm) (MS: ESI+ve 599.4 [M+H]). $^{1}$H NMR: (400 MHz, DMSO) δ ppm: 0.82-0.85 (t, 3H), 1.17-1.27 (m, 4H), 1.44-1.48 (t, 2H), 3.12-3.14 (d, 2H), 3.85-3.95 (q, 2H), 4.07-4.21 (m, 2H), 5.14 (s, 1H), 6.06-6.11 (d, J=16.4 Hz, 1H), 7.25-7.26 (t, 1H), 7.43-7.52 (m, 3H), 7.56-7.68 (m, 5H), 7.72-7.74 (d, J=7.2 Hz, 1H), 7.84-7.86 (d, J=5.2 Hz, 1H), 13.81 (s, 1H). Chiral HPLC (Fr-1): 100% (RT: 6.0), Isolated (0.009 g, 16.36%) of fraction 2 (Compound 025b), LCMS (Method-$C_3$): 100% (RT 2.041, 222.0 nm) (MS: ESI+ve 599.4 [M+H]). $^{1}$H NMR: (400 MHz, DMSO) δ ppm: 0.82-0.85 (t, 3H), 1.17-1.25 (m, 4H), 1.45-1.48 (t, 2H), 3.12-3.14 (d, 2H), 3.85-3.95 (q, 2H), 4.07-4.21 (m, 2H), 5.15 (s, 1H), 6.07-6.11 (d, J=16.4 Hz, 1H), 7.25 (m, 1H), 7.44-7.52 (m, 3H), 7.56-7.74 (m, 5H), 7.84-7.86 (d, J=5.2 Hz, 1H), 7.92-7.94 (d, J=7.6 Hz, 1H), 13.76 (s, 1H). Chiral HPLC (Fr-2): 97.02% (RT: 8.64).

Example 55b

Synthesis of 2-(but-3-en-1-yl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 024)

Compound 024

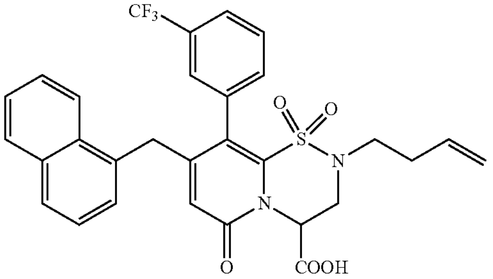

Prepared by a procedure similar to that reported for 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015)(Racemic) substituting 4-bromobut-1-ene in step 1. The crude product was purified using Prep HPLC Method 1 to give 2-(but-3-en-1-yl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 024), as an off white solid (0.031 g, 18.67%). LCMS (Method-J): 100% (RT: 5.478, 202.0 nm, 224.0 nm) (MS: ESI+ve 583.2 [M+H]). $^{1}$H NMR: (400 MHz, DMSO) δ ppm: 2.19-2.21 (d, J=6.4 Hz, 2H), 3.21-3.27 (m, 2H), 3.80-3.91 (m, 2H), 4.11 (s, 2H), 4.92-5.05 (m, 2H), 5.63-5.69 (m, 1H), 5.99-6.01 (d, J=10.0 Hz, 1H), 7.175 (s, 1H), 7.23-7.24 (d, J=3.6 Hz, 1H), 7.42-7.71 (m, 8H), 7.81-7.83 (m, 1H), 7.90-7.91 (d, J=7.6 Hz, 1H).

Example 56

Synthesis of 2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 056)

Compound 056

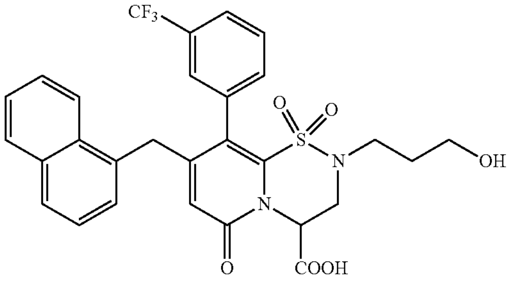

Prepared by a procedure similar to that reported for 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015)(Racemic) substituting 3-Bromo 1-propanol in step 1. The crude product was purified using Prep HPLC Method 1 to give 2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as a white solid (Compound 056) (0.062 g, 31.74%). LCMS (Method-C3): 100% (RT 1.751, 227.0 nm) (MS: ESI+ve 587.4 [M+H]). $^1$H NMR: (400 MHz, DMSO-$d_6$) δ ppm: 1.59 (m, 2H), 3.19-3.22 (m, 2H), 3.89-3.94 (m, 2H), 4.08-4.09 (m, 1H), 4.18-4.22 (m, 1H), 4.50 (bs, 1H), 5.14 (t, J=4 Hz, 1H), 6.06-6.10 (d, J=14.8 Hz, 1H), 7.23 (m, 1H), 7.45-7.48 (m, 3H), 7.55-7.72 (m, 5H), 7.82-7.84 (m, 1H), 7.90-7.91 (d, J=8 Hz, 1H), 13.69 (bs, 1H).

Example 57

Synthesis of 2-(5-hydroxypentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 086)

Compound 086

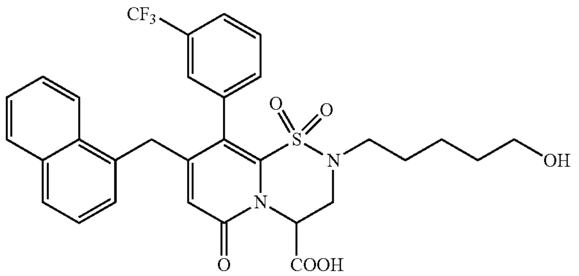

Prepared by a procedure similar to that reported for 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015)(Racemic) substituting 5-bromopentan-1-ol in step 1. The crude product was purified using Prep HPLC Method 1 to give 2-(5-hydroxypentyl)-8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylic acid 1,1-dioxide (Compound 086), as an off white solid (0.062 g, 21.38%). LCMS (Method-C3): 100% (RT 1.852) (MS: ESI+ve 615.38 [M+H]). $^1$H NMR: (400 MHz, DMSO) δ ppm: 1.19-1.21 (m, 2H), 1.34-1.45 (m, 4H), 3.10-3.11 (d, 2H), 3.89-3.94 (t, 2H), 4.06-4.20 (m, 2H), 5.14 (bs, 1H), 6.06-6.01 (d, 1H), 7.22-7.24 (d, J=5.2 Hz, 1H), 7.44-7.48 (m, 3H), 7.55-7.72 (m, 5H), 7.82-7.92 (m, 2H), 13.64 (bs, 1H).

Example 58

Synthesis of 2-(2-hydroxyethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 084)

Compound 084

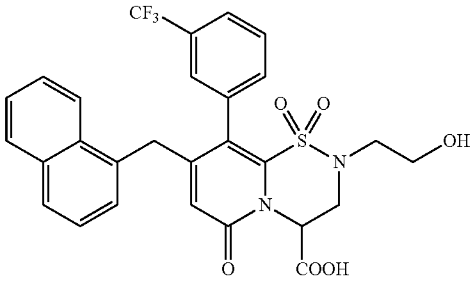

Prepared by a procedure similar to that reported for 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015)(Racemic) substituting 2-bromoethan-1-ol in step 1. The crude product was purified using Prep HPLC Method 1 to give 2-(2-hydroxyethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 084), as an off white solid (0.031 g, 18.68%). LCMS (Method-C3): 100% (RT 1.785, 226.0 nm) (MS: ESI+ve 573.39 [M+H]). $^1$H NMR: (400 MHz, DMSO) δ ppm: 3.12-3.16 (m, 1H), 3.25-3.26 (m, 2H), 3.42-3.43 (m, 2H), 3.83-3.93 (t, 2H), 4.15-4.28 (q, 2H), 5.08-5.09 (d, J=4 Hz, 1H), 6.04-6.08 (d, J=14.8 Hz, 1H), 7.23-7.24 (d, J=6.4 Hz, 1H), 7.43-7.50 (m, 3H), 7.56-7.70 (m, 5H), 7.82-7.84 (d, J=6 Hz, 1H), 7.90-7.92 (d, J=7.6 Hz, 1H).

Example 59

Synthesis of 2-(4-(1,3-dimethyl-2,6-dioxo-1,2,3,6-tetrahydro-7H-purin-7-yl)butyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 033)

Compound 033

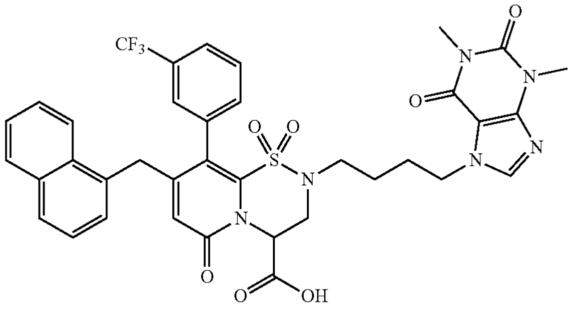

Step 1: Preparation of 7-(4-bromobutyl)-1,3-dimethyl-3,7-dihydro-1H-purine-2,6-dione

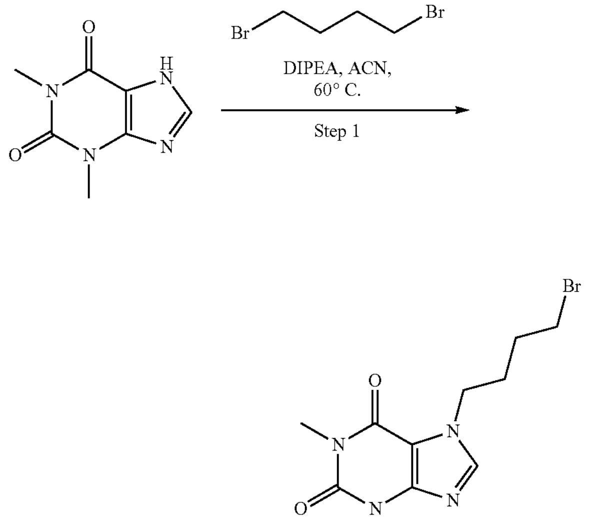

1,3-dimethyl-3,7-dihydro-1H-purine-2,6-dione (0.5 g, 2.774 mmol) was dissolved in anhydrous acetonitrile (5 mL). DIPEA (0.67 mL, 3.884 mmol) was added followed by 1,4-dibromobutane (2.3 g, 11.098 mmol), and the vial was sealed. The reaction vessel was heated to 60° C. for 16 h. The solution was allowed to cool to room temperature and sat. aq. sodium bicarbonate (30 mL) was added. The mixture was extracted with DCM (3×40 mL) and the organic layer was dried over sodium sulphate and concentrated under reduced pressure to give crude product which was purified using column chromatography, eluting with 60% ethyl acetate in hexane to give 7-(4-bromobutyl)-1,3-dimethyl-3,7-dihydro-1H-purine-2,6-dione as an off white solid (0.55 g, 66.14%) LCMS (Method-C3): 100% (RT: 1.455, 273.0 nm) (MS: ESI+ve 315.11 [M+H]). $^1$H NMR: (400 MHz, DMSO) δ ppm: 1.71-1.76 (m, 2H), 1.86-1.91 (m, 2H), 3.22 (s, 3H), 3.42 (s, 3H), 3.52-3.55 (t, J=13.2 Hz, 2H), 4.26-4.29 (t, J=13.2 Hz, 2H), 8.11 (s, 1H).

Step 2: Preparation of methyl 2-(4-(1,3-dimethyl-2,6-dioxo-1,2,3,6-tetrahydro-7H-purin-7-yl)butyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

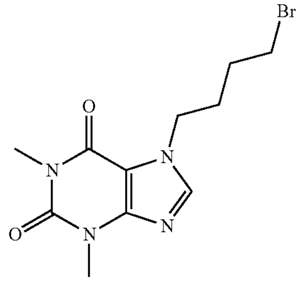

+

-continued

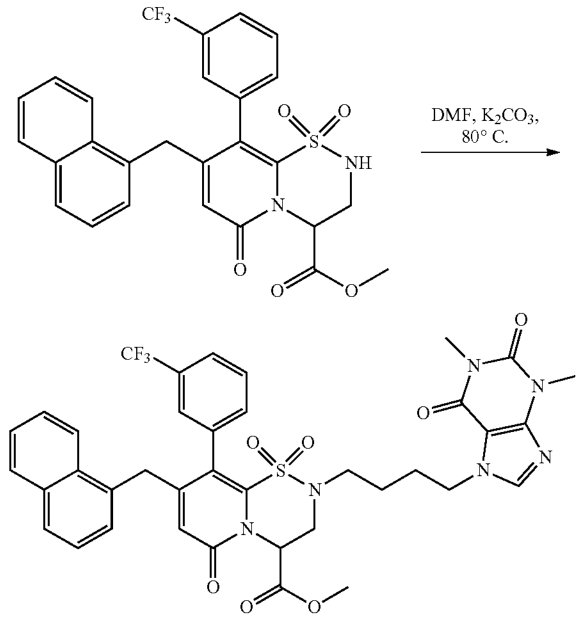

7-(4-bromobutyl)-1,3-dimethyl-3,7-dihydro-1H-purine-2,6-dione (0.2 g, 0.3686 mmol) and methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.174 g, 0.5529 mmol) were dissolved in DMF (3 ml) and potassium carbonate (0.077 g, 0.5529 mmol) was added. The resulting mixture was stirred at 80° C. 1 h. The reaction was quenched in ice water and extracted with ethyl acetate (3×15 mL). The organic layers were then combined and dried over sodium sulphate. The solvent was removed under reduced pressure and the crude was purified using column chromatography, eluting with 3% Methanol in DCM to give methyl 2-(4-(1,3-dimethyl-2,6-dioxo-1,2,3,6-tetrahydro-7H-purin-7-yl)butyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.2 g, 40.57%). LCMS (Method-C3): 90.0% (RT: 1.901, 220.0 nm) (MS: ESI+ve 777.5[M+H]).

Step 3: Preparation of 2-(4-(1,3-dimethyl-2,6-dioxo-1,2,3,6-tetrahydro-7H-purin-7-yl)butyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 033)

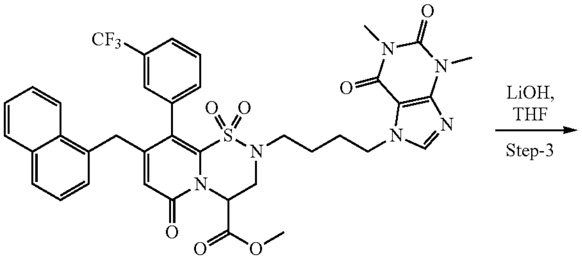

-continued

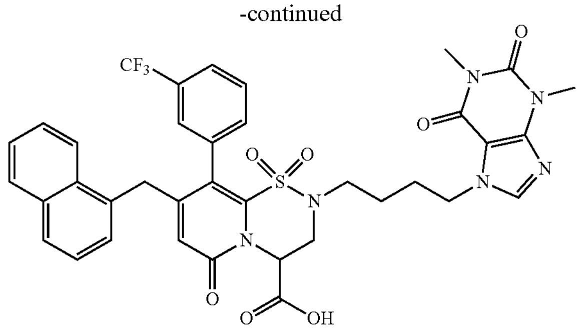

Compound 033

Methyl 2-(4-(1,3-dimethyl-2,6-dioxo-1,2,3,6-tetrahydro-7H-purin-7-yl)butyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.2 g, 0.257 mmol) was dissolved in THF:$H_2O$ (5 mL, 1:1) at room temperature. LiOH (0.033 g, 0.7724 mmol) was added at 0° C. and stirring was continued at room temperature for 4 h. The mixture was concentrated, then suspended in ice water (10 mL) and 1N aqueous HCl (10 mL). The resulting precipitate was collected by filtration and dried under vacuum. The crude product was purified using Prep HPLC Method 1 to give 2-(4-(1,3-dimethyl-2,6-dioxo-1,2,3,6-tetrahydro-7H-purin-7-yl)butyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid1,1-dioxide (Compound 033), as an off white solid (0.077 g, 39.21%). LCMS (Method-C3): 100% (RT: 1.745, 230.0 nm) (MS: ESI+ve 763.8[M+H]). 1H NMR: (400 MHz, DMSO) δ ppm: 1.42 (s, 2H), 1.71 (s, 2H), 3.14-3.16 (d, J=5.6 Hz, 2H), 3.22 (s, 3H), 3.42 (s, 3H), 3.90-3.95 (d, J=18.8 Hz, 2H), 4.05-4.106 (m, 1H), 4.16-4.22 (t, J=23.2 Hz, 3H) 5.14-5.17 (t, J=10.8 Hz, 1H), 6.08-6.12 (d, J=12.8, 1H), 7.24-7.25 (d, J=6.8 Hz, 1H), 7.44-7.52 (m, 3H), 7.56-7.72 (m, 5H), 7.84-7.86 (d, J=7.2 Hz, 1H), 7.91-7.93 (d, J=8 Hz, 1H), 8.05 (s, 1H), 13.66 (s, 1H).

Example 60

Synthesis of 2-(5-(1,3-dimethyl-2,6-dioxo-1,2,3,6-tetrahydro-7H-purin-7-yl)pentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 034)

Compound 034

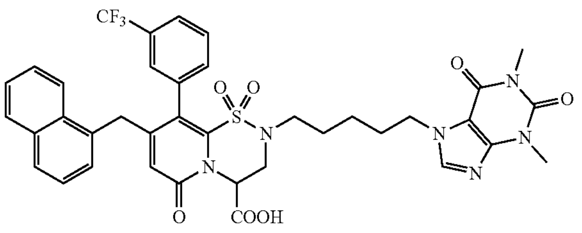

Prepared by a method similar to that reported for 2-(4-(1,3-dimethyl-2,6-dioxo-1,2,3,6-tetrahydro-7H-purin-7-yl)butyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid1,1-dioxide (Compound 033) substituting 1,5-dibromopentane in step 1. The crude product was purified using Prep HPLC Method 1 to give 2-(5-(1,3-dimethyl-2,6-dioxo-1,2,3,6-tetrahydro-7H-purin-7-yl)pentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as an off white solid (0.062 g, 11.27%) (Compound 034). LCMS (Method-C3): 100% (RT 1.775, 202.0 nm) (MS: ESI+ve 777.7 [M+H]). $^1$H NMR: (400 MHz, DMSO) δ ppm: 1.15-1.17 (m, 2H), 1.47-1.51 (m, 2H), 1.72-1.75 (m, 2H), 3.05-3.12 (m, 2H), 3.21 (s, 3H), 3.42 (S, 3H), 3.90 (s, 2H), 4.07-4.10 (m, 1H), 4.17-4.22 (m, 3H), 5.15 (d, J=5.6 Hz, 1H), 6.01 (d, J=14.8 Hz, 1H), 7.23 (d, J=8.0 Hz, 1H), 7.43-7.56 (m, 3H), 7.57-7.72 (m, 5H), 7.84-7.85 (d, J=4 Hz, 1H), 7.91-7.93 (d, J=8, 1H), 8.06 (s, 1H), 13.68 (bs, 1H).

Example 61

Synthesis of 2-(6-(1,3-dimethyl-2,6-dioxo-1,2,3,6-tetrahydro-7H-purin-7-yl)hexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 035)

Compound 035

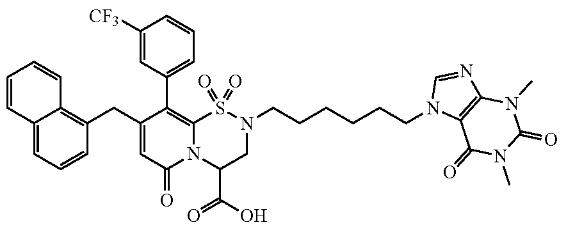

Prepared by a method similar to that reported for 2-(4-(1,3-dimethyl-2,6-dioxo-1,2,3,6-tetrahydro-7H-purin-7-yl)butyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid1,1-dioxide (Compound 033) substituting 1,6-dibromohexane in step 1. The crude residue was purified using Prep HPLC Method 1 to give 2-(6-(1,3-dimethyl-2,6-dioxo-1,2,3,6-tetrahydro-7H-purin-7-yl)hexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 035), as an off white solid (0.102 g, 34.60%). LCMS (Method-C3): 99.60% (RT: 5.218, 214.4 nm) (MS: ESI+ve 791.4[M+H]). $^1$H NMR: (400 MHz, DMSO) δ ppm: 1.19 (m, 4H), 1.45 (m, 2H), 1.74 (m, 2H), 3.10 (t, 2H), 3.22 (s, 3H), 3.35-3.42 (d, J=29.2 Hz, 3H), 3.90 (s, 2H), 4.06-4.09 (d, J=12 Hz, 2H), 4.19-4.22 (t, J=12 Hz, 2H), 5.15 (s, 1H), 6.08-6.12 (d, J=16, 1H), 7.25 (s, 1H), 7.46-7.50 (t, J=16.8, 3H), 7.55-7.67 (m, 4H), 7.71-7.72 (d, J=7.2 Hz, 1H), 7.83-7.86 (d, J=10 Hz, 1H), 7.91-7.93 (d, J=8.4 Hz, 1), 8.07 (s, 1H), 13.67 (s, 1H).

Example 62

Synthesis of 2-(6-(1,3-dimethyl-2,6-dioxo-1,2,3,6-tetrahydro-7H-purin-7-yl) heptyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 036)

Compound 036

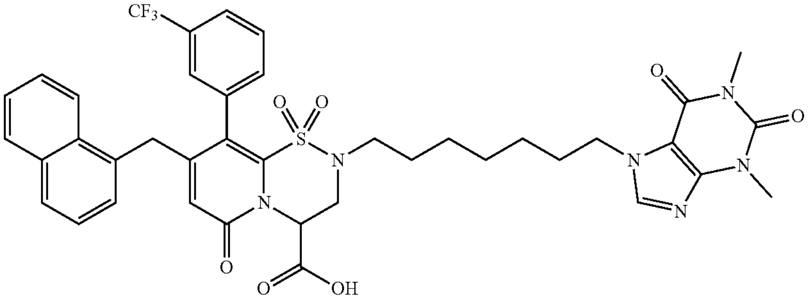

Prepared by a method similar to that reported for 2-(4-(1,3-dimethyl-2,6-dioxo-1,2,3,6-tetrahydro-7H-purin-7-yl) butyl)-8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylic acid1,1-dioxide (Compound 033) substituting 1,7-dibromoheptane in step 1. The crude product was purified using Prep HPLC Method 1 to give 2-(6-(1,3-dimethyl-2,6-dioxo-1,2,3,6-tetrahydro-7H-purin-7-yl) heptyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 036), as an off white solid (0.086 g, 29.18%). LCMS (Method-C3): 100% (RT 1.824) (MS: ESI+ve 805.6 [M+H]). $^1$H NMR: (400 MHz, DMSO) (δ ppm: 1.02-1.04 (d, J=6 Hz, 2H), 1.16 (m, 4H), 1.42 (m, 2H), 1.72 (m, 2H), 3.09 (m, 2H), 3.21 (s, 3H), 3.29-3.41 (t, J=4.8 Hz, 3H), 3.88 (s, 2H), 4.07-4.15 (d, J=30 Hz, 2H), 4.18-4.21 (t, J=14 Hz, 2H), 5.13 (s, 1H), 6.06-6.10 (d, J=16.4 Hz, 1H), 7.22-7.23 (d, J=4.4 Hz, 1H), 7.42-7.50 (m, 3H), 7.53-7.71 (m, 5H), 7.82-7.84 (d, J=5.6 Hz, 1H), 7.90-7.92 (d, J=8 Hz, 1H), 8.06 (s, 1H), 13.67 (s, 1H).

Example 63

Synthesis of 8-(naphthalen-1-ylmethyl)-6-oxo-9-(3-(trifluoromethyl)phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylic acid 1,1-dioxide (Compound 047)

Step 1: Preparation of 8-((tert-butyldimethylsilyl)oxy)octanoic acid

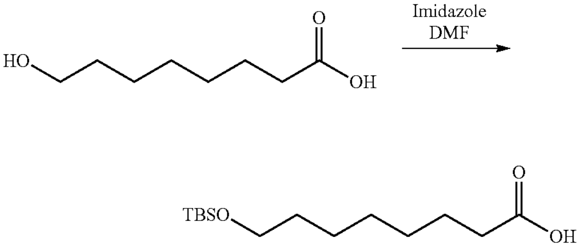

8-hydroxyoctanoic acid (1.0 g, 6.25 mmol) was dissolved in DMF (10 mL) and imidazole was added (1.0 g, 15.0 mmol) followed by tert-butyldimethylsilyl chloride (1.12 g, 8.125 mmol), and the reaction mixture was then stirred at room temperature for 30 min. The mixture was concentrated under reduced pressure, $H_2O$ was added, and the mixture was extracted with ethyl acetate (3x30 mL). The organic layers were combined and dried over sodium sulphate. The desiccant was removed by filtration and the solvent evaporated to give 8-((tert-butyldimethylsilyl)oxy)octanoic acid as a white solid (1.1 g, 64.21%), which was used directly in the next step.

Compound 047

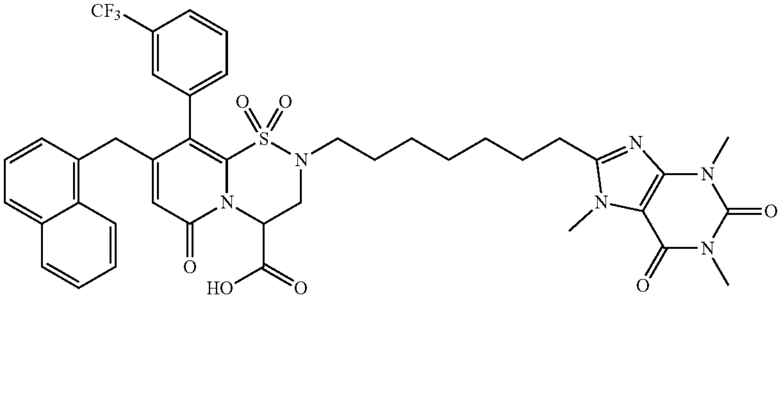

Step 2: Preparation of N-(6-amino-1,3-dimethyl-2,4-dioxo-1,2,3,4-tetrahydropyrimidin-5-yl)-8-((tert-butyldimethylsilyl)oxy)octanamide

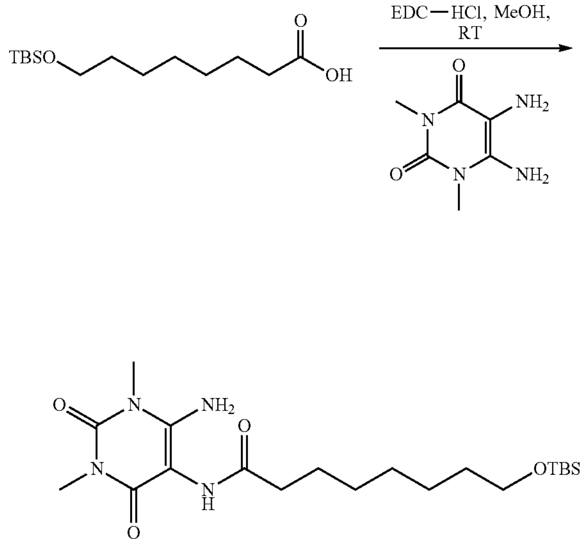

8-((tert-butyldimethylsilyl)oxy)octanoic acid (1.19 g, 4.014 mmol) and 5,6-diamino-1,3-dimethylpyrimidine-2,4(1H,3H)-dione (0.7 g, 4.014 mmol) were dissolved in MeOH (10 mL), EDC-HCl (1.07 g, 5.61 mmol) was added in one portion and the mixture was stirred for 16 h at room temperature. The reaction mixture was concentrated under reduced pressure, then quenched with water (30 mL) and extracted with DCM (3x30 mL). The organic layer was dried over sodium sulphate and concentrated under reduced pressure. The crude product was purified using column chromatography eluting with 3% methanol in DCM to give N-(6-amino-1,3-dimethyl-2,4-dioxo-1,2,3,4-tetrahydropyrimidin-5-yl)-8-((tert-butyldimethylsilyl)oxy)octanamide as a brown solid (1.1 g, 64.34%) LCMS (Method-C3): 92.48% (RT: 1.845, 268.0 nm) (MS: ESI+ve 427.7 [M+H]).

Step 3: Preparation of 8-(7-hydroxyheptyl)-1,3-dimethyl-3,7-dihydro-1H-purine-2,6-dione

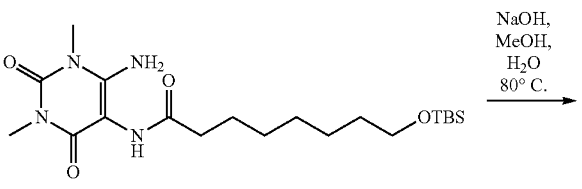

-continued

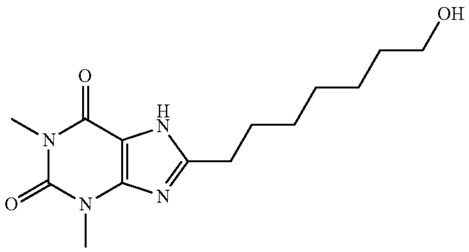

N-(6-amino-1,3-dimethyl-2,4-dioxo-1,2,3,4-tetrahydropyrimidin-5-yl)-8-((tert-butyl dimethyl silyl)oxy)octanamide (1.1 g, 2.58 mmol)) was dissolved in MeOH (5 ml). 10% aqueous NaOH solution (1.8 mL) was added, and the mixture was stirred for 16 h at 80° C. The solution was cooled to room temperature and 1N aqueous HCl (5 mL) was added, and the mixture was stirred for 15 min at 40° C. The pH was adjusted to 6-7 by adding aq. sodium bicarbonate solution (20 mL) and the solvent was removed under reduced pressure. The residue was suspended in water (30 mL) and extracted with ethyl acetate (3x30 mL). The organic layer was dried over sodium sulphate and concentrated under reduced pressure to give 8-(7-hydroxyheptyl)-1,3-dimethyl-3,7-dihydro-1H-purine-2,6-dione as a white solid (0.450 g, 59.29%) LCMS (Method-$C_3$): 99.13% (RT: 1.320, 275.0 nm) (MS: ESI+ve 295.3 [M+H]).

Step 4: Preparation of 8-(7-hydroxyheptyl)-1,3,7-trimethyl-3,7-dihydro-1H-purine-2,6-dione

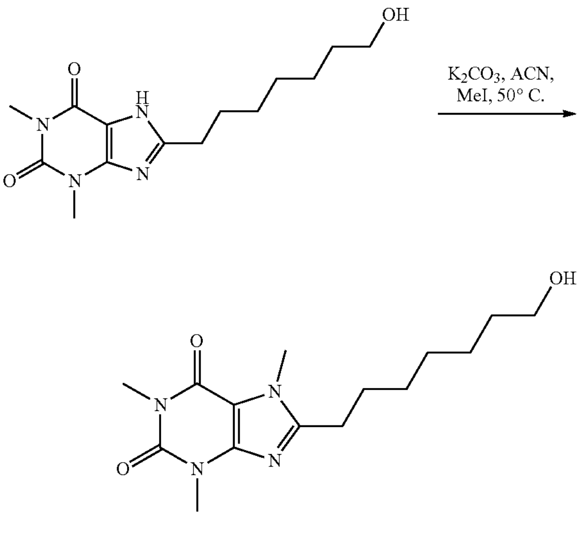

8-(7-hydroxyheptyl)-1,3-dimethyl-3,7-dihydro-1H-purine-2,6-dione (0.45 g, 1.530 mmol) was dissolved in anhydrous acetonitrile (5 mL). $K_2CO_3$ (0.823 g, 5.969 mmol) was added followed by methyl iodide (0.36 mL, 5.969 mmol). The reaction vial was sealed and heated to 50° C. for 16 h. The reaction mixture was allowed to cool to room temperature and water (10 mL) was added. The mixture was extracted with ethyl acetate (3×20 mL). The organic layers were then combined and dried over sodium sulphate. The solvent was removed under reduced pressure and the crude was purified using column chromatography eluting with 2% Methanol in DCM to give 8-(7-hydroxyheptyl)-1,3,7-trimethyl-3,7-dihydro-1H-purine-2,6-dione as a white solid (0.35 g, 74.24%) LCMS (Method-C): 99.28% (RT: 1.385, 275.0 nm) (MS: ESI+ve 309.3 [M+H]).

Step 5: Preparation of 8-(7-bromoheptyl)-1,3,7-trimethyl-3,7-dihydro-1H-purine-2,6-dione

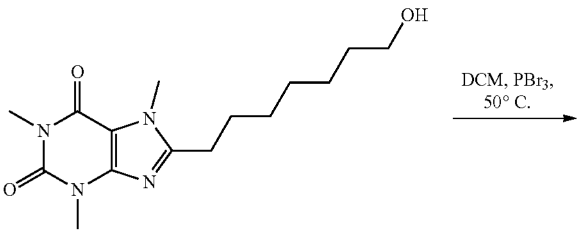

-continued

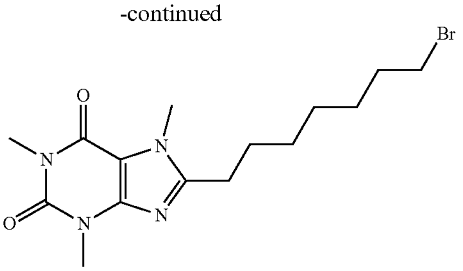

8-(7-hydroxyheptyl)-1,3,7-trimethyl-3,7-dihydro-1H-purine-2,6-dione (0.35 g, 1.136 mmol) was dissolved in DCM (5 mL). After cooling to 0° C., $PBr_3$ (0.22 mL, 2.272 mmol) was added dropwise. The reaction vial was sealed and heated to 50° C. for 16 h. The reaction mixture was cooled to room temperature and water (10 mL) was added. The mixture was extracted with ethyl acetate (3×20 mL) and the organic layers were combined and dried over sodium sulphate. The solvent was removed under reduced pressure and the crude product was purified using column chromatography eluting with 2% methanol/DCM to give 8-(7-bromoheptyl)-1,3,7-trimethyl-3,7-dihydro-1H-purine-2,6-dione as an orange solid (0.130 g, 30.85%) LCMS (Method-C3): 96.90% (RT: 1.670, 275.0 nm) (MS: ESI+ve 373.0 [M+H]).

Step 6: Preparation of methyl 8-(naphthalen-1-ylmethyl)-6-oxo-9-(3-(trifluoromethyl) phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylate 1,1-dioxide

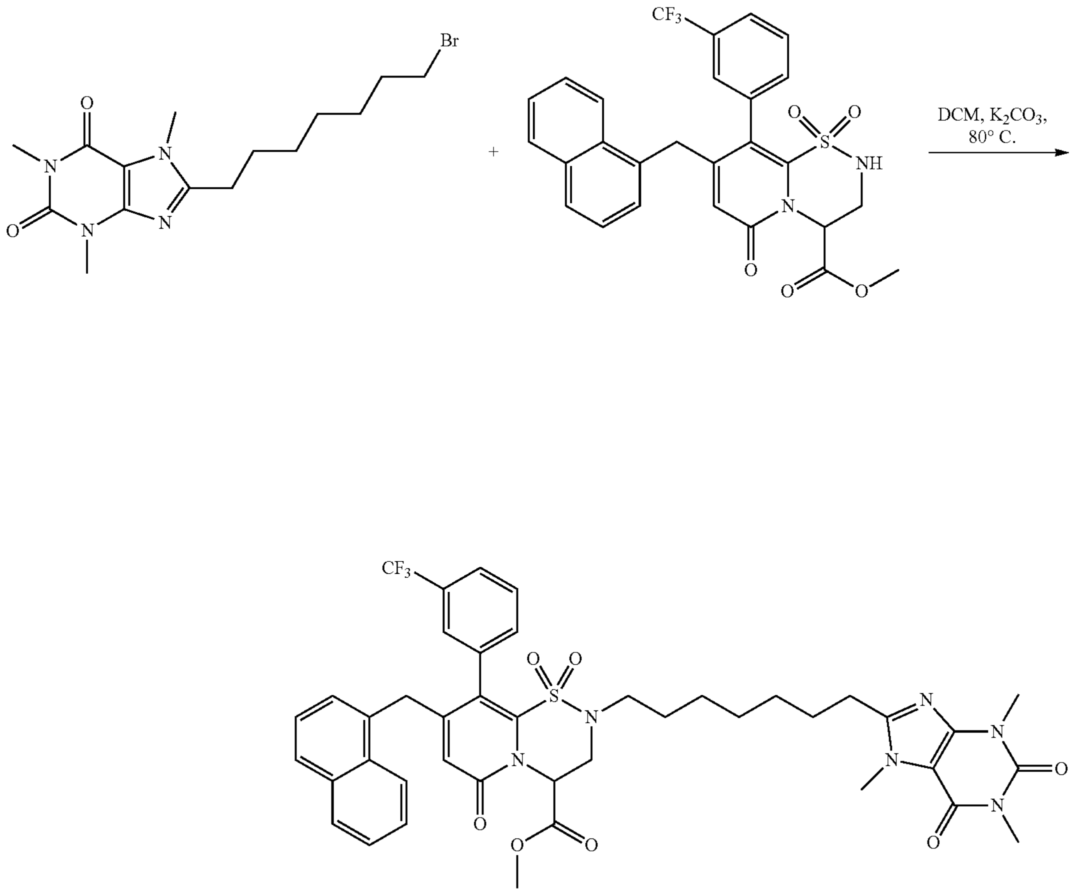

Methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.127 g, 0.2343 mmol) and 8-(7-bromoheptyl)-1,3,7-trimethyl-3,7-dihydro-1H-purine-2,6-dione (0.130 g, 0.3514 mmol) were dissolved in DMF (3 mL) and potassium carbonate was added (0.050 g, 0.3514 mmol). The reaction mixture was stirred at 80° C. for 1 h. The mixture was quenched with ice water and extracted with ethyl acetate (3×15 mL). The organic layers were combined and dried over sodium sulphate to give methyl 8-(naphthalen-1-ylmethyl)-6-oxo-9-(3-(trifluoromethyl)phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylate 1,1-dioxide as a brown solid (0.210 g, crude). LCMS (Method-C3): 48.86% (RT: 2.22, 275.0 nm) (MS: ESI+ve 833.8 [M+H]).

Step 7: Preparation of 8-(naphthalen-1-ylmethyl)-6-oxo-9-(3-(trifluoromethyl)phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylic acid 1,1-dioxide (Compound 047)

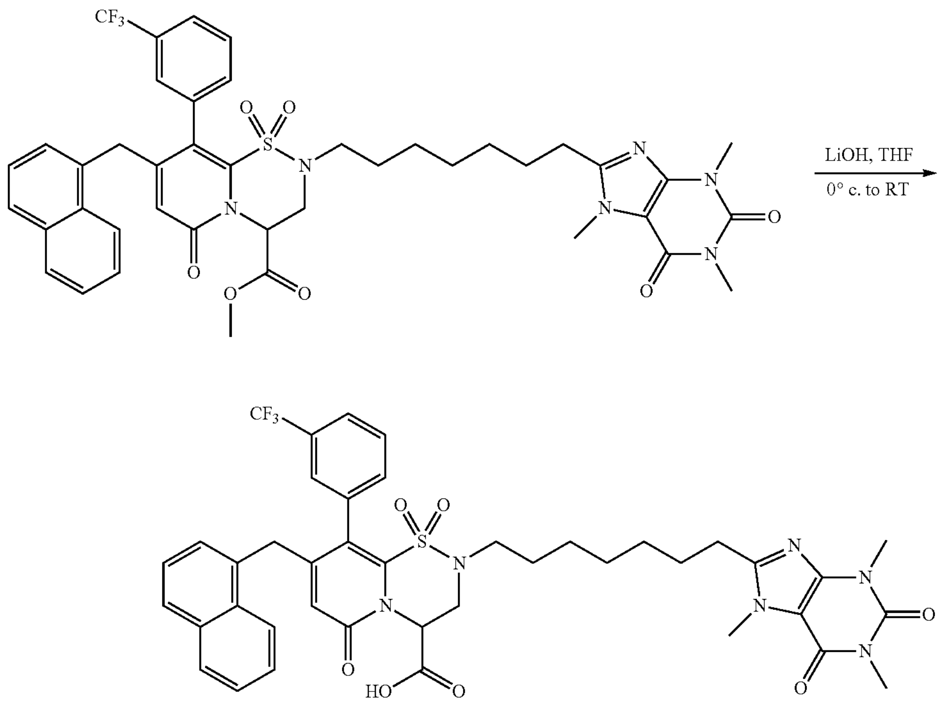

Compound 047

Methyl 8-(naphthalen-1-ylmethyl)-6-oxo-9-(3-(trifluoromethyl)phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylate 1,1-dioxide (0.210 g, 0.2524 mmol) was dissolved in THF:$H_2O$ (10 mL, 1:1) at room temperature. LiOH (0.033 g, 0.7572 mmol) was added at 0° C. and the mixture was stirred at room temperature for 4 h. The mixture was concentrated and cold water (10 mL) and 1N aqueous HCl solution (10 mL) were added. The resulting precipitate was collected by filtration and dried under vacuum. The crude product was purified using Prep HPLC Method 1 to give 8-(naphthalen-1-ylmethyl)-6-oxo-9-(3-(trifluoromethyl)phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylic acid 1,1-dioxide. (Compound 047) as an off white solid (0.106 g, 26.97%) LCMS (Method-C3): 100% (RT: 1.862, 220.0 nm) (MS: ESI+ve 819.5 [M+H]). $^1$H NMR: (400 MHz, DMSO) δ ppm: 1.22-1.64 (m, 10H), 2.69-2.75 (t, J=15.6 Hz, 2H), 3.14 (s, 2H), 3.22 (s, 3H), 3.34-3.39 (d, J=19.6 Hz, 3H), 3.82 (s, 3H), 3.89-3.94 (d, J=20.4 Hz, 2H), 4.07-4.21 (m, 2H), 5.14 (s, 1H), 6.07-6.11 (d, J=16 Hz, 1H), 7.25 (s, 1H), 7.45-7.50 (m, 3H), 7.55-7.72 (m, 5H), 7.83-7.85 (d, J=7.6 Hz, 1H), 7.91-7.93 (d, J=7.6 Hz, 1H), 13.69 (s, 1H)

Example 64

Synthesis of 8-(naphthalen-1-ylmethyl)-6-oxo-9-(3-(trifluoromethyl)phenyl)-2-(6-(1,3,7-trimethyl-2,6-dioxo-2,3,6,7-tetrahydro-1H-purin-8-yl)hexyl)-3,4-dihydro-2H,6H-pyrido[1,2-e][1,2,5]thiadiazine-4-carboxylic acid 1,1-dioxide (Compound 046)

Compound 046

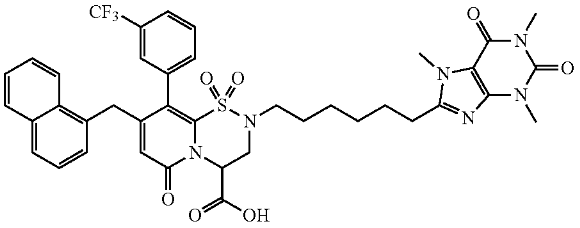

Prepared by a procedure similar to that reported for 8-(naphthalen-1-ylmethyl)-6-oxo-9-(3-(trifluoromethyl)phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylic acid 1,1-dioxide. (Compound 047), substituting 7-((tert-butyldimethylsilyl)oxy)heptanoic acid in step 2. The crude product was purified using Prep HPLC Method 3 to give 8-(naphthalen-1-ylmethyl)-6-oxo-9-(3-(trifluoromethyl)phenyl)-2-(6-(1,3,7-trimethyl-2,6-dioxo-2,3,6,7-tetrahydro-1H-purin-8-yl)hexyl)-3,4-dihydro-2H,6H-pyrido[1,2-e][1,2,5]thiadiazine-4-carboxylic acid 1,1-dioxide (Compound 046) as an off white solid (0.014 g, 12.95%).LCMS (Method-C3): 100% (RT: 1.828, 220.0 nm) (MS: ESI+ve 805.43 [M+H]). $^1$H NMR: (400 MHz, DMSO) δ ppm: 1.18-1.31 (m, 5H), 1.45 (s, 2H), 1.62-1.64 (d, J=6.4 Hz, 2H), 2.62-2.72 (m, 2H), 3.17 (s, 2H), 3.21 (s, 3H), 3.81-3.87 (m, 6H), 4.11 (s, 2H), 4.93 (s, 1H), 6.01-6.03 (d, J=8.8 Hz, 1H), 7.11 (s, 2H), 7.24 (s, 1H), 7.45-7.53 (m, 2H), 7.59-7.71 (m, 5H), 7.83-7.84 (d, J=4.8 Hz, 1H), 7.90-7.92 (d, J=8 Hz, 1H).

Example 65

Synthesis of 8-(naphthalen-1-ylmethyl)-6-oxo-9-(3-(trifluoromethyl)phenyl)-2-(5-(1,3,7-trimethyl-2,6-dioxo-2,3,6,7-tetrahydro-1H-purin-8-yl)pentyl)-3,4-dihydro-2H,6H-pyrido[1,2-e][1,2,5]thiadiazine-4-carboxylic acid 1,1-dioxide (Compound 045)

Compound 045

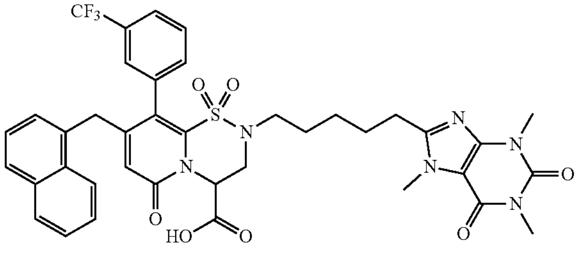

Prepared by a procedure similar to that reported for 8-(naphthalen-1-ylmethyl)-6-oxo-9-(3-(trifluoromethyl)phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylic acid 1,1-dioxide (Compound 047), substituting 6-((tert-butyldimethylsilyl)oxy)hexanoic acid in step 2. The crude product was purified using Prep HPLC Method 1 to give 8-(naphthalen-1-ylmethyl)-6-oxo-9-(3-(trifluoromethyl)phenyl)-2-(5-(1,3,7-trimethyl-2,6-dioxo-2,3,6,7-tetrahydro-1H-purin-8-yl)pentyl)-3,4-dihydro-2H,6H-pyrido[1,2-e][1,2,5]thiadiazine-4-carboxylic acid 1,1-dioxide (Compound 045) as an off white solid (0.106 g, 26.97%). LCMS (Method-$C_3$): 100% (RT: 1.862, 223.0 nm) (MS: ESI+ve 791.6 [M+H]). $^1$H NMR: (400 MHz, DMSO) δ ppm: 1.29-1.31 (d, J=6.8 Hz, 2H), 1.51-1.53 (d, J=6.4 Hz, 2H), 1.62-1.66 (t, J=6.8 Hz, 2H), 2.69-2.72 (t, J=7.2 Hz, 2H), 3.10-3.15 (m, 2H), 3.22 (s, 3H), 3.34-3.39 (d, J=18 Hz, 4H), 3.81 (s, 3H), 3.91 (s, 2H), 4.08-4.18 (t, 2H), 5.17 (s, 1H), 6.09-6.13 (d, 1H), 7.24-7.25 (d, J=6.4 Hz, 1H), 7.44-7.51 (m, 3H), 7.56-7.72 (m, 5H), 7.84-7.85 (d, J=5.96 Hz, 1H), 7.91-7.93 (d, J=7.6 Hz, 1H).

Example 66

Synthesis of 8-(naphthalen-1-ylmethyl)-6-oxo-9-(3-(trifluoromethyl)phenyl)-2-(4-(1,3,7-trimethyl-2,6-dioxo-2,3,6,7-tetrahydro-1H-purin-8-yl)butyl)-3,4-dihydro-2H,6H-pyrido[1,2-e][1,2,5]thiadiazine-4-carboxylic acid 1,1-dioxide (Compound 044)

Compound 044

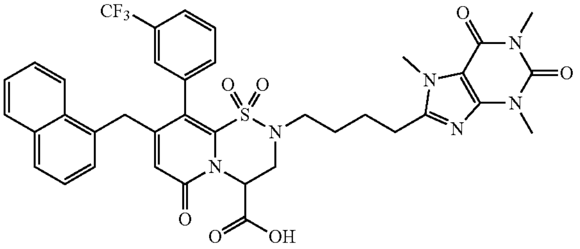

Prepared by a procedure similar to that reported for 8-(naphthalen-1-ylmethyl)-6-oxo-9-(3-(trifluoromethyl)phenyl)-2-(7-(1,3,7-trimethyl-2,6-dioxo-2,3,6,7-tetrahydro-1H-purin-8-yl)heptyl)-3,4-dihydro-2H,6H-pyrido[1,2-e][1,2,5]thiadiazine-4-carboxylic acid 1,1-dioxide. (Compound 047), substituting 5-((tert-butyldimethylsilyl)oxy)pentanoic acid (WO2018045464) in step 2. The crude product was purified using Prep HPLC Method 1 to give 8-(naphthalen-1-ylmethyl)-6-oxo-9-(3-(trifluoromethyl)phenyl)-2-(4-(1,3,7-trimethyl-2,6-dioxo-2,3,6,7-tetrahydro-1H-purin-8-yl)butyl)-3,4-dihydro-2H,6H-pyrido[1,2-e][1,2,5]thiadiazine-4-carboxylic acid 1,1-dioxide dioxide as a white solid (Compound 044) (0.020 g, 9.26%). LCMS (Method-C3): 100% (RT 1.77, 220 nm) (MS: ESI+ve 777.5[M+H]). $^1$H NMR: (400 MHz, DMSO-$d_6$) δ ppm: 1.59 (m, 4H), 2.70 (s, 2H), 3.20 (s, 6H), 3.71 (s, 3H), 3.94 (s, 2H), 4.17 (m, 2H), 5.16 (m, 1H), 6.08-6.11 (d, J=12 Hz, 1H), 7.23-7.24 (d, J=4 Hz, 1H), 7.45-7.49 (m, 3H), 7.61-7.71 (m, 5H), 7.83-7.84 (d, J=4 Hz, 1H), 7.90-7.90 (d, J=8 Hz, 1H).

Example 67

Synthesis of 2,2'-(hexane-1,6-diyl)bis(8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide) (Compound 043)

Compound 043

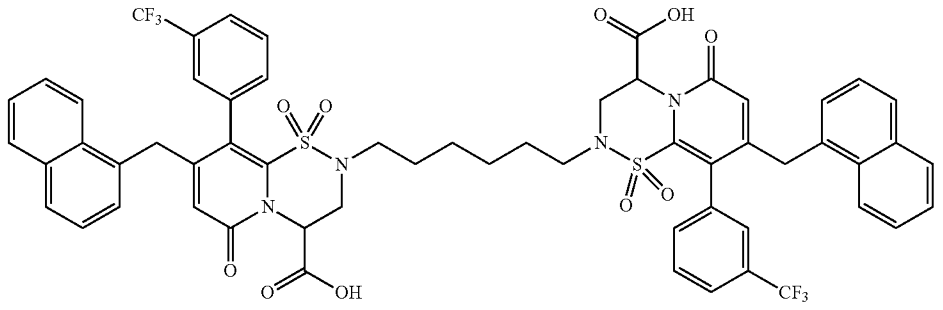

Step 1: preparation of methyl 2-(6-bromohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

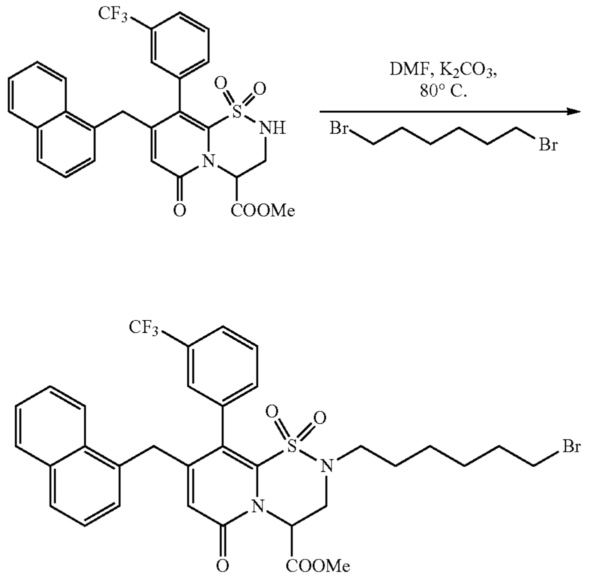

Methyl 8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylate 1,1-dioxide (0.5 g, 0.921 mmol) was dissolved in DMF (5 mL). Potassium carbonate (0.190 g, 0.138 mmol) was added followed by 1,6-dibromohexane (0.224 g, 0.921 mmol). The reaction mixture was stirred at 80° C. for 1 h in a sealed tube. The reaction mixture was diluted with water (50 mL) and extracted with ethyl acetate (3×50 mL). The organic layer was dried over sodium sulphate and concentrated under reduced pressure to give methyl 2-(6-bromohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a brown solid (0.55 g, 84.58%).LCMS (Method-C3): 87.43% (RT 2.280, 226.0 nm) (MS: ESI+ve 707.38 [M+H]).

Step 2: preparation of methyl 2-(6-bromohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

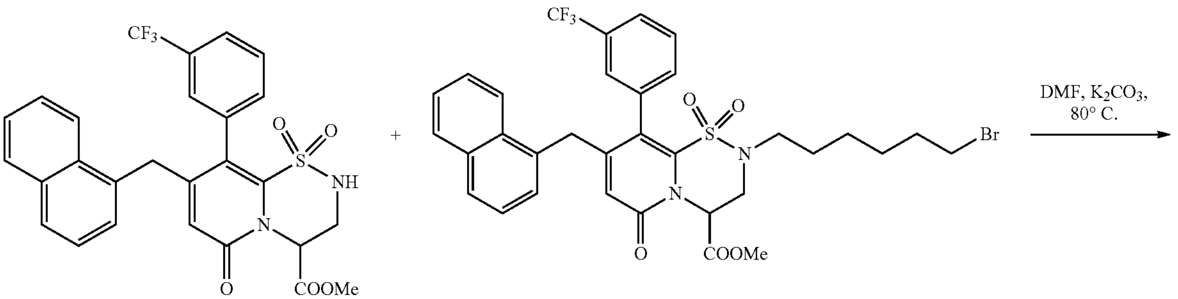

-continued

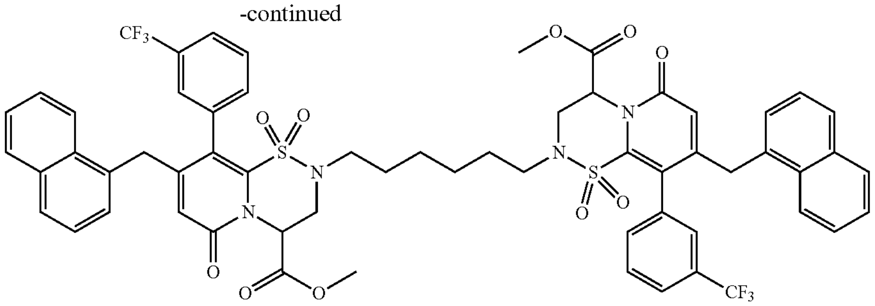

Methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.2 g, 0.368 mmol) was dissolved in DMF (5 mL). Potassium carbonate (0.076 g, 0.552 mmol) was added and after 5 min methyl 2-(6-bromohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.286 g, 0.405 mmol) was added. The reaction mixture was stirred at 80° C. for 1 h in a sealed tube. The reaction mixture was diluted with water (50 mL) and extracted with ethyl acetate (3×50 mL). The organic layer was dried over sodium sulphate and concentrated under reduced pressure to give dimethyl 2,2'-(hexane-1,6-diyl)bis(8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide) as a brown solid (0.45 g, 95.12%).LCMS (Method-C3): 81.98% (RT 2.439, 224.0 nm) (MS: ESI+ve 1167.63 [M+H]).

Step-3: Preparation of 2,2'-(hexane-1,6-diyl)bis(8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide) (Compound 043)

Dimethyl 2,2'-(hexane-1,6-diyl)bis(8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide) (0.45 g, 0.385 mmol) was dissolved in THF:$H_2O$ (1:1, 8 mL) at RT then LiOH—$H_2O$ (0.097 g, 2.31 mmol) was added and stirred at room temperature for 5 h. The mixture was concentrated and the residue was suspended in water (10 mL) and 1N HCl (3-4 mL). The resulting precipitate was collected by filtration and dried under vacuum. The crude product was purified using Prep HPLC Method 1 to give 2,2'-(hexane-1,6-diyl)bis(8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide) (Compound 043), as a mixture of meso compound (RS) (SR); (SS) and (RR) isomers, as an off white solid (0.106 g, 24.14%). LCMS (Method-$C_3$): 100% (RT 2.393, 225.0 nm) (MS: ESI−ve 1138.18 [M−H]). $^1H$ NMR: (400 MHz, DMSO) δ ppm: 1.13 (s, 4H), 1.40 (s, 4H), 3.07 (s, 4H), 3.88-3.93 (m, 4H), 4.06-4.12 (m, 4H), 5.11 (s, 2H), 6.05-6.09 (d, J=14.4 Hz, 2H), 7.23-7.91 (m, 22H), 13.66 (s, 2H).

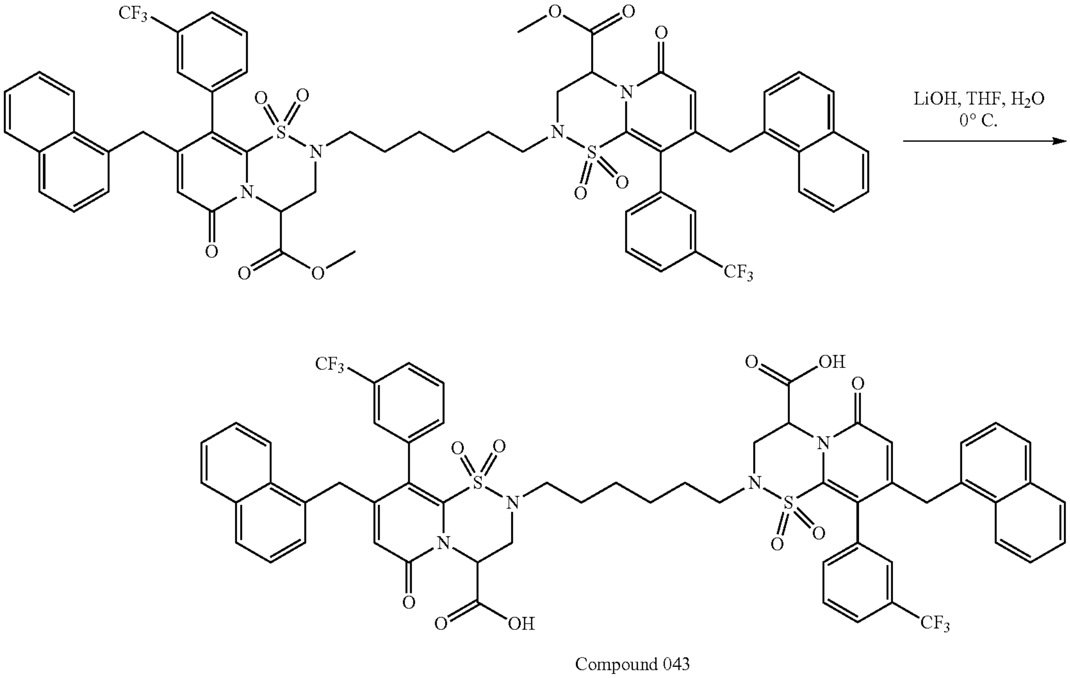

Compound 043

Example 68

Synthesis of 2-(2-amino-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 028)

Compound 028

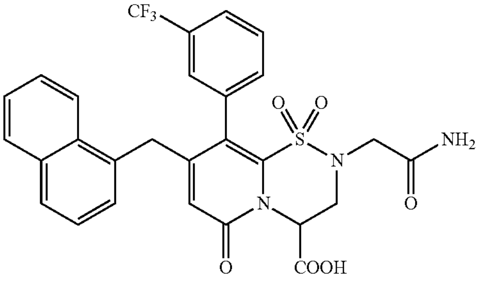

Prepared by a procedure similar to that described for 2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 015)(Racemic) substituting 2-bromoacetamide in step 1. The crude product was purified using Prep HPLC Method 1 to give 2-(2-amino-2-oxoethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 028), as an off white solid (0.008 g, 8.19%). LCMS (Method-J): 100% (RT 4.847, 202.4 nm) (MS: ESI+ve 586.2 [M+H]). $^1$H NMR: (400 MHz, DMSO) δ ppm: 3.74-3.78 (m, 1H), 3.86-3.89 (t, 3H), 4.08-4.11 (m, 1H), 4.18-4.21 (m, 1H), 5.32 (s, 1H), 6.07-6.10 (d, J=9.6 Hz, 1H), 7.19-7.25 (m, 2H), 7.43-7.65 (m, 9H), 7.82-7.84 (d, J=8.4 Hz, 1H), 7.90-7.92 (d, J=7.6 Hz, 1H), 13.51 (s, 1H).

Example 69

Synthesis of 2-(4-(methylamino)-4-oxobutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 037)

Compound 037

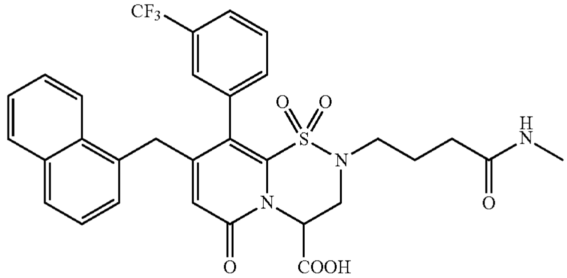

Step 1: preparation of methyl 2-(4-(tert-butoxy)-4-oxobutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

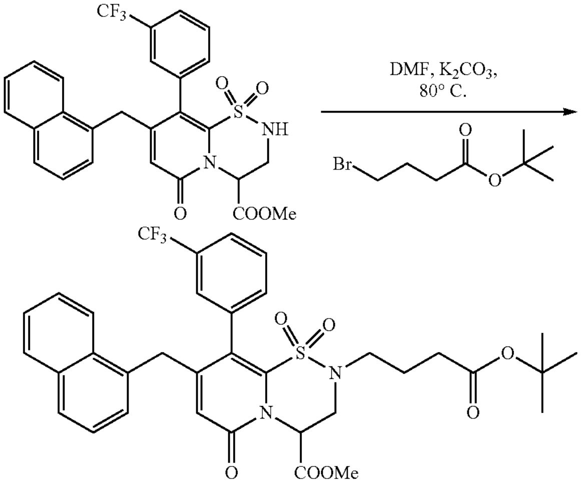

Methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.4 g, 0.737 mmol) was dissolved in DMF (5 mL). Potassium carbonate (0.152 g, 1.10 mmol) was added followed by tert-butyl 4-bromobutanoate (0.164 g, 0.737 mmol). The reaction mixture was heated at 80° C. for 1 h. The mixture was poured into crushed ice and the resulting precipitate was collected by filtration and dried to give crude product methyl 2-(4-(tert-butoxy)-4-oxobutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.410 g, 81.21%).LCMS (Method-C3): 90.23% (RT 2.167, 225.0 nm) (MS: ESI−ve 683.56 [M−H]).

Step-2: Preparation of 4-(4-(methoxycarbonyl)-8-(naphthalen-1-ylmethyl)-1,1-dioxido-6-oxo-9-(3-(trifluoromethyl)phenyl)-3,4-dihydro-2H,6H-pyrido[1,2-e][1,2,5]thiadiazin-2-yl)butanoic acid

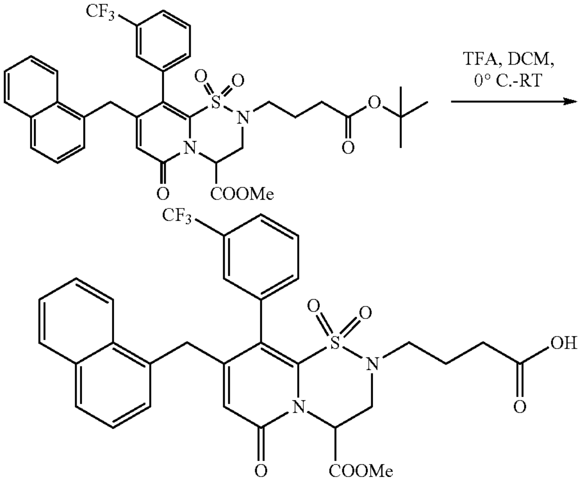

Methyl 2-(4-(tert-butoxy)-4-oxobutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.410 g, 0.598 mmol) was dissolved in DCM (5 mL) at room temperature. Trifluoroacetic acid (0.409 g, 3.59 mmol) was added at 0° C. and the mixture was stirred at room temperature for 16 h. The mixture was concentrated under reduced pressure then concentrated from DCM (3×10 mL) to give 4-(4-(methoxycarbonyl)-8-(naphthalen-1-ylmethyl)-1,1-dioxido-6-oxo-9-(3-(trifluoromethyl)phenyl)-3,4-dihydro-2H,6H-pyrido[1,2-e][1,2,5]thiadiazin-2-yl)butanoic acid as a yellow solid (0.35 g, 92.99%) LCMS (Method-C3): 88.00% (RT 1.861, 225.0 nm) (MS: ESI+ve 629.33 [M+H]).

Step-3: Preparation of methyl 2-(4-(methylamino)-4-oxobutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate1,1-dioxide

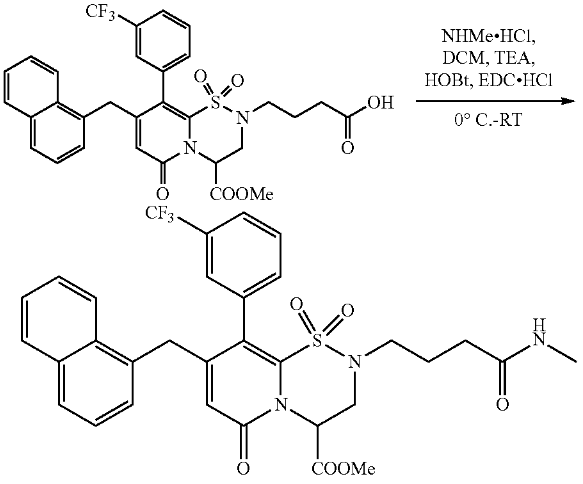

4-(4-(methoxycarbonyl)-8-(naphthalen-1-ylmethyl)-1,1-dioxido-6-oxo-9-(3 (trifluoromethyl)phenyl)-3,4-dihydro-2H,6H-pyrido[1,2-e][1,2,5]thiadiazin-2-yl)butanoic acid (0.25 g, 0.398 mmol) was dissolved in dichloromethane (5 mL). Methylamine hydrochloride (0.040 g, 0.597 mmol) was added at 0° C. and the mixture was stirred for 10 min. Triethyl amine (0.216 mL, 1.55 mmol) was added dropwise with stirring for an additional 10 min. EDC-HCl (0.114 g, 0.597 mmol) was added to the reaction mixture followed by HOBT (0.080 g, 0.597 mmol), the reaction mixture was stirred at room temperature for 16 h, quenched in $H_2O$ and extracted with DCM (3×20 mL). The organic layer was dried over $Na_2SO_4$ and concentrated under reduced pressure. The crude product was purified using column chromatography eluting with 6% methanol in DCM to give methyl 2-(4-(methylamino)-4-oxobutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as an off white solid (0.2 g, 78.37%). LCMS (Method-C3): 94.86% (RT 1.771, 230.0 nm) (MS: ESI+ve 642.43 [M+H])

Step-4: Preparation of 2-(4-(methylamino)-4-oxobutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 037)

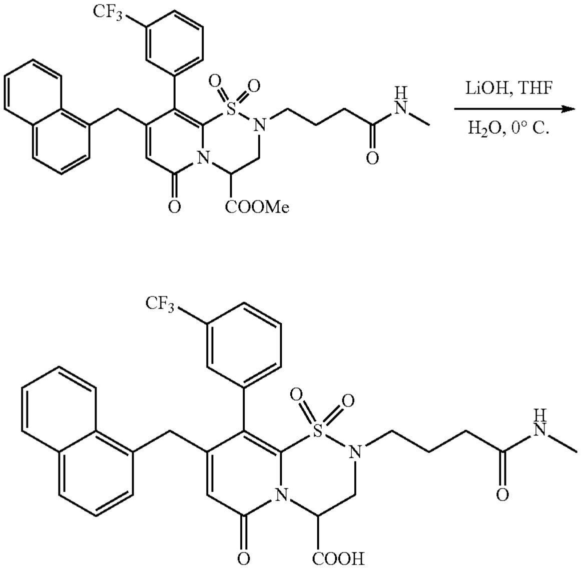

Compound 037

Methyl 2-(4-(methylamino)-4-oxobutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.180 g, 0.280 mmol) was dissolved in THF: $H_2O$ (6 mL, 1:1) at room temperature. LiOH (0.035 g, 0.842 mmol) was added at 0° C., and stirred for 5 h. The reaction mixture was concentrated then 0.1 N aqueous HCl solution (3 mL) was added. The resulting solid was collected by filtration, washed with $H_2O$ (5 mL) and dried under vacuum. The crude was purified using Prep HPLC Method 1 to give 2-(4-(methylamino)-4-oxobutyl)-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide (Compound 037), as an off white solid (0.039 g, 22.15%). LCMS (Method-C3): 100% (RT: 4.768, 224.0 nm, 230.0 nm) (MS: ESI+ve 628.2 [M+H]). $^1$H NMR: (400 MHz, DMSO) δ ppm: 1.68 (s, 2H), 2.00-2.04 (t, J=7.2 Hz, 2H), 2.53 (s, 3H), 3.14-3.15 (t, J=4.0 Hz, 2H), 3.89 (s, 2H), 4.06-4.21 (m, 2H), 5.12 (s, 1H), 6.07-6.10 (d, J=13.2 Hz, 1H), 7.24-7.25 (d, J=6.4 Hz, 1H), 7.43-7.74 (m, 9H), 7.84-7.85 (d, J=5.6 Hz, 1H), 7.91-7.93 (d, J=8.0 Hz, 1H), 13.70 (s, 1H).

Example 70

Synthesis of 2-(3-carboxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 029)

Compound 029

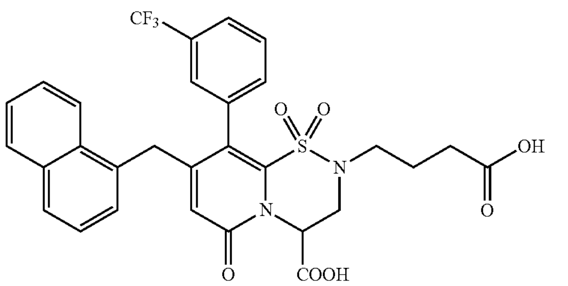

Step-1: Preparation of 2-(3-carboxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 029)

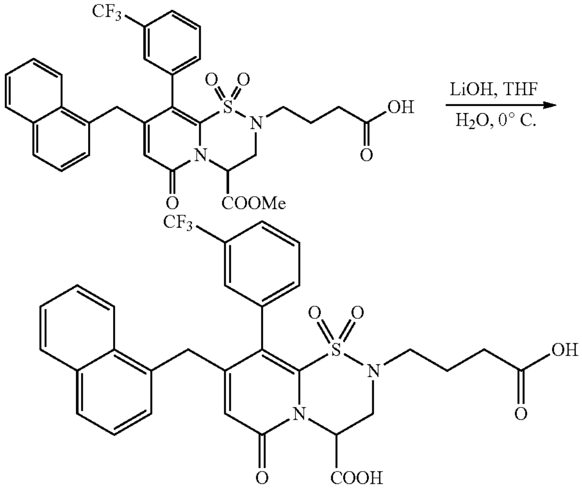

Compound 029

4-(4-(methoxycarbonyl)-8-(naphthalen-1-ylmethyl)-1,1-dioxido-6-oxo-9-(3-(trifluoromethyl)phenyl)-3,4-dihydro-2H,6H-pyrido[1,2-e][1,2,5]thiadiazin-2-yl)butanoic acid (0.1 g, 0.159 mmol) was dissolved in THF:$H_2O$ (6 mL, 1:1) at room temperature. LiOH (0.020 g, 0.477 mmol) was added at 0° C. and stirred at RT for 5 h. The reaction mixture was concentrated then diluted with 0.1 N HCl (3 mL). The resulting solid was collected by filtration and rinsed with $H_2O$ (5 mL) then dried under vacuum. The crude product was purified using Prep HPLC Method 1 to give 2-(3-carboxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 029) as an off white solid (0.047 g, 48.07%). LCMS (Method-C3): 100% (RT: 1.724, 202.0 nm, 225.0 nm) (MS: ESI+ve 615.50 [M+H]). $^1H$ NMR: (400 MHz, DMSO) δ ppm: 1.69 (s, 2H), 2.17-2.21 (t, J=7.2 Hz, 2H), 3.15-3.19 (t, J=6.8 Hz, 2H), 3.90 (s, 2H), 4.06-4.17 (m, 2H), 5.18 (s, 1H), 6.08-6.12 (d, J=14.4 Hz, 1H), 7.24-7.26 (d, J=7.6 Hz, 1H), 7.44-7.74 (m, 8H), 7.84-7.86 (d, J=6.8 Hz, 1H) 7.92-7.94 (d, J=7.6 Hz, 1H).

Example 71

Synthesis of 2-(5-(methylamino)-5-oxopentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 038)

Compound 038

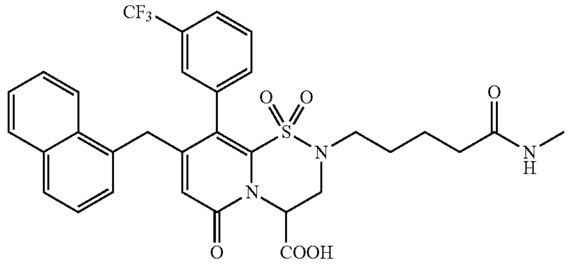

Prepared by a procedure similar to that reported for 2-(4-(methylamino)-4-oxobutyl)-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide (Compound 037) substituting 5-bromopentanoate in step 1 to give 2-(5-(methylamino)-5-oxopentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 038) (0.105 g, 89.21%) as a white solid, LCMS (Method-C3): 100% (RT 1.724, 220.0 nm) (MS: ESI+ve 642.55 [M+H]). $^1H$ NMR: (400 MHz, DMSO) δ ppm: 1.23 (s, 2H), 1.41 (s, 4H), 2.00 (s, 3H), 3.10 (s, 2H), 3.89 (s, 2H), 4.05-4.16 (m, 2H), 5.16 (s, 1H), 6.06-6.10 (d, J=13.2 Hz, 1H), 7.22-7.24 (d, J=6.4 Hz, 1H), 7.43-7.70 (m, 9H), 7.82-7.84 (d, J=8.8 Hz, 1H) 7.90-7.92 (d, J=7.2 Hz, 1H).

Example 72

Synthesis of 2-(4-carboxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 039)

Compound 039

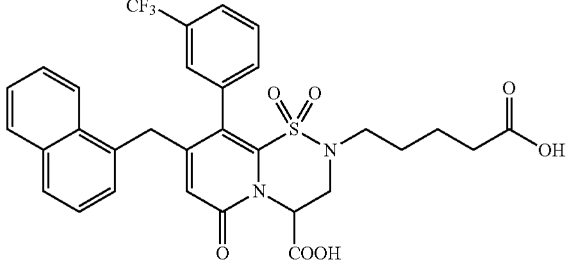

Prepared by a procedure similar to that reported for 2-(3-carboxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 029) substituting 5-(4-(methoxycarbonyl)-8-(naphthalen-1-ylmethyl)-1,1-dioxido-6-oxo-9-(3-(trifluoromethyl)phenyl)-3,4-dihydro-2H,6H-pyrido[1,2-e][1,2,5]thiadiazin-2-yl)pentanoic acid in step 1 to give 2-(4-carboxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 039) (0.148 g, 75.65%) as an off white solid, LCMS (Method-C3): 97.47% (RT 1.765, 283.0 nm) (MS: ESI−ve 627.6 [M+H])$^{1}$H NMR: (400 MHz, DMSO) δ ppm: 1.43-1.46 (m, 4H), 2.18 (s, 2H), 3.13 (s, 2H), 3.90 (s, 2H), 4.07-4.20 (m, 2H), 5.17 (s, 1H), 6.07-6.11 (d, J=14.4 Hz, 1H), 7.24-7.25 (d, J=6.8 Hz, 1H), 7.46-7.73 (m, 8H), 7.83-7.85 (d, J=8.0 Hz, 1H), 7.91-7.93 (d, J=7.2 Hz, 1H), 12.06 (bs, 1H), 13.62 (bs, 1H).

Example 72a

Synthesis of 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxamide 1,1-dioxide (Compound 030)

Compound 030

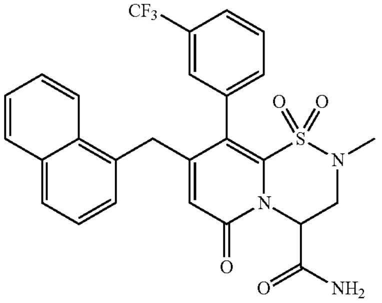

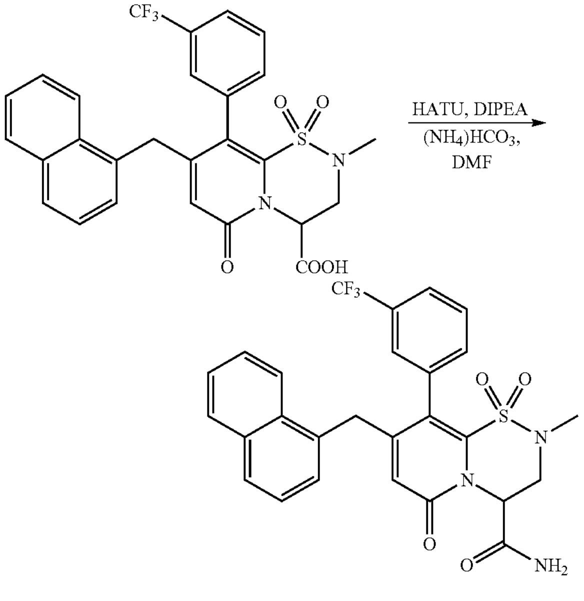

Compound 030

2-Methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (0.150 g, 0.276 mmol) was dissolved in DMF (3 mL). HATU (0.126 g, 0.331 mmol), ammonium bicarbonate (0.0437 g, 0.552 mmol) and DIPEA (0.141 mL, 0.829 mmol) were added sequentially, and the mixture was allowed to stir for 16 h. The reaction was quenched in ice water (20 mL) and extracted with ethyl acetate (3×50 mL). The organic layer was dried over sodium sulphate and concentrated under reduced pressure. The crude product was purified using Prep HPLC Method 6 to give 2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxamide 1,1-dioxide (Compound 030), as an off white solid (0.02 g, 13.36%). LCMS (Method-C3): 100.0% (RT 1.804, 254.0 nm) (MS: ESI+ve 542.36 [M+H]). 1H NMR: (400 MHz, DMSO) δ ppm: 2.86 (s, 3H), 3.89 (s, 2H), 3.97-4.02 (m, 1H), 4.20-4.25 (q, 2H), 4.96-4.98 (t, 1H), 6.04-6.07 (d, J=12.8 Hz, 1H), 7.24-7.26 (d, J=7.2 Hz, 1H), 7.44-7.48 (m, 4H), 7.56-7.73 (m, 4H), 7.83-7.86 (d, J=8.8 Hz, 2H), 7.91-7.93 (d, J=7.6 Hz, 1H).

Example 73

Synthesis of N,2-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxamide 1,1-dioxide (Compound 031)

Compound 031

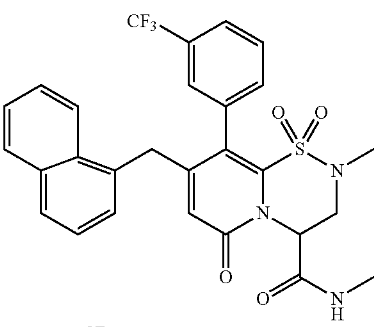

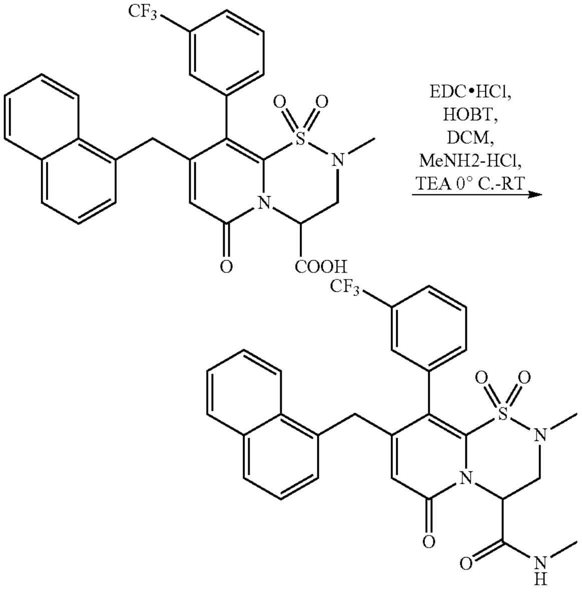

Compound 031

2-Methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (0.2 g, 0.36 mmol) was dissolved in DCM (10 mL) and cooled to 0° C. Methylamine hydrochloride (0.030 g, 0.442 mmol) was added followed by TEA (0.2 mL), EDC-HCl (0.105 g, 0.55 mmol) and HOBT (0.075 g, 0.55 mmol). The reaction mixture was stirred at for 16 h. The reaction was quenched in saturated aqueous $NaHCO_3$ (20 mL) and extracted with 10% MeOH/DCM (3×30 mL). The organic layer was dried over sodium sulphate and concentrated under reduced pressure to give crude product, which was purified by using column chromatography eluting with 0-70% ethyl acetate/hexane. The product was further purified using Prep HPLC Method to give N,2-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxamide 1,1-dioxide (Compound 031), (0.007 g, 3.74%) LCMS (Method-C3): 100% (RT 1.833, 202 nm) (MS: ESI+ve 525.3 [M+H]). $^1$H NMR: (400 MHz, DMSO) δ ppm: 2.61-2.62 (d, J=3.2 Hz, 3H), 2.81 (s, 3H), 3.88 (s, 2H), 3.96-3.97 (d, J=5.6 Hz, 1H), 4.16-4.17 (d, J=5.2 Hz, 1H), 4.96 (s, 1H), 6.03-6.05 (d, J=6.4 Hz, 1H), 7.22-7.23 (d, J=6.8 Hz, 1H), 7.43-7.50 (m, 3H), 7.55-7.70 (m, 5H), 7.82-7.84 (d, J=8 Hz, 1H), 7.90-7.92 (d, J=8 Hz, 1H), 8.30 (s, 1H).

Example 74

Synthesis of N,N-2-trimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxamide 1,1-dioxide (Compound 032)

Compound 032

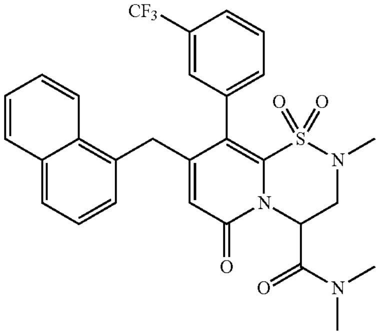

Prepared by a method similar to that reported for N,2-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxamide 1,1-dioxide (Compound 031), substituting dimethylamine. The crude product was purified using Prep HPLC Method to give N,N,2-trimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxamide 1,1-dioxide (Compound 032), (0.007 g, 3.74%) LCMS (Method-C3): 100% (RT 1.833, 202 nm) (MS: ESI+ve 525.3 [M+H]). $^1$H NMR: (400 MHz, DMSO) δ ppm: 2.83-2.85 (t, J=6 Hz, 6H), 3.15 (s, 3H), 3.88-3.90 (d, J=6.8 Hz, 2H), 3.96-3.97 (d, J=6 Hz, 1H), 4.20-4.25 (q, 1H), 5.46-5.47 (d, J=6 Hz, 1H), 6.05 (s, 1H), 7.20-7.23 (t, 1H), 7.42-7.46 (m, 3H), 7.53-7.71 (m, 5H), 7.82-7.84 (d, J=8 Hz 1H), 7.89-7.91 (d, J=8 Hz, 1H).

Example 75

Synthesis of 4-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 042)

Compound 042

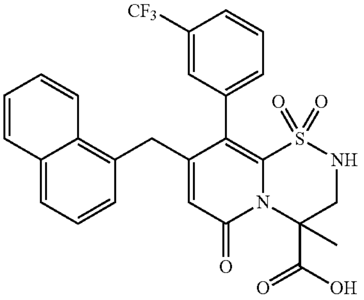

Step-1: Preparation of methyl 2-(4-methoxybenzyl)-4-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

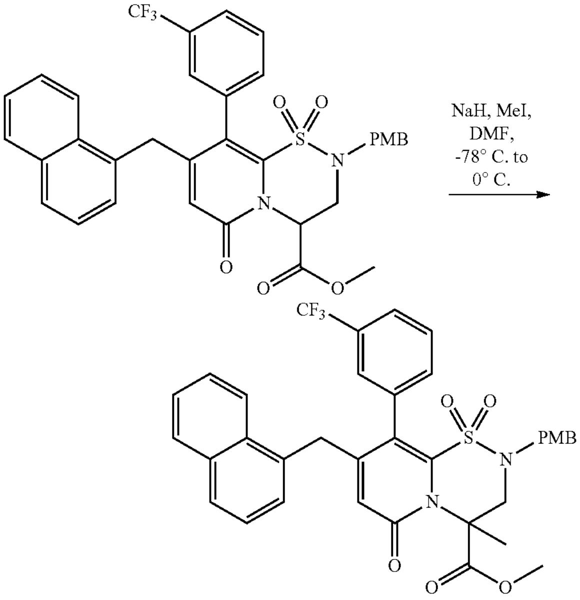

A suspension of sodium hydride (60%)(0.014 g, 0.603 mmol) in dimethylformamide (4 mL) was cooled to −78° C. Methyl 2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.400 g, 0.603 mmol) in DMF (2 mL) was added dropwise. After 15 min, methyl iodide (0.171 g, 1.20 mmol) was added and the mixture was warmed to 0° C. and stirred for 20 min. The reaction was quenched in water (20 mL) and extracted with ethyl acetate (3×20 mL). The organic layer was dried over sodium sulphate and concentrated under reduced pressure to give crude product which was purified by column chromatography eluting with 0-50% ethyl acetate/hexane to give methyl 2-(4-methoxybenzyl)-4-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a yellow solid (0.180 g, 44.07%). LCMS (Method-C3): 94.55% (RT 2.122, 225.0 nm) (MS: ESI+ve 677.66 [M+H]). $^1H$ NMR: (400 MHz, DMSO) δ ppm: 2.28 (s, 3H), 3.70-3.74 (m, 6H), 6.04-6.11 (t, 1H), 6.67-6.69 (d, J=7.6 Hz, 1H), 6.85-6.86 (d, J=6.4 Hz, 2H), 7.05-7.06 (d, J=5.6 Hz, 2H), 7.25-7.26 (m, 1H), 7.42-7.64 (m, 7H), 7.82-7.92 (m, 3H).

Step 2: Preparation of methyl 8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

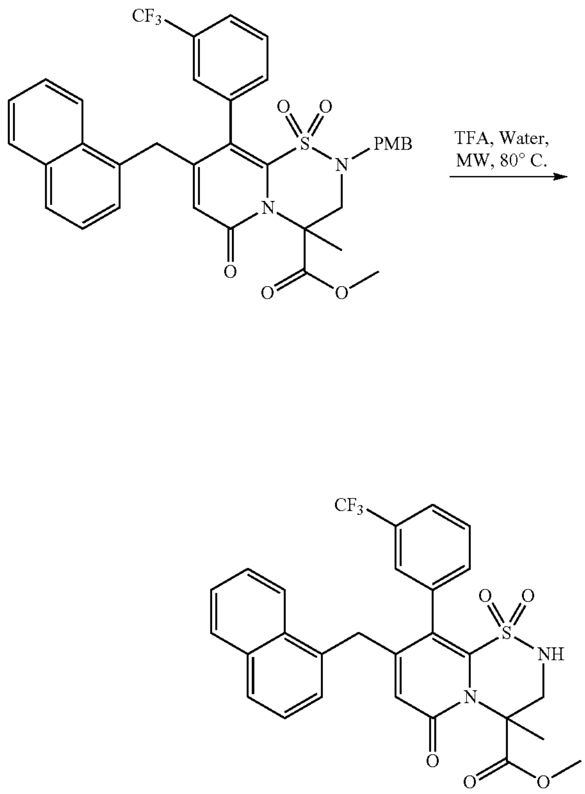

A mixture of methyl 2-(4-methoxybenzyl)-4-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.17 g), TFA (1.28 mL) and water (0.06 mL) was heated in a microwave reactor, under microwave irradiation, at 80° C. for 10 min. The reaction mixture was poured into ice water (20 mL) and sat. aq. sodium bicarbonate (20 mL) was added. The mixture was extracted with ethyl acetate (3×50 mL). The organic layer was dried over sodium sulphate and concentrated under reduced pressure to give methyl 4-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a brown solid (0.16 g, 92.98%), LCMS (Method-C3): 86.04% (RT 1.936, 220.0 nm) (MS: ESI−ve 555.38 [M−H]).

Step 3: Preparation of 2-(6-(methylthio)-4-(naphthalen-1-ylmethyl)-2-oxo-5-(3-(trifluoromethyl)phenyl)pyridin-1 (2H)-yl)acrylic acid (Compound 042)

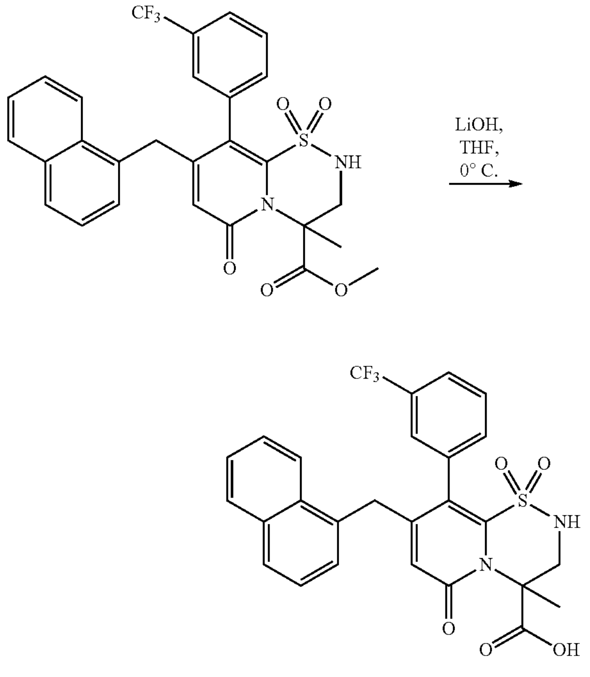

Compound 042

Methyl 4-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.16 g, 0.287 mmol) was dissolved in THF:$H_2O$ (1:1, 6 mL). LiOH—$H_2O$ (0.036 g, 0.862 mmol) was added and the mixture was stirred at room temperature for 5 h. The reaction mixture was concentrated then diluted with 0.1 N HCl (3 mL). The resulting solid was collected by filtration and rinsed with $H_2O$ (5 mL) then dried under vacuum. The crude product was purified using Prep HPLC Method 2 to give 4-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 042), as an off white solid (0.018 g, 11.54%). LCMS (Method-C3): 100% (RT: 1.799, 202.0 nm, 225.0 nm) (MS: ESI+ve 543.60 [M+H]). $^1H$ NMR: (400 MHz, DMSO) δ ppm: 2.85 (s, 3H), 3.79-3.90 (m, 1H), 4.05-4.12 (m, 2H), 4.73 (s, 1H), 5.96-5.98 (d, J=6.8 Hz, 1H), 7.11 (m, 1H), 7.25-7.270 (d, J=7.6 Hz, 1H), 7.43-7.72 (m, 8H) 7.83-7.85 (m, 1H) 7.91-7.93 (d, J=7.2 Hz, 1H).

Example 76

Synthesis of 7-(naphthalen-1-ylmethyl)-5-oxo-8-(3-(trifluoromethyl)phenyl)-5H-thiazolo[3,2-a]pyridine-3-carboxylic acid (Compound 019)

Compound 019

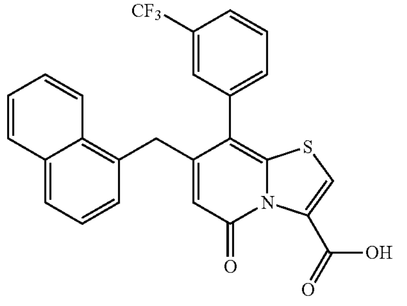

Step-1: Preparation of methyl 2-bromo-7-(naphthalen-1-ylmethyl)-5-oxo-8-(3-(trifluoromethyl)phenyl)-5H-thiazolo[3,2-a]pyridine-3-carboxylate

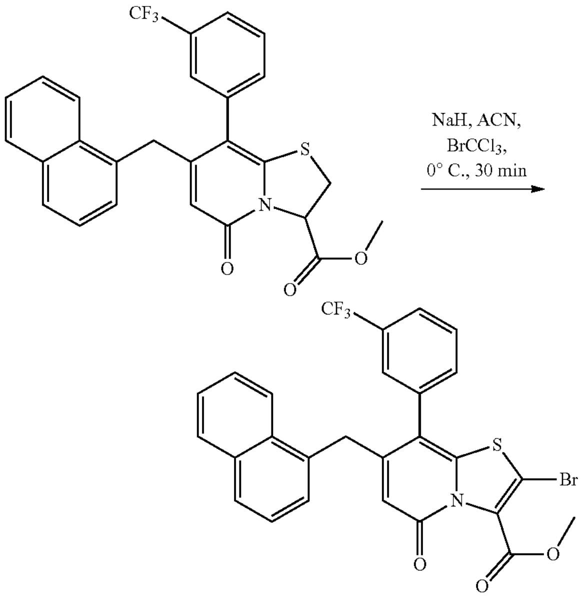

Methyl 7-(naphthalen-1-ylmethyl)-5-oxo-8-(3-(trifluoromethyl)phenyl)-2,3-dihydro-5H-thiazolo[3,2-a]pyridine-3-carboxylate (0.2 g, 0.404 mmol) was dissolved in dry acetonitrile (4.0 mL) and cooled to 0° C. Sodium hydride (0.032 g, 0.808 mmol) was added in portions and the mixture was stirred for 10 min. Bromotrichloromethane (0.0793 g, 0.399 mmol) was added dropwise at 0° C. and the mixture was stirred for 20 min. The reaction was quenched in ice water (50 mL) and extracted with ethyl acetate (3×50 mL). The organic layer was dried over sodium sulphate and concentrated under reduced pressure to give the crude product which was purified using column chromatography eluting with 0-20% ethyl acetate/hexane to give methyl 2-bromo-7-(naphthalen-1-ylmethyl)-5-oxo-8-(3-(trifluoromethyl)phenyl)-5H-thiazolo[3,2-a]pyridine-3-carboxylate as a yellow solid (0.18 g, 77.91%). LCMS (Method-$C_3$): 88.49% (RT: 2.335, 224.0 nm) (MS: ESI+ve 574.19[M+H]).

Step-2: Preparation of 7-(naphthalen-1-ylmethyl)-5-oxo-8-(3-(trifluoromethyl)phenyl)-5H-thiazolo[3,2-a]pyridine-3-carboxylic acid (Compound 019)

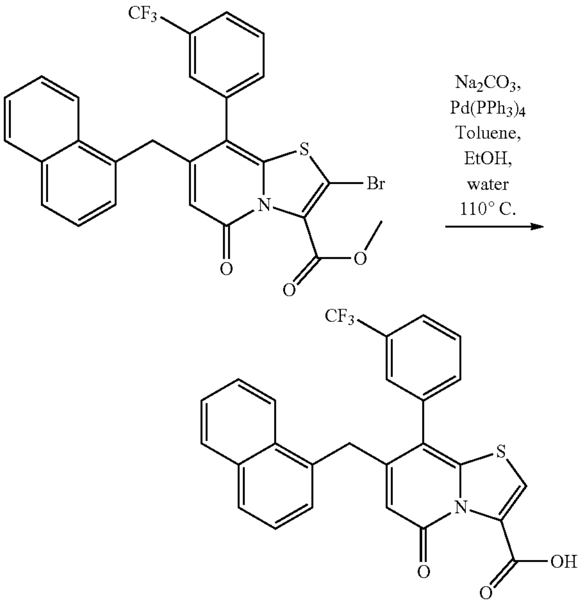

Compound 019

Methyl 2-bromo-7-(naphthalen-1-ylmethyl)-5-oxo-8-(3-(trifluoromethyl)phenyl)-5H-thiazolo[3,2-a]pyridine-3-carboxylate (0.18 g, 0.2797 mmol) was dissolved in a mixture of toluene (2 mL), ethanol (2 mL) and water (1 mL). Sodium carbonate (0.089 g, 0.839 mmol) was added and the mixture was degassed with nitrogen for 5 min. Palladium tetrakis (triphenylphosphine) (0.033 g, 0.027 mmol) was added and the mixture was heated in a sealed tube at 110° C. for 16 h. The reaction was quenched by adding ice water (50 mL) and 1N aqueous HCl solution (3-4 mL) then extracted with ethyl acetate (3×50 mL). The organic layer was dried over sodium sulphate and concentrated under reduced pressure. The crude product was purified using Prep HPLC Method 8 to give 7-(naphthalen-1-ylmethyl)-5-oxo-8-(3-(trifluoromethyl)phenyl)-5H-thiazolo[3,2-a]pyridine-3-carboxylic acid (Compound 019), as a yellow solid (0.08 g, 53.06%). LCMS (Method-C3): 95.19% (RT 2.171, 202 nm) (MS: ESI+ve 480.2 [M+H]). $^1H$ NMR: (400 MHz, DMSO) δ ppm: 4.22 (s, 2H), 6.053 (s, 1H), 7.24-7.26 (d, J=6.8 Hz, 1H), 7.40-7.52 (m, 3H), 7.71-7.84 (m, 6H), 7.91-7.93 (d, J=7.6 Hz, 1H), 8.00 (s, 1H).

Example 77

Synthesis of 7-(naphthalen-1-ylmethyl)-5-oxo-2-phenyl-8-(3-(trifluoromethyl)phenyl)-5H-thiazolo[3,2-a]pyridine-3-carboxylic acid (Compound 051)

Compound 051

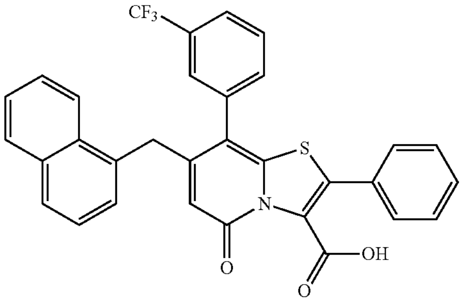

Step 1: Preparation of methyl 7-(naphthalen-1-ylmethyl)-5-oxo-2-phenyl-8-(3-(trifluoromethyl) phenyl)-5H-thiazolo [3, 2-a]pyridine-3-carboxylate

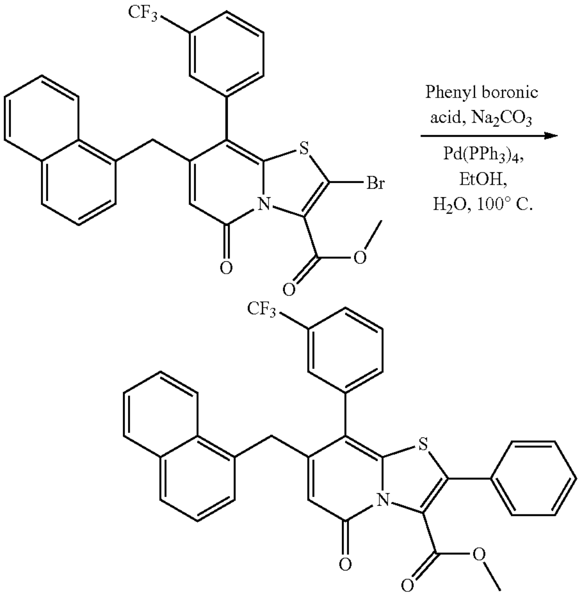

Methyl 2-bromo-7-(naphthalen-1-ylmethyl)-5-oxo-8-(3-(trifluoromethyl)phenyl)-5H-thiazolo[3,2-a]pyridine-3-carboxylate (0.2 g, 0.3466 mmol) was dissolved in ethanol (10 mL) and water (2 mL). Phenylboronic acid (0.063 g, 0.5199 mmol) was added followed by $Na_2CO_3$ (0.110 g, 1.0398 mmol) and the reaction mixture was purged with nitrogen for 20 min. $Pd(PPh_3)_4$ (0.040 g, 0.0346 mmol) was added and the reaction mixture was stirred at 100° C. for 16 h. The reaction mixture was cooled to room temperature and concentrated under vacuum then diluted with water and extracted with ethyl acetate (2×50 mL). The organic layer was washed with brine and dried over anhydrous sodium sulphate and concentrated. The crude product was purified using column chromatography eluting with 20% ethyl acetate/hexane to give methyl 7-(naphthalen-1-ylmethyl)-5-oxo-2-phenyl-8-(3-(trifluoromethyl) phenyl)-5H-thiazolo[3,2-a]pyridine-3-carboxylate. (0.19 g, 95.4%). LCMS (Method-C3): 92.31% (RT 2.31, 225.0 nm) (MS: ESI+ve 570 [M+H]).

Step 2: Preparation of 7-(naphthalen-1-ylmethyl)-5-oxo-2-phenyl-8-(3-(trifluoromethyl)phenyl)-5H-thiazolo[3,2-a]pyridine-3-carboxylic acid

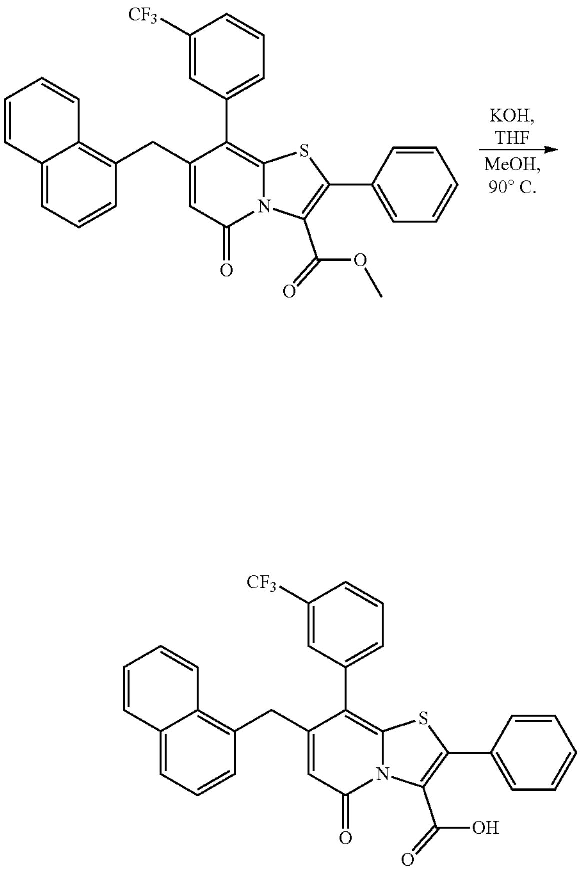

Compound 051

A mixture of methyl 7-(naphthalen-1-ylmethyl)-5-oxo-2-phenyl-8-(3-(trifluoromethyl)phenyl)-5H-thiazolo[3,2-a] pyridine-3-carboxylate (0.190 g, 0.3339 mmol), THF (2.5 mL), MeOH (1.5 mL) and KOH (0.320 g, 5.7117 mmol) was heated in a microwave reactor, under microwave irradiation, at 90° C. for 30 min. The reaction mixture was concentrated then diluted with water (20 mL) and 2N aqueous HCl solution (2 ml). The resulting solid was collected by filtration under vacuum. The crude product was purified using Prep HPLC Method 3 to give 7-(naphthalen-1-ylmethyl)-5-oxo-2-phenyl-8-(3-(trifluoromethyl)phenyl)-5H-thiazolo[3,2-a]pyridine-3-carboxylic acid (Compound 051). (0.01 g, 5.4%) LCMS (Method-C3): 100% (RT 2.609, 202 nm) (MS: ESI+ve 556 [M+H]). $^1$HNMR: (400 MHz, DMSO) δ ppm: 4.12 (s, 1H), 5.771 (s, 1H), 7.18 (m, 2H), 7.27-7.26 (d, J=6.8 Hz, 1H), 7.36-7.49 (m, 5H), 7.49-7.66 (m, 3H), 7.66-7.81 (m, 4H), 7.89-7.91 (d, J=7.6 Hz, 1H).

Example 78

Synthesis of 2-benzyl-7-(naphthalen-1-ylmethyl)-5-oxo-8-(3-(trifluoromethyl)phenyl)-5H-thiazolo[3,2-a]pyridine-3-carboxylic acid (Compound 060)

Compound 060

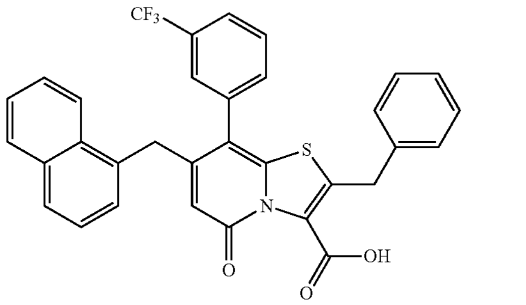

Step 1: Preparation of methyl 2-benzyl-7-(naphthalen-1-ylmethyl)-5-oxo-8-(3-(trifluoromethyl) phenyl)-5H-thiazolo[3,2-a]pyridine-3-carboxylate

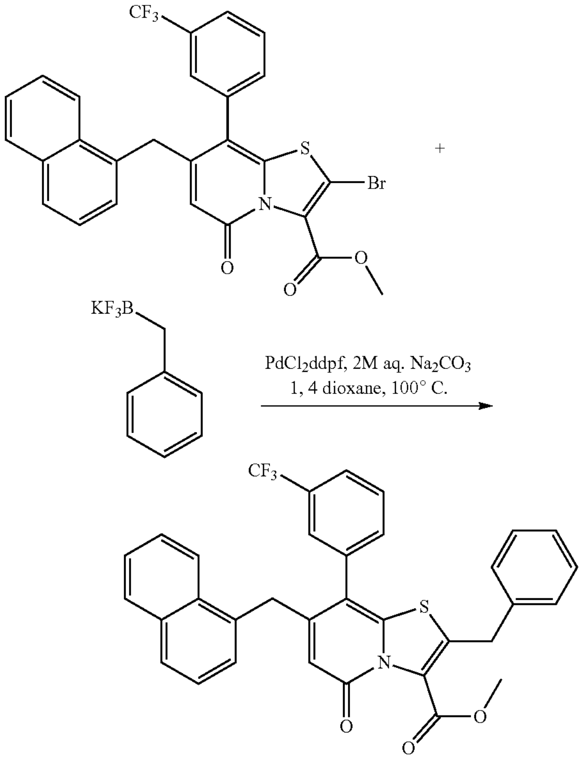

A mixture of methyl 2-bromo-7-(naphthalen-1-ylmethyl)-5-oxo-8-(3-(trifluoromethyl)phenyl)-5H-thiazolo[3,2-a] pyridine-3-carboxylate (0.2 g, 0.34 mmol), benzyltrifluoro-14-borane potassium salt (0.14 g, 6.9 mmol) and $Na_2CO_3$ (2.8 mL, 2M) was dissolved in 1,4-dioxane (6.0 ml). The reaction mixture was purged with N2 then $Pd(dppf)Cl_2$ (0.024 g, 0.34 mmol) was added and the mixture was stirred at 100° C. for 3 h. The reaction was quenched with water (20 mL) and extracted with ethyl acetate (3×20 mL). The organic layer was dried over sodium sulphate and concentrated. The crude product was purified using column chromatography to give methyl 2-benzyl-7-(naphthalen-1-ylmethyl)-5-oxo-8-(3-(trifluoromethyl)phenyl)-5H-thiazolo[3,2-a]pyridine-3-carboxylate (0.06 g, 30%). LCMS (Method-C3): 75.95% (RT: 2.391, 225 nm) (MS: ESI+ve 584.49 [M+1]).

Step 2: preparation of 2-benzyl-7-(naphthalen-1-ylmethyl)-5-oxo-8-(3-(trifluoromethyl) phenyl)-5H-thiazolo[3,2-a]pyridine-3-carboxylic acid (Compound 060)

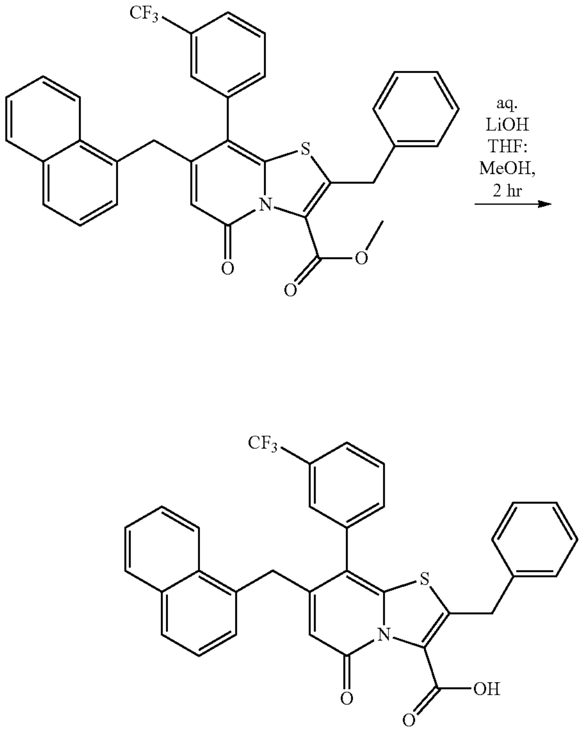

Compound 060

Methyl 2-benzyl-7-(naphthalen-1-ylmethyl)-5-oxo-8-(3-(trifluoromethyl)phenyl)-5H-thiazolo[3,2-a]pyridine-3-carboxylate (0.06 g, 0.1 mmol) was dissolved in THF:MeOH (1.8 ml, 3:1). A solution of LiOH (0.0017 g 0.41 mmol) in water (0.3 mL) was added and the mixture was stirred at 80° C. for 2 h. The reaction mixture was concentrated under reduced pressure. Water (3 mL) and 0.1N aqueous HCl solution were added and the resulting solid was collected by filtration and washed with water (10 mL). The crude compound was purified using Prep HPLC Method 1 to give 2-benzyl-7-(naphthalen-1-ylmethyl)-5-oxo-8-(3-(trifluoromethyl)phenyl)-5H-thiazolo[3,2-a]pyridine-3-carboxylic acid as a white solid (Compound 060) (0.006 g, 10%).LCMS (Method-C3): 100% (RT 2.174, 220.0 nm) (MS: ESI+ve 570.4 [M+H]): $^1$H NMR: (400 MHz, DMSO) δ ppm: 4.03 (s, 2H), 4.11 (s, 2H), 5.82 (s, 1H) 7.24-7.32 (m, 6H), 7.39-7.50 (m, 3H), 7.63-7.65 (m, 1H), 7.67-7.72 (m, 4H), 7.80-7.82 (dd, J=8.0, 1H), 7.89-7.91 (dd, J=8.01H).

Example 79

Synthesis of 7-(naphthalen-1-ylmethyl)-5-oxo-2-propyl-8-(3-(trifluoromethyl)phenyl)-5H-thiazolo[3,2-a]pyridine-3-carboxylic acid (Compound 061)

Compound 061

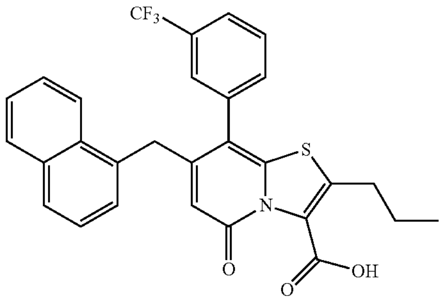

Prepared by a procedure similar to that reported for 2-benzyl-7-(naphthalen-1-ylmethyl)-5-oxo-8-(3-(trifluoromethyl)phenyl)-5H-thiazolo[3,2-a]pyridine-3-carboxylic (Compound 060) substituting trifluoro(propyl)-14-borane potassium salt in step 1. The crude product was purified using Prep HPLC Method 1 to give 7-(naphthalen-1-ylmethyl)-5-oxo-2-propyl-8-(3-(trifluoromethyl) phenyl)-5H-thiazolo[3,2-a]pyridine-3-carboxylic acid as a white solid (Compound 061) (0.0159 g, 20.65%). LCMS (Method-C3): 100% (RT: 5.764 (MS: ESI+ve 522.0 [M+H]). $^1$H NMR: (400 MHz, DMSO) δ ppm: 0.89-0.86 (t, 3H), 1.57-1.52 (m, 2H), 2.68-2.64 (t, 2H), 4.10 (s, 2H), 5.83 (s, 1H), 7.27-7.26 (d, J=6.8, 1H), 7.51-7.40 (m, 3H), 7.83-7.69 (m, 6H), 7.93-7.91 (d, J=7.6, 1H), 13.76 (s, 1H).

Example 80

Synthesis of 7-(naphthalen-1-ylmethyl)-5-oxo-2-phenethyl-8-(3-(trifluoromethyl)phenyl)-5H-thiazolo[3,2-a]pyridine-3-carboxylic acid (Compound 062)

Compound 062

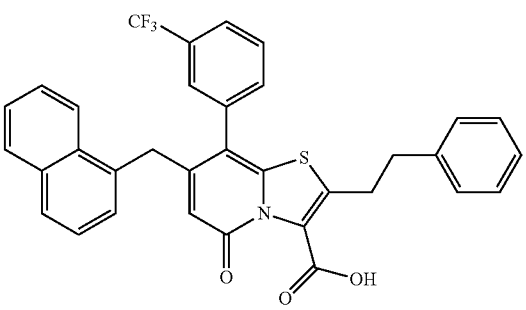

Prepared by a procedure similar to that reported for 2-benzyl-7-(naphthalen-1-ylmethyl)-5-oxo-8-(3-(trifluoromethyl)phenyl)-5H-thiazolo[3,2-a]pyridine-3-carboxylic (Compound 060) substituting trifluoro(phenethyl)-14-borane potassium salt in step 1. The crude product was purified using Prep HPLC Method 1 to give 2-benzyl-7-(naphthalen-1-ylmethyl)-5-oxo-8-(3-(trifluoromethyl)phenyl)-5H-thiazolo[3,2-a]pyridine-3-carboxylic acid as a white solid (Compound 062) (0.024 g, 24.5%).LCMS (Method-C3): 100% (RT 2.216, 224 nm) (MS: ESI+ve 584.5 [M+H]): $^1$H NMR: (400 MHz, DMSO) δ ppm: 2.85 (s, 2H), 2.98 (s, 2H), 4.16 (s, 2H) 5.83 (s, 1H), 7.21-7.30 (m, 6H), 7.40-7.50 (m, 3H), 7.71-7.83 (m, 6H), 7.91-7.93 (m, 1H) 13.86 (s, 1H).

Example 81

Synthesis of 6-amino-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 020 (Racemic), Compound 020a, Compound 029b)

Compound 020

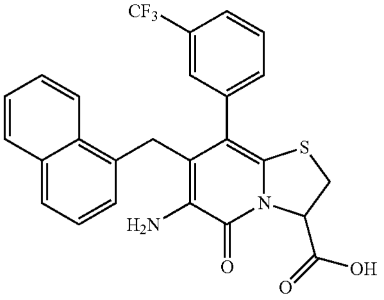

(Racemic)

Compound 020a
Arbitrary stereochemistry

Compound 020b
Arbitrary stereochemistry

Step 1: Preparation of methyl 7-(naphthalen-1-ylmethyl)-6-nitro-5-oxo-8-(3-(trifluoromethyl)phenyl)-2,3-dihydro-5H-thiazolo[3,2-a]pyridine-3-carboxylate

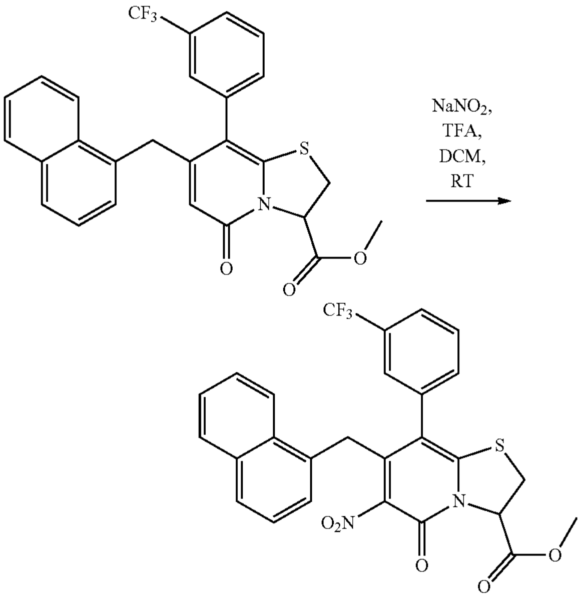

Methyl 7-(naphthalen-1-ylmethyl)-5-oxo-8-(3-(trifluoromethyl)phenyl)-2,3-dihydro-5H-thiazolo[3,2-a]pyridine-3-carboxylate (1.0 g, 2.0 mmol) was dissolved in DCM (56 mL), and $NaNO_2$ (0.167 g, 2.4 mmol) followed by TFA (1.8 mL) was added at room temperature. The reaction mixture was stirred for 16 h, quenched with saturated aqueous sodium bicarbonate (40 mL) and extracted with DCM (3×30 mL). The organic layer was dried over sodium sulphate and concentrated under reduced pressure to give methyl 7-(naphthalen-1-ylmethyl)-6-nitro-5-oxo-8-(3-(trifluoromethyl) phenyl)-2,3-dihydro-5H-thiazolo[3,2-a]pyridine-3-carboxylate, as a yellow solid (1.0 g, 91.68%), which was used without further purification. LCMS (Method-C3): 84.37% (RT: 2.020, 230 nm) (MS: ESI+ve 541.2 [M+H]).

Step 2: Preparation of methyl 6-amino-7-(naphthalen-1-ylmethyl)-5-oxo-8-(3-(trifluoromethyl)phenyl)-2,3-dihydro-5H-thiazolo[3,2-a]pyridine-3-carboxylate

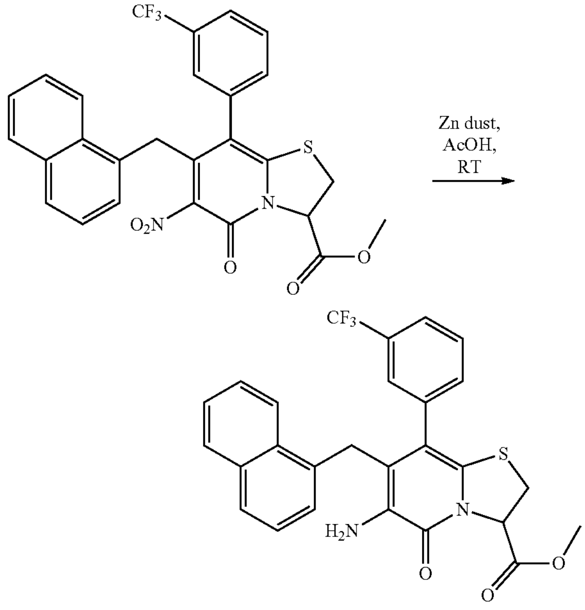

Methyl 7-(naphthalen-1-ylmethyl)-6-nitro-5-oxo-8-(3-(trifluoromethyl)phenyl)-2,3-dihydro-5H-thiazolo[3,2-a] pyridine-3-carboxylate (1.0 g, 1.85 mmol) was dissolved in acetic acid (15 mL) and freshly activated Zinc dust (0.604 g, 9.25 mmol) was added portion wise. The reaction was stirred at room temperature for 16 h. then passed through a pad of Celite and rinsed with DCM. The solvent was removed under reduced pressure and the residue was washed with saturated aqueous $NaHCO_3$ (30 mL) then extracted with DCM (3×30 mL). The organic layer was dried over sodium sulphate and concentrated under reduced pressure to give the crude product, which was purified by chromatography eluting with 0-70% ethyl acetate/hexane to give methyl 6-amino-7-(naphthalen-1-ylmethyl)-5-oxo-8-(3-(trifluoromethyl)phenyl)-2,3-dihydro-5H-thiazolo[3,2-a]pyridine-3-carboxylate, as a brown solid (0.7 g, 74.11%). LCMS (Method-C3): 85.17% (RT 1.934, 225 nm) (MS: ESI+ve 511.3 [M+H]).

Step 3: Preparation of 6-amino-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 020)(Racemic)

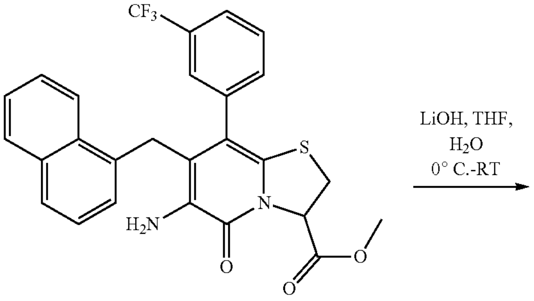

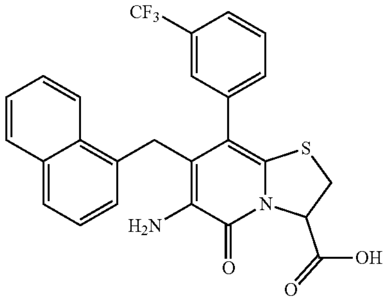

Compound 020(Reacemic)

Methyl 6-amino-7-(naphthalen-1-ylmethyl)-5-oxo-8-(3-(trifluoromethyl)phenyl)-2,3-dihydro-5H-thiazolo[3,2-a] pyridine-3-carboxylate (0.345 g, 0.67 mmol) was dissolved in THF:$H_2O$ (1:1, 10 mL). LiOH—$H_2O$ (0.055 g, 1.35 mmol) was added and stirred for 16 h. The mixture was concentrated under reduced pressure then cold water (30 mL) was added, followed by 1N aqueous HCl solution (4-5 mL). The resulting precipitate was collected by filtration and dried under vacuum. The crude product was purified using Prep HPLC Method 1 to give 6-amino-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 020)(Racemic), as an off white solid (0.010 g, 8.40%). LCMS (Method-J): 100% (RT 5.008, 254 nm) (MS: ESI+ve 497.4 [M+H]). $^1$H NMR: (400 MHz, DMSO) δ ppm: 3.46-3.49 (d, J=11.3 Hz, 1H), 3.80-3.94 (m, 2H), 4.02-4.12 (t, 2H), 4.93 (s, 2H), 5.59-5.61 (d, J=7.6 Hz, 1H), 6.98-6.99 (d, J=6 Hz 1H), 7.11 (s, 1H), 7.33-7.48 (m, 6H), 7.73-7.75 (d, J=8 Hz, 1H), 7.80-7.88 (m, 2H), 13.51 (s, 1H).

SFC separation of 6-amino-7-(naphthalen-1-ylmethyl)-5-oxo-8-(3-(trifluoromethyl)phenyl)-2,3-dihydro-5H-thiazolo[3,2-a]pyridine-3-carboxylic acid (Compound 020a, Compound 020b)

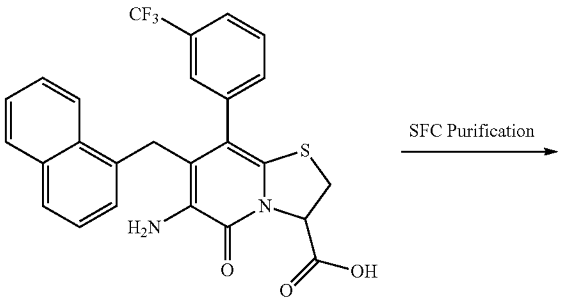

Compound 020 (Racemic)

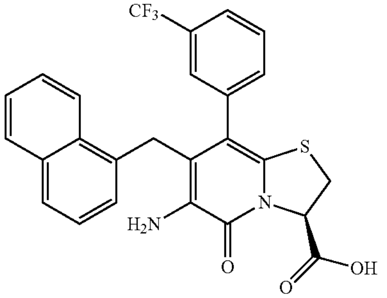

+

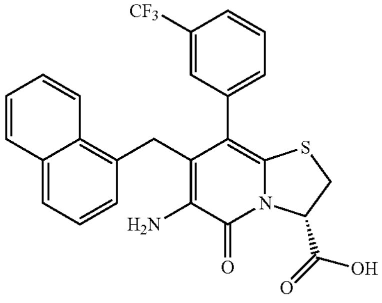

6-amino-7-(naphthalen-1-ylmethyl)-5-oxo-8-(3-(trifluoromethyl)phenyl)-2,3-dihydro-5H-thiazolo[3,2-a]pyridine-3-carboxylic acid (0.090 g) was separated on a Waters SFC 200 chromatography system with a UV detector. The column used was Chiralpak Ic (250*21.0) mm, 5 micron, column flow was 25.0 ml/min. Mobile phase (A) 0.1% DEA in Hexane (B) 0.1% DEA IN propan-1-ol:methanol (50:50). The gradient solvent B was 60-40% over 27 min.

Isolated (0.019 g, 21.11%) of fraction 1 (Compound 020a), as an off white solid. LCMS (Method-C3): 100.0% (RT 1.826, 225.0 nm) (MS: ESI−ve 495.4 [M+H]). $^1$H NMR: (400 MHz, DMSO) δ ppm: 2.54 (s, 1H), 3.36 (s, 1H); 3.80-3.85 (t, 1H); 3.85-4.08 (m, 3H); 5.60 (s, 1H); 6.98-7.00 (d, J=5.6 Hz, 1H); 7.17 (s, 1H); 7.36-7.46 (m, 6H); 7.73-7.75 (d, J=8 Hz, 1H); 7.81 (s, 1H); 7.86-7.88 (d, J=7.6 Hz, 1H). Chiral HPLC (Fr-1): 94.47% (RT: 6.19)

Isolated (0.01 g, 11.11%) of fraction 2 (Compound 020b), LCMS (Method-$C_3$): 100.0% (RT 1.823, 225.0 nm) (MS: ESI+ve 495.3 [M+H]). $^1$H NMR: (400 MHz, DMSO) δ ppm: 2.54 (s, 1H), 3.80-3.85 (t, 1H); 3.90 (s, 1H); 3.94 (s, 1H); 4.12 (s, 1H); 4.92 (s, 2H); 6.98-6.99 (d, 1H); 7.17 (s, 1H); 7.33-7.46 (m, 6H); 7.73-7.75 (d, J=8 Hz, 1H); 7.81 (s, 1H); 7.86-7.88 (d, J=7.6 Hz, 1H).Chiral HPLC (Fr-2): 82.68% (RT: 7.82).

Example 82

Synthesis of 6-amino-7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 023)

Compound 023

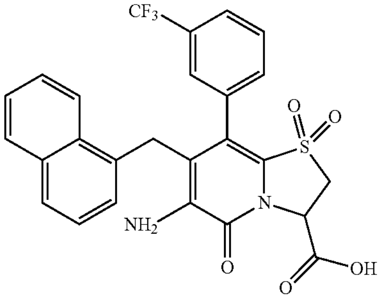

Step 1: preparation of methyl 7-(naphthalen-1-ylmethyl)-6-nitro-5-oxo-8-(3-(trifluoromethyl)phenyl)-2,3-dihydro-5H-thiazolo[3,2-a]pyridine-3-carboxylate 1,1-dioxide

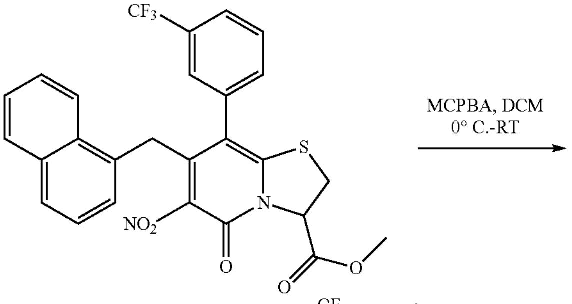

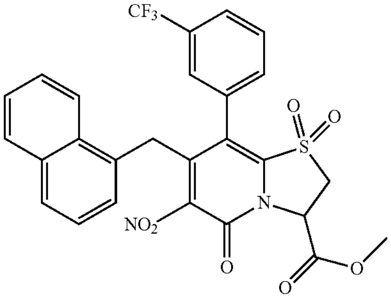

Methyl 7-(naphthalen-1-ylmethyl)-6-nitro-5-oxo-8-(3-(trifluoromethyl)phenyl)-2,3-dihydro-5H-thiazolo[3,2-a]pyridine-3-carboxylate (0.25 g, 0.462 mmol) was dissolved in DCM (5 mL). MCPBA (60%) (0.266 g, 1.15 mmol) dissolved in DCM (2 mL) was added at 0° C., and the reaction mixture was stirred for 16 h at room temperature. The reaction was quenched in water (50 mL) and sat. aq. $NaHCO_3$ (20 mL), then extracted with ethyl acetate (3×50 mL). The organic layer was dried over sodium sulphate and concentrated under reduced pressure to give the crude product which was purified by column chromatography eluting with 0-15% ethyl acetate/hexane to give methyl 7-(naphthalen-1-ylmethyl)-6-nitro-5-oxo-8-(3-(trifluoromethyl)phenyl)-2,3-dihydro-5H-thiazolo[3,2-a]pyridine-3-carboxylate 1,1-dioxide as a brown gum (0.15 g, 56.65%) LCMS (Method-J): 73.57% (RT 6.997, 222 nm) (MS: ESI+ve 574.2 [M+H]).

Step 2: Preparation of methyl 6-amino-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide

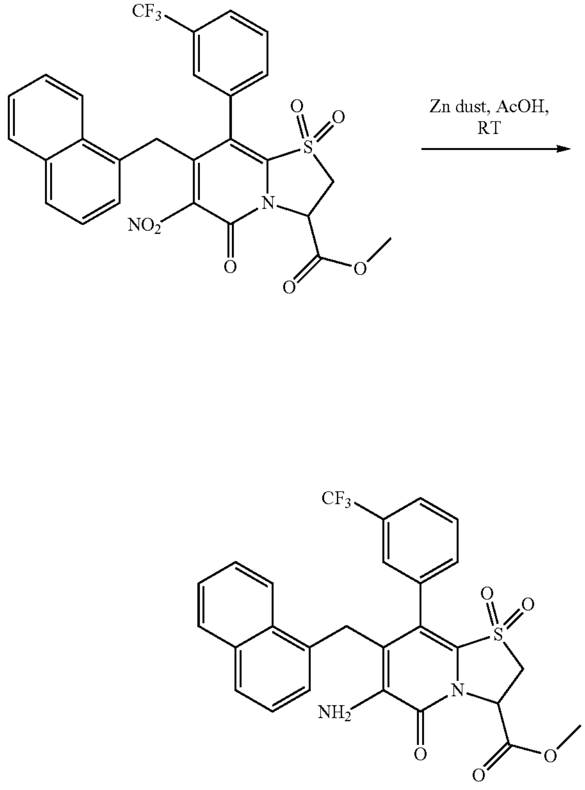

Methyl 7-(naphthalen-1-ylmethyl)-6-nitro-5-oxo-8-(3-(trifluoromethyl)phenyl)-2,3-dihydro-5H-thiazolo[3,2-a]pyridine-3-carboxylate 1,1-dioxide (0.13 g, 0.227 mmol) was dissolved in acetic acid (1.88 mL) at room temperature. Activated Zinc dust (0.103 g, 1.589 mmol) was added portion wise at room temperature and the reaction mixture was stirred at room temperature for 20 h. The mixture was then filtered through a Celite pad and rinsed with dichloromethane. The filtrate was concentrated, and the resulting solid was dissolved in DCM (150 mL), washed with sat. aq. $NaHCO_3$ (20 mL), and the organic layer was dried and concentrated under vacuum. The crude product was purified using column chromatography eluting with 0-50% ethyl acetate/hexane to give methyl 6-amino-7-(naphthalen-1-ylmethyl)-5-oxo-8-(3-(trifluoromethyl)phenyl)-5H-thiazolo[3,2-a]pyridine-3-carboxylate (0.11 g, 79.88%) as a brown solid. LCMS (Method-C3): 70.20% (RT: 2.218, 214.4 nm) (MS: ESI+ve 543.0[M+H]).

Step 3: Preparation of 6-amino-7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 023)

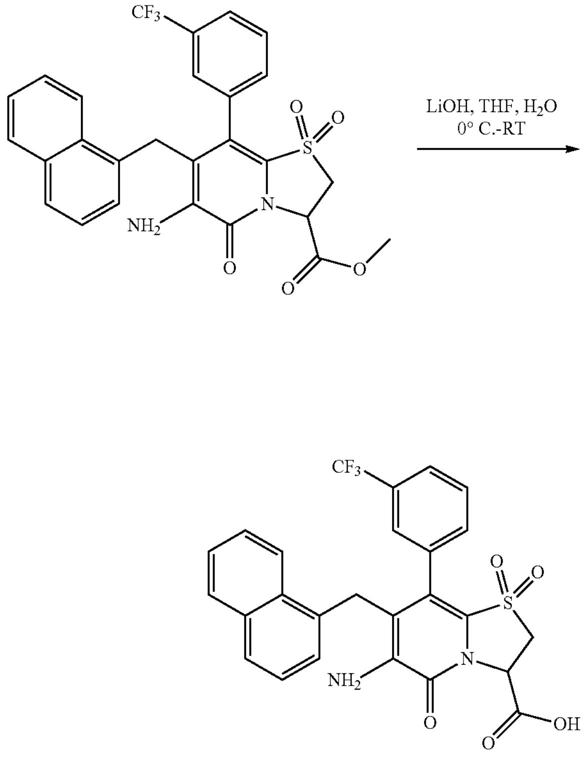

Compound 023

Methyl 6-amino-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.11 g, 0.313 mmol) was dissolved in $THF:H_2O$ (1:1, 10 mL). $LiOH—H_2O$ (0.025 g 0.626 mmol) was added and the reaction mixture was stirred at room temperature for 4 h. The mixture was concentrated then suspended in ice water (10 mL). 1N aqueous HCl solution (3-4 mL) was added and the resulting precipitate was collected by filtration and dried under vacuum. The crude product was purified using Prep HPLC Method 6 to give 6-amino-7-(naphthalen-1-ylmethyl)-5-oxo-8-(3-(trifluoromethyl)phenyl)-2,3-dihydro-5H-thiazolo[3,2-a]pyridine-3-carboxylic acid 1,1-dioxide (Compound 023), an off white solid (0.017 g, 16.20%). LCMS (Method-$C_3$): 100% (RT 1.933, 225 nm) (MS: ESI+ve 495.16 [M+H]). $^1H$ NMR: (400 MHz, DMSO) δ ppm: 3.85-3.89 (m, 1H), 4.03-4.14 (m, 3H), 5.52-5.54 (d, J=9.2 Hz, 1H), 5.80 (s, 2H), 6.96-6.98 (d, J=6.8 Hz, 1H), 7.33-7.46 (m, 7H) 7.71-7.78 (m, 2H) 7.84-7.86 (d, J=7.6 Hz, 1H).

Example 83

Synthesis of 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 120)

Compound 120

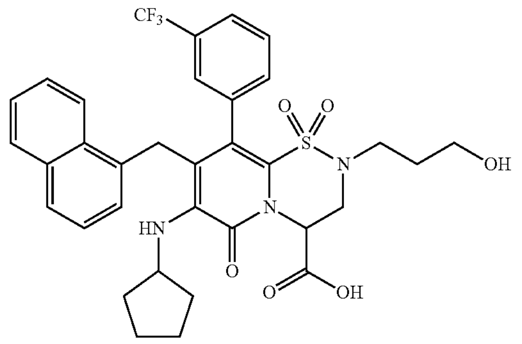

Step 1: Preparation of methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate

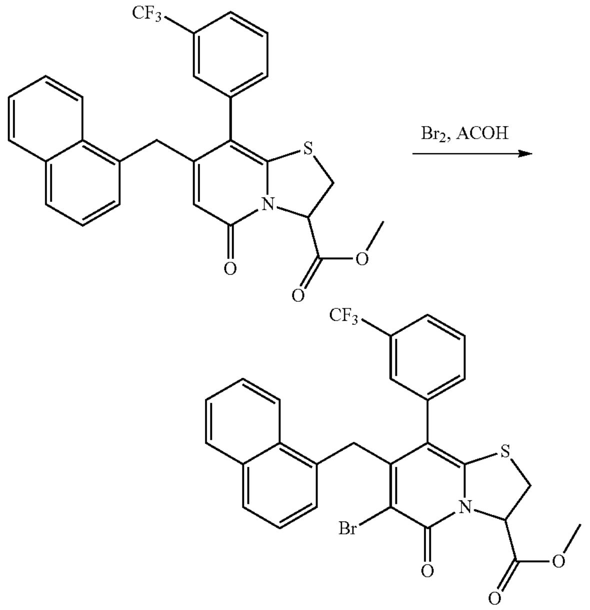

Methyl7-(naphthalen-1-ylmethyl)-5-oxo-8-(3-(trifluoromethyl)phenyl)-2,3-dihydro-5H-thiazolo[3,2-a]pyridine-3-carboxylate (25 g, 50.50 mmol) was dissolved in acetic acid (500 mL). Bromine (2.6 mL, 50.50 mmol) was added and the resulting mixture was stirred for 2 h. The solvent was removed under reduced pressure to give methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate (28 g, 96.62%). LCMS (Method-C3): 88.90% (RT: 2.115, 230.0 nm) (MS: ESI+ve 576.69 [M+H]).

Step 2: Preparation of methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide

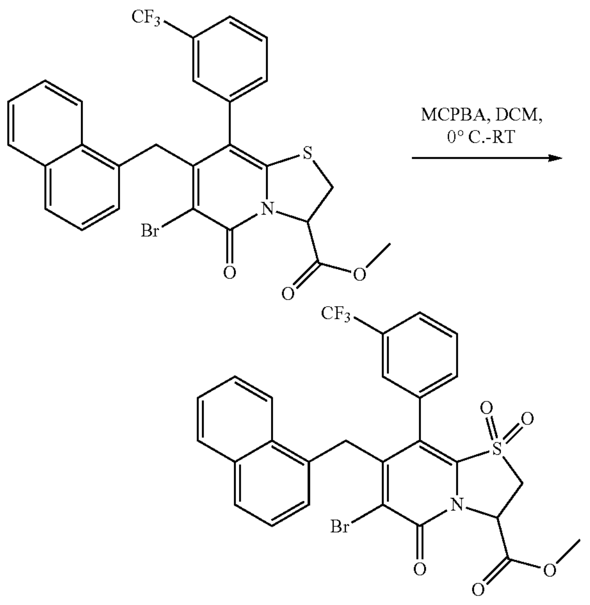

Methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate (28 g, 48.78 mmol) was dissolved in DCM (250 mL). MCPBA (55%) (38.13 g, 121.95 mmol) was dissolved in DCM (250 mL) and added to the mixture at 0° C. Stirring was continued at room temperature for 16 h. The reaction mixture was purified by column chromatography eluting with 30-40% Ethyl acetate/hexane to give methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (15.0 g, 50.74%). LCMS (Method-C3): 98.61% (RT: 2.293, 202.0 nm) (MS: ESI+ve 606.0 [M+H]).

Step 3: Preparation of methyl 7-bromo-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

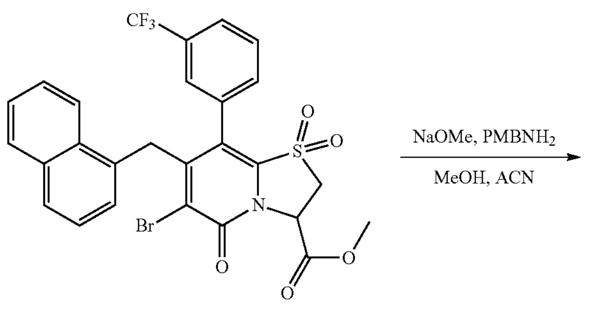

-continued

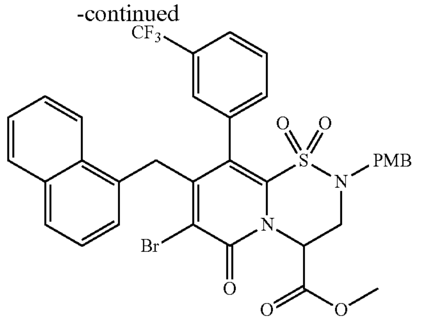

Methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (15.0 g, 24.75 mmol) was dissolved in methanol (150 mL), cooled to 0° C. and 4-methoxybenzylamine (5.07 g, 37.05 mmol) was added portion wise and stirred for 5 min. Then 0.2 M methanolic sodium methoxide solution (150 mL) was added dropwise at 0° C. and reaction mixture was stirred for 16 h at room temperature. The methanol was removed from the reaction mixture by rotary evaporation, and residue was then concentrated twice from chloroform. The reaction mixture was diluted with acetonitrile (270 mL) and cooled to 0° C. Pyridine (1.986 mL, 24.7 mmol) was added followed by bromine (4.71 g, 29.64 mmol) and the reaction mixture was stirred for 1 h at room temperature. The reaction was quenched in water (100 mL) and extracted with ethyl acetate (3×100 mL). The organic layer was dried over sodium sulphate and concentrated under reduced pressure to give crude product which was purified by column chromatography eluting with 0-20% ethyl acetate/hexane to give 7-bromo-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (9.0 g, 49.06%). LCMS (Method-C3): 92.93% (RT: 2.137, 225.0 nm) (MS: ESI+ve 743.3 [M+H]).

Step 4: Preparation of methyl 7-(cyclopentylamino)-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide -continued

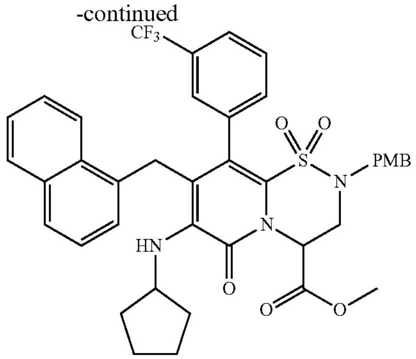

Methyl-7-bromo-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (1.2 g, 1.6 mmol) was added to a solution of cyclopentanamine (0.165 g, 0.0019 mmol) dissolved in dry toluene (20 mL) that was degassed with Argon. Potassium phosphate (0.515 g, 0.002 mmol) and Xantphos (0.074 g, 0.0001 mmol) were then added followed by tris(dibenzylideneacetone)dipalladium (0.066 g, 0.00006 mmol). The reaction mixture was degassed with argon, stirred at 110° C. for 16 h, quenched in water (50 mL) then extracted with ethyl acetate (2×30 mL). The organic layer was dried over sodium sulphate and concentrated under reduced pressure to give the crude product which was purified using column chromatography eluting with 30-40% ethyl acetate/hexane to give methyl 7-(cyclopentylamino)-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.180 g, 15.0%). LCMS (Method-C3): 64.5% (RT 2.437, 226 nm) (MS: ESI+ve 746.7 [M+1]).

Step 5: Preparation of methyl 7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

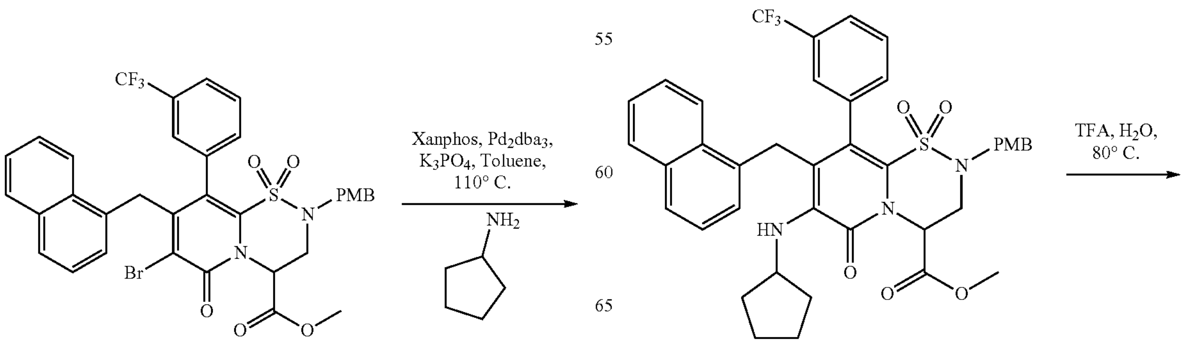

-continued

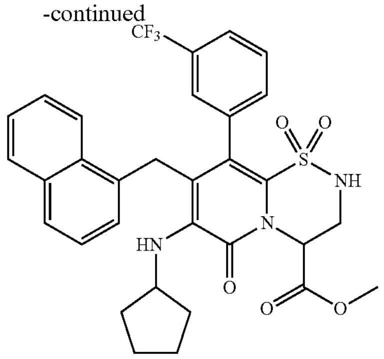

Methyl 7-(cyclopentylamino)-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.180 g, 0.2413 mmol) was dissolved in trifluoro acetic acid (3 mL) and water (0.3 mL) at room temperature, heated at 80° C. for 1 h, and quenched in saturated aqueous sodium bicarbonate solution (12 mL) then extracted into ethyl acetate (2×20 mL). The organic layer was dried over sodium sulphate and concentrated under reduced pressure to give methyl-7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.199 g, 100%), which was used without purification in the next step. LCMS (Method-C3): 67.5% (RT 2.609, 202 nm) (MS: ESI+ve 626.2 [M+1]).

Step 6: Preparation of methyl 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

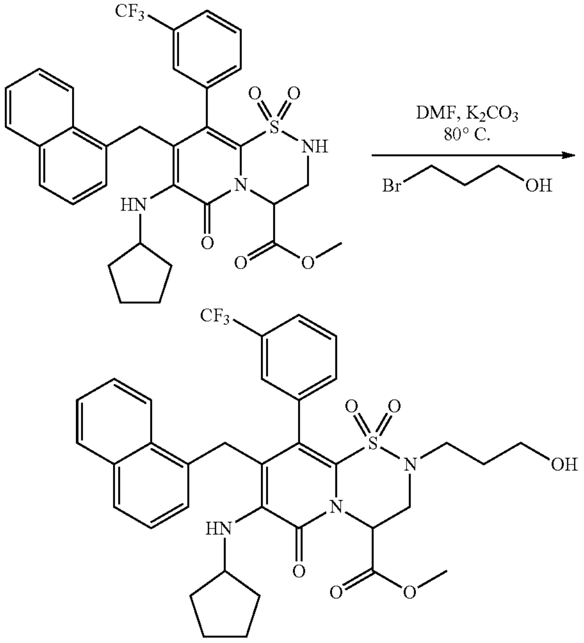

Methyl-7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.199 g, 0.3180 mmol) was dissolved in N,N-dimethylformamide (5 mL). Potassium carbonate (0.065 g, 0.4770 mmol) and 3-bromopropan-1-ol (0.065 g, 0.477 mmol) were added and the mixture was stirred at 80° C. for 2 h. The reaction was quenched in water (30 mL) and extracted into ethyl acetate (2×25 mL). The organic layer was dried over sodium sulphate and concentrated under reduced pressure to give the crude product which was purified by column chromatography eluting with 0-10% dichloromethane/methanol to give methyl 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.083 g, 38%). LCMS (Method-C3): 83.6% (RT 2.587, 254 nm) (MS: ESI+ve 684.4 [M+1]).

Step 7: Preparation of 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 120)

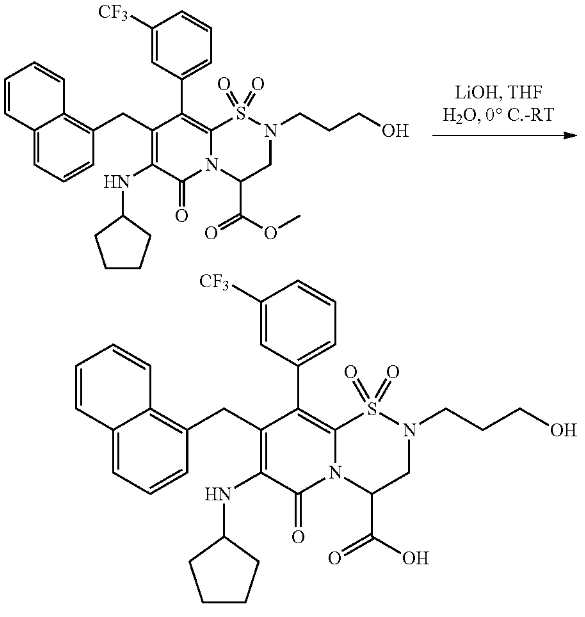

Compound 120

Methyl-7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.083 g, 0.1213 mmol) was dissolved in tetrahydrofuran (3 mL). An aqueous solution of lithium hydroxide (0.020 g, 0.4855 mmol) was added (3 mL) after cooling in an ice bath. The reaction mixture was stirred at room temperature for 16 h, then concentrated under reduced pressure, acidified with 1N aqueous HCl solution (7 mL) and extracted into ethyl acetate (2×10 mL). The organic layer was dried over sodium sulphate and concentrated under reduced pressure to give 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1, 2,5]thiadiazine-4-carboxylic acid 1,1-dioxide (0.112 g, 100%). LCMS (Method-J): 84.6% (RT 5.431, 5.464, 202 nm) (MS: ESI+ve 670.2 [M+1]). The crude product was purified by Preparative High Pressure Liquid Chromatography (Prep HPLC Method 1) to give 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 120) (0.017 g, 20.91%). LCMS (Method-$C_3$): 100% (RT 1.990, 2.006, 220 nm) (MS: ESI+ve 670.9 [M+1]). $^1$H NMR: (400 MHz, DMSO) δ ppm: 1.35-1.23 (m, 5H), 1.49 (s, 2H), 1.57 (s, 5H), 3.22 (s, 2H), 3.82 (s, 1H), 3.98 (s, 1H), 4.03 (s, 3H), 4.10 (m, 1H), 5.02 (s, 1H), 5.36-5.34 (d, J=8 Hz, 1H), 7.00-6.98 (m, 1H), 7.15 (m, 2H), 7.43-7.29 (m, 6H), 7.70 (m, 2H), 7.85-7.83 (d, J=8 Hz, 1H).

Example 84

Synthesis of 7-(cyclopentylamino)-2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 121)

Compound 121

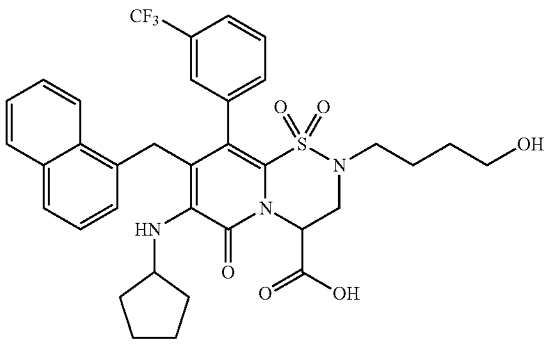

Prepared by a procedure similar to that described for 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 120) using 4-bromobutan-1-ol in step 6 to give 7-(cyclopentylamino)-2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 121) (0.012 g, 21.4%), as a white solid. Prep HPLC Method 2; LCMS (Method-H): 99.9% (RT 3.862, 3.899, 222 nm) (MS: ESI+ve 684.0 [M+1]). $^1$H NMR: (400 MHz, DMSO) δ ppm: 1.38-1.29 (m, 5H), 1.63-1.52 (m, 5H), 3.14 (s, 2H), 4.02-3.92 (m, 2H), 4.13-4.02 (m, 2H), 5.19 (s, 1H), 5.39 (s, 1H), 7.03 (s, 1H), 7.18 (s, 2H), 7.42-7.38 (m, 5H), 7.76 (s, 2H), 7.89-7.87 (d, J=8 Hz, 1H).

Example 85

Synthesis of 7-(cyclopentylamino)-2-(5-hydroxypentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 122)

Compound 122

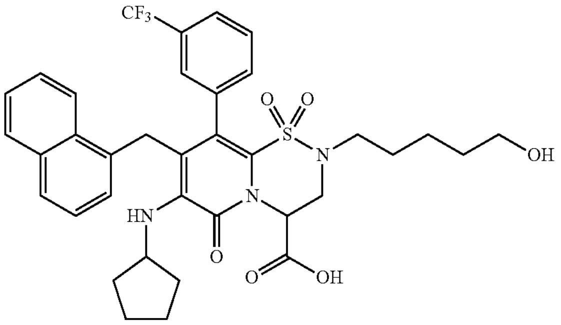

Prepared by a procedure similar to that described for 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 120) using 5-bromobutan-1-ol in step 6 to give 7-(cyclopentylamino)-2-(5-hydroxypentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 122) (0.023 g, 14.8%), as a white solid. Prep HPLC Method 2; LCMS (Method-J): 97.9% (RT 5.498, 5.534, 202 nm) (MS: ESI+ve 698.0 [M+1]). $^1$H NMR: (400 MHz, DMSO) δ ppm: 1.58-1.23 (m, 14H), 3.11 (s, 5H), 3.89-3.84 (d, J=20 Hz, 1H), 3.98-3.94 (d, J=16 Hz, 1H), 4.08 (s, 3H), 5.08 (s, 1H), 5.36-5.33 (d, J=12 Hz, 1H), 6.99-6.95 (m, 1H), 7.14 (s, 1H), 7.44-7.27 (m, 6H), 7.72-7.68 (t, J=16 Hz, 2H), 7.85-7.83 (d, J=8 Hz, 1H).

Example 86

Synthesis of 7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 002)

Compound 002

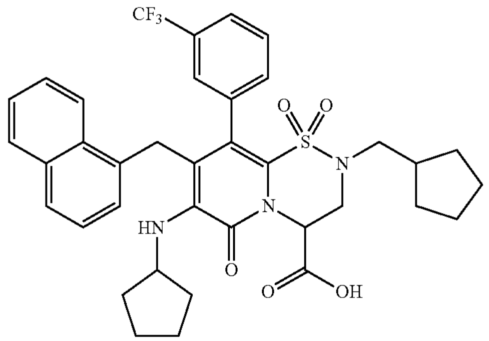

Prepared by a procedure similar to that described for 7-(cyclopentylamino)-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 120) using (bromomethyl) cyclopentane in step 6. The crude product was purified using Prep HPLC Method 1 to give 7-(cyclopentylamino)-2-(cyclopentylmethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 002), (0.010 g, 16.2%), as a white solid. LCMS (Method-C3): 40.70%, 58.18% (RT: 2.726, 2.748, 220 nm) (MS: ESI+ve 694.0 [M+1]). $^{1}$H NMR: (400 MHz, DMSO) δ ppm: 1.114 (s, 2H), 1.250 (s, 2H), 1.367 (s, 2H), 1.493 (s, 6H), 1.615 (s, 4H), 2.08-2.12 (m, 1H), 2.997 (s, 2H), 3.94-3.99 (m, 2H), 4.08-4.09 (m, 2H), 4.18-4.22 (d, J=16 Hz, 1H), 5.30-5.32 (m, 2H), 6.93-7.00 (m, 1H), 7.159 (s, 1H), 7.30-7.47 (m, 6H), 7.68-7.73 (dd, J=20 Hz, 2H), 7.85-7.87 (d, J=8 Hz, 1H).

Example 87

Synthesis of 7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 005)

Compound 005

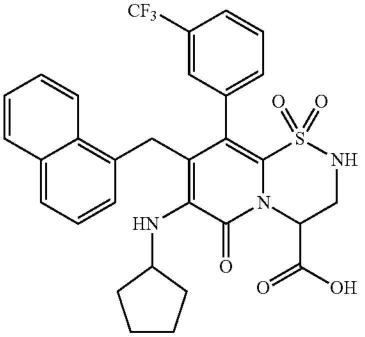

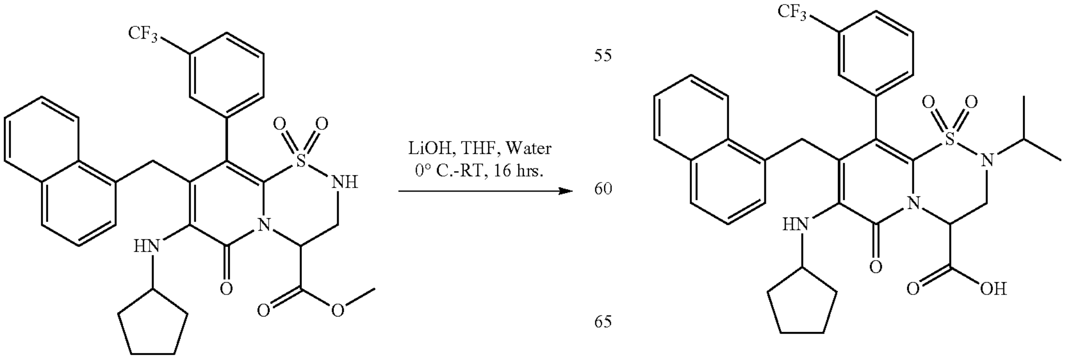

-continued

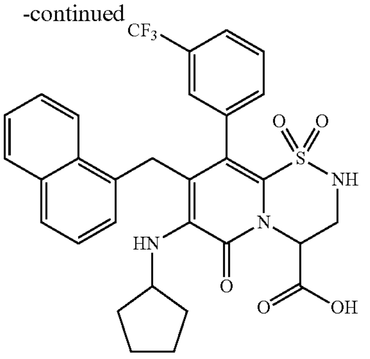

Compound 005

Methyl-7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.111 g, 0.1774 mmol) was dissolved in tetrahydrofuran (3 mL). A solution of lithium hydroxide (0.029 g, 0.7096 mmol) in water (3 mL) was added, the reaction mixture was stirred at room temperature for 16 h and then concentrated under reduced pressure. The residue was treated with 1N aqueous HCl solution (7 mL) and extracted into ethyl acetate (2×10 mL). The organic layer was dried over sodium sulphate and concentrated under reduced pressure. The crude product was purified using Prep HPLC Method 1 to give 7-(cyclopentylamino)-8-(naphthalen-1-ylmethyl)-6-oxo-9-(3 (trifluoromethyl)phenyl)-3,4-dihydro-2H,6H-pyrido[1,2-e][1,2,5]thiadiazine-4-carboxylic acid 1,1-dioxide (Compound 005), (0.021 g, 19.6%), as a white solid. LCMS (Method-C3): 38.56%, 60.17% (RT: 2.437, 2.454, 220 nm) (MS: ESI+ve 612.0 [M+1]). $^{1}$H NMR: (400 MHz, DMSO) δ ppm: 1.18-1.38 (m, 5H), 1.609 (s, 2H), 1.624 (s, 2H), 3.71-3.99 (m, 3H), 4.08-4.13 (m, 2H), 5.21 (s, 1H), 5.30-5.32 (d, J=8 Hz, 1H), 6.984 (s, 1H), 7.283 (s, 1H), 7.32-7.48 (m, 6H), 7.48-7.87 (m, 2H), 8.253 (s, 1H), 13.462 (s, 1H).

Example 88

Synthesis of 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123)

Compound 123

Step 1: Preparation of methyl 7-bromo-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

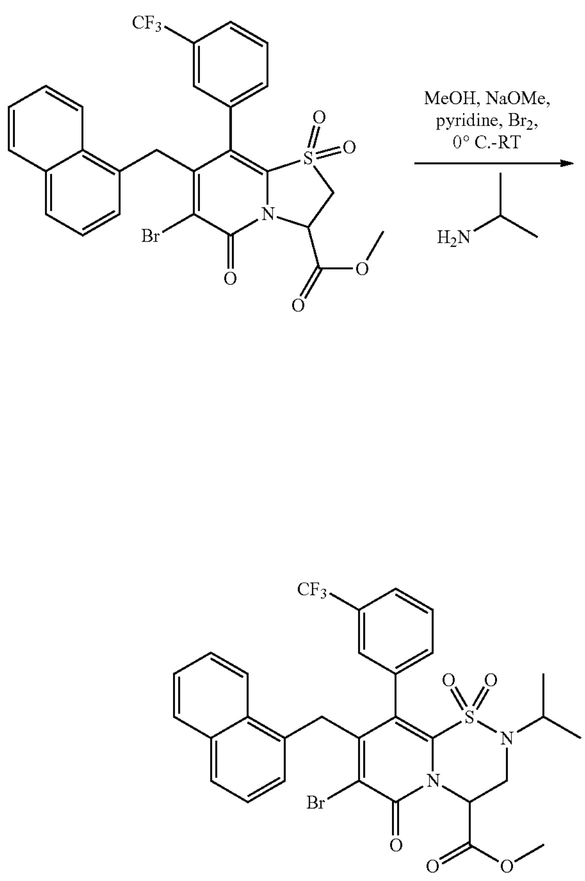

Methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (1.0 g, 1.65 mmol) was dissolved in methanol (10.0 mL), cooled to 0° C. and propan-2-amine (0.11 g, 1.98 mmol) was added portion wise then stirred for 5 min. 0.2 M sodium methoxide (freshly prepared) in methanol (10.0 mL) was added dropwise at 0° C. and the reaction mixture was stirred for 16 h at room temperature. The mixture was concentrated under reduced pressure, then concentrated twice from chloroform. The residue was dissolved in acetonitrile (16 mL) and cooled to 0° C. Pyridine (0.13 mL, 1.65 mmol) was added followed by bromine (0.314 g, 1.98 mmol), and stirring was continued for 1 h at room temperature. The reaction was quenched in water (100 mL) and extracted with ethyl acetate (3×100 mL). The organic layer was dried over sodium sulphate and concentrated under reduced pressure to give the crude product which was purified by using column chromatography eluting with 40% ethyl acetate/hexane to give methyl 7-bromo-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a brown solid (0.26 g, 23.76%). LCMS (Method-C3): 67.40% (RT: 2.576, 202.4 nm) (MS: ESI+ve 663.2 [M+0]).

Step 2: Preparation of methyl 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

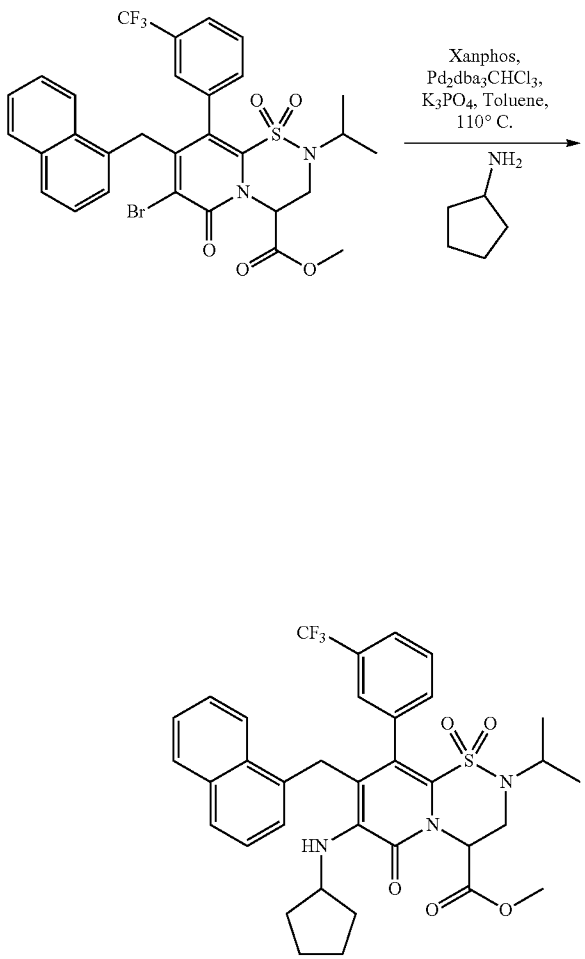

Methyl 7-bromo-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.26 g, 0.39 mmol) was dissolved in toluene (3.0 mL) and degassed with argon for 5 min. Potassium phosphate (0.208 g, 0.98 mmol) was added then Xantphos (0.018 g, 0.0313 mmol) and tris(dibenzylideneacetone)dipalladium-chloroform adduct (0.016 g, 0.0156 mmol) were added, followed by degassing under argon for 2 min. The reaction mixture was heated at 110° C. for 16 h, quenched in water (20 mL) and extracted with ethyl acetate (2×30 mL). The organic layer was dried over sodium sulphate and concentrated under reduced pressure to give the crude product which was purified by column chromatography eluting with 40% ethyl acetate/hexane to give methyl 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.07 g, 26.75%). LCMS (Method-C3): 95.35% (RT 2.813, 202.4.0 nm) (MS: ESI+ve 668.4[M+H]).

Step 3: Preparation of 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123)

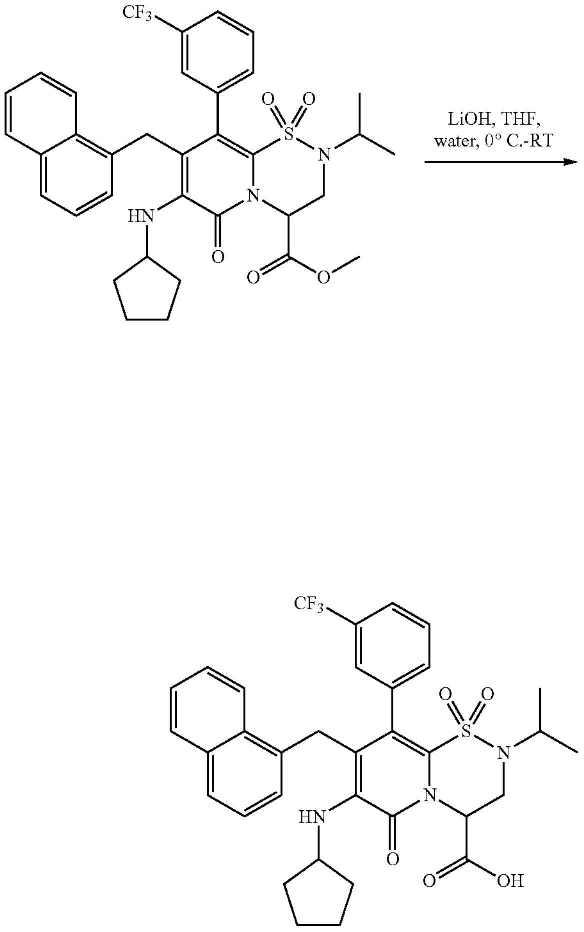

Methyl7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.07 g, 0.104 mmol) was dissolved in THF: $H_2O$ (1:1, 3 mL). LiOH—$H_2O$ (0.018 g, 0.419 mmol) was added and the mixture was stirred at room temperature for 4 h. The mixture was concentrated and ice-cold water (10 mL) was added followed by 1N aqueous HCl solution (3-4 mL). The resulting precipitate was collected by filtration and dried under vacuum to give 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123), as an off white solid (0.033 g, 48.15%). LCMS (Method-C3): 43.83% (RT 2.152, 225.0 nm) (MS: ESI+ve 654.53 [M+H]). 56.17% (RT 2.178, 225.0 nm) (MS: ESI+ve 654.53 [M+H]). (Atropisomer mixture)$^1$H NMR: (400 MHz, DMSO) δ ppm: 1.01-1.06 (m, 6H), 1.16-1.35 (m, 5H), 1.48-1.59 (m, 4H), 3.93-4.03 (m, 5H), 5.33 (s, 2H), 6.95 (m, 1H), 7.12 (s, 1H), 7.27-7.42 (m, 6H), 7.67-7.71 (m, 2H), 7.84-7.86 (d, J=6.4 Hz, 1H).

Example 89

Synthesis of 7-(cyclopentylamino)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 126)

Compound 126

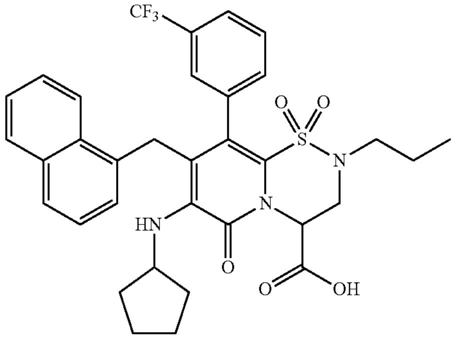

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123) using n-propyl amine in step 1 to give 8-(naphthalen-1-ylmethyl)-6-oxo-2-propyl-7-((tetrahydro-2H-pyran-4-yl) amino)-9-(3-(trifluoromethyl) phenyl)-3,4-dihydro-2H,6H-pyrido[1,2-e][1,2,5]thiadiazine-4-carboxylic acid 1,1-dioxide (Compound 126) (0.035 g, 35.75%), as an off white solid; Prep HPLC Method 3; LCMS (Method-C3): 96.28% (RT5.819: 202.0 nm) (MS: ESI+ve 654.2 [M+H]). $^1$H NMR: (400 MHz, DMSO) δ ppm: 0.75-0.77 (d, J=7.2 Hz, 3H), 1.23-1.58 (m, 10H), 3.07 (s, 2H), 3.87-4.14 (m, 5H), 5.15 (s, 1H), 5.34 (s, 1H), 6.95-6.99 (t, J=14 Hz, 1H), 7.14 (s, 2H), 7.28-7.44 (m, 5H), 7.72 (s, 2H), 7.83-7.85 (d, J=8.4 Hz, 1H).

Example 90

Synthesis of 8-(naphthalen-1-ylmethyl)-6-oxo-2-propyl-7-((tetrahydro-2H-pyran-4-yl)amino)-9-(3-(trifluoromethyl)phenyl)-3,4-dihydro-2H,6H-pyrido[1,2-e][1,2,5] thiadiazine-4-carboxylic acid 1,1-dioxide (Compound 127)

Compound 127

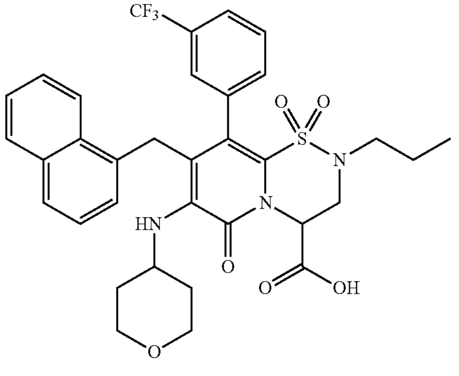

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H, 6H-pyrido[1,2-e][1,2,5]thiadiazine-4-carboxylic acid 1,1-dioxide (Compound 123) using n-propyl amine in step 1 and 4-amino tetrahydropyran in step 2 to give 8-(naphthalen-1-ylmethyl)-6-oxo-2-propyl-7-((tetrahydro-2H-pyran-4-yl) amino)-9-(3-(trifluoromethyl) phenyl)-3,4-dihydro-2H,6H-pyrido[1,2-e][1,2,5]thiadiazine-4-carboxylic acid 1,1-dioxide, (Compound 127) (0.032 g, 34.39%), as an off white solid; Prep HPLC Method 1, LCMS (Method-C3): 100.0% (RT: 1.940, 222.0 nm) (MS: ESI+ve 670.9 [M+H]). $^{1}$H NMR: (400 MHz, DMSO) δ ppm: 0.78-0.79 (d, J=6.8 Hz, 3H), 1.28 (s, 2H), 1.46-1.52 (m, 5H), 2.61-2.66 (t, J=21.2, 2H), 3.08 (s, 3H), 3.92-4.20 (m, 5H), 5.22 (s, 2H), 6.95-7.01 (s, 1H), 7.22-7.46 (m, 7H), 7.73-7.75 (d, J=7.6, 2H), 7.85-7.87 (d, J=7.2, 1H).

Example 91

Synthesis of 7-((cyclopentylmethyl)amino)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 128)

Compound 128

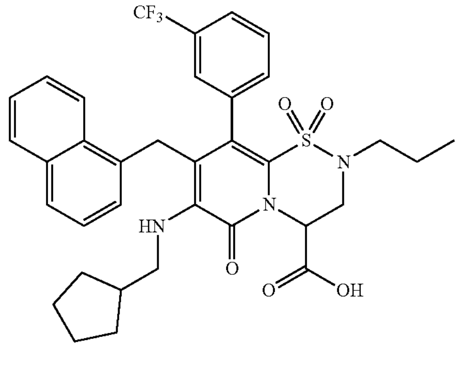

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H, 6H-pyrido[1,2-e][1,2,5]thiadiazine-4-carboxylic acid 1,1-dioxide (Compound 123) using n-propyl amine in step 1 and cyclopentylmethanamine in step 2 to give 7-((cyclopentylmethyl)amino)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 128) as an off white solid (0.12 g, 79.05%), LCMS (Method-C3): 100% (RT: 2.303, 225.0 nm) (MS: ESI+ve 668.95 [M+H]). $^{1}$H NMR: (400 MHz, DMSO) δ ppm: 0.74-0.78 (t, J=14 Hz, 3H), 0.88 (s, 2H), 1.29 (s, 4H), 1.44 (s, 4H), 1.91 (s, 1H), 2.97 (s, 2H), 3.09-3.15 (m, 2H), 3.87-4.02 (m, 2H), 4.09 (s, 2H), 4.93 (s, 1H), 5.60 (s, 1H), 6.99 (s, 1H), 7.16 (s, 1H) 7.30-7.40 (m, 6H), 7.71 (s, 2H), 7.83 (s, 1H).

Example 92

2-cyclohexyl-7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 131)

Compound 131

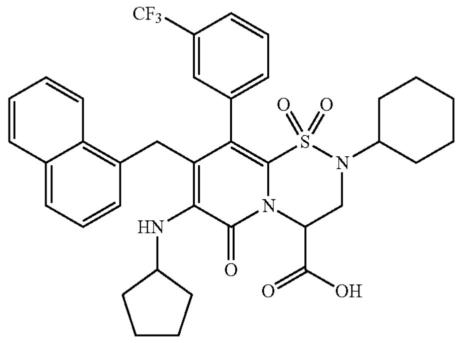

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H, 6H-pyrido[1,2-e][1,2,5]thiadiazine-4-carboxylic acid 1,1-dioxide (Compound 123) using cyclohexyl amine in step 1 and cyclopentylamine in step 2. The crude product was purified using prep HPLC Method 1 to give 2-cyclohexyl-7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 131) (0.028 g, 28.55%). LCMS (Method-C3): 100% (RT 2.284, 202.0 nm) (MS: ESI+ve 694.6 [M+H]). $^{1}$H NMR: (400 MHz, DMSO) δ ppm: 1.06 (m, 1H), 1.23 (m, 3H), 1.35 (m, 3H), 1.44-1.46 (m, 7H), 1.58 (m, 3H), 1.71-1.68 (m, 2H), 3.54 (m, 2H), 3.97-3.93 (m, 2H), 4.10-4.03 (m, 3H), 5.04 (s, 1H), 5.34-5.32 (m, 1H), 6.93 (m, 1H), 7.09-7.14 (m, 1H), 7.27-7.46 (m, 6H), 7.66-7.74 (m, 2H), 7.84-7.86 (d, J=8 Hz, 1H).

Example 93

Synthesis of 7-(isopropylamino)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 149)

Compound 149

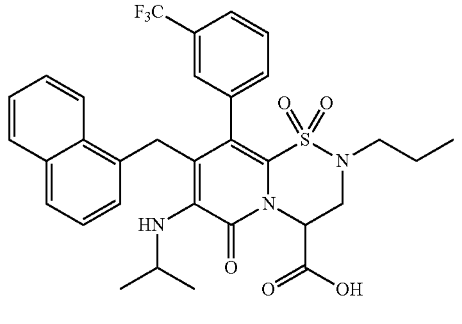

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123) using n-propyl amine in step 1 and 2-propylamine in step 2. The crude product was purified using Prep HPLC Method 1 to give 7-(isopropylamino)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide as a white solid (Compound 149) (0.003 g, 10.22%) LCMS (Method-C3): 33.53% and 66.47% (RT 2.050 and 2.067, 202 nm) (MS: ESI+ve 628 [M+H]). $^1$H NMR: (400 MHz, DMSO) δ ppm: 0.77-0.80 (t, 3H), 0.95-0.99 (t, 6H), 1.46-1.48 (d, J=6.4 Hz, 2H), 2.51 (s, 2H), 3.06-3.08 (d, J=6.4 Hz 2H), 3.81 (s, 1H), 3.93 (s, 1H), 4.05 (s, 2H), 5.13 (s, 1H), 5.29 (s, 1H), 6.94 (s, 1H), 7.13 (s, 1H), 7.30 (s, 1H), 7.34-7.41 (m, 5H), 7.67-7.75 (m, 2H), 7.85-7.87 (d, J=8 Hz, 1H).

Example 94

Synthesis of 2-cyclopentyl-7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 150)

Compound 150

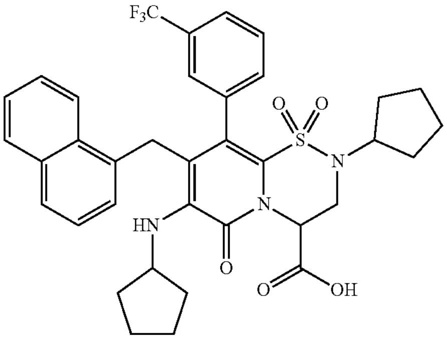

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123) using cyclopentylamine in step 1 and cyclopentylamine in step 2. The crude product was purified using Prep HPLC Method 1 to give 2-cyclopentyl-7-(cyclopentylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as a white solid (0.003 g, 12.76%). (Compound 150) LCMS (Method-C3): 39.49% and 55.60% (RT 2.227 and 2.251, 220 nm) (MS: ESI+ve 680 [M+H]). $^1$H NMR: (400 MHz, DMSO) δ ppm: 1.35-1.47 (m, 17H), 3.98 (s, 4H), 4.12 (s, 1H), 5.34-5.36 (d, J=8.4 Hz, 1H), 5.48 (s, 1H), 6.93-6.98 (m, 1H), 7.135 (s, 1H), 7.28-7.48 (m, 6H), 7.68-7.75 (m, 2H), 7.85-7.87 (d, J=8 Hz, 1H).

Example 95

Synthesis of 7-(cyclopentylamino)-2-isobutyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 145)

Compound 145

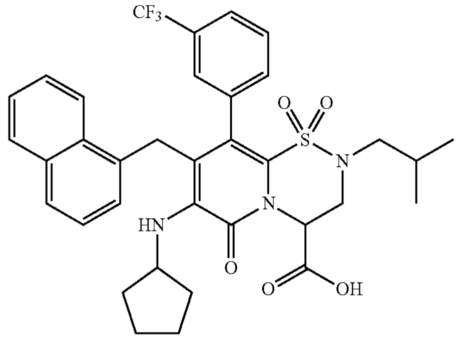

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123) using 2-methylpropan-1-amine in step 1 and cyclopentylamine in step 2. The crude product was purified using Prep HPLC Method 1 to give 7-(cyclopentylamino)-2-isobutyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as a white solid (0.005 g, 14.59%). (Compound 145) LCMS (Method-C3): 100% (RT 2.217, 202.0 nm) (MS: ESI+ve 668.6 [M+H]). $^1$H NMR: (400 MHz, DMSO) δ ppm: 0.78-0.85 (t, 6H), 1.23 (s, 2H), 1.35 (s, 2H), 1.48 (s, 2H), 1.58 (s, 2H), 1.75-1.78 (t, 1H), 2.83-2.92 (m, 2H), 3.93-3.97 (d, J=17.6 Hz, 2H), 4.02-4.11 (t, 2H), 4.18-4.22 (t, 1H), 5.26 (s, 1H), 5.34-5.36 (d, J=8.8 Hz, 1H), 6.92-6.99 (m, 1H), 7.15 (s, 1H), 7.29-7.33 (t, 1H), 7.37-7.46 (m, 5H), 7.68-7.74 (m, 2H), 7.84-7.86 (d, J=8 Hz, 1H), 13.77 (s, 1H).

Example 96

Synthesis of 7-isobutyramido-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 152)

Compound 152

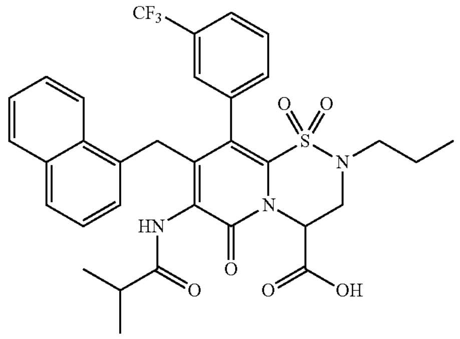

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123) using n-propylamine in step 1 and isobutyramide in step 2. The crude product was purified using Prep HPLC Method 1 to give 7-isobutyramido-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide as a white solid (0.040 g, 13.62%) (Compound 152). LCMS (Method-C3): 100% (RT: 1.819, 225 .0 nm) (MS: ESI+ve 657 [M+H]). $^{1}$H NMR: (400 MHz, DMSO) δ ppm: 0.75-0.78 (t, 3H); 0.86 (s, 3H); 0.93-0.97 (t, 3H); 1.23 (s, 1H); 1.43-1.48 (m, 2H); 3.08-3.10 (d, J=7.2 Hz, 2H); 3.90-3.97 (t, 1H); 4.03-4.12 (t, 2H); 4.22-4.25 (d, J=11.2 Hz, 1H); 5.237 (s, 1H); 6.84-6.95 (m, 2H); 7.26-7.32 (m, 5H); 7.406 (s, 1H); 7.49-7.51 (d, J=7.2 Hz, 1H); 7.69 (s, 1H); 7.80 (s, 1H); 9.48 (s, 1H); 13.81 (s, 1H).

Example 97

Synthesis of 7-isobutyramido-8-(naphthalen-1-ylmethyl)-6-oxo-2-propyl-9-(3 (trifluoromethyl)phenyl)-3,4-dihydro-2H,6H-pyrido[1,2-e][1,2,5]thiadiazine-4carboxylic acid 1,1-dioxide (Compound 153)

Compound 153

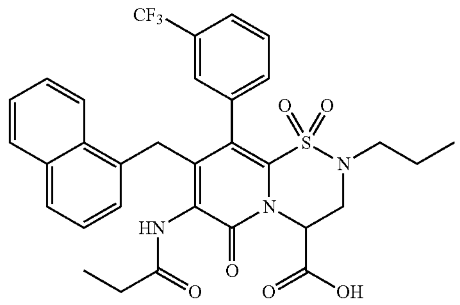

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123) using n-propylamine in step 1 and propionamide in step 2. The crude product was purified using Prep HPLC Method 1 to give 8-(naphthalen-1-ylmethyl)-6-oxo-7-propionamido-2-propyl-9-(3-(trifluoromethyl)phenyl)-3,4-dihydro-2H,6H-pyrido[1,2-e][1,2,5]thiadiazine-4-carboxylic acid 1,1-dioxide as a white solid (0.165 g, 29.5%). LCMS (Method-C3): 100% (RT: 2.174, 254.0 nm) (MS: ESI+ve 642.2 [M+H]). $^{1}$H NMR: (400 MHz, DMSO) δ ppm: 0.79-0.82 (m, 3H); 0.93-0.96 (q, J=12 Hz 3H); 1.47-1.53 (m, 2H); 2.23-2.26 (t, J=12 Hz, 2H); 3.13-3.16 (t, J=12 Hz, 2H); 3.96-4.16 (m, 3H); 4.25-4.33 (m, 1H); 5.26-5.31 (d, J=20 Hz, 1H); 6.91-6.99 (t, J=32 Hz, 2H); 7.29-7.46 (m, 5H); 7.53-7.56 (d, J=12 Hz, 1H), 7.72-7.75 (m, 1H), 7.83-7.86 (m, 2H), 9.55-9.60 (d, J=20 Hz, 2H).

Example 98

Synthesis of 8-(naphthalen-1-ylmethyl)-6-oxo-7-(2-oxopyrrolidin-1-yl)-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 151)

Compound 151

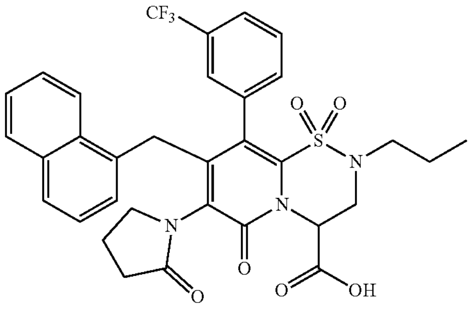

Prepared by a procedure similar to that described for 7-(cyclopentylamino)-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 123) using n-propylamine in step 1 and pyrrolidin-2-one in step 2. The crude product was purified using Prep HPLC Method 1 to give 8-(naphthalen-1-ylmethyl)-6-oxo-7-(2-oxopyrrolidin-1-yl)-2-propyl-9-(3-(trifluoromethyl)phenyl)-3,4-dihydro-2H,6H-pyrido[1,2-e][1,2,5]thiadiazine-4-carboxylic acid 1,1-dioxide as a white solid (0.03 g, 13.93%)(Compound 151). LCMS (Method-C3): 52.36% and 1.773 (RT: 1.719 and 1.773, 225.0 nm) (MS: ESI+ve 654.43 [M+H]). $^{1}$H NMR: (400 MHz, $CD_3OD$) δ ppm: 0.89-0.92 (t, 3H), 1.57-1.63 (m, 2H), 1.99-2.05 (m, 2H), 2.20-2.24 (m, 1H), 2.39-2.46 (m, 1H), 2.68-3.00 (m, 2H), 3.25-3.28 (t, 2H), 3.82-3.96 (m, 2H), 4.19-4.34 (m, 2H), 5.30-5.35 (d, J=18.4 Hz, 1H), 7.12-7.23 (m, 1H), 7.28-7.46 (m, 6H), 7.56 (s, 1H), 7.63-7.67 (t, 1H), 7.73-7.75 (d, J=8 Hz, 1H), 7.81-7.83 (d, J=7.6 Hz, 1H).

Example 99

Synthesis of 2-methyl-7-morpholino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 079)

Compound 079

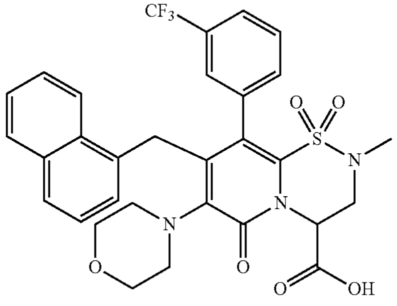

Step 1: Preparation of methyl 7-bromo-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

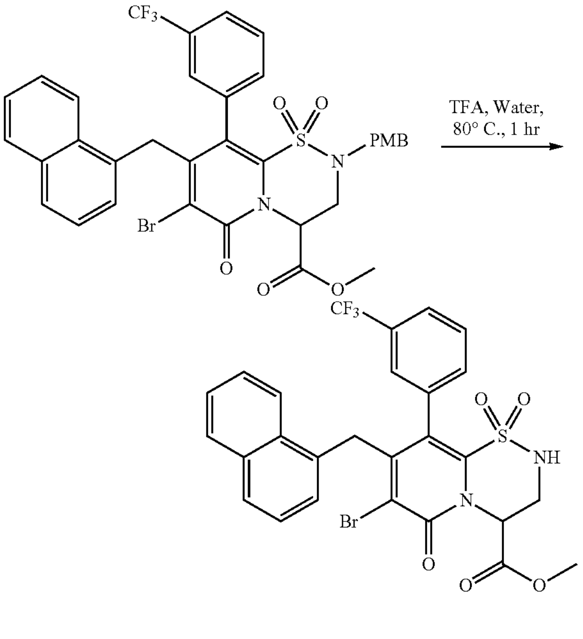

Methyl7-bromo-2-(4-methoxybenzyl)-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylate 1,1-dioxide (9 g, 12.14 mmol) was added to a mixture of TFA (30 mL) and water (3 mL). The reaction mixture was stirred for 1 h at 80° C. then quenched in saturated aqueous sodium bicarbonate (500 mL). The mixture was extracted with ethyl acetate (2×30 mL) and the organic layer was dried and concentrated to give methyl 7-bromo-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (7.5 g, 99.45%). LCMS (Method-C3): 100.0% (RT: 1.994, 230.0 nm) (MS: ESI+ve 623.56 [M+H]).

Step 2: Preparation of methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

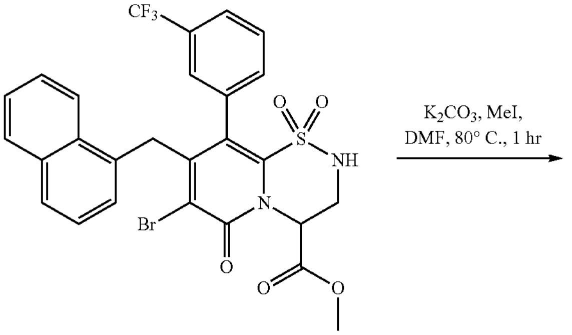

-continued

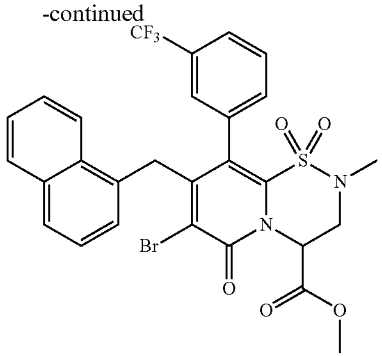

Methyl 7-bromo-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (2.2 g, 3.54 mmol) was dissolved in DMF (10 mL), methyl iodide (0.32 mL, 5.31 mmol) and potassium carbonate was added (0.73 g, 5.31 mmol) and the mixture was stirred at 80° C. for 1 h. The reaction was quenched in ice water (20 mL) and extracted into ethyl acetate (3×15 mL). The organic layers were dried over sodium sulphate and concentrated under reduced pressure. The crude residue was purified by column chromatography eluting with 30-40% ethyl acetate/hexane to give methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate1,1-dioxide (1.5 g, 66.68%). LCMS (Method-C3): 76.85% (RT: 24.65, 223.0 nm) (MS: ESI+ve 635.1 [M+H]). $^1$H NMR: (400 MHz, DMSO) δ ppm: 1.17-1.25 (m, 2H), 2.00 (s, 1H), 2.83-2.87 (d, J=16 Hz, 3H), 3.70 (s, 2H), 3.81 (s, 3H), 4.01-4.36 (m, 5H), 5.41 (s, 1H), 5.41-5.42 (d, J=4 Hz, 1H), 6.80 (s, 1H), 6.93-7.06 (m, 2H), 7.27-7.30 (d, J=12 Hz, 1H), 7.40-7.47 (m, 5H), 7.64 (s, 1H), 7.78-7.80 (d, J=8 Hz, 1H), 7.87-7.89 (d, J=8 Hz, 1H).

Step-3: Preparation of methyl 2-methyl-7-morpholino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

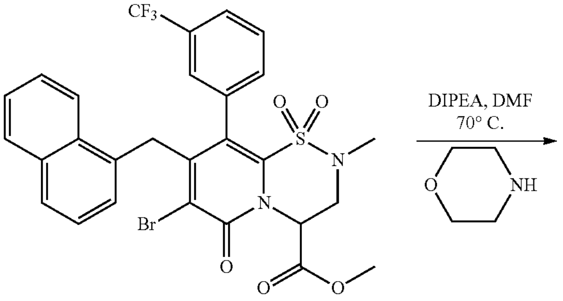

-continued

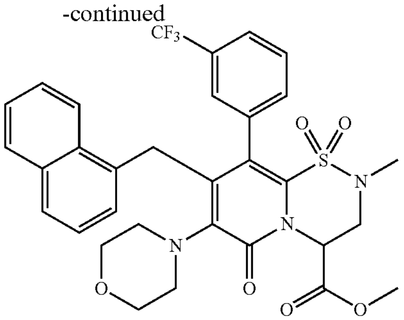

Methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.3 g, 0.47 mmol), morpholine (0.082 g, 0.94 mmol) and DIPEA (0.268 g, 2.07 mmol) in DMF (2 mL) and was stirred at 70° C. for 24 h. The reaction was quenched in ice water (50 mL) and extracted with ethyl acetate (3×50 mL). The organic layer was dried over sodium sulphate and concentrated under reduced pressure to give the crude product which was purified by column chromatography eluting with 0-40% ethyl acetate/hexane to give methyl 2-methyl-7-morpholino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a yellow solid (0.08 g, 27%). LCMS (Method-C3): 68.82% (RT 1.979, 226.0 nm) (MS: ESI+ve 641.43 [M+H]), which was used without further purification.

Step-4: Preparation of 2-methyl-7-morpholino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 079)

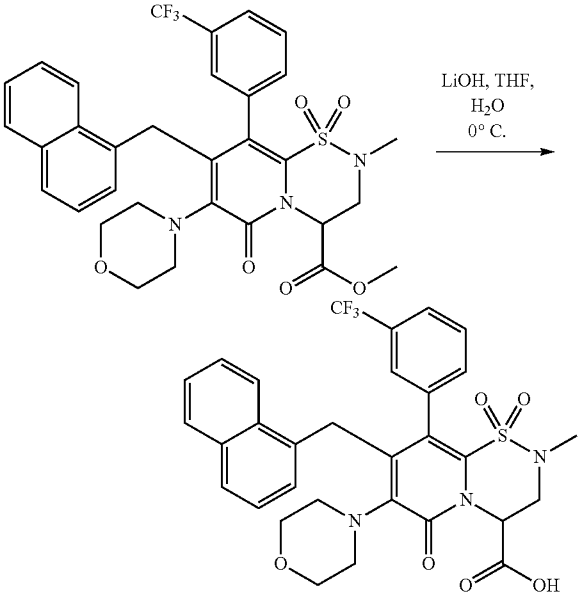

Compound 079

Methyl 2-methyl-7-morpholino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.08 g, 0.12 mmol) was dissolved in THF:MeOH (3:1, 4.0 mL). LiOH—$H_2O$ (0.02 g, 0.49 mmol) in (0.1 mL) $H_2O$ was added and the reaction mixture was stirred at room temperature for 2 h. The mixture was concentrated and cold water (10 mL) was added followed by 1N HCl (3-4 mL). The resulting precipitate was collected by filtration and purified using Prep HPLC Method 1 to give 2-methyl-7-morpholino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 079) (0.009 g, 11.50%). LCMS (Method-C3): 95.44% (RT 5.181, 202.4 nm)(MS: ESI+ve 628.2 [M+H]). $^{1}$H NMR: (400 MHz, DMSO) δ ppm: 2.83-2.88 (s, 3H), 3.00 (bs, 4H), 3.56 (m, 4H), 4.072-4.17 (m, 2H), 4.21-4.39 (m, 2H), 5.17-5.18 (d, J=6.4 Hz, 1H), 6.80-6.86 (q, 1H), 7.13-7.27 (m, 2H), 7.32-7.45 (m, 5H), 7.67-7.73 (m, 2H), 7.81-7.83 (d, J=8 Hz, 1H).

Example 100

Synthesis of 7-(cyclopentylamino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 070)

Compound 070

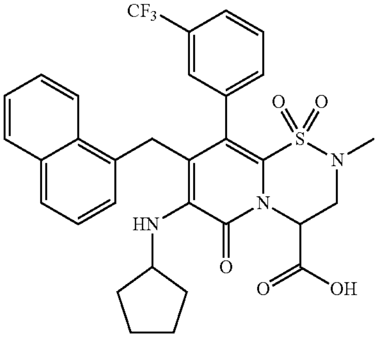

Step 1: Preparation of methyl 7-(cyclopentylamino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

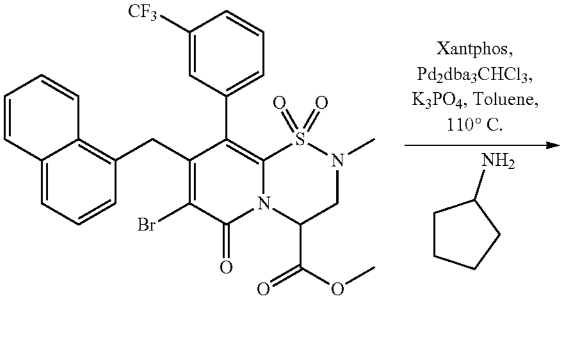

-continued

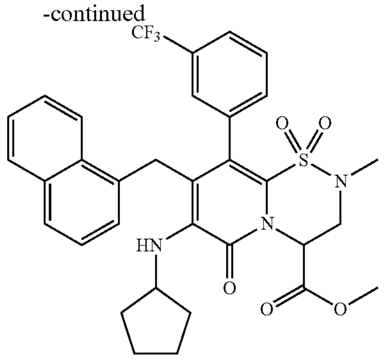

Methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (2.4 g, 3.776 mmol) was dissolved in dry toluene (50 mL), and the mixture was degassed with Argon. Potassium phosphate (1.207 g, 5.669 mmol). Xantphos (0.174 g, 0.3023 mmol) tris(dibenzylideneacetone)dipalladium-chloroform adduct (0.156 g, 0.151 mmol) and cyclopentanamine were added and the mixture was heated at 110° C. for 6 h under argon. The reaction was quenched in water (50 mL) and extracted with ethyl acetate (2×40 mL). The organic layer was dried over sodium sulphate and concentrated under reduced pressure to give the crude product which was purified using column chromatography eluting with 20-30% ethyl acetate/hexane to give methyl 7-(cyclopentylamino)-2-methyl-8-(naphthalen-1-ylmethyl)-6-oxo-9-(3-(trifluoromethyl) phenyl)-3,4-dihydro-2H,6H-pyrido[1,2-e][1,2,5] thiadiazine-4-carboxylate 1,1-dioxide (0.66 g, 27.32%). LCMS (Method-C3): 100% (RT 2.551, 202.0 nm) (MS: ESI+ve 640.0 [M+1]).

Step 2: Preparation of 7-(cyclopentylamino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 070)

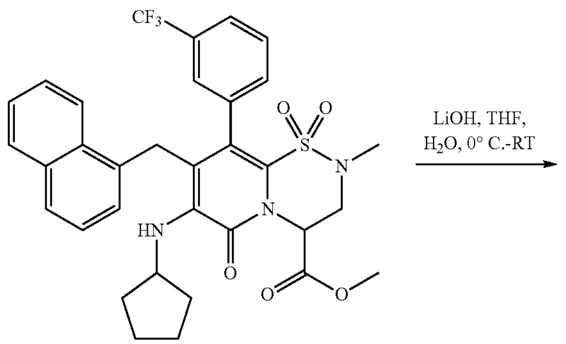

-continued

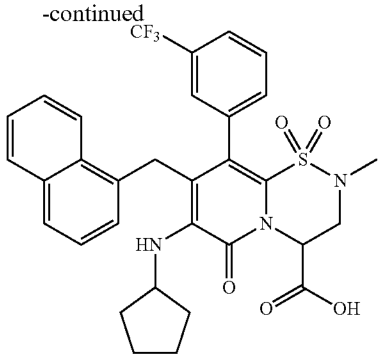

Compound 070

Methyl7-(cyclopentylamino)-2-methyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylate 1,1-dioxide (0.66 g, 1.031 mmol) was dissolved in THF: $H_2O$ (1:1, 10 mL) at room temperature. LiOH—$H_2O$ (0.169 g, 7.764 mmol) was added at 0° C. and the mixture was stirred at room temperature for 4 h. The mixture was concentrated then cold water (10 mL) and 1N aqueous HCl solution (7-8 mL) were added. The resulting solid was collected by filtration and dried under vacuum. to give 7-(cyclopentylamino)-2-methyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide (Compound 070) as a white solid (0.53 g, 82.10%). LCMS (Method-D) 97.01% (RT 7.150, 335.0 nm) (MS: ESI+ve 626.0 [M+H]). $^1H$ NMR: (400 MHz, DMSO) δ ppm: 1.16-1.59 (m, 8H), 2.80 (s, 3H), 3.96-4.25 (m, 5H), 5.26 (s, 2H), 6.93-7.00 (m, 1H), 7.15 (s, 1H), 7.30-7.44 (m, 6H), 7.72-7.74 (d, J=8 Hz, 2H), 7.84-7.86 (d, J=8 Hz, 1H), 13.628 (s, 1H).

Synthesis of 2-methyl-8-(naphthalen-1-ylmethyl)-6-oxo-7-(phenylamino)-9-(3-(trifluoromethyl)phenyl)-3,4-dihydro-2H,6H-pyrido[1,2-e][1,2,5]thiadiazine-4-carboxylic acid 1,1-dioxide (Compound 071)

Compound 071

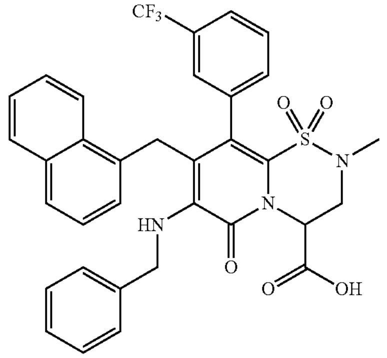

Prepared by a procedure similar to that reported for 7-(cyclopentylamino)-2-methyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide (Compound 070) substituting benzyl amine in step 1.

The crude product was purified using Prep HPLC Method 1 to give 2-methyl-8-(naphthalen-1-ylmethyl)-6-oxo-7-(phenylamino)-9-(3-(trifluoromethyl)phenyl)-3,4-dihydro-2H,6H-pyrido[1,2-e][1,2,5]thiadiazine-4-carboxylic acid 1,1-dioxide (Compound 071) (0.026 g, 38.2%) LCMS (Method-C3): 100% (RT 1.900, 202 nm) (MS: ESI+ve 648.38[M+H]). $^1$H NMR: (400 MHz, DMSO) δ: 2.80 (s, 3H), 3.77-3.85 (t, J=12 Hz, 1H), 4.00-4.09 (m, 1H), 3.95-4.09 (m, 2H), 4.20-4.26 (m, 2H), 5.26-5.27 (s, 1H), 6.39-6.40 (d, J=6 Hz, 1H), 6.85-6.95 (m, 1H), 7.069 (m, 3H), 7.18-7.24 (m, 3H), 7.26-7.34 (m, 1H), 7.33-7.36 (m, 3H), 7.38 (m, 2H), 7.72-7.74 (d, J=8.4 Hz, 1H), 7.836 (d, J=8 Hz, 1H), 13.64 (s, 1H).

Example 101

Synthesis of 2-methyl-8-(naphthalen-1-ylmethyl)-6-oxo-7-((tetrahydro-2H-pyran-4-yl)amino)-9-(3-(trifluoromethyl)phenyl)-3,4-dihydro-2H,6H-pyrido[1,2-e][1,2,5]thiadiazine-4-carboxylic acid 1,1-dioxide (Compound 072)

Compound 072

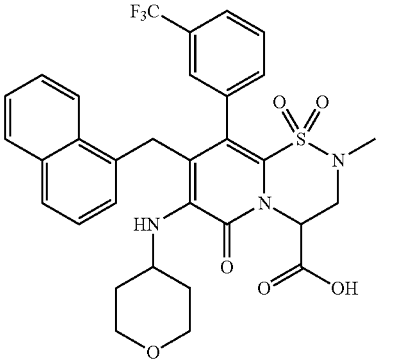

Prepared by a procedure similar to that reported for 7-(cyclopentylamino)-2-methyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide (Compound 070) substituting tetrahydro-2H-pyran-4-amine in step 1. The crude product was purified using Prep HPLC Method 1 to give 2-methyl-8-(naphthalen-1-ylmethyl)-6-oxo-7-((tetrahydro-2H-pyran-4-yl)amino)-9-(3-(trifluoromethyl)phenyl)-3,4-dihydro-2H,6H-pyrido[1,2-e][1,2,5]thiadiazine-4-carboxylic acid 1,1-dioxide (Compound 072) (8 mg, 1.02%) LCMS (Method-C3): 100% (RT 1.849, 230 nm) (MS: ESI+ve 642.4 [M+H]). $^1$HNMR: (400 MHz, DMSO) δ: 1.32 (2H, m), 1.54-1.66 (2H, m), 2.62-2.71 (2H, m), 2.83 (2H, s), 3.61 (3H, s), 4.22-4.26 (2H, m), 4.22-4.22 (1H, m), 5.23 (1H, m), 5.33-5.29 (1H, m), 7.04-6.96 (1H, m), 7.24 (1H, s), 7.50-7.32 (5H, m), 7.77-7.75 (2H, d, J=8), 7.89-7.87 (d, 1H, J=7.6).

Example 102

Synthesis of 2-methyl-8-(naphthalen-1-ylmethyl)-6-oxo-7-(piperidin-4-ylamino)-9-(3-(trifluoromethyl)phenyl)-3,4-dihydro-2H,6H-pyrido[1,2-e][1,2,5]thiadiazine-4-carboxylic acid 1,1-dioxide (Compound 091)

Compound 091

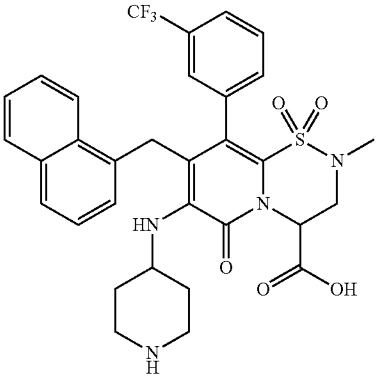

Step 1: preparation of methyl 7-((1-(tert-butoxycarbonyl)piperidin-4-yl)amino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

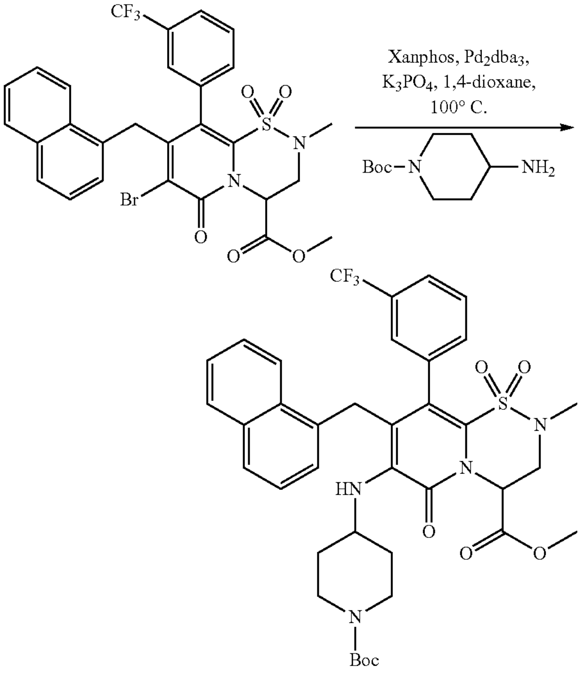

A mixture of methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.6 g, 0.94 mmol), tert-butyl 4-aminopiperidine-1-carboxylate (0.227 g, 1.1 mmol) and $K_3PO_4$ (0.250 g, 2.3 mmol) was dissolved in 1,4-dioxane (2.0 ml) and the reaction mixture was purged with nitrogen. $Pd_2(dba)_3$ $CHCl_3$ (0.02 g, 0.03 mmol) and Xanthphos (0.022 g, 0.03 mmol) were added and the reaction mixture was stirred at 100° C. for 16 h. The reaction was quenched with water (20 mL) and extracted with ethyl acetate (3×20 mL). The organic layer was dried over sodium sulphate and concentrated. The crude product was purified using column flash chromatography to give methyl 7-((1-(tert-butoxycarbonyl) piperidin-4-yl)amino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a brown solid (0.2 g, 28%).LCMS (Method-C3): 42% (RT 2.257, 225 nm) (MS: ESI+ve 755.2[M+H]).

Step-2: -preparation of 7-((1-(tert-butoxycarbonyl) piperidin-4-yl)amino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide

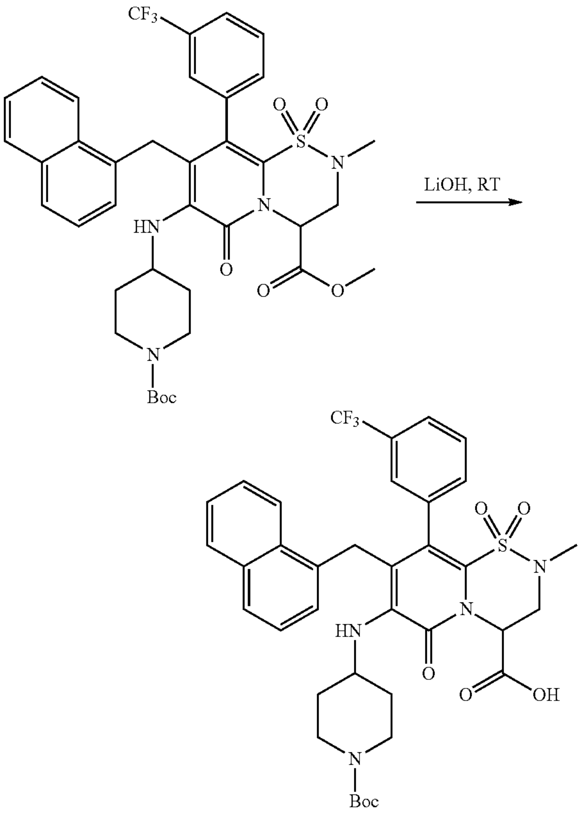

Methyl 7-((1-(tert-butoxycarbonyl)piperidin-4-yl) amino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.2 g, 0.26 mmol) was dissolved in THF:$H_2O$ (2 ml, 2:1). LiOH (0.04 g 1 mmol) was added and the mixture was stirred at room temperature for 4 h. The reaction mixture was acidified with 0.1 N HCl and the resulting solid was collected by filtration to give 7-((1-(tert-butoxycarbonyl)piperidin-4-yl)amino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (0.175 g, 100%). LCMS (Method-C3)(Crude): 36.82% (RT: 2.570, 214 nm) (MS+ve 741 [M+H]).

Step-3: Preparation of 2-methyl-8-(naphthalen-1-ylmethyl)-6-oxo-7-(piperidin-4-ylamino)-9-(3-(trifluoromethyl)phenyl)-3,4-dihydro-2H,6H-pyrido[1,2-e][1,2,5]thiadiazine-4-carboxylic acid 1,1-dioxide (Compound 091)

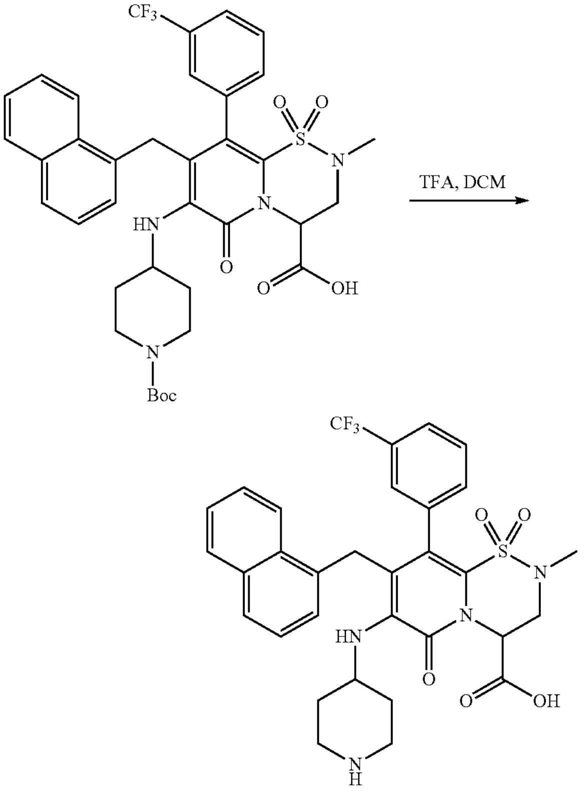

Compound 091

7-((1-(tert-butoxycarbonyl)piperidin-4-yl)amino)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (0.175 g, 0.09 mmol) was dissolved in DCM (1 mL) and cooled to 0° C. TFA (0.5 ml) was added and the mixture was allowed to slowly warm to room temperature over 4 h. The reaction mixture was concentrated and the crude residue was purified using Prep HPLC Method 1 to give 2-methyl-8-(naphthalen-1-ylmethyl)-6-oxo-7-(piperidin-4-ylamino)-9-(3-(trifluoromethyl)phenyl)-3,4-dihydro-2H,6H-pyrido[1,2-e][1,2,5]thiadiazine-4-carboxylic acid 1,1-dioxide as a white solid (0.012 g, 9.5%) (Compound 091). LCMS (Method $C_3$): 100% (RT 1.828, 225 nm) (MS: ESI+ve 641 [M+H]). $^1H$ NMR: (400 MHz, DMSO) δ ppm: 1.18-1.85 (m, 6H), 2.91-2.95 (m, 5H), 4.00-4.19 (m, 4H), 4.85-4.87 (d, J=4.8 Hz, 1H), 5.88-5.96 (d, J=28.4 Hz, 1H), 6.92-7.04 (m, 1H), 7.17 (s, 1H), 7.31-7.51 (m, 6H), 7.73-7.90 (m, 3H), 8.39 (s, 1H).

Example 103

Synthesis of 2-methyl-8-(naphthalen-1-ylmethyl)-6-oxo-7-(piperazin-1-yl)-9-(3-(trifluoromethyl)phenyl)-3,4-dihydro-2H,6H-pyrido[1,2-e][1,2,5]thiadiazine-4-carboxylic acid 1,1-dioxide (Compound 102)

Compound 102

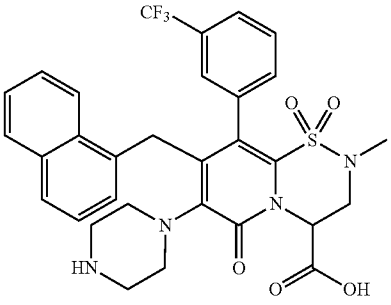

Prepared by a method similar to that reported for 2-methyl-8-(naphthalen-1-ylmethyl)-6-oxo-7-(piperidin-4-ylamino)-9-(3-(trifluoromethyl)phenyl)-3,4-dihydro-2H, 6H-pyrido[1,2-e][1,2,5]thiadiazine-4-carboxylic acid 1,1-dioxide (Compound 091), substituting tert-butyl piperazine-1-carboxylate I step 1. The crude product was purified using Prep HPLC Method 1 to give 2-methyl-8-(naphthalen-1-ylmethyl)-6-oxo-7-(piperazin-1-yl)-9-(3-(trifluoromethyl) phenyl)-3,4-dihydro-2H,6H-pyrido[1,2-e][1,2,5]thiadiazine-4-carboxylic acid 1,1-dioxide as a white solid (0.0075 g, 23%) (Compound 102). LCMS: 94.62% (RT: 1.561, 227.0 nm) (MS: ESI+ve 627.53 [M+H]). $^1$H NMR: (400 MHz, $CD_3OD$) δ ppm: 2.829 (bs, 4H), 3.01-3.00 (d, J=2.4 Hz, 3H), 4.26-4.25 (d, J=4.4, 2H), 4.31-4.30 (d, J=7.6, 1H), 4.35-4.34 (d, J=5.2, 1H), 4.66 (s, 4H), 5.11-5.10 (t, J=4.4, 1H), 7.12-7.09 (t, J=6 Hz, 1H), 7.25-7.23 (t, J=7.6 Hz, 1H), 7.49-7.33 (m, 6H), 7.72-7.70 (d, 8.4 Hz, 1H), 7.84-7.80 (t, J=7.2 Hz, 2H).

Example 104

Synthesis of 6-amino-7-(naphthalen-1-ylmethyl)-5-oxo-8-(3-(trifluoromethyl)phenyl)-5H-thiazolo[3,2-a]pyridine-3-carboxylic acid (Compound 050)

Compound 050

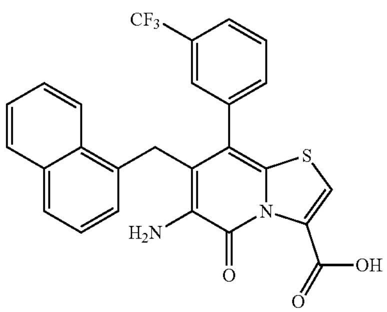

Step-1: Preparation of methyl 2-bromo-7-(naphthalen-1-ylmethyl)-6-nitro-5-oxo-8-(3-(trifluoromethyl) phenyl)-5H-thiazolo[3,2-a]pyridine-3-carboxylate

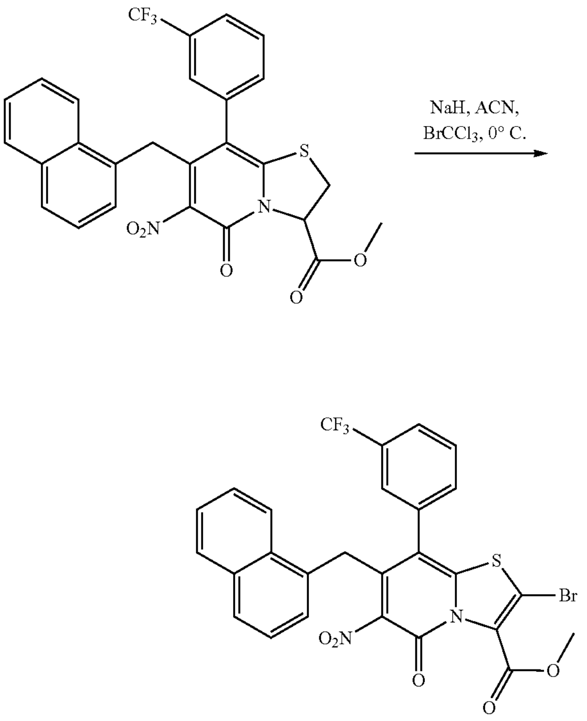

7-(Naphthalen-1-ylmethyl)-6-nitro-5-oxo-8-(3-(trifluoromethyl)phenyl)-2,3-dihydro-5H-thiazolo[3,2-a]pyridine-3-carboxylate (0.25 g, 0.462 mmol) was dissolved in dry acetonitrile (18 mL) and cooled to 0° C. Sodium hydride (0.046 g, 1.156 mmol) was added in portions and the mixture was stirred for 10 min. Bromotrichloromethane (0.137 g, 0.693 mmol) was added dropwise at 0° C. and the mixture was stirred for 20 min. The reaction was quenched with ice water (50 mL), extracted with ethyl acetate (3×50 mL) and the organic layer was dried over sodium sulphate and concentrated under reduced pressure to give the crude product which was purified using column chromatography eluting with 0-40% ethyl acetate/hexane to give methyl 2-bromo-7-(naphthalen-1-ylmethyl)-6-nitro-5-oxo-8-(3-(trifluoromethyl)phenyl)-5H-thiazolo[3,2-a]pyridine-3-carboxylate (0.13 g, 45.52%). LCMS (Method-C3): 95.22% (RT: 2.079, 224.0 nm) (MS: ESI+ve 617.04 [M+0]). $^1$H NMR: (400 MHz, DMSO) δ ppm: 3.98 (s, 3H), 4.24 (s, 2H), 7.22-7.24 (d, J=6.8 Hz, 1H), 7.34-7.36 (d, J=8 Hz, 1H), 7.38-7.59 (m, 6H), 7.75-7.79 (t, 2H), 7.85-7.87 (d, J=8 Hz, 1H).

Step 2: Preparation of methyl 6-amino-7-(naphthalen-1-ylmethyl)-5-oxo-8-(3-(trifluoromethyl)phenyl)-5H-thiazolo[3,2-a]pyridine-3-carboxylate

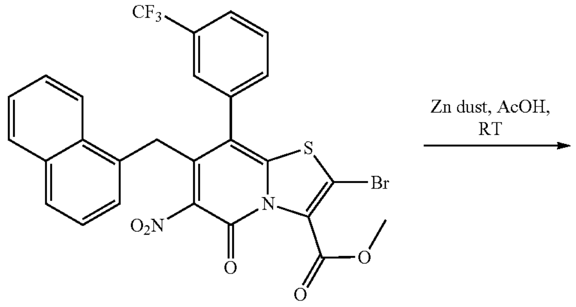

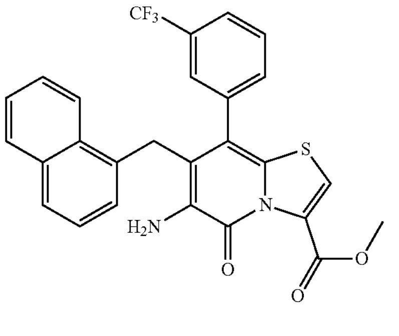

Methyl 2-bromo-7-(naphthalen-1-ylmethyl)-6-nitro-5-oxo-8-(3-(trifluoromethyl)phenyl)-5H-thiazolo[3,2-a]pyridine-3-carboxylate (0.21 g, 0.34 mmol) was dissolved in acetic acid (3.5 mL) at room temperature. Activated zinc dust (0.111 g, 1.701 mmol) was added in portions at room temperature and the mixture was stirred at room temperature for 16 h. The reaction mixture was filtered through a pad of Celite and rinsed with dichloromethane. The filtrate was concentrated, diluted with ice and sat. aq. sodium bicarbonate (20 mL), and extracted with DCM (3×50 mL). The organic layer was concentrated and the crude product was purified using column chromatography eluting with 0-50% ethyl acetate/hexane to give methyl 6-amino-7-(naphthalen-1-ylmethyl)-5-oxo-8-(3-(trifluoromethyl)phenyl)-5H-thiazolo[3,2-a]pyridine-3-carboxylate (0.17 g, 98.29%) as a yellow solid. LCMS (Method-C3): 95.27% (RT: 2.038, 225.0 nm) (MS: ESI+ve 509.29[M+H]). $^1$H NMR: (400 MHz, DMSO) δ ppm: 3.84 (s, 3H), 4.00-4.17 (m, 2H), 5.69 (s, 2H), 6.91 (s, 1H), 7.31-7.55 (m, 7H), 7.67-7.72 (m, 2H), 7.82-7.85 (m, 2H).

Step 3: Preparation of 6-amino-7-(naphthalen-1-ylmethyl)-5-oxo-8-(3-(trifluoromethyl)phenyl)-5H-thiazolo[3,2-a]pyridine-3-carboxylic acid (Compound 050)

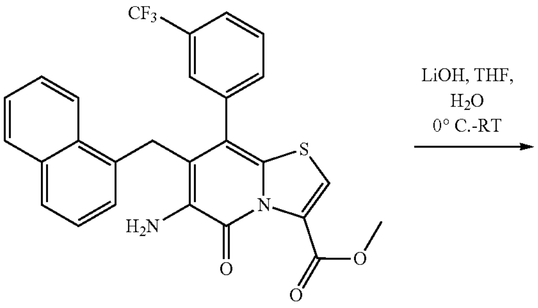

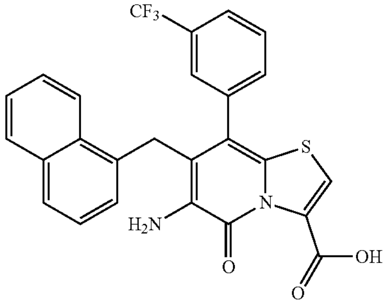

Compound 050

Methyl 6-amino-7-(naphthalen-1-ylmethyl)-5-oxo-8-(3-(trifluoromethyl)phenyl)-5H-thiazolo[3,2-a]pyridine-3-carboxylate (0.170 g, 0.334 mmol) was dissolved in THF:$H_2O$ (1:1, 10 mL). LiOH—$H_2O$ (0.047 g 1.12 mmol) was added and the mixture was stirred at room temperature for 4 h. The mixture was concentrated then cold water (10 mL) was added followed by 1N aqueous HCl solution (3-4 mL). The resulting precipitate was collected by filtration and purified using Prep HPLC Method 1 to give 6-amino-7-(naphthalen-1-ylmethyl)-5-oxo-8-(3-(trifluoromethyl)phenyl)-5H-thiazolo[3,2-a]pyridine-3-carboxylic acid (Compound 050), as an off white solid (0.030 g, 20.57%). LCMS (Method-C3): 100% (RT 1.933, 225 nm) (MS: ESI+ve 495.16 [M+H]). $^1$H NMR: (400 MHz, DMSO) δ ppm: 4.14-4.27 (q, 2H), 5.22 (s, 2H), 6.93-6.95 (d, J=7.2 Hz, 1H), 7.30-7.34 (t, 1H), 7.38 (s, 1H), 7.42-7.54 (m, 4H), 7.60-7.61 (d, J=6 Hz, 1H), 7.73-7.75 (d, J=8.4 Hz, 1H), 7.85-7.88 (t, 2H), 8.09 (s, 1H).

Example 105

Synthesis of 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 058)

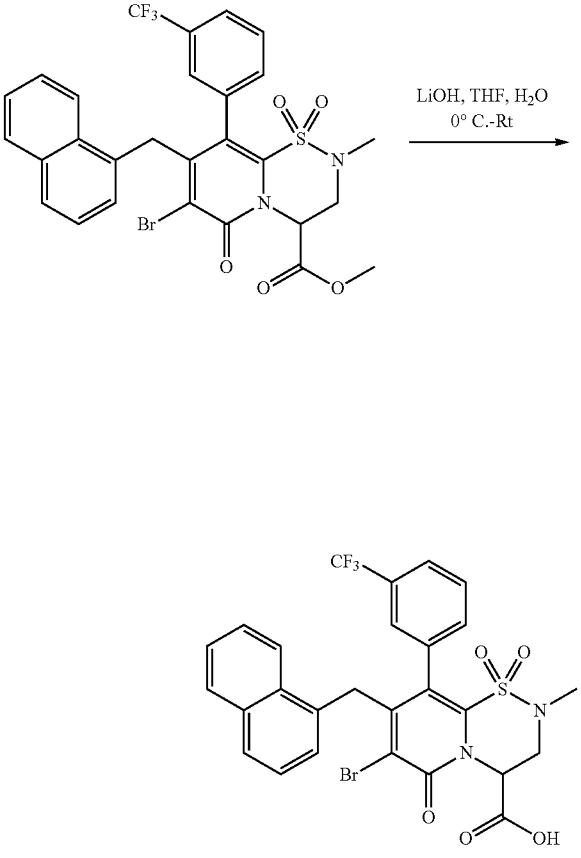

Compound 058

Methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.150 g, 0.2362 mmol) was dissolved in tetrahydrofuran (3 mL). Lithium hydroxide (0.039 g, 0.9448 mmol) in water (3 mL) was added and the mixture was stirred at room temperature for 16 h. The reaction mixture was concentrated and water and 1N aqueous HCl solution (5 mL) were added. The resulting solid was collected by filtration and rinsed with water. The solid was dissolved in dichloromethane and concentrated. The crude product was purified using Prep HPLC Method 1 to give 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 058) (15.2 mg, 11.2%), as a white solid. LCMS (Method-J): 100% (RT—5.203, 202.0 nm) (MS: ESI+ve 623.1 [M+2]). 1H NMR: (400 MHz, DMSO) δ ppm: 2.883 (s, 3H), 4.31-4.11 (m, 4H), 5.17-5.17 (d, J=3.2 Hz, 1H), 7.06-6.91 (m, 2H), 7.31-7.22 (m, 2H), 7.49-7.36 (m, 4H), 7.64-7.62 (d, J=8 Hz, 1H), 7.77-7.75 (d, J=8 Hz, 1H), 7.86-7.84 (d, J=8 Hz, 1H).

Example 106

Synthesis of 7-bromo-8-(naphthalen-1-ylmethyl)-6-oxo-2-propyl-9-(3-(trifluoromethyl) phenyl)-3,4-dihydro-2H,6H-pyrido[1,2-e][1,2,5]thiadiazine-4-carboxylic acid 1,1-dioxide (Compound 107)

Compound 107

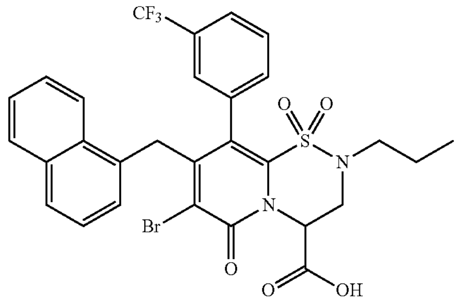

Step 1: Preparation of methyl 7-bromo-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

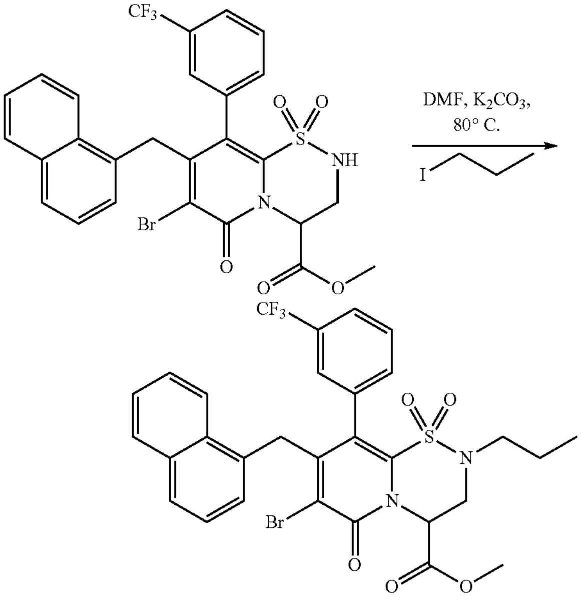

Methyl 7-bromo-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide and (0.2 g, 0.3220 mmol) and propyl iodide (0.082 g, 0.4830 mmol) was dissolved in DMF (3 mL) and $K_2CO_3$ was added (0.066 g, 0.4830 mmol). The resulting mixture was stirred at 80° C. 1 h. The reaction was quenched with ice water (10 mL) and extracted with ethyl acetate (3×15 mL). The organic layers were combined and dried over sodium sulphate. The solvent was removed under reduced pressure and the crude product was purified using column chromatography eluting with 20-30% ethyl acetate/hexane to give methyl 7-bromo-8-

(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide as a brown solid (0.075 g, 35.12%).LCMS (Method-C3): 81.48% (RT: 2.215, 226.0 nm) (MS: ESI+ve 665.8 [M+H]).

Step 2: Preparation of 7-bromo-8-(naphthalen-1-ylmethyl)-6-oxo-2-propyl-9-(3-(trifluoromethyl) phenyl)-3,4-dihydro-2H,6H-pyrido[1,2-e][1,2,5] thiadiazine-4-carboxylic acid 1,1-dioxide (Compound 107)

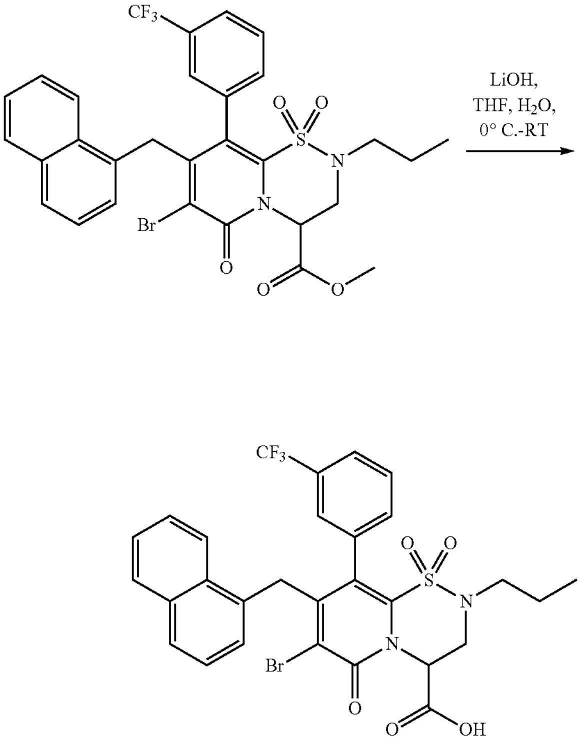

Compound 107

Methyl 7-bromo-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.075 g, 0.1131 mmol) was dissolved in THF:$H_2O$ (1:1, 5 mL). LiOH—$H_2O$ (0.019 g, 0.4524 mmol) was added at 0° C. and the reaction was stirred at room temperature for 4 h. The reaction mixture was concentrated, then water and 1N aqueous HCl solution (5 mL) were added. The resulting solid was collected by filtration. The crude product was purified using Prep HPLC Method 1 to give 7-bromo-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide. (Compound 107), as an off white solid (0.019 g, 25.88%). LCMS (Method-C3): 100% (RT 1.957, 224.0 nm) (MS: ESI+ve 586.4 [M+H]). $^1H$ NMR: (400 MHz, DMSO) δ ppm: 0.78-0.81 (t, J=14.4 Hz, 3H), 1.18 (s, 1H), 1.47-1.52 (m, 2H), 3.10-3.18 (m, 3H), 4.14-4.34 (m, 3H), 5.34 (s, 1H), 6.91-6.97 (m, 1H), 7.07-7.33 (m, 2H), 7.38-7.49 (m, 5H), 7.63-7.65 (d, J=8.4 Hz, 1H), 7.77-7.79 (d, J=6.8, 1H), 7.86-7.88 (d, J=8, 1H).

Example 107

Synthesis of methyl 7-chloro-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (Compound 142)

Compound 142

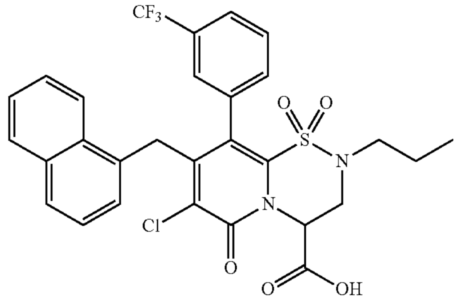

Step 1: Preparation of methyl 6-chloro-7-(naphthalen-1-ylmethyl)-5-oxo-8-(3-(trifluoromethyl)phenyl)-2,3-dihydro-5H-thiazolo[3,2-a]pyridine-3-carboxylate

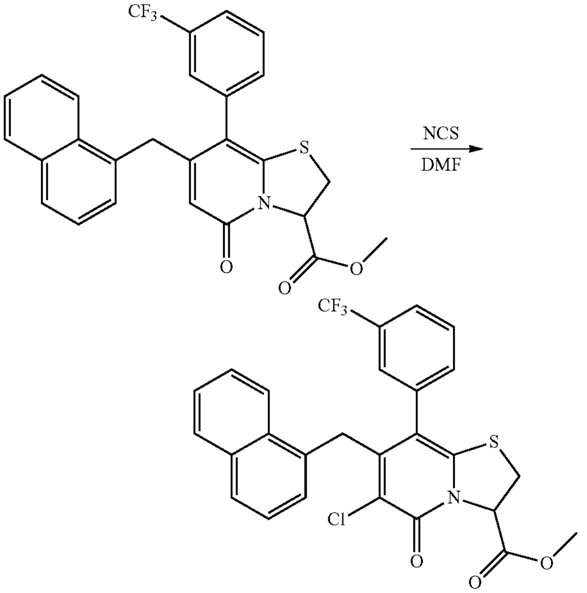

Methyl 6-chloro-7-(naphthalen-1-ylmethyl)-5-oxo-8-(3-(trifluoromethyl)phenyl)-2,3-dihydro-5H-thiazolo[3,2-a] pyridine-3-carboxylate dioxide (5 g, 10.10 mmol) was dissolved in DMF (50 mL), N-chlorosuccinimide (1.34 g, 10.10 mmol) was added and the reaction was stirred for 4 h. The reaction was quenched in ice water (100 mL) and the resulting precipitate was collected by filtration and dried to give methyl 6-chloro-7-(naphthalen-1-ylmethyl)-5-oxo-8-(3-(trifluoromethyl)phenyl)-2,3-dihydro-5H-thiazolo[3,2-a] pyridine-3-carboxylate (4.5 g, 93.26%). LCMS (Method-C3): 85.70% (RT: 2.474, 220 nm) (MS: ESI+ve 496.0 [M+1]).

Step 2: preparation of methyl 6-chloro-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide

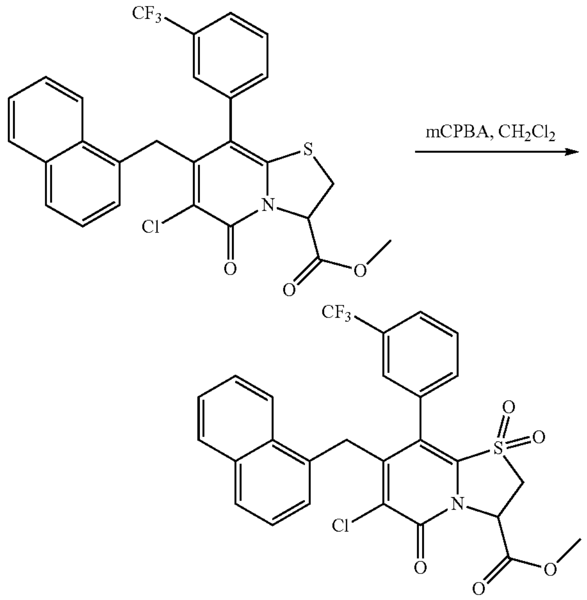

Methyl 6-chloro-7-(naphthalen-1-ylmethyl)-5-oxo-8-(3-(trifluoromethyl)phenyl)-2,3-dihydro-5H-thiazolo[3,2-a]pyridine-3-carboxylate (2 g, 3.78 mmol) was dissolved in DCM (30 mL), MCPBA (1.625 g, 9.44 mmol) was added and the mixture was stirred for 12 h., quenched with sat. aq. $NaHSO_3$ (20 mL) and washed with sat. aq. $NaHCO_3$ (20 mL). The organic layer was dried over sodium sulphate and concentrated under reduced pressure to give crude product which was purified using column chromatography eluting with 0-40% ethyl acetate/hexane to give methyl 6-chloro-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide as a white solid (1.2 g, 56.58%). LCMS (Method-C3): 77.26% (RT: 1.974, 202 nm) (MS: ESI+ve 561.8 [M+1]).

Step 3: preparation of methyl 7-chloro-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

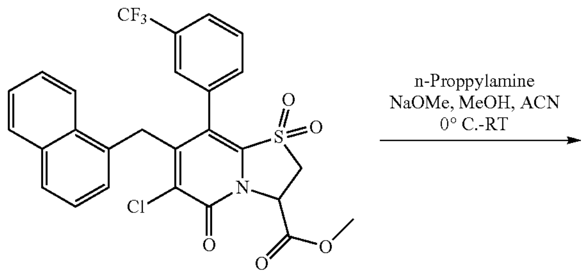

-continued

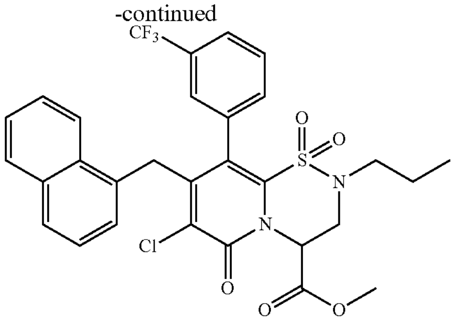

Methyl 6-chloro-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (1.2 g, 2.13 mmol) was dissolved in methanol (13 mL) and cooled to 0° C. n-Propylamine (0.151 g, 2.55 mmol) was added followed by freshly prepared sodium methoxide solution (0.2 M solution) (12.7 mL, 6 mL/1 mmol). The reaction mixture was stirred at room temperature for 16 h, concentrated under vacuum at 35° C., and then concentrated from chloroform (3x15 mL). The residue was dissolved in acetonitrile (20 mL) and cooled to 0° C., then pyridine (0.158 g, 2.13 mmol) and bromine (0.408 g, 2.56 mmol) were added. The reaction mixture was stirred at 0° C. for 10 min, then at room temperature for 1 h, quenched in ice water (20 mL) and extracted with ethyl acetate (3x20 mL). The organic layer was dried over sodium sulphate and concentrated to give methyl 7-chloro-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.390 g, 29.50%). LCMS (Method-C3): 95.47% (RT: 2.55, 214 nm) (MS: ESI+ve 619.0 [M+1]).

Step 4: preparation of 7-chloro-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 142)

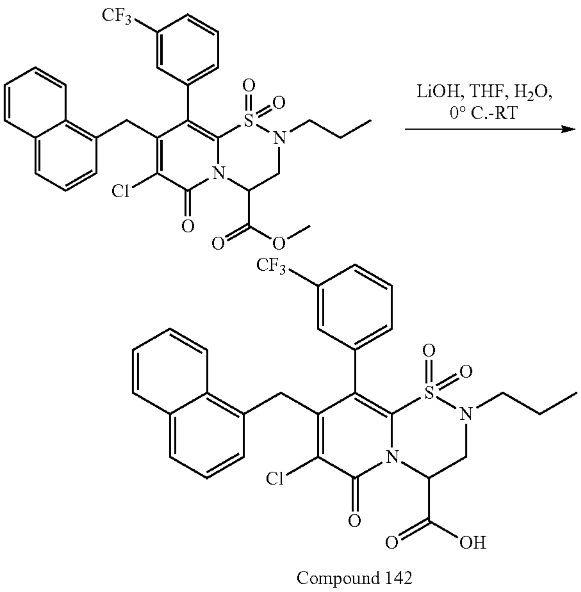

Compound 142

Methyl 7-chloro-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.1 g, 0.16 mmol) was dissolved in THF:$H_2O$ (1:1, 3 mL). LiOH (0.019 g 0.46 mmol) was added and the mixture was stirred at room temperature for 2 h. The mixture was concentrated then suspended in water (2 mL) and 1N aqueous HCl solution (2 mL). The resulting precipitate was collected by filtration and dried under vacuum. The crude product was purified using Prep HPLC Method 1 to give 7-chloro-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide as a white solid (Compound 142) (0.042 g, 42.97%). LCMS (Method-C3): 99.76% (RT 2.35, 220.0 nm) (MS: ESI+ve 605.0 [M+H]). $^1$H NMR: (400 MHz, DMSO) δ ppm: 0.78 (t, J=8 Hz, 3H), 1.48 (m, 2H), 3.12-3.14 (m, 2H), 4.08-4.31 (m, 4H), 5.33 (s, 1H), 6.89-6.95 (m, 2H), 7.07-7.26 (m, 2H), 7.38-7.48 (m, 5H), 7.62-7.64 (d, J=8 Hz, 1H), 7.76-7.78 (d, J=8 Hz, 1H), 7.85-7.87 (d, J=8 Hz, 1H), 13.94 (s, 1H).

Example 108

Synthesis of 2,7-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 068)

Compound 068

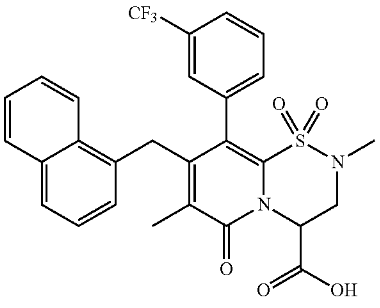

Step 1: Preparation of methyl 2,7-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

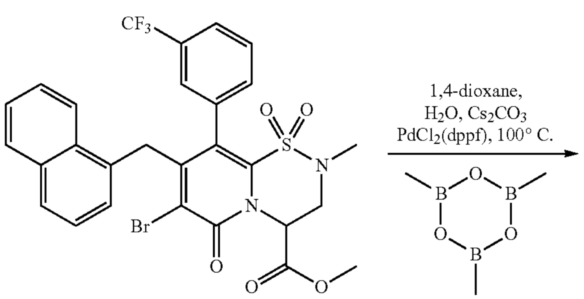

-continued

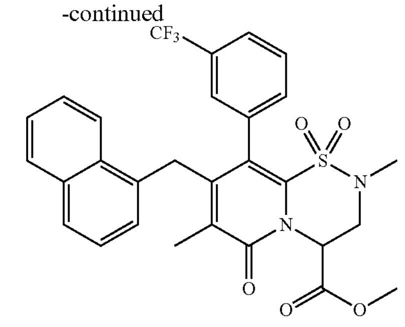

Methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.3 g, 0.4724 mmol) was dissolved in 1,4-dioxane (10 mL) and water (2.5 mL). Cesium carbonate (0.153 g, 0.4724 mmol) was added at room temperature, and the mixture was purged with N2 for 15 min. $PdCl_2$(dppf) (0.034 g, 0.0472 mmol) was added followed by trimethyl boroxine (0.059 g, 0.4724 mmoles) and purging with nitrogen was continued. The reaction mixture was heated at 100° C. for 5 h. The mixture was diluted with water and extracted with ethyl acetate (2×30 mL). The combined organic layers were dried over sodium sulphate and concentrated under reduced pressure to give crude product which was purified using column chromatography, product eluting with 70% ethyl acetate/hexane, to give methyl 2,7-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide, as a white solid (0.163 g, 60.4%). LCMS (Method-C3): 90.80% (RT 2.006, 228.0 nm) (MS: ESI+ve 571.3 [M+H]).

Step 2: Preparation of 2,7-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 068)

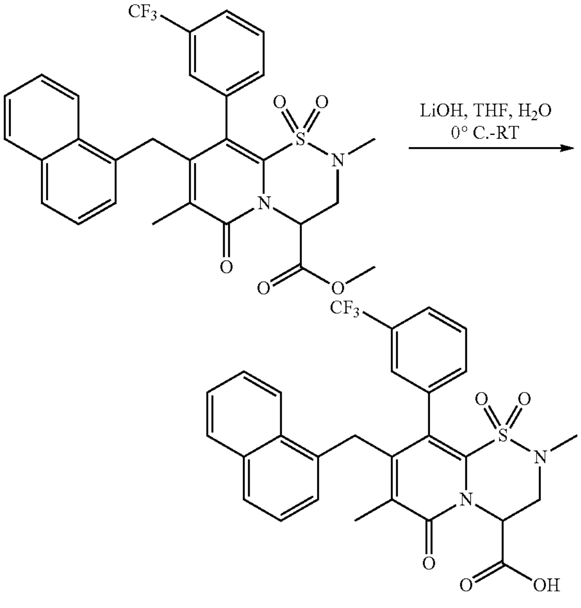

Compound 068

Methyl 2,7-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.163 g, 0.2856 mmol) was dissolved in tetrahydrofuran (4 mL). Lithium hydroxide (0.047 g, 1.1426 mmol) in water (4 mL) was added and the reaction mixture was stirred at room temperature for 16 h. The reaction mixture was concentrated under vacuum then ice and 0.1N aqueous HCl solution (7 mL) was added. The resulting solid was collected by filtration, washed with water, dissolved in dichloromethane and concentrated. The crude product was purified using Prep HPLC Method 1 to give 2,7-dimethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 068) (36.3 mg, 22.9%), as a white solid. LCMS (Method-C3): 100% (RT 1.785, 224.0 nm) (MS: ESI+ve 557.3 [M+1]). $^1$H NMR: (400 MHz, DMSO) δ ppm: 2.09-2.08 (s, 3H), 2.849 (s, 3H), 4.21-3.09 (m, 3H), 4.29-4.24 (m, 1H), 5.24-5.21 (m, 1H), 6.93-6.89 (m, 1H), 7.30-7.03 (m, 2H), 7.57-7.38 (m, 5H), 7.67-7.64 (m, 1H), 7.85-7.77 (m, 1H), 7.90-7.87 (m, 1H).

Example 109

Synthesis of 7-ethyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 076)

Compound 076

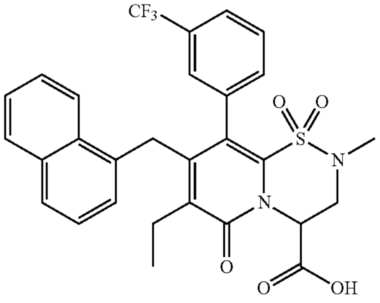

Step-1: Preparation of methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

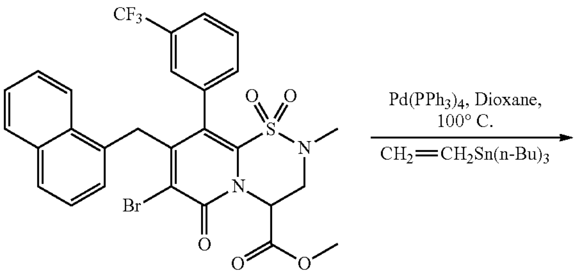

-continued

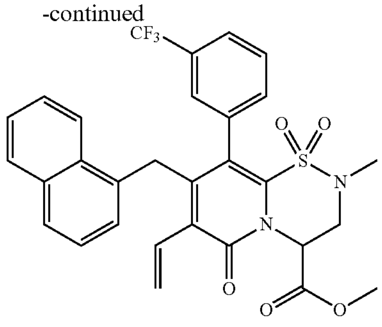

Methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.5 g, 0.787 mmol) was dissolved in dry dioxane (10 mL). Vinyl tributyl tin (0.25 g, 0.787 mmol) was added, and the mixture degassed for 5 min with argon. Paladium tetrakis (triphenylphosphine) (0.091 g, 0.0787 mmol) was added and the mixture was heated in a sealed tube at 100° C. for 16 h. The reaction was quenched in ice water (50 mL) and extracted with ethyl acetate (3×50 mL). The organic layer was dried over sodium sulphate and concentrated under reduced pressure to give crude product which was purified using chromatography eluting with 0-40% ethyl acetate/hexane to give methyl 2-methyl-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (0.4 g, 87%). LCMS (Method-C3): 77.80% (RT 2.087, 227.0 nm) (MS: ESI+ve 583.51 [M+H]) which was used directly in the next step without further purification.

Step 2: Preparation of methyl 7-ethyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

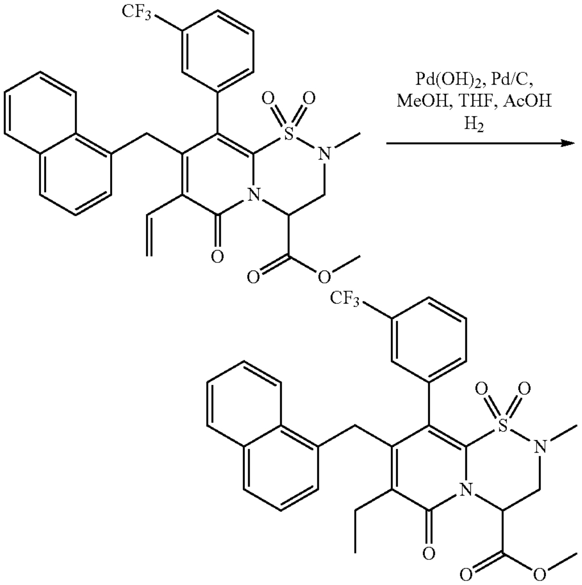

Methyl 2-methyl-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (0.15 g, 0.257 mmol) was dissolved in a mixture of methanol (3 mL), THF (1.5 mL) and acetic acid (0.1 mL). 10% palladium hydroxide (50% moisture) (0.15 g) and 10% Pd/C (50% moisture) (0.05 g) was added and the mixture was stirred under hydrogen for 16 h. The mixture was passed through a pad of Celite then concentrated to give methyl 7-ethyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a yellow solid (0.12 g, 79.5%). LCMS (Method-C3): 88.4% (RT 2.081, 223.0 nm) (MS: ESI+ve 585.61 [M+H]).

Step-3: Preparation of 7-ethyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 076)

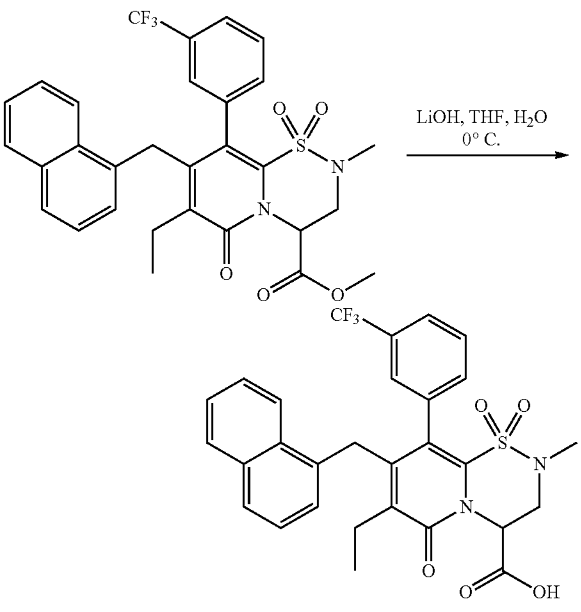

Compound 076

Methyl 7-ethyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.12 g, 0.205 mmol) was dissolved in THF:MeOH (1:2, 3.6 mL) at room temperature. LiOH—$H_2O$ (0.043 g, 1.047 mmol) in (0.1 mL) $H_2O$ was added and the mixture was stirred at room temperature for 4 h. The mixture was concentrated under reduced pressure and water (10 mL) and 1N aqueous HCl solution (3-4 mL) were added. The resulting precipitate was collected by filtration and dried under vacuum. The crude product was purified using Prep HPLC Method 1 to give 7-ethyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 076), as a white solid (0.035 g, 29.91%). LCMS (Method-C3): 100.00% (RT: 1.918, 225.0 nm) (MS: ESI+ve 571.6 [M+H]). $^1H$ NMR: (400 MHz, DMSO) δ ppm: 0.90-1.06 (m, 1H), 1.00-1.16 (m, 3H), 1.29-1.60 (m, 1H), 2.93 (s, 3H), 3.94-4.12 (m, 3H), 4.25-4.28 (m, 1H), 5.22 (s, 1H), 6.87-6.93 (m, 1H), 7.05-7.14 (m, 1H) 7.21-7.46 (m, 6H), 7.65-7.67 (d, J=8.4 Hz, 1H), 7.73-7.75 (d, J=6.8 Hz, 1H), 7.83-7.85 (d, J=8 Hz, 1H).

Example 110

Synthesis of 2-methyl-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylic acid 1,1-dioxide (Compound 078)

Compound 078

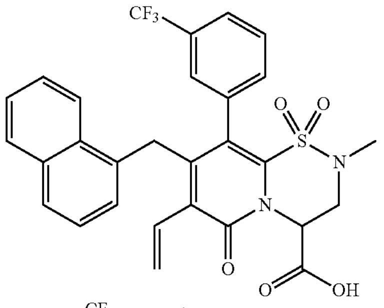

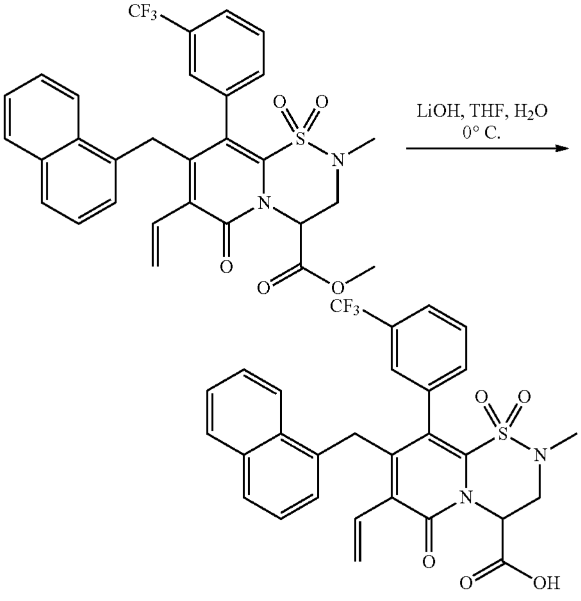

Compound 078

Methyl 2-methyl-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (0.1 g, 0.171 mmol) was dissolved in THF:MeOH (1:2, 3.0 mL). A solution of LiOH—$H_2O$ (0.036 g, 0.859 mmol) in $H_2O$ (0.1 mL) was added and the mixture was stirred at room temperature for 4 h. The mixture was concentrated and water (10 mL) and 1N aqueous HCl solution (3-4 mL) were added. The resulting precipitate was collected by filtration and dried under vacuum. The crude product was purified using Prep HPLC Method 1 to give 2-methyl-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylic acid 1,1-dioxide (Compound 078), was a white solid (0.026 g, 26.6%). LCMS (Method-J): 100% (RT 5.181 (MS: ESI+ve 569.1 [M+H]). $^1H$ NMR: (400 MHz, DMSO) δ ppm: 2.88 (s, 3H), 3.99-4.28 (m, 4H), 5.28 (s, 1H), 5.49-5.52 (d, J=12

Hz, 1H), 6.35-6.39 (d, J=17.4 Hz, 1H), 6.62-6.69 (m, 1H), 6.92-6.96 (m, 1H), 7.08 (s, 1H), 7.22-7.47 (m, 6H), 7.65-7.66 (d, J=6.4 Hz, 1H), 7.77-7.79 (d, J=7.2 Hz, 1H), 7.86-7.88 (d, J=7.6 Hz, 1H), 13.69 (bs, 1H).

Example 111

Synthesis of 7-(1,2-dihydroxyethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 101)

Compound 101

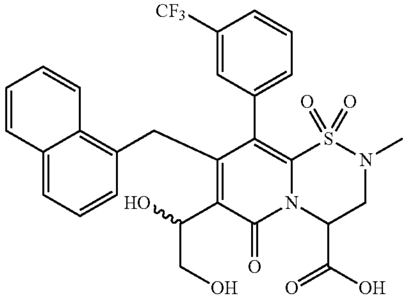

Step 1: Preparation of methyl 7-(1,2-dihydroxyethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

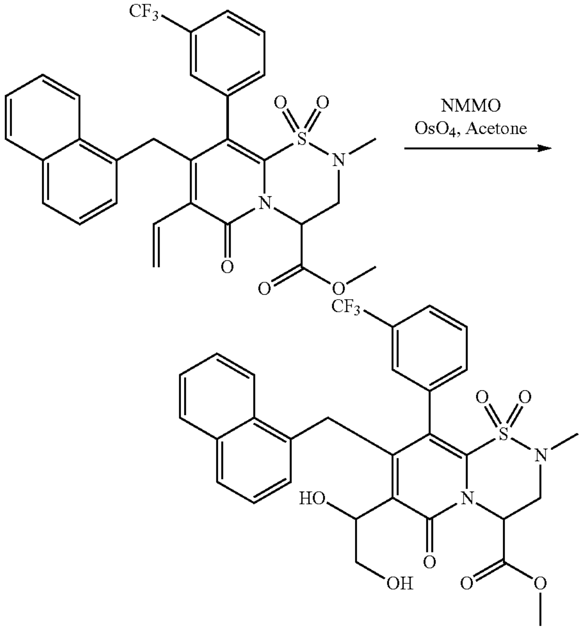

Methyl 2-methyl-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (0.2 g, 0.343 mmol) was dissolved in acetone (10 mL), N-methyl morpholine N-oxide (0.011 g in 0.2 mL $H_2O$) and osmium (VIII) oxide (0.016 mL 10%) was added and the mixture was stirred for 16 h. The mixture was concentrated and aq. sodium thiosulphate (20 mL) was added. The mixture was extracted with ethyl acetate (3×20 mL). The organic layer was dried over sodium sulphate and concentrated under reduced pressure to give the crude product which was purified using column chromatography eluting with 5% methanol in DCM to give methyl 7-(1,2-dihydroxyethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a white solid (0.1 g, 47.39%). LCMS (Method-C3): 85.99% (RT: 1.770, 225 nm) (MS: ESI+ve 616.7 [M+H]).

Step-3: Preparation of 7-(1,2-dihydroxyethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 101)

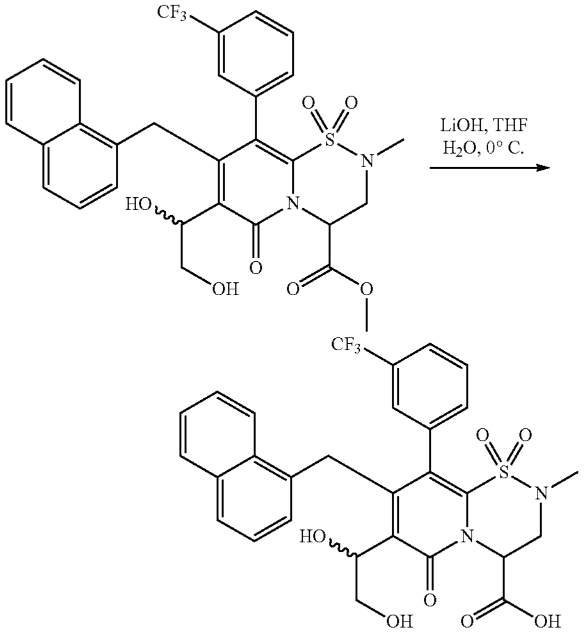

Compound 101

Methyl 7-(1,2-dihydroxyethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.1 g, 0.162 mmol) was dissolved in THF: MeOH (1:2, 3.6 mL). A solution of LiOH—$H_2O$ (0.034 g, 0.811 mmol) in (0.1 mL) $H_2O$ was added and the mixture was stirred at room temperature for 3 h. The mixture was concentrated and water (10 mL) and 1N aqueous HCl solution (3-4 mL) were added. The resulting precipitate was collected by filtration and dried under vacuum. The crude product was purified using Prep HPLC Method 1 to give 7-(1,2-dihydroxyethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 101), as a white solid (0.016 g, 16.34%). LCMS (Method-J): 100.00% (RT: 4.471, 202.4 nm) (MS: ESI+ve 603.2 [M+H]). $^1H$ NMR: (400 MHz, DMSO) δ ppm: 2.85 (s, 3H), 3.53 (s, 2H), 4.10-4.14 (d, 1H), 4.27-4.30 (m, 1H), 4.37-4.61 (m, 2H), 4.84 (s, 1H), 5.03 (s, 1H), 5.20-5.22 (t, 1H), 5.39-5.48 (m, 1H), 6.90-6.97 (m, 2H), 7.12-7.42 (m, 6H), 7.55-7.59 (t, 1H), 7.70-7.72 (d, J=8 Hz, 1H), 7.80-7.82 (d, J=6.8 Hz, 1H).

Example 112

Synthesis of 7-(hydroxymethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 077)

Compound 077

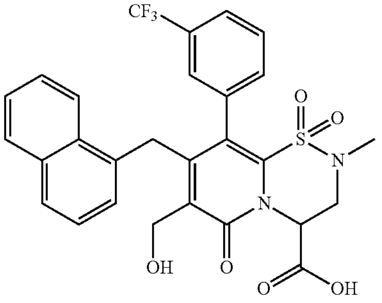

Step 1: Preparation of methyl 7-formyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

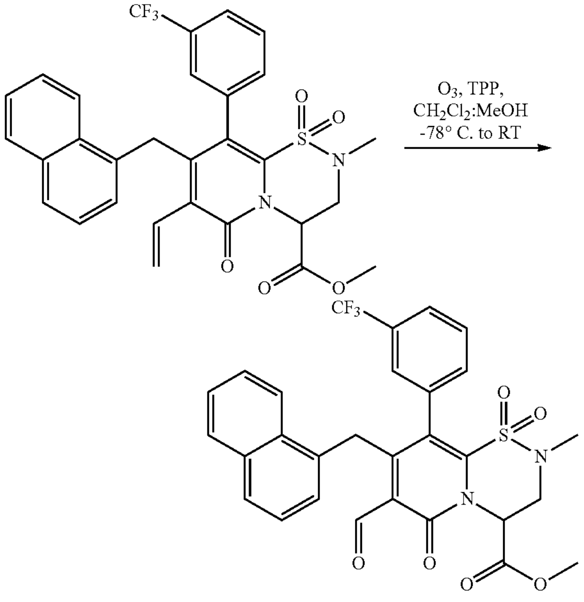

Methyl 2-methyl-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (1.60 g, 2.749 mmol) was dissolved in $CH_2Cl_2$:MeOH (1:3)(48 mL), 03 was purged through the reaction mixture over 20 min at −78° C. The reaction was then quenched with TPP. The mixture was stirred at room temperature for 16 h, then concentrated and purified using column chromatography eluting with 10% MeOH/$CH_2Cl_2$, to give methyl 7-formyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (1.63 g, 80.98%). LCMS (Method-C3): 85.84% (RT: 4.937, 222 nm) (MS: ESI+ve 585.32 [M+1]).

Step 2: Preparation of methyl 7-(hydroxymethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

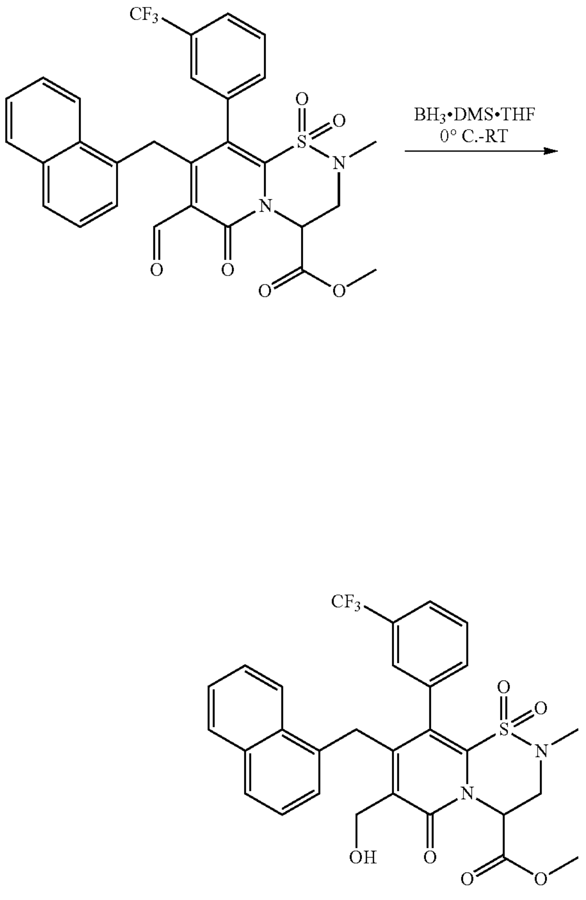

Methyl 7-formyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.15 g, 0.25 mmol) was dissolved in THF (2 mL) and $BH_3$.dimethylsulfide in THF, 1M (0.028 g, (0.28 mL) 0.28 mmol) was added dropwise over 15 min. The mixture was stirred in room temperature for 1 h, quenched with methanol and concentrated twice from methanol. The residue was purified using column chromatography (DCM:MeOH, 9:1) to give methyl 7-(hydroxymethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.14 g, 93.01%). LCMS (Method-C3): 36.40% (RT: 1.538, 221 nm) (MS: ESI+ve 587.27 [M+1]).

Step 3: preparation of 7-(hydroxymethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 077)

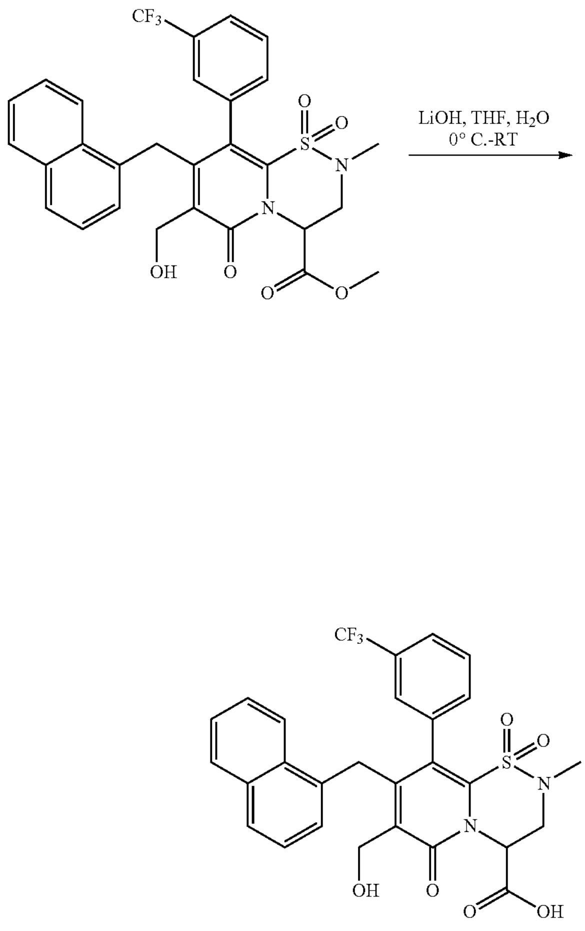

Compound 077

Methyl 7-(hydroxymethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.14 g, 0.238 mmol) was dissolved in THF:$H_2O$, (1:1, 2 mL). LiOH (0.029 g 0.716 mmol) was added and the mixture was stirred for 2 h. The mixture was concentrated and water (10 mL) and 1N aqueous HCl solution (3-4 mL) were added. The resulting precipitate was collected by filtration and dried under vacuum. The crude product was purified using Prep HPLC Method 1 to give 7-(hydroxymethyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as a white solid (Compound 077) (0.010 g, 10.24%). LCMS (Method-C3): 100% (RT 1.493, 202.0 nm) (MS: ESI+ve 573.39 [M+H]). $^1H$ NMR: (400 MHz, DMSO-$d_6$) δ ppm: 2.84 (s, 3H), 4.10-4.12 (m, 1H), 4.25 (m, 1H), 4.40 (m, 1H), 4.53 (m, 2H), 5.04 (m, 2H), 5.19 (m, 1H), 7.01 (m, 1H), 7.20 (m, 2H), 7.37-7.39 (d, J=8 Hz, 2H), 7.56-7.67 (m, 4H), 7.83-7.85 (m, 2H).

Example 113

Synthesis of 7-((dimethylamino)methyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 108)

Compound 108

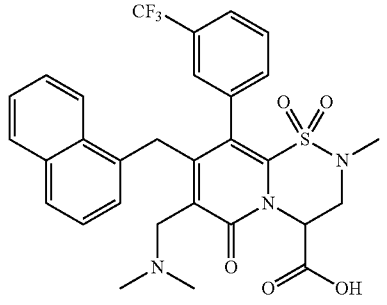

Step 1: Preparation of methyl 7-((dimethylamino)methyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

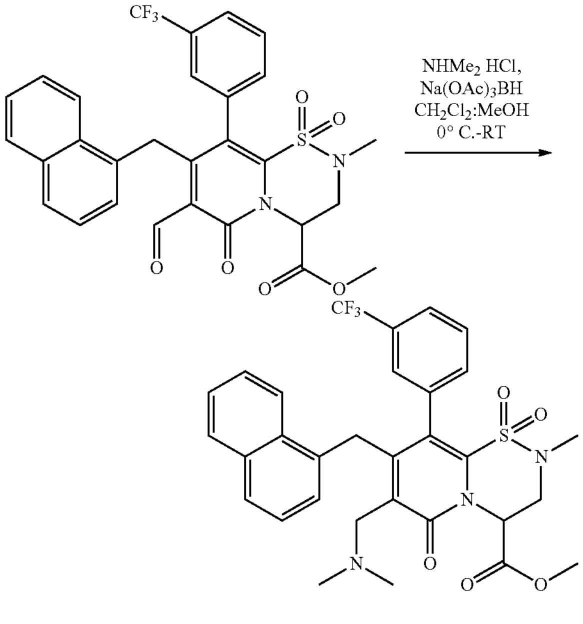

Methyl 7-formyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.2 g, 0.34 mmol) was dissolved in MeOH: $CH_2Cl_2$ (1:1, 3 mL) containing 3 Å molecular sieves. Dimethylamine hydrochloride (0.027 g, 0.34 mmol) was added and the mixture was stirred at 0° C. for 0.5 h. Sodium triacetoxyborohydride (0.616 g, 2.919 mmol) was added and the mixture was stirred at room temperature for 16 h. The reaction was quenched with sat. aq. $NaHCO_3$ solution (2 mL) and extracted with $CH_2Cl_2$ (3×3 mL). The organic layer was dried over sodium sulphate and concentrated under reduced pressure. The crude product was purified by using column chromatography eluting with 0-10% MeOH/DCM to give 7-((dimethylamino)methyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a solid (0.18 g, 90.0%) LCMS (Method-C3): 41.77% (RT: 1.660, 223 nm) (MS: ESI+ve 614.72 [M+1]).

Step 2: preparation of 7-((dimethylamino)methyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 108)

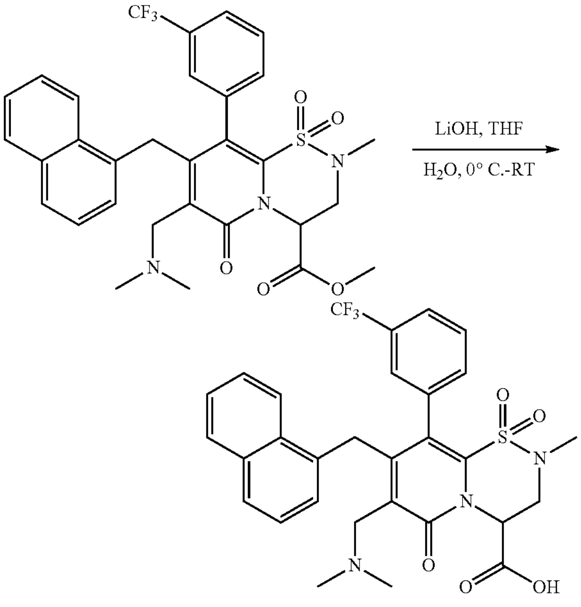

Compound 108

7-((dimethylamino)methyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.18 g, 0.29 mmol) was dissolved in THF:$H_2O$ (1:1, 2 mL). LiOH (0.036 g 0.88 mmol) was added and the mixture was stirred for 2 h. The mixture was concentrated, then ice water (1 mL) and 1N aqueous HCl solution (1 mL) were added. The resulting solid was collected by filtration and dried under vacuum. The crude product was purified using Prep HPLC Method 1 to give 7-((dimethylamino)methyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as a white solid (Compound 108) (0.015 g, 8.53%). LCMS (Method-C3): 100% (RT 1.961, 202.0 nm) (MS: ESI+ve 600.2 [M+H]). $^1H$ NMR: (400 MHz, DMSO-$d_6$) δ ppm: 2.89 (s, 6H), 3.03 (s, 3H), 4.30-4.25 (m, 4H), 4.36-4.46 (m, 2H), 5.13-5.14 (d, J=4 Hz, 1H), 7.07 (m, 3H), 7.27 (m, 1H) 7.40-7.48 (m, 3H), 7.50 (m, 1H), 7.64-7.66 (d, J=8 Hz, 1H), 7.76-7.78 (d, J=8 Hz, 1H), 7.83-7.85 (d, J=8 Hz, 1H).

Example 114

Synthesis of 7-carbamoyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 109)

Compound 109

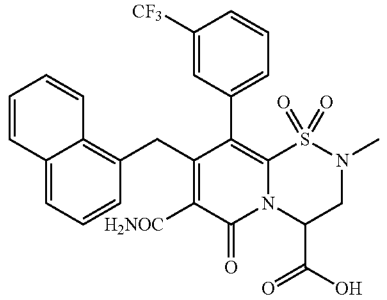

Step 1: Preparation of 4-(methoxycarbonyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-7-carboxylic acid 1,1-dioxide

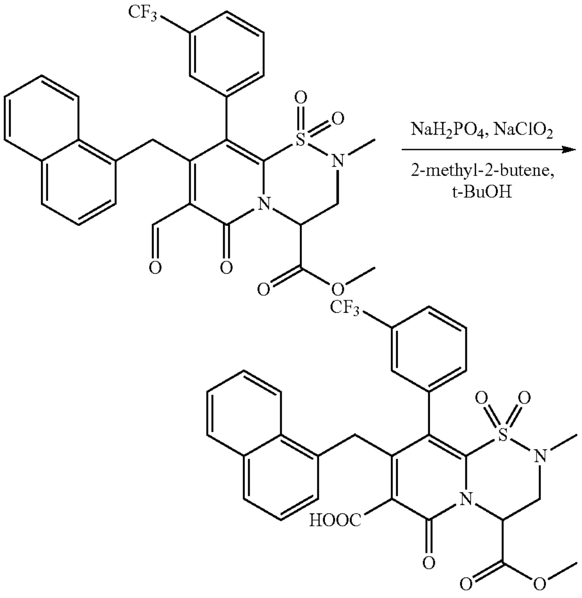

Methyl 7-formyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.2 g, 0.34 mmol) was dissolved in $H_2O$:tert-butyl alcohol, (1:1) (3 mL). $NaH_2PO_4$ (0.061 g, 0.51 mmol), $NaClO_2$ (0.09 g, 1.29 mmol) and 2-methyl-2-butene (0.16 g, 2.28 mmol) were added sequentially and the reaction was stirred at room temperature for 16 h. The mixture was quenched with 1N aqueous HCl solution (2 mL) and the resulting solid was collected by filtration and dried under vacuum to give 4-(methoxycarbonyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-7-carboxylic acid 1,1-dioxide (0.18 g, 87.60%) LCMS (Method-C3): 84.60% (RT: 1.772, 228 nm) (MS: ESI+ve 601.33 [M+H]).

Step 2: preparation of methyl 7-carbamoyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

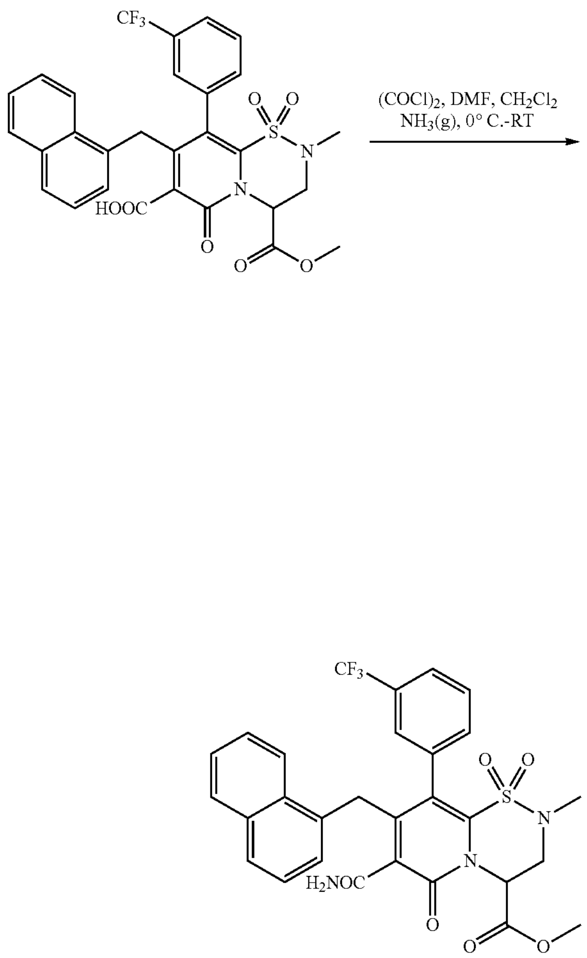

4-(Methoxycarbonyl)-2-methyl-8-(naphthalen-1-ylmethyl)-6-oxo-9-(3-(trifluoromethyl)phenyl)-3,4-dihydro-2H, 6H-pyrido[1,2-e][1,2,5]thiadiazine-7-carboxylic acid 1,1-dioxide (0.21 g, 0.35 mmol) was dissolved in DCM (2 mL) and cooled to 0° C. DMF (0.1 mL) and oxalyl chloride (0.052 g, 0.42 mmol) were added and the mixture was stirred at room temperature for 1 h. Ammonia gas was purged through the mixture for 30 min. The reaction was quenched with water (3 mL) and extracted with $CH_2Cl_2$ (3×10 mL). The organic layer was dried over sodium sulphate and concentrated under reduced pressure to give the crude product which was purified using column chromatography eluting with 5% MeOH/DCM to give methyl 7-carbamoyl-2-methyl-8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylate 1,1-dioxide (0.15 g, 71.55%). LCMS (Method-C3): 72.44% (RT: 1.816, 225 nm) (MS: ESI+ve 600.7 [M+1]).

Step 3: preparation of 7-carbamoyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 109)

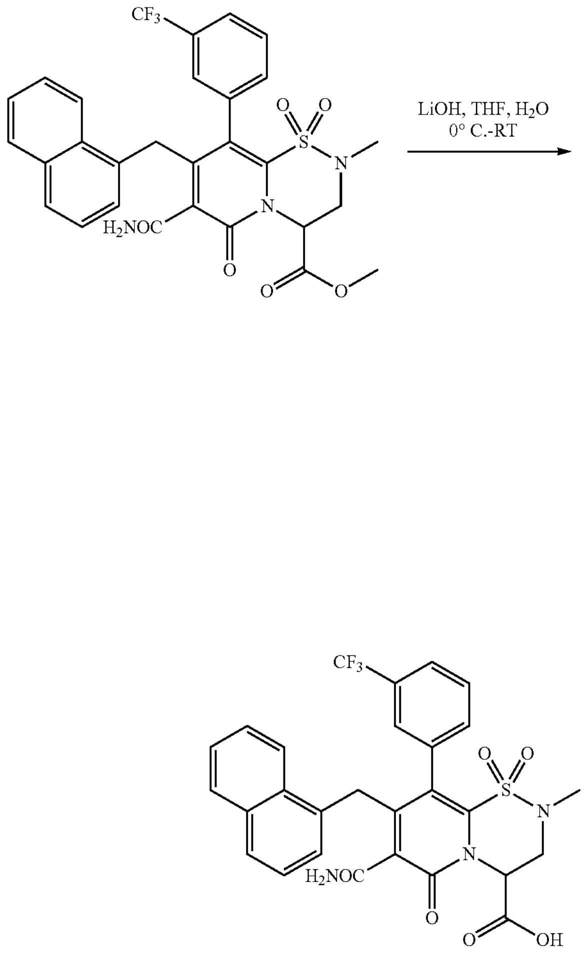

Compound 109

Methyl 7-carbamoyl-2-methyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylate 1,1-dioxide (0.15 g, 0.25 mmol) was dissolved in THF:$H_2O$ (1:1, 2 mL). LiOH (0.030 g 0.75 mmol) was added and the mixture was stirred at room temperature for 2 h. The mixture was concentrated and water and 1N aqueous HCl solution (1 mL) were added. The resulting precipitate was collected by filtration and dried under vacuum. The crude product was purified using Prep HPLC Method 1 give 7-carbamoyl-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as a white solid (Compound 109) (0.045 g, 30.72%). LCMS (Method-C3): 100% (RT 4.423, 202.0 nm) (MS: ESI+ve 586.2 [M+H]). $^1$H NMR: (400 MHz, $CD_3OD$) δ ppm: 2.94 (s, 3H), 4.24-4.37 (m, 4H), 5.43 (s, 1H), 7.01-7.19 (m, 5H), 7.27-7.30 (m, 2H), 7.37-7.39 (d, J=8 Hz, 1H), 7.49-7.51 (d, J=8 Hz, 1H), 7.69-7.78 (m, 2H).

Example 115

Synthesis of 2-methyl-8-(naphthalen-1-ylmethyl)-6-oxo-7-propyl-9-(3-(trifluoromethyl)phenyl)-3,4-dihydro-2H,6H-pyrido[1,2-e][1,2,5]thiadiazine-4-carboxylic acid 1,1-dioxide (Compound 090)

Compound 090

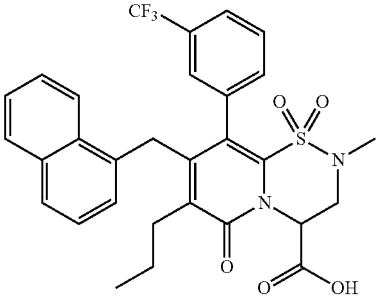

Step-1: Preparation of methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

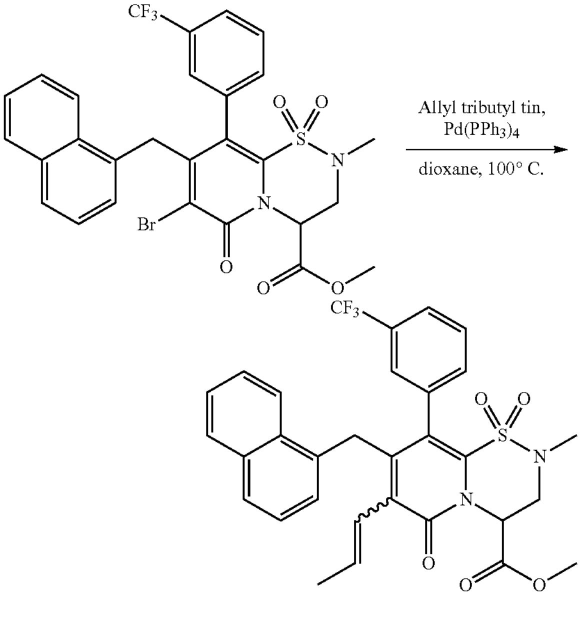

Methyl 7-bromo-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.3 g, 0.472 mmol) was dissolved in dry dioxane (6 mL). Allyl tributyl tin (0.156 g, 0.472 mmol) was added and the mixture was purged with argon for 5 minutes. Palladium tetrakis(triphenylphosphine) (0.055 g, 0.0472 mmol) was added and the mixture was heated in a sealed tube at 100° C. for 16 h. The reaction was quenched in ice water (50 mL) and extracted with ethyl acetate (3×50 mL). The organic layer was dried over sodium sulphate and concentrated under reduced pressure to give crude product which was purified using column chromatography eluting with 0-40% ethyl acetate/hexane to give a mixture of methyl (E) and (Z)-2-methyl-8-(naphthalen-1-ylmethyl)-6-oxo-7-(prop-1-en-1-yl)-9-(3-(trifluoromethyl)phenyl)-3,4-dihydro-2H,6H-pyrido[1,2-e][1,2,5]thiadiazine-4-carboxylate 1,1-dioxide (0.2 g, 71%). LCMS (Method-C3): 84.2% (RT 2.152, 225.0 nm) (MS: ESI+ve 597.4 [M+H]), which was used in the next step without further purification.

Step 2: Preparation of methyl 2-methyl-8-(naphthalen-1-ylmethyl)-6-oxo-7-propyl-9-(3-(trifluoromethyl)phenyl)-3,4-dihydro-2H,6H-pyrido[1,2-e][1,2,5]thiadiazine-4-carboxylate 1,1-dioxide

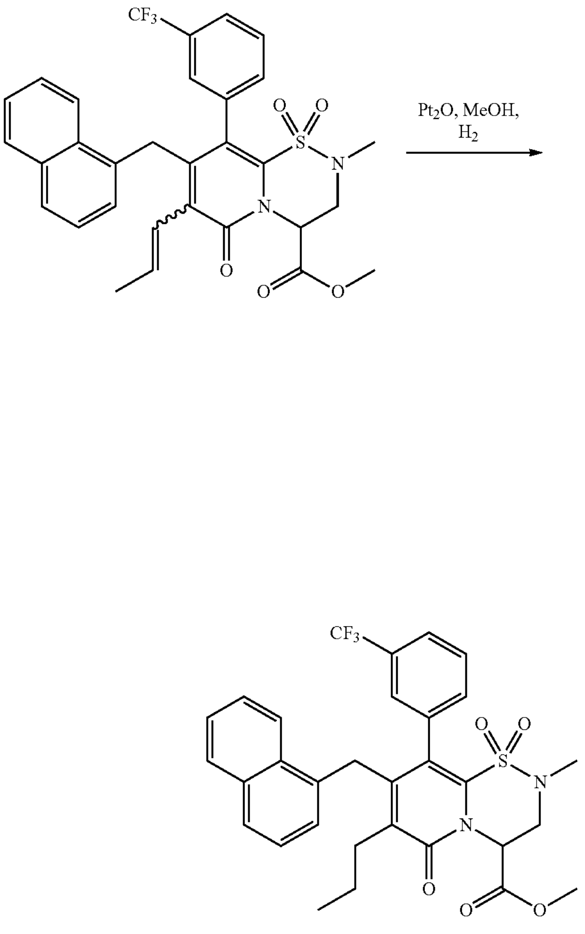

A mixture of (E) and (Z)-methyl-2-methyl-8-(naphthalen-1-ylmethyl)-6-oxo-7-(prop-1-en-1-yl)-9-(3-(trifluoromethyl)phenyl)-3,4-dihydro-2H,6H-pyrido[1,2-e][1,2,5]thiadiazine-4-carboxylate 1,1-dioxide (0.2 g, 0.335 mmol) was dissolved in methanol (5 mL). Platinum oxide (50% w/w) (0.1 g) was added and the mixture was stirred under hydrogen gas for 16 h. The mixture was passed through a pad of Celite and the solvent was evaporated to give methyl 2-methyl-8-(naphthalen-1-ylmethyl)-6-oxo-7-propyl-9-(3-(trifluoromethyl)phenyl)-3,4-dihydro-2H,6H-pyrido[1,2-e][1,2,5]thiadiazine-4-carboxylate 1,1-dioxide (0.18 g, 89.6%). LCMS (Method-C3): 90.85% (RT 2.193, 225.0 nm) (MS: ESI+ve 599.81 [M+H]).

Step-3: Preparation of 2-methyl-8-(naphthalen-1-ylmethyl)-6-oxo-7-propyl-9-(3-(trifluoromethyl)phenyl)-3,4-dihydro-2H,6H-pyrido[1,2-e][1,2,5]thiadiazine-4-carboxylic acid 1,1-dioxide (Compound 090)

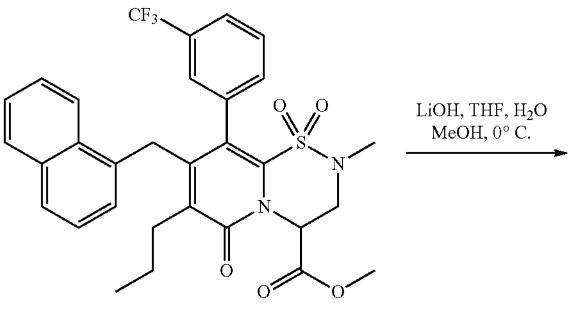

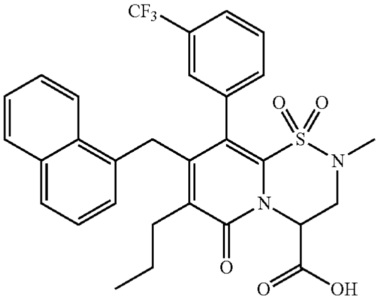

Compound 090

Methyl 2-methyl-8-(naphthalen-1-ylmethyl)-6-oxo-7-propyl-9-(3-(trifluoromethyl)phenyl)-3,4-dihydro-2H,6H-pyrido[1,2-e][1,2,5]thiadiazine-4-carboxylate 1,1-dioxide (0.12 g, 0.334 mmol) was dissolved in THF:MeOH (1:3, 5 mL). A solution of LiOH—$H_2O$ (0.070 g, 0.167 mmol) in $H_2O$ (0.1 mL) was added and the mixture was stirred at room temperature for 2 h. The mixture was concentrated and water (10 mL) and 1N aqueous HCl solution (3-4 mL) were added. The resulting solid was collected by filtration and dried under vacuum. The crude product was purified using Prep HPLC Method 1 to give 2-methyl-8-(naphthalen-1-ylmethyl)-6-oxo-7-propyl-9-(3-(trifluoromethyl)phenyl)-3,4-dihydro-2H,6H-pyrido[1,2-e][1,2,5]thiadiazine-4-carboxylic acid 1,1-dioxide (Compound 090), as a white solid (0.045 g, 23.07%). LCMS (Method-C3): 99.43% (RT 1.919, 225 nm) (MS: ESI+ve 585.7 [M+H]). $^1$H NMR: (400 MHz, DMSO) δ ppm: 0.83-0.85 (t, 3H), 1.16-1.24 (m, 2H), 2.55-2.68 (m, 2H), 2.85 (s, 3H), 3.98-4.14 (m, 3H), 4.27-4.30 (m, 1H), 5.21-5.23 (s, 1H), 6.87-6.93 (d, J=8.0 Hz, 1H), 7.03-7.13 (d, 1H), 7.22-7.47 (m, 6H), 7.65-7.67 (d, J=8.8 Hz, 1H), 7.75-7.76 (m, J=7.2 Hz, 1H), 7.84-7.86 (m, J=8.0 Hz, 1H), 13.66 (bs, 1H).

Example 116

Synthesis of (Z)-2-methyl-8-(naphthalen-1-ylmethyl)-6-oxo-7-(prop-1-en-1-yl)-9-(3-(trifluoromethyl)phenyl)-3,4-dihydro-2H,6H-pyrido[1,2-e][1,2,5]thiadiazine-4-carboxylic acid 1,1-dioxide (Compound 087) and (E)-2-methyl-8-(naphthalen-1-ylmethyl)-6-oxo-7-(prop-1-en-1-yl)-9-(3-(trifluoromethyl)phenyl)-3,4-dihydro-2H,6H-pyrido[1,2-e][1,2,5]thiadiazine-4-carboxylic acid 1,1-dioxide (Compound 088)

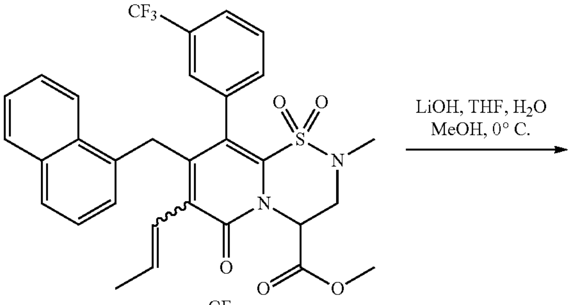

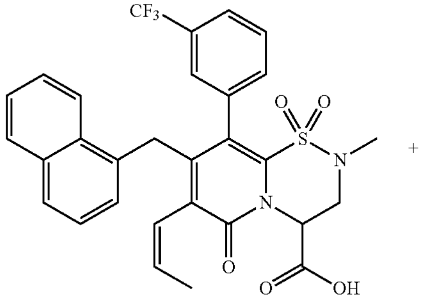

Compound 087

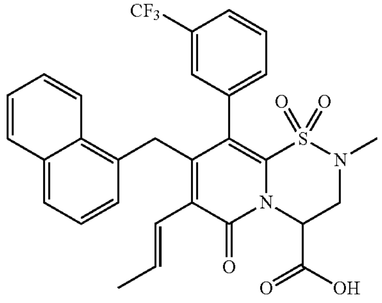

Compound 088

A mixture of (E) and (Z)-methyl-2-methyl-8-(naphthalen-1-ylmethyl)-6-oxo-7-(prop-1-en-1-yl)-9-(3-(trifluoromethyl)phenyl)-3,4-dihydro-2H,6H-pyrido [1,2-e][1,2,5]thiadiazine-4-carboxylate 1,1-dioxide (0.2 g, 0.335 mmol) was dissolved in THF:MeOH (1:3), (5 mL). A solution of LiOH—$H_2O$ (0.070 g, 0.167 mmol) in $H_2O$ (0.1 mL) was added. The mixture was stirred at room temperature for 3 h. The mixture was concentrated and water (10 mL) and 1N aqueous HCl solution (3-4 mL) were added. The resulting solid was collected by filtration and dried under vacuum. The crude product was purified using Prep HPLC Method 1 to give (Z)-2-methyl-8-(naphthalen-1-ylmethyl)-6-oxo-7-(prop-1-en-1-yl)-9-(3-(trifluoromethyl)phenyl)-3,4-dihydro-2H,6H-pyrido[1,2-e][1,2,5]thiadiazine-4-carboxylic acid 1,1-dioxide (Compound 087), as a white solid (0.035 g, 17.92%). LCMS (Method-C3): 98.70% (RT 1.947, 229 nm) (MS: ESI+ve 583.4 [M+H]). $^1$H NMR: (400 MHz, DMSO) δ ppm: 1.60 (s, 3H), 2.87 (s, 3H), 4.00-4.16 (m, 3H), 4.28-4.33 (m, 1H), 5.23-5.25 (t, 1H), 5.83-5.88 (m, 1H), 6.08-6.14 (t, 1H), 6.83-6.91 (dd, J=6.4 Hz, J=6.8 Hz, 1H), 7.06-7.08 (d, J=6.4 Hz, 1H), 7.26-7.45 (m, 6H), 7.56-7.60 (t, 1H), 7.72-7.74 (d, J=8.0 Hz, 1H), 7.82-7.84 (m, J=8.0 Hz, 1H), 13.68 (bs, 1H).

A second fraction was collected to give (E)-2-methyl-8-(naphthalen-1-ylmethyl)-6-oxo-7-(prop-1-en-1-yl)-9-(3-(trifluoromethyl)phenyl)-3,4-dihydro-2H,6H-pyrido[1,2-e][1,2,5]thiadiazine-4-carboxylic acid 1,1-dioxide dioxide (Compound 088), as a white solid (0.035 g, 17.92%). LCMS (Method-J): 97.78% (RT 5.307, 202.4) (MS: ESI+ve 583.2 [M+H]). $^1$H NMR: (400 MHz, DMSO) δ ppm: 1.66-1.74 (t, 3H), 2.86 (s, 3H), 3.99-4.30 (m, 4H), 5.25-5.26 (d, J=5.2 Hz, 1H), 4.24 (m, 1H), 6.35-6.39 (d, J=15.2 Hz, 1H), 6.88-7.02 (m, 2H), 7.22-7.48 (m, 6H), 7.62-7.64 (d, J=8.4 Hz, 1H), 7.76-7.7 (d, J=8.0 Hz, 1H), 7.85-7.87 (m, J=8.0 Hz, 1H).

Example 117

Synthesis of 7-ethyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 112)

Compound 112

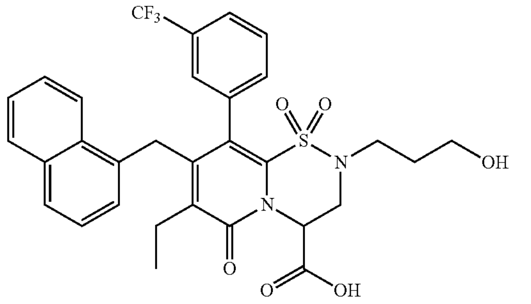

Step 1: Preparation of methyl 2-(4-methoxybenzyl)-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide

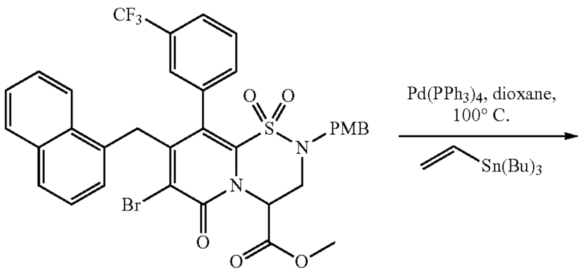

-continued

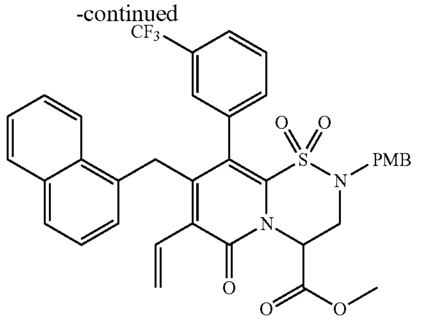

Methyl 2-(4-methoxybenzyl)-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (2 g, 2.66 mmol) was dissolved in 1,4-dioxane (20 mL). Vinyl tributyl tin (0.85 g, 2.66 mmol) was added and the mixture was degassed for 5 min under argon. Tetrakis (triphenylphosphine) palladium (0) (0.31 g, 0.26 mmol) was added and the reaction mixture was heated in a sealed tube at 100° C. for 16 h. The reaction was quenched in ice water (50 mL) and extracted with ethyl acetate (3×50 mL). The organic layer was dried over sodium sulphate and concentrated under reduced pressure to give the crude product, which was purified using column chromatography eluting with 0-40% ethyl acetate/DCM to give methyl 2-(4-methoxybenzyl)-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (1.29 g, 64.5%). LCMS (Method-C3): 98.38% (RT: 2.645, 254 nm) (MS: ESI+ve 689.4 [M+1]).

Step 2: Preparation of methyl 7-ethyl-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

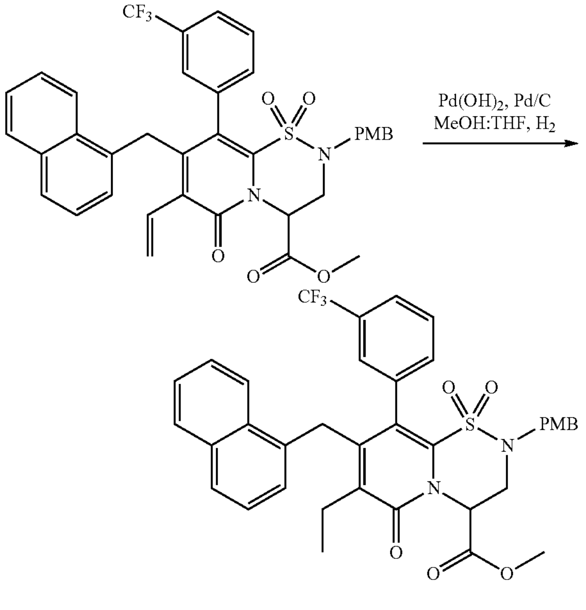

Methyl 7-ethyl-2-(4-methoxybenzyl)-8-(naphthalen-1-ylmethyl)-6-oxo-9-(3-(trifluoromethyl)phenyl)-3,4-dihydro- 2H,6H-pyrido[1,2-e][1,2,5]thiadiazine-4-carboxylate 1,1-dioxide (0.6 g, 0.8 mmol), was dissolved in MeOH:THF (1:1.12 mL), 30 wt % Pd/C (0.060 g), Pd(OH) 2 (0.600 g) and acetic acid (0.1 mL) were added and the mixture was stirred under hydrogen at room temperature for 16 h. The reaction mixture was filtered through Celite, washed with methanol (10 mL) and concentrated to give methyl 7-ethyl-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a pale yellow solid (0.550 g, 91.40%). LCMS (Method-$C_3$): 96.22% (RT 2.666, 202.4 nm) (MS: ESI+ve 691.3 [M+H]).

Step 3: Preparation of methyl 7-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

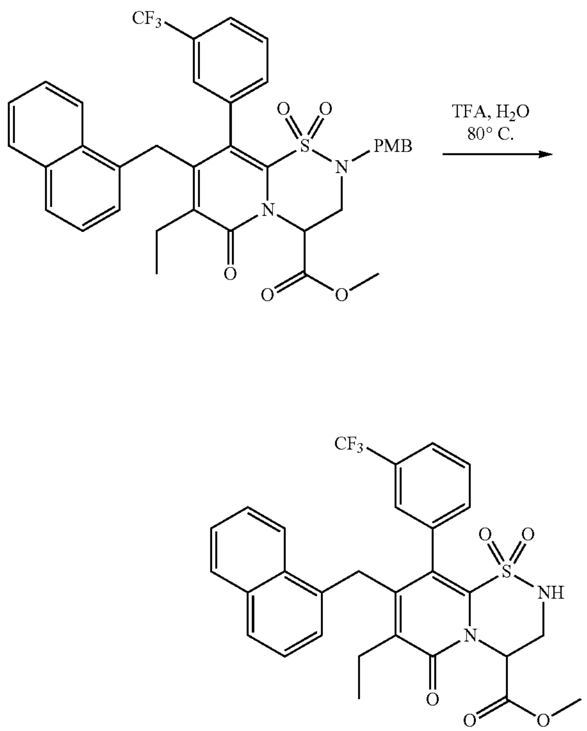

Methyl 7-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.69 g, 0.77 mmol) was dissolved in a mixture of TFA (4 mL) and water (0.5 mL) and heated at 80° C. for 1 h. The mixture was then poured into ice water (20 mL)/sat. aq. sodium bicarbonate solution (20 mL) and extracted with ethyl acetate (3×50 mL). The organic layer was dried over sodium sulphate and concentrated under reduced pressure to give the crude product which was purified using column chromatography eluting with 0-50% ethyl acetate/hexane to give methyl 7-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a brown solid (0.4 g, 70.18%). LCMS (Method-C3): 83.34% (RT 2.013, 227.0 nm) (MS: ESI+ve 571.54 [M+H]).

Step 4: Preparation of methyl 7-ethyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

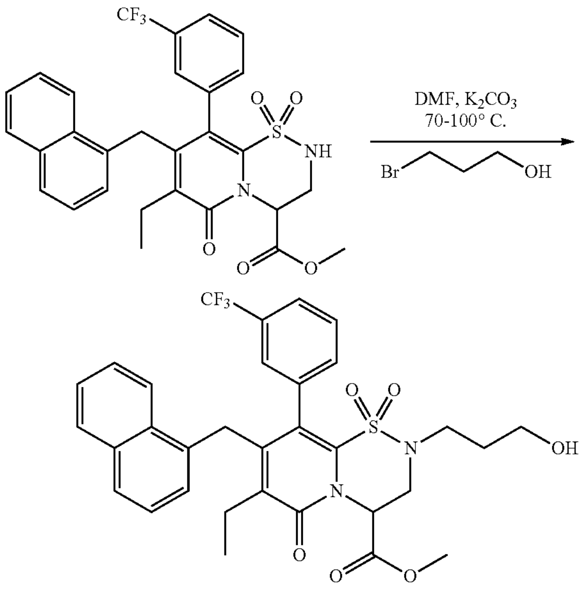

Methyl 7-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.41 g, 0.7 mmol) was dissolved in DMF (5 mL) and 3-bromo-1-propanol added (0.176 g, 1.2 mmol) followed by $K_2CO_3$ (0.176 g, 1.2 mmol). The reaction mixture was stirred for 2 h at 100° C. The reaction was quenched in ice water then extracted with ethyl acetate (3×15 mL). The organic layer was dried over sodium sulphate. The crude product was purified by column chromatography to give methyl 7-ethyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide. (0.4 g, 88.85%). LCMS (Method-C3): 86.65% (RT 2.377, 223.0 nm) (MS: ESI+ve 629.2 [M+H]).

Step 5: preparation of 7-ethyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 112)

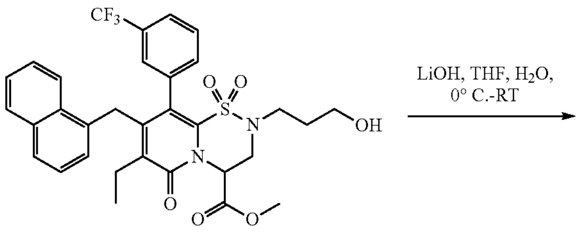

-continued

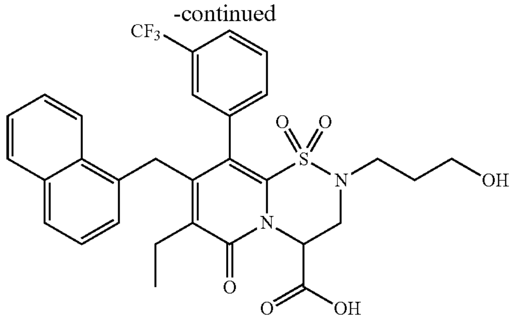

Compound 112

Methyl 7-ethyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.4 g, 0.6 mmol) was dissolved in THF:$H_2O$ (1:1.4 mL). LiOH (0.78 g 1.9 mmol) was added and the mixture was stirred at room temperature for 2 h. The mixture was concentrated then suspended in ice water (10 mL) and 1N aqueous HCl solution (3-4 mL). The resulting solid was collected by filtration and dried under vacuum. The crude product was triturated with n-pentane to give 7-ethyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as an off white solid (Compound 112) (0.230 g, 58.21%). LCMS (Method-C3): 97.91% (RT 2.240, 214.0 nm) (MS: ESI+ve 615.37 [M+H]). $^1$H NMR: (400 MHz, DMSO-$d_6$) δ ppm: 1.03 (t, J=8 Hz, 3H), 1.61 (m, 2H), 3.20 (t, J=8 Hz, 2H), 4.07 (m, 3H), 4.25 (m, 1H), 4.53 (bs, 1H), 5.29 (m, 1H), 6.89 (m, 1H), 7.10 (m, 1H), 7.26 (m, 1H), 7.31 (m, 1H), 7.37-7.46 (m, 4H), 7.65-7.69 (m, 1H), 7.75 (m, 1H), 7.85-7.87 (d, J=8 Hz, 1H), 13.16 (s, 1H).

Example 118

Synthesis of 7-ethyl-2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 113)

Compound 113

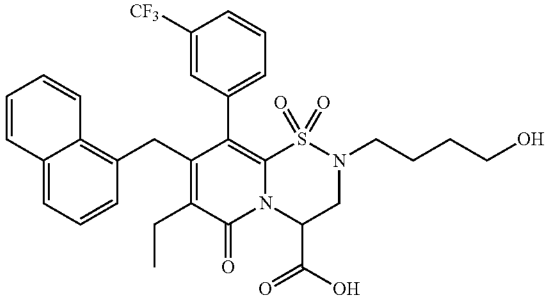

Prepared by a procedure similar to that reported for 7-ethyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 112) substituting 4-bromo-1-butanol in step 4. The crude product was purified using Prep HPLC Method 1 to give 7-ethyl-2-(4-hydroxybutyl)-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide as a white solid (Compound 113) (0.025 g, 11%). LCMS (Method-C3): 100% (RT 2.237, 202.0 nm) (MS: ESI+ve 629.2 [M+H]. $^1$H NMR: (400 MHz, DMSO-$d_6$) δ ppm: 1.14 (t, J=8 Hz, 3H), 1.53 (m, 2H), 1.62 (m, 2H), 2.61 (m, 2H), 3.23 (m, 2H), 3.50 (t, J=8 Hz, 2H), 4.10 (m, 2H), 4.25 (m, 2H), 5.27 (s, 1H), 7.09 (m, 1H), 7.26 (m, 1H), 7.31 (m, 2H), 7.35-7.46 (m, 4H), 7.65-7.67 (m, 1H), 7.74 (m, 1H), 7.83-7.85 (d, J=8 Hz, 1H).

Example 119

Synthesis of 7-ethyl-2-(5-hydroxypentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 114)

Compound 114

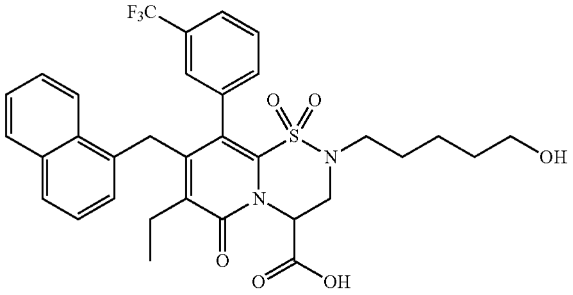

Prepared by a procedure similar to that reported for 7-ethyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 112) substituting 5-bromo-1-pentanol in step 4. The crude product was purified using Prep HPLC Method 1 to give 7-ethyl-2-(5-hydroxypentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as a white solid (Compound 114) (0.03 g, 16.13%). LCMS (Method-C3): 100% (RT 2.66, 214.0 nm) (MS: ESI+ve 643.3 [M+H]). $^1$H NMR: (400 MHz, $CD_3OD$) δ ppm: 1.16-1.13 (t, J=8 Hz, 3H), 1.30 (m, 2H), 1.62-1.48 (m, 4H), 2.70-2.67 (m, 2H), 3.27-3.23 (m, 2H), 3.54-3.51 (t, J=8 Hz, 2H), 4.07-4.17 (m, 2H), 4.24-4.27 (m, 2H), 5.46 (s, 1H), 6.98 (m, 1H), 7.27-7.25 (m, 2H), 7.44-7.32 (m, 3H), 7.62-7.64 (d, J=8 Hz, 1H), 7.72-7.72 (d, J=8 Hz, 1H). 7.80-7.82 (d, J=8 Hz, 1H).

Example 120

Synthesis of 7-ethyl-8-(naphthalen-1-ylmethyl)-6-oxo-2-propyl-9-(3-(trifluoromethyl) phenyl)-3,4-dihydro-2H,6H-pyrido[1,2-e][1,2,5]thiadiazine-4-carboxylic acid 1,1-dioxide (Compound 117)

Compound 117

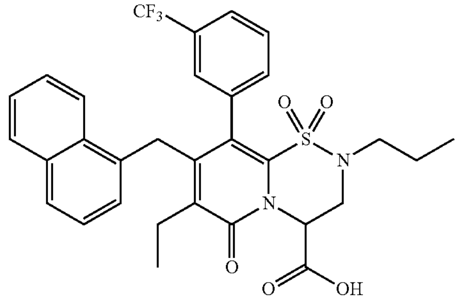

Step 1: Preparation of methyl 8-(naphthalen-1-ylmethyl)-6-oxo-2-propyl-9-(3-(trifluoromethyl)phenyl)-7-vinyl-3,4-dihydro-2H,6H-pyrido[1,2-e][1,2,5]thiadiazine-4-carboxylate 1,1-dioxide

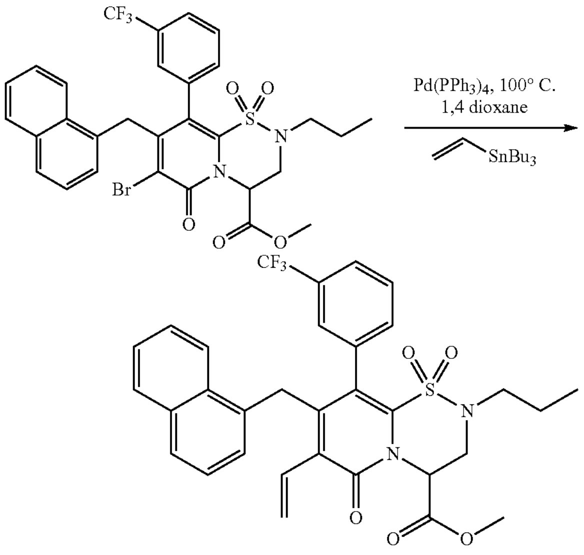

Methyl 7-bromo-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate1,1-dioxide (0.3 g, 0.452 mmol) and tributyl vinyl tin (0.3 g, 0.4524 mmol) was dissolved in 1,4 dioxane (5 mL). N2 gas was purged through the reaction mixture for 5 min, then palladium tetrakis(triphenylphosphine) (0.053 g, 0.04524 mmol) was added. N2 gas was purged through the reaction mixture for a further 5 min and the reaction mixture was stirred and heated at 100° C. for 16 h. The reaction was quenched with water (20 mL) and extracted with ethyl acetate (3×20 mL), and the organic layer was dried over sodium sulphate and concentrated. The crude product was purified using column chromatography to give methyl 2-methyl-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide as a pale brown solid (0.2 g, 72.44%).LCMS (Method-C3): 94.43% (RT: 2.602, 223.0 nm) (MS: ESI+ve 611.2 [M+H]).

Step 2: Preparation of methyl 7-ethyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

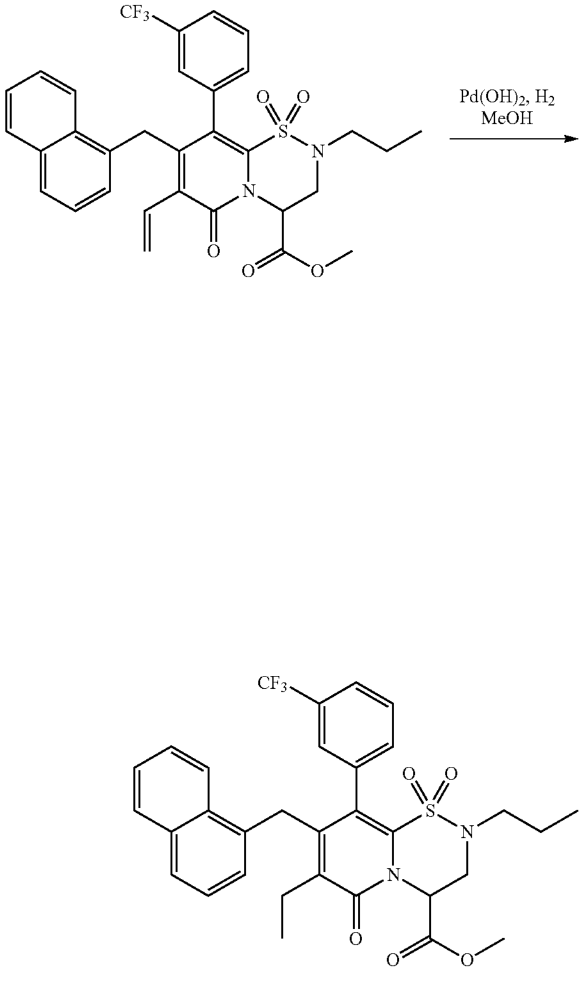

Methyl 8-(naphthalen-1-ylmethyl)-6-oxo-2-propyl-9-(3-(trifluoromethyl)phenyl)-7-vinyl-3,4-dihydro-2H,6H-pyrido[1,2-e][1,2,5]thiadiazine-4-carboxylate 1,1-dioxide (0.21 g, 0.343 mmol) was dissolved in MeOH (5 mL) and palladium hydroxide (0.2 g) was added. The reaction mixture was purged with $H_2$ gas and stirred for 1 h. The mixture was filtered through Celite and the filtrate was concentrated under reduced pressure to give methyl 7-ethyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.2 g, 94.92%). LCMS (Method-C3): 89.23% (RT: 2.619, 225.0 nm) (MS: ESI+ve 613.2 [M+H]).

Step 3: Preparation of 7-ethyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 117)

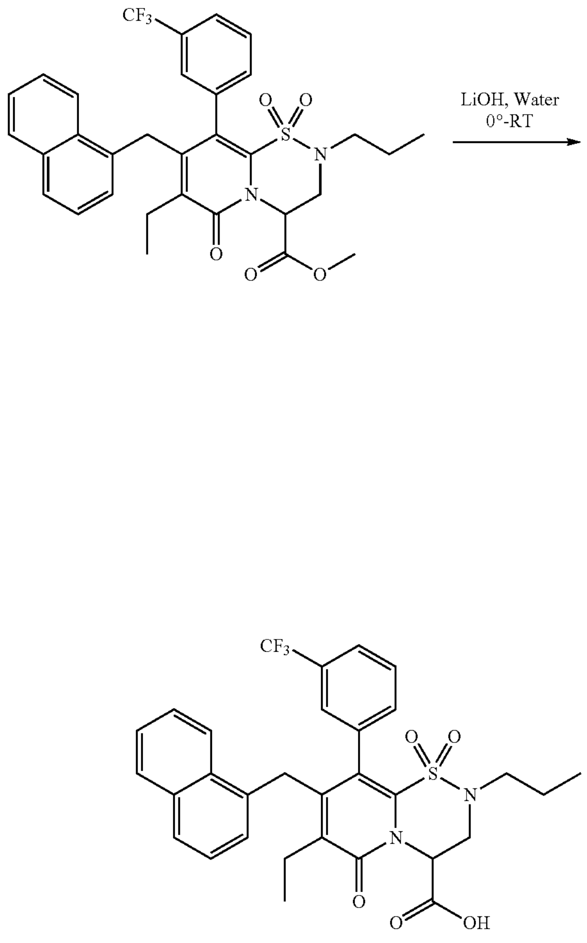

Compound 117

Methyl 7-ethyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.2 g, 3267 mmol) was dissolved in THF:$H_2O$ (1:1, 5 mL). LiOH—$H_2O$ (0.054 g, 1.3068 mmol) was added and the mixture was stirred at room temperature for 4 h. The mixture was concentrated then suspended in ice water (10 mL) and 1N aqueous HCl solution (3-4 mL). The resulting solid was collected by filtration and dried under vacuum. The crude product was purified using Prep HPLC Method 1 to give 7-ethyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 117) as an off white solid (0.053 g, 27.12%). LCMS (Method-C3): 100% (RT 1.863, 223.0 nm) (MS: ESI+ve 600.42 [M+H]). $^1H$ NMR: (400 MHz, DMSO) δ ppm: 0.75-0.79 (d, J=8 Hz, 3H), 1.02 (s, 3H), 1.46-1.47 (d, J=4 Hz, 2H), 3.08-3.10 (d, J=8 Hz, 2H), 3.95-4.24 (m, 5H), 5.28 (s, 1H), 6.85-6.90 (t, J=20 Hz, 1H), 7.04-7.13 (m 1H), 7.22-7.42 (m, 6H), 7.65-7.67 (d, J=8 Hz, 1H), 7.74 (s, 1H), 7.83-7.85 (d, J=8 Hz, 1H), 19.72 (s, 1H).

Example 121

7-isobutyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 139)

Compound 139

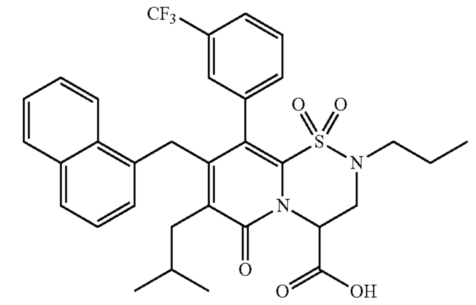

Step 1: Preparation of methyl 7-isobutyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

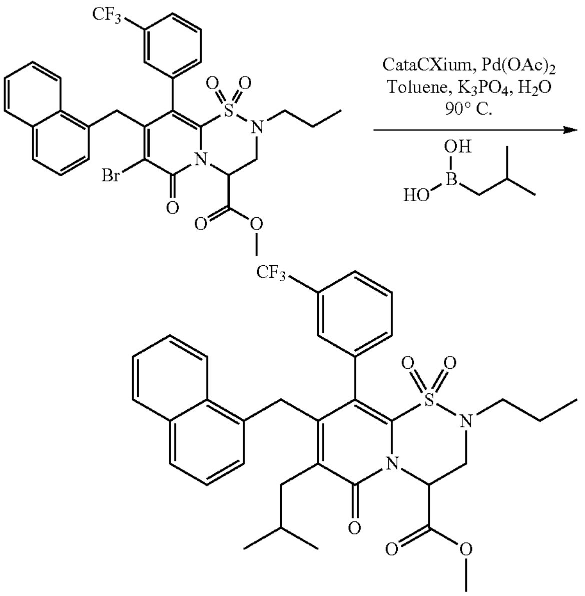

Methyl 7-bromo-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.40 g, 0.61 mmol) was added to isobutyl-boronic acid (0.248 g, 2.45 mmol) dissolved in dry toluene and water (6 mL+0.6 mL). The mixture was degassed with argon and potassium phosphate (0.179 g, 2.45 mmol) was added. CataCXium A (0.023 g, 0.0641 mmol) and $Pd(OAc)_2$ (0.003 g, 0.013 mmol) were added under argon. The reaction mixture was stirred at 90° C. for 16 h. The reaction was quenched in water (5 mL) and extracted in ethyl acetate (2×10 mL). The organic layer was dried over sodium sulphate and concentrated under reduced pressure to give the crude product which was purified using column chromatography eluting with 20-40% ethyl acetate/hexane to give methyl 7-isobutyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide as a solid (0.10 g, 25.89%). LCMS (Method-C3): 95.71% (RT 2.748, 202 nm) (MS: ESI+ve 641.3 [M+1]).

Step 2: Preparation Of 7-isobutyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 139)

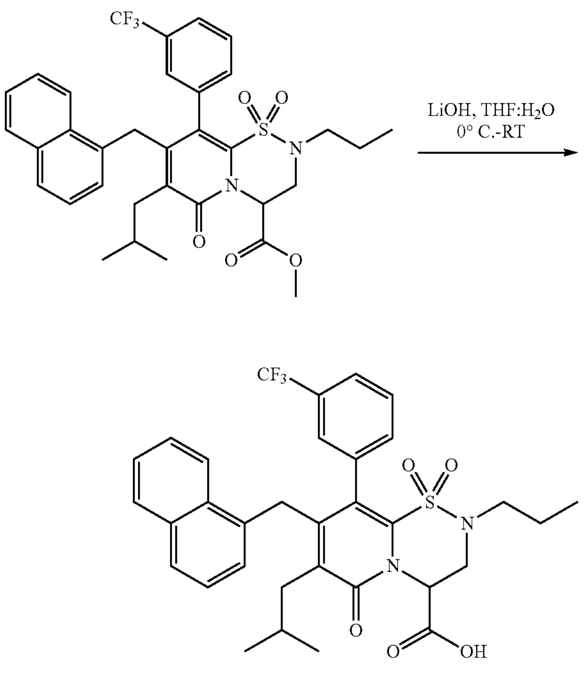

Compound 139

Methyl 7-isobutyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.1 g, 0.15 mmol) was dissolved in THF:$H_2O$ (1:1, 2 mL). LiOH—$H_2O$ (0.019 g, 0.46 mmol) was added and the mixture was stirred at room temperature for 2 h. The mixture was concentrated then suspended in ice water (1 mL) and 1N aqueous HCl solution (2 mL). The resulting solid was collected by filtration, triturated with n-pentane then dried under vacuum to give 7-isobutyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide as an off white solid (0.050 g, 51.12%) (Compound 139). LCMS (Method-j): 100%) (RT: 5.165, 222 nm) (MS:ESI+ve 627.5 [M+1]). $^1H$ NMR: (400 MHz, DMSO-$d_6$) δ ppm: 0.77 (m, 3H), 0.87-0.81 (m, 6H), 1.49-1.43 (m, 2H), 1.94 (m, 1H), 3.11-3.03 (m, 2H), 4.21-4.00 (m, 2H), 4.24-4.26 (m, 1H), 5.26 (m, 1H), 6.80-6.85 (q, J=4 Hz, 1H), 6.97-7.06 (m, 1H), 7.19-7.26 (m, 2H), 7.33-7.45 (m, 3H), 7.59-7.60 (m, 1H), 7.73 (m, 1H), 7.82-7.84 (d, J=8 Hz, 1H), 13.64 (bs, 1H).

Example 122

Synthesis of 7-isopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 125)

Compound 125

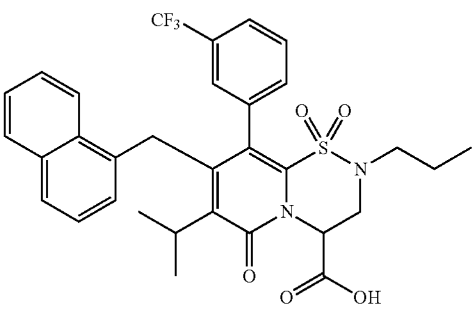

Step-1: Preparation of methyl 8-(naphthalen-1-ylmethyl)-6-oxo-7-(prop-1-en-2-yl)-2-propyl-9-(3-(trifluoromethyl)phenyl)-3,4-dihydro-2H,6H-pyrido[1,2-e][1,2,5]thiadiazine-4-carboxylate 1,1-dioxide

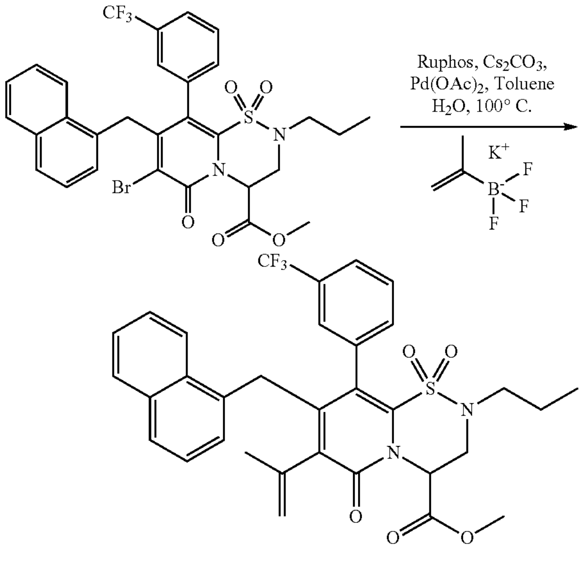

Methyl 7-bromo-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.4 g, 0.60 mmol) was dissolved in toluene (2 mL), and water (0.5 mL), and potassium trifluoro(prop-1-en-2-yl)borate (0.107 g, 0.72 mmol), cesium carbonate (0.588 g, 1.80 mmol), and RuPhos (0.028, 0.06 mmol) were added and the reaction mixture was degassed for 5 min with argon. $Pd(OAc)_2$ (0.007 g, 0.03 mmol) was added and the mixture was heated in a sealed tube at 100° C. for 16 h. The reaction was quenched in ice water (50 mL) and extracted with ethyl acetate (3×50 mL). The organic layer was dried over sodium sulphate and concentrated under reduced pressure to give the crude product which was purified using column chromatography eluting with 0-40% ethyl acetate/hexane to give methyl 8-(naphthalen-1-ylmethyl)-6-oxo-7-(prop-1-en-2-yl)-2-propyl-9-(3-(trifluoromethyl)phenyl)-3,4-dihydro-2H,6H-pyrido[1,2-e][1,2,5]thiadiazine-4-carboxylate 1,1-dioxide, as a brown solid (0.25 g, 67.56%). LCMS (Method-C3): 62.70% (RT: 2.602, 202.4 nm) (MS: ESI+ve 625.2 [M+1]).

Step 2: Preparation of methyl 7-isopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

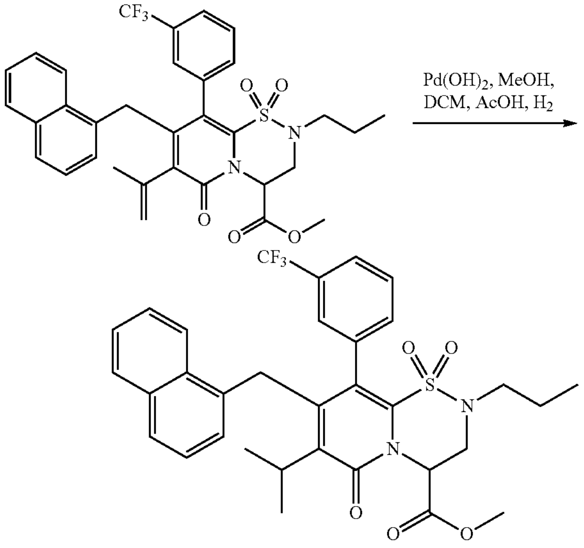

Methyl 8-(naphthalen-1-ylmethyl)-6-oxo-7-(prop-1-en-2-yl)-2-propyl-9-(3-(trifluoromethyl)phenyl)-3,4-dihydro-2H,6H-pyrido[1,2-e][1,2,5]thiadiazine-4-carboxylate 1,1-dioxide (0.25 g, 0.400 mmol) was dissolved in methanol:DCM (1:1, 5 mL). 10% Palladium hydroxide (50% moisture, 0.25 g) was added and the mixture was stirred under hydrogen for 30 min. The mixture was passed through a pad of Celite and concentrated to give methyl 7-isopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide as a brown solid (0.80 g, 31.90%) .LCMS (Method-C3): 83.21% (RT 2.683, 202.4 nm) (MS: ESI+ve 627.2 [M+H]).

Step-3: Preparation of 7-isopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 125)

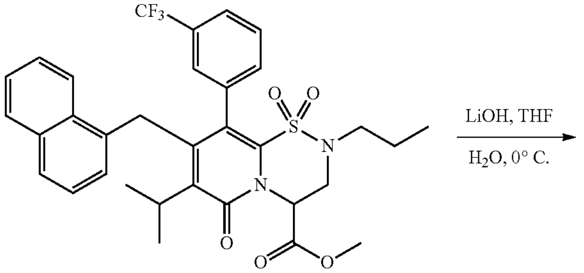

-continued

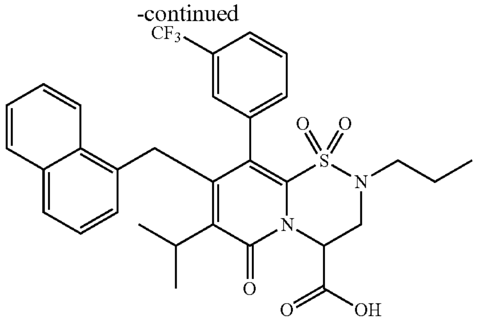

Compound 125

Methyl 7-isopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.08 g, 0.127 mmol) was dissolved in THF:$H_2O$ (1:1, 10 mL). LiOH—$H_2O$ (0.0214 g, 0.511 mmol) was added and the mixture was stirred at room temperature for 2 h. The mixture was concentrated then suspended in ice water (1 mL) and 1N aqueous HCl solution (2 mL). The resulting solid was collected by filtration and triturated with n-pentane then dried under vacuum. The crude product was purified using Prep HPLC Method 1 to give 7-isopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 125), as an off white solid (0.018 g, 23.02%). LCMS (Method-J): 100% (RT 5.730, 202.4 nm) (MS: ESI+ve 613.2 [M+H]). $^1H$ NMR: (400 MHz, DMSO) δ ppm: 0.76-0.80 (m, 3H), 1.21-1.25 (m, 6H), 1.44-1.49 (m, 2H), 2.89-2.92 (m, 1H), 3.12 (s, 2H), 3.94-4.22 (m, 4H), 5.17 (s, 1H). 6.91-6.95 (t, 1H), 7.09 (s, 1H), 7.24-7.47 (m, 6H), 7.67-7.69 (d, J=8.4 Hz, 1H), 7.74-7.77 (t, 1H), 7.85-7.86 (d, J=5.6 Hz, 1H), 13.78 (bs, 1H).

Example 123

Synthesis of 7-cyclopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 132)

Compound 132

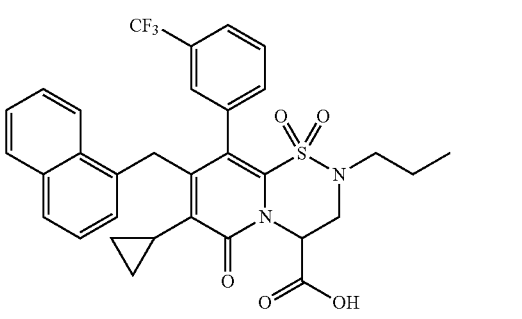

Step-1: Preparation of methyl 7-cyclopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

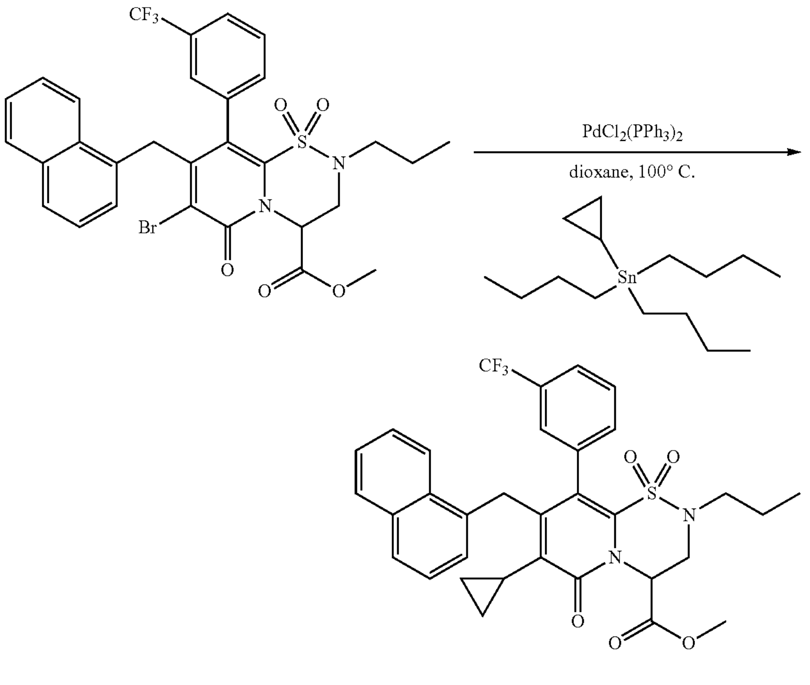

Methyl 7-bromo-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.4 g, 0.6033 mmol) and tributyl(cyclopropyl)stannane (0.219 g, 0.6636 mmol) was dissolved in dry 1,4 dioxane (4.0 mL) then degassed with nitrogen for 10 min. Bis (triphenylphosphine)palladium(II) dichloride (0.0423 g, 0.0603 mmol) was added, and the reaction was stirred for 72 h at 100° C. The reaction was quenched in water (50 mL) and extracted with ethyl acetate (3×50 mL). The organic layer was dried over sodium sulphate and concentrated under reduced pressure to give the crude product which was purified using column chromatography eluting with 0-30% ethyl acetate/hexane to give methyl 7-cyclopropyl-8-(naphthalen-1-ylmethyl)-6-oxo-2-propyl-9-(3-(trifluoromethyl) phenyl)-3,4-dihydro-2H,6H-pyrido[1,2-e][1,2,5]thiadiazine-4-carboxylate 1,1-dioxide (0.22 g, 58.42%). LCMS (Method-H): 72.31% (RT: 5.534, 222.0 nm) (MS: ESI+ve 625.0 [M+H]).

Step-2: Preparation of 7-cyclopropyl-8-(naphthalen-1-ylmethyl)-6-oxo-2-propyl-9-(3-(trifluoromethyl) phenyl)-3,4-dihydro-2H,6H-pyrido[1,2-e][1,2,5] thiadiazine-4-carboxylic acid 1,1-dioxide (Compound 132)

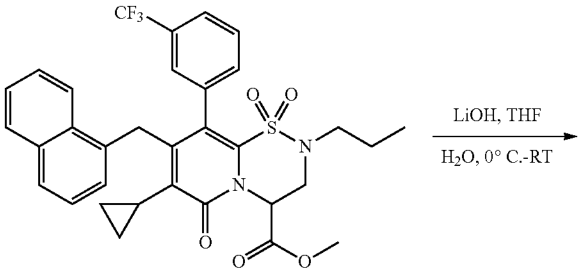

-continued

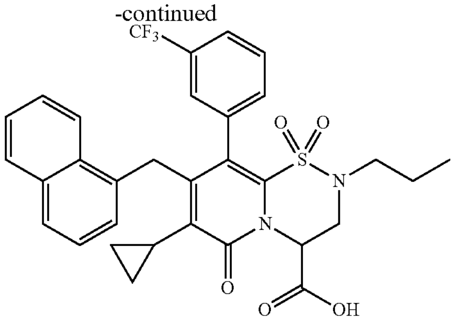

Compound 132

Methyl 7-cyclopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.20 g, 0.320 mmol) was dissolved in THF:$H_2O$ (1:1, 4 mL) at room temperature. LiOH—$H_2O$ (0.053 g, 1.282 mmol) was added and the mixture was stirred at room temperature for 4 h. The mixture was concentrated then ice water (10 mL) and 1N aqueous HCl solution (3-4 mL) were added. The resulting solid was collected by filtration and dried under vacuum. The crude product was purified by using Prep HPLC Method 1 to give 7-cyclopropyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 132), as a white solid (0.065 g, 33.25%). LCMS (Method-C3): 100% (RT 2.008, 225.0 nm) (MS: ESI+ve 611.5 [M+H]). $^1$H NMR: (400 MHz, DMSO) δ ppm: 0.70-0.79 (m, 5H), 1.160-1.20 (d, J=16.4 Hz, 2H), 1.45-1.47 (m, 2H), 1.63 (s, 1H), 3.06-3.08 (d, J=8 Hz, 2H), 4.09-4.35 (m, 4H), 5.20 (s, 1H), 6.90-6.95 (t, J=18.8 Hz, 1H), 7.02-7.13 (m, 1H), Example 124

Synthesis of 7-ethyl-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 124)

Compound 124

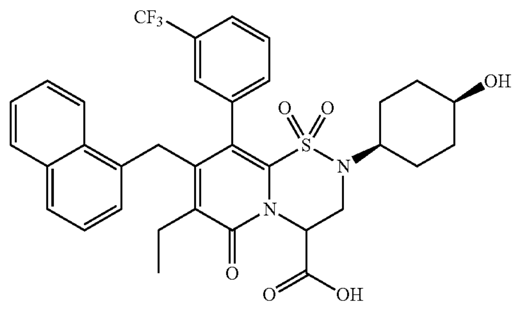

Step 1: preparation of methyl 7-bromo-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

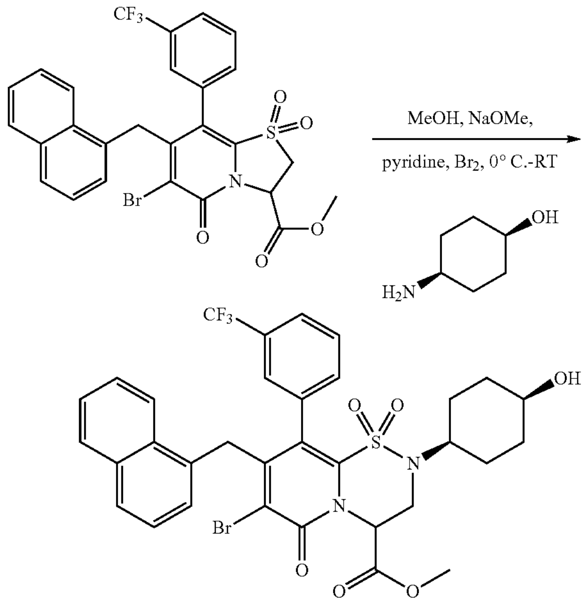

Methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.5 g, 0.82 mmol) was dissolved in methanol (5.0 mL). After cooling to 0° C., (1s,4s)-4-aminocyclohexan-1-ol (0.11 g, 0.98 mmol) was added in portions and the mixture was stirred for 5 min. 0.2 M sodium methoxide in methanol (5.0 mL) was added dropwise at 0° C. and the mixture was stirred for 16 h at room temperature. The mixture was concentrated, then concentrated twice from chloroform. The residue was dissolved in acetonitrile (10 mL) and cooled to 0° C. Pyridine (0.061 mL, 0.82 mmol), followed by bromine (0.157 g, 0.98 mmol) was added and the reaction mixture was stirred for 1 h at room temperature. The reaction was quenched in water (100 mL) and extracted with ethyl acetate (3×100 mL). The organic layer was dried over sodium sulphate and concentrated under reduced pressure to give crude product which was purified using column chromatography eluting with 0-40% ethyl acetate/DCM to give methyl 7-bromo-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a brown solid (0.32 g, 53.94%). LCMS (Method-C3): 72.07% (RT: 2.427, 202.4 nm) (MS: ESI+ve 719.2 [M+0]).

Step-2: Preparation of methyl 2-((1s,4s)-4-hydroxycyclohexyl)-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide

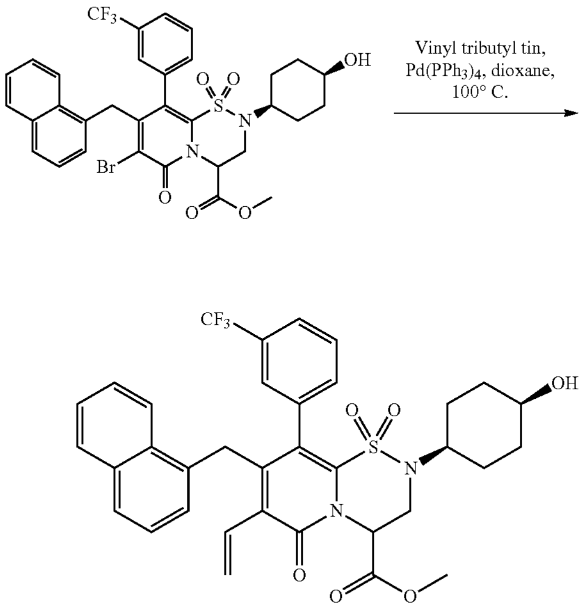

Methyl 7-bromo-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.32 g, 0.445 mmol) was dissolved in dry dioxane (10 mL). Vinyl tributyl tin (0.141 g, 0.445 mmol) was added and the mixture was degassed for 5 min with argon. Palladium (0) tetrakis(triphenylphosphine) (0.051 g, 0.0445 mmol) was added and the mixture was heated in a sealed tube at 100° C. for 16 h. The reaction was quenched in ice water (50 mL) and extracted with ethyl acetate (3×50 mL). The organic layer was dried over sodium sulphate and concentrated under reduced pressure to give the crude product which was purified using column chromatography eluting with 0-40% ethyl acetate/DCM to give methyl 2-((1s,4s)-4-hydroxycyclohexyl)-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (0.29 g, 97.81%). LCMS (Method-C3): 63.07% (RT: 2.443, 202.4 nm) (MS: ESI+ve 667.2 [M+1]).

Step 3: Preparation of methyl 7-ethyl-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

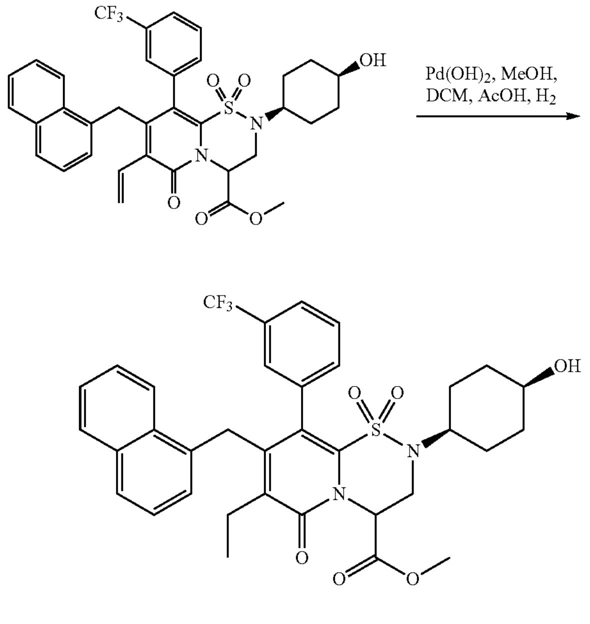

Methyl 2-((1s,4s)-4-hydroxycyclohexyl)-8-(naphthalen-1-ylmethyl)-6-oxo-9-(3-(trifluoromethyl)phenyl)-7-vinyl-3,4-dihydro-2H,6H-pyrido[1,2-e][1,2,5]thiadiazine-4-carboxylate 1,1-dioxide (0.32 g, 0.480 mmol) was dissolved in methanol (15 mL). 10% palladium hydroxide (50% moisture) (0.32 g) was added and the mixture was stirred under hydrogen for 30 min. The mixture was filtered through Celite and the filtrate was concentrated and to give methyl 7-ethyl-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide as a brown solid (0.24 g, 74.77%).LCMS (Method-C3): 55.77% (RT 2.442, 202.4 nm) (MS: ESI+ve 669.3 [M+H]).

Step-4: Preparation of 7-ethyl-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 124)

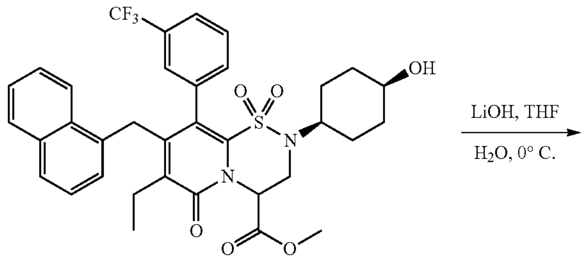

-continued

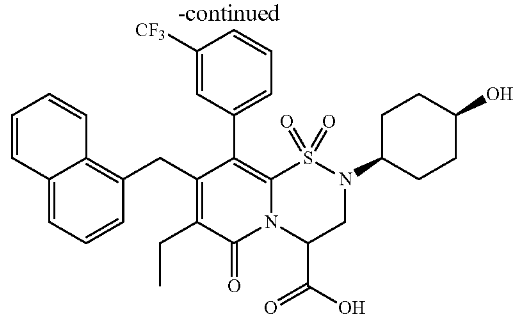

Compound 124

Methyl 7-ethyl-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.24 g, 0.359 mmol) was dissolved in THF:$H_2O$ (1:1, 10 mL). LiOH—$H_2O$ (0.060 g, 1.43 mmol) was added and the reaction mixture was stirred for 2 h. The mixture was concentrated then suspended in cold water (10 mL) and 1N aqueous HCl solution (3-4 mL). The resulting precipitate was collected by filtration and dried under vacuum. The crude product was purified using Prep HPLC Method 1 to give 7-ethyl-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 124), as an off white solid (0.056 g, 23.83%). LCMS (Method-C3): 100% (RT 2.279, 214.4 nm) (MS: ESI+ve 655.2 [M+H]). 1H NMR: (400 MHz, DMSO) δ ppm: 1.02 (s, 3H), 1.21-1.40 (m, 5H), 1.65-1.84 (m, 6H), 3.59-3.61 (m, 1H), 3.71 (s, 1H), 3.95-4.09 (q, 3H), 4.44 (s, 1H), 5.42 (s, 1H), 6.85 (s, 1H), 7.01-7.11 (d, 1H), 7.22-7.44 (m, 6H), 7.65 (m, 1H), 7.74 (m, 1H), 7.83 (m, 1H), 13.57 (s, 1H).

Example 125

Synthesis of 2-cyclohexyl-7-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 116)

Compound 116

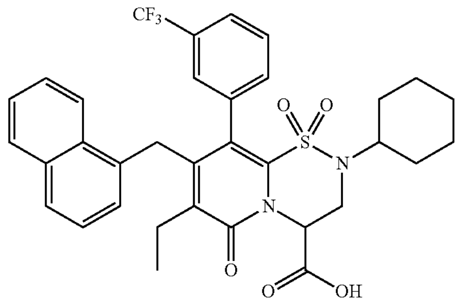

Prepared by a procedure similar to that reported for Preparation of 7-ethyl-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 124) substituting cyclohexanamine in step 1. The crude product was purified using Prep HPLC Method 1 to give 2-cyclohexyl-7-ethyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide, as an off white solid (Compound 116) (0.032 g, 20.4%). LCMS (Method-C3): 100% (RT 2.54, 202.0 nm) (MS: ESI+ve 639.3 [M+H]). $^1$H NMR: (400 MHz, DMSO) δ ppm: 1.00-1.06 (m, 3H), 1.10-1.22 (m, 3H), 1.44-1.47 (m, 5H), 1.68-1.71 (m, 2H), 3.56 (m, 1H), 3.95-4.14 (m, 4H), 5.39 (s, 1H), 6.83-6.83 (m, 1H), 7.11-6.99 (m, 1H), 7.22-7.29 (m, 2H), 7.35-7.44 (m, 4H), 7.60-7.64 (m, 1H), 7.74-7.76 (m, 1H), 7.85 (t, J=4 Hz, 1H), 13.56 (s, 1H).

Example 126

Synthesis of 7-ethyl-2-isopropyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide (Compound 115)

Compound 115

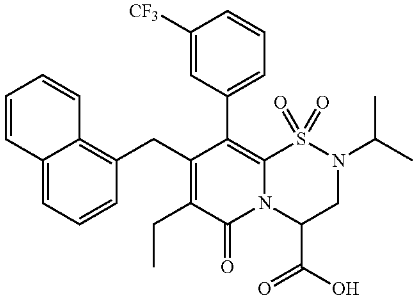

Prepared by a procedure similar to that reported for Preparation of 7-ethyl-2-((1s,4s)-4-hydroxycyclohexyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 124) substituting isopropyl amine in step 1. The crude product was purified using Prep HPLC Method 1 to give 7-ethyl-2-isopropyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 115). LCMS (Method-C3): 100% (RT: 5.461) (MS: ESI+ve 599.2 [M+H]). $^1$H NMR: (400 MHz, MeDO) (332793) δ ppm: 1.15-1.19 (t, J=9H), 2.67 (s, 2H), 4.122-4.198 (t, 5H), 5.649 (s, 1H), 6.965 (s, 1H), 7.150-7.459 (m, 7H), 7.622-7.636 (d, 1H), 7.720-7.740 (d, J=8, 1H), 7.802-7.821 (d, J=8.1H).

Compound 082

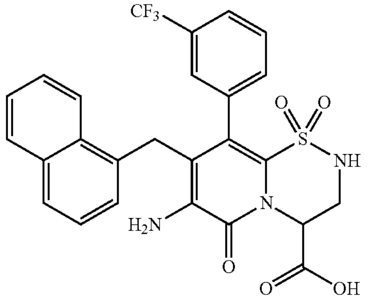

Step 1: Preparation of methyl 7-(benzylamino)-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

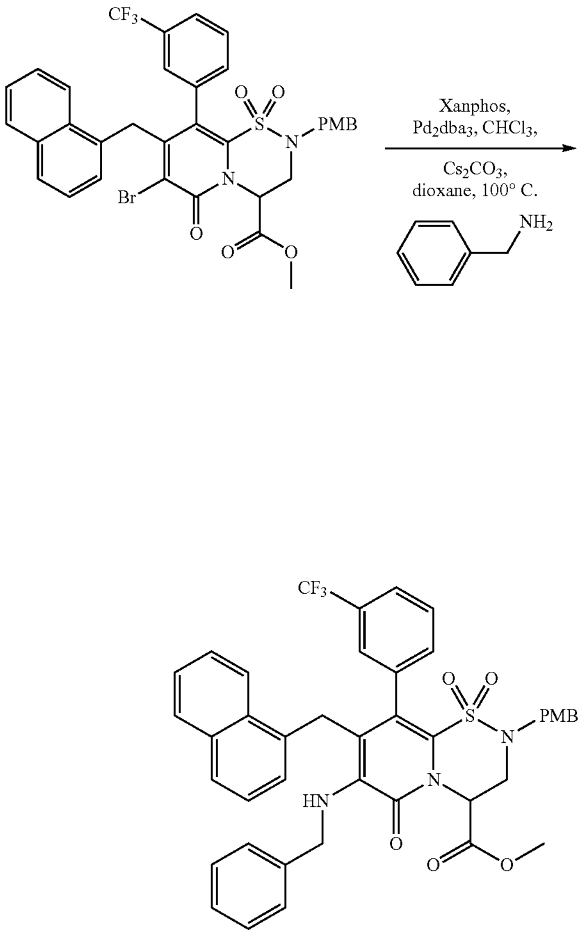

7-Bromo-2-(4-methoxybenzyl)-8-(naphthalen-1-ylmethyl)-6-oxo-9-(3-(trifluoromethyl) phenyl)-3, 4-dihydro-2H,6H-pyrido[1,2-e][1,2,5]thiadiazine-4-carboxylate 1,1-dioxide (3.5 g, 4.723 mmol) was dissolved in dry 1,4 dioxane (40 mL) and degassed with argon. Cesium carbonate (3.9 g, 11.7 mmol), Xantphos (0.213 g, 0.377 mmol) and tris(dibenzylideneacetone) dipalladium-chloroform adduct (0.195 g, 0.188 mmol) were added sequentially under argon. The reaction mixture was stirred at 100° C. for 16 h then quenched in water (50 mL) and extracted with ethyl acetate (2×30 mL). The organic layer was dried over sodium sulphate and concentrated under reduced pressure to give crude product which was purified by column chromatography eluting with 20-30% ethyl acetate/hexane to give methyl 7-(benzylamino)-2-(4-methoxybenzyl)-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylate 1,1-dioxide (2.0 g, 55.19%). LCMS (Method-J): 84.80% (RT: 5.652, 225.0 nm) (MS: ESI+ve 768.25 [M+H]).

Step 2: Preparation of methyl 7-(benzylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

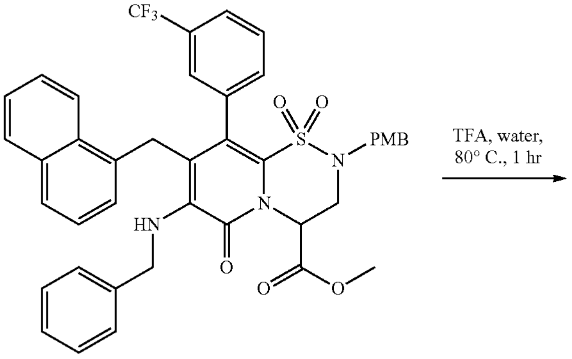

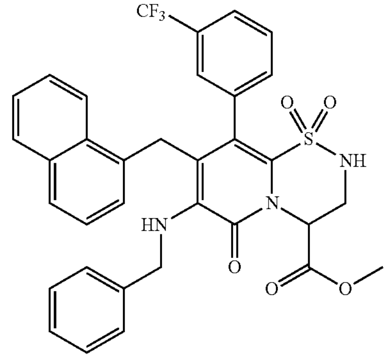

Methyl 7-(benzylamino)-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (2.0 g, 2.60 mmol) was added to TFA (20 mL) and water (2.0 mL). The mixture was stirred for 1 h at 80° C. The mixture was quenched in sat. aq. bicarbonate solution (1000 mL) and extracted with ethyl acetate (2×50 mL). The organic layer was dried and concentrated to give methyl 7-(benzylamino)-8-(naphthalen-1-ylmethyl)-6-oxo-9-(3-(trifluoromethyl)phenyl)-3, 4-dihydro-2H,6H-pyrido [1,2-e][1,2,5] thiadiazine-4-carboxylate1,1-dioxide (1.6 g, 94.84%) LCMS (Method-C3): 87.67% (RT: 2.133, 225.0 nm) (MS: ESI+ve 647.3 [M+H]).

Step 3: Preparation of methyl 7-amino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

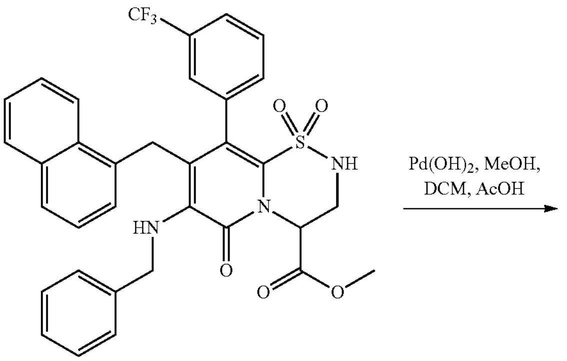

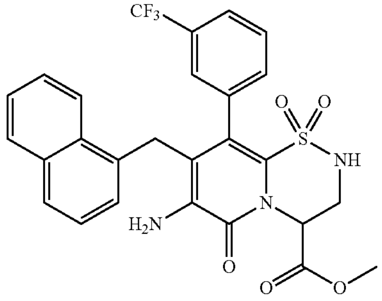

Methyl 7-(benzylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.1 g, 0.154 mmol) dissolved in (DCM:MeOH)(1:1, 10 mL) and acetic acid (0.2 mL). Palladium hydroxide (0.1 g) was added and the reaction mixture was purged with $H_2$ gas and stirred for 1 h. The reaction mixture was filtered through a pad of Celite and the filtrate was concentrated under reduced pressure to give methyl 7-amino-8-(naphthalen-1-ylmethyl)-6-oxo-9-(3-(trifluoromethyl)phenyl)-3,4-dihydro-2H, 6H-pyrido[1,2-e][1,2,5]thiadiazine-4-carboxylate 1,1-dioxide (0.08 g, 98.74%). LCMS (Method-C3): 85.86% (RT: 1.818, 225.0 nm) (MS: ESI+ve 558.6 [M+H]).

Step 4: Preparation of 7-amino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 082)

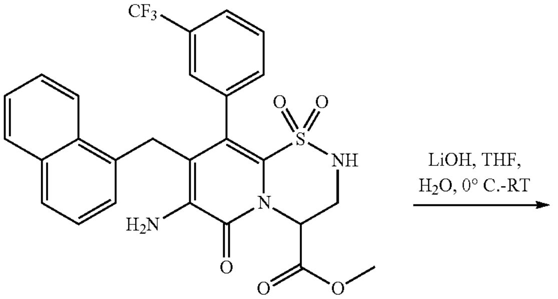

-continued

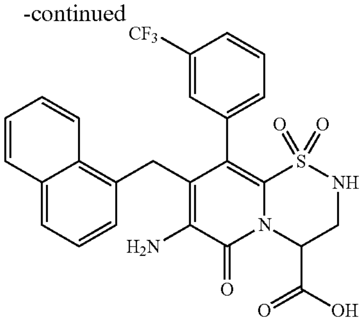

Compound 082

Methyl 7-amino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.08 g, 0.1795 mmol) was dissolved in THF:$H_2O$ (1:1, 5 mL) at room temperature. LiOH—$H_2O$ (0.023 g, 0.5385 mmol) was added at 0° C. and the mixture was stirred at room temperature for 4 h. The mixture was concentrated then suspended in ice water (10 mL) and 1N aqueous HCl solution (3-4 mL). The resulting precipitate solid was collected by filtration and dried under vacuum. The crude product was purified using Prep HPLC Method 5 to give 7-amino-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 082) as an off white solid (0.019 g, 22.93%). LCMS (Method-C3): 100% (RT 1.4701, 202.0 nm) (MS: ESI+ve 544.0 [M+H]). $^1$H NMR: (400 MHz, DMSO) δ ppm: 3.78-4.00 (m, 4H), 5.23 (s, 1H), 5.991 (s, 2H), 6.88-6.89 (d, J=4.4, 1H), 6.99 (s, 1H), 7.25-7.27 (d, J=6.8, 1H), 7.36-7.44 (m, 5H), 7.61-7.64 (d, J=8.4, 1H), 7.71-7.74 (m, 1H), 7.83-7.85 (d, J=5.6, 1H), 8.12 (s, 1H), Example 127

Synthesis of 7-amino-2-butyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide (Compound 093)

Compound 093

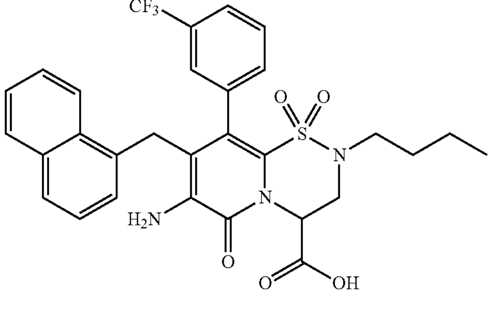

Step 1: Preparation of methyl 7-(benzylamino)-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

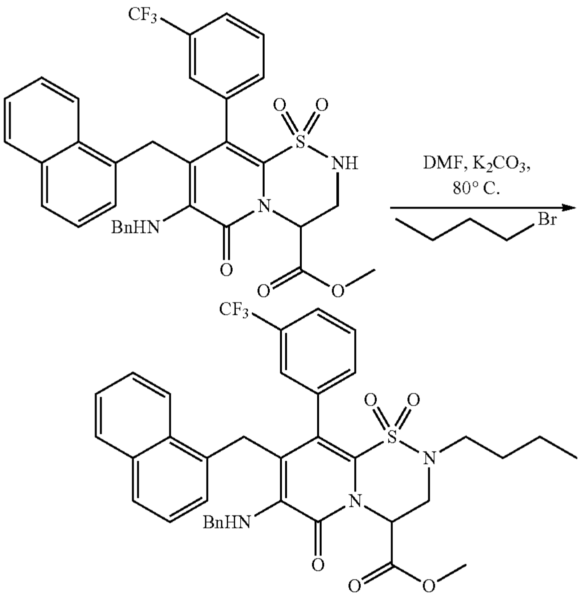

Methyl 7-(benzylamino)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.2 g, 0.3091 mmol) and 1-bromobutane (0.065 g, 0.4636 mmol) was dissolved in DMF (3 mL). $K_2CO_3$ (0.064 g, 0.4636 mmol) was added and the reaction mixture was stirred at 80° C. for 1 h. The reaction was quenched with ice water (10 mL) and extracted with ethyl acetate (3×15 mL). The organic layers were combined and dried over sodium sulphate. The solvent was removed under reduced pressure and the crude product was purified by column chromatography eluting with 20% ethyl acetate/hexane to give methyl 7-(benzylamino)-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide, as a brown solid (0.13 g, 59.82%) LCMS (Method-C3): 91.36% (RT: 2.336, 225.0 nm) (MS: ESI+ve 704.8 [M+H]).

Step 2: Preparation of methyl 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

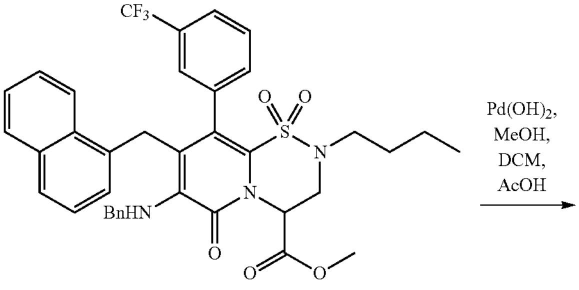

-continued

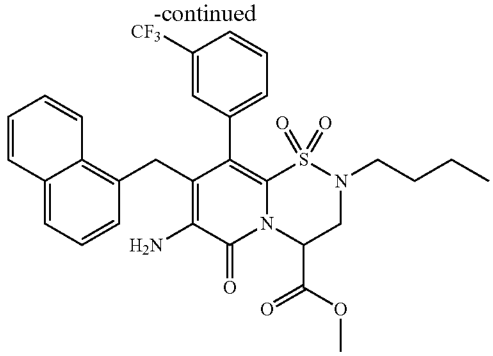

Methyl7-(benzylamino)-2-butyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylate 1,1-dioxide (0.13 g, 0.1844 mmol) was dissolved in (DCM: MeOH) (1:1, 10 mL) and acetic acid (0.2 mL). Palladium hydroxide (0.13 g) was added and the reaction mixture was purged with $H_2$. After 1 h, the reaction mixture was filtered through a pad of Celite and the filtrate was concentrated under reduced pressure to give methyl 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.11 g, 97.04%). LCMS (Method-C3): 81.41% (RT: 2.160, 229.0 nm) (MS: ESI+ve 614.48 [M+H]).

Step 3: Preparation of 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093)

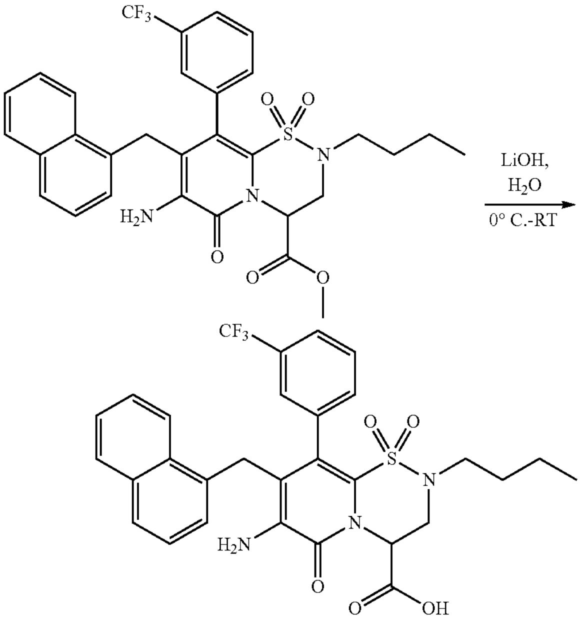

Compound 093

Methyl 7-amino-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.11 g, 0.1794 mmol) was dissolved in THF:$H_2O$ (1:1, 5 mL) at rt then LiOH—$H_2O$ (0.022 g, 0.5383 mmol) was added at 0° C. with stirring continued for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093), as an off white solid (0.023 g, 21.40%). LCMS (Method-C3): 100% (RT 1.863, 223.0 nm) (MS: ESI+ve 600.42 [M+H]). $^1$H NMR: (400 MHz, DMSO) δ ppm: 0.82-0.85 (t, J=14.8 Hz, 3H), 1.118-1.28 (m, 2H), 1.41-1.47 (m, 2H), 3.08-3.18 (m, 2H), 3.81-3.88 (m, 1H), 3.97-4.10 (m, 2H), 4.10-4.21 (m, 1H), 5.39 (s, 1H), 6.08 (s, 2H), 6.89-6.94 (t, J=16.8 Hz, 1H), 7.04 (s, 1H), 7.29-7.474 (m, 6H), 7.64-7.66 (d, J=8.4, 1H), 7.73-7.75 (d, J=7.6, 1H), 7.85-7.87 (d, J=8 Hz, 1H).

Example 128

Synthesis of 7-amino-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 074)

Compound 074

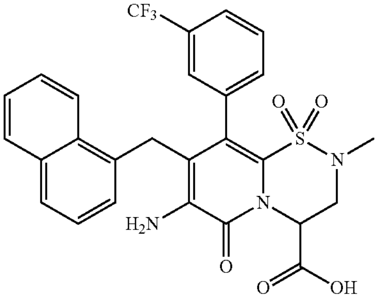

Prepared by a method similar to that reported for 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093) substituting methyl iodide in step 1. The crude product was purified using Prep HPLC Method 1 to give 7-amino-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 074), as an off white solid (0.011 g, 18.79%). LCMS (Method-C3): 100% (RT 1.747, 283 nm) (MS: ESI+ve 558.66 [M+H]). $^1$H NMR: (400 MHz, DMSO) δ ppm: 2.80 (s, 3H), 3.80-3.90 (m, 1H), 3.97-4.11 (m, 2H), 4.21-4.27 (m, 1H), 5.32 (s, 1H), 6.12 (s, 1H), 6.89-6.95 (m, 2H), 7.04-7.14 (m, 1H), 7.28-7.30 (m, 1H), 7.34-7.47 (m, 5H), 7.64-7.66 (d, J=8 Hz, 1H), 7.73-7.75 (d, J=8.4 Hz, 1H), 7.85-7.87 (d, J=8 Hz, 1H), 13.60 (s, 1H).

Example 129

Synthesis of 7-amino-8-(naphthalen-1-ylmethyl)-6-oxo-2-propyl-9-(3-(trifluoromethyl) phenyl)-3,4-dihydro-2H,6H-pyrido[1,2-e][1,2,5]thiadiazine-4-carboxylic acid 1,1-dioxide. (Compound 089)

Compound 089

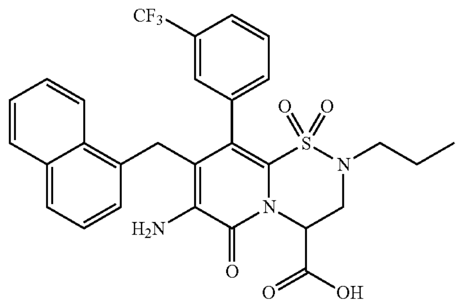

Prepared by a method similar to that reported for 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093) substituting propyl iodide in step 1. The crude product was purified using Prep HPLC Method 1 to give 7-amino-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 089), as an off white solid (0.058 g, 27%). LCMS (Method-C3): 100% (RT 1.957, 224.0 nm) (MS: ESI+ve 586.4 [M+H]). $^1$H NMR: (400 MHz, DMSO) δ ppm: 0.79 (s, 3H), 1.47-1.487 (d, J=6.4, 2H), 3.07 (s, 2H), 3.81-4.16 (m, 4H), 5.303 (s, 1H), 6.02 (s, 2H), 6.90 (s, 1H), 7.01-7.08 (d, J=26.4, 1H), 7.31-7.43 (m, 6H), 7.62-7.85 (m, 3H), Example 130

Synthesis of 7-amino-8-(naphthalen-1-ylmethyl)-6-oxo-2-pentyl-9-(3-(trifluoromethyl) phenyl)-3,4-dihydro-2H,6H-pyrido[1,2-e][1,2,5]thiadiazine-4-carboxylic acid 1,1-dioxide (Compound 094)

Compound 094

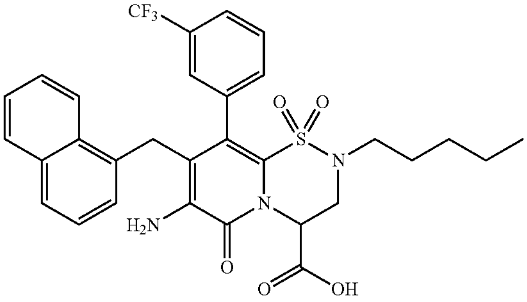

Prepared by a method similar to that reported for 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093) substituting 1-bromopentane in step 1. The crude product was purified using Prep HPLC Method 1 to give 7-amino-8-(naphthalen-1-ylmethyl)-6-oxo-2-pentyl-9-(3-(trifluoromethyl)phenyl)-3,4-dihydro-2H,6H-pyrido[1,2-e][1,2,5]thiadiazine-4-carboxylic acid 1,1-dioxide (Compound 094), as an off white solid (0.040 g, 29.22%). LCMS (Method-C3): 100% (RT 1.929,224.0 nm) (MS: ESI+ve 614.4 [M+H]). $^1$H NMR: (400 MHz, DMSO) δ ppm: 0.82-0.85 (t, J=14 Hz, 3H), 1.89-1.27 (m, 4H), 1.45-1.48 (t, J=6.8 Hz, 2H), 3.06-3.09 (t, J=13.6 Hz, 2H), 3.81-3.88 (m, 1H), 3.97-4.10 (m, 2H), 4.17-4.22 (m, 1H), 5.410 (s, 1H), 6.09 (s, 2H), 6.89-6.94 (t, J=17.6 Hz, 1H) 7.04-7.13 (m, 1H), 7.30-7.47 (m, 6H), 7.64-7.66 (d, J=8.4 Hz, 1H), 7.74-7.76 (d, J=8 Hz, 1H), 7.85-7.87 (d J=8 Hz, 1H).

Example 131

Synthesis of 7-amino-2-(2-hydroxyethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 098)

Compound 098

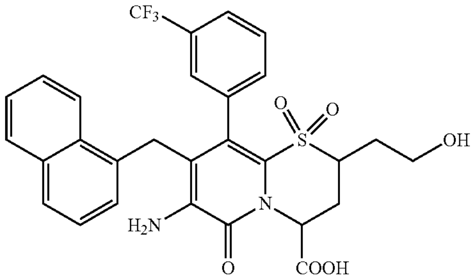

Prepared by a method similar to that reported for 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093) substituting 2-bromoethan-1-ol in step 1. The crude product was purified using Prep HPLC Method 1 to give 7-amino-2-(2-hydroxyethyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 098), as an off white solid (0.040 g, 27.30%). LCMS (Method-C3): 100% (RT 1.702, 230 nm) (MS: ESI+ve 588.76 [M+H]). 1H NMR: (400 MHz, DMSO) δ ppm: 3.15-3.23 (m, 2H), 3.46 (s, 2H), 3.80-3.89 (t, 1H), 3.96-4.03 (m, 1H), 4.15-4.32 (m, 2H), 4.86 (s, 1H), 5.36 (s, 1H), 6.07 (s, 2H), 6.89-6.94 (q, 1H), 7.05-7.13 (d, J=31.6 Hz, 1H), 7.28-7.46 (m, 6H), 7.64-7.66 (d, J=8.4 Hz, 1H), 7.73-7.75 (d, J=8 Hz, 1H), 7.85-7.87 (d, J=8 Hz, 1H), 13.58 (s, 1H).

Example 132

Synthesis of 7-amino-2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 099)

Compound 099

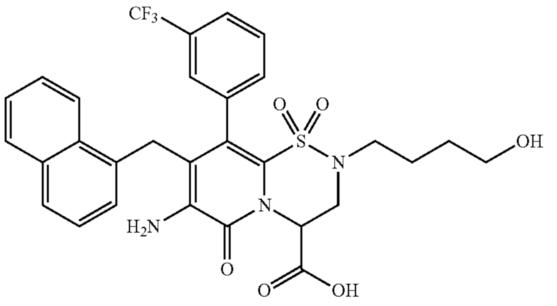

Prepared by a method similar to that reported for 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093) substituting 4-bromobutan-1-ol in step 1. The crude product was purified using Prep HPLC Method 1 to give 7-amino-2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 099), as an off white solid (0.011 g, 8.30%). LCMS (Method-C3): 100% (RT 1.758, 285.0 nm) (MS: ESI+ve 616 [M+H]). $^1$H NMR: (400 MHz, DMSO) δ ppm: 1.33-1.38 (m, 2H), 1.48-1.52 (m, 2H), 3.09-3.10 (d, J=3.2 Hz, 2H), 3.32-3.35 (t, 2H), 3.81-3.87 (m, 1H), 3.96-4.02 (m, 1H), 4.06-4.20 (m, 2H), 5.35 (s, 1H), 6.07 (s, 2H), 6.89-6.93 (m, 2H), 7.04-7.87 (m, 9H).

Example 133

Synthesis of 7-amino-2-(5-hydroxypentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 100)

Compound 100

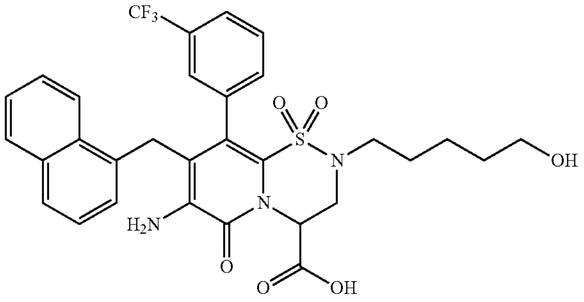

Prepared by a method similar to that reported for 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093) substituting 5-bromopentan-1-ol in step 1. The crude product was purified using Prep HPLC Method 1 to give 7-amino-2-(5-hydroxypentyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 100), as an off white solid (0.035 g, 38.34%). LCMS (Method-C3): 100% (RT 1.758, 285.0 nm) (MS: ESI+ve 630 [M+H]). $^1$H NMR: (400 MHz, DMSO) δ ppm: 1.22 (s, 2H), 1.37-1.47 (d, J=40 Hz, 4H), 3.07 (s, 2H), 3.81-3.88 (m, 1H), 3.98-4.09 (m, 2H), 4.17-4.37 (m, 2H), 5.40 (s, 1H), 6.09 (s, 2H), 6.91 (s, 1H), 7.04-7.13 (d, J=35 Hz, 1H), 7.30-7.45 (m, 6H), 7.63-7.65 (d, J=8 Hz, 1H), 7.73-7.75 (d, J=6.8 Hz, 1H), 7.85-7.87 (d, J=6.8 Hz, 1H), 13.61 (s, 1H).

Example 134

Synthesis of 7-amino-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 097)

Compound 097

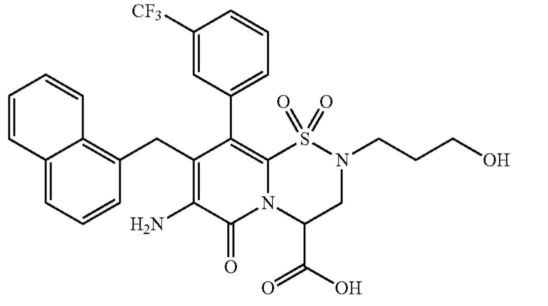

Prepared by a method similar to that reported for 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093) substituting 3-bromopropan-1-ol in step 1. The crude product was purified using Prep HPLC Method 1 to give 7-amino-2-(3-hydroxypropyl)-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylic acid 1,1-dioxide (Compound 097) as a white solid (0.069 g, 25.00%). LCMS (Method-C3): 95.74% (RT: 4.932, 254.4 nm) (MS: ESI+ve 602.2 [M+H]). $^1$H NMR: (400 MHz, DMSO) (18121) δ ppm: 2.688 (s, 2H) 3.200 (m, 2H), 3.346 (s, 2H), 3.85-4.01 (m, 1H), 4.22-4.32 (m, 2H), 4.62 (bs, 1H), 4.96 (bs, 1H), 5.33 (bs, 1H), 6.06 (s, 2H), 6.91 (m, 1H), 7.05-7.13 (m, 1H), 7.30-7.39 m, 6H), 7.63 (d, J=8.4 Hz, 1H) 7.73 (d, J=7.6 Hz, 1H) 7.84 (d, J=8.0 Hz 1H); 13.599 (bs, 1H).

Example 135

Synthesis of 7-amino-2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 092)

Compound 092

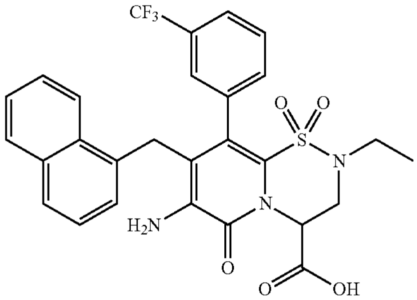

Prepared by a method similar to that reported for 7-amino-2-butyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 093) substituting ethyl iodide in step 1. The crude product was purified Prep HPLC Method 1 to give 7-amino-2-ethyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 092) as an off white solid (0.014 g, 23.91%). LCMS (Method-C3): 100% (RT 2.095, 202.0 nm) (MS: ESI+ve 572.2 [M+H]). $^1$H NMR: (400 MHz, DMSO) δ ppm: 1.06-1.09 (t, J=13.2 Hz, 3H), 3.09-3.21 (m, 2H), 3.80-3.88 (m, 1H), 3.97-4.03 (m, 1H), 4.07-4.12 (m, 1H), 4.17-4.22 (3, 1H), 5.41-5.42 (d, J=3.2 Hz, 1H), 6.10 (s, 2H), 6.88-6.93 (m, 1H), 7.04-7.12 (s, 1H), 7.29-7.47 (m, 6H), 7.64-7.66 (d, J=8 Hz, 1H), 7.73-7.75 (d, J=8, 1H), 7.85-7.87 (d, J=8, 1H), 13.65 (s, 1H).

Example 136

Synthesis of 7-amino-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylic acid 1,1-dioxide (Compound 105)

Compound 105

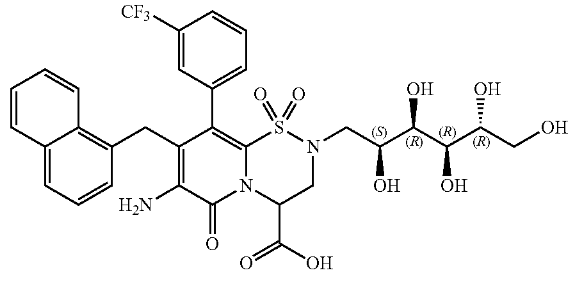

Step 1: Preparation of methyl 7-bromo-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylate 1,1-dioxide

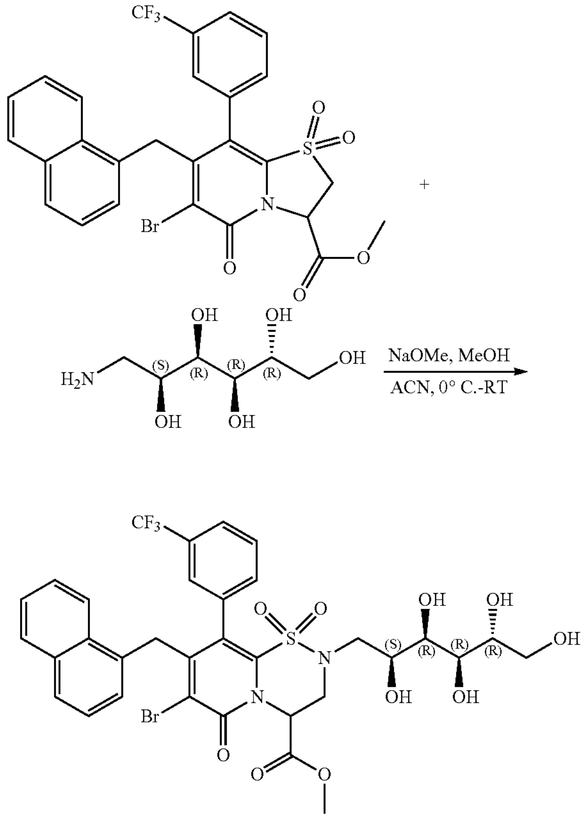

Methyl 6-bromo-7-(naphthalen-1-ylmethyl)-5-oxo-8-(3-(trifluoromethyl)phenyl)-2,3-dihydro-5H-thiazolo[3,2-a]pyridine-3-carboxylate 1,1-dioxide (0.5 g, 0.825 mmol) was dissolved in methanol 5 mL) and cooled to 0° C. (2R,3R,4R,5S)-6-aminohexane-1,2,3,4,5-pentaol (0.174 g, 0.961 mmol) was added followed by freshly prepared sodium methoxide solution (0.2 M solution) (5 mL, 6 mL/1 mmol). The reaction mixture was stirred at room temperature for 16 h then concentrated under vacuum and concentrated from chloroform (3×10 mL). The residue was dissolved in acetonitrile (10 mL) and cooled to 0° C. Pyridine (0.061 g, 0.77 mmol) and bromine (0.157 g, 1.013 mmol) were added and stirring was continued at 0° C. for 10 min, then at room temperature for 1 h. The reaction was quenched in ice water (10 mL) and extracted with ethyl acetate (3×20 mL). The organic layer was dried over sodium sulphate and concentrated under reduced pressure to give the crude product which was purified using column chromatography eluting with 5-10% MeOH/$CH_2Cl_2$ to give methyl 7-bromo-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylate 1,1-dioxide as a white solid (0.54 g, 37.85%). LCMS (Method-C3): 74.63% (RT: 1.724, 225 nm) (MS: ESI+ve 787.7 [M+1]).

Step 2: Preparation Of methyl 7-(benzylamino)-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylate 1,1-dioxide

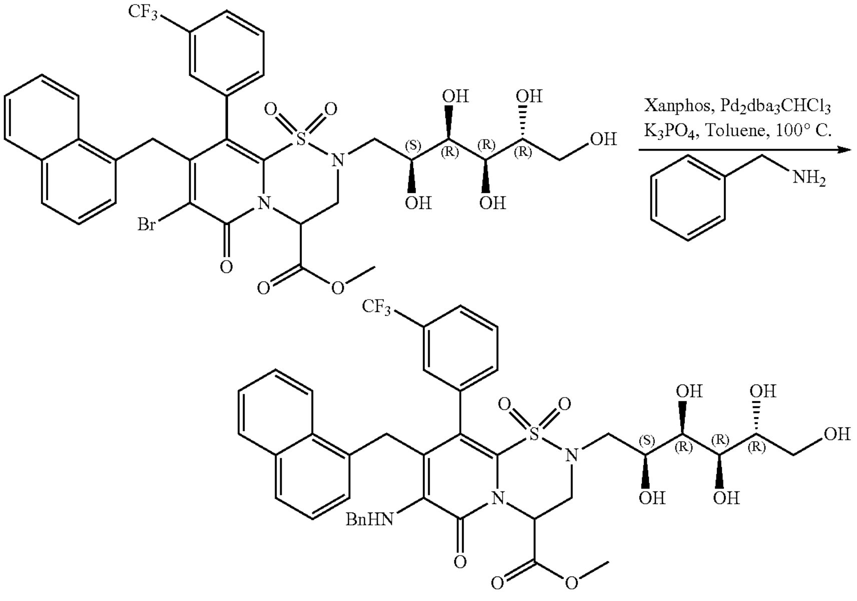

Methyl 7-bromo-2-cyclohexyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.3 g, 0.38 mmol) was added to benzylamine (0.049 g, 0.45 mmol) dissolved in dry toluene (5 mL). The mixture was degassed under argon and potassium phosphate (0.202 g, 0.952 mmol) was added, followed by Xantphos (0.0085 g, 0.015 mmol) and tris(dibenzylideneacetone)dipalladium-chloroform adduct (0.0316 g, 0.034 mmol). The reaction mixture was heated at 100° C. for 16 h, quenched in water (10 mL) and extracted with ethyl acetate (2×20 mL). The organic layer was dried over sodium sulphate and concentrated under reduced pressure to give the crude product which was purified using column chromatography eluting with 5-10% MeOH/DCM to give methyl 7-(benzylamino)-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylate 1,1-dioxide as a solid (0.10 g, 32.26%). LCMS (Method-C3): 74.10% (RT 1.877, 250 nm) (MS: ESI+ve 813.0 [M+1]).

Step 3: Preparation Of methyl 7-amino-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylate 1,1-dioxide

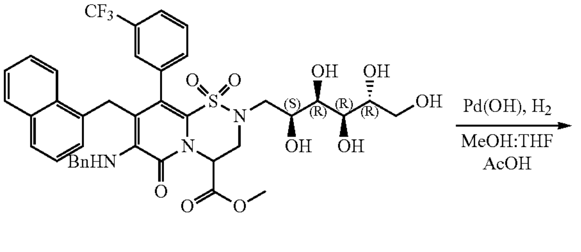

-continued

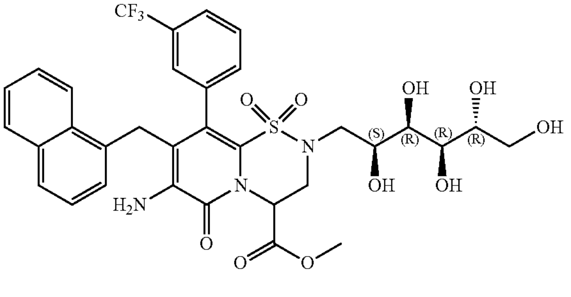

Methyl 7-(benzylamino)-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylate 1,1-dioxide (0.1 g, 0.12 mmol), was dissolved in MeOH:THF (1:1)(2 mL). Pd(OH) 2 (0.100 g) and acetic acid (0.1 mL) were added and the mixture was stirred under hydrogen at room temperature for 4 h. The reaction mixture was filtered through Celite, rinsed with methanol (10 mL) and the combined filtrates concentrated to give methyl 7-amino-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylate 1,1-dioxide as a solid (0.090 g, crude). LCMS (Method-C3): 79.33% (RT 1.602, 225.0 nm) (MS: ESI+ve 722.7 [M+H]).

Step 4: Preparation Of 7-amino-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylic acid 1,1-dioxide (Compound 105)

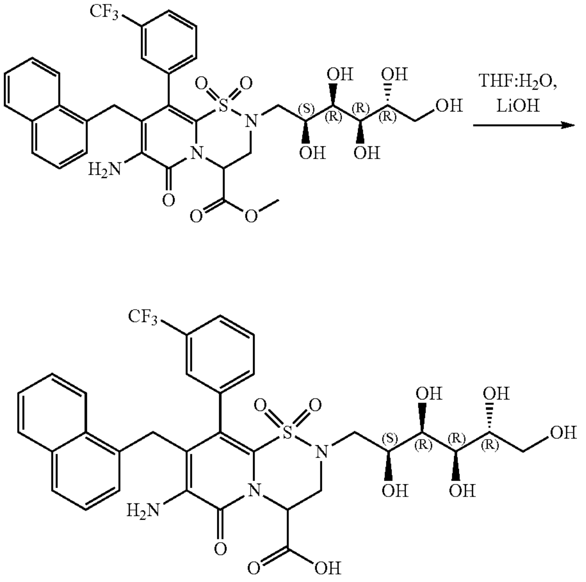

Compound 105

Methyl 7-amino-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylate 1,1-dioxide (0.09 g, 0.12 mmol) was dissolved in THF:$H_2O$ (1:1, 2 mL). LiOH—$H_2O$ (0.015 g, 0.036 mmol) was added and the mixture was stirred at room temperature for 3h. The mixture was concentrated then suspended in ice water (10 mL) and 1N aqueous HCl solution (3-4 mL). The resulting precipitate was collected by filtration and dried under vacuum. The crude product was purified using Prep HPLC Method 9 to give 7-amino-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylic acid 1,1-dioxide. (Compound 105) (0.018 g, 21.53%) as a mixture of diastereomers. LCMS (Method-$C_3$): 100% (RT 1.593, 225.0 nm) (MS: ESI+ve 708.91 [M+H]). $^1H$ NMR: (400 MHz, DMSO) δ ppm: 2.99 (m, 1H) 3.18 (m, 1H), 3.54-3.57 (m, 3H), 3.86 (m, 2H), 3.94 (m, 1H), 4.24 (m, 1H), 4.27 (m, 1H), 4.36-4.44 (m, 2H), 4.99-5.09 (m, 2H), 5.83 (s, 2H), 6.95 (m, 1H), 7.13 (m, 1H), 7.39 (m, 6H), 7.66 (m, 1H), 7.73 (m, 1H), 7.85 (m, 1H).

Example 137

Synthesis of 7-amino-2-((S)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 095)

Compound 095

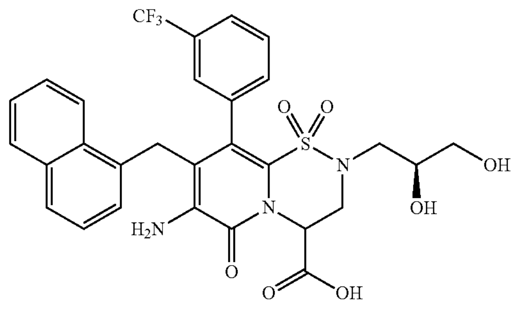

Prepared by a procedure similar to that reported for 7-amino-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylic acid 1,1-dioxide (Compound 105) substituting (S)-3-aminopropane-1,2-diol in step 1. The crude product was purified using Prep HPLC Method 1 to give 7-amino-2-((S)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide as an off white solid (0.041 g, 45.87%) (Compound 095). LCMS (Method-C3)$_{100}$% (RT: 1.610, 225.0 nm, 225.0 nm) (MS: ESI+ve 618.33 [M+H]). $^1H$ NMR: (400 MHz, DMSO) δ ppm: 3.00 (m, 2H), 3.85-4.01 (m, 2H), 4.22-4.32 (m, 2H), 4.62 (bs, 1H), 4.96 (bs, 1H), 5.33 (bs, 1H), 6.06 (s, 2H), 6.91 (m, 1H), 7.05-7.13 (m, 1H), 7.30-7.39 (m, 6H), 7.63 (d, 1H) 7.73 (d, 1H) 7.84 (d, 1H), 13.56 (bs, 1H).

Example 138

Synthesis of 7-amino-2-((R)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 096)

Compound 096

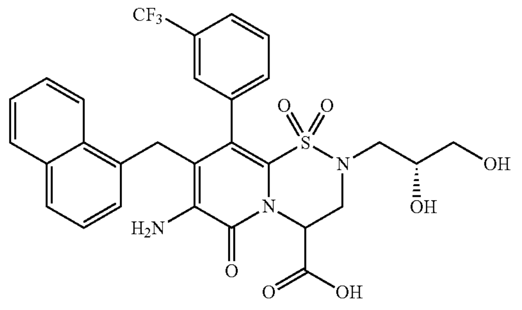

Prepared by a procedure similar to that reported for 7-amino-8-(naphthalen-1-ylmethyl)-6-oxo-2-((2S,3R,4R,5R)-2,3,4,5,6-pentahydroxyhexyl)-9-(3-(trifluoromethyl)phenyl)-3,4-dihydro-2H,6H-pyrido[1,2-e][1,2,5]thiadiazine-4-carboxylic acid 1,1-dioxide (Compound 105) substituting (R)-3-aminopropane-1,2-diol in step 1. The crude product was purified using Prep HPLC Method 1 to give 7-amino-2-((R)-2,3-dihydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 096), as an off white solid (0.029 g, 30.37%). LCMS (Method-C3): 100% (RT: 1.574, 225.0 nm, 225.0 nm) (MS: ESI+ve 618.33 [M+H]). $^1$H NMR: (400 MHz, DMSO) (22414) δ ppm: 2.94-3.06 (m, 1H), 3.22-3.30 (m, 3H), 3.51-3.11 (bs, 1H), 3.80-3.89 (m, 1H), 3.97-4.02 (m, 1H), 4.18-4.23 (m, 1H), 4.33-4.37 (m, 1H) 4.63 (bs, 1H), 4.98 (bs, 1H), 5.32 (m, 1H), 6.08 (s, 1H) 6.89-6.94 (m, 1H) 7.05-7.13 (d, 1H); 7.29-7.46 (m, 6H); 7.64-7.66 (d, J=8.4 Hz, 1H); 7.73-7.75 (d, J=8 Hz, 1H) 7.85-7.87 (d, J=8 Hz, 1H) 13.61 (s, 1H).

Example 139

Synthesis of 7-hydroxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 141)

Compound 141

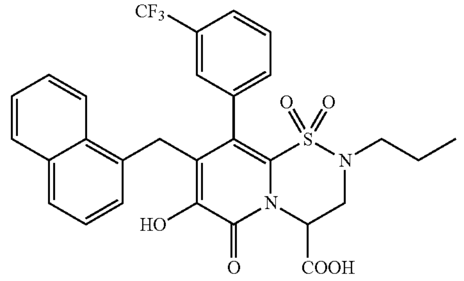

Step 1: preparation of methyl 7-hydroxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

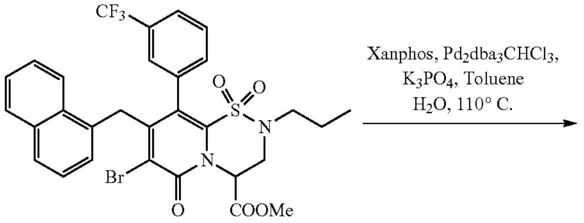

-continued

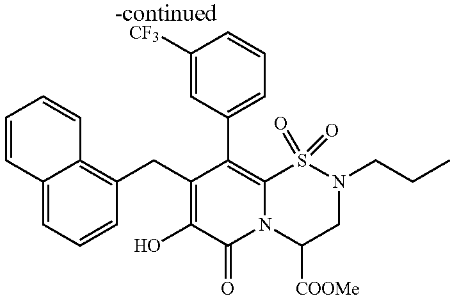

Methyl 7-bromo-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.3 g, 0.452 mmol) was dissolved in a mixture of toluene (10 mL) and water (1 mL). After degassing the mixture with argon, potassium phosphate (0.144 g, 0.678 mmol) and Xantphos (0.0209 g, 0.0361 mmol) were added, followed by tris(dibenzylideneacetone)dipalladium-chloroform adduct (0.0187 g, 0.0018 mmol). The mixture was again degassed with argon, then heated at 110° C. for 16 h. The reaction was quenched in water (50 mL) and extracted with ethyl acetate (2×40 mL). The organic layer was dried over sodium sulphate and concentrated under reduced pressure to give the crude product which was purified using column chromatography eluting with 40% ethyl acetate/hexane to give methyl 7-hydroxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.1 g, 36.82%). LCMS (Method-$C_3$): 86.41% (RT 2.438, 214.0 nm) (MS: ESI+ve 601.0 [M+1]).

Step 2: Preparation of 7-hydroxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 141)

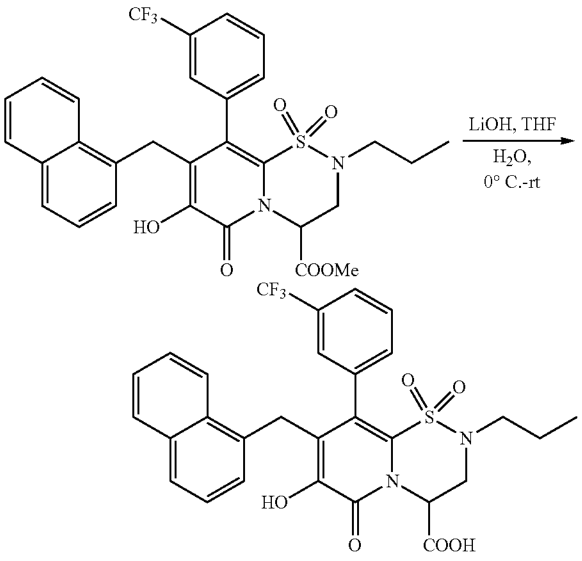

Compound 141

Methyl 7-hydroxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.1 g, 0.166 mmol) was dissolved in THF:$H_2O$ (1:1, 10 mL). LiOH—$H_2O$ (0.0209 g, 0.499 mmol) was added and the mixture was stirred at room temperature for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 7-hydroxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 141), as an off white solid (0.024 g, 24.57%). LCMS (Method-C3): 100% (RT 2.270, 220 nm) (MS: ESI+ve 587.0 [M+H]). $^1H$ NMR: (400 MHz, DMSO) δ ppm: 0.76-0.80 (t, 3H), 1.44-1.50 (q, 2H), 3.06-3.09 (t, 2H), 3.83-4.23 (m, 4H), 5.36 (s, 1H), 6.81-6.86 (t, 1H), 7.05-7.15 (d, J=40 Hz, 1H), 7.34-7.44 (m, 6H), 7.67-7.72 (t, 2H), 7.83-7.85 (d, J=8.4 Hz, 1H), 10.41 (s, 1H), 13.80 (s, 1H).

Example 140

Synthesis of 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 143)

Compound 143

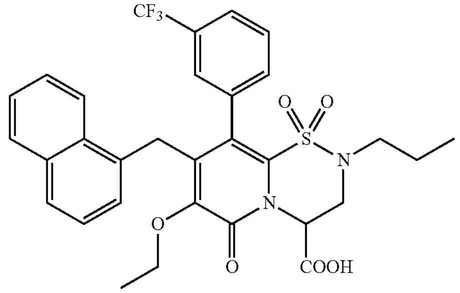

Step 1: preparation of methyl 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

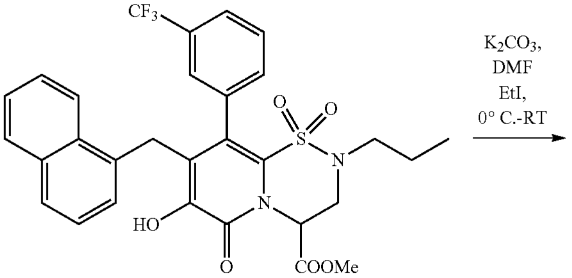

-continued

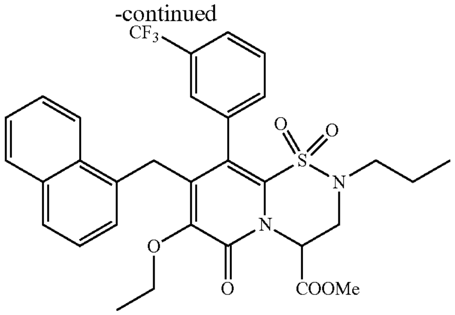

Methyl 7-hydroxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.09 g, 0.15 mmol) was dissolved in DMF (5 mL) and potassium carbonate (0.0.031 g, 0.225 mmol) was added at 0° C. The mixture was stirred for 5 min, and ethyl iodide (0.028 g, 0.18 mmol) was added with stirring continued for 16 h. The mixture was quenched in water (50 mL) and extracted with ethyl acetate (2×40 mL). The organic layer was dried over sodium sulphate and concentrated under reduced pressure to give crude product which was purified using column chromatography eluting with 40% ethyl acetate/hexane to give methyl 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.085 g, 90.23%). LCMS (Method-C3): 79.67% (RT 2.611, 220.4 nm) (MS: ESI+ve 629.0 [M+1]).

Step 2: Preparation of 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 143)

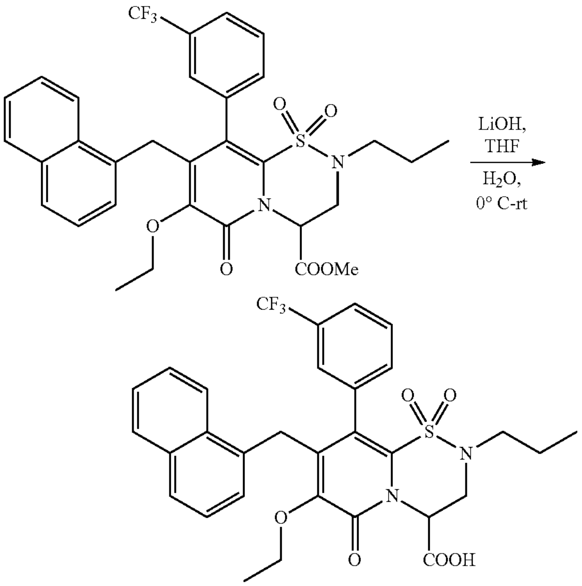

Compound 143

Methyl 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.085 g, 0.135 mmol) was dissolved in THF:$H_2O$ (1:1, 6 mL). LiOH—$H_2O$ (0.017 g, 0.406 mmol) was added and the mixture was stirred at room temperature for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 143), as an off white solid (0.013 g, 15.64%). LCMS (Method-C3): 100% (RT 1.977, 225 nm) (MS: ESI+ve 615.5 [M+H]). $^1$H NMR: (400 MHz, DMSO) δ ppm: 0.72-0.79 (t, 3H), 1.07-1.10 (t, 3H), 1.44-1.49 (m, 2H), 3.03-3.16 (m, 2H), 3.80-3.86 (m, 1H), 4.08-4.15 (m, 3H), 4.19-4.27 (m, 2H), 5.28-5.32 (m, 1H), 6.84-6.89 (q, 1H), 7.05-7.15 (d, J=38 Hz, 1H), 7.24-7.50 (m, 6H), 7.64-7.66 (d, J=6.8 Hz, 1H), 7.70-7.73 (dd, J=0.8 Hz, J=3.2 Hz, 1H), 7.82-7.84 (d, J=8 Hz, 1H).

Example 141

Synthesis of 8-(naphthalen-1-ylmethyl)-6-oxo-7-propoxy-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 147)

Compound 147

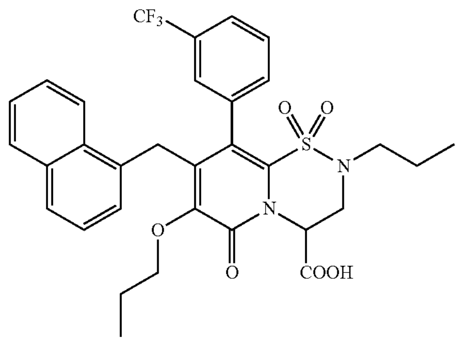

Prepared by a procedure similar to that reported for 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 143) substituting 1-iodopropane in step 1. The crude product was purified using Prep HPLC Method 1 to give 8-(naphthalen-1-ylmethyl)-6-oxo-7-propoxy-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 147), as an off white solid (0.03 g, 34.08%). LCMS (Method-C3): 98.60% (RT 2.084, 224 nm) (MS: ESI+ve 629.34 [M+H]). $^1$H NMR: (400 MHz, DMSO) δ ppm: 0.70-0.87 (m, 6H), 1.23 (s, 1H), 1.46-1.50 (t, 3H), 3.08-3.09 (d, J=6.4 Hz, 2H), 3.91-4.24 (m, 6H), 5.29 (s, 1H), 6.85-6.90 (m, 1H), 7.06-7.16 (d, J=38.4 Hz, 1H), 7.25-7.43 (m, 6H), 7.65-7.71 (m, 2H), 7.82-7.84 (d, J=7.6 Hz, 1H), 13.79 (s, 1H).

Example 142

Synthesis of 7-(benzyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 146)

Compound 146

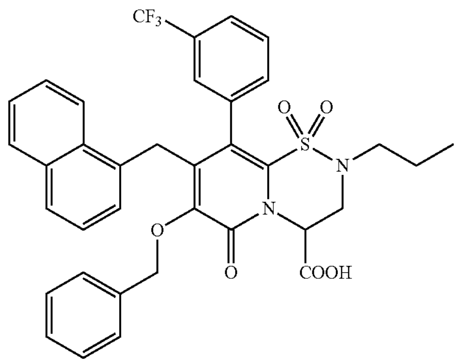

Prepared by a procedure similar to that reported for 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 143) substituting benzyl bromide in step 1. The crude product was purified using Prep HPLC Method 1 to give 7-(benzyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 146), as an off white solid (0.02 g, 9.28%). LCMS (Method-C3): 100% (RT 2.188, 202 nm) (MS: ESI+ve 676.71 [M+H]). $^1$H NMR: (400 MHz, DMSO) δ ppm: 0.88-0.92 (t, 3H), 1.57-1.62 (q, 2H), 3.18-3.22 (t, 2H), 3.88-4.03 (m, 2H), 4.30 (s, 2H), 5.22-5.36 (m, 2H), 5.56 (s, 1H), 6.80-6.81 (d, J=6.8 Hz, 1H), 7.10-7.32 (m, 11H), 7.38-7.42 (t, 1H), 7.47-7.50 (d, J=8.4 Hz, 1H), 7.66-7.68 (d, J=8 Hz, 1H), 7.77-7.79 (d, J=8 Hz, 1H).

Example 143

Synthesis of 8-(naphthalen-1-ylmethyl)-6-oxo-7-phenethoxy-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 001)

Compound 001

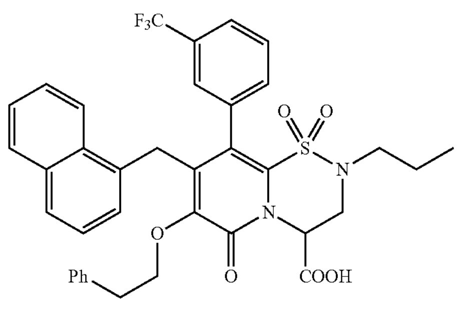

Prepared by a procedure similar to that reported for 7-ethoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 143) substituting (2-bromoethyl)benzene in step 1. The crude product was purified using Prep HPLC Method 1 to give 8-(naphthalen-1-ylmethyl)-6-oxo-7-phenethoxy-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 001), as an off white solid (0.029 g, 29.59%). LCMS (Method-C3): 100.0% (RT 2.055, 225 nm) (MS: ESI+ve 691.78 [M+H]). 1H NMR: (400 MHz, DMSO) δ ppm: 0.76-0.80 (t, 3H), 1.45-1.50 (q, 2H), 2.75-2.78 (t, 2H), 3.08-3.11 (q, 2H), 3.70-3.93 (m, 2H), 4.10-4.14 (t, 1H), 4.20-4.24 (t, 1H), 4.34-4.38 (t, 1H), 4.45-4.47 (d, J=7.2 Hz, 1H), 5.30 (s, 1H), 6.80-6.86 (q, 1H), 7.06-7.15 (m, 6H), 7.28-7.46 (m, 6H), 7.52-7.54 (d, J=8.4 Hz, 1H), 7.72-7.73 (d, J=5.2 Hz, 1H), 7.83-7.85 (d, J=8 Hz, 1H), 13.84 (s, 1H).

Example 144

Synthesis of 7-(cyclopentyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 144)

Compound 144

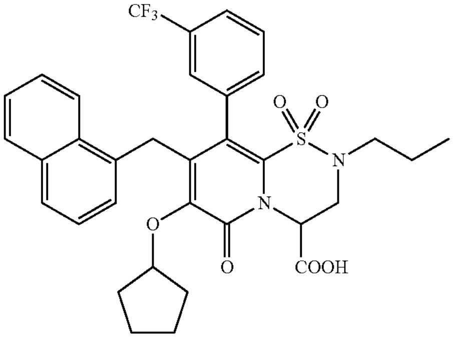

Step 1: preparation of methyl 7-(cyclopentyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide

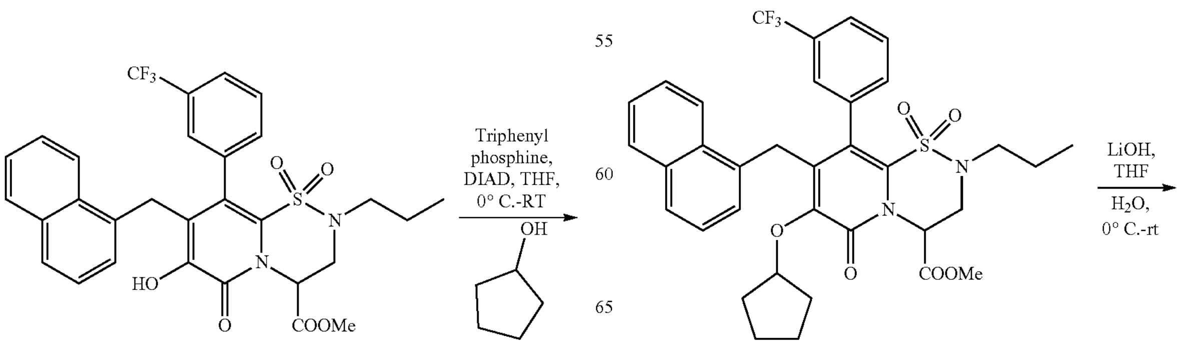

-continued

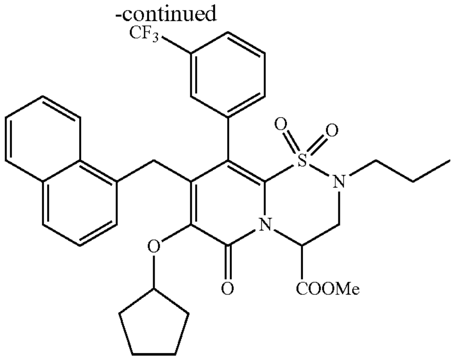

Methyl 7-hydroxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.15 g, 0.25 mmol) was dissolved in THF (5 mL). Cyclopentanol (0.0258 g, 0.3 mmol) and triphenyl phosphine (0.0983 g, 0.375 mmol) was added and cooled to 0° C., DIAD (0.0758 g, 0.375 mmol) was added with stirring continued for 16 h. The reaction was quenched in water (50 mL) and extracted with ethyl acetate (2×40 mL). The organic layer was dried over sodium sulphate and concentrated under reduced pressure to give the crude product which was purified using column chromatography eluting with 30% ethyl acetate/hexane to give methyl 7-(cyclopentyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.165 g, 98.8%). LCMS (Method-C3): 65.84% (RT 2.378, 202.0 nm) (MS: ESI+ve 669.95 [M+1]).

Step 2: Preparation of 7-(cyclopentyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 144)

-continued

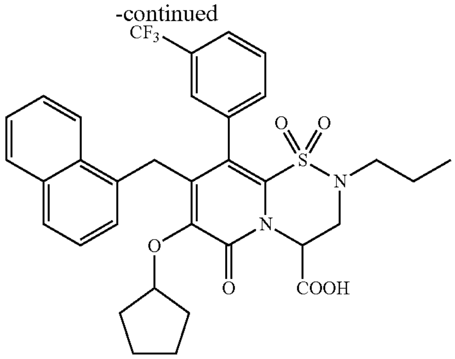

Compound 144

Methyl 7-(cyclopentyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylate 1,1-dioxide (0.21 g, 0.314 mmol) was dissolved in THF:$H_2O$ (1:1, 10 mL). LiOH—$H_2O$ (0.0395 g, 0.9424 mmol) was added and stirring continued at room temperature for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 7-(cyclopentyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 144), as an off white solid (0.038 g, 18.48%). LCMS (Method-H): 100.0% (RT 3.153, 223 nm) (MS: ESI+ve 655.28 [M+H]). $^1$H NMR: (400 MHz, DMSO) δ ppm: 0.76-0.79 (t, 3H), 1.14-1.48 (t, 5H), 1.65 (s, 3H), 2.33-2.39 (m, 2H), 3.08-3.09 (d, 2H), 3.92-3.99 (t, 1H), 4.09-4.24 (m, 3H), 5.29 (s, 1H), 5.47-5.48 (d, J=3.6 Hz, 1H), 6.84-6.86 (m, 1H), 7.10-7.14 (d, J=17.6 Hz, 1H), 7.23-7.42 (m, 6H), 7.65-7.70 (m, 2H), 7.81-7.83 (d, J=7.6 Hz, 1H), 13.71 (s, 1H).

Example 145

Synthesis of 7-isopropoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 148)

Compound 148

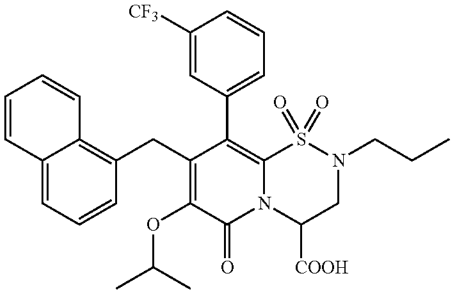

Prepared by a procedure similar to that reported for 7-(cyclopentyloxy)-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 144) substituting propan-2-ol in step 1. The crude product was purified using Prep HPLC Method 1 to give 7-isopropoxy-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 148), as an off white solid (0.030 g, 13.94%). LCMS (Method-H): 44.85%, 55.15% (RT 2.073, 2.077, 225 nm) MS: ESI+ve 629.30 [M+H]) (Atropisomers). $^1$H NMR: (400 MHz, DMSO) δ ppm: 0.76-0.80 (t, 3H), 1.14-1.24 (m, 6H), 1.44-1.50 (q, 2H), 3.03-3.13 (m, 2H), 3.97-4.24 (m, 4H), 5.04-5.07 (t, 1H), 5.27-5.29 (t, 1H), 6.81-6.86 (q, 1H), 7.06-7.11 (d, J=16.8 Hz, 1H), 7.21-7.44 (m, 6H), 7.63-7.72 (m, 2H), 7.81-7.83 (d, J=7.6 Hz, 1H), 13.78 (s, 1H).

Example 146

Synthesis of 7-(cyclopentylamino)-8-(naphthalen-1-ylmethyl)-6-oxo-2-propyl-3,4-dihydro-2H,6H-pyrido[1,2-e][1,2,5]thiadiazine-4-carboxylic acid 1,1-dioxide (Compound 006)

Compound 006

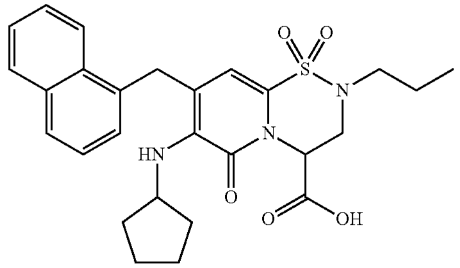

Step 1: preparation of methyl 6-bromo-8-(3-fluorophenyl)-7-(naphthalen-1-ylmethyl)-5-oxo-2,3-dihydro-5H-thiazolo[3,2-a]pyridine-3-carboxylate 1,1-dioxide

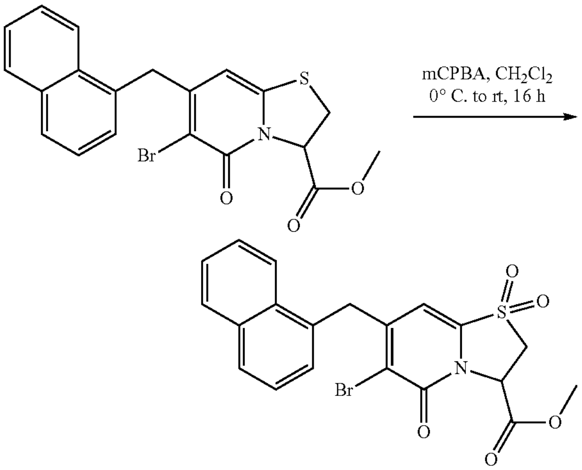

6-Bromo-7-(naphthalen-1-ylmethyl)-5-oxo-2,3-dihydro-5H-thiazolo[3,2-a]pyridine-3-carboxylic acid (1.5 g, 3.48 mmol) was dissolved in DCM (30 mL) and MCPBA (1.79 g, 10.40 mmol) was added. The reaction mixture was stirred for 12 h, quenched with sat. aq. $NaHSO_3$ (40 mL) and washed with sat. aq. $NaHCO_3$ (40 mL). The organic layer was dried over sodium sulphate and concentrated under reduced pressure. The crude product was purified using column chromatography eluting with 2-4% ethyl acetate/dichloromethane to give methyl 6-bromo-8-(3-fluorophenyl)-7-(naphthalen-1-ylmethyl)-5-oxo-2,3-dihydro-5H-thiazolo[3,2-a]pyridine-3-carboxylate 1,1-dioxide as a white solid (0.8 g, 48.02%). LCMS (Method-C3): 92.66% (RT: 2.210, 202 nm) (MS: ESI+ve 463.8 [M+2]).

Step 2: Preparation of methyl 7-bromo-8-(naphthalen-1-ylmethyl)-6-oxo-2-propyl-3,4-dihydro-2H,6H-pyrido[1,2-e][1,2,5]thiadiazine-4-carboxylate 1,1-dioxide

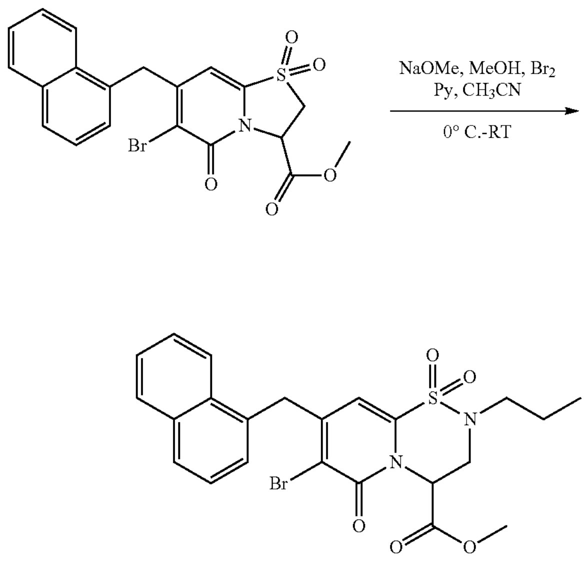 [SMILES: COC(=O)C1CS(=O)(=O)c2cc(Cc3cccc4ccccc34)c(Br)c(=O)n21 ; CCCN1CC(C(=O)OC)n2c(cc(Cc3cccc4ccccc34)c(Br)c2=O)S1(=O)=O]

Methyl 6-bromo-8-(3-fluorophenyl)-7-(naphthalen-1-ylmethyl)-5-oxo-2,3-dihydro-5H-thiazolo[3,2-a]pyridine-3-carboxylate 1,1-dioxide (1 g, 2.16 mmol) was dissolved in methanol (13.4 mL) and cooled to 0° C. n-Propylamine (0.0.198 g, 3.35 mmol) was added followed by sodium methoxide (0.2 M) (13.4 mL). The reaction mixture was stirred at room temperature for 16 h, concentrated under vacuum and then concentrated from chloroform (3×20 mL). The crude residue was dissolved in acetonitrile (22 mL) and cooled to 0° C. Pyridine (0.172 g, 2.16 mmol) then bromine (0.427 g, 2.68 mmol) were added and the reaction mixture was stirred at 0° C. for 10 min then at room temperature for 1 h. The reaction was quenched in ice water (30 mL) and extracted with ethyl acetate (3×30 mL). The organic layer was dried over sodium sulphate and concentrated under reduced pressure. The crude product was purified using column chromatography eluting with 2-4% ethyl acetate/dichloromethane to give methyl 7-bromo-8-(naphthalen-1-ylmethyl)-6-oxo-2-propyl-3,4-dihydro-2H,6H-pyrido[1,2-e][1,2,5]thiadiazine-4-carboxylate 1,1-dioxide as a yellow solid (0.4 g, 35.60%). LCMS (Method-C3): 98.39% (RT: 2.416, 222 nm) (MS: ESI+ve 518.8.0 [M+1]).

Step 3: Preparation of methyl 7-(cyclopentylamino)-8-(naphthalen-1-ylmethyl)-6-oxo-2-propyl-3,4-dihydro-2H,6H-pyrido[1,2-e][1,2,5]thiadiazine-4-carboxylate 1,1-dioxide

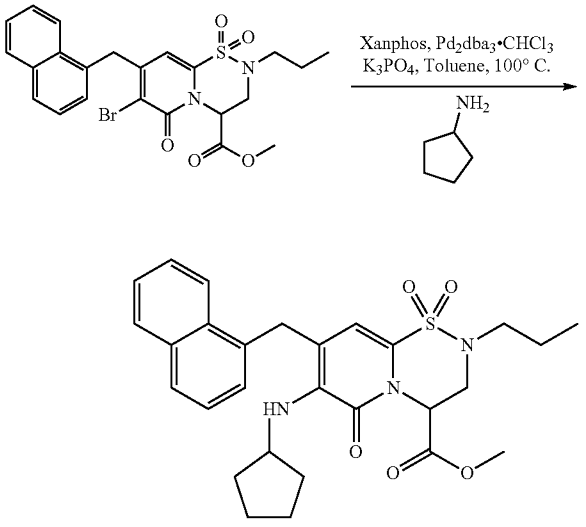 [SMILES: CCCN1CC(C(=O)OC)n2c(cc(Cc3cccc4ccccc34)c(Br)c2=O)S1(=O)=O ; NC1CCCC1 ; CCCN1CC(C(=O)OC)n2c(cc(Cc3cccc4ccccc34)c(NC3CCCC3)c2=O)S1(=O)=O]

Methyl 7-bromo-8-(naphthalen-1-ylmethyl)-6-oxo-2-propyl-3,4-dihydro-2H,6H-pyrido[1,2-e][1,2,5]thiadiazine-4-carboxylate 1,1-dioxide (0.35 g, 0.676 mmol) was added to a solution of cyclopentylamine (0.018 g, 0.21 mmol) in dry toluene (3 mL). Potassium phosphate (0.216 g, 1.01 mmol) was added and the mixture was degassed under argon. Xantphos (0.031 g, 0.053 mmol) and tris(dibenzylideneacetone)dipalladium-chloroform adduct (0.027 g, 0.026 mmol) were added and the mixture was stirred at 100° C. for 16 h. The reaction was quenched in water (8 mL) and extracted with ethyl acetate (2×8 mL). The organic layer was dried over sodium sulphate and concentrated under reduced pressure. The crude product was purified using column chromatography eluting with 20-30% ethyl acetate/hexane to give methyl 7-(cyclopentylamino)-8-(naphthalen-1-ylmethyl)-6-oxo-2-propyl-3,4-dihydro-2H,6H-pyrido[1,2-e][1,2,5]thiadiazine-4-carboxylate 1,1-dioxide as a solid (0.20 g, 56.68%). LCMS (Method-C3): 95.24% (RT 2.188, 223 nm) (MS: ESI+ve 524.49 [M+1]).

Step 4: Preparation Of 7-(cyclopentylamino)-8-(naphthalen-1-ylmethyl)-6-oxo-2-propyl-3,4-dihydro-2H,6H-pyrido[1,2-e][1,2,5]thiadiazine-4-carboxylic acid 1,1-dioxide (Compound 006)

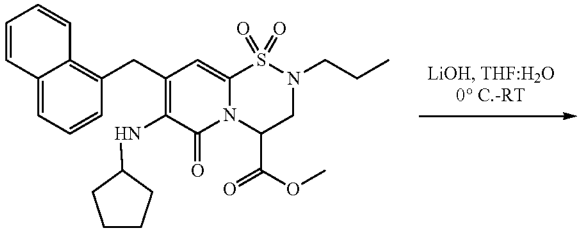

-continued

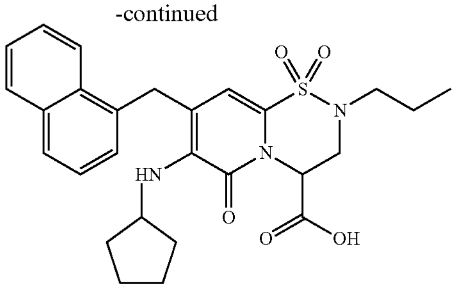

Compound 006

7-(Cyclopentylamino)-8-(naphthalen-1-ylmethyl)-6-oxo-2-propyl-3,4-dihydro-2H,6H-pyrido[1,2-e][1,2,5]thiadiazine-4-carboxylic acid 1,1-dioxide (0.15 g, 0.28 mmol) was dissolved in THF:$H_2O$ (1:1, 2 mL). LiOH—$H_2O$ (0.035 g, 0.85 mmol) was added and the mixture was stirred at room temperature for 6 h. The mixture was concentrated then ice water (1 mL) and 1N aqueous HCl solution (2 mL) were added. The resulting solid was collected by filtration and dried under vacuum. The crude product was purified using Prep HPLC Method 1 to give 7-(cyclopentylamino)-8-(naphthalen-1-ylmethyl)-6-oxo-2-propyl-3,4-dihydro-2H,6H-pyrido[1,2-e][1,2,5]thiadiazine-4-carboxylic acid 1,1-dioxide (0.035 g, 23.98%) (Compound 006). LCMS (Method-C3): 100% (RT 1.900, 254.0 nm) (MS: ESI+ve 510.4 [M+H]). $^1$H NMR: (400 MHz, DMSO) δ ppm: 0.82 (t, J=7.2 Hz, 3H), 1.44-1.50 (m, 6H), 1.59-1.61 (m, 2H), 1.74-1.79 (m, 2H), 2.92-3.06 (m, 1H), 4.01-4.14 (m, 3H), 4.38-4.47 (m, 2H), 5.02 (m, 1H), 5.03 (m, 1H), 6.45 (s, 1H), 7.31-7.33 (d, J=8 Hz, 1H), 7.49-7.59 (m, 3H), 7.87-7.89 (d, J=8 Hz, 1H), 7.95-7.99 (m, 2H), 13.57 (s, 1H).

Example 147

Synthesis of 7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 080)

Compound 080

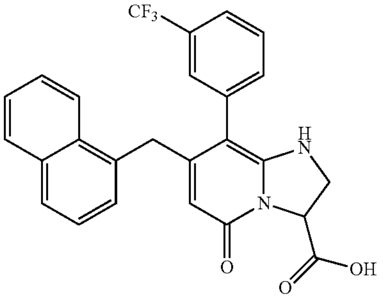

Step-1: Preparation of methyl (S)-2,3-diaminopropanoate hydrogen chloride

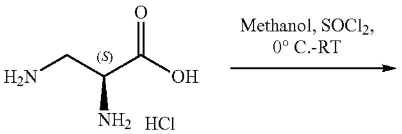

-continued

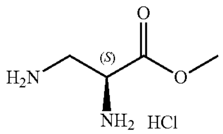

(S)-2,3-diaminopropanoic acid hydrochloride (10.0 g, 71.13 mmol) was dissolved in methanol (800 mL) and cooled to 0° C. Thionyl chloride (50.0 mL) was added dropwise and stirring was continued at room temperature for 16 h. The reaction mixture was concentrated under reduced pressure to give methyl (S)-2,3-diaminopropanoate hydrochloride as a white solid (Crude weight, 13.0 g), which was used in the next step without purification. $^1$H NMR: (400 MHz, DMSO) δ ppm: 3.29-3.37 (m, 2H), 3.76 (s, 3H), 4.42-4.45 (t, 1H), 8.92 (bs, 4H).

Step-2: Preparation methyl (S)-2-(3-(trifluoromethyl)benzyl)-4,5-dihydro-1H-imidazole-4-carboxylate

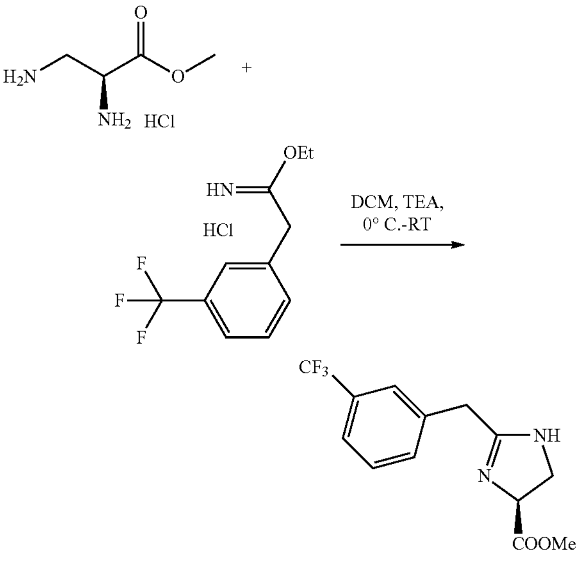

Methyl (S)-2,3-diaminopropanoate hydrogen chloride (9.0 g, 76.1 mmol) was dissolved in dichloromethane (100 mL) and cooled to 0° C. Triethylamine (10.47 mL, 74.65 mmol) was added and the mixture was stirred at 0° C. for 30 min. A solution of ethyl 2-(3-(trifluoromethyl)phenyl)acetimidate hydrogen chloride (13.03 g, 56.3 mmol) in dichloromethane (30 mL) was added at 0° C. The reaction mixture was stirred at room temperature for 16 h then quenched with sat. aq. sodium bicarbonate solution (400 mL) and extracted with dichloromethane (3×300 mL). The organic layer was dried over sodium sulphate and concentrated under reduced pressure to give the crude product which was purified using column chromatography eluting with 35% ethyl acetate/hexane to give methyl (S)-2-(3-(trifluoromethyl)benzyl)-4,5-dihydro-1H-imidazole-4-carboxylate as a light yellow solid (12.20 g, 55.94%). LCMS (Method-H): 78.44% (RT: 3.037, 215 nm) (MS: ESI+ve 287.05 [M+H]).

Step-3: Preparation of methyl 7-(naphthalen-1-ylmethyl)-5-oxo-8-(3-(trifluoromethyl)phenyl)-1,2,3,5-tetrahydroimidazo[1,2-a]pyridine-3-carboxylate

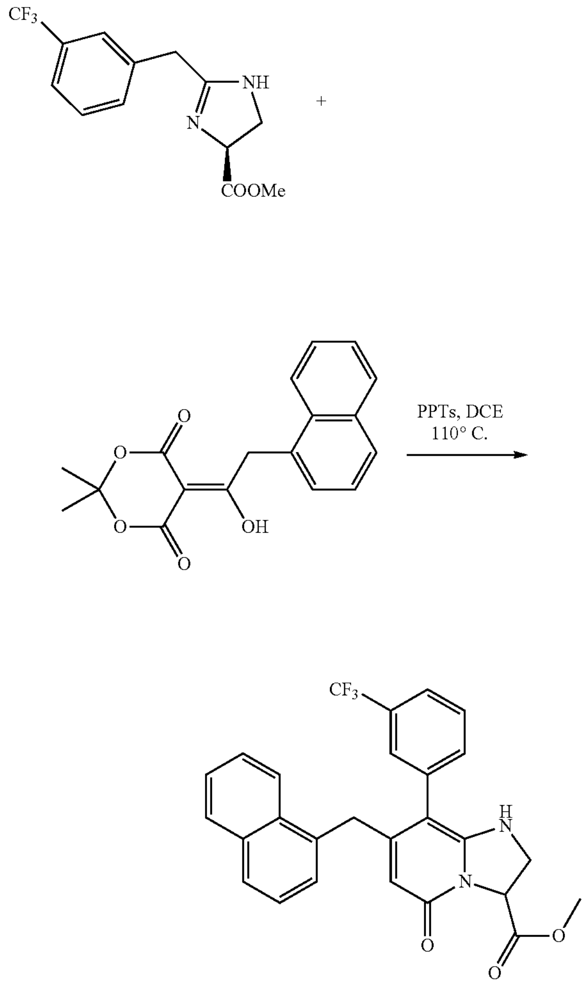

Methyl (S)-2-(3-(trifluoromethyl)benzyl)-4,5-dihydro-1H-imidazole-4-carboxylate (5.0 g, 17.46 mmol) and 5-(1-hydroxy-2-(naphthalen-1-yl)ethylidene)-2,2-dimethyl-1,3-dioxane-4,6-dione (10.91 g, 34.93 mmol) were dissolved in 1,2 dichloroethane (70 mL). Pyridinium p-toluenesulfonate (4.38 g, 17.46 mmol) was added and the mixture was stirred at 110° C. for 16 h. The reaction was quenched with sat. aq. sodium bicarbonate solution (400 mL) and extracted with DCM (3×300 mL). The organic layer was dried over sodium sulphate and concentrated under reduced pressure. The crude product was purified using column chromatography eluting with 3% methanol in DCM to give methyl 7-(naphthalen-1-ylmethyl)-5-oxo-8-(3-(trifluoromethyl)phenyl)-1,2,3,5-tetrahydroimidazo[1,2-a]pyridine-3-carboxylate (3.1 g, 37.09%) as a brown gum. LCMS (Method-C3): 100% (RT: 1.839, 214.0 nm) (MS: ESI+ve 479.5 [M+H]). $^1H$ NMR: (400 MHz, $CD_3OD$) δ ppm: 3.78 (s, 1H), 3.84 (s, 3H), 3.93-3.99 (m, 3H), 4.25 (s, 1H), 5.20-5.24 (m, 1H), 5.66 (s, 1H), 7.20-7.21 (d, J=6.8 Hz, 1H), 7.27-7.45 (3, 6H), 7.49-7.53 (d, J=18.4 Hz, 1H), 7.62-7.64 (d, J=8 Hz, 1H), 7.71-7.73 (d, J=8 Hz, 1H), 7.81-7.83 (d, J=8 Hz, 1H).

Step-4: Preparation of 7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 080)

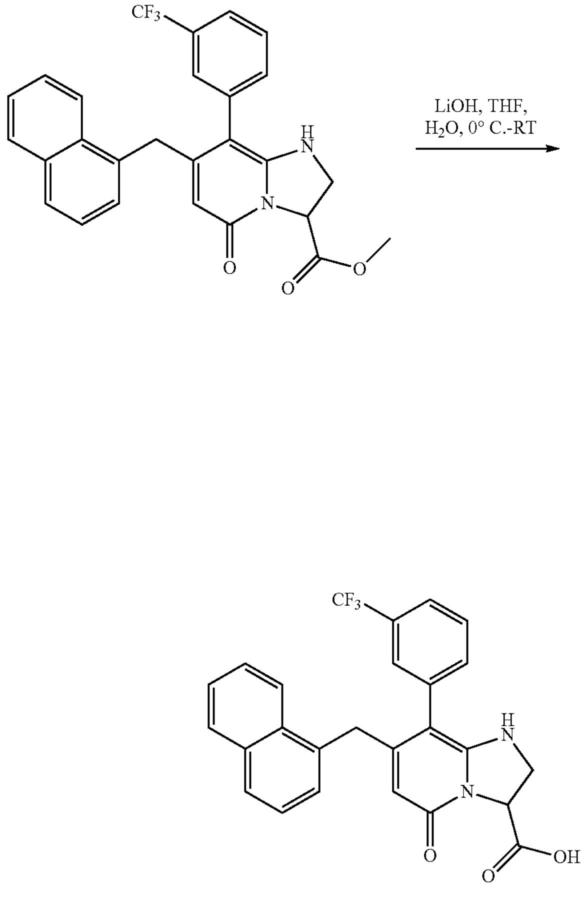

Compound 080

Methyl 7-(naphthalen-1-ylmethyl)-5-oxo-8-(3-(trifluoromethyl)phenyl)-1,2,3,5-tetrahydroimidazo[1,2-a]pyridine-3-carboxylate (0.18 g, 0.376 mmol) was dissolved in THF:$H_2O$ (1:1, 4 mL). LiOH—$H_2O$ (0.047 g 1.128 mmol) was added and the mixture was stirred at room temperature for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 080), as a white solid (0.042 g, 24.04%). LCMS (Method-C3): 100% (RT 1.744, 202.0 nm) (MS: ESI+ve 465.5 [M+H]). $^1H$ NMR: (400 MHz, DMSO) δ ppm: 3.46-3.48 (m, 1H), 3.83-3.92 (m, 3H), 4.88-4.90 (d, J=6.8 Hz, 1H), 5.05 (s, 1H), 6.86 (s, 1H), 7.25-7.26 (d, J=6.8 Hz, 1H), 7.39-7.46 (m, 3H), 7.55-7.69 (m, 5H), 7.77-7.79 (d, J=8.4 Hz, 1H), 7.87-7.89 (d, J=7.6 Hz, 1H). Analytical Chiral HPLC: (RT 5.74, 5.4% and RT 7.67, 93.8%), The column used was Chiralpak IH (250*4.6) mm, 5 micron, column flow 4.0 ml/min. Mobile phase (A) liquid carbon dioxide (B) 0.1% diethylamine in methanol.

Example 148

Synthesis of 1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 104)

Compound 104

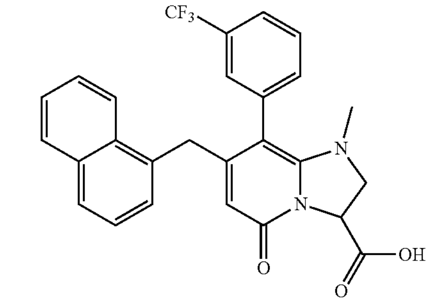

Step-1: Preparation of methyl 1-methyl-7-(naphthalen-1-ylmethyl)-5-oxo-8-(3-(trifluoromethyl)phenyl)-1,2,3,5-tetrahydroimidazo[1,2-a]pyridine-3-carboxylate

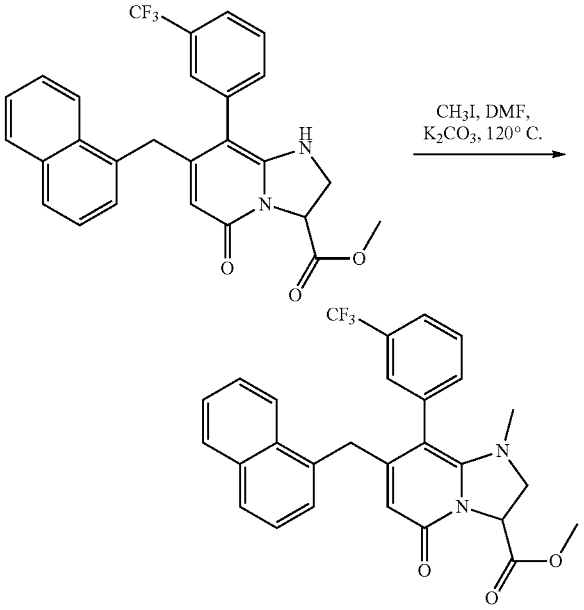

Methyl 7-(naphthalen-1-ylmethyl)-5-oxo-8-(3-(trifluoromethyl)phenyl)-1,2,3,5-tetrahydroimidazo[1,2-a]pyridine-3-carboxylate (0.4 g, 0.835 mmol) was dissolved in DMF (4.0 mL). Potassium carbonate (0.231 g, 1.67 mmol) was added and the mixture was stirred for 10 min. Methyl iodide (0.142 g, 1.003 mmol) was added dropwise at room temperature and the reaction mixture was stirred at 120° C. for 16 h. The mixture was quenched in ice water (50 mL) and extracted with ethyl acetate (3×50 mL). The organic layer was dried over sodium sulphate and concentrated under reduced pressure to give the crude product which was purified using column chromatography eluting with 0-3% methanol in dichloromethane to give methyl 1-methyl-7-(naphthalen-1-ylmethyl)-5-oxo-8-(3-(trifluoromethyl)phenyl)-1,2,3,5-tetrahydroimidazo[1,2-a]pyridine-3-carboxylate as a brown gum. (0.13 g, 31.57%). LCMS (Method-C3): 67.13% (RT: 1.934, 227.0 nm) (MS: ESI+ve 493.34 [M+H]).

Step-2: Preparation of 1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 104)

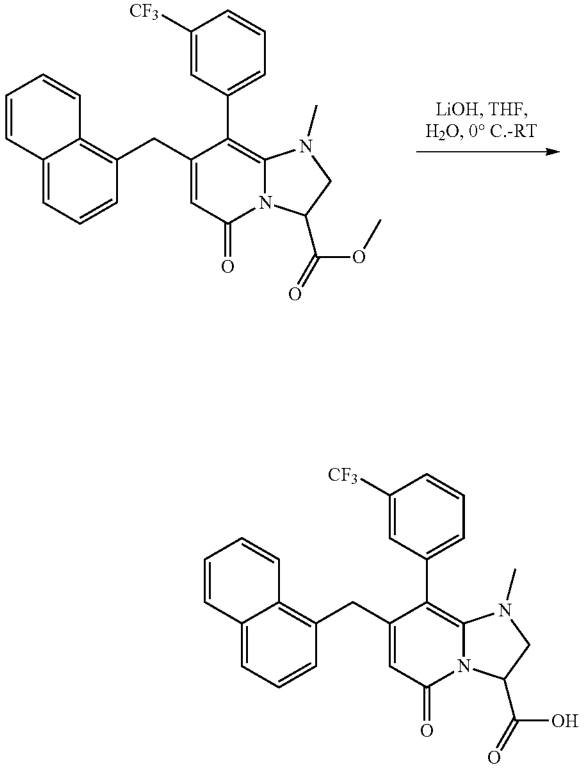

Compound 104

Methyl 1-methyl-7-(naphthalen-1-ylmethyl)-5-oxo-8-(3-(trifluoromethyl)phenyl)-1,2,3,5-tetrahydroimidazo[1,2-a]pyridine-3-carboxylate (0.13 g, 0.263 mmol) was dissolved in THF:$H_2O$ (1:1, 3 mL). LiOH—$H_2O$ (0.033 g 0.791 mmol) was added and stirred at room temperature for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 104), as a white solid (0.046 g, 36.42%). LCMS (Method-C3): 100% (RT 1.824, 202.0 nm) (MS: ESI+ve 479.3 [M+H]). $^1$H NMR: (400 MHz, DMSO) δ ppm: 2.11-2.17 (m, 3H), 3.60 (s, 1H), 3.82-3.89 (m, 3H), 4.88-4.90 (d, J=6.8 Hz, 1H), 5.10-5.13 (d, J=11.6 Hz, 1H), 7.27-7.29 (d, J=6.8 Hz, 1H), 7.42-7.48 (m, 3H), 7.57-7.67 (m, 5H), 7.80-7.82 (d, J=8.4 Hz, 1H), 7.90-7.91 (d, J=7.6 Hz, 1H), 13.28 (s, 1H).

Example 149

Synthesis of 7-(naphthalen-1-ylmethyl)-5-oxo-8-(3-(trifluoromethyl)phenyl)-1,5-dihydroimidazo[1,2-a]pyridine-3-carboxylic acid (Compound 110)

Compound 110

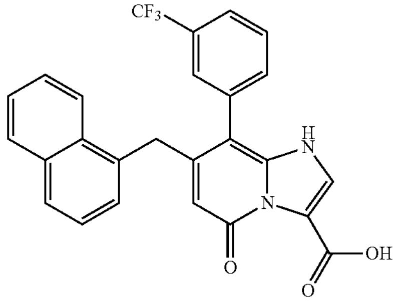

Step-1: Preparation of methyl 2-bromo-7-(naphthalen-1-ylmethyl)-5-oxo-8-(3-(trifluoromethyl)phenyl)-1,5-dihydroimidazo[1,2-a]pyridine-3-carboxylate

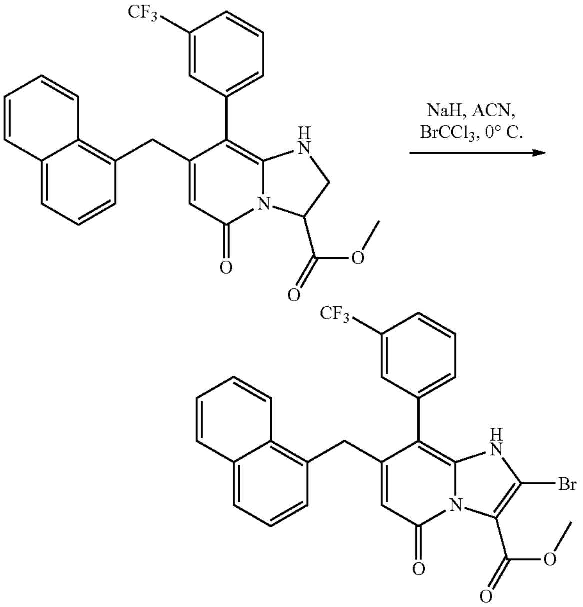

Methyl 7-(naphthalen-1-ylmethyl)-5-oxo-8-(3-(trifluoromethyl)phenyl)-1,2,3,5-tetrahydroimidazo[1,2-a]pyridine-3-carboxylate (1.0 g, 2.090 mmol) was dissolved in dry acetonitrile (10.0 mL) and cooled to 0° C. Sodium hydride (0.25 g, 6.270 mmol) was added in portions and stirring was continued for 10 min. Bromotrichloromethane (1.038 g, 5.254 mmol) was added dropwise at 0° C. and the mixture was stirred for 1 h. The reaction was quenched in ice water (100 mL) and extracted with ethyl acetate (3×100 mL). The organic layer was dried over sodium sulphate and concentrated under reduced pressure. The crude product was purified using column chromatography eluting with 0-2% ethyl acetate/hexane to give methyl 2-bromo-7-(naphthalen-1-ylmethyl)-5-oxo-8-(3-(trifluoromethyl)phenyl)-1,5-dihydroimidazo[1,2-a]pyridine-3-carboxylate (0.38 g, 32.74%). LCMS (Method-C3): 63.15% (RT: 2.331, 222.0 nm) (MS: ESI+ve 557.0 [M+2]).

Step-2: Preparation of 7-(naphthalen-1-ylmethyl)-5-oxo-8-(3-(trifluoromethyl)phenyl)-1,5-dihydroimidazo[1,2-a]pyridine-3-carboxylic acid (Compound 110)

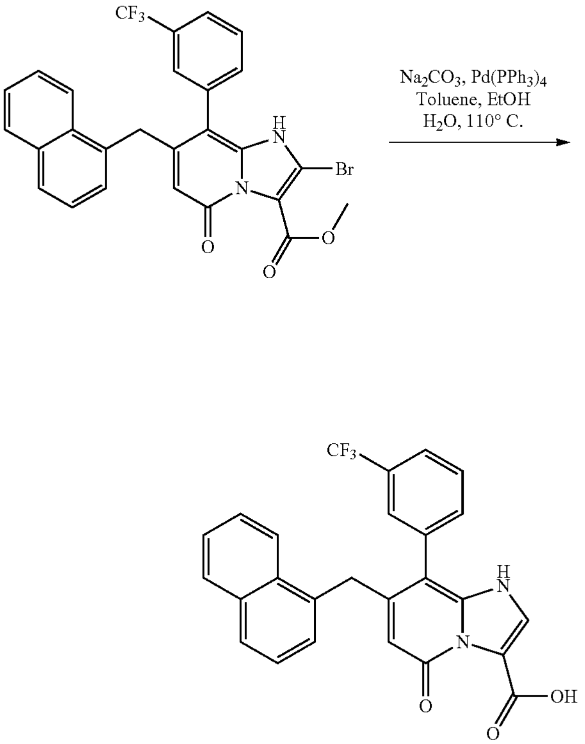

Compound 110

A solution of ethyl 2-bromo-7-(naphthalen-1-ylmethyl)-5-oxo-8-(3-(trifluoromethyl)phenyl)-1,5-dihydroimidazo[1,2-a]pyridine-3-carboxylate (0.2 g, 0.360 mmol) was dissolved in Toluene (2 mL), ethanol (2 mL), water (1 mL) and sodium carbonate (0.057 g, 0.540 mmol), and the mixture was degassed under nitrogen for 5 min. Palladium tetrakis-triphenylphosphine (0.041 g, 0.036 mmol) was added and the mixture was heated in a sealed tube at 110° C. for 16 h. The reaction was quenched in ice water (50 mL) and sat. aq. 1N aqueous HCl solution (3-4 mL). The mixture was extracted with ethyl acetate (3×50 mL) and the organic layer was dried over sodium sulphate and concentrated under reduced pressure. The crude product was purified using Prep HPLC Method 1 to give 7-(naphthalen-1-ylmethyl)-5-oxo-8-(3-(trifluoromethyl)phenyl)-1,5-dihydroimidazo[1,2-a]pyridine-3-carboxylic acid (Compound 110), as a white solid (0.015 g, 9.01%). LCMS (Method-J): 99.31% (RT 4.555, 254.0 nm) (MS: ESI+ve 463.0 [M+H]). $^1$H NMR: (400 MHz, DMSO) δ ppm: 4.068 (s, 2H), 5.39 (s, 1H), 7.24-7.26 (d, J=6.4 Hz, 1H), 7.39-7.46 (m, 3H), 7.64-7.67 (d, J=12.4 Hz, 5H), 7.78-7.80 (d, J=8 Hz, 1H), 7.88-7.90 (d, J=8, 1H), 8.066 (s, 1H).

Example 150

Synthesis of 1-methyl-7-(naphthalen-1-ylmethyl)-5-oxo-8-(3-(trifluoromethyl)phenyl)-1,5-dihydroimidazo[1,2-a]pyridine-3-carboxylic acid (Compound 111)

Compound 111

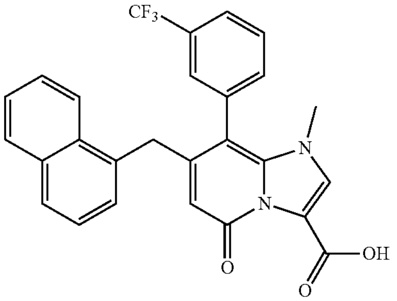

Prepared by a procedure similar to that described for 7-(naphthalen-1-ylmethyl)-5-oxo-8-(3-(trifluoromethyl)phenyl)-1,5-dihydroimidazo[1,2-a]pyridine-3-carboxylic acid (Compound 110) substituting methyl 1-methyl-7-(naphthalen-1-ylmethyl)-5-oxo-8-(3-(trifluoromethyl)phenyl)-1,2,3,5-tetrahydroimidazo[1,2-a]pyridine-3-carboxylate in step 1. The crude product was purified using Prep HPLC Method 1 to give 1-methyl-7-(naphthalen-1-ylmethyl)-5-oxo-8-(3-(trifluoromethyl)phenyl)-1,5-dihydroimidazo[1,2-a]pyridine-3-carboxylic acid (Compound 111), as a white solid (0.032 g, 22.32%). LCMS (Method-C3): 100% (RT 2.363, 202.0 nm) (MS: ESI+ve 477.2 [M+H]). $^1$H NMR: (400 MHz, DMSO) δ ppm: 3.05 (s, 3H), 4.08 (s, 2H), 5.89 (s, 1H), 7.21-7.22 (d, J=6.8 Hz, 1H), 7.41-7.48 (m, 3H), 7.66 (s, 2H), 7.74-7.82 (m, 4H), 7.90-7.92 (d, J=8.0 Hz, 1H), 8.46 (s, 1H).

Example 151

Synthesis of 1-((benzyloxy)carbonyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 103)

Compound 103

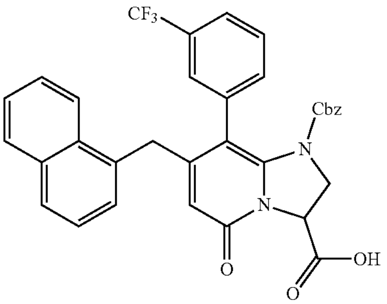

Step-1: Preparation of 1-benzyl 4-methyl (S)-2-(3-(trifluoromethyl)benzyl)-4,5-dihydro-1H-imidazole-1,4-dicarboxylate

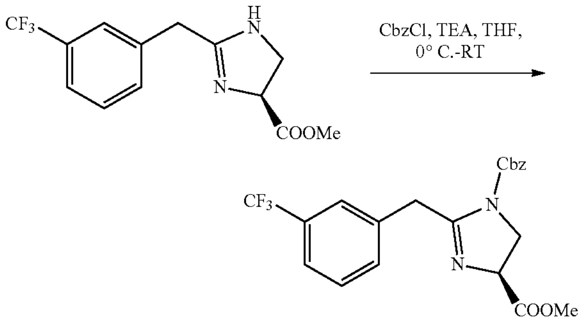

Methyl (S)-2-(3-(trifluoromethyl)benzyl)-4,5-dihydro-1H-imidazole-4-carboxylate (1.0 g, 3.49 mmol) was dissolved in tetrahydrofuran (10 mL) and cooled to 0° C. Triethylamine (0.98 mL, 6.98 mmol) was added and the reaction mixture was stirred for 10 min. Benzylchloroformate (1.43 mL, 4.19 mmol) was added and the mixture was stirred at room temperature for 2 h. The reaction was quenched with water (50 mL) and extracted with ethyl acetate (3×30 mL). The organic layer was dried over sodium sulphate and concentrated under reduced pressure to give the crude product which was purified using column chromatography eluting with 30% ethyl acetate/hexane to give 1-benzyl 4-methyl (S)-2-(3-(trifluoromethyl)benzyl)-4,5-dihydro-1H-imidazole-1,4-dicarboxylate as a light yellow liquid (0.6 g, 40.86%). LCMS (Method-C3): 75.35% (RT: 2.167, 220 nm) (MS: ESI+ve 421.0 [M+H]).

Step-2: Preparation of 1-benzyl 3-methyl7-(naphthalen-1-ylmethyl)-5-oxo-8-(3-(trifluoromethyl)phenyl)-2,3-dihydroimidazo[1,2-a]pyridine-1,3 (5H)-dicarboxylate

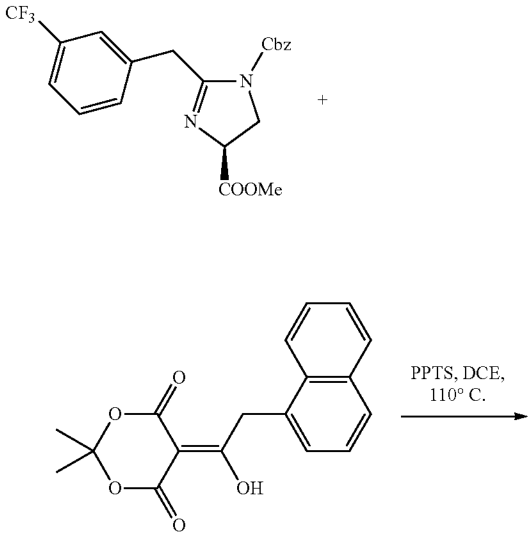

-continued

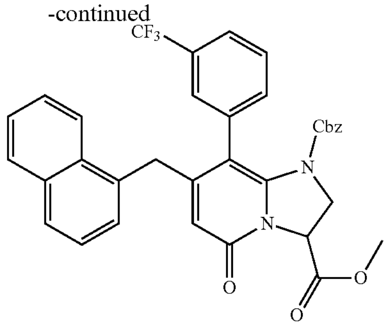

1-Benzyl 4-methyl (S)-2-(3-(trifluoromethyl)benzyl)-4,5-dihydro-1H-imidazole-1,4-dicarboxylate (0.5 g, 1.19 mmol) and 5-(1-hydroxy-2-(naphthalen-1-yl)ethylidene)-2,2-dimethyl-1,3-dioxane-4,6-dione (0.92 g, 2.97 mmol) was dissolved in 1,2 dichloroethane (20 mL). Pyridinium p-toluenesulfonate (0.29 g, 1.19 mmol) was added and the mixture was stirred at 110° C. for 16 h. The reaction was quenched with saturated aqueous sodium bicarbonate solution (50 mL) and extracted with DCM (3×50 mL). The organic layer was dried over sodium sulphate and concentrated under reduced pressure to give the crude product which was purified using column chromatography eluting with 50% ethyl acetate/hexane to give 1-benzyl 3-methyl 7-(naphthalen-1-ylmethyl)-5-oxo-8-(3-(trifluoromethyl)phenyl)-2,3-dihydroimidazo[1,2-a]pyridine-1,3 (5H)-dicarboxylate (0.1 g, 13.72%) as a brown gum. LCMS (Method-C3): 74.69% (RT: 1.903, 225.0 nm) (MS: ESI+ve 613.4 [M+H]).

Step-3: Preparation of 1-((benzyloxy)carbonyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 103)

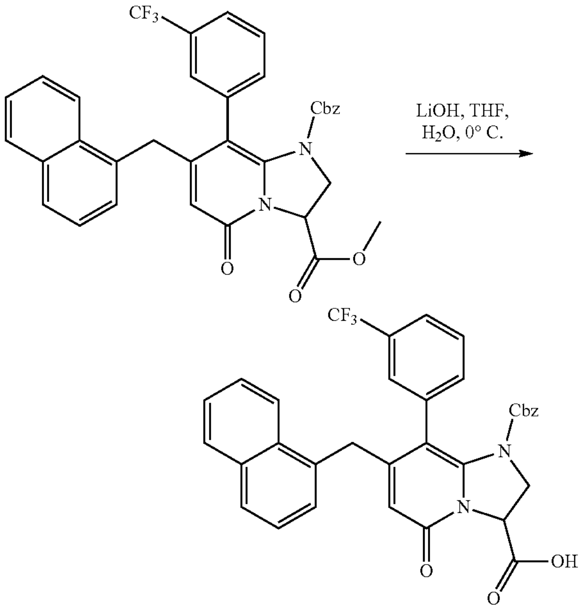

Compound 103

1-Benzyl 3-methyl 7-(naphthalen-1-ylmethyl)-5-oxo-8-(3-(trifluoromethyl)phenyl)-2,3-dihydroimidazo[1,2-a]pyridine-1,3 (5H)-dicarboxylate (0.10 g, 0.163 mmol) was dissolved in THF:$H_2O$ (1:1, 3 mL). LiOH—$H_2O$ (0.02 g 0.489 mmol) was added and the mixture was stirred at room temperature for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 1-((benzyloxy)carbonyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 103), as a white solid (0.014 g, 14.33%). LCMS (Method-J): 100% (RT 4.666, 202.0 nm) (MS: ESI+ve 599.2 [M+H]). $^1$H NMR: (400 MHz, DMSO) δ ppm: 4.26-4.30 (d, J=14.2 Hz, 1H), 4.46-4.56 (m, 3H), 4.90-4.93 (d, J=12.8 Hz, 1H), 5.12 (s, 2H), 5.51 (s, 1H), 7.03 (s, 2H), 7.30-7.31 (d, J=2.4 Hz, 3H), 7.46-7.65 (m, 8H), 7.96-8.00 (m, 3H), 14.35 (m, 1H).

Example 152

Synthesis of 6-bromo-1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 119)

Compound 119

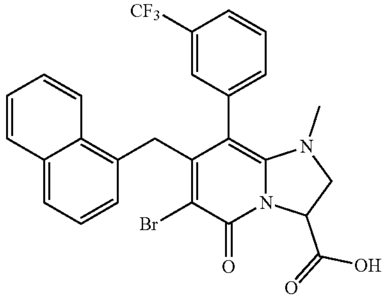

Step-1: Preparation of methyl 6-bromo-1-methyl-7-(naphthalen-1-ylmethyl)-5-oxo-8-(3-(trifluoromethyl)phenyl)-1,2,3,5-tetrahydroimidazo[1,2-a]pyridine-3-carboxylate

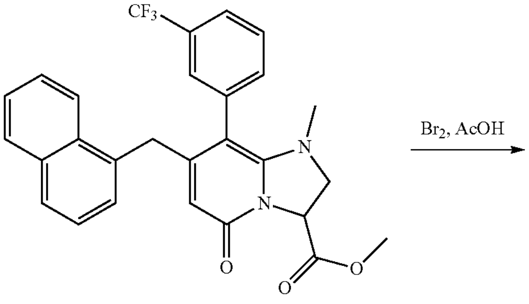

-continued

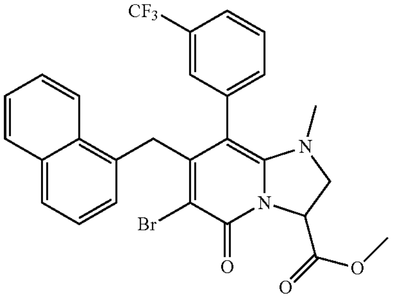

Methyl 1-methyl-7-(naphthalen-1-ylmethyl)-5-oxo-8-(3-(trifluoromethyl)phenyl)-1,2,3,5-tetrahydroimidazo[1,2-a]pyridine-3-carboxylate (0.25 g, 0.507 mmol) was dissolved in acetic acid (3.0 mL). Bromine (0.081 g, 0.507 mmol) was added dropwise and the mixture was stirred for 2 h. The mixture was concentrated and quenched in saturated aqueous sodium bicarbonate solution (50 mL) then extracted with ethyl acetate (3×50 mL). The organic layer was dried over sodium sulphate and concentrated under reduced pressure to give the crude product which was purified using column chromatography eluting with 0-2% methanol/dichloromethane to give methyl 6-bromo-1-methyl-7-(naphthalen-1-ylmethyl)-5-oxo-8-(3-(trifluoromethyl)phenyl)-1,2,3,5-tetrahydroimidazo[1,2-a]pyridine-3-carboxylate (0.20 g, 68.95%). LCMS (Method-C3): 88.48% (RT: 2.412, 202.0 nm) (MS: ESI+ve 473.2 [M+2]).

Step-2: Preparation of 6-bromo-1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 119)

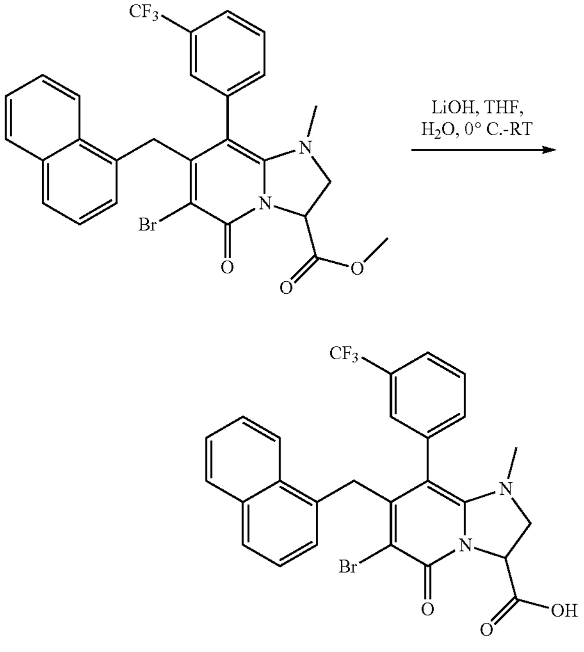

Compound 119

Methyl 6-bromo-1-methyl-7-(naphthalen-1-ylmethyl)-5-oxo-8-(3-(trifluoromethyl)phenyl)-1,2,3,5-tetrahydroimidazo[1,2-a]pyridine-3-carboxylate (0.070 g, 0.122 mmol) was dissolved in THF:$H_2O$ (1:1, 2 mL). LiOH—$H_2O$ (0.015 g 0.367 mmol) was added and the mixture was stirred for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 6-bromo-1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 119), as a white solid (0.024 g, 35.15%). LCMS (Method-C3): 100% (RT 2.241, 202.0 nm) (MS: ESI+ve 559.0 [M+2]). $^1$H NMR: (400 MHz, DMSO) δ ppm: 2.07 (s, 3H), 3.64 (s, 1H), 3.87-3.92 (t, J=20 Hz, 1H), 3.99-4.20 (m, 2H), 4.99-5.01 (d, J=7.2 Hz, 1H), 7.07-7.08 (m, 1H), 7.16 (s, 1H), 7.23-7.45 (m, 6H), 7.70-7.76 (m, 2H), 7.85-7.87 (d, J=8 Hz, 1H).

Example 153

Synthesis of 6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 133)

Compound 133

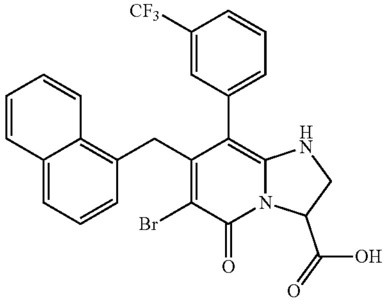

Prepared by a procedure similar to that described for 6-bromo-1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 119) substituting methyl 7-(naphthalen-1-ylmethyl)-5-oxo-8-(3-(trifluoromethyl)phenyl)-1,2,3,5-tetrahydroimidazo[1,2-a]pyridine-3-carboxylate in step 1. The crude product was purified using Prep HPLC Method 3 to give 6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 133), as a white solid (0.045 g, 46.16%). LCMS (Method-H): 97.78% (RT 3.403, 202.0 nm) (MS: ESI+ve 545.0 [M+2]). $^1$H NMR: (400 MHz, DMSO) δ ppm: 3.83 (s, 1H), 4.14 (s, 2H), 4.28-4.30 (d, J=9.6 Hz, 1H), 4.94 (s, 1H), 6.89 (s, 1H), 7.05-7.09 (t, 1H), 7.23 (s, 1H), 7.40-7.47 (m, 5H), 7.74-7.75 (d, J=7.2 Hz, 1H), 7.80-7.82 (d, J=7.6 Hz, 1H), 7.86-7.88 (d, J=8, 1H).

Example 154

Synthesis of 1-benzyl-6-ethyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 140)

Compound 140

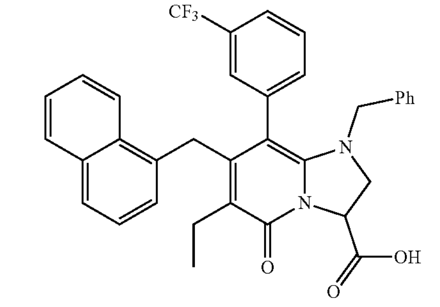

Step-1: Preparation of methyl 6-bromo-7-(naphthalen-1-ylmethyl)-5-oxo-8-(3-(trifluoromethyl)phenyl)-1,2,3,5-tetrahydroimidazo[1,2-a]pyridine-3-carboxylate

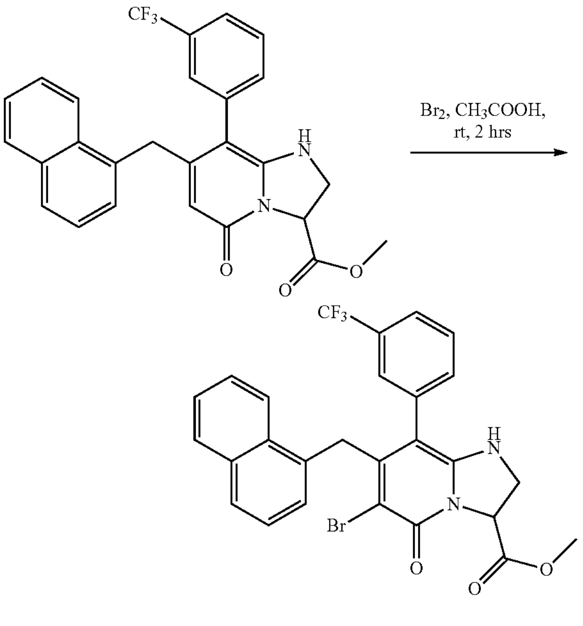

Methyl 7-(naphthalen-1-ylmethyl)-5-oxo-8-(3-(trifluoromethyl)phenyl)-1,2,3,5-tetrahydroimidazo[1,2-a]pyridine-3-carboxylate (1 g, 2.09 mmol) was dissolved in acetic acid (10.0 mL). Bromine (0.33 g, 2.09 mmol) was added dropwise and the mixture was stirred for 2 h. The mixture was concentrated and quenched in saturated aqueous sodium bicarbonate solution (100 mL) then extracted into ethyl acetate (3×100 mL). The organic layer was dried over sodium sulphate and concentrated under reduced pressure to give the crude product which was purified using column chromatography eluting with 0-2% methanol/dichloromethane to give methyl 6-bromo-7-(naphthalen-1-ylmethyl)-5-oxo-8-(3-(trifluoromethyl)phenyl)-1,2,3,5-tetrahydroimidazo[1,2-a]pyridine-3-carboxylate as a brown solid (0.90 g, 77.26%). LCMS (Method-C3): 99.02% (RT: 1.900, 225.0 nm) (MS: ESI+ve 559.2 [M+2]).

Step-2: Preparation of methyl 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylate

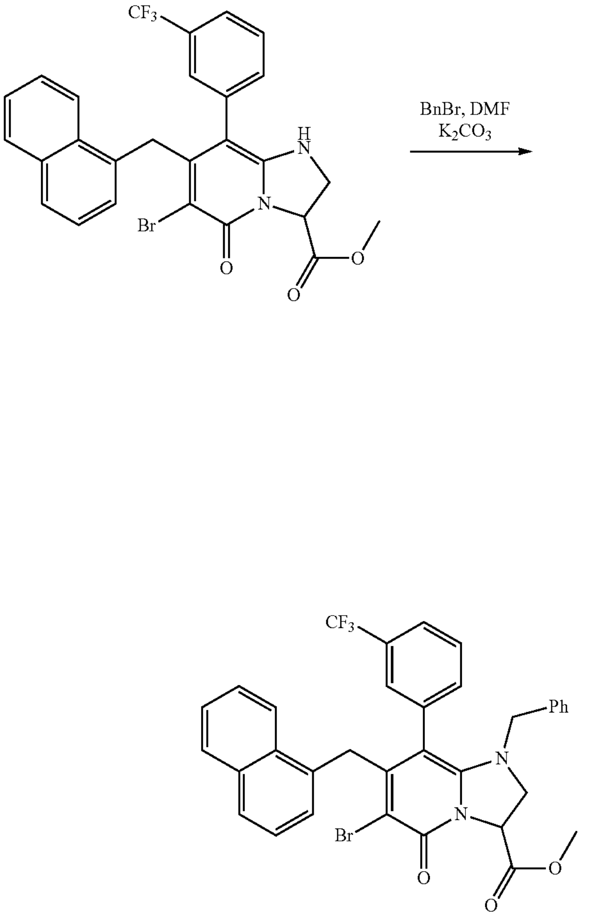

Methyl 6-bromo-7-(naphthalen-1-ylmethyl)-5-oxo-8-(3-(trifluoromethyl)phenyl)-1,2,3,5-tetrahydroimidazo[1,2-a]pyridine-3-carboxylate (0.9 g, 1.615 mmol) was dissolved in DMF (10.0 mL). Potassium carbonate (0.663 g, 4.847 mmol) was added and the mixture was stirred for 10 min. Benzylbromide (0.303 g, 1.777 mmol) was added dropwise at room temperature and stirring was continued for 16 h. The reaction was quenched in ice water (100 mL) and extracted with ethyl acetate (3×100 mL). The organic layer was dried over sodium sulphate and concentrated under reduced pressure to give the crude product which was purified using column chromatography eluting with 0-3% methanol/dichloromethane to give methyl 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylate as a brown gum. (0.7 g, 66.95%). LCMS (Method-C3): 80.00% (RT: 2.588, 202.0 nm) (MS: ESI+ve 649.2 [M+2]).

Step-3: Preparation of methyl 1-benzyl-7-(naphthalen-1-ylmethyl)-5-oxo-8-(3-(trifluoromethyl)phenyl)-6-vinyl-1,2,3,5-tetrahydroimidazo[1,2-a]pyridine-3-carboxylate

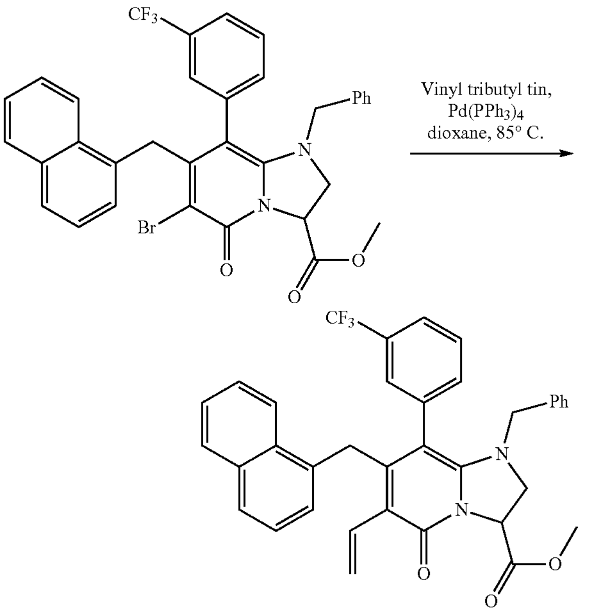

Methyl 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylate (0.7 g, 1.081 mmol) was dissolved in dry dioxane (10 mL). Vinyl tributyl tin (0.342 g, 1.081 mmol) was added and the mixture was degassed for 5 min under argon. $Pd(PPh_3)_4$ (0.124 g, 0.108 mmol) was added and the mixture was heated in a sealed tube at 85° C. for 16 h. The reaction was quenched in ice water (100 mL) and extracted with ethyl acetate (3×100 mL). The organic layer was dried over sodium sulphate and concentrated under reduced pressure to give the crude product which was purified using column chromatography eluting with 0-40% ethyl acetate/DCM to give methyl 1-benzyl-7-(naphthalen-1-ylmethyl)-5-oxo-8-(3-(trifluoromethyl)phenyl)-6-vinyl-1,2,3,5-tetrahydroimidazo[1,2-a]pyridine-3-carboxylate (0.30 g, 46.67%). LCMS (Method-C3): 40.63% (RT: 2.630, 202.4 nm) (MS: ESI+ve 595.2 [M+1]).

Step 4: Preparation of methyl 1-benzyl-6-ethyl-7-(naphthalen-1-ylmethyl)-5-oxo-8-(3-(trifluoromethyl)phenyl)-1,2,3,5-tetrahydroimidazo[1,2-a]pyridine-3-carboxylate

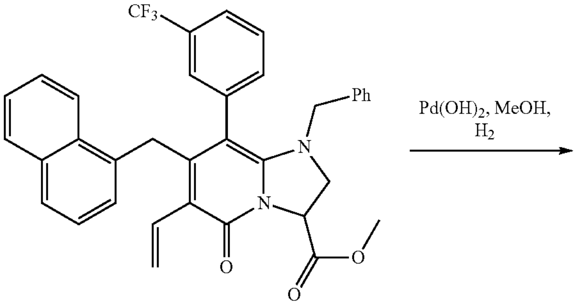

-continued

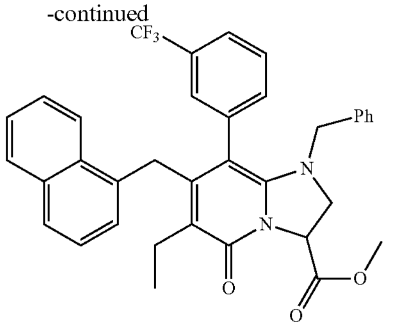

Methyl 1-benzyl-7-(naphthalen-1-ylmethyl)-5-oxo-8-(3-(trifluoromethyl)phenyl)-6-vinyl-1,2,3,5-tetrahydroimidazo[1,2-a]pyridine-3-carboxylate (0.27 g, 0.454 mmol) was dissolved in methanol (5 mL). 10% Palladium hydroxide (50% moisture) (0.27 g) was added and the mixture was stirred under hydrogen for 30 min. The mixture was filtered through a pad of Celite and the filtrate was concentrated to give methyl 1-benzyl-6-ethyl-7-(naphthalen-1-ylmethyl)-5-oxo-8-(3-(trifluoromethyl)phenyl)-1,2,3,5-tetrahydroimidazo[1,2-a]pyridine-3-carboxylate as a brown solid (0.19 g, 70.13%).LCMS (Method-C3): 37.93% (RT 2.626, 202.4 nm) (MS: ESI+ve 597.2 [M+H]).

Step-5: Preparation 1-benzyl-6-ethyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 140).

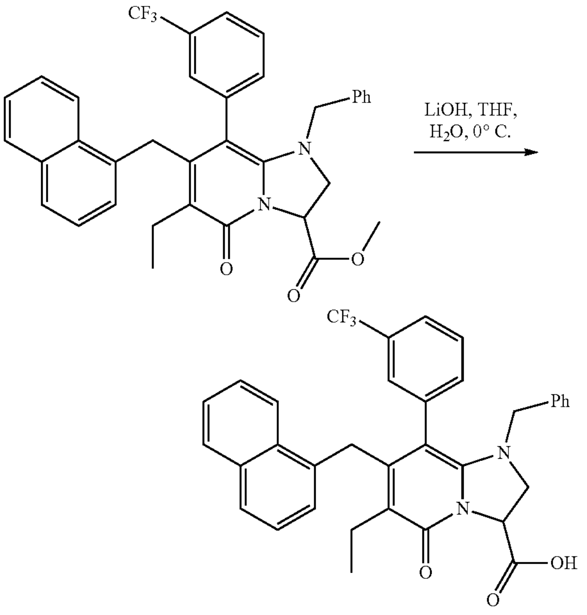

Compound 140

Methyl 1-benzyl-6-ethyl-7-(naphthalen-1-ylmethyl)-5-oxo-8-(3-(trifluoromethyl)phenyl)-1,2,3,5-tetrahydroimidazo[1,2-a]pyridine-3-carboxylate (0.190 g, 0.318 mmol) was dissolved in THF:$H_2O$ (1:1, 4 mL) at room temperature. LiOH—$H_2O$ (0.040 g 0.956 mmol) was added and the mixture was stirred at room temperature for 4 h. The mixture was concentrated then ice-cold water (10 mL) and 1 N aqueous HCl solution (4-5 mL) were added. The resulting solid was collected by filtration and dried under vacuum.

The crude product was purified using Prep HPLC Method 1 to give 1-benzyl-6-ethyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 140), as a white solid (0.021 g, 11.32%). LCMS (Method-C3): 96.70% (RT 2.439, 220.4 nm) (MS: ESI+ve 583.2 [M+H]). $^{1}$H NMR: (400 MHz, DMSO) δ ppm: 0.94 (s, 3H), 2.26-2.32 (m, 2H), 3.60-3.73 (m, J=20 Hz, 2H), 3.84 (s, 1H), 3.98-4.04 (t, 2H), 4.23-4.25 (d, J=8 Hz, 1H), 4.36-4.43 (t, 1H), 6.53 (s, 1H), 6.78 (s, 1H), 6.85 (s, 1H), 6.96-6.98 (d, J=6.8 Hz, 2H), 7.15-7.18 (d, J=10.8 Hz, 3H), 7.26 (s, 1H), 7.38-7.42 (t, 5H), 7.67-7.72 (t, 2H,), 7.82 (s, 1H), 13.36 (s, 1H).

Example 155

Synthesis of 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 003)

Compound 003

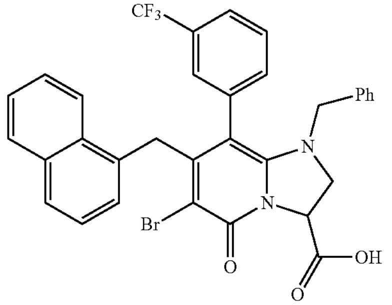

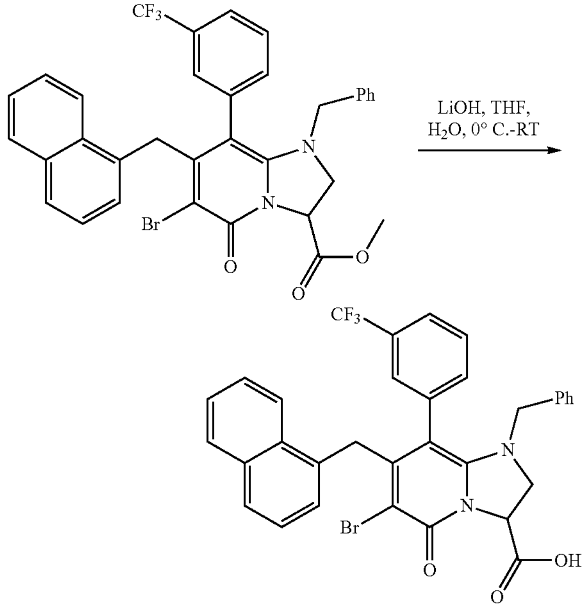

Compound 003

Methyl 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylate (0.115 g, 0.177 mmol) was dissolved in THF:$H_2O$ (1:1, 4 mL). LiOH—$H_2O$ (0.022 g 0.533 mmol) was added and the mixture was stirred at room temperature for 4 h. The mixture was concentrated then ice water (10 mL) and 1 N HCl (3-4 mL) were added. The resulting solid was collected by filtration and dried under vacuum. The crude product was purified using Prep HPLC Method 1 to give 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid as white solid (0.037 g, 32.89%) (Compound 003). LCMS (Method-C3): 100% (RT 2.443, 224.0 nm) (MS: ESI+ve 635.0 [M+2]). $^{1}$H NMR: (400 MHz, DMSO) δ ppm: 3.58 (s, 1H), 3.69-383 (m, 2H), 3.96-4.18 (m, 3H), 5.14-5.16 (d, J=8.4 Hz, 1H), 6.85 (s, 2H), 6.93-6.98 (m, 1H), 7.04-7.07 (t, 1H), 7.13-7.32 (m, 6H), 7.35-7.44 (m, 3H), 7.66-7.67 (d, J=4.4 Hz, 1H), 7.73-7.75 (d, J=8 Hz, 1H), 7.83-7.85 (d, J=8 Hz, 1H), 13.57 (s, 1H).

Example 156

Synthesis of 6-ethyl-1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 136)

Compound 136

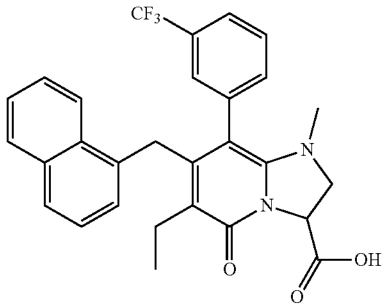

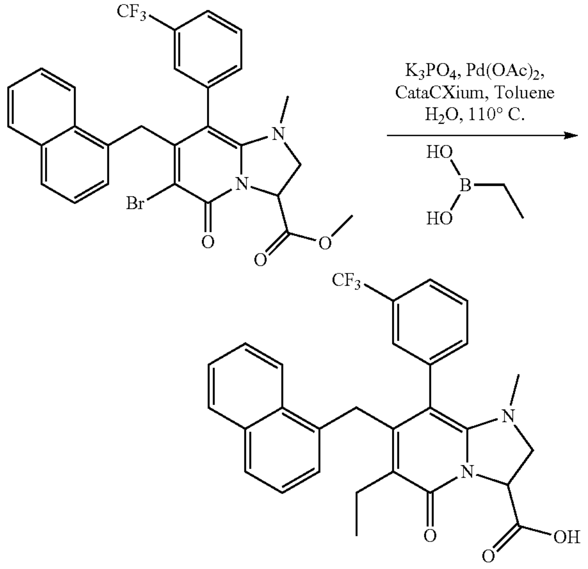

Compound 136

Methyl 6-bromo-1-methyl-7-(naphthalen-1-ylmethyl)-5-oxo-8-(3-(trifluoromethyl)phenyl)-1,2,3,5-tetrahydroimidazo[1,2-a]pyridine-3-carboxylate (0.16 g, 0.28 mmol) and ethylboronic acid (0.081 g, 1.12 mmol) were dissolved in toluene (4 mL) and water (2 mL) at room temperature. $K_3PO_4$ (0.237 g, 1.12 mmol) was added and the mixture was degassed for 10 min under nitrogen. $Pd(OAc)_2$ (0.0012 g, 0.0056 mmol) and cataCXium A (0.01 g, 0.028 mmol) were added and the mixture was heated in a sealed tube at 110° C. for 16 h. The reaction was quenched in ice water (50 mL) and extracted with ethyl acetate (3×50 mL). The organic layer was dried over sodium sulphate and concentrated under reduced pressure. The crude product was purified using Prep HPLC Method 3 to give 6-ethyl-1-methyl-7-(naphthalen-1-ylmethyl)-5-oxo-8-(3-(trifluoromethyl)phenyl)-1,2,3,5-tetrahydroimidazo[1,2-a]pyridine-3-carboxylic acid as a white solid (0.016 g, 11.28%) (Compound 136). LCMS (Method-C3): 100% (RT 2.371, 202.0 nm) (MS: ESI+ve 507.0 [M+2]). $^{1}$H NMR: (400 MHz, DMSO) δ ppm: 0.91 (s, 3H), 2.03 (s, 3H), 2.33 (s, 2H), 3.53 (s, 1H), 3.74 (s, 1H), 3.86-3.90 (d, J=14.8 Hz, 1H), 3.97 (s, 1H), 4.84-4.86 (d, J=6.8 Hz, 1H), 7.08 (s, 1H), 7.15 (s, 1H), 7.27-7.47 (m, 6H), 7.72-7.74 (d, J=8 Hz, 2H), 7.85-7.86 (d, J=3.6 Hz, 1H).

Example 157

Synthesis of 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004)

Compound 004

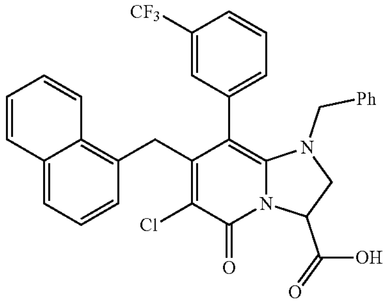

Step-1: Preparation of methyl 6-chloro-7-(naphthalen-1-ylmethyl)-5-oxo-8-(3-(trifluoromethyl)phenyl)-1,2,3,5-tetrahydroimidazo[1,2-a]pyridine-3-carboxylate

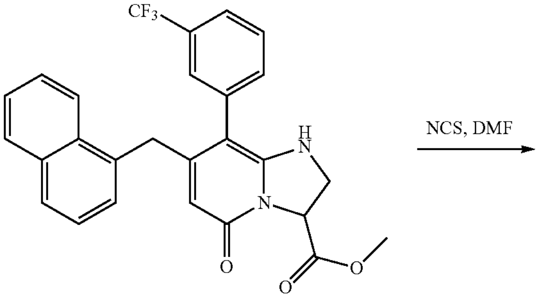

-continued

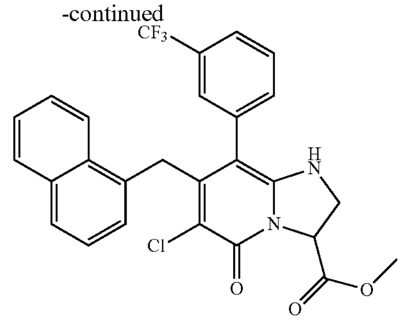

Methyl 7-(naphthalen-1-ylmethyl)-5-oxo-8-(3-(trifluoromethyl)phenyl)-1,2,3,5-tetrahydroimidazo[1,2-a]pyridine-3-carboxylate (0.3 g, 0.627 mmol) was dissolved in DMF (5.0 mL). N-Chlorosuccinimide (0.088 g, 0.658 mmol) was added in portions and the reaction mixture was stirred for 2 h. The reaction was quenched in water (100 mL) and extracted with ethyl acetate (3×100 mL). The organic layer was dried over sodium sulphate and concentrated under reduced pressure. The crude product was purified using column chromatography eluting with 0-2% methanol/dichloromethane to give methyl 6-chloro-7-(naphthalen-1-ylmethyl)-5-oxo-8-(3-(trifluoromethyl)phenyl)-1,2,3,5-tetrahydroimidazo[1,2-a]pyridine-3-carboxylate as a brown solid (0.240 g, 74.63%). LCMS (Method-C3): 93.62% (RT: 1.983, 283.0 nm) (MS: ESI+ve 515.4 [M+2]). Analytical Chiral HPLC: (RT 4.5, 86.1% and RT 4.86, 12.4%), The column used was Chiralpak IH (250*4.6 mm), 5 micron, column flow 4.0 ml/min. Mobile phase (A) liquid carbon dioxide (B) 0.1% diethylamine in methanol.

Step-2: Preparation of methyl 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylate

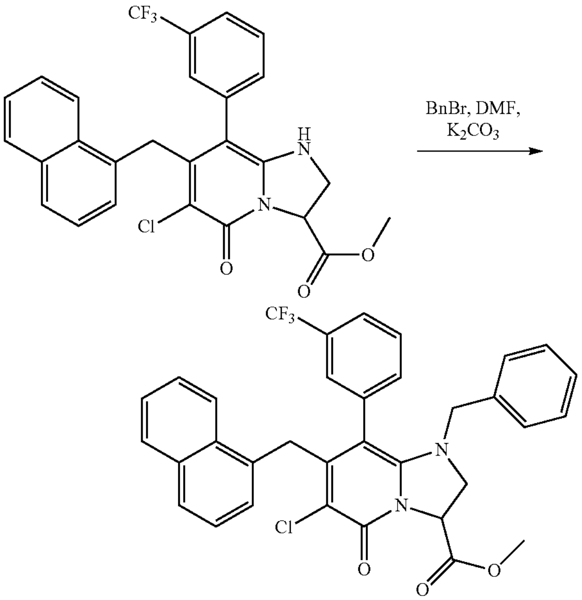

Methyl 6-chloro-7-(naphthalen-1-ylmethyl)-5-oxo-8-(3-(trifluoromethyl)phenyl)-1,2,3,5-tetrahydroimidazo[1,2-a]

pyridine-3-carboxylate (0.24 g, 0.468 mmol) was dissolved in DMF (4.0 mL). Potassium carbonate (0.194 g, 1.40 mmol) was added and the mixture was stirred for 10 min. Benzyl bromide (0.088 g, 0.515 mmol) was added dropwise and the reaction mixture was stirred for 16 h. The reaction was quenched in ice water (50 mL) and extracted with ethyl acetate (3×50 mL). The organic layer was dried over sodium sulphate and concentrated under reduced pressure. The crude product was purified using column chromatography eluting with 0-3% methanol/dichloromethane to give methyl 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylate as a brown gum. (0.210 g, 74.42%). LCMS (Method-C3): 92.51% (RT: 2.162, 225.0 nm) (MS: ESI+ve 605.8 [M+2]). Analytical Chiral HPLC: (RT 5.38, 86.8% and RT 6.01, 10.6%), The column used was Chiralpak IH (250*4.6 mm), 5 micron, column flow 4.0 ml/min. Mobile phase (A) liquid carbon dioxide (B) 0.1% diethylamine in methanol.

Step-3: Preparation 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004)

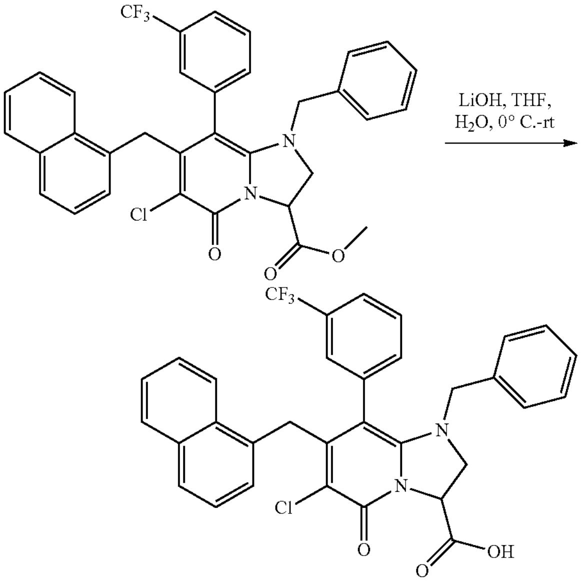

Compound 004

Methyl 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylate (0.210 g, 0.348 mmol) was dissolved in THF:$H_2O$ (1:1, 4 mL). LiOH—$H_2O$ (0.043 g, 1.046 mmol) was added and the mixture was stirred at room temperature for 4 h. The mixture was concentrated then ice water (10 mL) and 1N aqueous HCl solution (4-5 mL) were added. The resulting solid was collected by filtration and dried under vacuum. The crude product was purified using Prep HPLC Method 1 to give 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid as a white solid (Compound 004) (0.025 g, 12.19%). LCMS (Method-C3): 97.86% (RT 2.440, 224.0 nm) (MS: ESI+ve 589.0 [M+0]). $^1$H NMR: (400 MHz, DMSO) δ ppm: 3.56 (s, 1H), 3.68-3.82 (m, 2H), 3.91-4.16 (m, 3H), 5.07 (s, 1H), 6.85-6.87 (d, J=6 Hz, 2H), 6.96-7.05 (m, 1H), 7.18-7.28 (m, 6H), 3.37-7.44 (m, 4H), 7.70-7.75 (t, 2H), 7.84-7.86 (d, J=7.6 Hz, 1H). Analytical Chiral HPLC: (RT 4.59, 89.5% and RT, 14.63, 10.5%), The column used was Chiralcel OX-H (150*4.6 mm), 5 micron, column flow 1.0 ml/min. Mobile phase (A) 0.1% diethylamine in n-hexane (B) 0.1% diethylamine in propanol:methanol (1:1).

Step-4: SFC separation of 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid Compound 004a (S-Isomer); Compound 004b (R-Isomer)

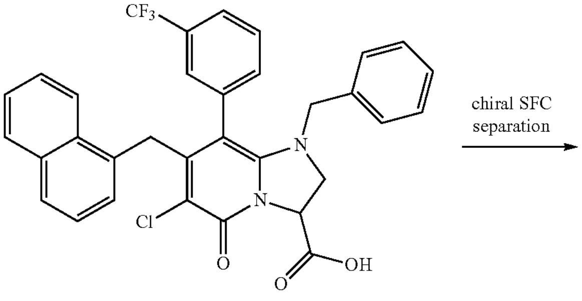

Compound 004

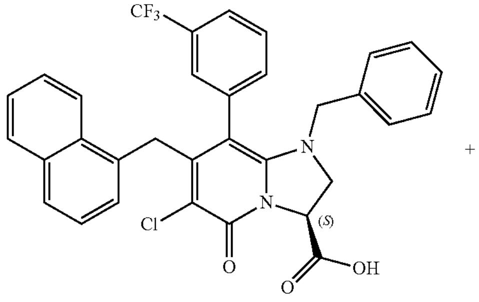

Compound 004a
(S-Isomer)

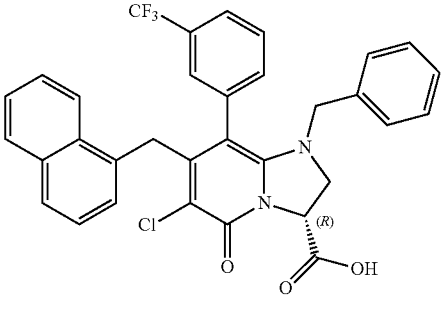

Compound 004b
(R-Isomer)

1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004), (90 mg) was separated on a Shimadzu LC-20AP and UV detector. The column used was Chiralcel OX-H (250*21.0) mm, 5 micron, column flow 20.0 ml/min. Mobile phase (A) 0.1% diethylamine in hexane (B) 0.1% diethylamine in propanol:methanol (1:1).

Isolated (0.030 g) of fraction 1 (S)-1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid Compound 004a_Fraction-1 (S-Isomer) LCMS (Method-C3): 100% (RT 2.018, 220.0 nm) (MS: ESI+ve 589.8 [M+H]). $^{1}$H NMR: (400 MHz, DMSO) δ ppm: 3.56 (s, 1H), 3.68-3.82 (m, 2H), 3.91-4.16 (m, 3H), 5.07 (s, 1H), 6.85-6.87 (d, J=6 Hz, 2H), 6.96-7.05 (m, 1H), 7.18-7.28 (m, 6H), 3.37-7.44 (m, 4H), 7.70-7.75 (t, 2H), 7.84-7.86 (d, J=7.6 Hz, 1H). Analytical Chiral HPLC (Fraction-1): 100% (RT: 4.93). The column used was Chiralcel OX-H (150*21.0) mm, 5 micron, column flow 1.0 ml/min. Mobile phase (A) 0.1% diethylamine in hexane (B) 0.1% diethylamine in propanol:methanol (1:1).

Isolated (0.002 g) of fraction 2 (R)-1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid Compound 004b_Fraction-2 (R-Isomer) LCMS (Method-C3): 100% (RT 2.010, 220.0 nm) (MS: ESI+ve 589.8 [M+H]). Analytical Chiral HPLC (Fraction-2): 96.6% (RT: 17.04). The column used was Chiralcel OX-H (150*21.0) mm, 5 micron, column flow 1.0 ml/min. Mobile phase (A) 0.1% diethylamine in hexane (B) 0.1% diethylamine in propanol:methanol (1:1).

Example 158

Synthesis of 7-(difluoro(naphthalen-1-yl)methyl)-5-oxo-8-(3-(trifluoromethyl)phenyl)-1,2,3,5-tetrahydroimidazo[1,2-a]pyridine-3-carboxylic acid (Compound 134)

Compound 134

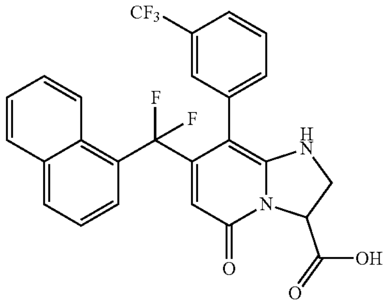

Step-1: Preparation of methyl 7-(difluoro(naphthalen-1-yl)methyl)-5-oxo-8-(3-(trifluoromethyl)phenyl)-1,2,3,5-tetrahydroimidazo[1,2-a]pyridine-3-carboxylate

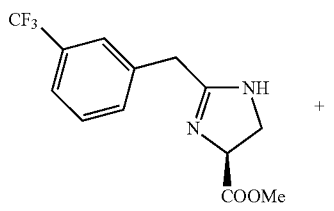

-continued

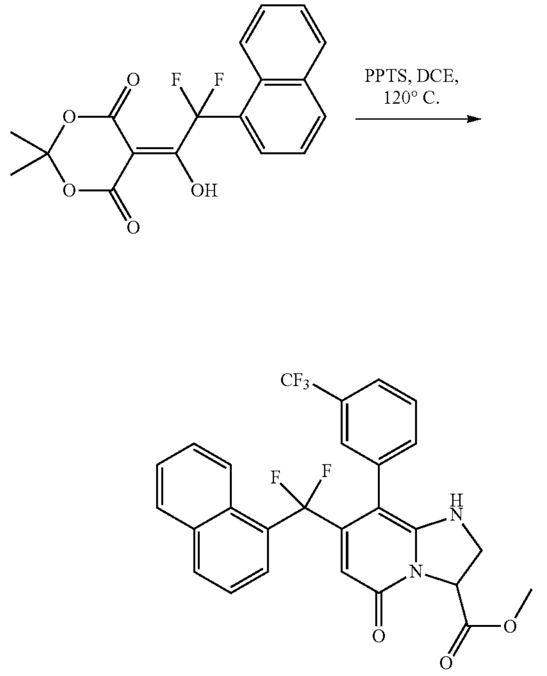

Methyl (S)-2-(3-(trifluoromethyl)benzyl)-4,5-dihydro-1H-imidazole-4-carboxylate (0.4 g, 1.39 mmol) and 5-(2,2-difluoro-1-hydroxy-2-(naphthalen-1-yl)ethylidene)-2,2-dimethyl-1,3-dioxane-4,6-dione (1.21 g, 3.44 mmol) were dissolved in 1,2 dichloroethane (15 mL). Pyridinium p-toluenesulfonate (0.35 g, 1.39 mmol) was added and the mixture was stirred at 120° C. for 16 h. The reaction was quenched with saturated aqueous sodium bicarbonate solution (50 mL) and extracted with DCM (3×50 mL). The organic layer was dried over sodium sulphate and concentrated under reduced pressure. The crude product was purified using column chromatography eluting with 3% methanol/DCM then again with 1% methanol/DCM to give methyl 7-(difluoro(naphthalen-1-yl)methyl)-5-oxo-8-(3-(trifluoromethyl)phenyl)-1,2,3,5-tetrahydroimidazo[1,2-a]pyridine-3-carboxylate. (0.49 g, 68.16%) LCMS (Method-$C_3$): 97.76% (RT: 2.119, 222.0 nm) (MS: ESI+ve 515.0 [M+H]).

Step-2: Preparation of 7-(difluoro(naphthalen-1-yl)methyl)-5-oxo-8-(3-(trifluoromethyl)phenyl)-1,2,3,5-tetrahydroimidazo[1,2-a]pyridine-3-carboxylic acid (Compound 134)

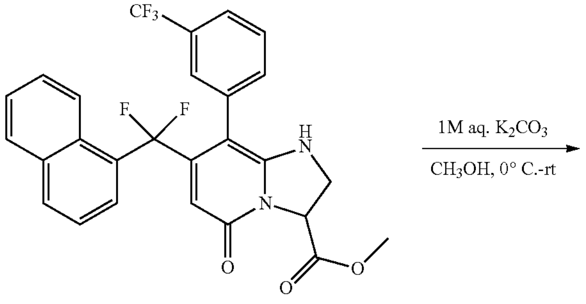

-continued

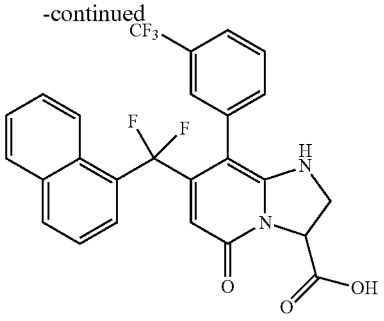

Compound 134

Methyl 7-(difluoro(naphthalen-1-yl)methyl)-5-oxo-8-(3-(trifluoromethyl)phenyl)-1,2,3,5-tetrahydroimidazo[1,2-a] pyridine-3-carboxylate (0.1 g, 0.194 mmol) was dissolved in methanol (2 mL). 1M $K_2CO_3$ (2 mL) was added and the mixture was stirred at room temperature for 4 h. The mixture was concentrated then ice-cold water (10 mL) and 1N aqueous HCl solution (3-4 mL) were added. The resulting solid was collected by filtration and dried under vacuum. The crude product was purified using Prep HPLC Method 1 to give 7-(difluoro(naphthalen-1-yl)methyl)-5-oxo-8-(3-(trifluoromethyl)phenyl)-1,2,3,5-tetrahydroimidazo[1,2-a]pyridine-3-carboxylic acid (Compound 134), as a white solid (0.03 g, 30.84%). LCMS (Method-J): 100% (RT 4.662, 254.0 nm) (MS: ESI+ve 501.0 [M+H]). $^1$H NMR: (400 MHz, DMSO) δ ppm: 4.14-4.19 (t, 1H), 4.30-4.35 (t, 2H), 6.0 (s, 1H) 6.68-6.79 (m, 1H), 7.01-7.18 (m, 3H), 7.37-7.42 (m, 1H), 7.51-7.55 (m, 3H), 7.89-7.94 (t, 3H), 13.16 (s, 1H).

Example 159

Synthesis of 7-(difluoro(naphthalen-1-yl)methyl)-1-methyl-5-oxo-8-(3-(trifluoromethyl)phenyl)-1,2,3,5-tetrahydroimidazo[1,2-a]pyridine-3-carboxylic acid (Compound 135)

Compound 135

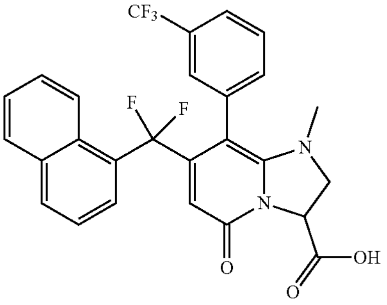

Step-1: Preparation of methyl 7-(difluoro(naphthalen-1-yl)methyl)-1-methyl-5-oxo-8-(3-(trifluoromethyl)phenyl)-1,2,3,5-tetrahydroimidazo[1,2-a]pyridine-3-carboxylate

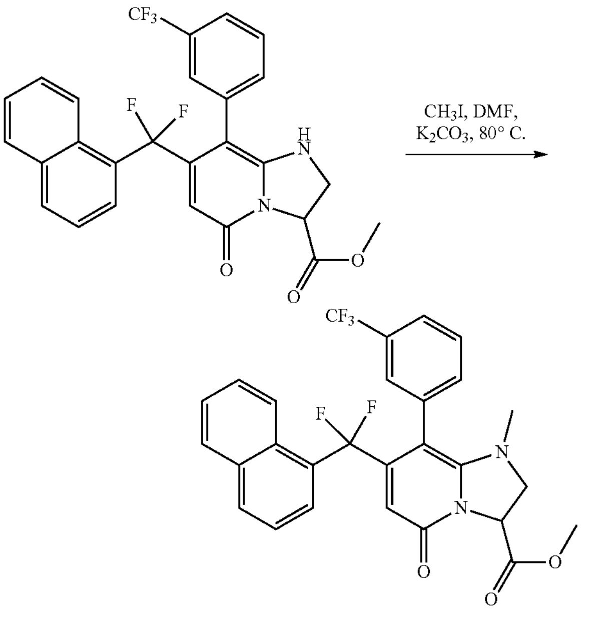

Methyl 7-(difluoro(naphthalen-1-yl)methyl)-5-oxo-8-(3-(trifluoromethyl)phenyl)-1,2,3,5-tetrahydroimidazo[1,2-a] pyridine-3-carboxylate (0.2 g, 0.38 mmol) was dissolved in DMF (2.0 mL). Potassium carbonate (0.107 g, 0.77 mmol) was added and the mixture was stirred for 10 min. Methyl iodide (0.12 g, 0.855 mmol) was added dropwise at room temperature and the reaction mixture was stirred at 80° C. for 16 h. The reaction was quenched in ice water (50 mL) and extracted with ethyl acetate (3×50 mL). The organic layer was dried over sodium sulphate and concentrated under reduced pressure to give methyl 7-(difluoro(naphthalen-1-yl)methyl)-1-methyl-5-oxo-8-(3-(trifluoromethyl) phenyl)-1,2,3,5-tetrahydroimidazo[1,2-a]pyridine-3-carboxylate (0.27 g, crude product) as a brown gum. LCMS (Method-C3): 58.24% (RT: 1.920, 225.0 nm) (MS: ESI+ve 529.39 [M+H]).

Step-2: Preparation of 7-(difluoro(naphthalen-1-yl)methyl)-1-methyl-5-oxo-8-(3-(trifluoromethyl)phenyl)-1,2,3,5-tetrahydroimidazo[1,2-a]pyridine-3-carboxylic acid (Compound 135)

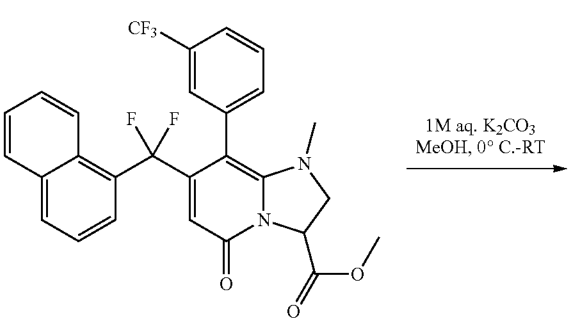

-continued

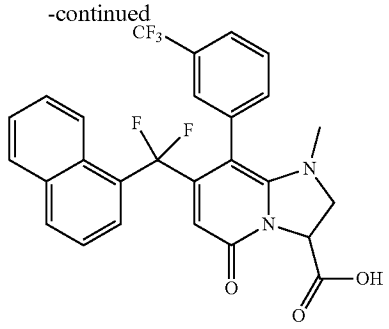

Compound 135

Methyl 7-(difluoro(naphthalen-1-yl)methyl)-1-methyl-5-oxo-8-(3-(trifluoromethyl)phenyl)-1,2,3,5-tetrahydroimidazo[1,2-a]pyridine-3-carboxylate (0.27 g, 0.511 mmol) was dissolved in methanol (3 mL) at room temperature. 1M aqueous $K_2CO_3$ solution (3 mL) was added and the mixture was stirred at room temperature for 4 h. The mixture was concentrated then ice-cold water (10 mL) and 1N aqueous HCl solution (3-4 mL) were added. The resulting solid was collected by filtration and dried under vacuum. The crude product was purified using Prep HPLC Method 1 to give 7-(difluoro(naphthalen-1-yl)methyl)-1-methyl-5-oxo-8-(3-(trifluoromethyl)phenyl)-1,2,3,5-tetrahydroimidazo[1,2-a] pyridine-3-carboxylic acid as a white solid (0.023 g, 8.75%) (Compound 135). LCMS (Method-C3): 100% (RT 2.220, 202.0 nm) (MS: ESI+ve 515.2 [M+H]). $^1$H NMR: (400 MHz, DMSO) δ ppm: 1.89-1.91 (d, J=5.6 Hz, 3H), 3.54 (s, 1H), 3.79-3.84 (t, 1H) 4.89 (s, 1H), 6.05-6.07 (d, J=8.8 Hz, 1H), 6.73-6.83 (m, 1H), 7.07-7.20 (m, 2H), 7.29-7.39 (t, 2H), 7.54-7.56 (d, 3H), 7.92-7.98 (t, 3H).

Example 160

Synthesis of 7-(naphthalen-1-ylmethyl)-5-oxo-8-(3-(trifluoromethyl)phenyl)-2,3-dihydro-5H-thiazolo[3,2-c]pyrimidine-3-carboxylic acid (Compound 022)

Compound 022

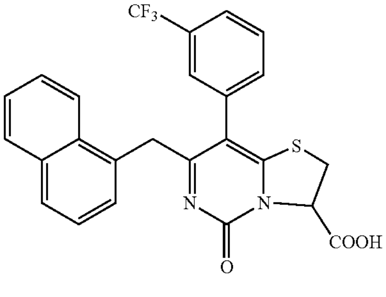

Step 1: Preparation of ethyl 4-(naphthalen-1-yl)-3-oxobutanoate

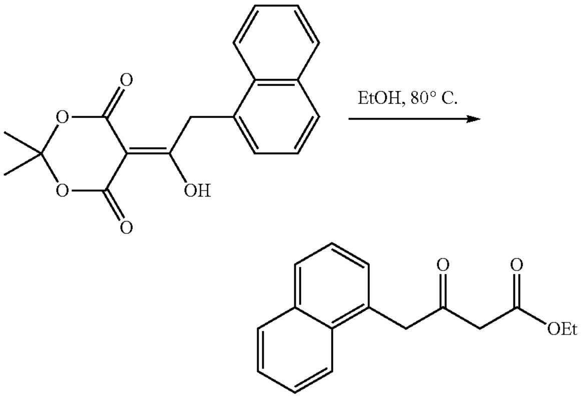

5-(1-Hydroxy-2-(naphthalen-1-yl)ethylidene)-2,2-dimethyl-1,3-dioxane-4,6-dione (4 g, 12.82 mmol) was dissolved in ethanol (16 mL) and allowed to stir at 80° C. for 2 h. The mixture was cooled to room temperature, concentrated under reduced pressure then diluted with water (100 mL) and extracted with ethyl acetate (3×50 mL). The combined organic layers were dried over sodium sulfate ($Na_2SO_4$) and concentrated. The crude product was purified using column chromatography eluting with 10% ethyl acetate/hexane to give ethyl 4-(naphthalen-1-yl)-3-oxobutanoate as a yellow solid. (2 g, 60.93%) LCMS (Method-C3): 89.89% (RT: 1.820, 230.0 nm) (MS: ESI+ve 257.3 [M+H]).

Step 2: Preparation of 6-(naphthalen-1-ylmethyl)-2-thioxo-2,3-dihydropyrimidin-4 (1H)-one

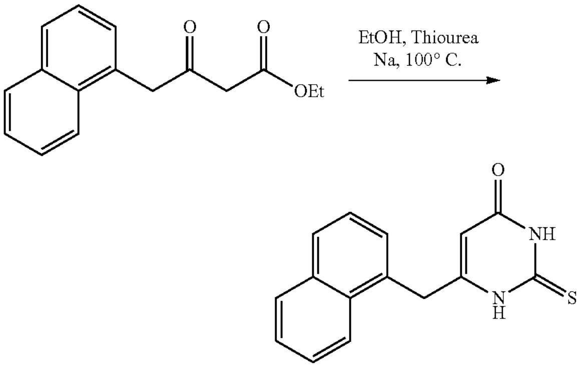

Sodium metal (0.358 g, 15.6 mmol) was dissolved in ethanol (10 mL), then thiourea (0.889 g, 11.7 mmol) was added at room temperature. Ethyl 4-(naphthalen-1-yl)-3-oxobutanoate (1 g, 3.90 mmol) was added at room temperature, and the reaction mixture was heated at 100° C. for overnight. The reaction mixture was cooled to room temperature then evaporated to dryness under reduced pressure. The residue was dissolved in water (50 mL), and the resulting solution was acidified with 3M aqueous HCl solution (10 mL) to pH 4. The resulting precipitate was filtered, washed with $H_2O$ and diethyl ether successively, then dried to give 6-(naphthalen-1-ylmethyl)-2-thioxo-2,3-dihydropyrimidin-4 (1H)-one as a white solid. (0.4 g, 38.21%) LCMS (Method-C3): 98.59% (RT: 1.508, 224.0 nm) (MS: ESI−ve 267.4 [M−H]). $^{1}$H NMR: (400 MHz, DMSO) δ ppm: 4.24 (s, 2H), 5.15 (s, 1H), 7.48-7.54 (m, 2H), 7.56-7.61 (m, 2H), 7.91-7.93 (d, J=8 Hz, 1H), 7.98-7.99 (t, J=2.4 Hz, 2H), 12.43 (s, 1H), 12.58 (s, 1H).

Step 3: Preparation of 6-(naphthalen-1-ylmethyl)pyrimidine-2,4 (1H,3H)-dione

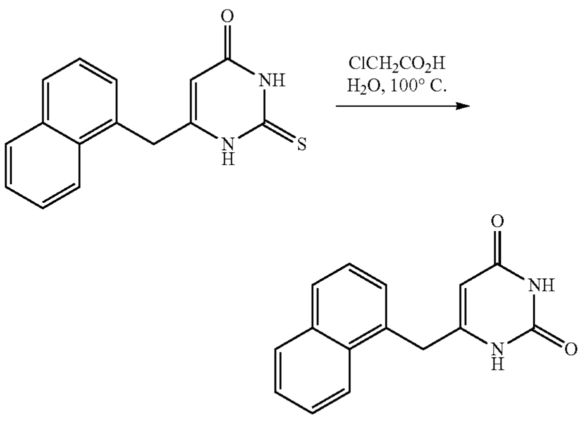

6-(naphthalen-1-ylmethyl)-2-thioxo-2,3-dihydropyrimidin-4 (1H)-one (4 g, 14.92 mmol) was added to a solution of chloroacetic acid (42 g, 447.75 mmol) in water (10 mL) and allowed to stir at 100° C. for 18 h. The reaction mixture was cooled to room temperature and the resulting solid was collected by filtration then washed with water (3×15 mL), ethanol (5 mL) and diethyl ether (3 mL) to give 6-(naphthalen-1-ylmethyl)pyrimidine-2,4 (1H,3H)-dione as an off white solid. (2.5 g, 66.48%) LCMS (Method-C3): 98.89% (RT: 1.449, 228.0 nm) (MS: ESI+ve 253.3 [M+H]). $^{1}$H NMR: (400 MHz, DMSO) δ ppm: 4.15 (S, 2H), 4.86 (s, 1H), 7.50-7.56 (m, 2H), 7.58-7.61 (m, 2H), 7.90-7.92 (d, J=6.8 Hz, 1H), 7.97-7.99 (d, J=8.8 Hz, 2H), 11.01 (s, 1H), 11.15 (s, 1H).

Step 4: Preparation of 5-bromo-6-(naphthalen-1-ylmethyl)pyrimidine-2,4 (1H,3H)-dione

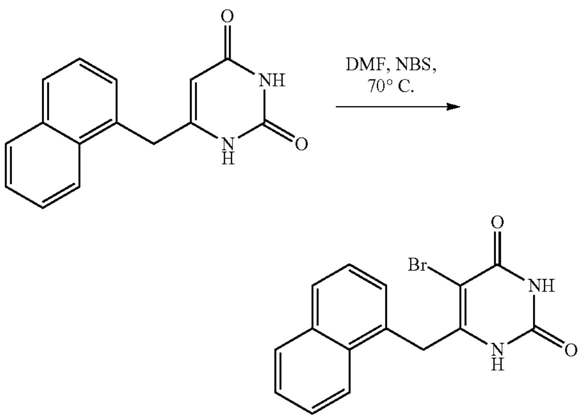

6-(Naphthalen-1-ylmethyl)pyrimidine-2,4 (1H,3H)-dione (2.5 g, 9.92 mmol) was dissolved in DMF (20 mL). N-Bromosuccinimide (1.94 g, 10.91 mmol) was added in portions over 30 min then stirred at 70° C. for 6 h. The reaction mixture was cooled to room temperature and quenched in ice water (100 mL). The resulting solid was collected by filtration and washed with water. The crude product was purified using column chromatography eluting with 37% ethyl acetate/hexane to give 5-bromo-6-(naphthalen-1-ylmethyl)pyrimidine-2,4 (1H,3H)-dione as a yellow solid. (1.5 g, 45.71%). LCMS (Method-C3): 96.88% (RT: 1.545, 225.0 nm) (MS: ESI+ve 331.26 [M+H]). $^{1}$H NMR: (400 MHz, DMSO) δ ppm: 4.36 (s, 2H), 7.17-7.19 (d, J=7.2 Hz, 1H), 7.44-7.48 (t, J=7.6 Hz, 1H), 7.57-7.65 (m, 2H), 7.85-7.88 (d, J=8.4 Hz, 1H), 7.95-7.99 (t, J=7.6 Hz, 1H), 8.10-8.12 (d, J=8 Hz, 1H), 11.47 (s, 1H), 11.63 (s, 1H).

Step 5: Preparation of 6-(naphthalen-1-ylmethyl)-5-(3-(trifluoromethyl)phenyl) pyrimidine-2,4 (1H,3H)-dione

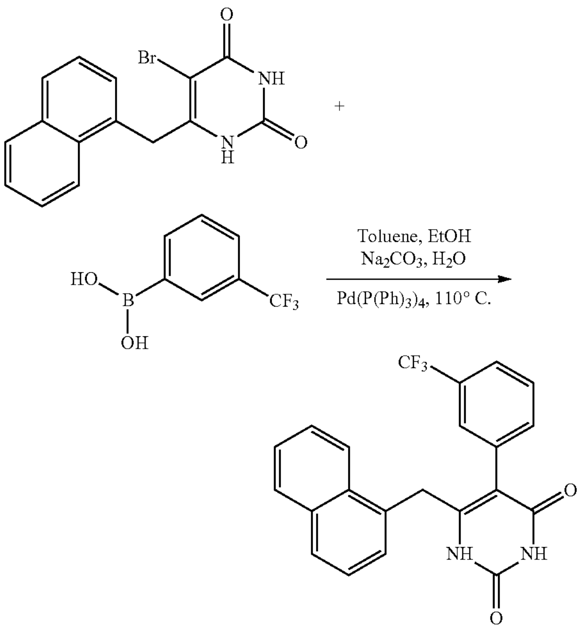

$Na_2CO_3$ (0.48 g, 4.529 mmol) was added to a solution of 5-bromo-6-(naphthalen-1-ylmethyl)pyrimidine-2,4 (1H, 3H)-dione (0.5 g, 1.509 mmol) and (3-(trifluoromethyl) phenyl)boronic acid (0.43 g, 2.264 mmol) in toluene:ethanol:water (1:1:1, 9 mL). Palladium tetrakis triphenylphosphine (0.174 g, 0.150 mmol) was added under argon. The reaction mixture was stirred for 2 h at 110° C., in a microwave reactor, under microwave irradiation. After cooling, $H_2O$ (10 mL) was added and the mixture was extracted with ethyl acetate (3×20 mL). The organic layers were combined and dried over sodium sulphate. The solvent was removed under reduced pressure to give the crude product which was purified using column chromatography eluting with 63% ethyl acetate/hexane. The product was further purified by using Prep HPLC Method 2 to give 6-(naphthalen-1-ylmethyl)-5-(3-(trifluoromethyl)phenyl) pyrimidine-2,4 (1H,3H)-dione as an off white solid (0.034 g, 5.68%). LCMS (Method-H): 100% (RT: 4.183, 202 nm) (MS: ESI+ve 397 [M+H]). 1H NMR: (400 MHz, DMSO) δ ppm: 4.07 (s, 2H), 7.33-7.34 (d, J=6.8 Hz, 1H), 7.42-7.54 (m, 7H), 7.79-7.83 (t, 2H), 7.92-7.94 (d, J=7.6 Hz, 1H), 11.25 (s, 2H).

Step 6: Preparation of 6-(naphthalen-1-ylmethyl)-4-thioxo-5-(3-(trifluoromethyl)phenyl)-3,4-dihydropyrimidin-2 (1H)-one

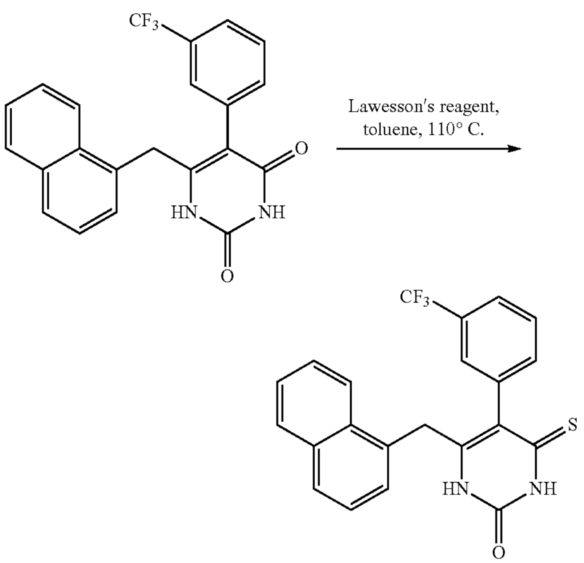

6-(Naphthalen-1-ylmethyl)-5-(3-(trifluoromethyl)phenyl) pyrimidine-2,4 (1H,3H)-dione (0.1 g, 0.252 mmol) was dissolved in toluene (2 mL). Lawesson's reagent (0.111 g, 0.277 mmol) was added and the mixture was stirred at 110° C. for 16 h. The reaction was quenched in water (8 mL) and extracted with ethyl acetate (3×10 mL). The organic layer was dried over sodium sulphate and concentrated under reduced pressure to give the crude product which was purified using column chromatography eluting with 50% ethyl acetate/hexane to give 6-(naphthalen-1-ylmethyl)-4-thioxo-5-(3-(trifluoromethyl)phenyl)-3,4-dihydropyrimidin-2 (1H)-one as a yellow solid. (0.04 g, 38.44%). LCMS (Method-H): 97.617% (RT: 4.091, 222 nm) (MS: ESI+ve 413 [M+H]). $^{1}$H NMR: (400 MHz, DMSO) δ ppm: 3.99 (s, 2H), 7.26-7.27 (d, J=5.6 Hz, 2H), 7.32-7.52 (m, 6H), 7.69-7.71 (d, J=8.4 Hz, 1H), 7.78-7.80 (d, J=8 Hz, 1H), 7.89-7.91 (d, J=7.6 Hz, 1H), 11.98 (s, 1H), 12.77 (s, 1H).

Step-7: Preparation of methyl 7-(naphthalen-1-ylmethyl)-5-oxo-8-(3-(trifluoromethyl)phenyl)-2,3-dihydro-5H-thiazolo[3,2-c]pyrimidine-3-carboxylate

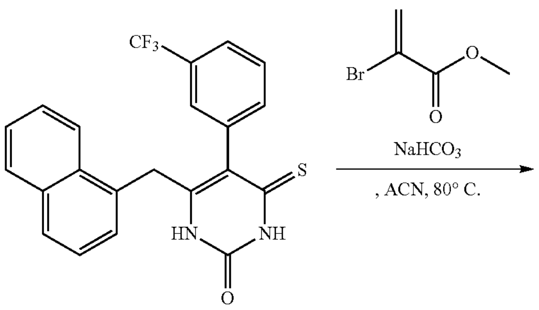

-continued

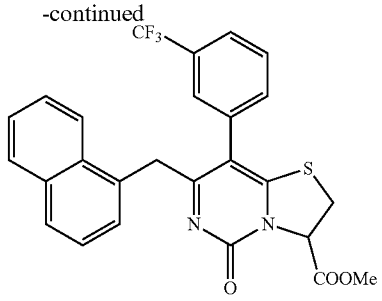

6-(Naphthalen-1-ylmethyl)-4-thioxo-5-(3-(trifluoromethyl)phenyl)-3,4-dihydropyrimidin-2 (1H)-one (0.7 g, 1.697 mmol) was dissolved in acetonitrile (20 mL). Methyl 2-bromoacrylate (0.42 g, 2.546 mmol) and sodium bicarbonate (1.28 g, 15.28 mmol) were added. The mixture was stirred at 80° C. in a sealed tube for 16 h. The reaction was quenched in water (100 mL) and extracted with ethyl acetate (3×100 mL). The organic layer was dried over sodium sulphate and concentrated under reduced pressure. The crude product was purified using column chromatography eluting with 0-70% ethyl acetate/hexane to give methyl 7-(naphthalen-1-ylmethyl)-5-oxo-8-(3-(trifluoromethyl)phenyl)-2,3-dihydro-5H-thiazolo[3,2-c]pyrimidine-3-carboxylate as a brown solid (0.23 g, 27.29%). LCMS (Method-C3): 88.42% (RT: 1.859, 225.0 nm) (MS: ESI–ve 495.3 [M–H]).

Step 8: Preparation of 7-(naphthalen-1-ylmethyl)-5-oxo-8-(3-(trifluoromethyl)phenyl)-2,3-dihydro-5H-thiazolo[3,2-c]pyrimidine-3-carboxylic acid (Compound 022)

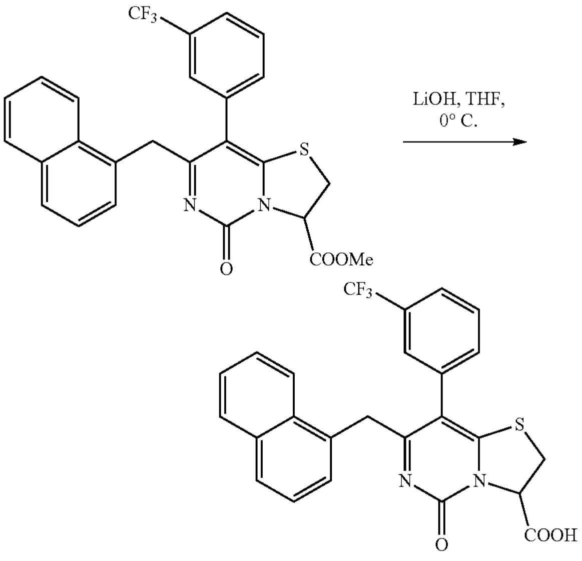

Compound 022

Methyl 7-(naphthalen-1-ylmethyl)-5-oxo-8-(3-(trifluoromethyl)phenyl)-2,3-dihydro-5H-thiazolo[3,2-c]pyrimidine-3-carboxylate (0.2 g, 0.402 mmol) was dissolved in THF:$H_2O$ (1:1, 10 mL). LiOH—$H_2O$ (0.057 g 1.208 mmol) was added and the mixture stirred at room temperature for 4 h. The mixture was concentrated then suspended in ice water (10 mL) and 1N aqueous HCl solution (3-4 mL). The resulting precipitate was collected by filtration and dried under vacuum. The crude product was purified using Prep HPLC Method 1 to give 7-(naphthalen-1-ylmethyl)-5-oxo-8-(3-(trifluoromethyl)phenyl)-2,3-dihydro-5H-thiazolo[3,2-c]pyrimidine-3-carboxylic acid (Compound 022), as an off white solid (0.035 g, 18.01%). LCMS (Method-J): 100% (RT 4.598, 202.4 nm) (MS: ESI+ve 483.0 [M+H]). $^{1}H$ NMR: (400 MHz, DMSO) δ ppm: 3.54-3.57 (d, J=10.4 Hz, 1H), 3.68-3.73 (t, 1H), 4.13-4.21 (d, J=32.4 Hz, 2H), 5.43-5.45 (d, J=9.6 Hz, 1H), 6.99-7.01 (d, J=7.2 Hz, 1H), 7.28-7.32 (t, 1H), 7.39-7.47 (m, 2H), 7.53 (s, 1H), 7.63-7.64 (d, J=6.8 Hz, 2H), 7.70-7.79 (m, 3H), 7.85-7.87 (d, J=7.2 Hz, 1H), 13.67 (bs, 1H).

Example 161

Synthesis of 2,2-dimethyl-7-(naphthalen-1-ylmethyl)-5-oxo-8-(3-(trifluoromethyl) phenyl)-2,3-dihydro-5H-thiazolo[3,2-c]pyrimidine-3-carboxylic acid (Compound 059)

Compound 059

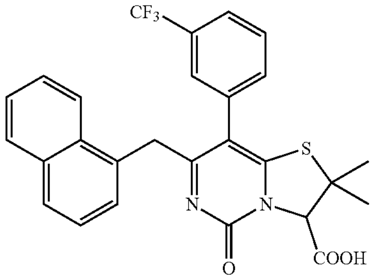

Step 1: Preparation of ethyl 2-bromo-3-methylbut-2-enoate

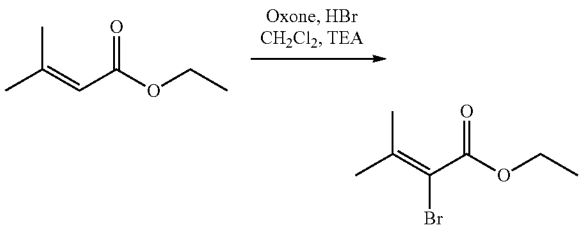

A mixture of ethyl 3-methylbut-2-enoate (2 g, 15.604 mmol), DCM (40 mL) and Oxone (11.5 g, 18.72 mmol) was cooled to 0° C. 2N HBr solution 37% in water (2.71 g, 34.329 mmol) was added dropwise and the mixture was stirred at room temperature for 2 h. The reaction mixture turned colorless and TEA (11.5 ml, 82.234 mmol) was added at 0° C. The mixture was stirred at room temperature for 12 hours, diluted with water (50 mL) and extracted with DCM (50 mL×2). The organic layer was dried over anhydrous sodium sulphate and concentrated. The crude product was purified using column chromatography eluting with 20% ethyl acetate/hexane to give ethyl 2-bromo-3-methylbut-2-enoate (0.4 g, 12.4%). LCMS (Method-C3): 72.74% (RT: 2.109, 202.0 nm) (MS: ESI+ve 208.9 [M+2]).

Step 2: Preparation of ethyl 2,2-dimethyl-7-(naphthalen-1-ylmethyl)-5-oxo-8-(3-(trifluoromethyl)phenyl)-2,3-dihydro-5H-thiazolo[3,2-c]pyrimidine-3-carboxylate

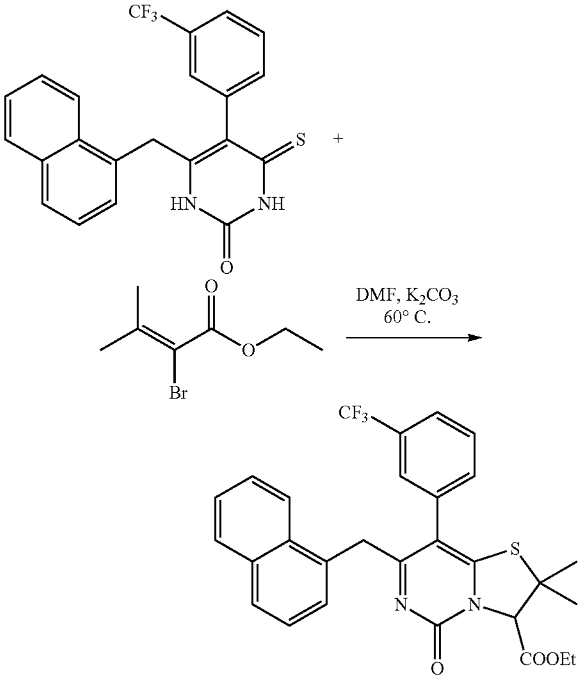

To a stirred solution of 6-(naphthalen-1-ylmethyl)-4-thioxo-5-(3-(trifluoromethyl)phenyl)-3,4-dihydropyrimidin-2 (1H)-one (0.5 g, 1.21 mmol) in DMF (5 mL), ethyl 2-bromo-3-methylbut-2-enoate (0.3 g, 1.4547 mmol) was added, followed by $K_2CO_3$ (1.5 g, 10.91 mmol). The reaction mixture was stirred at 60° C. for 2 h. then cooled to room temperature. The mixture was diluted with water (20 mL) and extracted with ethyl acetate (2×30 mL). The organic layer was dried over anhydrous sodium sulphate and concentrated under vacuum to afford ethyl 2,2-dimethyl-7-(naphthalen-1-ylmethyl)-5-oxo-8-(3-(trifluoromethyl)phenyl)-2,3-dihydro-5H-thiazolo[3,2-c]pyrimidine-3-carboxylate (0.07 g, 10.7%). LCMS (Method-C3): 66.06% (RT 2.038, 230 nm) (MS: ESI+ve 539.55 [M+H]).

Step 3: Preparation of 2,2-dimethyl-7-(naphthalen-1-ylmethyl)-5-oxo-8-(3-(trifluoromethyl)phenyl)-2,3-dihydro-5H-thiazolo[3,2-c]pyrimidine-3-carboxylic acid (Compound 059)

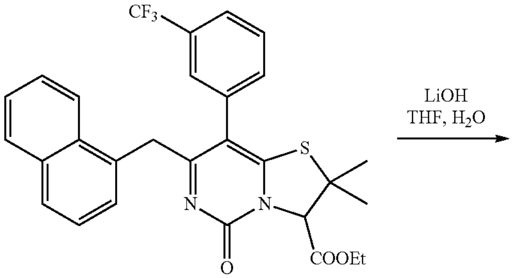

-continued

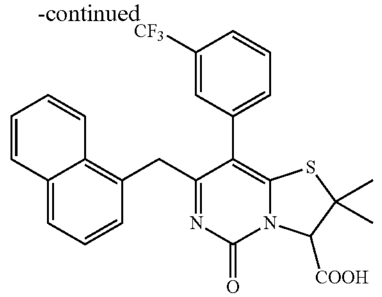

Compound 059

To a stirred solution of ethyl 2,2-dimethyl-7-(naphthalen-1-ylmethyl)-5-oxo-8-(3-(trifluoromethyl)phenyl)-2,3-dihydro-5H-thiazolo[3,2-c]pyrimidine-3-carboxylate (0.07 g, 0.1301 mmol) in THF (4 mL) and water (4 mL), LiOH—$H_2O$ (0.026 g, 0.6505 mmol) was added at 0° C. The reaction mixture was stirred at room temperature for 16 h. The mixture was concentrated then diluted with water (20 mL), and the pH of the aqueous layer was adjusted to pH 1-2 with 2N aqueous HCl solution (2 mL). The resultant solid was collected by filtration and dried under vacuum. The crude product was purified using Prep HPLC Method 2 to give 2,2-dimethyl-7-(naphthalen-1-ylmethyl)-5-oxo-8-(3-(trifluoromethyl)phenyl)-2,3-dihydro-5H-thiazolo[3,2-c]pyrimidine-3-carboxylic acid (Compound 059) (0.03 g, 45.4%). LCMS (Method-C3) 100% (RT 4.679, 202 nm) (MS: ESI+ve 525 [M+H]). $^1$H NMR: (400 MHz, DMSO) δ ppm: 1.49 (s, 3H), 1.90 (s, 3H), 4.10 (s, 2H), 4.45 (s, 1H), 6.75-6.99 (d, J=8 Hz, 1H), 7.27-7.31 (t, J=8 Hz, 1H), 7.41-7.45 (m, 2H), 7.56 (s, 1H), 7.64 (m, 2H), 7.69-7.74 (m, 2H), 7.79-7.80 (d, J=4 Hz, 1H), 7.85-7.87 (d, J=8 Hz, 1H).

Example 162

Synthesis of 7-(1-naphthoyl)-5-oxo-8-(3-(trifluoromethyl)phenyl)-2,3-dihydro-5H-thiazolo[3,2-c]pyrimidine-3-carboxylic acid (Compound 055)

Compound 055

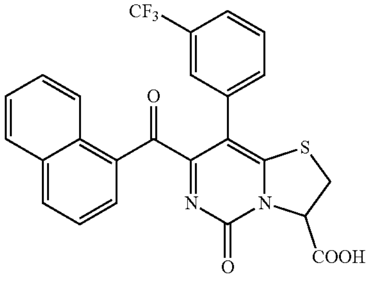

Step-1: Preparation of methyl 7-(1-naphthoyl)-5-oxo-8-(3-(trifluoromethyl)phenyl)-2,3-dihydro-5H-thiazolo[3,2-c]pyrimidine-3-carboxylate

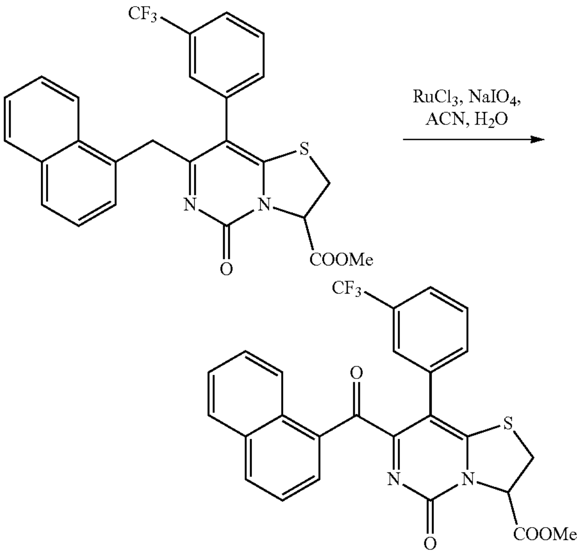

Methyl 7-(naphthalen-1-ylmethyl)-5-oxo-8-(3-(trifluoromethyl)phenyl)-2,3-dihydro-5H-thiazolo[3,2-c]pyrimidine-3-carboxylate (0.270 g, 0.543 mmol) was dissolved in acetonitrile (10 mL) and water (10 mL). Sodium periodate (0.174 g, 0.815 mmol) and ruthenium trichloride (0.0112 g, 0.0543 mmol) were added and the mixture was allowed to stir for 16 h. The reaction was quenched in ice water (50 mL) and extracted with ethyl acetate (3×50 mL). The organic layer was dried over sodium sulphate and concentrated under reduced pressure. The crude product was purified using column chromatography eluting with 0-70% ethyl acetate/hexane to give methyl 7-(1-naphthoyl)-5-oxo-8-(3-(trifluoromethyl)phenyl)-2,3-dihydro-5H-thiazolo[3,2-c]pyrimidine-3-carboxylate, as a brown solid (0.11 g, 39.62%). LCMS (Method-C3): 100.0% (RT 1.815, 230.0 nm) (MS: ESI+ve 511.27 [M+H]). $^1$H NMR: (400 MHz, $CDCl_3$) δ ppm: 3.69-3.72 (m, 1H), 3.87-3.97 (m, 3H), 5.79-5.81 (q, 1H), 7.30-7.34 (m, 1H), 7.36-7.62 (m, 7H), 7.87-7.89 (d, J=7.6 Hz, 1H), 8.03-8.09 (m, 2H), 8.77-8.79 (d, J=8 Hz, 1H).

Step-2: Preparation of 7-(1-naphthoyl)-5-oxo-8-(3-(trifluoromethyl)phenyl)-2,3-dihydro-5H-thiazolo[3,2-c]pyrimidine-3-carboxylic acid (Compound 055)

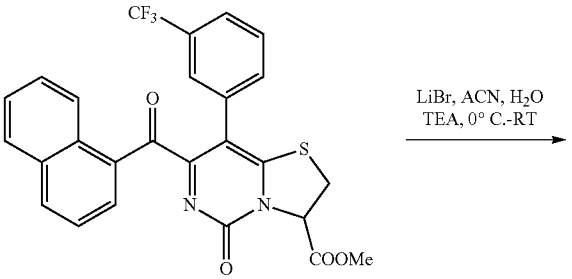

-continued

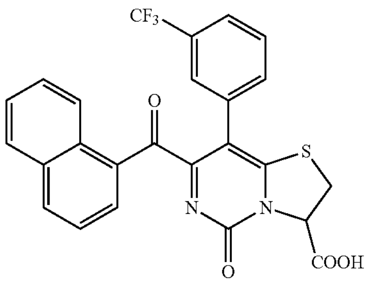

Compound 055

Methyl 7-(1-naphthoyl)-5-oxo-8-(3-(trifluoromethyl)phenyl)-2,3-dihydro-5H-thiazolo[3,2-c]pyrimidine-3-carboxylate (0.05 g, 0.09803 mmol) was dissolved in acetonitrile (0.6 mL) and water (0.03 mL) then cooled to 0° C. LiBr (0.0849 g, 0.9803 mmol) and triethylamine (0.04 mL, 0.2941 mmol) were added and the mixture was stirred at room temperature for 4 h. The mixture was concentrated, then cold water (10 mL) and 1N aqueous HCl solution (3-4 mL) were added. The resulting solid was collected by filtration and dried under vacuum. The crude product was purified using Prep HPLC Method 1 to give 7-(1-naphthoyl)-5-oxo-8-(3-(trifluoromethyl)phenyl)-2,3-dihydro-5H-thiazolo[3,2-c]pyrimidine-3-carboxylic acid (Compound 055), as an off white solid (0.009 g, 18.51%). LCMS (Method-C3): 97.15% (RT 1.596, 227 nm) (MS: ESI+ve 497.29 [M+H]). 1H NMR: (400 MHz, DMSO) δ ppm: 3.72-3.75 (d, J=10 Hz, 1H), 3.96-4.02 (t, 1H), 5.61-5.63 (t, 1H), 7.48-7.64 (m, 7H), 8.02-8.11 (m, 2H), 8.24-8.26 (d, J=8 Hz, 1H), 8.66-8.68 (d, J=8 Hz, 1H), 14.03 (s, 1H).

Example 163

Synthesis of 7-(difluoro(naphthalen-1-yl)methyl)-5-oxo-8-(3-(trifluoromethyl)phenyl)-2,3-dihydro-5H-thiazolo[3,2-c]pyrimidine-3-carboxylic acid (Compound 063)

Compound 063

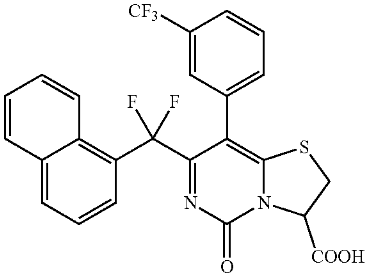

Step-1: Preparation of methyl 7-(difluoro(naphthalen-1-yl)methyl)-5-oxo-8-(3-(trifluoromethyl)phenyl)-2,3-dihydro-5H-thiazolo[3,2-c]pyrimidine-3-carboxylate

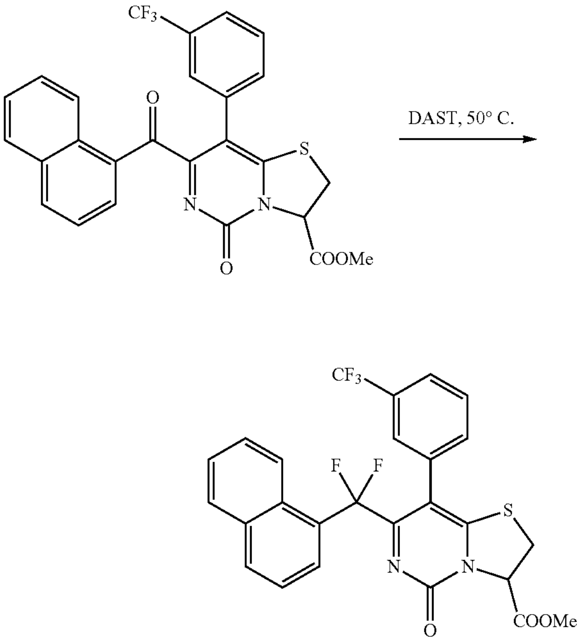 [SMILES: COC(=O)C1CSc2c(-c3cccc(C(F)(F)F)c3)c(Cc3cccc4ccccc34)nc(=O)n21 ; COC(=O)C1CSc2c(-c3cccc(C(F)(F)F)c3)c(C(=O)c3cccc4ccccc34)nc(=O)n21]

Methyl 7-(1-naphthoyl)-5-oxo-8-(3-(trifluoromethyl)phenyl)-2,3-dihydro-5H-thiazolo[3,2-c]pyrimidine-3-carboxylate (0.4 g, 0.782 mmol) was dissolved in DAST (2.0 mL) and stirred at 50° C. for 12 h. The reaction was quenched in ice water (50 mL) and sat. aq. sodium bicarbonate solution, then extracted with ethyl acetate (3×100 mL). The organic layer was dried over sodium sulphate and concentrated under reduced pressure. The crude product was purified using column chromatography eluting with 0-50% ethyl acetate/hexane to give methyl 7-(difluoro(naphthalen-1-yl)methyl)-5-oxo-8-(3-(trifluoromethyl)phenyl)-2,3-dihydro-5H-thiazolo[3,2-c]pyrimidine-3-carboxylate, as a brown solid (0.11 g, 26.36%). LCMS (Method-C3): 91.33% (RT 1.936, 220.0 nm) (MS: ESI+ve 533.34 [M+H].

Step-2: Preparation of 7-(1-naphthoyl)-5-oxo-8-(3-(trifluoromethyl)phenyl)-2,3-dihydro-5H-thiazolo[3,2-c]pyrimidine-3-carboxylic acid (Compound 063)

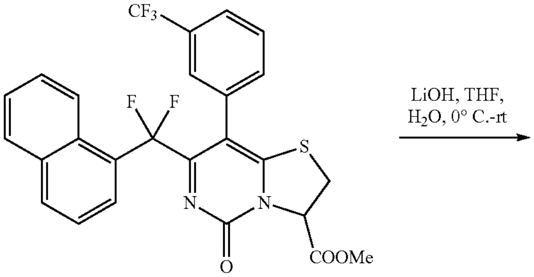

-continued

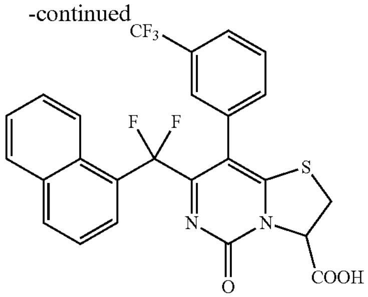

Compound 063

Methyl 7-(difluoro(naphthalen-1-yl)methyl)-5-oxo-8-(3-(trifluoromethyl)phenyl)-2,3-dihydro-5H-thiazolo[3,2-c] pyrimidine-3-carboxylate (0.15 g, 0.281 mmol) was dissolved in THF:$H_2O$ (1:1, 10 mL). LiOH—$H_2O$ (0.060 g 1.43 mmol) was added at 0° C. and the mixture was stirred at room temperature for 2 h. The mixture was concentrated then cold water (10 mL) and 1N aqueous HCl solution (3-4 mL) were added. The resulting solid was collected by filtration and dried under vacuum. The crude product was purified using Prep HPLC Method 1 to give 7-(difluoro (naphthalen-1-yl)methyl)-5-oxo-8-(3-(trifluoromethyl)phenyl)-2,3-dihydro-5H-thiazolo[3,2-c]pyrimidine-3-carboxylic acid (Compound 063), as an off white solid (0.031 g, 21.23%). LCMS (Method-J): 98.40% (RT 4.722, 202.4 nm) (MS: ESI+ve 519.0 [M+H]). 1H NMR: (400 MHz, DMSO) δ ppm: 3.59-3.62 (d, 1H), 3.88-3.93 (t, 1H), 5.55-5.57 (d, J=8.4 Hz, 1H), 7.01 (s, 1H), 7.16-7.20 (t, 1H), 7.26-7.32 (q, 1H), 7.35-7.42 (m, 3H), 7.72 (s, 1H), 8.00-8.02 (m, 3H), 14.03 (s, 1H).

Example 164

Synthesis of 7'-(naphthalen-1-ylmethyl)-5'-oxo-8'-(3-(trifluoromethyl)phenyl)-3'H,5'H-spiro[cyclopentane-1,2'-thiazolo[3,2-c]pyrimidine]-3'-carboxylic acid (Compound 053)

Compound 053

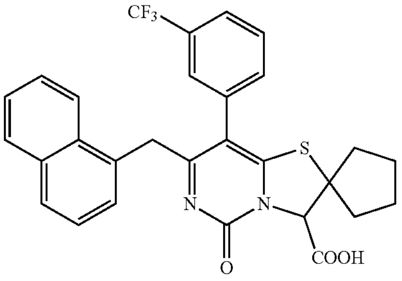

Step 1: Preparation of ethyl 2-cyclopentylideneacetate

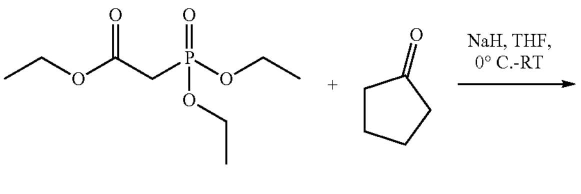

-continued

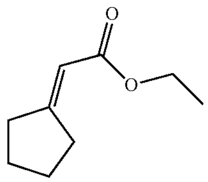

Ethyl 2-(diethoxyphosphoryl)acetate (8.7 g, 9.200 mmol) was dissolved in tetrahydrofuran (30 mL). Sodium hydride (0.940 g, 9.200 mmol) was added under a nitrogen atmosphere at 0° C. The mixture was stirred at room temperature for 1 h. A solution of cyclopentanone (3.0 g, 5.600 mmol) in tetrahydrofuran was added dropwise at 0° C. The reaction mixture was stirred at room temperature for 2 h, quenched in water (40 mL) and extracted with diethyl ether (3×40 mL). The organic layer was dried over sodium sulphate and concentrated under reduced pressure without heating to give ethyl 2-cyclopentylideneacetate (2.4 g, 43.6%). LCMS (Method-F): 100% (RT: 7.055, 225.0 nm) (MS: ESI+ve 155.0 [M+H]).

Step-2: Preparation of ethyl 2-bromo-2-cyclopentylideneacetate

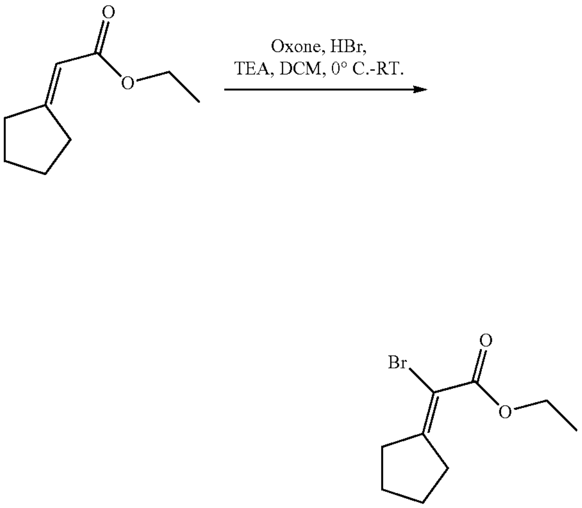

Ethyl 2-cyclopentylideneacetate (1.1 g, 7.100 mmol) and Oxone (5.2 g, 8.500 mmol) were dissolved in dichloromethane (15 mL) at 0° C. Hydrogen bromide (2 N) (0.9 mL, 5.600 mmol) was added dropwise at 0° C., and the mixture was stirred at room temperature for 1 h. Triethyl amine (5.6 mL, 0.700 mmol) was added dropwise, and the reaction mixture was stirred at room temperature for 16 h. The reaction was quenched in water (40 mL) and extracted with ether (3×40 mL). The organic layer was dried over sodium sulphate and concentrated under reduced pressure without heating to give ethyl 2-bromo-2-cyclopentylideneacetate (1.0 g, 60.1%). $^{1}$H NMR: (400 MHz, DMSO) δ ppm: 1.36-1.41 (t, J=18.4 Hz, 3H), 1.74-1.77 (m, J=14 Hz, 2H), 1.86-1.89 (m, J=14 Hz, 2H), 2.56-2.59 (t, J=14 Hz, 2H), 2.80-2.83 (t, J=14 Hz 2H), 4.25-4.29 (q, J=14 Hz, 2H).

Step 3: Preparation of ethyl 7'-(naphthalen-1-ylmethyl)-5'-oxo-8'-(3-(trifluoromethyl)phenyl)-3'H,5'H-spiro[cyclopentane-1,2'-thiazolo[3,2-c]pyrimidine]-3'-carboxylate

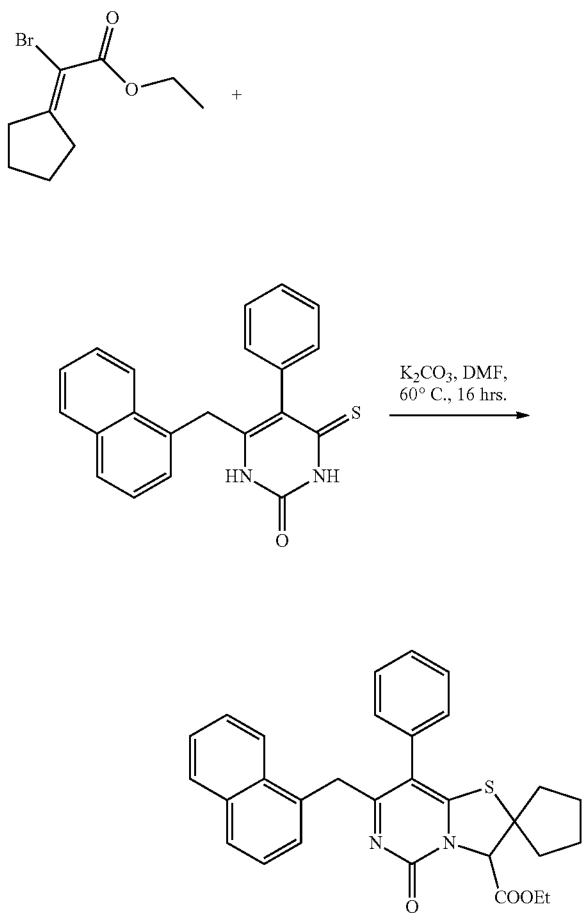

Ethyl 2-bromo-2-cyclopentylideneacetate (0.300 g, 0.0007 mmol) and 6-(naphthalen-1-ylmethyl)-4-thioxo-5-(3-(trifluoromethyl)phenyl)-3,4-dihydropyrimidin-2 (1H)-one (0.254 g, 0.0010 mmol) were dissolved in DMF (9 mL). $K_2CO_3$ (0.940 g, 0.0065 mmol) was added in portions at 0° C. and the mixture was stirred at 60° C. for 16 h. The reaction was quenched in water (40 mL) and extracted with ether (3×40 mL). The organic layer was dried over sodium sulphate and concentrated under reduced pressure without heating to give ethyl 7'-(naphthalen-1-ylmethyl)-5'-oxo-8'-(3-(trifluoromethyl)phenyl)-3'H,5'H-spiro[cyclopentane-1,2'-thiazolo[3,2-c]pyrimidine]-3'-carboxylate (0.180 g, 43.8%). LCMS (Method-C3): 65.2% (RT 2.093, 233.0 nm) (MS: ESI+ve 565.5 [M+H]).

Step 4: Preparation of 7'-(naphthalen-1-ylmethyl)-5'-oxo-8'-(3-(trifluoromethyl)phenyl)-3'H,5'H-spiro[cyclopentane-1,2'-thiazolo[3,2-c]pyrimidine]-3'-carboxylic acid (Compound 053)

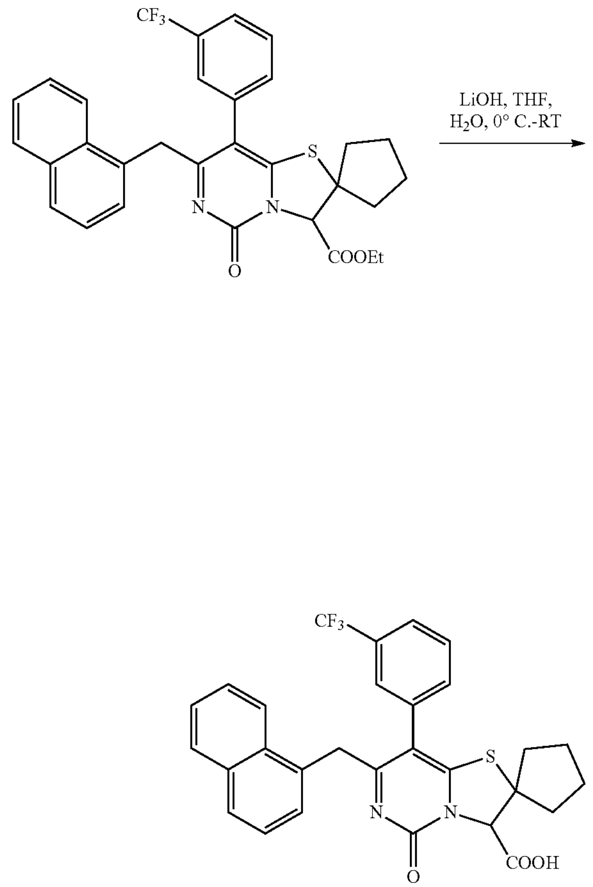

Compound 053

Ethyl 7'-(naphthalen-1-ylmethyl)-5'-oxo-8'-(3-(trifluoromethyl)phenyl)-3'H,5'H-spiro[cyclopentane-1,2'-thiazolo[3,2-c]pyrimidine]-3'-carboxylate (0.180 g, 0.0003 mmol) was dissolved in THF:$H_2O$ (4:4 mL). Lithium hydroxide (0.065 g, 0.0015 mmol) was added at 0° C. and the mixture was stirred at room temperature for 16 h. The reaction mixture was concentrated then water (40 mL) and 1N aqueous HCl solution were added. The mixture was extracted with ethyl acetate (3×40 mL). The organic layer was dried over sodium sulphate and concentrated under reduced pressure. The crude product was purified using Prep HPLC Method 1 to give 7'-(naphthalen-1-ylmethyl)-5'-oxo-8'-(3-(trifluoromethyl)phenyl)-3'H,5'H-spiro[cyclopentane-1,2'-thiazolo[3,2-c]pyrimidine]-3'-carboxylic acid (Compound 053) (0.030 g, 17.7%), as a white solid. LCMS (Method-C3): 100% (RT 2.256, 202.0 nm) (MS: ESI+ve 537.2 [M+H]) $^1$H NMR (400 MHz, DMSO) δ ppm: 1.59-1.65 (t, 2H), 1.79-1.81 (q, 1H), 1.96-1.99 (t, 2H), 2.07-2.18 (t, 2H), 2.61-2.66 (m, 1H), 4.17 (s, 2H), 4.38 (s, 1H), 6.98-7.00 (d, J=7.2 Hz, 1H), 7.27-7.31 (t, 1H), 7.39-7.47 (m, 2H), 7.55 (s, 1H), 7.63 (s, 2H), 7.71-7.81 (m, 3H), 7.85-7.87 (d, J=7.6 Hz, 1H), 13.62 (bs, 1H).

Example 165

Synthesis of 7-(naphthalen-1-ylmethyl)-5-oxo-8-(3-(trifluoromethyl)phenyl)-2,3-dihydro-5H-oxazolo[3,2-a]pyridine-3-carboxylic acid (Compound 064)

Compound 064

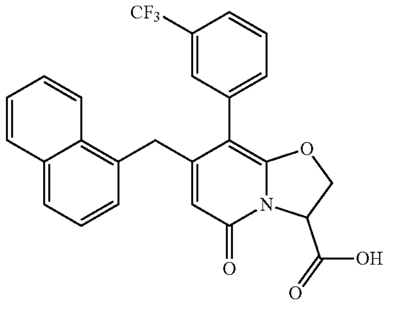

Step-1: Preparation of methyl 2-(3-(trifluoromethyl)benzyl)-4,5-dihydrooxazole-4-carboxylate

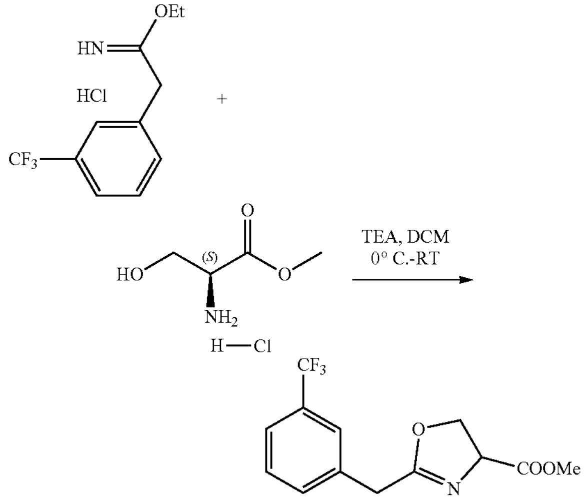

L-Serine methyl ester hydrochloride (10.0 g, 64.26 mmol) was dissolved in dichloromethane (100 mL) and cooled to 0° C. Triethylamine (8.83 mL, 62.90 mmol) was added and the reaction mixture was stirred at room temperature for 30 min. A solution of ethyl 2-(3-(trifluoromethyl)phenyl)acetimidate (10.99 g, 47.5 mmol) in dichloromethane (25 mL) was added at 0° C. and the reaction mixture was stirred at room temperature for 16 h. The reaction was quenched with saturated aqueous sodium bicarbonate solution (400 mL) and extracted with dichloromethane (3x300 mL). The organic layer was dried over sodium sulphate and concentrated under reduced pressure. The crude product was purified using column chromatography eluting with 35% ethyl acetate/hexane to give methyl 2-(3-(trifluoromethyl)benzyl)-4,5-dihydrooxazole-4-carboxylate as a colorless liquid (3.7 g, 27.10%). LCMS (Method-C3): 44.35% (RT: 1.604, 214 nm) (MS: ESI+ve 288.5 [M+H]). $^{1}$H NMR: (400 MHz, DMSO) δ ppm: 3.16 (s, 3H), 3.80 (s, 2H), 4.35-4.44 (m, 2H), 4.74-4.78 (t, 1H), 7.53-7.71 (m, 4H).

Step-2: Preparation of methyl 7-(naphthalen-1-ylmethyl)-5-oxo-8-(3-(trifluoromethyl)phenyl)-2,3-dihydro-5H-oxazolo[3,2-a]pyridine-3-carboxylate

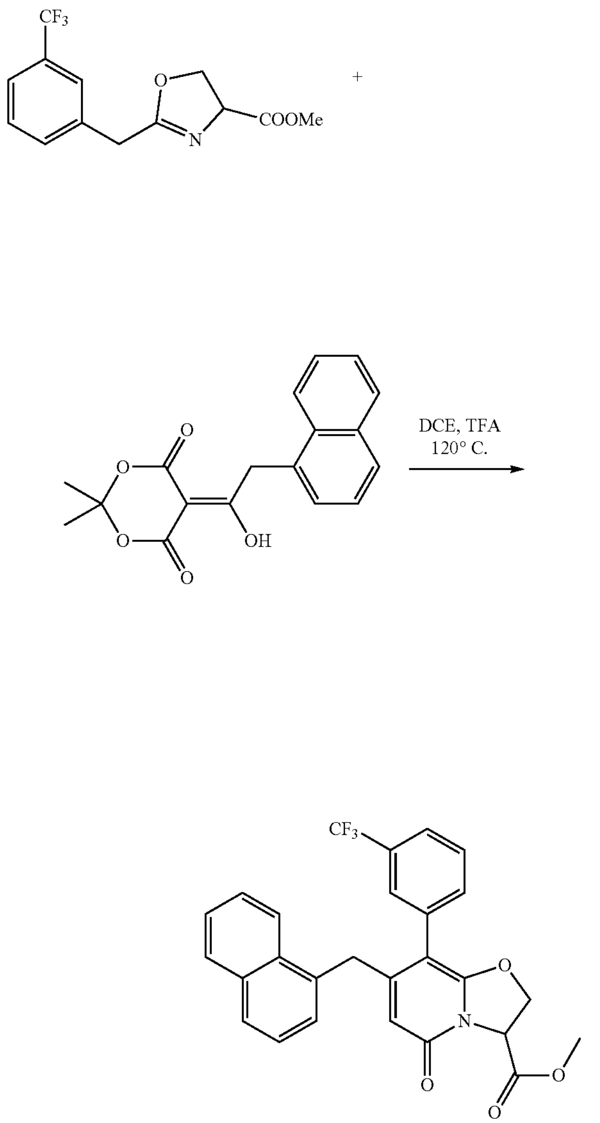

Methyl 2-(3-(trifluoromethyl)benzyl)-4,5-dihydrooxazole-4-carboxylate (0.3 g, 1.04 mmol) and 5-(1-hydroxy-2-(naphthalen-1-yl)ethylidene)-2,2-dimethyl-1,3-dioxane-4,6-dione (0.65 g, 2.08 mmol) was dissolved in 1,2 dichloroethane (4 mL). Trifluoroacetic acid (0.17 mL, 2.29 mmol) was added and the mixture was stirred at 120° C. for 16 h. The reaction was quenched with saturated aqueous sodium bicarbonate solution (40 mL) and extracted with 1, 2 dichloroethane (3x30 mL). The organic layer was dried over sodium sulphate and concentrated under reduced pressure. The crude product was purified using column chromatography eluting with 55% ethyl acetate/hexane to give methyl 7-(naphthalen-1-ylmethyl)-5-oxo-8-(3-(trifluoromethyl)phenyl)-2,3-dihydro-5H-oxazolo[3,2-a]pyridine-3-carboxylate (0.15 g, 29.95%) LCMS (Method-C3): 75.89% (RT: 1.924, 225.0 nm) (MS: ESI+ve 480.34 [M+H]).

Step-3: Preparation of 7-(naphthalen-1-ylmethyl)-5-oxo-8-(3-(trifluoromethyl)phenyl)-2,3-dihydro-5H-oxazolo[3,2-a]pyridine-3-carboxylic acid (Compound 064)

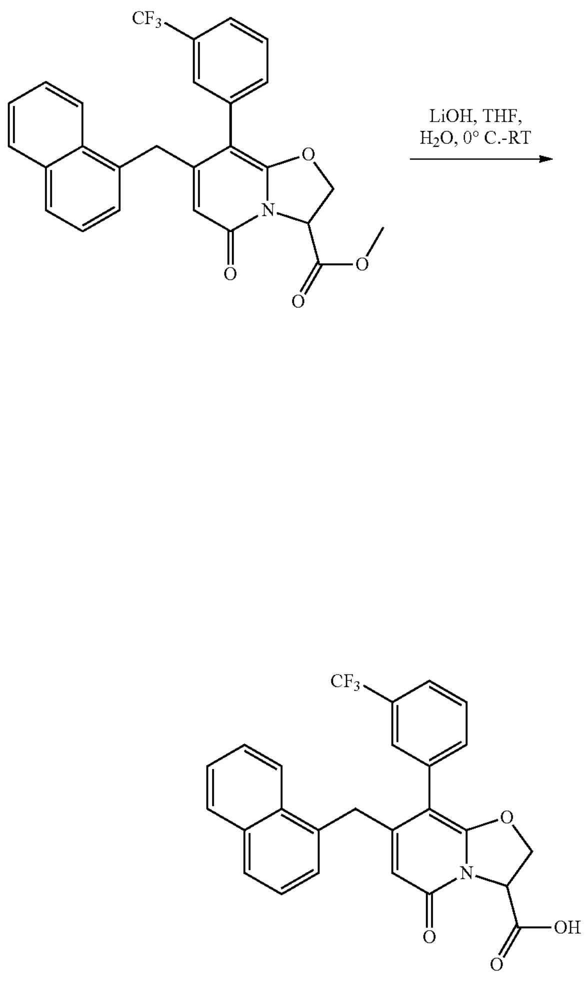

Compound 064

Methyl 7-(naphthalen-1-ylmethyl)-5-oxo-8-(3-(trifluoromethyl)phenyl)-2,3-dihydro-5H-oxazolo[3,2-a]pyridine-3-carboxylate (0.14 g, 0.291 mmol) was dissolved in THF: $H_2O$ (1:1, 4 mL). LiOH—$H_2O$ (0.036 g 0.875 mmol) was added and the mixture was stirred at room temperature for 4 h. The mixture was concentrated then cold water (10 mL) and 1N aqueous HCl solution (3-4 mL) were added. The resulting solid was collected by filtration and dried under vacuum. The crude product was purified using Prep HPLC Method 1 to give 7-(naphthalen-1-ylmethyl)-5-oxo-8-(3-(trifluoromethyl)phenyl)-2,3-dihydro-5H-oxazolo[3,2-a]pyridine-3-carboxylic acid (Compound 064), as an off white solid (0.0129 g, 9.49%). LCMS (Method-J): 100% (RT 4.970, 254.4 nm) (MS: ESI+ve 466.0 [M+H]). 1H NMR: (400 MHz, DMSO) δ ppm: 4.06-4.19 (m, 2H), 4.73-4.76 (m, 1H), 4.88-4.93 (m, 1H), 5.10-5.913 (m, 1H), 5.45 (s, 1H), 7.27-7.29 (d, J=7.2 Hz, 1H), 7.42-7.51 (m, 3H), 7.59-7.72 (m, 5H), 7.81-7.83 (d, J=8.4 Hz, 1H), 7.90-7.92 (d, J=7.6 Hz, 1H).

Example 166

Synthesis of 6-amino-7-(naphthalen-1-ylmethyl)-5-oxo-8-(3-(trifluoromethyl) phenyl)-2,3-dihydro-5H-oxazolo[3,2-a]pyridine-3-carboxylic acid (Compound 069)

Compound 069

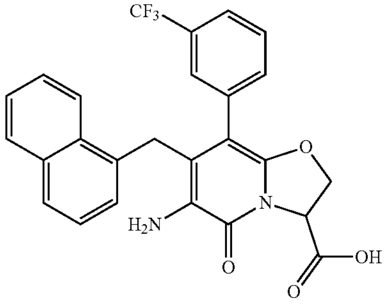

Step 1: Methyl 7-(naphthalen-1-ylmethyl)-6-nitro-5-oxo-8-(3-(trifluoromethyl)phenyl)-2,3-dihydro-5H-oxazolo[3,2-a]pyridine-3-carboxylate

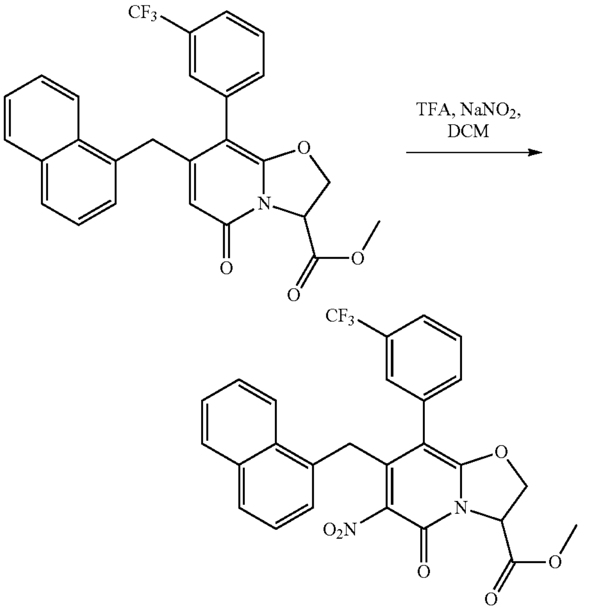

Methyl-7-(naphthalen-1-ylmethyl)-5-oxo-8-(3-(trifluoromethyl)phenyl)-2,3-dihydro-5H-oxazolo[3,2-a]pyridine-3-carboxylate (1 g, 0.200 mmol) was dissolved in dichloromethane (54 mL). Sodium nitrite (0.071 g, 0.10 mmol) was added and the mixture was stirred at room temperature for several hours. Trifluoroacetic acid (1.8 mL) was added and the mixture was stirred for 16 h. The reaction mixture was diluted with sat. aq. sodium bicarbonate solution (30 mL) and extracted with ethyl acetate (2×30 mL). The organic layer was dried over sodium sulphate and concentrated under reduced pressure. The crude product was purified using column chromatography eluting with 0-40% ethyl acetate/hexane to give methyl 7-(naphthalen-1-ylmethyl)-6-nitro-5-oxo-8-(3-(trifluoromethyl)phenyl)-2,3-dihydro-5H-oxazolo[3,2-a]pyridine-3-carboxylate as a yellow solid (0.303 g, 27.7%).LCMS (Method-C3): 100% (RT 1.997, 225.0 nm) (MS: ESI+ve 525.4 [M+H]).

Step 2: Preparation of methyl 6-amino-7-(naphthalen-1-ylmethyl)-5-oxo-8-(3-(trifluoromethyl)phenyl)-2,3-dihydro-5H-oxazolo[3,2-a]pyridine-3-carboxylate

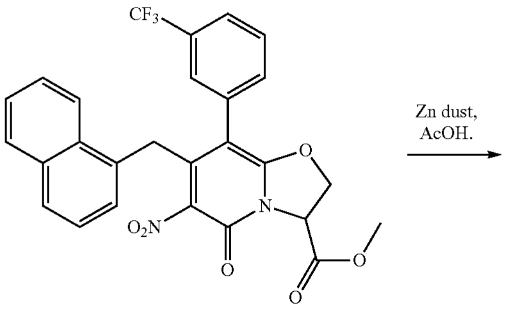

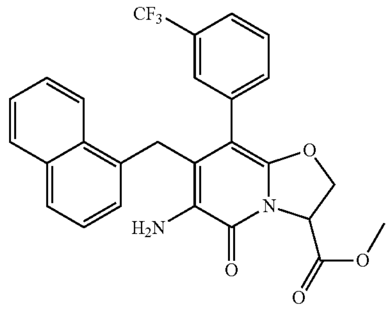

Methyl 7-(naphthalen-1-ylmethyl)-6-nitro-5-oxo-8-(3-(trifluoromethyl) phenyl)-2,3-dihydro-5H-oxazolo[3,2-a] pyridine-3-carboxylate (0.300 g, 0.570 mmol) was dissolved in acetic acid (3.6 mL). Activated Zinc dust (0.186 g, 2.8601 mmol) was added and the mixture was stirred at room temperature for 16 h. The reaction mixture was filtered through Celite and rinsed with dichloromethane. The filtrate was concentrated, then ice and sat. aq. bicarbonate solution (20 mL) were added. The resulting solid was collected by filtration, dissolved in dichloromethane then dried and concentrated to give methyl 6-amino-7-(naphthalen-1-ylmethyl)-5-oxo-8-(3-(trifluoromethyl)phenyl)-2,3-dihydro-5H-oxazolo[3,2-a]pyridine-3-carboxylate, as a brown solid (0.291 g, 100%).LCMS (Method-C3): 83.53% (RT 1.888, 232.0 nm) (MS: ESI+ve 495.3 [M+1]).

Step 3: Preparation of 6-amino-7-(naphthalen-1-ylmethyl)-5-oxo-8-(3-(trifluoromethyl)phenyl)-2,3-dihydro-5H-oxazolo[3,2-a]pyridine-3-carboxylic acid (Compound 069)

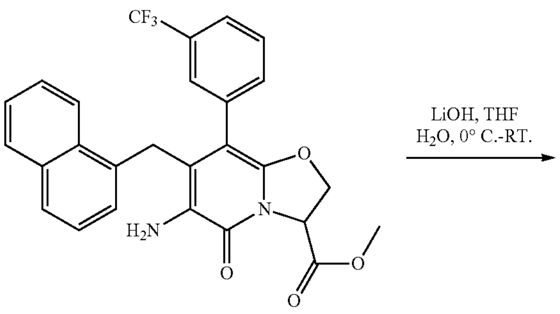

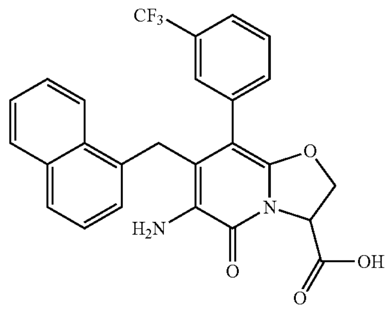

Compound 069

Methyl 6-amino-7-(naphthalen-1-ylmethyl)-5-oxo-8-(3-(trifluoromethyl) phenyl)-2,3-dihydro-5H-oxazolo[3,2-a] pyridine-3-carboxylate (0.270 g, 0.5460 mmol) was dissolved in tetrahydrofuran (5 mL). A solution of lithium hydroxide (0.091 g, 2.1841 mmol) in water (5 mL) was added and the mixture was stirred for 16 h. The reaction mixture was concentrated then ice and 0.1N aqueous HCl solution (10 mL) were added. The resulting solid was collected by filtration then washed with water, dissolved in dichloromethane, dried and concentrated. The crude product was purified using Prep HPLC Method 1 to give 6-amino-7-(naphthalen-1-ylmethyl)-5-oxo-8-(3-(trifluoromethyl) phenyl)-2,3-dihydro-5H-oxazolo[3,2-a]pyridine-3-carboxylic acid (Compound 069), (36.26 mg, 13.8%), as a brown solid. LCMS (Method-C3): 100% (RT 1.723, 225.0 nm) (MS: ESI+ve 481.5 [M+1]). $^1$H NMR: (400 MHz, DMSO) δ ppm: 4.14-4.08 (dd, J=24 Hz, 2H,), 4.68-4.65 (m, 1H), 4.84-4.79 (m, 1H), 5.28-5.25 (m, 1H), 7.04-7.02 (d, J=8 Hz, 1H), 7.218 (s, 1H), 7.50-7.37 (m, 6H), 7.77-7.75 (d, J=8 Hz, 1H), 7.90-7.88 (d, J=8.8 Hz, 2H).

For all methods, chromatographic retention times (RT) are reported in minutes, followed by a chromatographic system's UV detector wavelength setting, as monitored, in nanometers (nm). The term "ABPR" refers to the automated back pressure regulator feature of a chromatography apparatus.

Example 167

Synthesis of 2-methyl-8-(naphthalen-1-ylmethyl)-6-oxo-7-(propylcarbamoyl)-9-(3-(trifluoromethyl)phenyl)-3,4-dihydro-2H,6H-pyrido[1,2-e][1,2,5]thiadiazine-4-carboxylic acid 1,1-dioxide (Compound 154)

Compound 154

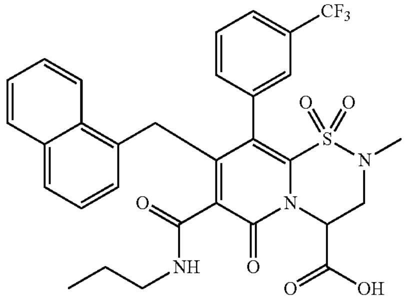

Step 1: Preparation of methyl 2-methyl-8-(naphthalen-1-ylmethyl)-6-oxo-7-(propylcarbamoyl)-9-(3-(trifluoromethyl)phenyl)-3,4-dihydro-2H,6H-pyrido[1,2-e][1,2,5]thiadiazine-4-carboxylate 1,1-dioxide

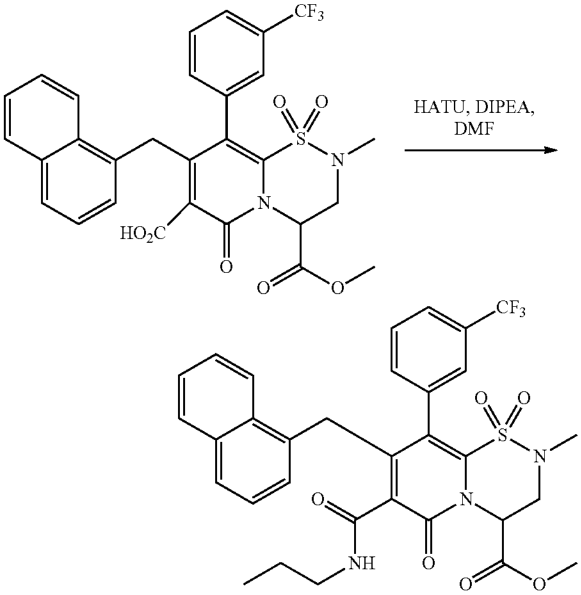

4-(methoxycarbonyl)-2-methyl-8-(naphthalen-1-ylmethyl)-6-oxo-9-(3-(trifluoromethyl) phenyl)-3,4-dihydro-2H,6H-pyrido[1,2-e][1,2,5]thiadiazine-7-carboxylic acid 1,1-dioxide (0.2 g, 0.33 mmol) was dissolved in DMF (5 mL) and cooled to 0° C. HATU (0.15 g, 0.39 mmol) was added followed by propylamine (0.039 g, 0.6 mmol) and DIPEA (0.2 mL, 0.99 mmol). The reaction mixture was stirred at room temperature for 3 hours. Water was added (20 mL) and the resulting precipitate collected by filtration and dried under vacuum to give methyl 2-methyl-8-(naphthalen-1-ylmethyl)-6-oxo-7-(propylcarbamoyl)-9-(3-(trifluoromethyl)phenyl)-3,4-dihydro-2H,6H-pyrido[1,2-e][1,2,5]thiadiazine-4-carboxylate 1,1-dioxide as an off white solid. (0.18 g, 84%).

Step 2: Preparation of 2-methyl-8-(naphthalen-1-ylmethyl)-6-oxo-7-(propylcarbamoyl)-9-(3-(trifluoromethyl)phenyl)-3,4-dihydro-2H,6H-pyrido[1,2-e][1,2,5]thiadiazine-4-carboxylic acid 1,1-dioxide (Compound 154)

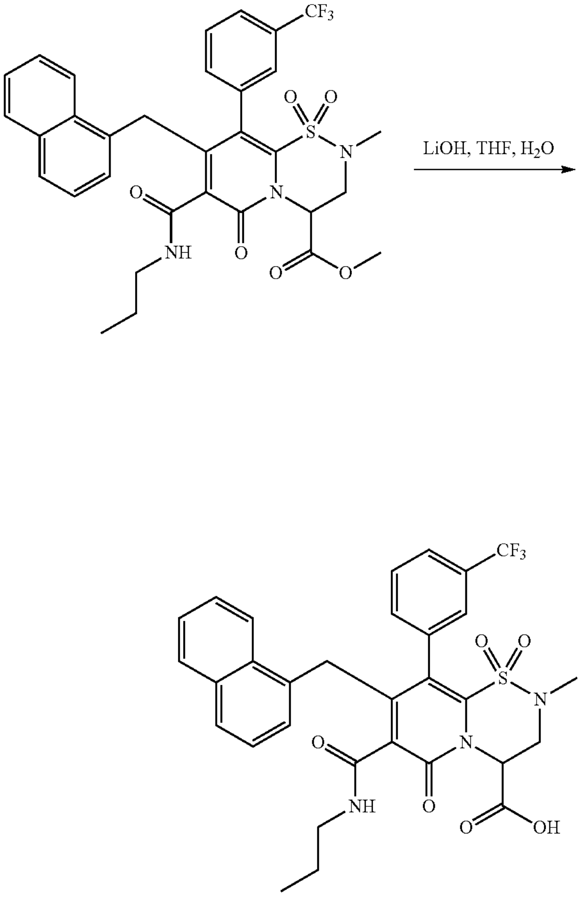

Compound 154

2-methyl-8-(naphthalen-1-ylmethyl)-6-oxo-7-(propylcarbamoyl)-9-(3-(trifluoromethyl) phenyl)-3,4-dihydro-2H,6H-pyrido[1,2-e][1,2,5]thiadiazine-4-carboxylate 1,1-dioxide (0.18 g, 0.28 mmol) was hydrolyzed using the standard method as in Example 114, Step 3. The crude product was purified using Prep HPLC Method 1 to give 2-methyl-8-(naphthalen-1-ylmethyl)-6-oxo-7-(propylcarbamoyl)-9-(3-(trifluoromethyl) phenyl)-3,4-dihydro-2H,6H-pyrido[1,2-e][1,2,5]thiadiazine-4-carboxylic acid 1,1-dioxide (Compound 154) (0.051 g, 28.49%). LCMS (Method-$C_3$): 96.36% (RT 2.126, 220.0 nm) (MS: ESI+ve 628 [M+H]). $^1H$ NMR: (400 MHz, MeOD) δ ppm: 0.75-0.80 (m, 3H), 1.40-1.48 (m, 2H), 2.95 (s, 4H), 3.22-3.27 (m, 2H), 4.17 (s, 2H), 4.26-4.36 (m, 2H), 5.38 (s, 1H), 7.09-7.20 (m, 2H), 7.21-7.28 (m, 3H), 7.28-7.32 (m, 1H), 7.36-7.39 (m, 2H), 7.41-7.47 (m, 1H), 7.50-7.63 (m, 1H), 7.70-7.78 (m, 2H), 8.609 (s, 1H).

Example 168

Synthesis of methyl 7-(ethylcarbamoyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (Compound 156)

Compound 156

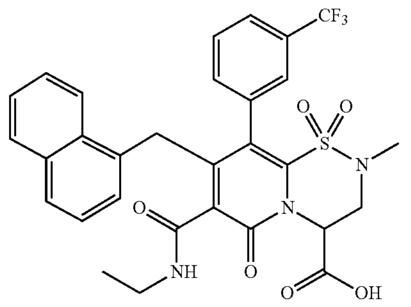

Prepared by a method similar to that reported for 2-methyl-8-(naphthalen-1-ylmethyl)-6-oxo-7-(propylcarbamoyl)-9-(3-(trifluoromethyl) phenyl)-3,4-dihydro-2H,6H-pyrido[1,2-e] [1,2,5] thiadiazine-4-carboxylic acid 1,1-dioxide (Compound 154). The crude product was purified using Prep HPLC Method 1 to give 7-(ethylcarbamoyl)-2-methyl-8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylic acid 1,1-dioxide as a white solid (Compound 156) (0.045 g, 20.01%). LCMS (Method-C3): 100% (RT 1.690, 202.0 nm) (MS: ESI+ve 614 [M+H]). $^1$H NMR: (400 MHz, MeOD) δ ppm: 1.00-1.03 (t, 3H), 2.93 (s, 3H), 3.22-3.32 (t, 2H), 4.21 (s, 2H), 4.28-4.36 (m, 2H), 5.41 (s, 1H), 7.06-7.16 (m, 5H), 7.29-7.30 (d, J=7.2 Hz, 1H), 7.37-7.38 (d, J=6 Hz, 3H), 7.49-7.51 (d, J=8 Hz, 1H), 7.69-7.71 (d, J=8 Hz, 1H), 7.75-7.77 (d, J=8 Hz, 1H), 8.59 (s, 1H)

Synthesis of 7-(isopropylcarbamoyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 157)

Compound 157

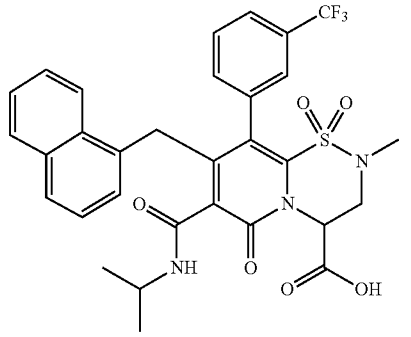

Prepared by a method similar to that reported for 2-methyl-8-(naphthalen-1-ylmethyl)-6-oxo-7-(propylcarbamoyl)-9-(3-(trifluoromethyl) phenyl)-3,4-dihydro-2H,6H-pyrido[1,2-e] [1,2,5] thiadiazine-4-carboxylic acid 1,1-dioxide (Compound 154). The crude product was purified using Prep HPLC Method 1 to give 7-(isopropylcarbamoyl)-2-methyl-8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylic acid 1,1-dioxide as a white solid (Compound 157) (0.060 g, 30.6%). LCMS (Method-C3): 98.8% (RT 1.779, 225.0 nm) (MS: ESI+ve 628 [M+H]). $^1$H NMR: (400 MHz, MeOD) δ ppm: 0.96-1.00 (m, 3H), 1.07-1.11 (m, 3H), 2.95 (s, 3H), 4.01 (s, 3H), 4.15 (s, 2H), 4.29-4.32 (d, J=14 Hz, 2H), 5.29 (s, 1H), 7.09-7.18 (m, 6H), 7.30 (s, 1H), 7.38 (s, 2H), 7.51 (s, 1H), 7.70-7.78 (m, 2H), 8.50 (s, 1H).

Example 169

Synthesis of 7-(isopropylcarbamoyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 158)

Compound 158

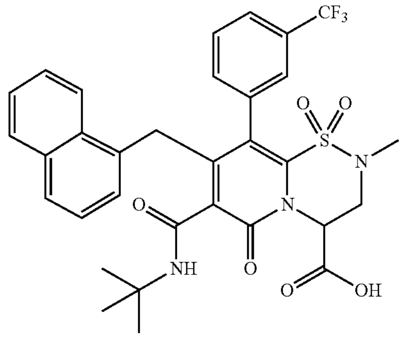

Prepared by a method similar to that reported for 2-methyl-8-(naphthalen-1-ylmethyl)-6-oxo-7-(propylcarbamoyl)-9-(3-(trifluoromethyl) phenyl)-3,4-dihydro-2H,6H-pyrido[1,2-e] [1,2,5] thiadiazine-4-carboxylic acid 1,1-dioxide (Compound 154). The crude product was purified using Prep HPLC Method 1 to give 7-(tert-butylcarbamoyl)-2-methyl-8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylic acid 1,1-dioxide as a white solid (Compound 158) (0.060 g, 26.2%). LCMS (Method-C3): 97.0% (RT 1.746, 225.0 nm) (MS: ESI+ve 642 [M+H]). $^1$H NMR: (400 MHz, MeOD) δ ppm: 1.22 (s, 9H), 2.93 (s, 3H), 4.16 (s, 2H), 4.25-4.36 (m, 2H), 5.38-5.41 (t, 1H), 7.04-7.15 (m, 5H), 7.29-7.33 (m, 1H), 7.38-7.41 (m, 2H), 7.53-7.55 (d, J=8.4 Hz, 1H), 7.71-7.73 (d, J=8 Hz, 1H), 7.77-7.79 (d, J=8 Hz, 1H), 8.06 (s, 1H)

Example 170

Synthesis of 7-(isobutylcarbamoyl)-2-methyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 159)

Compound 159

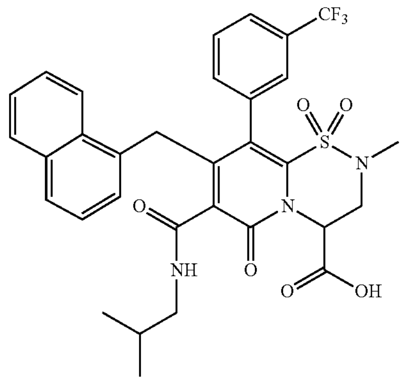

Prepared by a method similar to that reported for 2-methyl-8-(naphthalen-1-ylmethyl)-6-oxo-7-(propylcarbamoyl)-9-(3-(trifluoromethyl) phenyl)-3,4-dihydro-2H,6H-pyrido[1,2-e] [1,2,5] thiadiazine-4-carboxylic acid 1,1-dioxide (Compound 154). The crude product was purified using Prep HPLC Method 1 to give 7-(isobutylcarbamoyl)-2-methyl-8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylic acid 1,1-dioxide as a white solid (Compound 159) (0.045 g, 20.9%). LCMS (Method-C3): 100% (RT 1.838, 232.0 nm) (MS: ESI+ve 642 [M+H]). $^1$H NMR: (400 MHz, MeOD) δ ppm: 0.75-0.77 (d, J=6.4 Hz, 6H), 1.65-1.72 (m, 1H), 2.93 (s, 3H), 3.03-3.15 (m, 2H), 4.18 (s, 2H), 4.29-4.33 (m, 2H), 5.42 (s, 1H), 7.03-7.05 (d, J=8.4 Hz, 2H), 7.10-7.16 (t, 3H), 7.21-7.31 (t, 1H), 7.35-7.40 (m, 2H), 7.49-7.51 (d, J=8 Hz, 1H) 7.69-7.77 (m, 2H), 8.62 (s, 1H)

Example 171

Synthesis of 2-methyl-7-(morpholine-4-carbonyl)-8-(naphthalen-1-ylmethyl)-6-oxo-9-(3-(trifluoromethyl) phenyl)-3,4-dihydro-2H,6H-pyrido[1,2-e][1,2,5] thiadiazine-4-carboxylic acid 1,1-dioxide (Compound 160)

Compound 160

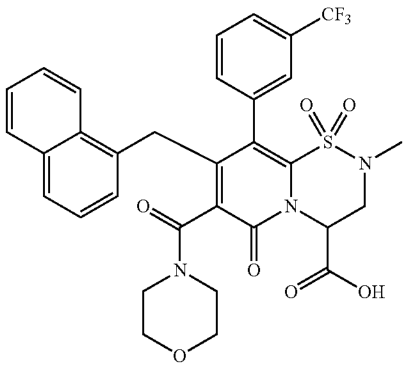

Prepared by a method similar to that reported for 2-methyl-8-(naphthalen-1-ylmethyl)-6-oxo-7-(propylcarbamoyl)-9-(3-(trifluoromethyl) phenyl)-3,4-dihydro-2H,6H-pyrido[1,2-e] [1,2,5] thiadiazine-4-carboxylic acid 1,1-dioxide (Compound 154). The crude product was purified using Prep HPLC Method 1 to give 2-methyl-7-(morpholine-4-carbonyl)-8-(naphthalen-1-ylmethyl)-6-oxo-9-(3-(trifluoromethyl) phenyl)-3,4-dihydro-2H,6H-pyrido[1,2-e] [1,2,5] thiadiazine-4-carboxylic acid 1,1-dioxide as a white solid (Compound 160) (0.031 g, 16%). LCMS (Method-C3): 100% (RT 1.749, 225.0 nm) (MS: ESI+ve 656 [M+H]). $^1$H NMR: (400 MHz, MeOD) δ ppm: 2.91 (s, 1H), 2.97 (s, 3H), 3.13-3.14 (m, 1H), 3.18 (s, 1H), 3.52-3.65 (m, 4H), 3.85-3.93 (t, 1H), 4.25-4.39 (m, 4H), 5.31-5.43 (m, 1H), 7.18 (s, 1H), 7.37-7.45 (m, 6H), 7.51-7.61 (m, 2H), 7.80-7.82 (d, J=4.8, 2H).

Example 172

Synthesis of 7-(dimethylcarbamoyl)-2-methyl-8-(naphthalen-1-ylmethyl)-6-oxo-9-(3-(trifluoromethyl) phenyl)-3,4-dihydro-2H,6H-pyrido[1,2-e] [1,2,5] thiadiazine-4-carboxylic acid 1,1-dioxide (Compound 173)

Compound 173

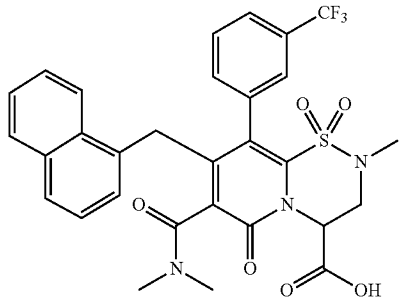

Prepared by a method similar to that reported for 2-methyl-8-(naphthalen-1-ylmethyl)-6-oxo-7-(propylcarbamoyl)-9-(3-(trifluoromethyl) phenyl)-3,4-dihydro-2H,6H-pyrido[1,2-e] [1,2,5] thiadiazine-4-carboxylic acid 1,1-dioxide (Compound 154). The crude product was purified using Prep HPLC Method 5 to give 7-(dimethylcarbamoyl)-2-methyl-8-(naphthalen-1-ylmethyl)-6-oxo-9-(3-(trifluoro methyl) phenyl)-3,4-dihydro-2H,6H-pyrido[1,2-e] [1,2,5] thiadiazine-4-carboxylic acid 1,1-dioxide as a white solid (Compound 173) (0.034 g, 13%). LCMS (Method-$C_3$): 100% (RT 1.705, 223.0 nm) (MS: ESI+ve 613 [M+H]). $^1$H NMR: (400 MHz, MeOD) δ ppm: 2.67-2.79 (m, 6H), 2.96 (s, 3H), 3.88 (s, 1H), 4.27-4.38 (m, H), 5.40 (s, 1H), 7.11-7.14 (m, 2H), 7.36-7.43 (m, 5H), 7.53-7.61 (m, 2H), 7.71-7.73 (d, J=8 Hz, 1H), 7.78-7.80 (d, J=7.6 Hz, 1H).

Example 173

Synthesis of 2-methyl-8-(naphthalen-1-ylmethyl)-6-oxo-7-(pyrrolidine-1-carbonyl)-9-(3-(trifluoromethyl) phenyl)-3,4-dihydro-2H,6H-pyrido[1,2-e] [1,2,5] thiadiazine-4-carboxylic acid 1,1-dioxide (Compound 186)

Compound 186

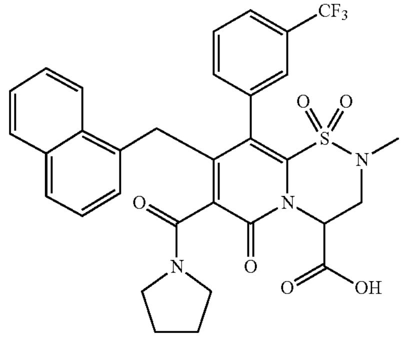

Prepared by a method similar to that reported for 2-methyl-8-(naphthalen-1-ylmethyl)-6-oxo-7-(propylcarbamoyl)-9-(3-(trifluoromethyl) phenyl)-3,4-dihydro-2H, 6H-pyrido[1,2-e] [1,2,5] thiadiazine-4-carboxylic acid 1,1-dioxide (Compound 154). The crude product was purified using Prep HPLC Method 1 to give 2-methyl-8-(naphthalen-1-ylmethyl)-6-oxo-7-(pyrrolidine-1-carbonyl)-9-(3-(trifluoromethyl) phenyl)-3,4-dihydro-2H,6H-pyrido[1,2-e] [1,2,5] thiadiazine-4-carboxylic acid 1,1-dioxide as a white solid (Compound 186) (0.02 g, 7.86%). LCMS (Method-H): 67.55%, 15.18 and 17.25% (RT 2.60, 2.70 and 2.74 225.0 nm) (MS: ESI+ve 613 [M+H]). $^1$H NMR: (400 MHz, MeOD) δ ppm: 1.32 (s, 2H), 1.77 (s, 2H), 2.85 (s, 2H), 2.93 (s, 3H), 3.81-3.88 (t, 1H), 4.25-4.29 (t, 1H), 4.34-4.39 (m, 2H), 5.25-5.26 (d, J=5.2, 1H), 7.15-7.21 (m, 1H), 7.28-7.44 (m, 6H) 7.61-7.65 (t, 3H), 7.78-7.80 (d, J=8, 1H).

Example 174

Synthesis of 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 176)

Compound 176

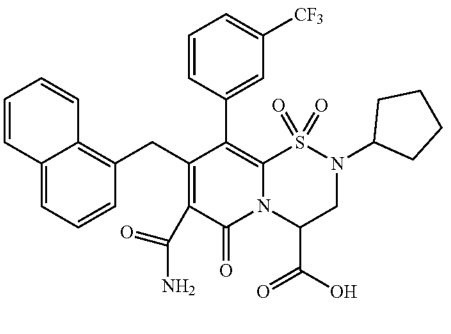

Step-1: Preparation of methyl 7-formyl-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

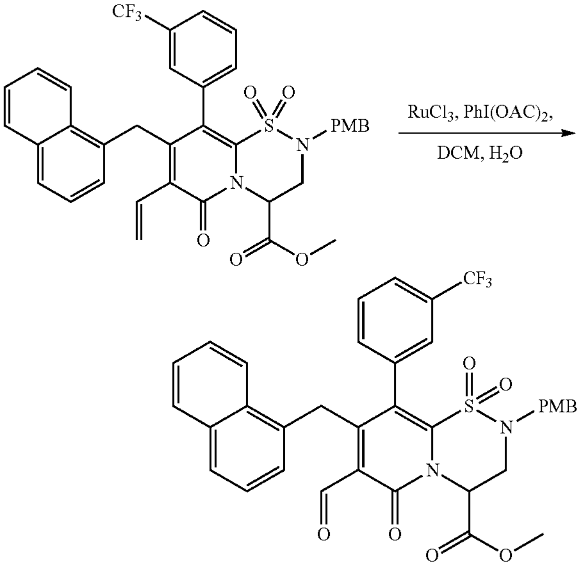

Methyl-2-(4-methoxybenzyl)-8-(naphthalen-1-ylmethyl)-6-oxo-9-(3-(trifluoromethyl) phenyl)-7-vinyl-3,4-dihydro-2H,6H-pyrido[1,2-e][1,2,5]thiadiazine-4-carboxylate 1,1-dioxide (2 g, 0.002 mmol) was dissolved in Dichloromethane (50 mL). Diacetoxyiodo benzene (2.8 g, 0.008 mmol) and ruthenium trichloride (0.060 g, 0.0002 mmol) were added followed by $H_2O$ (50 mL). The reaction mixture was stirred at room temperature for 16 hr then portioned between dichloromethane (2×40 mL) and water (2×40 mL). The combined organic layers were washed with brine dried and concentrated to give methyl-7-formyl-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide. The crude residue was purified using column chromatography eluting with 20-40% ethyl acetate/hexane gradient. (0.540 g, 27% yield).

Step-2: Preparation of 2-(4-methoxybenzyl)-4-(methoxycarbonyl)-8-(naphthalen-1-ylmethyl)-6-oxo-9-(3-(trifluoromethyl)phenyl)-3,4-dihydro-2H, 6H-pyrido[1,2-e][1,2,5]thiadiazine-7-carboxylic acid 1,1-dioxide

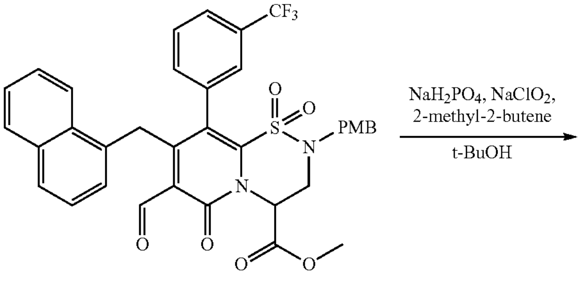

-continued

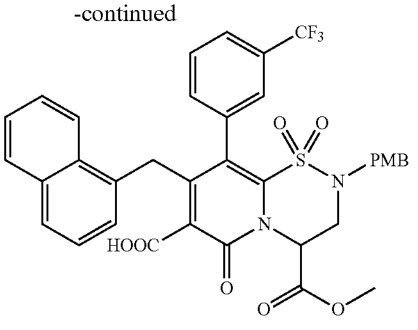

Methyl-7-formyl-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.540 g, 0.781 mmol) was dissolved in tert-butanol (7 mL) and water (7 mL). Sodium dihydrogen phosphate (0.140 g, 1.172 mmol) and sodium chlorite (0.176 g, 1.954 mmol). 2-methyl-2-butene (0.394 g, 5.629 mmol) were added dropwise at room temperature. The reaction mixture was concentrated with no heating then acidified with 1N HCl. The resulting precipitate was collected by filtration, dissolved in dichloromethane (20 mL) then concentrated to give 2-(4-methoxybenzyl)-4-(methoxycarbonyl)-8-(naphthalen-1-ylmethyl)-6-oxo-9-(3-(trifluoromethyl)phenyl)-3,4-dihydro-2H,6H-pyrido[1,2-e][1,2,5]thiadiazine-7-carboxylic acid 1,1-dioxide (0.550 g, 99.8% crude). LCMS (Method-C3): 89.3%, (RT: 1.945, 282 nm) (MS: ESI+ve 707.4 [M+1]).

Step-3: Preparation of methyl 7-carbamoyl-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

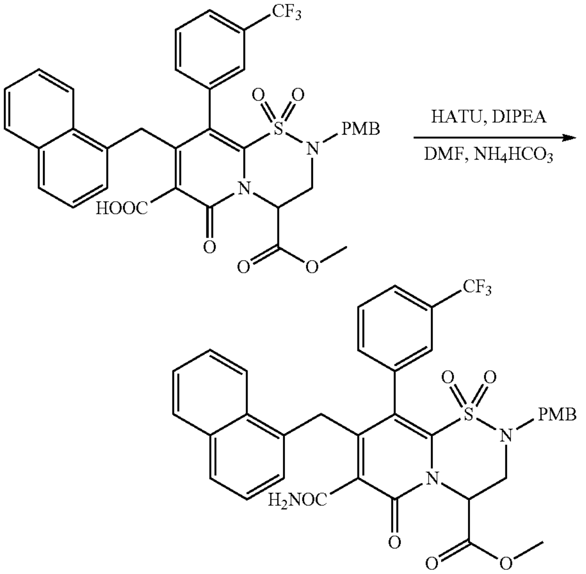

2-(4-methoxybenzyl)-4-(methoxycarbonyl)-8-(naphthalen-1-ylmethyl)-6-oxo-9-(3-(trifluoromethyl)phenyl)-3,4-dihydro-2H,6H-pyrido[1,2-e][1,2,5]thiadiazine-7-carboxylic acid 1,1-dioxide (1.9 g, 0.002 mmol) was dissolved in N,N-Dimethylformamide (25 mL) and cooled to 0° C. HATU (1.5 g, 0.004 mmol) was added followed by Ammonium bicarbonate (0.425 g, 0.005 mmol) and the reaction mixture was stirred for 15 mins. DIPEA (1.4 mL) was added and the mixture warmed to room temperature for 16 hr. The reaction was quenched into ice-cold water and the resulting precipitate was collected by filtration then dissolved in dichloromethane (25 mL). After concentration, isolated methyl 7-carbamoyl-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide. (1.7 g, 89.4% crude). LCMS (Method-C3): 88.3%, (RT: 1.870, 222 nm) (MS: ESI+ve 706.5 [M+1]).

Step-5: Preparation of methyl 7-carbamoyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 11-dioxide

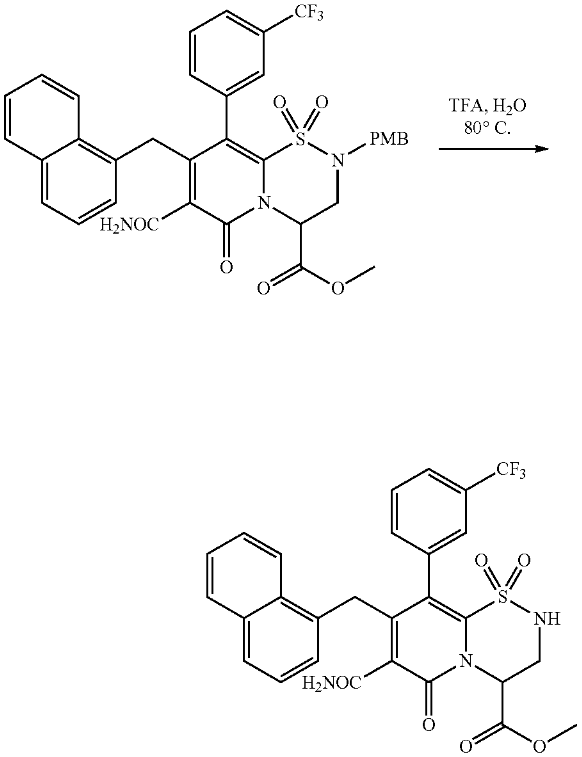

A mixture of methyl-7-carbamoyl-2-(4-methoxybenzyl)-8-(naphthalen-1-ylmethyl)-6-oxo-9-(3-(trifluoro methyl) phenyl)-3,4-dihydro-2H,6H-pyrido[1,2-e][1,2,5]thiadiazine-4-carboxylate 1,1-dioxide (1 g, 0.001 mmol), TFA (6 mL) and water (0.2 mL) was heated at 80° C. for 1 hr. The mixture was concentrated, and ice-cold water was added. The resulting precipitate was collected, rinsed with sodium bicarbonate (10% aqueous) and dissolved in dichloromethane (25 mL). Concentrated under reduced pressure to give methyl 7-carbamoyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (1.1 g, crude). LCMS (Method-C3): 98.5%, (RT: 1.630, 222 nm) (MS: ESI+ve 586.3 [M+1]).

Step-6: Preparation of methyl 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide

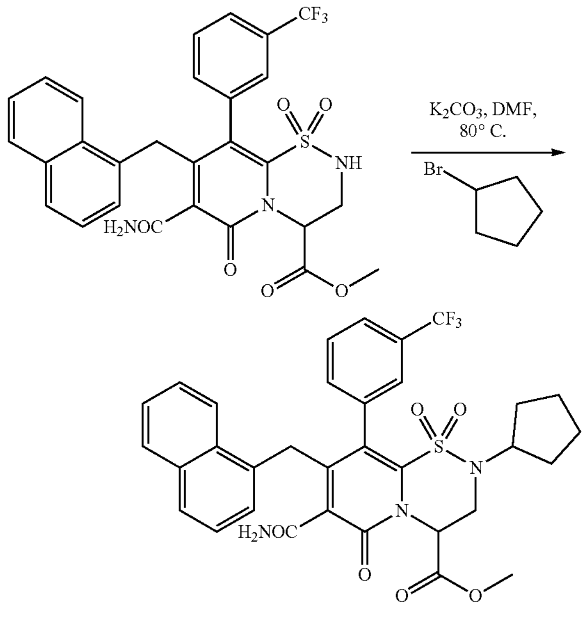

A mixture of methyl 7-carbamoyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylate 1,1-dioxide (0.300 g, 0.512 mmol), N,N-Dimethylformamide (5 mL), potassium carbonate (0.106 g, 0.768 mmol) and bromocyclopentane (0.114 g, 0.768 mmol) was heated at 80° C. for 3 hr. The reaction mixture was partitioned between ethyl acetate (2×20 mL) and water (2×20 mL). The organic layer was concentrated to give methyl 7-carbamoyl-2-cyclopentyl-8-(naphthalen-1-ylmethyl)-6-oxo-9-(3-(trifluoromethyl) phenyl)-3,4-dihydro-2H,6H-pyrido[1,2-e] [1,2,5]thiadiazine-4-carboxylate 1,1-dioxide. (0.269 g, 80.5%). LCMS (Method-C3): 71.1%, (RT: 1.886, 227 nm) (MS: ESI+ve 654.4 [M+1]).

Step-7: Preparation of 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 176)

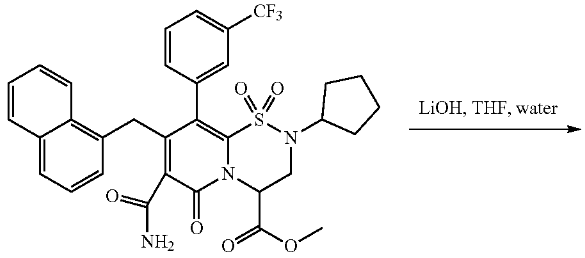

-continued

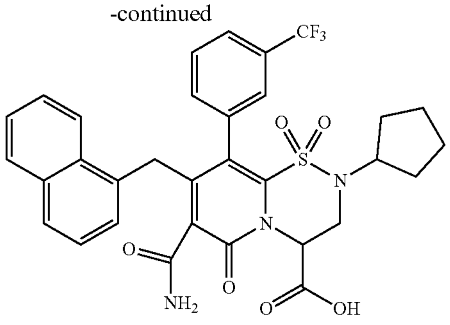

Compound 176

Methyl 7-carbamoyl-2-cyclopentyl-8-(naphthalen-1-ylmethyl)-6-oxo-9-(3-(trifluoro methyl)phenyl)-3,4-dihydro-2H,6H-pyrido[1,2-e][1,2,5]thiadiazine-4-carboxylate 1,1-dioxide (0.269 g, 0.411 mmol) was hydrolyzed using the standard method as in Example 114 Step 3. The crude product was purified Prep HPLC Method 5 to give 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 176) (0.036 g, 13.8%), as a white solid. LCMS (Method-C3): 97.6% (RT: 1.681, 225 nm) (MS: ESI+ve 614.4 [M+1]). $^{1}$H NMR: (400 MHz, DMSO) δ ppm: 1.561-1.662 (m, 4H), 1.732 (m, 3H), 1.859 (s, 1H), 4.076-4.123 (m, 2H), 4.173-4.178 (m, 1H), 4.210-4.236 (m, 2H), 5.658-5.677 (m, 1H), 6.970-7.008 (m, 1H), 7.046-7.200 (m, 4H), 7.271-7.308 (m, 1H), 7.354-7.410 (m, 2H), 7.494-7.515 (d, 8.4 Hz, 1H), 7.702-7.723 (d, 8.4 Hz, 1H), 7.763-7.783 (d, 8.0 Hz, 1H).

Example 175

Synthesis of 7-carbamoyl-2-isopropyl-8-(naphthalen-1-ylmethyl)-6-oxo-9-(3-(trifluoro methyl)phenyl)-3,4-dihydro-2H,6H-pyrido[1,2-e][1,2,5]thiadiazine-4-carboxylic acid 1,1-dioxide (Compound 175)

Compound 175

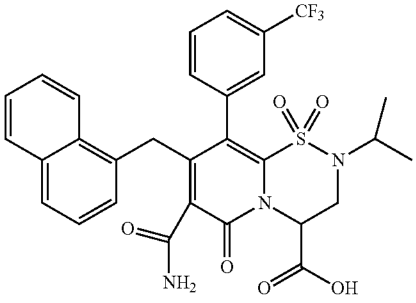

Prepared by a method similar to that reported for 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 176). The crude product was purified using Prep HPLC Method 5 to give methyl 7-carbamoyl-2-isopropyl-8-(naphthalen-1-ylmethyl)-6-oxo-9-(3-(trifluoromethyl) phenyl)-3,4-dihydro-2H,6H-pyrido[1,2-e][1,2,5]thiadiazine-4-carboxylate 1,1-dioxide (Compound 175) (0.044 g, 17.2%), as a white solid. LCMS (Method-C3): 97.6% (RT: 1.681, 225 nm) (MS: ESI+ve 614.4 [M+1]). $^1$H NMR: (400 MHz, DMSO) δ ppm: 1.134-1.196 (m, 6H), 4.061-4.130 (m, 2H), 4.191-4.235 (m, 3H), 5.652-5.665 (s, 1H), 6.986 (s, 1H), 7.005-7.205 (m, 4H), 7.253-7.306 (m, 1H), 7.353-7.409 (m, 2H), 7.491-7.509 (d, J=7.2 Hz, 1H), 7.701-7.722 (d, J=8.4 Hz, 1H), 7.762-7.782 (d, J=8.0 Hz, 1H).

Example 176

Synthesis of 7-carbamoyl-8-(naphthalen-1-ylmethyl)-6-oxo-2-propyl-9-(3-(trifluoro methyl)phenyl)-3,4-dihydro-2H,6H-pyrido[1,2-e][1,2,5]thiadiazine-4-carboxylic acid 1,1-dioxide (Compound 172)

Compound 172

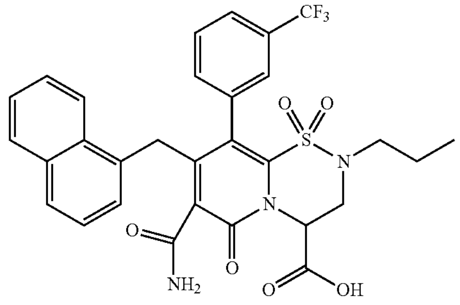

Prepared by a method similar to that reported for 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 176). The crude product was purified using Prep HPLC Method 5 to give 7-carbamoyl-8-(naphthalen-1-ylmethyl)-6-oxo-2-propyl-9-(3-(trifluoromethyl)phenyl)-3,4-dihydro-2H,6H-pyrido[1,2-e][1,2,5]thiadiazine-4-carboxylic acid 1,1-dioxide (Compound 172) (0.012 g, 4%), as a white solid. LCMS (Method-J): 98.8% (RT: 4.747, 202 nm) (MS: ESI+ve 614.2 [M+1]). $^1$H NMR: (400 MHz, DMSO) δ ppm: 0.865-0.901 (m, 3H), 1.554-1.608 (m, 2H), 3.193 (s, 2H), 4.231-4.330 (m, 4H), 5.438-5.449 (d, J=4.4 Hz, 1H), 6.982-7.018 (m, 1H), 7.064-7.181 (m, 4H), 7.259-7.297 (m, 1H), 7.366-7.397 (m, 2H), 7.486-7.506 (d, J=8 Hz, 1H), 7.689-7.771 (dd, J=24.4 Hz, 2H).

Example 177

Synthesis of 7-carbamoyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 184)

Compound 184

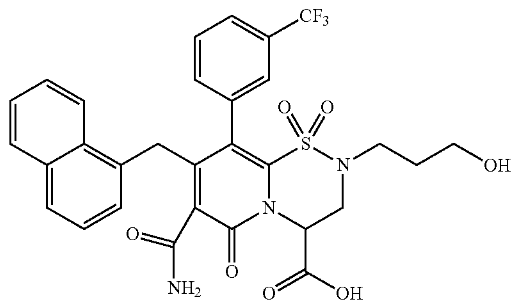

Prepared by a method similar to that reported for 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 176). The crude product was purified using Prep HPLC Method 5 to give 7-carbamoyl-2-(3-hydroxypropyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 184) (0.020 g, 8.2%), as a white solid. LCMS (Method-C3): 100% (RT: 1.558, 225 nm) (MS: ESI+ve 630.9 [M+1]). $^1$H NMR: (400 MHz, DMSO) δ ppm: 1.735-1.766 (t, J=12.4 Hz, 2H), 3.361-3.367 (s, 2H), 3.354-3.573 (t, J=87.6 Hz, 2H), 4.228 (s, 2H), 4.316-4.328 (t, J=4.8 Hz, 2H), 5.453-5.463 (d, J=4 Hz, 1H), 6.979-7.018 (m, 1H), 7.066-7.129 (m, 3H), 7.168-7.184 (m, 1H), 7.259-7.296 (m, 1H), 7.351-7.380 (dd, J=11.6 Hz, 2H), 7.487-7.506 (d, J=7.6 Hz, 1H), 7.689-7.750 (dd, J=24.4 Hz, 2H).

Example 178

Synthesis of 2-butyl-7-carbamoyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 177)

Compound 177

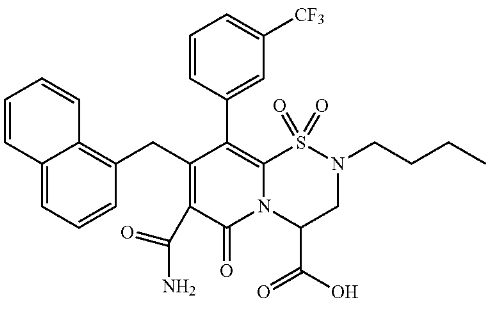

Prepared by a method similar to that reported for 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 176). The crude product was purified using Prep HPLC Method 5 to give 2-butyl-7-carbamoyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 177) (0.075 g, 29.4%), as a white solid. LCMS (Method-C3): 100% (RT: 1.737, 202 nm) (MS: ESI+ve 628.4 [M+1]). $^1$H NMR: (400 MHz, MeOH) δ ppm: 0.899-0.936 (m, 3H), 1.297-1.367 (m, 2H), 1.517-1.567 (m, 2H), 3.180-3.263 (m, 2H), 4.240-4.289 (m, 4H), 5.496-5.518 (m, 1H), 6.983-7.010 (m, 1H), 7.061-7.200 (m, 4H), 7.271-7.308 (m, 1H), 7.357-7.409 (m, 2H), 7.495-7.517 (d, J=8.8 Hz, 1H), 7.702-7.782 (dd, 32 Hz, 2H)

Example 179

Synthesis of 7-carbamoyl-2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 183)

Compound 183

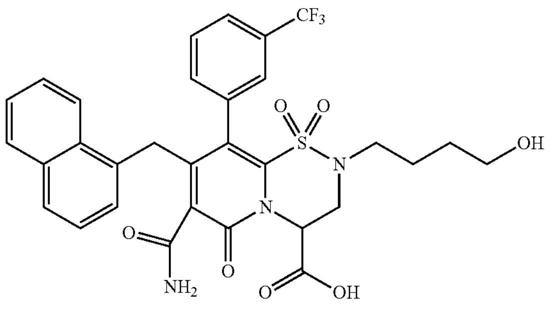

Prepared by a method similar to that reported for 7-carbamoyl-2-cyclopentyl-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 176). The crude product was purified using Prep HPLC Method 5 to give 7-carbamoyl-2-(4-hydroxybutyl)-8-(naphthalen-1-ylmethyl)-6-oxo-9-(3-(trifluoromethyl)phenyl)-3,4-dihydro-2H,6H-pyrido[1,2-e][1,2,5]thiadiazine-4-carboxylic acid 1,1-dioxide (Compound 183) (0.084 g, 33.5%), as a white solid. LCMS (Method-C3): 95.3% (RT: 1.567, 225 nm) (MS: ESI+ve 644.5 [M+1]). $^1$H NMR: (400 MHz, MeOH) δ ppm: 1.508-1.524 (m, 2H), 1.613-1.631 (m, 2H), 3.516-3.546 (t, J=12 Hz, 2H), 4.110-4.180 (m, 2H), 4.283 (s, 2H), 5.245 (s, 1H), 7.019-7.161 (m, 4H), 7.205-7.294 (m, 2H), 7.355-7.391 (t, J=14.4 Hz, 2H), 7.478-7.513 (m, 1H), 7.682-7.702 (d, aJ=8 hz, 1H), 7.747-7.767 (d, J=8 Hz, 1H), 8.163 (s, 1H).

Example 180

Synthesis of 6-ethyl-1-(4-methoxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 161)

Compound 161

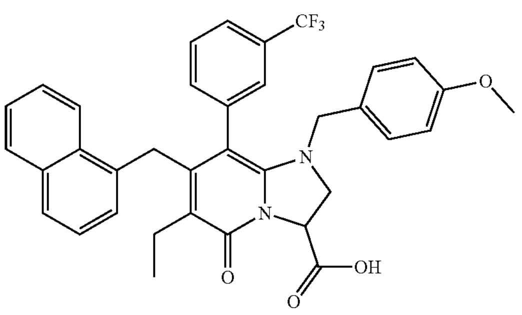

Prepared by a method similar to that reported for 1-benzyl-6-ethyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 140). The crude product was purified using Prep HPLC Method 6 to give 6-ethyl-1-(4-methoxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 161), as a white solid (0.021 g, 11.32%). LCMS (Method-C3): 100.00% (RT 2.031, 223.0 nm) (MS: ESI+ve 614.0 [M+H]). $^1$H NMR: (400 MHz, DMSO) δ ppm: 0.84-0.96 (t, 3H), 2.26-2.40 (m, 2H), 3.54-3.58 (m, 1H), 3.69 (s, 3H), 3.77-3.92 (q, 2H), 4.00-4.03 (m, 1H), 4.21-4.34 (m, 3H), 6.74-6.83 (m, 4H), 7.00-7.13 (m, 2H), 7.28-7.44 (m, 6H), 7.71-7.80 (m, 2H), 7.85-7.87 (d, J=8.0 Hz, 1H).

Example 181

SFC separation of 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 003) to give (S)-1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 189) and (R)-1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 190)

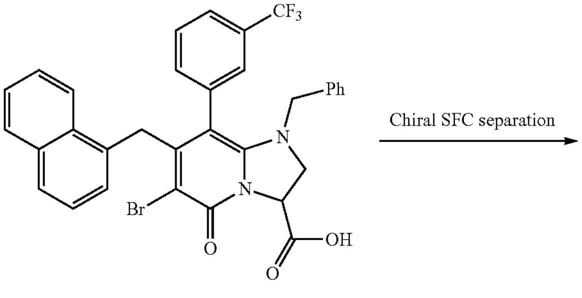

Compound 003

-continued

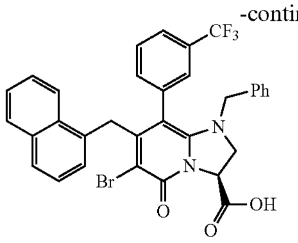

Compound 189

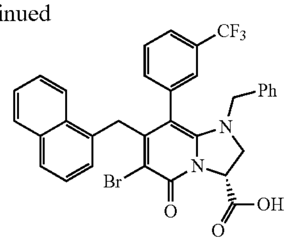

Compound 190

Methyl 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylate (0.3 g, 0.46 mmol)(Compound 003) (Chiral HPLC: 88.81% (Fraction 1, RT: 4.71), 11.19%, (Fraction 2, RT: 13.69) was separated using a Shimadzu LC-20AP chromatography system and UV detector. The column used was CHIRALCEL OX-H (250*21.0) mm, 5 micron, column flow was 20.0 ml/min. Mobile phases (A) 0.1% DEA in hexane (B) 0.1% DEA in propan-1-ol: methanol (50:50) to give;

Fraction 1; (S)-1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 189) (0.034 g,). After SFC purification, the DEA was removed by reverse phase combi-flash chromatography (0.1% formic acid in water and acetonitrile) LCMS (Method-C3): 100.0% (RT 1.999, 220.0 nm) (MS: ESI+ve 635.38 [M+2]). $^1$H NMR: (400 MHz, DMSO) δ ppm: 3.50 (s, 1H), 3.59-3.83 (m, 2H), 3.96-4.18 (m, 3H), 5.16-5.18 (d, J=8.0 Hz, 1H), 6.85 (s, 2H), 6.93-6.98 (d, J=20.0 Hz, 1H), 7.04-7.07 (t, J=12.0 Hz, 1H), 7.11-7.20 (m, 4H), 7.25-7.32 (m, 2H), 7.35-7.43 (m, 3H), 7.67-7.85 (d, J=7.2 Hz, 1H), 7.74-7.76 (d, J=8.0 Hz, 1H), 7.84-7.86 (d, J=8.0 Hz, 1H), 13.52 (s, 1H).

Fraction 2; (R)-1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 190) (0.002 g). After SFC purification, the DEA was removed by reverse phase combi-flash chromatography (0.1% formic acid in water and acetonitrile) LCMS (Method-C3): 100.0% (RT 2.006, 220.0 nm) (MS: ESI+ve 636.6 [M+2]).

Example 182

Synthesis of 6-chloro-7-(naphthalen-1-ylmethyl)-5-oxo-1-propyl-8-(3-(trifluoromethyl)phenyl)-1,2,3,5-tetrahydroimidazo[1,2-a]pyridine-3-carboxylic acid (Compound 162)

Compound 162

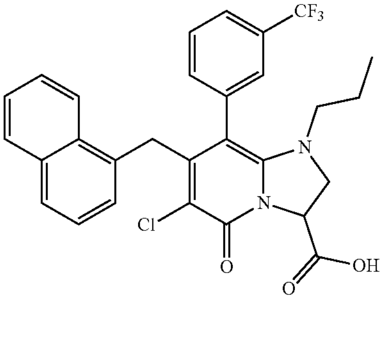

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 1 to give 6-chloro-7-(naphthalen-1-ylmethyl)-5-oxo-1-propyl-8-(3-(trifluoromethyl)phenyl)-1,2,3,5-tetrahydroimidazo[1,2-a]pyridine-3-carboxylic acid (Compound 162) as an off-white solid (0.035 g, 12.82%). LCMS (Method-C3): 100% (RT 1.961, 202 nm) (MS: ESI+ve 541.32 [M+1]). $^1$H NMR: (400 MHz, DMSO) δ ppm: 0.25-0.31 (m, 3H), 1.06-1.23 (m, 2H), 2.27-2.33 (t, J=4.8 Hz, 2H), 3.62-3.68 (t, J=4.8 Hz, 1H), 3.96-4.19 (m, 3H), 5.04-5.07 (d, J=12 Hz, 1H), 7.04-7.06 (d, J=6 Hz, 1H), 7.18 (s, 1H), 7.33-7.48 (m, 6H), 7.71-7.76 (m, 2H), 7.86-7.88 (d, J=8 Hz, 1H).

Example 183

Synthesis of 1-butyl-6-chloro-7-(naphthalen-1-ylmethyl)-5-oxo-8-(3-(trifluoromethyl) phenyl)-1,2,3,5-tetrahydroimidazo[1,2-a]pyridine-3-carboxylic acid (Compound 163)

Compound 163

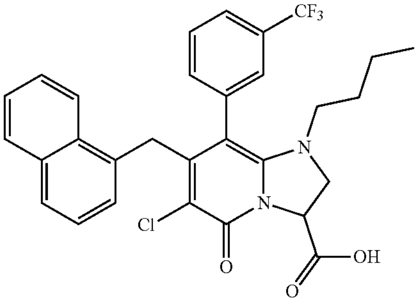

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 1 to give 1-butyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 163) (0.012 g, 12.30%). LCMS (Method-C3): 100% (RT 2.046, 225.0 nm) (MS: ESI+ve 554.8 [M+]). $^1$H NMR: (400 MHz, DMSO) δ ppm: 0.53-0.57 (t, 3H), 0.62-0.69 (q, 2H), 1.05-1.23 (m, 2H), 2.28-2.44 (m, 2H), 3.62-3.70 (m, 1H), 3.97-4.19 (m, 3H), 5.08-5.11 (m, 1H), 7.03-7.06 (t, 1H), 7.19 (s, 1H), 7.29-7.48 (m, 6H), 7.71-7.77 (m, 2H), 7.86-7.88 (d, J=8.0 Hz, 1H), 13.50 (s, 1H).

Example 184

Synthesis of 6-chloro-1-isobutyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 164)

Compound 164

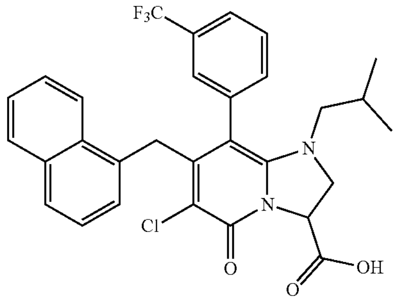

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 1 to give 6-chloro-1-isobutyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 164) (0.030 g, 20.51%). LCMS (Method-C3): 100% (RT 2.104, 225.0 nm) (MS: ESI+ve 554.82 [M+]). $^{1}$H NMR: (400 MHz, DMSO) δ ppm: 0.37-0.47 (m, 6H), 1.23-1.42 (m, 1H), 2.18-2.33 (m, 2H), 1.60 (s, 1H), 3.80-4.16 (m, 3H), 4.84 (s, 1H), 7.05 (s, 1H), 7.16-7.18 (d, J=8.8 Hz, 1H), 7.33-7.45 (m, 6H), 7.73-7.75 (m, 2H), 7.85-7.87 (d, J=7.6 Hz, 1H).

Example 185

Synthesis of 6-chloro-1-(2-cyanobenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 165)

Compound 165

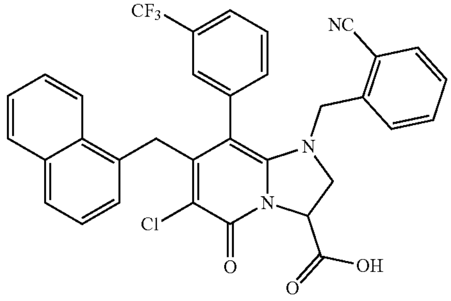

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 6 to give 6-chloro-1-(2-cyanobenzyl)-7-(naphthalen-1-ylmethyl)-5-oxo-8-(3-(trifluoromethyl) phenyl)-1,2,3,5-tetrahydroimidazo[1,2-a]pyridine-3-carboxylic acid (Compound 165) (0.045 g, 8.95%). LCMS (Method-J): 100% (RT 5.30, 202 nm) (MS: ESI+ve 614.2 [M+1]). $^{1}$H NMR: (400 MHz, DMSO) δ ppm: 3.78-3.83 (s, 2H J=5.6 Hz), 3.87-4.04 (s, 2H), 4.18-4.23 (s, 2H), 5.15 (bs, 1H), 6.72 (s, 1H), 6.99-7.04 (m, 3H), 7.08-7.17 (m, 1H), 7.33-7.42 (m, 4H), 7.63-7.67 (t, 2H), 7.71-7.73 (s 1H), 7.82-7.84 (d, 1H).

Example 186

Synthesis of 6-chloro-7-(naphthalen-1-ylmethyl)-5-oxo-1-(pyridin-2-ylmethyl)-8-(3-(trifluoromethyl)phenyl)-1,2,3,5-tetrahydroimidazo[1,2-a]pyridine-3-carboxylic acid (Compound 166)

Compound 166

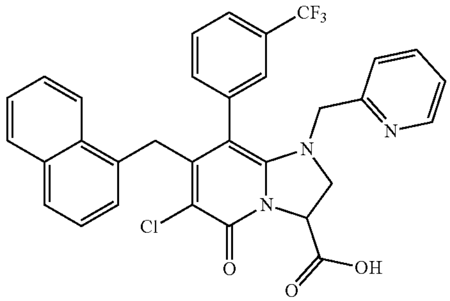

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 1 to give 6-chloro-7-(naphthalen-1-ylmethyl)-5-oxo-1-(pyridin-2-ylmethyl)-8-(3-(trifluoromethyl)phenyl)-1,2,3,5-tetrahydroimidazo[1,2-a]pyridine-3-carboxylic acid (Compound 166) as a white solid (0.40 g, 11.70%). LCMS (Method-C3): 96.43.0% (RT 1.755, 225.0 nm) (MS: ESI+ve 590.8 [M+2]). $^{1}$H NMR: (400 MHz, DMSO) δ ppm: 3.97-4.17 (m, 6H), 5.19 (s, 1H), 6.56 (s, 1H), 6.86-7.03 (m, 3H), 7.19 (s, 1H), 7.25-7.30 (3, 2H), 7.37-7.44 (3, 3H), 7.60-7.70 (m, 2H), 7.73-7.75 (d, J=8.0 Hz, 1H), 7.84-7.86 (s, J=8.0 Hz, 1H), 8.35-8.38 (d, J=12 Hz, 1H).

Example 187

Synthesis of 6-chloro-1-(cyclopentylmethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 167)

Compound 167

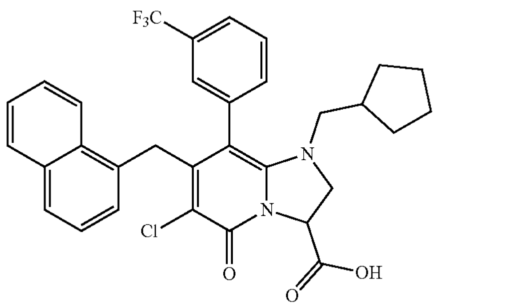

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. (FN-Target-335). The crude product was purified using Prep HPLC Method 6 to give 6-chloro-1-(cyclopentylmethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 167) (0.030 g, 15.36%). LCMS (Method-C3): 100% (RT 2.195, 225.0 nm) (MS: ESI+ve 581.90 [M+2]). $^1$H NMR: (400 MHz, DMSO) δ ppm: 0.61-0.69 (m, 2H), 1.22-1.35 (m, 6H), 1.71-1.73 (d, J=6.8 Hz, 1H), 2.27-2.43 (m, 2H), 3.63-3.71 (m, 1H), 3.96-4.18 (m, 3H0, 5.07-5.12 (m, 1H), 7.02-7.05 (t, 1H), 7.17-7.27 (m, 1H), 7.37-7.49 (m, 6H), 7.70-7.75 (t, 2H), 7.85-7.87 (d, J=8.0 Hz, 1H), 13.53 (s, 1H).

Example 188

Synthesis of 6-chloro-1-(3-cyanobenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 168)

Compound 168

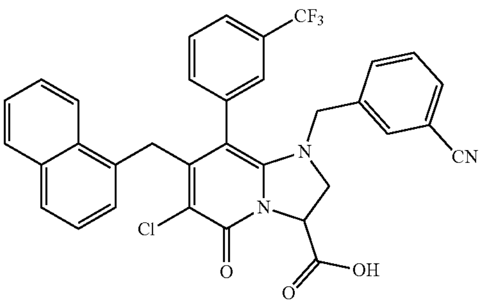

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 1 to give 6-chloro-1-(3-cyanobenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 168) as an off-white solid (0.035 g, 14.92%). LCMS (Method-C3): 100% (RT 1.904, 220.0 nm) (MS: ESI+ve 614.9 [M+H]). $^1$H NMR: (400 MHz, DMSO) δ ppm: 3.62 (m, 1H), 4.08 (m, 5H), 4.98 (s, 1H), 6.79-6.83 (d, J=15.6 Hz, 1H), 7.02-7.04 (t, 1H), 7.13-7.24 (m, 4H), 7.33-7.43 (m, 5H), 7.60-7.75 (m, 3H), 7.83-7.85 (d, J=8 Hz, 1H).

Example 189

Synthesis of 6-chloro-7-(naphthalen-1-ylmethyl)-5-oxo-1-(pyridin-3-ylmethyl)-8-(3-(trifluoromethyl)phenyl)-1,2,3,5-tetrahydroimidazo[1,2-a]pyridine-3-carboxylic acid (Compound 169)

Compound 169

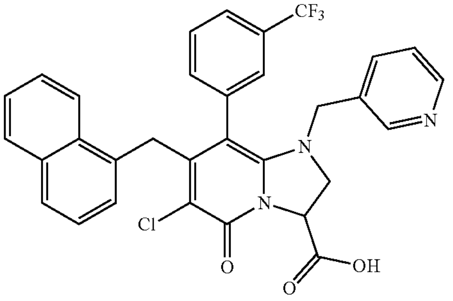

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 6 to give 6-chloro-7-(naphthalen-1-ylmethyl)-5-oxo-1-(pyridin-3-ylmethyl)-8-(3-(trifluoromethyl)phenyl)-1,2,3,5-tetrahydroimidazo[1,2-a]pyridine-3-carboxylic acid (Compound 169) as an off-white solid (0.036 g, 24.57%). LCMS (Method-C3): 100% (RT 1.580, 202 nm) (MS: ESI+ve 590.4 [M]). $^1$H NMR: (400 MHz, DMSO) δ ppm: 3.66-3.72 (m, 1H), 3.80-4.06 (m, 3H), 4.13-4.32 (m, 2H), 5.16-5.18 (d, J=5.2 Hz, 1H), 6.96-6.98 (d, J=6.8 Hz, 2H), 7.04-7.46 (m, 8H), 7.68-8.04 (m, 4H), 8.15 (s, 1H), 8.37 (s, 1H).

Example 190

Synthesis of 6-chloro-1-(4-(hydroxymethyl)benzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 170)

Compound 170

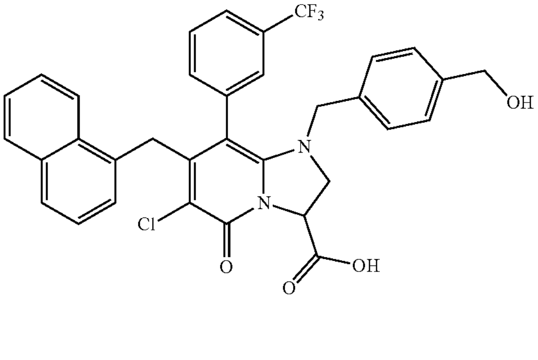

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 1 to give 6-chloro-1-(4-(hydroxymethyl)benzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 170) as an off-white solid (0.015 g, 6.09%). LCMS (Method-C3): 100% (RT 1.802, 225.0 nm) (MS: ESI+ve 619.90 [M+H]). $^1$H NMR: (400 MHz, DMSO) δ ppm: 3.51 (m, 1H), 3.65-3.76 (m, 2H), 3.93-4.17 (m, 3H), 4.41 (s, 2H), 5.12 (s, 2H), 6.82-6.85 (t, 2H), 7.03-7.08 (m, 2H), 7.14-7.16 (d, J=8 Hz, 2H), 7.18-7.46 (m, 6H), 7.69-7.76 (m, 2H), 7.84-7.86 (d, J=8.4 Hz, 1H), 13.71 (s, 1H).

Example 191

Synthesis of 6-chloro-1-(4-cyanobenzyl)-7-(naphthalen-1-ylmethyl)-5-oxo-8-43 (trifluoromethyl) phenyl)-1,2,3,5-tetrahydroimidazo[1,2-a]pyridine-3-carboxylic acid (Compound 171)

Compound 171

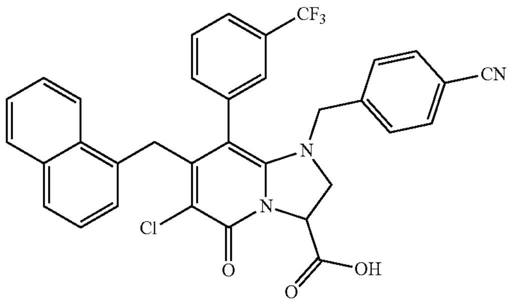

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 6 to give 6-chloro-1-(4-cyanobenzyl)-7-(naphthalen-1-ylmethyl)-5-oxo-8-(3-(trifluoromethyl) phenyl)-1,2,3,5-tetrahydroimidazo[1,2-a]pyridine-3-carboxylic acid (Compound 171) (0.016 g, 8.18%). LCMS (Method-C3): 98.86% (RT 1.94, 224 nm) (MS: ESI+ve 615.4 [M+1]). $^1$H NMR: (400 MHz, DMSO) δ ppm: 3.56-3.59 (d, 2H J=11.2 Hz), 3.80-4.10 (m, 4H), 4.71-4.81 (s, 1H), 6.72-6.82 (s, 1H), 7.04-7.25 (m, 4H), 7.34-7.44 (m, 5H), 7.70-7.74 (m, 2H), 7.83-7.85 (m, 2H J=8 Hz).

Example 192

Synthesis of 6-chloro-7-(naphthalen-1-ylmethyl)-5-oxo-1-(pyridin-4-ylmethyl)-8-(3-(trifluoromethyl) phenyl)-1,2,3,5-tetrahydroimidazo[1,2-a]pyridine-3-carboxylic acid (Compound 174)

Compound 174

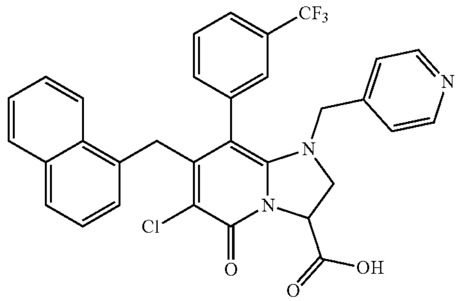

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 6 to give 6-chloro-7-(naphthalen-1-ylmethyl)-5-oxo-1-(pyridin-4-ylmethyl)-8-(3-(trifluoromethyl)phenyl)-1,2,3,5-tetrahydroimidazo[1,2-a]pyridine-3-carboxylate (Compound 174) as an off-white solid (0.036 g, 24.57%). LCMS (Method-C3): 100% (RT 1.555, 202 nm) (MS: ESI+ve 590.32 [M]). $^1$H NMR: (400 MHz, DMSO) δ ppm: 3.72-4.04 (m, 4H), 4.10-4.18 (m, 2H), 5.18-5.20 (d, J=10.4 Hz, 1H), 6.85-6.89 (t, J=2 Hz, 3H), 7.01-7.43 (m, 7H), 7.66-7.68 (d, J=12.1H), 7.30-7.749 (d, J=7.6, 1H), 7.83-7.85 (d, J=8.1H), 8.34-8.35 (d, J=5.2, 2H).

Example 193

Synthesis of 6-chloro-7-(naphthalen-1-ylmethyl)-5-oxo-1-phenethyl-8-(3-(trifluoro methyl) phenyl)-1,2,3,5-tetrahydroimidazo[1,2-a]pyridine-3-carboxylic (Compound 178)

Compound 178

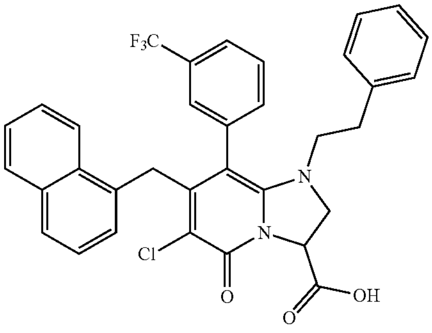

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 5 to give 6-chloro-7-(naphthalen-1-ylmethyl)-5-oxo-1-phenethyl-8-(3-(trifluoromethyl)phenyl)-1,2,3,5-tetrahydroimidazo[1,2-a]pyridine-3-carboxylic acid (Compound 178) (0.025 g, 25.58%). LCMS (Method-C3): 100% (RT 2.066, 254.0 nm) (MS: ESI+ve 603.93 [M+1]). $^1$H NMR: (400 MHz, $CDCl_3$) δ ppm: 2.44-2.54 (m, 2H), 2.77-2.87 (m, 2H), 3.87-3.94 (m, 1H), 4.13-4.35 (m, 3H), 5.41-5.44 (m, 1H), 6.69-6.70 (d, J=3.6 Hz, 2H), 7.04-7.06 (d, J=7.2 Hz, 1H), 7.10-7.14 (m, 1H), 7.16-7.30 (m, 4H), 7.40-7.54 (m, 5H), 7.55-7.58 (m, 1H), 7.74-7.76 (m, 1H), 7.84-7.86 (d, J=8.0 Hz, 1H).

Example 194

Synthesis of 6-chloro-1-isopropyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 179)

Compound 179

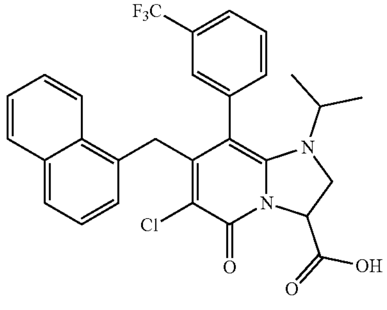

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 5 to give 6-chloro-1-isopropyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 179) (0.025 g, 25.58%). LCMS (Method-C3): 98.71% (RT 1.855, 225.0 nm) (MS: ESI+ve 541.82 [M+1]). $^1$H NMR: (400 MHz, $CDCl_3$) δ ppm: 0.73-0.83 (m, 6H), 2.66-2.67 (m, 1H), 3.60-3.64 (t, 1H), 3.92-4.19 (m, 3H), 5.07-5.09 (d, J=10.8 Hz, 1H), 7.04 (s, 1H), 7.23 (s, 1H), 7.29-7.35 (m, 1H), 7.39-7.50 (m, 5H), 7.73-7.75 (d, J=8.0 Hz, 1H), 7.85-7.87 (d, J=8.0 Hz, 1H), 13.58 (s, 1H).

Example 195

Synthesis of 6-chloro-1-(cyclohexylmethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 180)

Compound 180

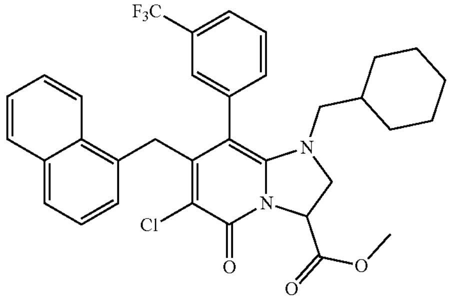

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 5 to give 6-chloro-1-(cyclohexylmethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 180) (0.030 g, 15.36%). LCMS (Method-C3): 100% (RT 2.147, 225.0 nm) (MS: ESI+ve 595.5 [M+2]). $^1$H NMR: (400 MHz, DMSO) δ ppm: 0.34-0.37 (m, 2H), 0.91-1.31 (m, 5H), 1.46 (broad s, 1H), 2.23-2.32 (m, 2H), 3.60-3.67 (m, 1H), 3.95-4.18 (m, 3H), 5.05-5.10 (m, 1H), 7.03 (s, 1H), 7.16 (s, 1H), 7.28-7.50 (m, 6H), 7.70-7.76 (t, 2H), 7.85-7.87 (d, J=8.0 Hz, 1H), 13.53 (s, 1H).

Example 196

Synthesis of 6-chloro-1-(2-(hydroxymethyl)benzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 181)

Compound 181

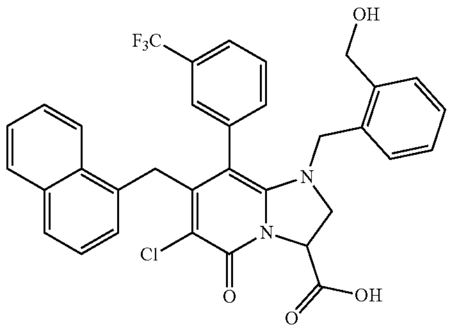

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 5 to give 6-chloro-1-(2-(hydroxymethyl)benzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 181) (0.043 g, 29.81%). LCMs (Method C-3) 100% (RT—1.79, 202 nm) (MS: ESI+ve 621.3 [M+1]). $^{1}$H NMR: (400 MHz, DMSO) δ ppm: 3.60-3.62 (t, 1H J=4 Hz), 3.73-3.77 (m, 2H), 3.85-3.98 (s, 2H), 4.05-4.14 (s, 2H), 4.87 (bs, 1H), 5.18-5.21 (dd, 1H), 6.83-6.87 (d, 1H), 7.02-7.08 (m, 2H), 7.13-7.25 (m, 6H), 7.34-7.35 (s 1H), 7.37-7.44 (d, 2H), 7.64-7.68 (t, 1H), 7.72-7.74 (d, 1H), 7.83-7.85 (m, 6H J=7.6 Hz).

Example 197

Synthesis of methyl 6-chloro-7-(naphthalen-1-ylmethyl)-5-oxo-1-((tetrahydro-2H-pyran-4-yl)methyl)-8-(3-(trifluoromethyl)phenyl)-1,2,3,5-tetrahydroimidazo[1,2-a]pyridine-3-carboxylate (Compound 182)

Compound 182

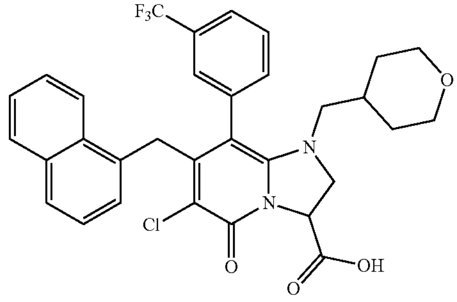

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 5 to give 6-chloro-7-(naphthalen-1-ylmethyl)-5-oxo-1-((tetrahydro-2H-pyran-4-yl)methyl)-8-(3-(trifluoro methyl)phenyl)-1,2,3,5-tetrahydroimidazo[1,2-a]pyridine-3-carboxylic acid (Compound 182) (0.035 g, 19.90%). LCMS (Method-C3): 100% (RT 1.846, 202.0 nm) (MS: ESI+ve 597.03 [M+2]). $^{1}$H NMR: (400 MHz, DMSO) δ ppm: 0.56-0.66 (m, 2H), 1.01-1.08 (m, 2H), 2.32-2.39 (m, 2H), 2.96-3.06 (m, 2H), 3.61-3.64 (m, 3H), 3.87-4.17 (m, 3H), 4.86-4.88 (m, 1H), 7.05-(broad s, 1H), 7.18 (s, 1H), 7.27-7.47 (m, 6H), 7.73-7.75 (m, 2H), 7.85-7.87 (d, J=8.0 Hz, 1H).

Example 198

Synthesis of 6-chloro-1-(3-methoxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 191)

Compound 191

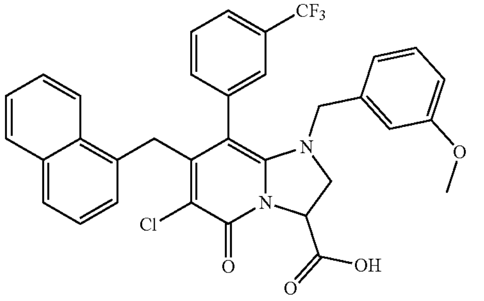

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 1 to give 6-chloro-1-(3-methoxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 191) (0.060 g, 30.00%). LCMS (Method-C3): 100% (RT 2.009, 225.0 nm) (MS: ESI+ve 619.48 [M+2]). $^{1}$H NMR: (400 MHz, DMSO) δ ppm: 3.49-3.67 (m, 4H), 3.74-3.88 (m, 2H), 3.92-4.16 (m, 3H), 5.18-5.20 (m, 1H), 6.40-6.45 (m, 2H), 6.74 (s, 1H), 6.94-6.98 (m, 1H), 7.03-7.13 (m, 2H), 7.18-7.22 (m, 1H), 7.29 (s, 2H), 7.36-7.71 (m, 3H), 7.75-7.85 (m, 2H), 7.87-8.15 (m, 1H), 13.57 (s, 1H).

Example 199

Synthesis of 6-chloro-1-(3-hydroxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 196)

Compound 196

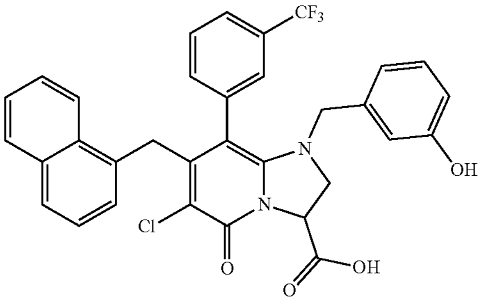

Step-1: Preparation of methyl 6-chloro-1-(3-hydroxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylate

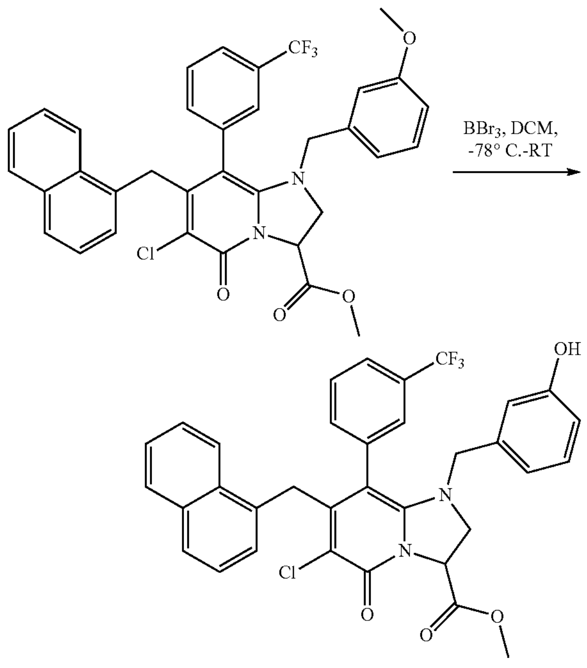

Methyl 6-chloro-1-(3-methoxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylate (0.3 g, 0.47 mmol) was dissolved in DCM (3.0 mL) and cooled to −78° C. A 1M solution of $BBr_3$ in DCM (1.89 mL, 1.89 mmol) was added at −78° C. and the reaction mixture was stirred for 16 hr slowly warming to room temperature. The reaction mixture was cooled to −78° C. and quenched by the addition of methanol (5.0 mL) and evaporated to dryness under vacuum to give methyl 6-chloro-1-(3-hydroxybenzyl)-7-(naphthalen-1-ylmethyl)-5-oxo-8-(3-(trifluoro methyl)phenyl)-1,2,3,5-tetrahydroimidazo[1,2-a]pyridine-3-carboxylate, as a brown gum crude product (0.3 g) which was directly used in the next step without further purification. LCMS (Method-C3): 67.98% (RT: 1.054, 227.0 nm) (MS: ESI+ve 619.43 [M+2]).

Step-2: Preparation of 6-chloro-1-(3-hydroxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 196)

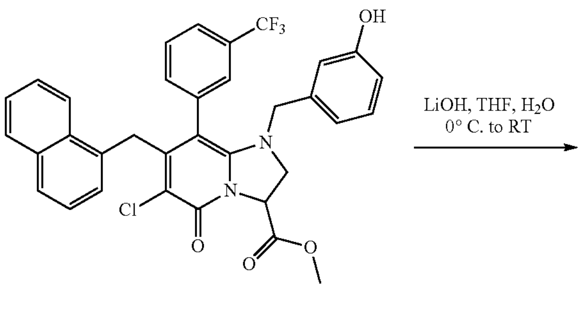

-continued

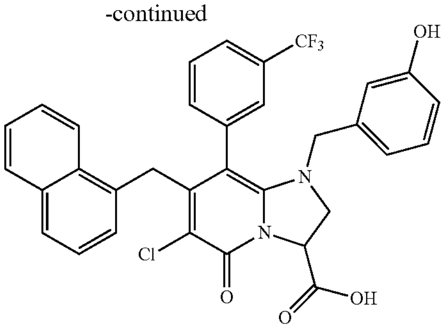

Compound 196

Methyl 6-chloro-1-(3-hydroxybenzyl)-7-(naphthalen-1-ylmethyl)-5-oxo-8-(3-(trifluoro methyl)phenyl)-1,2,3,5-tetrahydroimidazo[1,2-a]pyridine-3-carboxylate (0.3 g, 0.48 mmol) was hydrolyzed using the standard method as for (Compound 004) Step 3, and the crude product was purified using Prep HPLC Method 9 to give 6-chloro-1-(3-hydroxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 196) (0.080 g, 27.28%). LCMS (Method-J): 100% (RT 5.086, 254.0 nm) (MS: ESI+ve 602.5 [M+2]). $^1$H NMR: (400 MHz, DMSO) δ ppm: 3.53-3.59 (m, 2H), 3.67-3.74 (m, 1H), 3.88-4.01 (m, 2H), 4.09-4.18 (t, J=16.8 Hz, 1H), 4.99-5.01 (d, J=8.4 Hz, 1H), 6.28 (s, 2H), 6.55-6.57 (d, J=7.6 Hz, 2H), 6.96-7.00 (m, 2H), 7.08-7.17 (m, 2H), 7.22-7.32 (m, 2H), 7.40-7.45 (m, 3H), 7.70-7.76 (m, 2H), 7.85-7.87 (d, J=7.6 Hz, 1H), 9.42 (s, 1H).

Example 200

Synthesis of 6-chloro-1-(4-methoxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 192)

Compound 192

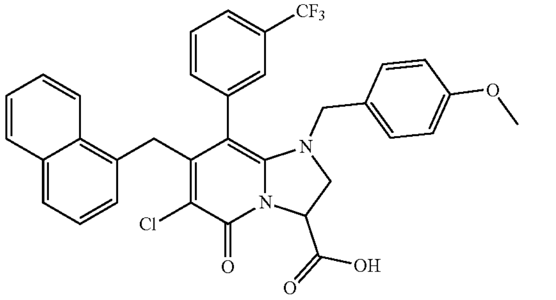

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 9 to give 6-chloro-1-(4-methoxybenzyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 192) as an off-white solid (0.06 g, 23.9%). LCMS (Method-J): 100% (RT 5.512, 202.0 nm) (MS: ESI+ve 620 [M+1]). $^1$H NMR: (400 MHz, DMSO) δ ppm: 3.61 (s, 2H), 3.69 (s, 6H), 3.97-4.14 (m, 3H), 5.14 (s, 1H), 6.77 (s, 3H), 7.05-7.29 (m, 2H), 7.39-7.45 (m, 7H), 7.75-7.77 (d, J=8, 2H), 7.85-7.87 (d, J=7.6, 1H).

Example 201

Synthesis of 6-chloro-1-(2-methoxybenzyl)-7-(naphthalen-1-ylmethyl)-5-oxo-8-(3-(trifluoromethyl) phenyl)-1,2,3,5-tetrahydroimidazo[1,2-a]pyridine-3-carboxylic acid (Compound 195)

Compound 195

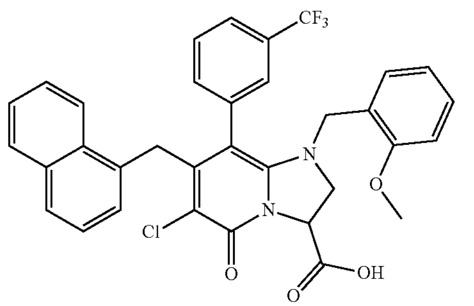

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 9 to give 6-chloro-1-(2-methoxybenzyl)-7-(naphthalen-1-ylmethyl)-5-oxo-8-(3-(trifluoromethyl) phenyl)-1,2,3,5-tetrahydroimidazo[1,2-a]pyridine-3-carboxylic acid (Compound 195) as a white solid (0.004 g, 2.05%). LCMS (Method-J): 100% (RT 5.587, 202.0 nm) (MS: ESI+ve 620 [M+H]). $^1$H NMR: (400 MHz, DMSO) δ ppm: 3.46 (s, 3H), 3.66 (s, 1H), 3.85-3.92 (m, 1H), 4.02-4.11 (m, 2H), 4.29-4.31 (d, J=9.2, 2H), 5.1 (s, 1H), 6.46-6.48 (d, J=8.4, 1H), 6.71-6.74 (m, 1H), 6.86-6.92 (m, 2H), 6.98-7.05 (m, 2H), 7.16-7.22 (m, 2H), 7.37-7.46 (m, 4H), 7.66-7.74 (m, 2H), 7.84-7.86 (d, J=8, 1H).

Example 202

Synthesis of 6-chloro-1-(3-hydroxypropyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 197)

Compound 197

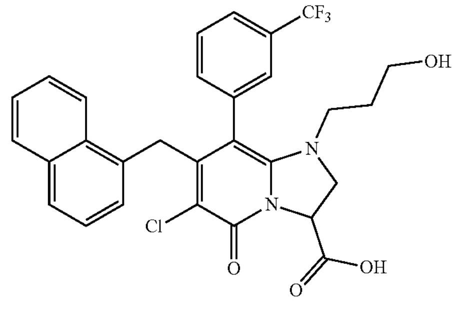

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 9 to give 6-chloro-1-(3-hydroxypropyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 197), as a white solid (0.03 g, 20.50%). LCMS (Method-C3): 99.10% (RT 1.852, 223.0 nm) (MS: ESI–ve 555.0 [M+2]). $^1$H NMR: (400 MHz, DMSO) δ ppm: 1.23-1.30 (m, 2H), 2.67 (s, 2H), 2.82-2.92 (m, 2H), 3.67-3.68 (m, 1H), 3.95-4.18 (m, 3H), 4.25 (s, 1H), 5.08-5.11 (d, J=10.4 Hz, 1H), 7.02-7.05 (t, 1H), 7.17-7.27 (m, 1H), 7.30-7.48 (m, 6H), 7.71-7.76 (t, 2H), 7.86-7.88 (d, J=8 Hz, 1H).

Example 203

Synthesis of 6-chloro-1-(5-hydroxypentyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 199)

Compound 199

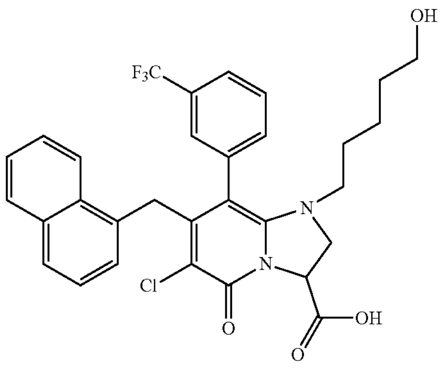

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 9 to give 6-chloro-1-(5-hydroxypentyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 199) as an off-white solid (0.025 g, 14.22%). LCMS (Method-J): 98.64% (RT 4.845, 254.0 nm) (MS: ESI+ve 585.2 [M]). $^1$H NMR: (400 MHz, DMSO) δ ppm: 0.72-0.75 (t, J=6.8 Hz, 2H), 1.09-1.15 (m, 4H), 2.33-2.50 (m, 2H), 3.203.23 (t, J=6 Hz, 2H), 3.61 (s, 1H), 3.84 (s, 1H), 4.03-4.16 (m, 2H), 4.76 (s, 1H), 7.08-7.10 (d, J=6.8, 1H), 7.19 (s, 1H), 7.36-7.43 (m, 6H), 7.71-7.74 (m, 2H), 7.84-7.86 (d, J=7.6 Hz, 1H).

Example 204

Synthesis of 6-chloro-1,7-bis(naphthalen-1-ylmethyl)-5-oxo-8-(3-(trifluoromethyl)phenyl)-1,2,3,5-tetrahydroimidazo[1,2-a]pyridine-3-carboxylic acid (Compound 200)

Compound 200

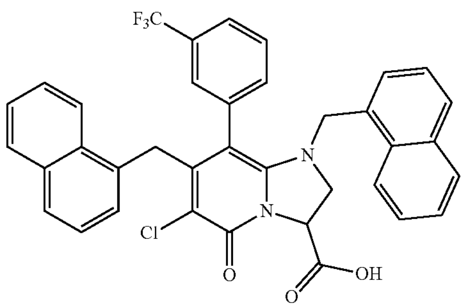

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 9 to give 6-chloro-1,7-bis(naphthalen-1-ylmethyl)-5-oxo-8-(3-(trifluoromethyl)phenyl)-1,2,3,5-tetrahydroimidazo[1,2-a]pyridine-3-carboxylic acid (Compound 200) as an off-white solid (0.025 g, 12.77%). LCMS (Method-J): 100% (RT 5.749, 254.0 nm) (MS: ESI+ve 639.2 [M]). $^{1}$H NMR: (400 MHz, DMSO) δ ppm: 3.64-3.68 (t, J=18.4 Hz, 1H), 3.86-4.34 (m, 5H), 4.74 (d, J=8 Hz, 1H), 6.79-6.92 (m, 3H), 7.06 (s, 1H), 7.13-7.21 (m, 2H), 7.29-7.43 (m, 7H), 7.62-7.66 (t, J=16.4 Hz, 1H), 7.72-7.83 (m, 4H).

Example 205

Synthesis of 1-([1,1'-biphenyl]-4-ylmethyl)-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 202)

Compound 202

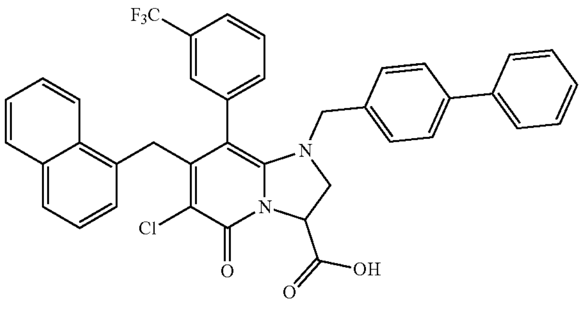

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 9 to give 1-([1,1'-biphenyl]-4-ylmethyl)-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 202) as an off-white solid (0.036 g, 12.25%). LCMS (Method-C3): 95.23% (RT 2.152, 222.0 nm) (MS: ESI+ve 665.23 [M]). $^{1}$H NMR: (400 MHz, DMSO) δ ppm: 3.55 (s, 1H), 3.68-4.15 (m, 5H), 4.74 (s, 1H), 6.96 (s, 3H), 7.09 (s, 1H), 7.21-7.47 (m, 13H), 7.58-7.60 (d, J=8 Hz, 2H), 7.84-7.86 (d, J=8 Hz, 1H), 8.48 (s, 1H).

Example 206

Synthesis of 6-chloro-1-(2-cyclohexylethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 207)

Compound 207

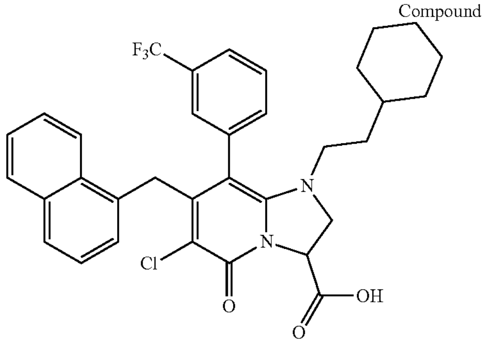

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 6 to give 6-chloro-7-(naphthalen-1-ylmethyl)-5-oxo-1-(pyridin-3-ylmethyl)-8-(trifluoromethyl)phenyl)-1,2,3,5-tetrahydroimidazo[1,2-a]pyridine-3-carboxylic acid (Compound 207) as an off-white solid (0.036 g, 24.57%). LCMS (Method-C3): 100% (RT 2.557, 230.0 nm) (MS: ESI+ve 609.25 [M+1]). $^{1}$H NMR: (400 MHz, DMSO) δ ppm: 0.50 (s, 3H), 0.93-1.28 (m, 5H), 1.46 (s, 3H), 2.50-2.54 (d, J=15.6 Hz, 4H), 3.61-3.68 (m, 1H), 3.93-4.19 (m, 3H), 5.07-5.09 (d, J=8 Hz, 1H), 7.01-7.04 (s, 1H), 7.16 (s, 1H), 7.28-7.46 (m, 6H), 7.70-7.88 (m, 3H), 13.55 (s, 1H).

Example 207

Synthesis of 1-(4-(tert-butyl)benzyl)-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 208)

Compound 208

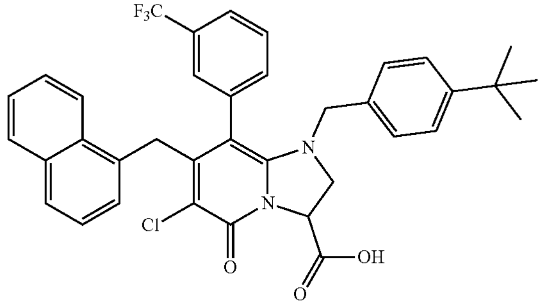

Prepared by a method similar to that reported for 1-benzyl-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 004) as a white solid. The crude product was purified using Prep HPLC Method 5 to give 1-(4-(tert-butyl)benzyl)-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 208) (0.028 g, 7.5%), as a white solid. LCMS (Method-C3): 100% (RT: 2.345, 225 nm) (MS: ESI+ve 646.2 [M+1]). $^{1}$H NMR: (400 MHz, DMSO) δ ppm: 1.228 (s, 9H), 3.641-3.901 (m, 3H), 3.941-4.165 (m, 3H), 5.162 (s, 1H), 6.754-6.774 (m, 2H), 6.863-6.911 (d, J=19.2 Hz, 1H), 7.050 (s, 1H), 7.182-7.454 (m, 8H), 7.711-7.766 (m, 2H), 7.855-7.874 (d, J=7.6 Hz, 1H), 13.763 (s, 1H)

Example 208

Synthesis of 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 238)

Compound 238

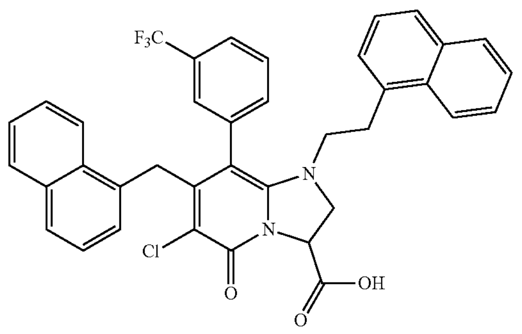

Step 1: Preparation of 3-(tert-butyl) 4-methyl (4S)-1,2,3-oxathiazolidine-3,4-dicarboxylate 2-oxide

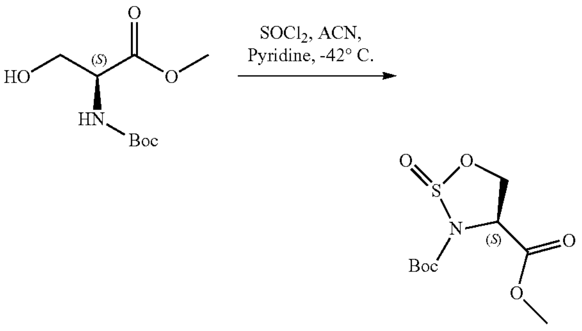

Thionyl chloride (8.32 mL, 114.03 mmol) was dissolved in dry acetonitrile (60 mL) under a N2 atmosphere and cooled to −42° C. A solution of methyl (tert-butoxycarbonyl)-L-serinate (10.0 g, 45.61 mmol) in dry acetonitrile (60 mL) was added drop wise at −42° C. over 1 hr. Pyridine (19.3 mL, 239.47 mmol) was added over 30 min then the mixture was stirred for 2 hrs at −42° C. The reaction was quenched into crushed ice (100 g) and acidified with aq. 10% $NaHSO_4$. The mixture was extracted into DCM (3×100 mL). The organic layer was washed with water (100 mL), sat. aq $NaHCO_3$ (100 mL) and brine (100 mL). The organic layer was then dried over sodium sulphate and concentrated under reduced pressure to give (12.97 g) 3-(tert-butyl) 4-methyl 1,2,3-oxathiazolidine-3,4-dicarboxylate 2-oxide, which was used directly in the next step.

Step 2: Preparation of 3-(tert-butyl) 4-methyl (S)-1,2,3-oxathiazolidine-3,4-dicarboxylate 2,2-dioxide

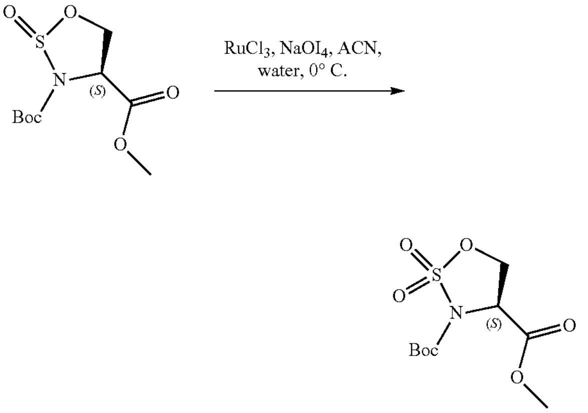

3-(tert-butyl) 4-methyl (4S)-1,2,3-oxathiazolidine-3,4-dicarboxylate 2-oxide (12.97 g, 48.90 mmol) was dissolved in acetonitrile (120 mL) and cooled to 0° C. Ruthenium trichloride hydrate (5.07 g, 24.45 mmol), sodium periodate (11.48 g, 53.79 mmol) and water (120 mL) was added and stirring continued at room temperature for 4 hr. The reaction was quenched in brine (100 mL) and extracted in diethyl ether (2×100 mL). The organic layer was washed with sat. aq $NaHCO_3$ (50 mL) and dried over sodium sulphate then concentrated under reduced pressure to give the crude product which was purified by column chromatography eluting with 20% Ethyl acetate/Hexane to give 3-(tert-butyl) 4-methyl (S)-1,2,3-oxathiazolidine-3,4-dicarboxylate 2,2-dioxide as a white solid. (6.0 g, 47.16%). $^{1}$H NMR: (400 MHz, DMSO) δ ppm: 1.54-1.60 (m, 9H), 3.89 (s, 3H), 4.70-4.85 (m, 3H).

Step 3: Preparation of methyl 2-((tert-butoxycarbonyl)amino)-3-((2-(naphthalen-1-yl)ethyl)amino)propanoate

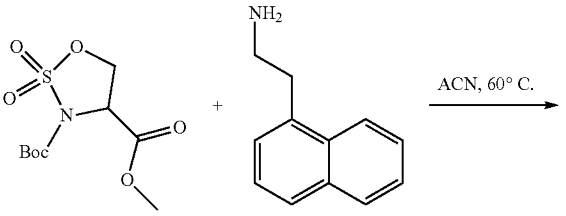

-continued

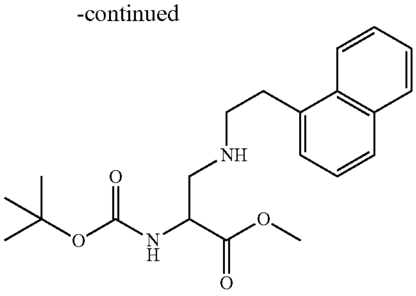

3-(tert-butyl) 4-methyl 1,2,3-oxathiazolidine-3,4-dicarboxylate 2,2-dioxide (0.426 g, 1.518 mmol) and 2-(naphthalen-1-yl)ethan-1-amine (0.520 g, 3.037 mmol) was dissolved in dry acetonitrile (10 mL). The reaction mixture was heated at 60° C. for 16 hr. The resulting precipitate was collected by filtration to give methyl (S)-2-((tert-butoxycarbonyl)amino)-3-((2-(naphthalen-1-yl)ethyl)amino)propanoate as a white solid. (0.550 g, 98.89%). LCMS (Method-C3): 100% (RT: 1.561, 223.0 nm) (MS: ESI+ve 316.9 [M−56]).

Step-4: Preparation of methyl 2-amino-3-((2-(naphthalen-1-yl)ethyl)amino)propanoate hydrochloride

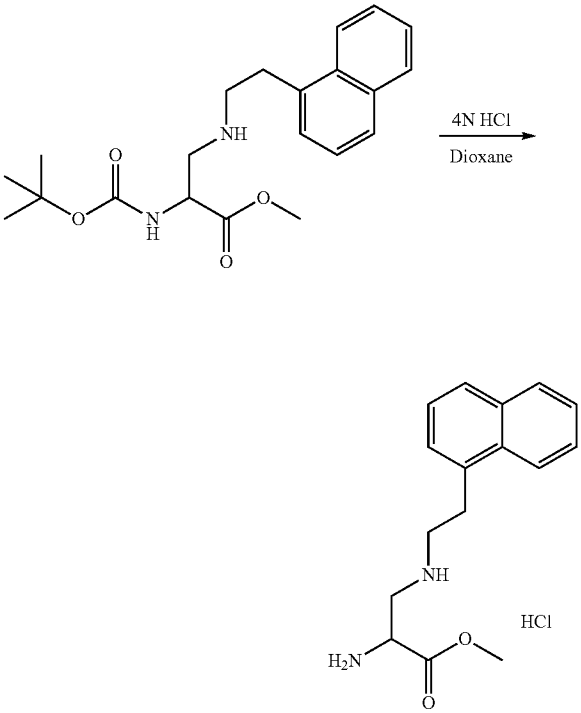

Methyl 2-((tert-butoxycarbonyl)amino)-3-((2-(naphthalen-1-yl)ethyl)amino)propanoate (0.550 g, 1.47 mmol) was dissolved in 1,4 dioxane (3 mL). 4 N HCl in Dioxane (1.5 mL) was added dropwise and the reaction mixture was stirred at room temperature for 24 hr. The mixture was concentrated to dryness and extracted with DCM (2 X) to give methyl 2-amino-3-((2-(naphthalen-1-yl)ethyl)amino) propanoate hydrochloride (0.53 g, Crude). (MS: ESI+ve 273.24 [M+1]).

Step-5: Preparation of methyl 1-(2-(naphthalen-1-yl)ethyl)-2-(3-(trifluoromethyl)benzyl)-4,5-dihydro-1H-imidazole-4-carboxylate

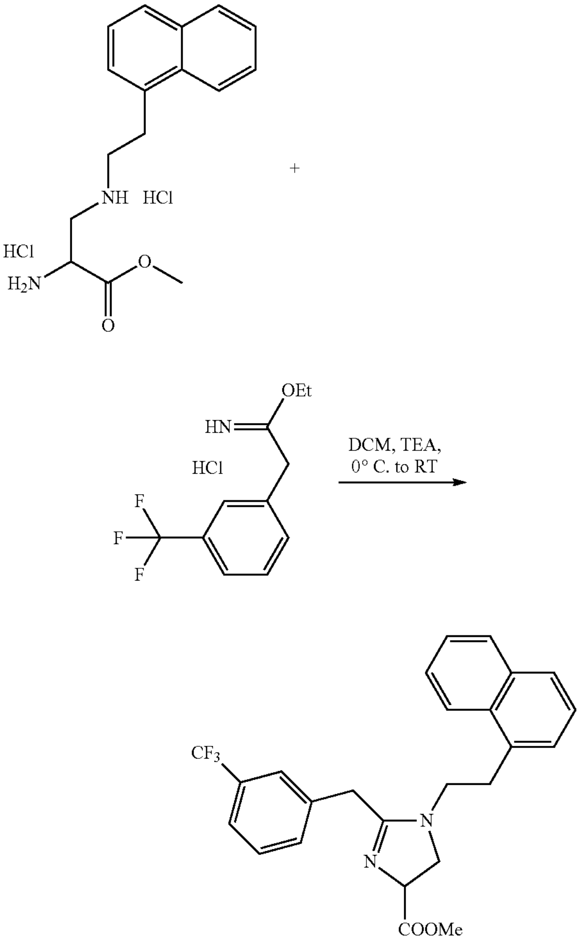

Methyl 2-amino-3-((2-(naphthalen-1-yl)ethyl)amino)propanoate hydrochloride (0.530 g, 1.944 mmol) was dissolved in dichloromethane (5 mL) and cooled to 0° C. Triethylamine (0.27 mL, 1.944 mmol) was added and the mixture was stirred for 30 min. Ethyl 2-(3-(trifluoromethyl)phenyl)acetimidate hydrochloride (0.45 g, 1.944 mmol) dissolved in dichloromethane (5 mL) was added. The mixture was stirred at room temperature for 48 hr. The reaction was quenched with saturated sodium bicarbonate solution (50 mL) and extracted with dichloromethane (3×50 mL). The organic layer was dried over sodium sulphate and concentrated under reduced pressure to give methyl 1-(2-(naphthalen-1-yl)ethyl)-2-(3-(trifluoromethyl)benzyl)-4,5-dihydro-1H-imidazole-4-carboxylate as a brown gum (0.75 g). LCMS (Method-C2): 85.63% (RT: 1.225, 227 nm) (MS: ESI+ve 441.63 [M+H]).

Step-6: Preparation of methyl 1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylate

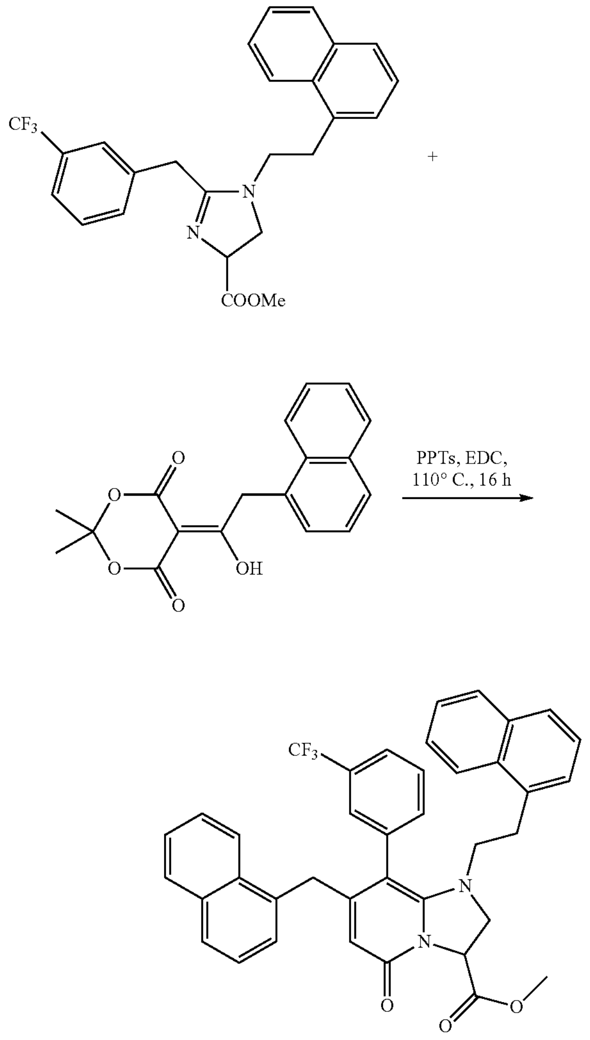

Methyl 1-(2-(naphthalen-1-yl)ethyl)-2-(3-(trifluoromethyl)benzyl)-4,5-dihydro-1H-imidazole-4-carboxylate (0.700 g, 1.589 mmol) and 5-(1-hydroxy-2-(naphthalen-1-yl)ethylidene)-2,2-dimethyl-1,3-dioxane-4,6-dione (1.73 g, 5.561 mmol) were dissolved in 1,2 dichloroethane (15 mL). Pyridinium p-toluenesulfonate (0.439 g, 1.748 mmol) was added and the mixture was stirred at 120° C. for 16 hrs. The reaction was quenched with saturated sodium bicarbonate solution (40 mL) and extracted with DCM (3×50 mL). The organic layer was dried over sodium sulphate and concentrated under reduced pressure. The crude product was purified using column chromatography eluting with 50-100% ethyl acetate/Hexane to give methyl 1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylate (0.6 g, 55.7%) as a brown gum. LCMS (Method-C2): 59.13% (RT: 1.621, 230.0 nm) (MS: ESI+ve 633.46 [M+H]).

Step-7: Preparation of methyl 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylate

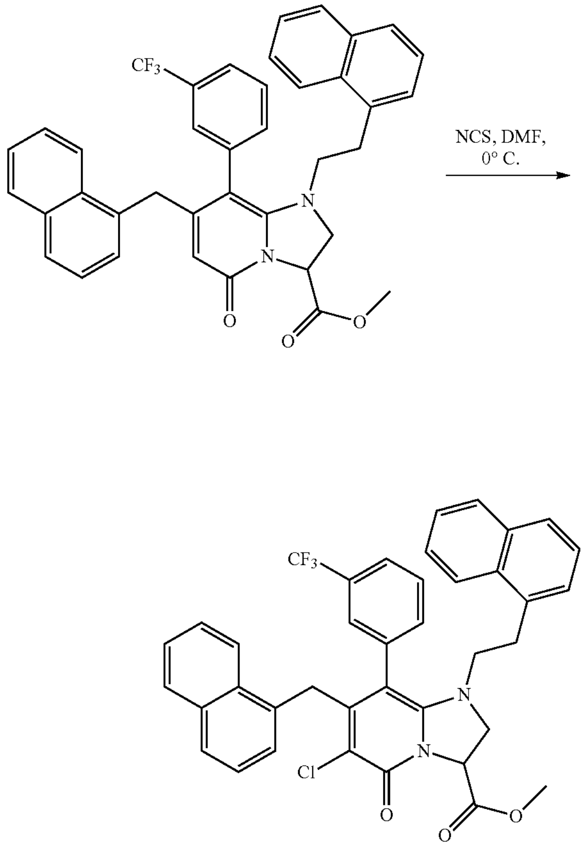

Methyl 1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylate (0.35 g, 0.553 mmol) was dissolved in DMF (10 mL). N-chlorosuccinimide (0.088 g, 0.664 mmol) was added portion-wise at 0° C. and the reaction mixture was stirred for 1 hr at 0° C. The reaction was quenched with cold water (50 mL) and the resulting solid was collected by filtration and dissolved in dichloromethane (50 mL). The organic layer was dried over sodium sulphate then concentrated under reduced pressure to give the crude product which was purified using column chromatography eluting with 70% ethyl acetate/Hexane to give methyl 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylate as a brown solid (0.21 g, 66%). LCMS (Method-C3): 71.89% (RT: 1.635, 229.0 nm) (MS: ESI+ve 667.48 [M+1]).

Step-8: Preparation 6-chloro-1-(2-(naphthalen-1-yl) ethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 238)

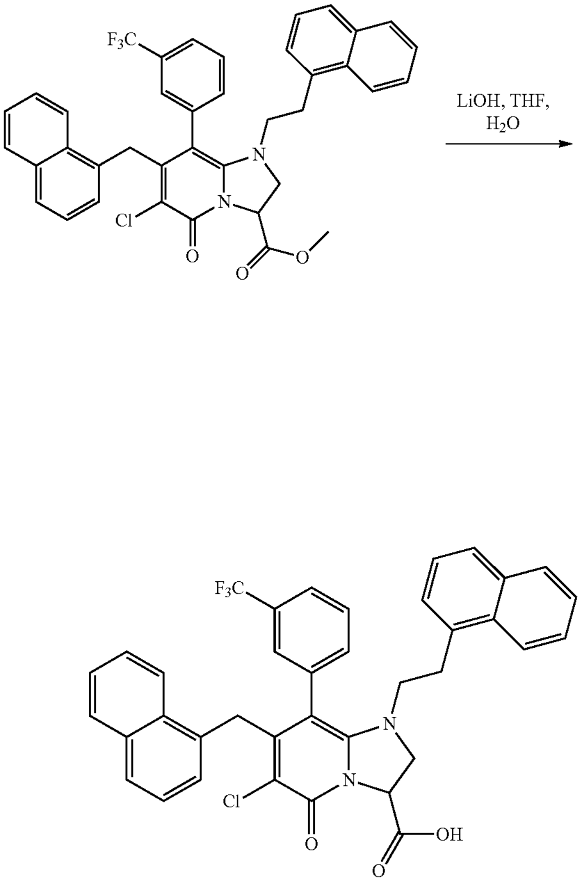

Compound 238

Methyl 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylate (0.21 g, 0.314 mmol) was hydrolyzed using the standard method as for (Compound 004) Step 3, and the crude product was purified using Prep HPLC Method 1 to give 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 238) as a white solid (0.092 g, 44.47%). LCMS (Method-C3): 100% (RT 2.238, 225.0 nm) (MS: ESI+ve 653.08 [M+1]). $^1H$ NMR: (400 MHz, DMSO) δ ppm: 2.78-2.96 (m, 4H), 3.86-4.02 (m, 2H), 4.06-4.18 (m, 2H), 5.11-5.15 (q, 1H), 6.75-6.79 (t, 1H), 7.01-7.06 (t, 1H), 7.22-7.48 (m, 10H), 7.65-7.77 (m, 4H), 7.83-7.88 (t, 2H), 13.56 (bs, 1H).

Example 209

Synthesis of 1-benzyl-8-(3-bromophenyl)-6-chloro-7-(naphthalen-1-ylmethyl)-5-oxo-1,2,3,5-tetrahydroimidazo[1,2-a]pyridine-3-carboxylic acid (Compound 198)

Compound 198

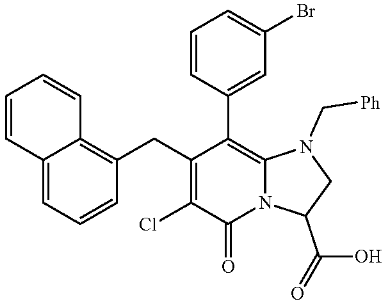

Prepared by a procedure similar to that reported for 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 238) as a white solid. The crude product was purified using Prep HPLC Method 7 to give 1-benzyl-8-(3-bromophenyl)-6-chloro-7-(naphthalen-1-ylmethyl)-5-oxo-1,2,3,5-tetrahydroimidazo[1,2-a]pyridine-3-carboxylic acid (Compound 198) as a white solid (0.23 g, 87.18%). LCMS (Method-C3): 100% (RT 2.007, 223 nm) (MS: ESI+ve 600.9 [M+2]). $^1H$ NMR: (400 MHz, DMSO) δ ppm: 3.56-3.59 (d, J=12.4 Hz, 1H), 3.73-3.86 (m, 2H), 3.98-4.06 (m, 2H), 4.11-4.15 (d, J=16.8 Hz, 1H), 5.14-5.16 (d, J=6 Hz, 1H), 6.89-6.94 (m, 4H), 6.98-7.02 (d, J=16 Hz, 2H), 7.19-7.26 (m, J=8 Hz, 4H), 7.42-7.50 (m, 3H), 7.75-7.82 (m, 2H), 7.87-7.95 (t, 1H), 13.51 (s, 1H).

Example 210

Synthesis of 1-benzyl-8-(4-bromophenyl)-6-chloro-7-(naphthalen-1-ylmethyl)-5-oxo-1,2,3,5-tetrahydroimidazo[1,2-a]pyridine-3-carboxylic acid (Compound 201)

Compound 201

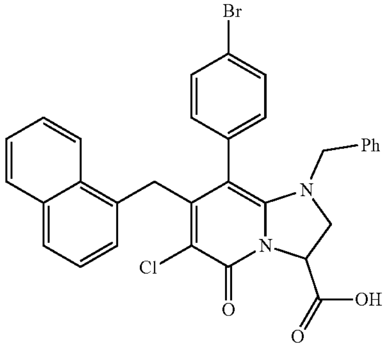

Prepared by a procedure similar to that reported for 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 238) as a white solid. The crude product was purified using Prep HPLC Method 7 to give 1-benzyl-8-(4-bromophenyl)-6-chloro-7-(naphthalen-1-ylmethyl)-5-oxo-1,2,3,5-tetrahydroimidazo[1,2-a]pyridine-3-carboxylic acid, as a white solid (Compound 201) (0.045 g, 35.42%). LCMS (Method-C3): 100% (RT 5.671, 202.4 nm) (MS: ESI+ve 601.2 [M+2]). $^1$H NMR: (400 MHz, DMSO) δ ppm: 3.48-3.50 (d, J=7.2 Hz, 1H), 3.71-3.81 (m, 2H), 3.85-3.90 (m, 1H), 3.95-3.99 (m, J=16 Hz, 1H), 4.10-4.14 (d, J=16 Hz, 1H), 5.08-5.11 (d, J=10.4 Hz, 1H), 6.84-6.86 (d, J=7.6 Hz, 1H), 6.89-6.91 (d, J=8 Hz, 1H), 6.94-6.96 (d, J=6.8 Hz, 2H), 7.03-7.05 (d, J=7.2 Hz, 1H), 7.08-7.10 (d, J=8 Hz, 1H), 7.14-7.16 (d, J=7.6 Hz, 1H), 7.23-7.25 (d, J=7.6 Hz, 3H), 7.43-7.51 (m, 3H), 7.75-7.77 (d, J=8.4 Hz, 1H), 7.81-7.83 (d, J=7.6 Hz, 1H), 7.88-7.90 (d, J=8 Hz, 1H).

Example 211

Synthesis of 1-(4-(tert-butyl)phenethyl)-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 239)

Compound 239

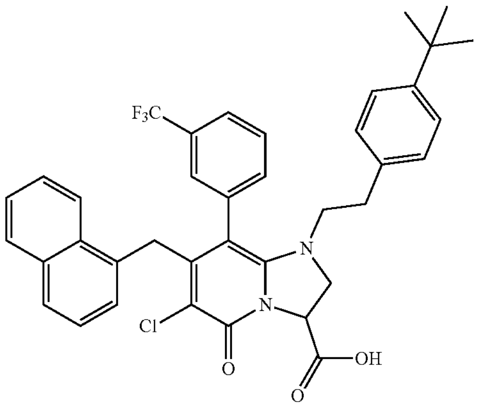

Prepared by a method similar to that reported for 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 238) as a white solid. The crude product was purified using Prep HPLC Method 1 to give 1-(4-(tert-butyl)phenethyl)-6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 239) (0.054 g, 36.77%). LCMS (Method-J): 100.0% (RT 6.270, 202.0 nm) (MS: ESI+ve 659.2 [M+1]). $^1$H NMR: (400 MHz, DMSO) δ ppm: 1.20-1.25 (s, 9H), 2.62-2.69 (m, 4H), 3.75-3.80 (m, 1H), 3.96-4.22 (m, 3H), 5.12-5.16 (dd, J=4.4 Hz, J=4.4 Hz, 1H), 6.59-6.63 (t, 2H), 7.03-7.07 (t, 1H), 7.12-7.14 (d, J=8.8 Hz, 2H), 7.25-7.50 (m, 7H), 7.73-7.78 (q, 2H), 7.87-7.89 (d, J=8 Hz, 1H), 13.51 (s, 1H).

Example 212

Synthesis of 1-benzyl-6-chloro-5-oxo-7-phenethyl-8-(3-(trifluoromethyl)phenyl)-1,2,3,5-tetrahydroimidazo[1,2-a]pyridine-3-carboxylic acid (Compound 240)

Compound 240

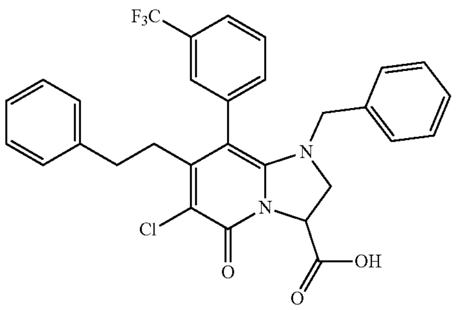

Prepared by a method similar to that reported for 6-chloro-1-(2-(naphthalen-1-yl)ethyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 238) as a white solid. The crude product was purified using Prep HPLC Method 5 to give 1-benzyl-6-chloro-5-oxo-7-phenethyl-8-(3-(trifluoromethyl)phenyl)-1,2,3,5-tetrahydroimidazo[1,2-a]pyridine-3-carboxylic acid (Compound 240) (0.007 g, 9.2%), as a white solid. LCMS (Method-J): 100% (RT: 5.527, 202 nm) (MS: ESI+ve 553.2 [M+1]). $^1$H NMR: (400 MHz, DMSO) δ ppm: 2.417 (m, 4H), 3.520-3.567 (m, 1H), 3.769-3.885 (m, 2H), 4.006-4.018 (m, 1H), 5.067-5.094 (m, 1H), 6.754-6.771 (m, 2H), 6.890-6.904 (m, 2H), 7.134-7.219 (m, 7H), 7.508-7.684 (m, 3H), 13.488 (s, 1H).

Example 213

Synthesis of 1-benzyl-5-oxo-7-phenethyl-8-(3-(trifluoromethyl)phenyl)-1,2,3,5-tetrahydroimidazo[1,2-a]pyridine-3-carboxylic acid (Compound 236)

Compound 236

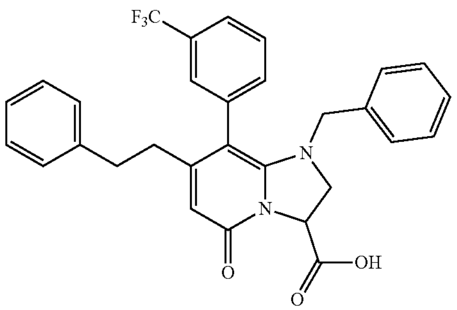

Prepared by a procedure similar to that reported for 1-benzyl-6-chloro-5-oxo-7-phenethyl-8-(3-(trifluoromethyl)phenyl)-1,2,3,5-tetrahydroimidazo[1,2-a]pyridine-3-carboxylic acid (Compound 240) omitting the chlorination step. The crude product was purified using Prep HPLC Method 5 to give 1-benzyl-5-oxo-7-phenethyl-8-(3-(trifluoromethyl)phenyl)-1,2,3,5-tetrahydroimidazo[1,2-a]pyridine-3-carboxylic acid (Compound 236) (0.012 g, 12.8%), as a white solid. LCMS (Method-J): 96.1% (RT: 5.303, 202 nm) (MS: ESI+ve 519.0 [M+1]). $^{1}$H NMR: (400 MHz, DMSO) δ ppm: 2.229-2.506 (m, 2H), 2.554 (s, 1H), 3.402 (s, 1H), 3.780-3.940 (m, 2H), 3.966-4.013 (m, 1H), 4.977-5.031 (m, 1H), 5.777 (s, 1H), 6.838-6.900 (m, 4H), 7.093-7.309 (m, 7H), 7.483-7.542 (dd, J=19.2 Hz, 2H), 7.633-7.646 (m, 1H).

Example 214

Synthesis of 1-benzyl-6-cyano-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 185)

Compound 185

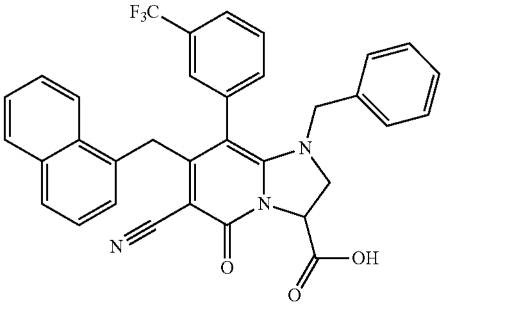

Step-1: Preparation of methyl 1-benzyl-6-cyano-7-(naphthalen-1-ylmethyl)-5-oxo-8-(3-(trifluoromethyl)phenyl)-1,2,3,5-tetrahydroimidazo[1,2-a]pyridine-3-carboxylate

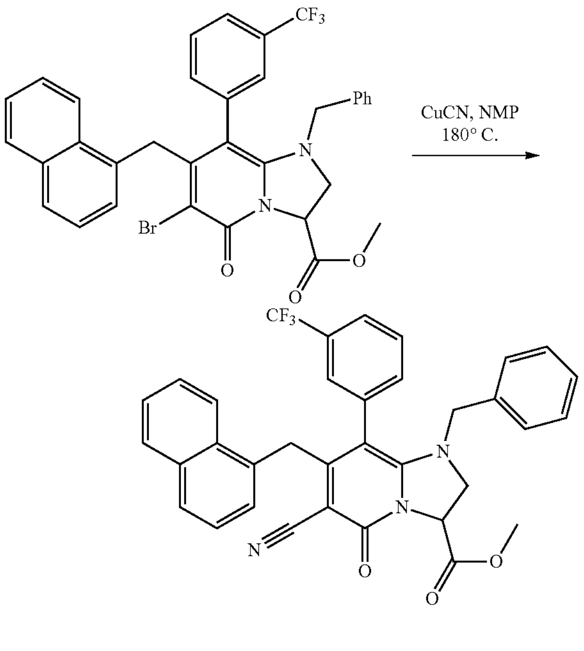

Methyl 1-benzyl-6-bromo-7-(naphthalen-1-ylmethyl)-5-oxo-8-(3-(trifluoromethyl)phenyl)-1,2,3,5-tetrahydroimidazo[1,2-a]pyridine-3-carboxylate (0.300 g, 0.463 mmol) was dissolved in NMP (4.5 mL). Copper cyanide (0.348 g, 3.891 mmol) was added and the mixture was degassed with nitrogen gas. The reaction mixture was heated in a in microwave reactor at 180° C. for 30 minutes. The mixture was poured into $H_2O$ and the resulting precipitate was collected by filtration, dissolved in dichloromethane and concentrated to dryness. The crude product was purified using column chromatography eluting with 0-25% dichloromethane/ethyl acetate (0.129 g, 46.9% yield). LCMS (Method-C3): 100% (RT: 2.064, 220.0 nm) (MS: ESI+ve 594.9 [M+1]).

Step-2: Preparation of 1-benzyl-6-cyano-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 185)

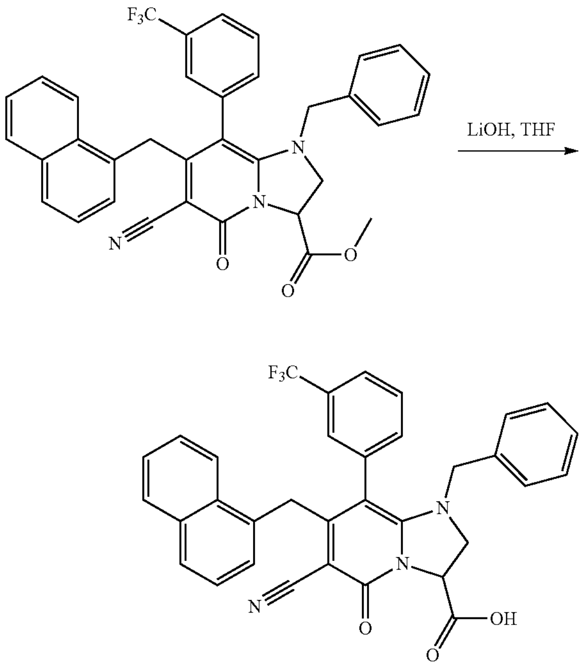

Compound 185

Methyl 1-benzyl-6-cyano-7-(naphthalen-1-ylmethyl)-5-oxo-8-(3-(trifluoromethyl)phenyl)-1,2,3,5-tetrahydroimidazo[1,2-a]pyridine-3-carboxylate (0.110 g, 0.185 mmol) was hydrolyzed using the standard method as for (Compound 004) Step 3. The crude product was purified using Prep HPLC Method 5 to give 1-benzyl-6-cyano-7-(naphthalen-1-ylmethyl)-5-oxo-8-(3-(trifluoromethyl)phenyl)-1,2,3,5-tetrahydroimidazo[1,2-a]pyridine-3-carboxylic acid (FN-Target-410) (0.033 g, 30.8%), as a white solid. LCMS (Method-C3): 100% (RT: 1.818, 227 nm) (MS: ESI+ve 580.5 [M+1]). $^{1}$H NMR: (400 MHz, DMSO) δ ppm: 3.694-3.803 (m, 1H), 3.823-3.902 (m, 2H), 3.945-4.063 (m, 2H), 4.157-4.213 (m, 1H), 5.161-5.218 (m, 1H), 6.840-6.890 (dd, J=7.6 Hz, 2H), 6.983 (s, 1H), 7.080-7.124 (m, 1H), 7.149-7.295 (m, 5H), 7.328-7.397 (m, 2H), 7.441-7.471 (t, J=12 Hz, 2H), 7.656-7.783 (d, J=50.8 Hz, 1H), 7.763-7.783 (d, J=8 Hz, 1H), 7.849-7.869 (d, J=8 Hz, 1H).

Example 215

Synthesis of 1-benzyl-6-fluoro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 194)

Compound 194

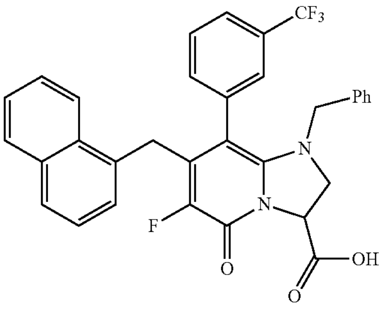

Step 1: Preparation of methyl 1-benzyl-6-fluoro-7-(naphthalen-1-ylmethyl)-5-oxo-8-(3-(trifluoromethyl)phenyl)-1,2,3,5-tetrahydroimidazo[1,2-a]pyridine-3-carboxylate

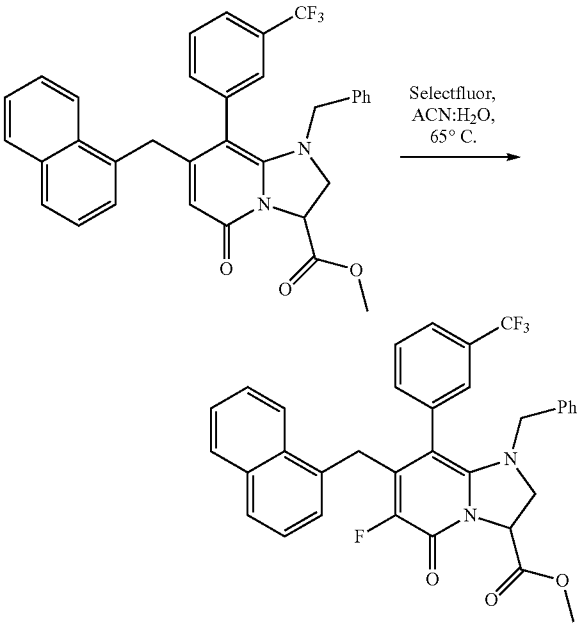

Methyl 1-benzyl-7-(naphthalen-1-ylmethyl)-5-oxo-8-(3-(trifluoromethyl)phenyl)-1,2,3,5-tetrahydroimidazo[1,2-a]pyridine-3-carboxylate (0.5 g, 0.088 mmol) was dissolved in a mixture of acetonitrile (5 mL)/water (0.5 mL). Selectfluor (0.342 g, 0.096) was added at room temperature and the reaction mixture was stirred at 65° C. for 3 hr. The mixture quenched into cold water (5 mL) and extracted with ethyl acetate (3×10 mL). The organic layer was dried over sodium sulphate and concentrated under reduced pressure. The crude product was purified by using column chromatography eluting with 30-40% ethyl acetate/Hexane to give methyl 1-benzyl-6-fluoro-7-(naphthalen-1-ylmethyl)-5-oxo-8-(3-(trifluoromethyl)phenyl)-1,2,3,5-tetrahydroimidazo[1,2-a]pyridine-3-carboxylate (0.160 g, 31%). LCMS (Method-C3): 60.29% (RT 1.121, 225 nm) (MS: ESI+ve 587.5 [M+H]).

Step 2: Preparation 1-benzyl-6-fluoro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 194)

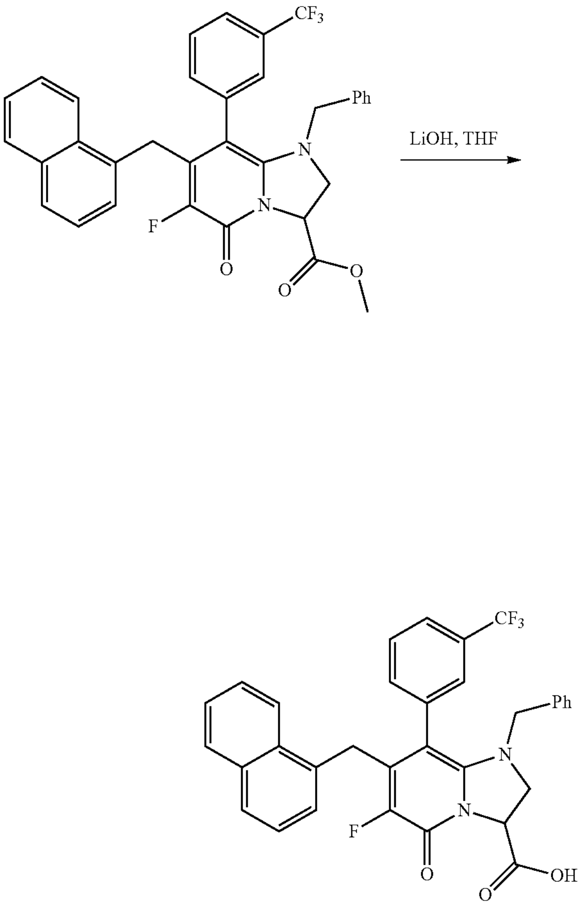

Compound 194

Methyl 1-benzyl-6-fluoro-7-(naphthalen-1-ylmethyl)-5-oxo-8-(3-(trifluoromethyl)phenyl)-1,2,3,5-tetrahydroimidazo[1,2-a]pyridine-3-carboxylate (0.140 g, 0.023 mmol) was hydrolyzed using the standard method as for (Compound 004) Step 3. The crude product was purified using Prep HPLC Method 9 to give 1-benzyl-6-fluoro-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 194) (0.020 g, 14.64%), as a white solid. LCMS (Method-C3): 100% (RT 1.947, 225 nm) (MS: ESI+ve 573.1 [M+1]). $^1H$ NMR: (400 MHz, DMSO) δ ppm: 3.55 (s, 1H), 3.69-3.86 (m, 3H), 3.98-4.08 (m, 2H), 5.15-5.17 (m, 1H), 6.84 (s, 2H), 6.96-7.04 (m, 2H), 7.17 (s, 4H), 7.28-7.30 (m, 2H), 7.38-7.44 (m, 3H), 7.69-7.75 (m, 2H), 7.84-7.86 (m, 2H), 13.59 (s, 1H).

Example 216

Synthesis of 1-benzyl-6-carbamoyl-7-(naphthalen-1-ylmethyl)-5-oxo-8-(3-(trifluoro methyl)phenyl)-1,2,3,5-tetrahydroimidazo[1,2-a]pyridine-3-carboxylic acid (Compound 203)

Compound 203

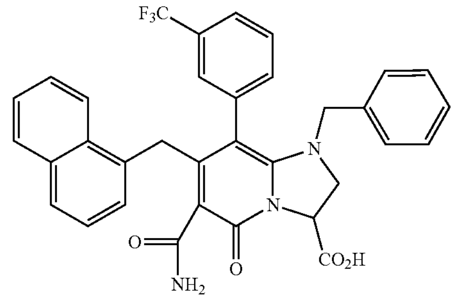

Step-1: Preparation of methyl 1-benzyl-6-formyl-7-(naphthalen-1-ylmethyl)-5-oxo-8-(3-(trifluoromethyl)phenyl)-1,2,3,5-tetrahydroimidazo[1,2-a]pyridine-3-carboxylate

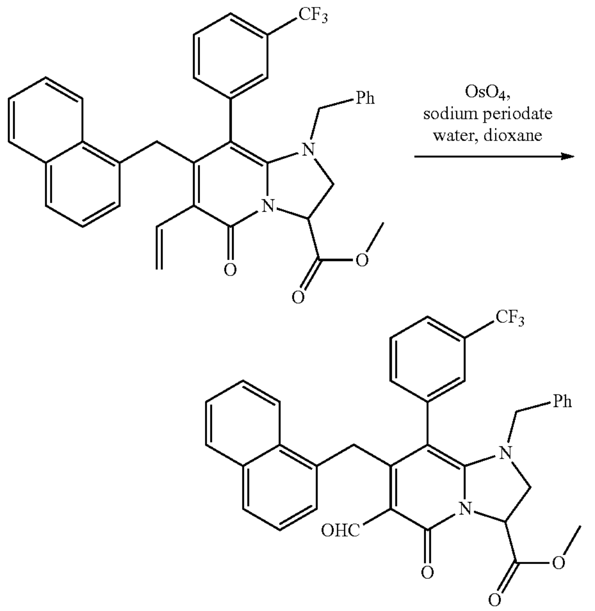

Methyl 1-benzyl-7-(naphthalen-1-ylmethyl)-5-oxo-8-(3-(trifluoromethyl)phenyl)-6-vinyl-1,2,3,5-tetrahydroimidazo [1,2-a]pyridine-3-carboxylate (5.46 g, 9.182 mmol) was dissolved in 1,4-Dioxane (100 mL). Water (27.5 mL), sodium periodate (5.86 g, 27.546 mmol) and osmium tetroxide (4.6 mL) was added. The reaction mixture was stirred for 2 hours quenched in ice water (500 mL) and extracted with ethyl acetate (3×250 mL). The organic layer was dried over sodium sulphate and concentrated under reduced pressure. The crude product was purified using column chromatography eluting with 30-40% Ethyl acetate/DCM to give methyl 1-benzyl-6-formyl-7-(naphthalen-1-ylmethyl)-5-oxo-8-(3-(trifluoromethyl)phenyl)-1,2,3,5-tetrahydroimidazo [1,2-a] pyridine-3-carboxylate (1.18 g, 21.8% yield). LCMS (Method-C3): 72.9% (RT: 2.379, 254.0 nm) (MS: ESI+ve597.2 [M+1]).

Step-2: Preparation of 1-benzyl-3-(methoxycarbonyl)-7-(naphthalen-1-ylmethyl)-5-oxo-8-(3-(trifluoromethyl)phenyl)-1,2,3,5-tetrahydroimidazo[1,2-a]pyridine-6-carboxylic acid

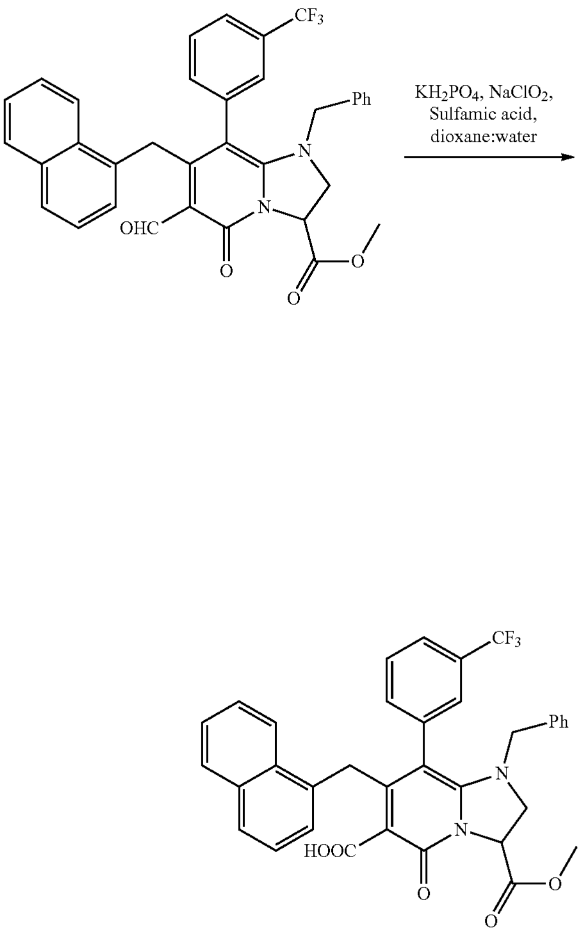

Methyl 1-benzyl-6-formyl-7-(naphthalen-1-ylmethyl)-5-oxo-8-(3-(trifluoromethyl)phenyl)-1,2,3,5-tetrahydroimidazo[1,2-a]pyridine-3-carboxylate (0.3 g, 0.5028 mmol) was dissolved in 1,4-Dioxane (12.5 mL). Water (2.5 mL) was added and the mixture was cooled to 0° C. Sulfamic acid, Sodium chlorite (0.059 g, 0.653 mmol) and Potassium phosphate (0.821 g, 6.034 mmol) in water (2.5 mL) were added and the mixture was stirred at room temperature for 2 hr. The reaction mixture was quenched into a mixture of ice (200 mL) and 1N HCl. The resulting precipitate was collected by filtration and dried under vacuum to give 1-benzyl-3-(methoxycarbonyl)-7-(naphthalen-1-ylmethyl)-5-oxo-8-(3-(trifluoromethyl)phenyl)-1,2,3,5-tetrahydroimidazo [1,2-a]pyridine-6-carboxylic acid (0.891 g, 95.1% yield). LCMS (Method-C3): 86.4%, (RT: 1.992, 355.0 nm) (MS: ESI+ve 613.2 [M+1]).

Step-3: Preparation of methyl 1-benzyl-6-carbamoyl-7-(naphthalen-1-ylmethyl)-5-oxo-8-(3-(trifluoromethyl)phenyl)-1,2,3,5-tetrahydroimidazo[1,2-a]pyridine-3-carboxylate

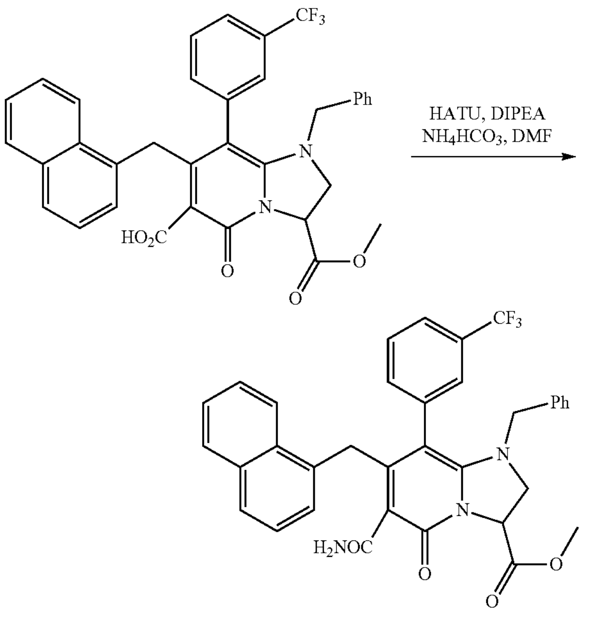

1-benzyl-3-(methoxycarbonyl)-7-(naphthalen-1-ylmethyl)-5-oxo-8-(3-(trifluoromethyl) phenyl)-1,2,3,5-tetrahydroimidazo[1,2-a]pyridine-6-carboxylic acid (0.292 g, 0.476 mmol) was dissolved in N,N-Dimethylformamide (10 mL). After cooling to 0° C., HATU (0.271 g, 0.7149 mmol) and Ammonium bicarbonate (0.075 g, 0.953 mmol) were added sequentially. The reaction mixture was stirred for 15 min then DIPEA (0.24 mL) was added. The reaction mixture was then stirred at room temperature for 16 hr. Water was added and the resulting precipitate was collected by filtration, dissolved in DCM (25 mL) then concentrated to give methyl 7-carbamoyl-2-(4-methoxybenzyl)-8-(naphthalen-1-ylmethyl)-6-oxo-9-(3-(trifluoromethyl)phenyl)-3,4-dihydro-2H,6H-pyrido[1,2-e][1,2,5] thiadiazine-4-carboxylate 1,1-dioxide. (0.179 g, 61.5% crude). LCMS (Method-C3): 65.1%, (RT: 1.910, 225.0 nm) (MS: ESI+ve 612.2 [M+1]).

Step-4: Preparation of 1-benzyl-6-carbamoyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 203)

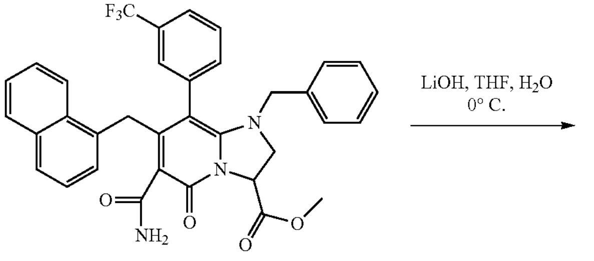

-continued

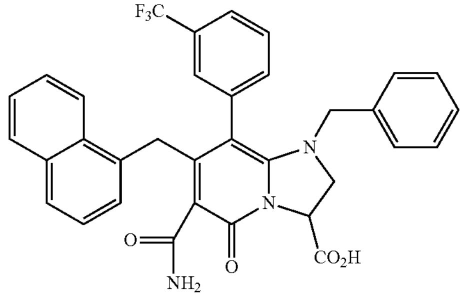

Compound 203

Methyl 1-benzyl-6-carbamoyl-7-(naphthalen-1-ylmethyl)-5-oxo-8-(3-(trifluoromethyl)phenyl)-1,2,3,5-tetrahydroimidazo[1,2-a]pyridine-3-carboxylate (0.179 g, 0.292 mmol) was hydrolyzed using the standard method as for (Compound 004) Step 3, and purified using Prep HPLC Method 9 to give 1-benzyl-6-carbamoyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 203 (0.014 g, 11.3%), as a white solid. LCMS (Method-C3): 100% (RT: 4.985, 254 nm) (MS: ESI+ve 598.2 [M+1]). $^1$H NMR: (400 MHz, DMSO) δ ppm: 3.58-3.79 (m, 3H), 4.03-4.17 (m, 1H), 4.46-4.57 (m, 1H), 4.86-4.89 (m, 1H), 5.13-5.15 (m, 1H), 6.76 (s, 1H), 6.82-6.84 (d, J=6 Hz, 1H), 6.98-7.39 (m, 11H), 7.50-7.52 (d, J=8 Hz, 1H), 7.65-7.67 (d, J=8 Hz, 1H), 7.77-7.79 (d, J=8 Hz, 1H), 8.68 (s, 2H).

Example 217

Synthesis of 1-benzyl-6-((dimethylamino)methyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 204)

Compound 204

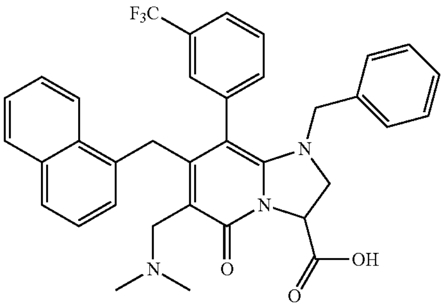

Step-1: Preparation of methyl 1-benzyl-6-((dimethylamino)methyl)-7-(naphthalen-1-ylmethyl)-5-oxo-8-(3-(trifluoromethyl)phenyl)-1,2,3,5-tetrahydroimidazo[1,2-a]pyridine-3-carboxylate

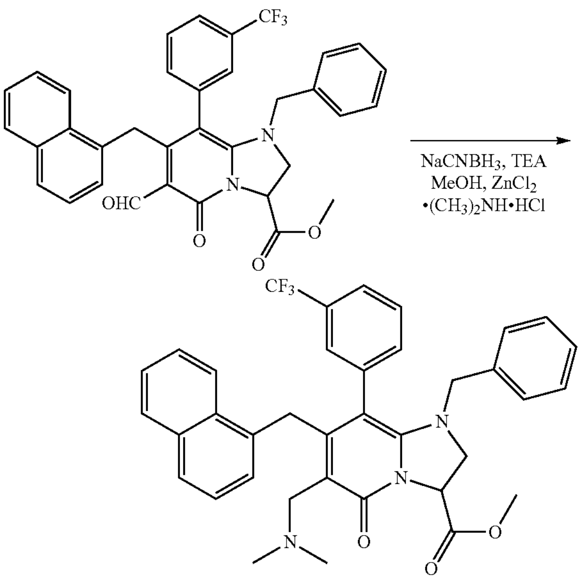

Methyl-1-benzyl-6-formyl-7-(naphthalen-1-ylmethyl)-5-oxo-8-(3-(trifluoro methyl)phenyl)-1,2,3,5-tetrahydroimidazo[1,2-a]pyridine-3-carboxylate (0.377 g, 0.631 mmol) and dimethyl amine hydrochloride (0.051 g, 0.631 mmol) was dissolved in methanol (8 mL) and cooled to 0° C. Triethylamine (0.35 mL) and zinc chloride (0.086 g, 0.063 mmol) and the reaction mixture was heated at 50° C. for 6 hr. After cooling to room temperature, sodium cyanoborohydride (0.158 g, 2.527 mmol) was added and the mixture was stirred for 16 hr. The mixture was concentrated then partitioned between dichloromethane (2×20 mL) and water (2×20 mL). The organic layers were dried and concentrated to give methyl 1-benzyl-6-((dimethylamino)methyl)-7-(naphthalen-1-ylmethyl)-5-oxo-8-(3-(trifluoromethyl) phenyl)-1,2,3,5-tetrahydroimidazo[1,2-a]pyridine-3-carboxylate. LCMS (Method-C3): 63.0% (RT: 1.745, 254.0 nm) (MS: ESI+ve 626.2 [M+1]).

Step-2: Preparation of 1-benzyl-6-((dimethylamino)methyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 204)

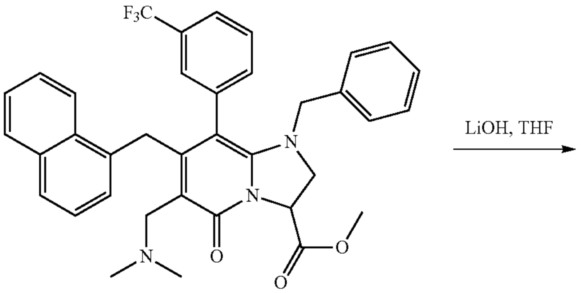

-continued

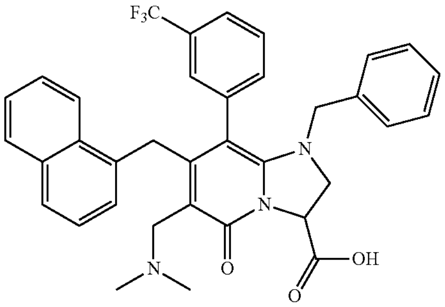

Compound 204

Methyl 1-benzyl-6-((dimethylamino)methyl)-7-(naphthalen-1-ylmethyl)-5-oxo-8-(3-(trifluoromethyl)phenyl)-1,2,3,5-tetrahydroimidazo[1,2-a]pyridine-3-carboxylate (0.500 g, 0.799 mmol) was dissolved in tetrahydrofuran (5 mL) was hydrolyzed using the standard method as for (Compound 004) Step 3, and the crude product was purified using Prep HPLC Method 5 to give 11-benzyl-6-((dimethylamino) methyl)-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 204) (0.033 g, 30.8%), as a white solid. LCMS (Method-J): 100% (RT: 4.647, 254 nm) (MS: ESI+ve 612.2s [M+1]). $^1$H NMR: (400 MHz, DMSO) δ ppm: 2.105 (s, 6H), 2.684 (s, 2H), 3.140 (s, 1H), 3.620-3.661 (d, J=16.4 Hz, 1H), 3.731-3.770 (m, 2H), 3.973-4.212 (m, 2H), 4.673-4.696 (d, J=9.2 Hz, 1H), 6.886-6.976 (m, 3H), 7.071-7.296 (m, 7H), 7.376-7.452 (m, 3H), 7.707-7.726 (m, 2H), 7.830-7.849 (d, J=7.6 Hz, 1H).

Example 218

Synthesis of 1-benzyl-7-(naphthalen-1-ylmethyl)-5-oxo-8-(3-(trifluoromethyl)phenyl)-1,2,3,5-tetrahydroimidazo[1,2-a]pyridine-3,6-dicarboxylic acid (Compound 209)

Compound 209

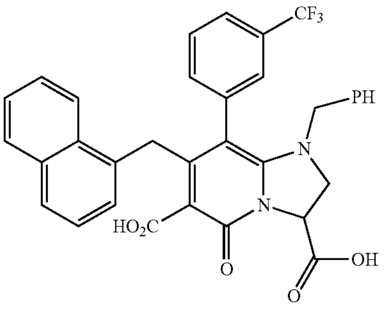

Step-1: Preparation of 1-benzyl-3-(methoxycarbonyl)-7-(naphthalen-1-ylmethyl)-5-oxo-8-(3-(trifluoromethyl)phenyl)-1,2,3,5-tetrahydroimidazo[1,2-a]pyridine-6-carboxylic acid

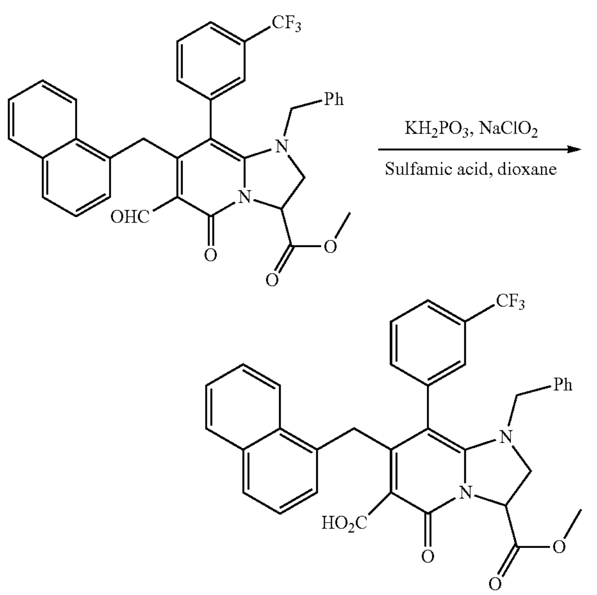

Methyl-1-benzyl-6-formyl-7-(naphthalen-1-ylmethyl)-5-oxo-8-(3-(trifluoromethyl)phenyl)-1,2,3,5-tetrahydroimidazo[1,2-a]pyridine-3-carboxylate (0.220 g, 0.368 mmol) was dissolved in 1,4-dioxane (9.1 mL) and water (1.8 mL). After cooling to 0° C., sulfamic acid (0.214 g, 2.215 mmol) and sodium chlorite (0.043 g, 0.479 mmol) were added followed by the dropwise addition of a solution of a solution of monopotassium phosphate (0.602 g, 4.425 mmol) in water (7 mL) over 15 min. The reaction mixture was stirred at room temperature for 2 hrs then poured into cold 1N HCl (pH=2). The resulting precipitate was collected by filtration, dissolved in dichloromethane (20 mL), dried and concentrated to give 1-benzyl-3-(methoxycarbonyl)-7-(naphthalen-1-ylmethyl)-5-oxo-8-(3-(trifluoromethyl)phenyl)-1,2,3,5-tetrahydroimidazo[1,2-a]pyridine-6-carboxylic acid (0.167 g, 73.9% yield). LCMS (Method-C3): 59.2% (RT: 2.021, 225.0 nm) (MS: ESI+ve 613.2 [M+1]).

Step-2: Preparation of 1-benzyl-7-(naphthalen-1-ylmethyl)-5-oxo-8-(3-(trifluoro methyl)phenyl)-1,2,3,5-tetrahydroimidazo[1,2-a]pyridine-3,6-dicarboxylic acid (Compound 209)

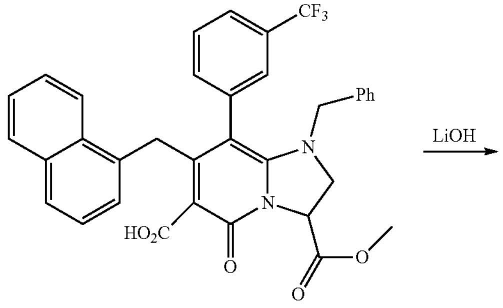

-continued

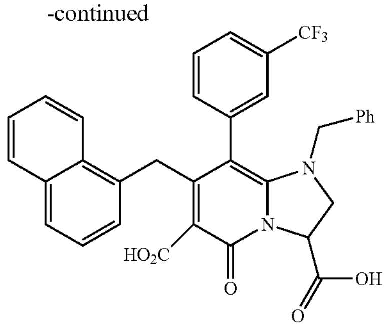

Compound 209

1-Benzyl-3-(methoxycarbonyl)-7-(naphthalen-1-ylmethyl)-5-oxo-8-(3-(trifluoromethyl) phenyl)-1,2,3,5-tetrahydroimidazo[1,2-a]pyridine-6-carboxylic acid (0.167 g, 0.272 mmol) was hydrolyzed using the standard method as for (Compound 004) Step 3, and the crude product was purified using Prep HPLC Method 5 to give 1-benzyl-7-(naphthalen-1-ylmethyl)-5-oxo-8-(3-(trifluoromethyl)phenyl)-1,2,3,5-tetrahydroimidazo[1,2-a]pyridine-3,6-dicarboxylic acid (Compound 209) (0.017 g, 10.9%), as a white solid. LCMS (Method-J): 98.4% (RT: 5.199, 214 nm) (MS: ESI+ve 599.2 [M+1]). $^1$H NMR: (400 MHz, DMSO) δ ppm: 3.674-3.700 (m, 1H), 3.756-3.883 (m, 2H), 4.095-4.223 (m, 2H), 4.593 (s, 1H), 4.960-5.087 (m, 1H), 6.888-6.906 (m, 2H), 6.974-7.000 (d, J=10.4 Hz, 1H), 7.158-7.207 (m, 5H), 7.290-7.432 (m, 5H), 7.592-7.603 (d, J=4.4 Hz, 1H), 7.686-7.706 (d, J=8 Hz, 1H), 7.814-7.834 (d, J=8 Hz, 1H), 15.323 (s, 1H).

Example 219

Synthesis of 1,1'-(hexane-1,6-diyl)bis(6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid)(Compound 193)

Compound 193

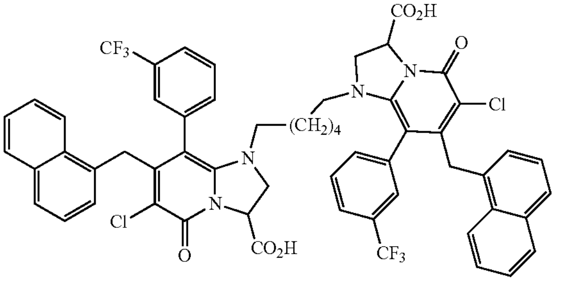

Step-1: Preparation of methyl 1-(6-bromohexyl)-6-chloro-7-(naphthalen-1-ylmethyl)-5-oxo-8-(3-(trifluoromethyl)phenyl)-1,2,3,5-tetrahydroimidazo[1,2-a]pyridine-3-carboxylate Step-2: Preparation of dimethyl 1,1'-(hexane-1,6-diyl)bis(6-chloro-7-(naphthalen-1-ylmethyl)-5-oxo-8-(3-(trifluoromethyl)phenyl)-1,2,3,5-tetrahydroimidazo[1,2-a]pyridine-3-carboxylate)

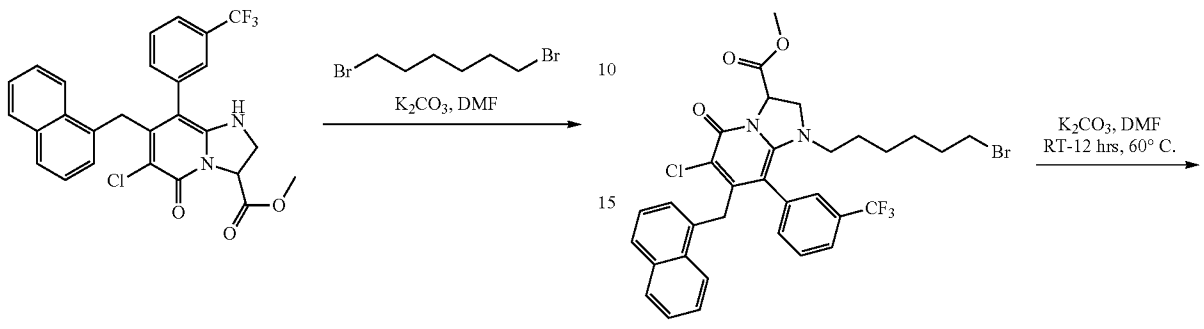

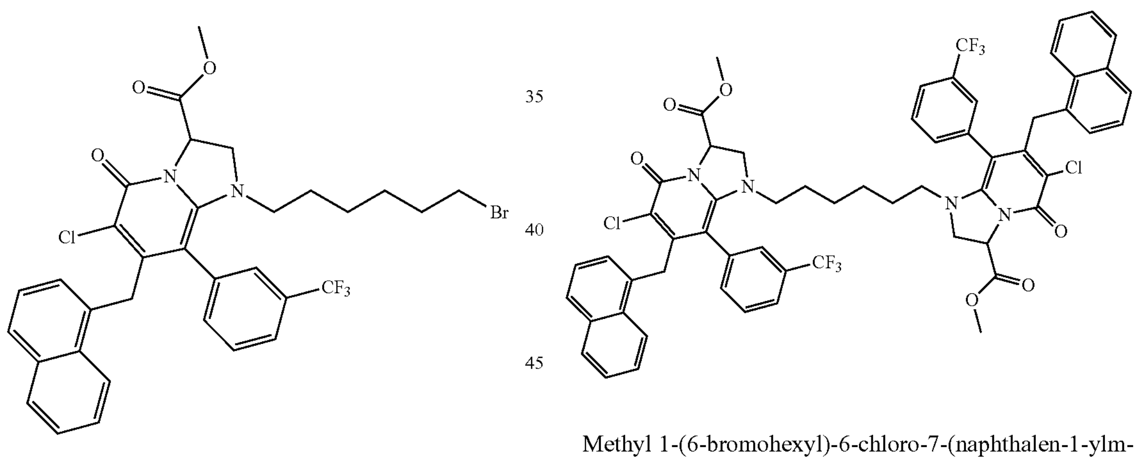

Methyl 6-chloro-7-(naphthalen-1-ylmethyl)-5-oxo-8-(3-(trifluoromethyl)phenyl)-1,2,3,5-tetrahydroimidazo[1,2-a]pyridine-3-carboxylate (5.0 g, 9.74 mmol) was dissolved in DMF (25.0 mL) and cooled to 0° C. Potassium carbonate (4.0 g, 29.2 mmol) was added and the mixture was stirred for 15 minutes. 1,6-Dibromohexane (2.85 g, 11.6 mmol) was added dropwise and the reaction mixture was stirred for 16 hr slowly warming to room temperature. Cool water (100 mL) was added and the mixture was extracted with ethyl acetate (3×150 mL), dried over sodium sulphate and concentrated under reduced pressure. The crude product was purified using column chromatography eluting with 10% ethyl acetate/dichloromethane to give methyl 1-(6-bromohexyl)-6-chloro-7-(naphthalen-1-ylmethyl)-5-oxo-8-(3-(trifluoromethyl)phenyl)-1,2,3,5-tetrahydroimidazo[1,2-a]pyridine-3-carboxylate (0.8 g, 12.14%). LCMS (Method-C3): 71.63% (RT: 6.207, 254.0 nm) (MS: ESI+ve 677.34 [M+2]).

Methyl 1-(6-bromohexyl)-6-chloro-7-(naphthalen-1-ylmethyl)-5-oxo-8-(3-(trifluoromethyl) phenyl)-1,2,3,5-tetrahydroimidazo[1,2-a]pyridine-3-carboxylate (0.8 g, 1.18 mmol) and methyl 6-chloro-7-(naphthalen-1-ylmethyl)-5-oxo-8-(3-(trifluoromethyl)phenyl)-1,2,3,5-tetrahydroimidazo[1,2-a]pyridine-3-carboxylate (0.606 g, 1.18 mmol) was dissolved in DMF (8.0 mL). Potassium carbonate (0.489 g, 3.55 mmol) was added and reaction mixture was stirred for 12 hr at room temperature then at 80° C. for 6 hr. The reaction mixture was cooled to room temperature, quenched in ice water (150 mL) and extracted with ethyl acetate (2×50 mL). The organic layer was dried over sodium sulphate and concentrated under reduced pressure to give Dimethyl 1,1'-(hexane-1,6-diyl)bis(6-chloro-7-(naphthalen-1-ylmethyl)-5-oxo-8-(3-(trifluoromethyl)phenyl)-1,2,3,5-tetrahydroimidazo[1,2-a]pyridine-3-carboxylate)(1.0 g) which was directly used for the next step without further purification. LCMS (Method-C3): 38.00% (RT: 2.442, 223.0 nm) (MS: ESI+ve 1109.1 [M+2]).

Step-3: Preparation 1,1'-(hexane-1,6-diyl)bis(6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid)(Compound 193)

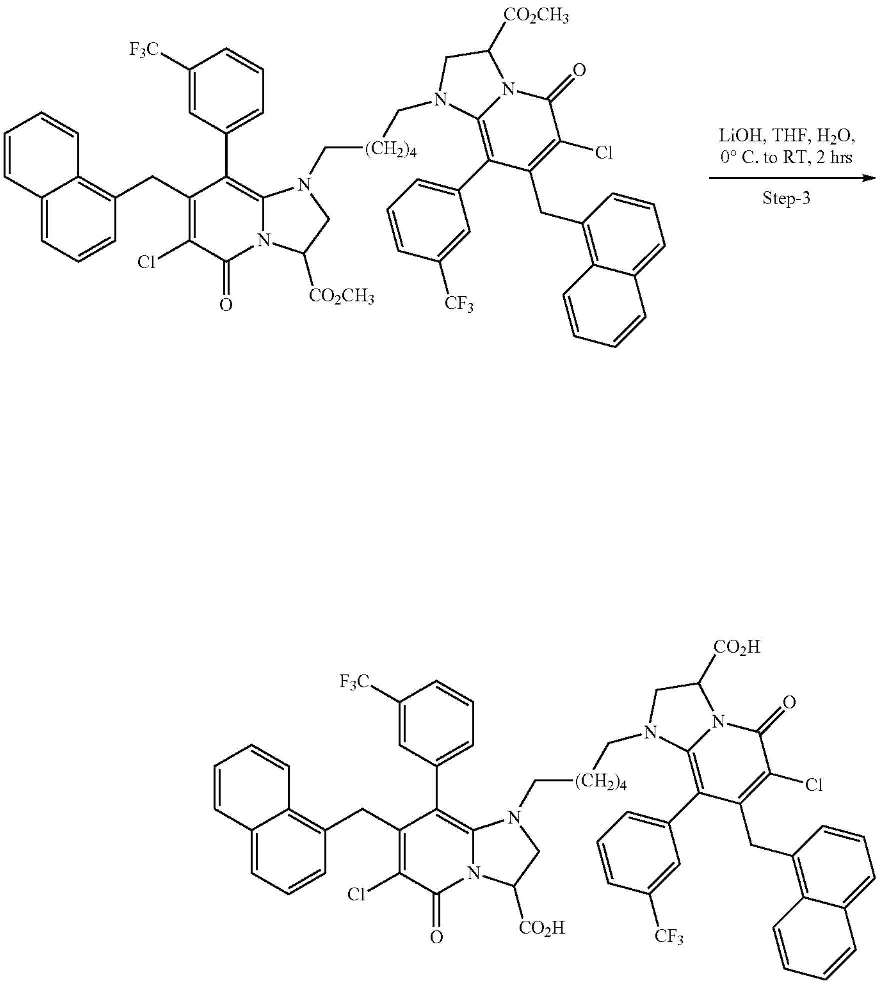

Compound 193

Dimethyl 1,1'-(hexane-1,6-diyl)bis(6-chloro-7-(naphthalen-1-ylmethyl)-5-oxo-8-(3-(trifluoro methyl)phenyl)-1,2,3,5-tetrahydroimidazo[1,2-a]pyridine-3-carboxylate) (1.0 g, 0.902 mmol) was hydrolyzed using the standard method as for (Compound 004) Step 3. The crude product was purified using Prep HPLC Method to give 1,1'-(hexane-1,6-diyl)bis(6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid)(Compound 193) (0.078 g, 8.00%). LCMS (Method-C3): 100% (RT 2.246, 225.0 nm) (MS: ESI+ve 1079.2 [M+]). $^1H$ NMR: (400 MHz, DMSO) δ ppm: 0.51 (s, 4H), 1.022 (s, 4H), 2.08-2.50 (m, 4H), 3.43-3.85 (m, 4H), 3.91-4.16 (m, 4H), 4.87 (s, 1H), 4.90 (s, 1H), 7.03-7.19 (m, 4H), 7.23-7.45 (m, 12H), 7.72-7.74 (m, 4H), 7.84-7.86 (d, J=8.0 Hz, 2H).

Example 220

Synthesis of 1,1'-(heptane-1,7-diyl)bis(6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid)(Compound 188)

Compound 188

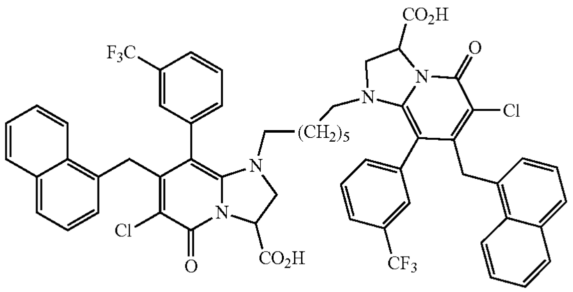

Prepared by a procedure similar to that reported for 1,1'-(hexane-1,6-diyl)bis(6-chloro-7-(naphthalen-1-ylmethyl)-5-oxo-8-(3-(trifluoromethyl)phenyl)-1,2,3,5-tetrahydroimidazo[1,2-a]pyridine-3-carboxylic acid)(Compound 193). The crude product was purified using Prep HPLC Method to give 1,1'-(heptane-1,7-diyl)bis(6-chloro-7-(naphthalen-1-ylmethyl)-5-oxo-8-(3-(trifluoromethyl) phenyl)-1,2,3,5-tetrahydroimidazo[1,2-a]pyridine-3-carboxylic acid) (Compound 188) (0.050 g, 5.13%). LCMS (Method-C3): 100% (RT 2.205, 225.0 nm) (MS: ESI+ve 1079.92 [M+]). $^1$H NMR: (400 MHz, DMSO) δ ppm: 0.41 (s, 4H), 0.60 (m, 2H), 0.88-1.24 (m, 4H), 2.27-2.34 (m, 4H), 3.59-3.65 (q, 2H), 3.96-4.17 (m, 6H), 5.06 (s, 1H), 5.08 (s, 1H), 7.03-7.13 (m, 3H), 7.23-7.49 (m, 13H), 7.71-7.77 (q, 4H), 7.86-7.88 (d, J=8.0 Hz, 2H).

Example 221

Synthesis of 1-benzyl-6-chloro-7-(isoquinolin-8-ylmethyl)-5-oxo-8-(3-(trifluoromethyl)phenyl)-1,2,3,5-tetrahydroimidazo[1,2-a]pyridine-3-carboxylic acid (Compound 205)

Compound 205

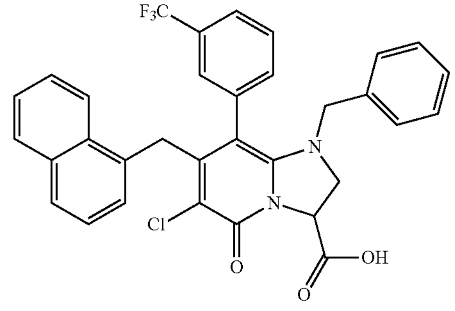

Step 1: Preparation of 5-(2-chloro-1-hydroxyethylidene)-2,2-dimethyl-1,3-dioxane-4,6-dione

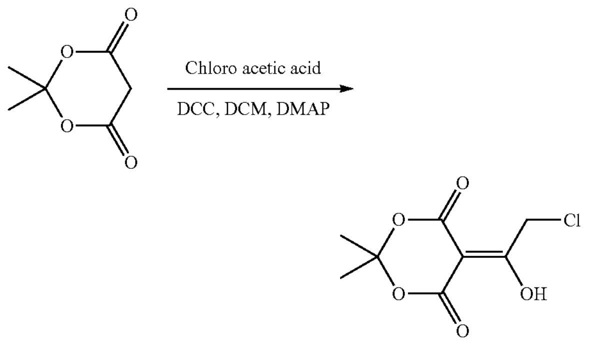

Chloroacetic acid (4.72 g, 49.94 mmol), Meldrum's acid (7.2 g, 49.94 mmol) and 4-Dimethylaminopyridine (DMAP) (7.32 g, 59.92 mmol) were dissolved in DCM (250 mL) and cooled to 0° C. A solution of N,N'-Dicyclohexylcarbodiimide (DCC)(9.97 g, 48.33 mmol) in DCM (50 mL) was added dropwise at 0° C. and stirred for 16 hr warming to room temperature. The reaction mixture was filtered and 6% aq. $KHSO_4$ solution (150 mL) was added. The mixture was extracted with DCM (2×250 mL) and the organic layers were dried over sodium sulphate and concentrated to give 5-(2-chloro-1-hydroxyethylidene)-2,2-dimethyl-1,3-dioxane-4,6-dione as a yellow solid. (11 g, crude). The crude product was used without further purification in the next step.

Step-2: Preparation of methyl 1-benzyl-7-(chloromethyl)-5-oxo-8-(3-(trifluoromethyl)phenyl)-1,2,3,5-tetrahydroimidazo[1,2-a]pyridine-3-carboxylate

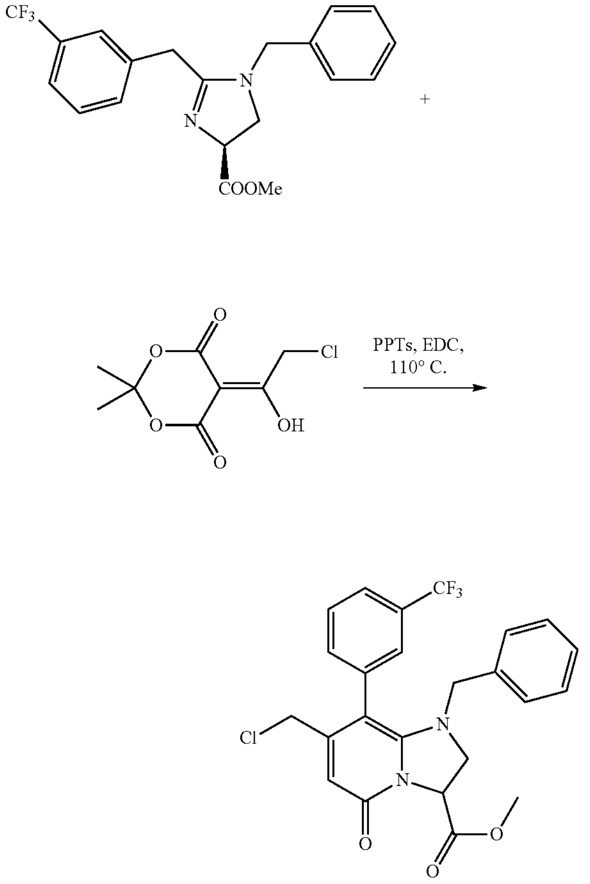

Methyl (S)-1-benzyl-2-(3-(trifluoromethyl)benzyl)-4,5-dihydro-1H-imidazole-4-carboxylate (2.7 g, 7.173 mmol) and 5-(2-chloro-1-hydroxyethylidene)-2,2-dimethyl-1,3-dioxane-4,6-dione (4.74 g, 21.52 mmol) dissolved in 1,2 dichloroethane (60 mL). Pyridinium p-toluenesulfonate (PPTs)(1.98 g, 7.89 mmol) was added and the mixture was stirred at 120° C. for 16 hr. The reaction mixture was quenched with saturated aqueous sodium bicarbonate (50 mL) and extracted with DCM (3×50 mL). The organic layer was dried over sodium sulphate and concentrated under reduced pressure. The crude product was purified using column chromatography eluting with 3% methanol/DCM to give methyl 1-benzyl-7-(chloromethyl)-5-oxo-8-(3-(trifluoromethyl)phenyl)-1,2,3,5-tetrahydroimidazo[1,2-a]pyridine-3-carboxylate (1 g, 17.13%). LCMS (Method-X): 77.16% (RT: 1.021, 241 nm) (MS: ESI+ve 477.3 [M+H]).

Step-3: Preparation of methyl 1-benzyl-7-(isoquinolin-8-ylmethyl)-5-oxo-8-(3-(trifluoromethyl)phenyl)-1,2,3,5-tetrahydroimidazo[1,2-a]pyridine-3-carboxylate

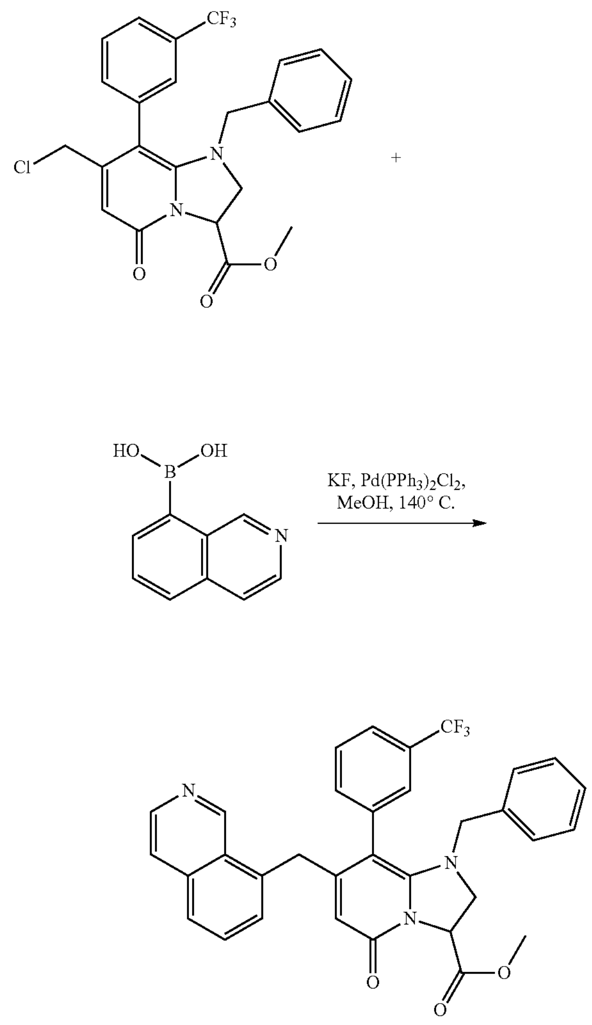

Methyl 1-benzyl-7-(chloromethyl)-5-oxo-8-(3-(trifluoromethyl)phenyl)-1,2,3,5-tetrahydroimidazo[1,2-a]pyridine-3-carboxylate (1.2 g, 2.518 mmol), isoquinolin-8-ylboronic acid (0.87 g, 5.037 mmol) and potassium fluoride (0.292 g, 5.037 mmol) were dissolved in methanol (12.0 mL) and degassed with N2 for 10-15 minutes at room temperature. Bis(triphenylphosphine)palladium chloride (0.088 g, 0.125 mmol) was added and the reaction mixture was heated in a microwave reactor, under microwave irradiation at 140° C. for 10 minutes. The mixture was concentrated then partitioned between water (50 mL) and ethyl acetate (3×50 mL). The combined organic layers were dried over sodium sulphate and concentrated. The crude product was purified using column chromatography eluting with 4% Methanol/Dichloromethane to give methyl 1-benzyl-7-(isoquinolin-8-ylmethyl)-5-oxo-8-(3-(trifluoromethyl)phenyl)-1,2,3,5-tetrahydroimidazo[1,2-a]pyridine-3-carboxylate as a brown gum. (0.3 g, 13.4%). LCMS (Method-C3): 30.87% (RT: 1.575, 230.0 nm) (MS: ESI+ve 570.2 [M+1]).

Step-4: Preparation of methyl 1-benzyl-6-chloro-7-(isoquinolin-8-ylmethyl)-5-oxo-8-(3-(trifluoromethyl)phenyl)-1,2,3,5-tetrahydroimidazo[1,2-a]pyridine-3-carboxylate

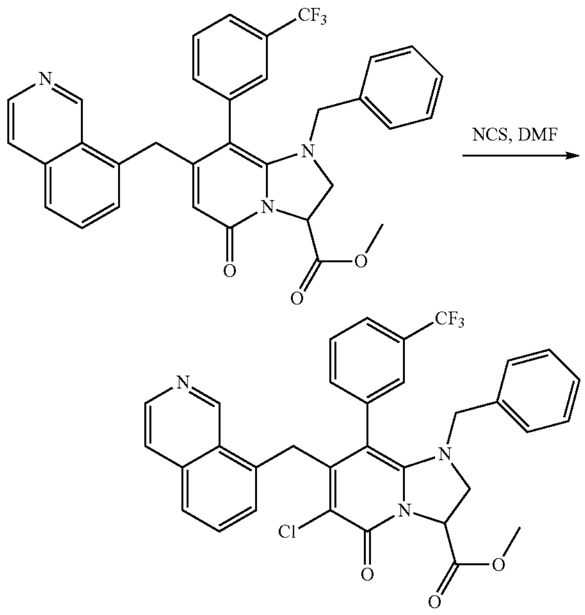

Methyl 1-benzyl-7-(isoquinolin-8-ylmethyl)-5-oxo-8-(3-(trifluoromethyl)phenyl)-1,2,3,5-tetrahydroimidazo[1,2-a]pyridine-3-carboxylate (0.3 g, 0.526 mmol) was dissolved in DMF (10 mL). N-Chlorosuccinimide (NCS) (0.077 g, 0.579 mmol) was added in portions at 10° C. The reaction mixture was stirred for 2 hr then quenched with water (100 mL). The resulting precipitate was dissolved in dichloromethane (50 mL), dried over sodium sulphate and concentrated under reduced pressure to give the crude product which was purified using column chromatography eluting with 0-50% ethyl acetate/dichloromethane to give methyl 1-benzyl-6-chloro-7-(isoquinolin-8-ylmethyl)-5-oxo-8-(3-(trifluoromethyl)phenyl)-1,2,3,5-tetrahydroimidazo[1,2-a]pyridine-3-carboxylate as a brown solid (0.2 g, 62.8%). LCMS (Method-C3): 75.58% (RT: 1.632, 230.0 nm) (MS: ESI+ve 604.13 [M+1]).

Step-5: Preparation 1-benzyl-6-chloro-7-(isoquinolin-8-ylmethyl)-5-oxo-8-(3-(trifluoromethyl)phenyl)-1,2,3,5-tetrahydroimidazo[1,2-a]pyridine-3-carboxylic acid (Compound 205)

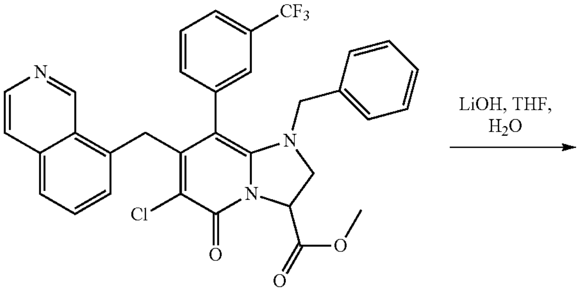

-continued

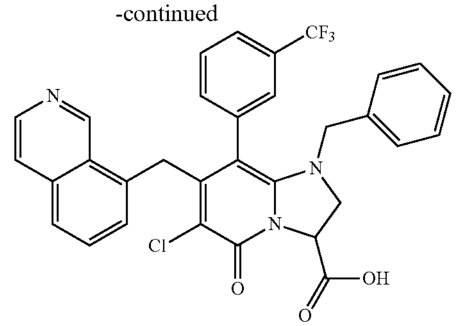

Compound 205

Methyl 1-benzyl-6-chloro-7-(isoquinolin-8-ylmethyl)-5-oxo-8-(3-(trifluoromethyl)phenyl)-1,2,3,5-tetrahydroimidazo[1,2-a]pyridine-3-carboxylate (0.2 g, 0.331 mmol) was hydrolyzed using the standard method as for (Compound 004) Step 3, and the crude product was purified using Prep HPLC Method 1 to give 1-benzyl-6-chloro-7-(isoquinolin-8-ylmethyl)-5-oxo-8-(3-(trifluoromethyl)phenyl)-1,2,3,5-tetrahydroimidazo[1,2-a]pyridine-3-carboxylic acid as a white solid (Compound 205) (0.028 g, 14.33%). LCMS (Method-C3): 100.0% (RT 1.474, 232.0 nm) (MS: ESI+ve 590.21 [M+1]). $^{1}H$ NMR: (400 MHz, DMSO) δ ppm: 3.41-3.49 (t, 2H), 3.63-3.85 (m, 2H), 4.06-4.30 (m, 2H), 4.73-4.75 (d, J=8.8 Hz, 1H), 6.80-9.85 (d, J=21.6 Hz, 3H), 7.16-7.29 (m, 7H), 7.64-7.78 (m, 3H), 8.42-8.43 (d, J=5.6 Hz, 1H), 9.10-9.13 (d, J=9.2 Hz, 1H).

Example 222

Synthesis of 1-benzyl-6-chloro-5-oxo-7-(quinolin-4-ylmethyl)-8-(3-(trifluoromethyl)phenyl)-1,2,3,5-tetrahydroimidazo[1,2-a]pyridine-3-carboxylic acid (Compound 206)

Compound 206

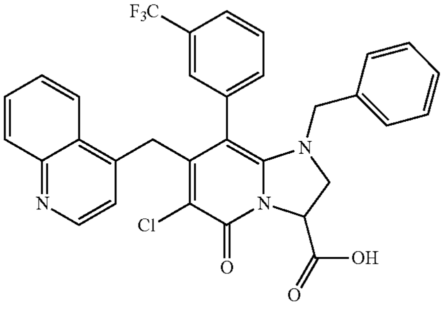

Prepared by a procedure similar to that reported for 1-benzyl-6-chloro-7-(isoquinolin-8-ylmethyl)-5-oxo-8-(3-(trifluoromethyl)phenyl)-1,2,3,5-tetrahydroimidazo[1,2-a]pyridine-3-carboxylic acid (Compound 205) as a white solid. The crude product was purified using Prep HPLC Method to give 1-benzyl-6-chloro-5-oxo-7-(quinolin-4-ylmethyl)-8-(3-(trifluoromethyl)phenyl)-1,2,3,5-tetrahydroimidazo[1,2-a]pyridine-3-carboxylic acid (Compound 206) as a white solid (0.03 g, 15.36%). LCMS (Method-C3): 100.0% (RT 1.790, 230.0 nm) (MS: ESI+ve 590.15 [M+1]). $^{1}H$ NMR: (400 MHz, DMSO) δ ppm: 3.59-3.61 (m, 1H), 3.73-3.86 (m, 2H), 3.96-4.02 (m, 1H), 4.06-4.21 (m, 2H), 5.16-5.19 (d, J=10.8 Hz, 1H), 6.86-6.96 (t, 2H), 7.04-7.06 (t, 2H), 7.16-7.36 (m, 6H), 7.44-7.48 (t, 1H), 7.66-7.70 (t, 1H), 7.76-7.80 (t, 1H), 7.94-7.96 (d, J=8.4 Hz, 1H), 8.77-8.79 (t, 1H), 13.59 (s, 1H).

Example 223

Synthesis of 1-benzyl-6-chloro-7-(isoquinolin-4-ylmethyl)-5-oxo-8-(3-(trifluoromethyl) phenyl)-1,2,3,5-tetrahydroimidazo[1,2-a] pyridine-3-carboxylic acid (Compound 210)

Compound 210

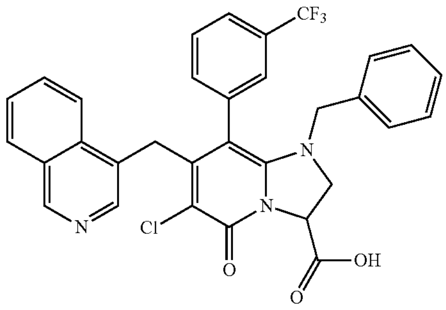

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo[,2-a]pyridine-3-carboxylic acid (Compound 206) as a white solid. The crude product was purified using Prep HPLC Method 6 to give 1-benzyl-6-chloro-7-(isoquinolin-4-ylmethyl)-5-oxo-8-(3-(trifluoromethyl)phenyl)-1,2,3,5-tetrahydroimidazo[1,2-a]pyridine-3-carboxylic acid (Compound 210) (0.0021 g, 17.92%). LCMS (Method-C3): 96.56% (RT 3.917, 230.0 nm) (MS: ESI+ve 590.41 [M+2]). $^{1}H$ NMR: (400 MHz, DMSO) δ ppm: 3.56-3.63 (m, 1H), 3.73-3.92 (m, 2H), 3.96-4.17 (m, 3H), 5.16-5.19 (m, 1H), 6.84-6.87 (t, 2H), 6.94 (s, 1H), 7.18-7.23 (m, 4H), 7.27-7.35 (m, 2H), 7.59-7.70 (m, 3H), 7.97-7.99 (d, J=8.4 Hz, 1H), 8.05-8.07 (d, J=8.4 Hz, 1H), 9.142 (s, 1H).

Example 224

Synthesis of 1-benzyl-7-(isoquinolin-4-ylmethyl)-5-oxo-8-(3-(trifluoromethyl)phenyl)-1,2,3,5-tetrahydroimidazo[1,2-a]pyridine-3-carboxylic acid (Compound 221)

Compound 221

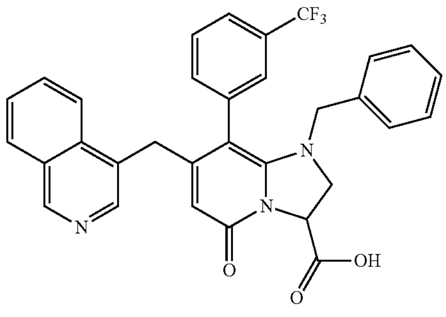

Prepared by a procedure similar to that reported for 1-benzyl-6-chloro-7-(isoquinolin-4-ylmethyl)-5-oxo-8-(3-(trifluoromethyl)phenyl)-1,2,3,5-tetrahydroimidazo[1,2-a] pyridine-3-carboxylic acid (Compound 210), omitting the chlorination step. The crude product was purified using Prep HPLC Method 5 to give 1-benzyl-7-(isoquinolin-4-ylmethyl)-5-oxo-8-(3-(trifluoromethyl)phenyl)-1,2,3,5-tetrahydroimidazo[1,2-a]pyridine-3-carboxylic acid (Compound 221) (0.009 g, 7.8%), as a white solid. LCMS (Method-J): 100% (RT: 4.106, 202 nm) (MS: ESI+ve 556.2 [M+1]). $^1$H NMR: (400 MHz, DMSO) δ ppm: 3.172 (s, 1H), 3.482-3.535 (m, 1H), 3.729-3.881 (m, 2H), 3.956-4.031 (m, 1H), 4.979 (s, 1H), 5.210-5.243 (d, J=13.2 Hz, 1H), 6.890 (s, 2H), 7.210-7.238 (m, 3H), 7.373-7.448 (m, 3H), 7.523-7.601 (m, 1H), 7.652-7.737 (m, 3H), 8.093-8.113 (d, J=8 Hz, 1H), 8.185 (s, 1H), 9.188 (s, 1H).

Example 225

Synthesis of 1-benzyl-6-chloro-5-oxo-7-(quinolin-5-ylmethyl)-8-(3-(trifluoromethyl) phenyl)-1,2,3,5-tetrahydroimidazo[1,2-a]pyridine-3-carboxylic acid (Compound 211)

Compound 211

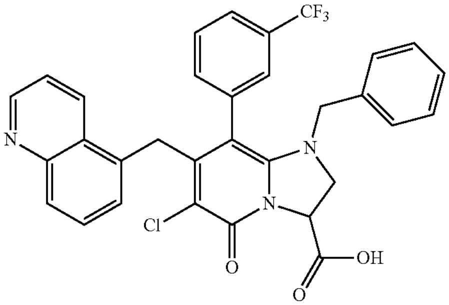

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo[1,2-a]pyridine-3-carboxylic acid (Compound 206) as a white solid. The crude product was purified using Prep HPLC Method 1 to give 1-benzyl-6-chloro-5-oxo-7-(quinolin-5-ylmethyl)-8-(3-(trifluoromethyl)phenyl)-1,2,3,5-tetrahydroimidazo[1,2-a]pyridine-3-carboxylic acid (Compound 211) (0.0011 g, 12.51%). LCMS (Method-J): 100% (RT 3.817, 235.0 nm) (MS: ESI+ve 590.12 [M+2]). $^1$H NMR: (400 MHz, DMSO) δ ppm: 3.63-4.17 (m, 6H), 4.725 (s, 1H), 6.86 (s, 3H), 7.16-7.26 (m, 6H), 7.36 (s, 1H), 7.65-7.68 (t, J=7.6 Hz, 1H), 7.83-7.85 (d, J=8.0 Hz, 1H), 8.13-8.15 (m, 1H), 8.47 (s, 1H), 8.81 (s, 1H).

Example 226

Synthesis of 1-benzyl-5-oxo-7-(quinolin-5-ylmethyl)-8-(3-(trifluoromethyl) phenyl)-1,2,3,5-tetrahydroimidazo[1,2-a] pyridine-3-carboxylic acid (Compound 222)

Compound 222

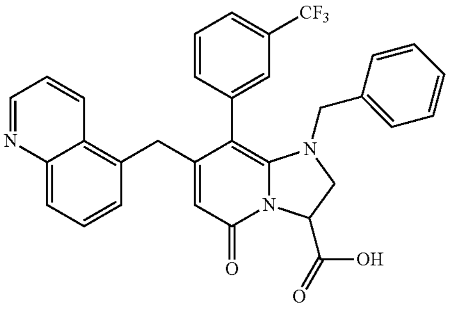

Prepared by a procedure similar to that reported for 1-benzyl-6-chloro-5-oxo-7-(quinolin-5-ylmethyl)-8-(3-(trifluoromethyl)phenyl)-1,2,3,5-tetrahydroimidazo[1,2-a]pyridine-3-carboxylic acid (Compound 211), omitting the chlorination step. The crude product was purified using Prep HPLC Method 1 to give 1-benzyl-5-oxo-7-(quinolin-5-ylmethyl)-8-(3-(trifluoromethyl) phenyl)-1,2,3,5-tetrahydroimidazo[1,2-a]pyridine-3-carboxylic acid (Compound 222) as a white solid (0.023 g, 9%). LCMS (Method-J): 100% (RT 4.138, 254.0 nm) (MS: ESI+ve 556 [M+1]). $^1$H NMR: (400 MHz, DMSO) δ ppm: 3.58 (s, 1H), 3.74-3.87 (m, 5H), 4.71-4.73 (d, J=8, 1H), 5.30 (s, 1H), 6.90-6.92 (d, J=6, 2H), 7.18-7.20 (d, J=6, 4H), 7.29-7.31 (d, J=6.8, 2H), 7.38-7.35 (d, J=6, 2H), 7.45 (s, 1H), 7.61-7.65 (t, 1H), 7.85-7.87 (d, J=8.4, 1H), 8.05-8.07 (d, J=8.4, 1H), 8.83 (s, 1H).

Example 227

Synthesis of 1-benzyl-6-chloro-7-(isoquinolin-5-ylmethyl)-5-oxo-8-(3-(trifluoromethyl)phenyl)-1,2,3,5-tetrahydroimidazo[1,2-a]pyridine-3-carboxylic acid (Compound 212)

Compound 212

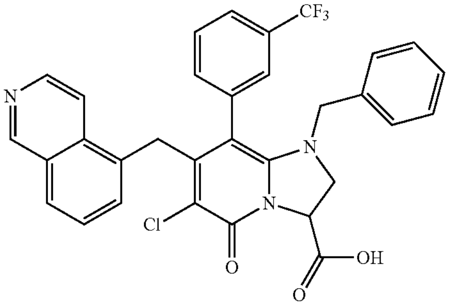

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo1,2-a]pyridine-3-carboxylic acid (Compound 206) as a white solid.

The crude product was purified using Prep HPLC Method 1 to give 1-benzyl-6-chloro-7-(isoquinolin-5-ylmethyl)-5-oxo-8-(3-(trifluoromethyl)phenyl)-1,2,3,5-tetrahydroimidazo[1,2-a]pyridine-3-carboxylic acid (Compound 212) (0.120 g, 72.27%). LCMS (Method-C3): 100% (RT 1.525, 202.0 nm) (MS: ESI+ve 590.6 [M+2]). $^{1}$H NMR: (400 MHz, DMSO) δ ppm: 3.53 (s, 1H), 3.66-3.77 (m, 3H), 3.87-4.12 (m, 3H), 4.94-4.97 (d, J=9.6 Hz, 1H), 6.79-6.85 (t, 3H), 7.16-7.21 (d, J=20.4 Hz, 3H), 7.25-7.31 (m, 4H), 7.50-7.53 (t, 1H), 7.57-7.61 (t, 1H), 7.92-7.94 (d, J=8 Hz, 1H), 8.32-8.33 (d, J=5.6 Hz, 1H), 9.21 (s, 1H).

Example 228

Synthesis of methyl 1-benzyl-7-(isoquinolin-5-ylmethyl)-5-oxo-8-(3-(trifluoromethyl) phenyl)-1,2,3,5-tetrahydroimidazo[1,2-a] pyridine-3-carboxylate (Compound 223)

Compound 223

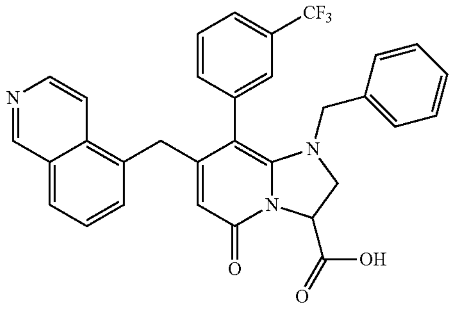

Prepared by a procedure similar to that reported for 1-benzyl-6-chloro-7-(isoquinolin-5-ylmethyl)-5-oxo-8-(3-(trifluoromethyl)phenyl)-1,2,3,5-tetrahydroimidazo[1,2-a] pyridine-3-carboxylic acid (Compound 212), omitting the chlorination step. The crude product was purified using Prep HPLC Method 1 to give 1-benzyl-7-(isoquinolin-5-ylmethyl)-5-oxo-8-(3-(trifluoromethyl) phenyl)-1,2,3,5-tetrahydroimidazo[1,2-a] pyridine-3-carboxylate (Compound 223) as a white solid (0.033 g, 12.6%). LCMS (Method-J): 100% (RT 4.006, 340.0 nm) (MS: ESI+ve 556 [M+1]). $^{1}$H NMR: (400 MHz, DMSO) δ ppm: 3.47 (s, 1H), 3.69-3.83 (m, 5H), 4.63 (s, 1H), 5.20 (s, 1H), 6.89 (s, 2H), 7.23 (s, 4H), 7.38 (s, 2H), 7.46-7.48 (d, J=6.8, 2H), 7.56-7.60 (t, 1H), 7.95-7.97 (d, J=8, 1H), 8.36-8.38 (d, J=5.2, 1H), 8.46 (s, 1H), 9.24 (s, 1H).

Example 229

Synthesis of 1-benzyl-6-chloro-5-oxo-7-(quinolin-8-ylmethyl)-8-(3-(trifluoromethyl) phenyl)-1,2,3,5-tetrahydroimidazo[1,2-a]pyridine-3-carboxylic acid (Compound 213)

Compound 213

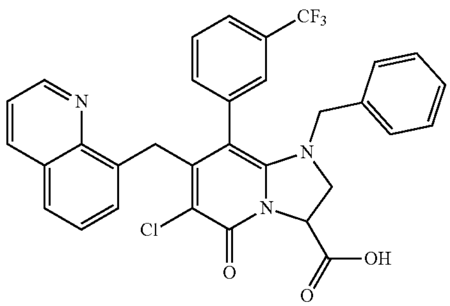

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo1,2-a]pyridine-3-carboxylic acid (Compound 206) as a white solid. The crude product was purified using Prep HPLC Method 7 to give 1-benzyl-6-chloro-5-oxo-7-(quinolin-8-ylmethyl)-8-(3-(trifluoromethyl)phenyl)-1,2,3,5-tetrahydroimidazo[1,2-a]pyridine-3-carboxylic acid (Compound 213), (0.0011 g, 09.38%). LCMS (Method-C2): 100% (RT 1.367, 202.0 nm) (MS: ESI+ve 590.4 [M+2]). 1H NMR: (400 MHz, DMSO) δ ppm: 3.494 (m, 1H), 3.64-3.80 (m, 2H), 3.91 (s, 1H), 4.16-4.37 (m, 2H), 4.89 (s, 1H), 6.81-6.85 (m, 3H), 7.11-7.31 (m, 7H), 7.44-7.45 (m, 1H), 7.51-7.55 (t, J=7.6 Hz, 1H), 7.79-7.81 (d, J=8.0 Hz, 1H), 8.26-8.28 (d, J=8.0 Hz, 1H), 8.68 (s, 1H).

Example 230

Synthesis of 1-benzyl-5-oxo-7-(quinolin-8-ylmethyl)-8-(3-(trifluoromethyl) phenyl)-1,2,3,5-tetrahydroimidazo[1,2-a] pyridine-3-carboxylic acid (Compound 224)

Compound 224

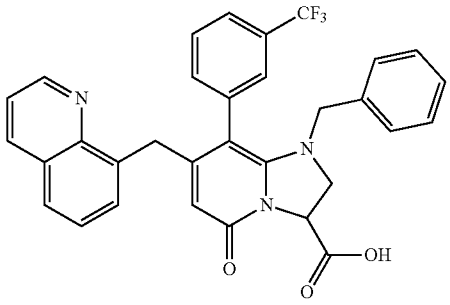

Prepared by a procedure similar to that reported for 1-benzyl-6-chloro-5-oxo-7-(quinolin-8-ylmethyl)-8-(3-(trifluoromethyl)phenyl)-1,2,3,5-tetrahydroimidazo1,2-a]pyridine-3-carboxylic acid (Compound 213), omitting the chlorination step. The crude product was purified using Prep HPLC Method 1 to give 1-benzyl-5-oxo-7-(quinolin-8-ylmethyl)-8-(3-(trifluoromethyl) phenyl)-1,2,3,5-tetrahydroimidazo[1,2-a]pyridine-3-carboxylic acid (Compound 224), as a white solid (0.005 g, 3.94%). LCMS (Method-J): 99.8% (RT 4.893, 230.0 nm) (MS: ESI+ve 556 [M+1]). $^1$H NMR: (400 MHz, DMSO) δ ppm: 3.45-3.48 (d, J=10, 2H), 3.79-3.90 (m, 2H), 3.94-3.96 (d, J=8.4, 2H), 4.94-4.97 (d, J=9.6, 1H), 5.40-5.43 (d, J=10.8, 1H), 6.88 (s, 2H), 7.12 (s, 1H), 7.20-7.22 (d, J=6, 3H), 7.29-7.31 (m, 1H), 7.45-7.48 (m, 3H), 7.47-7.54 (m, 1H), 7.81-7.83 (d, J=8, 1H), 8.28-8.30 (d, J=7.2, 1H), 8.74 (s, 1H).

Example 231

Synthesis of 1,7-dibenzyl-6-chloro-5-oxo-8-(3-(trifluoromethyl)phenyl)-1,2,3,5-tetrahydroimidazo[1,2-a]pyridine-3-carboxylic acid (Compound 214)

Compound 214

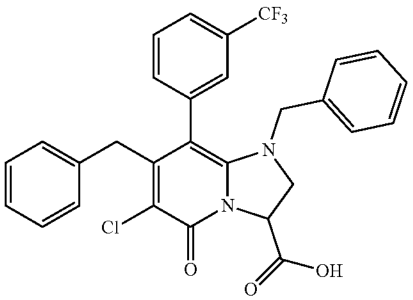

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo[1,2-a]pyridine-3-carboxylic acid (Compound 206), as a white solid. The crude product was purified using Prep HPLC Method 6 to give 1,7-dibenzyl-6-chloro-5-oxo-8-(3-(trifluoromethyl) phenyl)-1,2,3,5-tetrahydroimidazo[1,2-a]pyridine-3-carboxylic acid (Compound 214), (0.110 g, 53.74%). LCMS (Method-J): 100% (RT 4.839, 222.0 nm) (MS: ESI+ve 539.1 [M+2]). $^1$H NMR: (400 MHz, DMSO) δ ppm: 3.58-3.60 (m, 1H), 3.72-3.85 (m, 2H), 3.92-4.18 (m, 3H), 5.17-5.19 (t, 1H), 6.86-7.04 (m, 4H), 7.14-7.36 (m, 6H), 7.48-7.52 (t, 1H), 7.62-7.65 (t, 2H), 7.78-7.82 (t, 1H), 8.14-8.16 (d, J=8.4 Hz, 1H), 13.52-13.63 (d, J=45.2 Hz, 1H).

Example 232

Synthesis of 1,7-dibenzyl-5-oxo-8-(3-(trifluoromethyl)phenyl)-1,2,3,5-tetrahydroimidazo[1,2-a]pyridine-3-carboxylic acid (Compound 235)

Compound 235

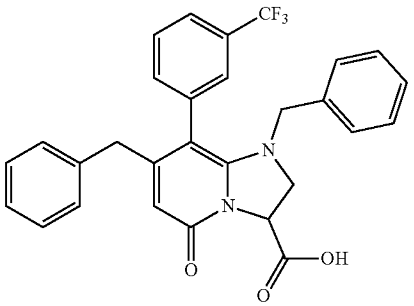

Prepared by a procedure similar to that reported for 1,7-dibenzyl-6-chloro-5-oxo-8-(3-(trifluoromethyl)phenyl)-1,2,3,5-tetrahydroimidazo[1,2-a]pyridine-3-carboxylic acid (Compound 214), omitting the chlorination step. The crude product was purified using Prep HPLC Method 1 to give 1,7-dibenzyl-5-oxo-8-(3-(trifluoromethyl) phenyl)-1,2,3,5-tetrahydroimidazo[1,2-a] pyridine-3-carboxylic acid (Compound 235), as a white solid (0.045 g, 17.79%). LCMS (Method-J): 99.20% (RT 5.194, 254.0 nm) (MS: ESI+ve 505 [M+1]). $^1$H NMR: (400 MHz, DMSO) δ ppm: 3.41 (s, 3H), 3.78 (s, 2H), 3.91-4.0 (m, 1H), 4.97-4.99 (d, J=10, 1H), 5.59 (s, 1H), 6.76-6.78 (d, J=6, 4H), 7.00 (s, 1H), 7.18 (s, 6H), 7.39 (s, 2H), 7.53 (s, 1H).

Example 233

Synthesis of 1-benzyl-7-(3-(tert-butyl) benzyl)-6-chloro-5-oxo-8-(3-(trifluoromethyl) phenyl)-1,2,3,5-tetrahydroimidazo[1,2-a] pyridine-3-carboxylic acid (Compound 215)

Compound 215

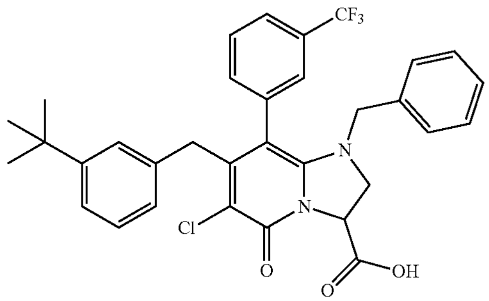

Prepared by a procedure similar to that reported for 1-benzyl-6-chloro-5-oxo-7-(quinolin-4-ylmethyl)-8-(3-(trifluoromethyl) phenyl)-1,2,3,5-tetrahydroimidazo[1,2-a]pyridine-3-carboxylic acid (Compound 206) as a white solid. The crude product was purified using Prep HPLC Method 1 to give 1-benzyl-7-(3-(tert-butyl) benzyl)-6-chloro-5-oxo-8-(3-(trifluoromethyl) phenyl)-1,2,3,5-tetrahydroimidazo[1,2-a]pyridine-3-carboxylic acid (Compound 215) as an off-white solid (0.10 g, 44%). LCMS (Method-J): 100% (RT 5.451, 224.0 nm) (MS: ESI+ve 595 [M+1]). $^1$H NMR: (400

MHz, DMSO) δ ppm: 1.15 (s, 9H), 3.36 (s, 2H), 3.72-3.80 (m, 4H), 3.86-3.97 (m, 1H), 5.03-5.06 (d, J=10, 1H), 6.59-6.61 (d, J=6.8, 1H), 6.69-6.70 (d, J=6.4, 1H), 6.84 (s, 2H), 6.93 (s, 1H), 7.06-7.12 (m, 2H), 7.17 (s, 3H), 7.28 (s, 1H), 7.33 (s, 1H), 7.48-7.50 (d, J=7.6, 1H).

Example 234

Synthesis of 1-benzyl-7-(3-(tert-butyl) benzyl)-5-oxo-8-(3-(trifluoromethyl) phenyl)-1,2,3,5-tetrahydroimidazo[1,2-a] pyridine-3-carboxylic acid (Compound 226)

Compound 226

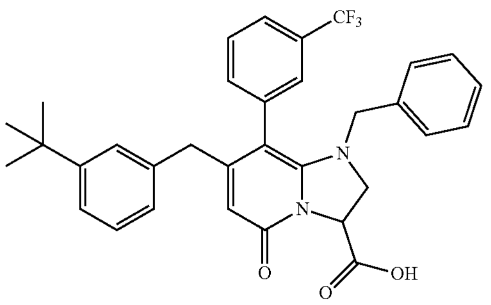

Prepared by a procedure similar to that reported for 1-benzyl-7-(3-(tert-butyl) benzyl)-6-chloro-5-oxo-8-(3-(trifluoromethyl) phenyl)-1,2,3,5-tetrahydroimidazo[1,2-a] pyridine-3-carboxylic acid (Compound 215) omitting the chlorination step, as an off-white solid. The crude product was purified using Prep HPLC Method 1 to give 1-benzyl-7-(3-(tert-butyl) benzyl)-5-oxo-8-(3-(trifluoromethyl)phenyl)-1,2,3,5-tetrahydroimidazo[1,2-a] pyridine-3-carboxylic acid (Compound 226) as a white solid (0.050 g, 42.71%). LCMS (Method-J): 96.29% (RT 5.828, 220.0 nm) (MS: ESI+ve 561 [M+1]). $^1$H NMR: (400 MHz, DMSO) δ ppm: 1.164 (s, 9H), 3.17 (s, 2H), 3.41 (s, 1H), 3.76 (s, 2H), 3.90-4.00 (m, 1H), 6.59 (s, 1H), 6.73 (s, 1H), 6.85 (s, 2H), 7.07-7.13 (m, 3H), 7.18 (s, 3H), 7.35-7.39 (m, 2H), 7.49-7.51 (d, J=7.2, 1H).

Example 235

Synthesis of 1-benzyl-7-(4-(tert-butyl) benzyl)-6-chloro-5-oxo-8-(3-(trifluoromethyl) phenyl)-1,2,3,5-tetrahydroimidazo[1,2-a] pyridine-3-carboxylic acid (Compound 216)

Compound 216

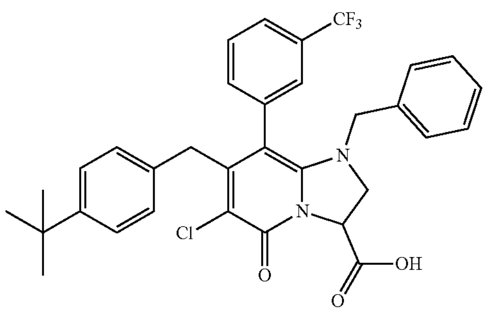

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo1,2-a]pyridine-3-carboxylic acid (Compound 206) as a white solid. The crude product was purified using Prep HPLC Method 1 to give 1-benzyl-7-(4-(tert-butyl) benzyl)-6-chloro-5-oxo-8-(3-(trifluoromethyl) phenyl)-1,2,3,5-tetrahydroimidazo[1,2-a]pyridine-3-carboxylic acid (Compound 216) as an off-white solid (0.087 g, 44%). LCMS (Method-J): 100% (RT 5.607, 218.0 nm) (MS: ESI+ve 596 [M+1]). $^1$H NMR: (400 MHz, DMSO) δ ppm: 1.20 (s, 9H), 3.52 (s, 2H), 3.75 (s, 2H), 3.87-3.95 (m, 1H), 3.95-4.04 (m, 1H), 5.08-5.13 (m, 1H), 6.59-6.61 (d, J=7.6, 2H), 6.83 (s, 3H), 7.12-7.19 (m, 5H), 7.38-7.39 (d, J=5.2, 2H), 7.51 (s, 1H).

Example 236

Synthesis of 1-benzyl-7-(4-(tert-butyl) benzyl)-5-oxo-8-(3-(trifluoromethyl) phenyl)-1,2,3,5-tetrahydroimidazo[1,2-a] pyridine-3-carboxylic acid (Compound 227)

Compound 227

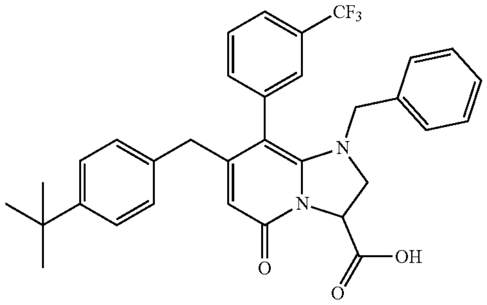

Prepared by a procedure similar to that reported for 1-benzyl-7-(4-(tert-butyl) benzyl)-6-chloro-5-oxo-8-(3-(trifluoromethyl) phenyl)-1,2,3,5-tetrahydroimidazo[1,2-a] pyridine-3-carboxylic acid (Compound 216) omitting the chlorination step, as an off-white solid. The crude product was purified using Prep HPLC Method # to give 1-benzyl-7-(4-(tert-butyl) benzyl)-5-oxo-8-(3-(trifluoromethyl) phenyl)-1,2,3,5-tetrahydroimidazo[1,2-a] pyridine-3-carboxylic acid (Compound 227) as a white solid (0.026 g, 37.01%). LCMS (Method-J): 99.14% (RT 5.886, 254.0 nm) (MS: ESI+ve 561 [M+1]). $^1$H NMR: (400 MHz, DMSO) δ ppm: 1.214 (s, 9H), 3.47-3.57 (m, 2H), 3.89-3.99 (m, 2H), 4.94-4.97 (m, 1H), 5.60-5.61 (d, J=5.2, 1H), 6.65-6.67 (d, J=7.2, 2H), 6.85 (s, 2H), 6.92 (s, 1H), 7.18 (s, 5H), 7.439 (s, 2H), 7.53 (s, 1H).

Example 237

Synthesis of 1-benzyl-6-chloro-7-((4-methoxynaphthalen-1-yl)methyl)-5-oxo-8-(3-(trifluoromethyl)phenyl)-1,2,3,5-tetrahydroimidazo[1,2-a]pyridine-3-carboxylic acid (Compound 219)

Compound 219

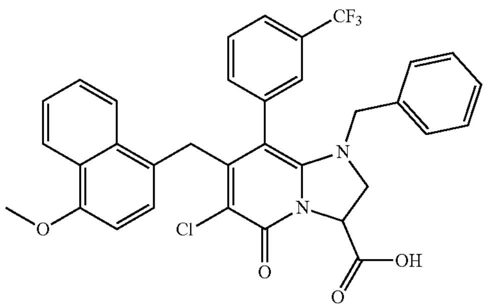

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo[1,2-a]pyridine-3-carboxylic acid (Compound 206) as a white solid. The crude product was purified using Prep HPLC Method 1 to give 1-benzyl-6-chloro-7-((4-methoxynaphthalen-1-yl)methyl)-5-oxo-8-(3-(trifluoromethyl)phenyl)-1,2,3,5-tetrahydroimidazo[1,2-a]pyridine-3-carboxylic acid (Compound 219), (0.0011 g, 12.51%). LCMS (Method-J): 100% (RT 5.566, 202.4 nm) (MS: ESI+ve 619.2 [M+2]). $^1$H NMR: (400 MHz, DMSO) δ ppm: 3.58 (s, 1H), 3.77-3.79 (m, 2H), 3.84-3.88 (m, 1H), 3.94 (s, 3H), 3.96-4.04 (m, 2H), 5.15 (m, 1H), 6.87-7.00 (m, 5H), 7.17-7.29 (m, 5H), 7.37-7.43 (m, 2H), 7.62 (m, 1H), 8.11-8.13 (d, J=8.8 Hz, 1H), 13.59 (s, 1H).

Example 238

Synthesis of 1-benzyl-7-((4-methoxynaphthalen-1-yl)methyl)-5-oxo-8-(3-(trifluoromethyl)phenyl)-1,2,3,5-tetrahydroimidazo[1,2-a]pyridine-3-carboxylic acid (Compound 220)

Compound 220

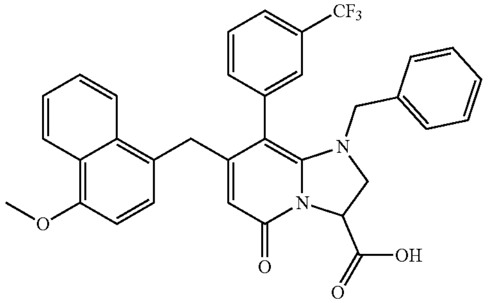

Prepared by a procedure similar to that reported for 1-benzyl-6-chloro-7-((4-methoxynaphthalen-1-yl)methyl)-5-oxo-8-(3-(trifluoromethyl)phenyl)-1,2,3,5-tetrahydroimidazo[1,2-a]pyridine-3-carboxylic acid (Compound 219), omitting the chlorination step. The crude product was purified using Prep HPLC Method 1 to give 1-benzyl-7-((4-methoxynaphthalen-1-yl)methyl)-5-oxo-8-(3-(trifluoromethyl)phenyl)-1,2,3,5-tetrahydroimidazo[1,2-a]pyridine-3-carboxylic acid (Compound 220), (0.0011 g, 12.51%). LCMS (Method-J): 100% (RT 5.534, 254.4 nm) (MS: ESI+ve 585.2 [M+2]). $^1$H NMR: (400 MHz, DMSO) δ ppm: 3.39-3.50 (m, 1H), 3.66 (s, 2H), 3.85 (s, 2H), 3.96-3.99 (m, 4H), 4.95 (s, 1H), 6.91 (s, 3H), 7.17-7.34 (m, 4H), 7.45-7.64 (m, 7H), 8.15-8.17 (m, 1H).

Example 239

Synthesis of 1-benzyl-6-chloro-7-((4-chloronaphthalen-1-yl)methyl)-5-oxo-8-(3-(trifluoromethyl)phenyl)-1,2,3,5-tetrahydroimidazo[1,2-a]pyridine-3-carboxylic acid (Compound 225)

Compound 225

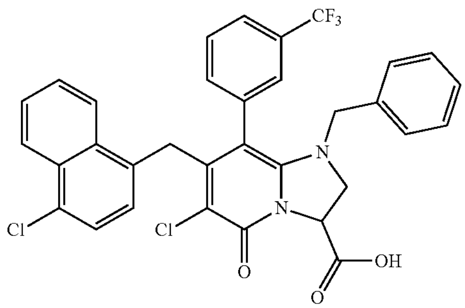

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo1,2-a]pyridine-3-carboxylic acid (Compound 206) as a white solid. The crude product was purified using Prep HPLC Method 1 to give 1-benzyl-6-chloro-7-((4-chloronaphthalen-1-yl)methyl)-5-oxo-8-(3-(trifluoromethyl)phenyl)-1,2,3,5-tetrahydroimidazo[1,2-a]pyridine-3-carboxylic acid (Compound 225), (0.100 g, 56.81%). LCMS (Method-C3): 100% (RT 2.168, 202.0 nm) (MS: ESI+ve 623.1 [M+2]). $^1$H NMR: (400 MHz, DMSO) δ ppm: 3.58-3.60 (m, 1H), 3.72-3.85 (m, 2H), 3.92-4.18 (m, 3H), 5.17-5.19 (t, 1H), 6.86-7.04 (m, 4H), 7.14-7.36 (m, 6H), 7.48-7.52 (t, 1H), 7.62-7.65 (t, 2H), 7.78-7.82 (t, 1H), 8.14-8.16 (d, J=8.4 Hz, 1H), 13.52-13.63 (d, J=45.2 Hz, 1H).

Example 240

Synthesis of 1-benzyl-7-((4-chloronaphthalen-1-yl) methyl)-5-oxo-8-(3-(trifluoromethyl) phenyl)-1,2,3,5-tetrahydroimidazo[1,2-a] pyridine-3-carboxylic acid (Compound 232)

Compound 232

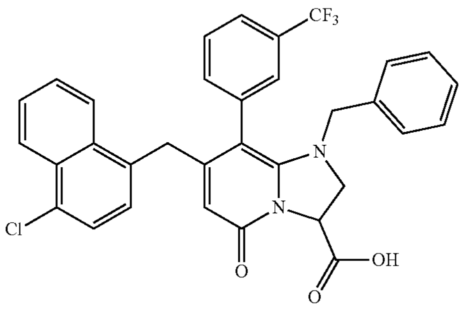

Prepared by a procedure similar to that reported for 1-benzyl-6-chloro-7-((4-chloronaphthalen-1-yl)methyl)-5-oxo-8-(3-(trifluoromethyl)phenyl)-1,2,3,5-tetrahydroimidazo[1,2-a]pyridine-3-carboxylic acid (Compound 225), omitting the chlorination step. The crude product was purified using Prep HPLC Method # to give 1-benzyl-7-((4-chloronaphthalen-1-yl) methyl)-5-oxo-8-(3-(trifluoromethyl) phenyl)-1,2,3,5-tetrahydroimidazo[1,2-a] pyridine-3-carboxylic acid (Compound 232) as a white solid (0.018 g, 25.24%). LCMS (Method-J): 100% (RT 5.744, 202.0 nm) (MS: ESI+ve 589 [M+1]). $^{1}$H NMR: (400 MHz, DMSO) δ ppm: 3.77-3.85 (t, 6H), 4.72 (s, 1H), 5.15 (s, 1H), 6.90 (s, 2H), 7.19 (s, 4H), 7.42 (s, 3H), 7.60-7.62 (d, J=6.8, 3H), 7.71-7.73 (d, J=8, 1H), 8.15-8.21 (m, 2H).

Example 241

Synthesis of 1-benzyl-6-chloro-7-((3-methoxynaphthalen-1-yl)methyl)-5-oxo-8-(3-(trifluoromethyl) phenyl)-1,2,3,5-tetrahydroimidazo[1,2-a]pyridine-3-carboxylic acid (Compound 234)

Compound 234

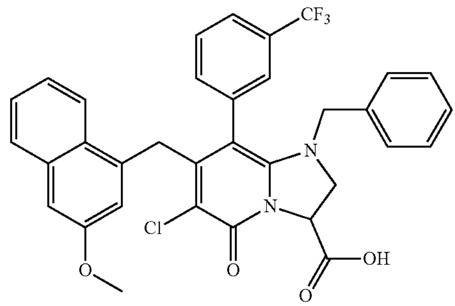

Prepared by a procedure similar to that reported for 1-benzyl-6-chloro-5-oxo-7-(quinolin-4-ylmethyl)-8-(3-(trifluoromethyl)phenyl)-1,2,3,5-tetrahydroimidazo1,2-a]pyridine-3-carboxylic acid (Compound 206). The crude product was purified using Prep HPLC Method 1 to give methyl 1-benzyl-7-((3-methoxynaphthalen-1-yl) methyl)-5-oxo-8-(3-(trifluoromethyl) phenyl)-1,2,3,5-tetrahydroimidazo[1,2-a]pyridine-3-carboxylate (Compound 234), (0.005 g, 4.51%). LCMS (Method-J): 100% (RT 5.612, 202.0 nm) (MS: ESI+ve 619 [M+1]). $^{1}$H NMR: (400 MHz, DMSO) δ ppm: 3.99 (s, 8H), 5.15 (s, 1H), 6.16 (s, 5H), 7.19 (s, 5H), 7.40 (s, 2H), 7.61 (s, 2H), 8.11 (s, 1H).

Example 242

Synthesis of 1-benzyl-7-((3-methoxynaphthalen-1-yl)methyl)-5-oxo-8-(3-(trifluoromethyl)phenyl)-1,2,3,5-tetrahydroimidazo[1,2-a]pyridine-3-carboxylic acid (Compound 233)

Compound 233

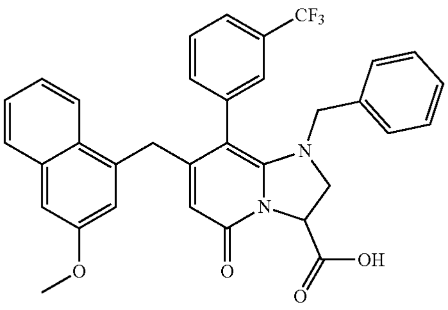

Prepared by a procedure similar to that reported for methyl 1-benzyl-7-((3-methoxynaphthalen-1-yl) methyl)-5-oxo-8-(3-(trifluoromethyl) phenyl)-1,2,3,5-tetrahydroimidazo[1,2-a] pyridine-3-carboxylate (Compound 234), omitting the chlorination step. The crude product was purified using Prep HPLC Method 1 to give 1-benzyl-7-((3-methoxynaphthalen-1-yl)methyl)-5-oxo-8-(3-(trifluoromethyl)phenyl)-1,2,3,5-tetrahydroimidazo[1,2-a]pyridine-3-carboxylic acid (Compound 233) as a white solid (0.022 g, 25.60%). LCMS (Method-J): 100% (RT 5.571, 202.0 nm) (MS: ESI+ve 585 [M+1]). $^{1}$H NMR: (400 MHz, DMSO) δ ppm: 3.46 (s, 2H), 3.65 (s, 2H), 3.79 (s, 2H), 3.95 (s, 3H), 4.93 (s, 1H), 5.10-5.14 (d, J=13.6, 1H), 6.90 (s, 2H), 7.16-7.23 (m, 5H), 7.44-7.46 (d, J=8.8, 6H), 7.63 (s, 1H), 8.15 (s, 1H).

Example 243

Synthesis of 1-benzyl-6-chloro-7-((3,4-dihydroquinolin-1 (2H)-yl)methyl)-5-oxo-8-(3-(trifluoromethyl)phenyl)-1,2,3,5-tetrahydroimidazo[1,2-a]pyridine-3-carboxylic acid (Compound 217)

Compound 217

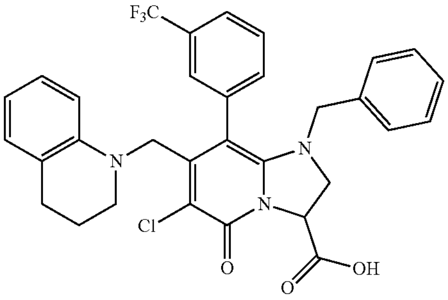

Step-1: Preparation of methyl 1-benzyl-7-((3,4-dihydroquinolin-1 (2H)-yl)methyl)-5-oxo-8-(3-(trifluoromethyl)phenyl)-1,2,3,5-tetrahydroimidazo[1,2-a]pyridine-3-carboxylate

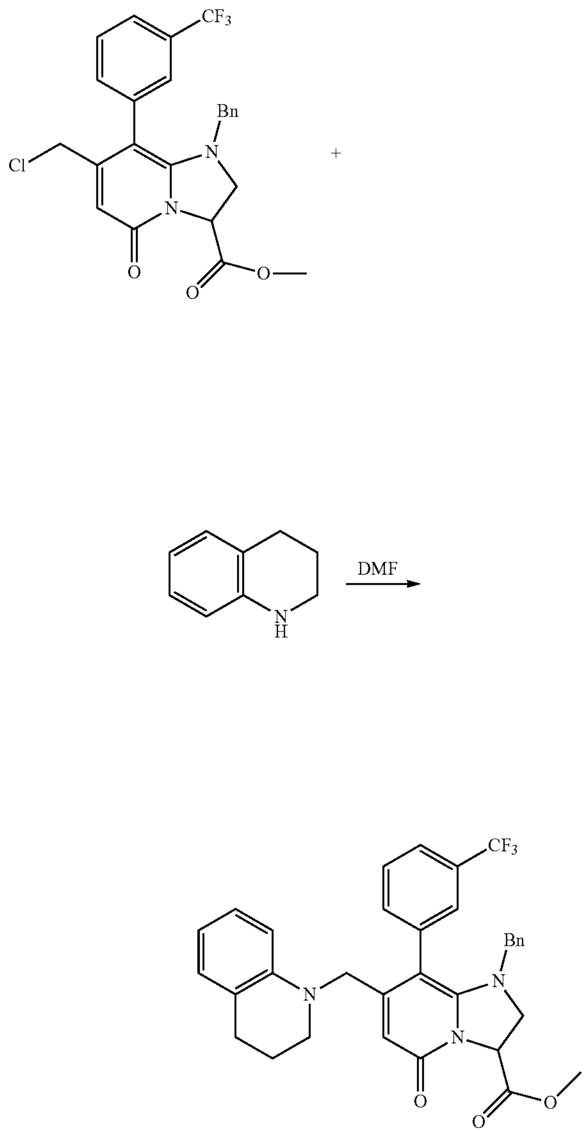

Methyl 1-benzyl-7-(chloromethyl)-5-oxo-8-(3-(trifluoromethyl) phenyl)-1,2,3,5-tetrahydroimidazo[1,2-a] pyridine-3-carboxylate (0.35 g, 0.73 mmol) and 1,2,3,4-tetrahydroquinoline (0.3 mL, 2.2 mmol) were dissolved in N,N-Dimethylformamide (5.0 mL) then stirred at room temperature for 16 hr. The reaction mixture was poured into ice cold water (30 mL) and the resulting precipitate was collected by filtration and dried under vacuum. The crude product was purified using column chromatography eluting with 4% Methanol/Dichloromethane to give methyl 1-benzyl-7-((3,4-dihydroquinolin-1 (2H)-yl)methyl)-5-oxo-8-(3-(trifluoromethyl)phenyl)-1,2,3,5-tetrahydroimidazo[1,2-a] pyridine-3-carboxylate as an off-white solid (0.1 g, 23.7%). LCMS (Method-C2): 91.0% (RT: 1.561, 254.0 nm) (MS: ESI+ve 574 [M+1]).

Step-2: Preparation of methyl 1-benzyl-6-chloro-7-((3,4-dihydroquinolin-1 (2H)-yl) methyl)-5-oxo-8-(3-(trifluoromethyl) phenyl)-1, 2, 3, 5-tetrahydroimidazo [1,2-a] pyridine-3-carboxylate

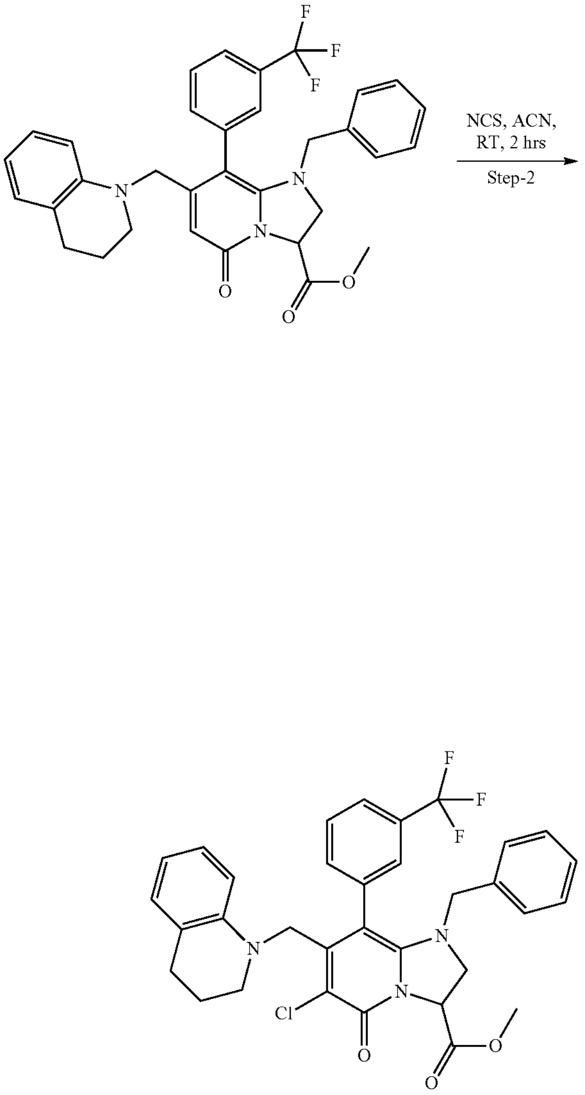

Methyl 1-benzyl-7-((3, 4-dihydroquinolin-1 (2H)-yl) methyl)-5-oxo-8-(3-(trifluoromethyl) phenyl)-1, 2, 3, 5-tetrahydroimidazo [1, 2-a] pyridine-3-carboxylate (0.1 g, 0.17 mmol) was dissolved in ACN (3.0 mL). N-Chlorosuccinimide (NCS) (0.024 g, 0.17 mmol) was added in portions and the reaction mixture was stirred for 2 hr. The reaction mixture was quenched in cool water (20 mL) and extracted with ethyl acetate (3×20 mL). The organic layer was dried over sodium sulphate and concentrated under reduced pressure to give methyl 1-benzyl-6-chloro-7-((3, 4-dihydroquinolin-1 (2H)-yl) methyl)-5-oxo-8-(3-(trifluoromethyl) phenyl)-1, 2, 3, 5-tetrahydroimidazo [1, 2-a]pyridine-3-carboxylate as an off-white solid (0.09 g, crude) which was used directly in the next step without further purification. LCMS (Method-C2): 82.3% (RT: 1.606, 254.0 nm) (MS: ESI+ve 608 [M+1]).

Step-3: Preparation of 1-benzyl-6-chloro-7-((3,4-dihydroquinolin-1 (2H)-yl)methyl)-5-oxo-8-(3-(trifluoromethyl)phenyl)-1,2,3,5-tetrahydroimidazo[1,2-a]pyridine-3-carboxylic acid (Compound 217)

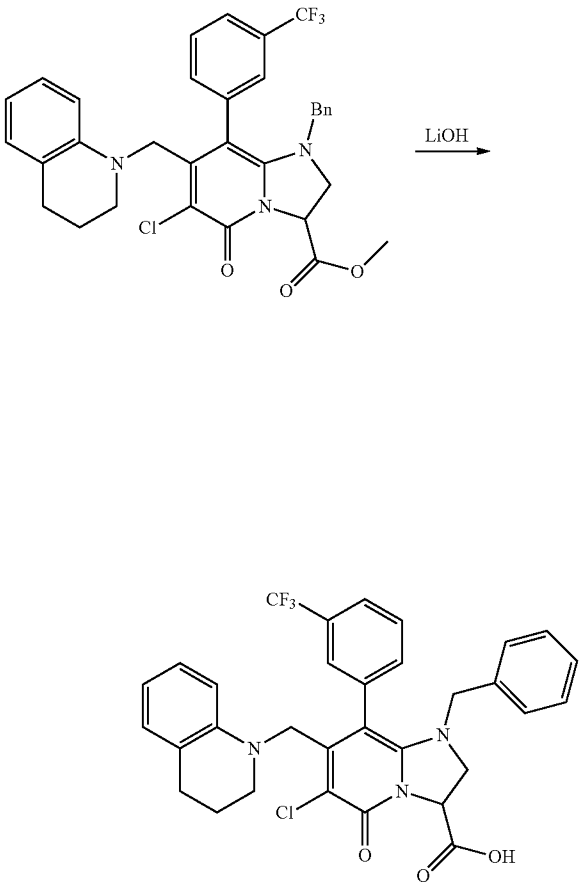

Compound 217

Methyl 1-benzyl-6-chloro-7-((3, 4-dihydroquinolin-1 (2H)-yl) methyl)-5-oxo-8-(3-(trifluoromethyl) phenyl)-1, 2, 3, 5-tetrahydroimidazo [1, 2-a] pyridine-3-carboxylate (0.09 g, 0.14 mmol) was hydrolyzed using the standard method as for (Compound 004) Step 3, and the crude product was purified using Prep HPLC Method 1 to give 1-benzyl-6-chloro-7-((3,4-dihydroquinolin-1 (2H)-yl)methyl)-5-oxo-8-(3-(trifluoromethyl)phenyl)-1,2,3,5-tetrahydroimidazo[1,2-a]pyridine-3-carboxylic acid (Compound 217) as an off-white solid (0.016 g, 18.20%). LCMS (Method-J): 96.5% (RT 5.281, 254.0 nm) (MS: ESI+ve 594 [M+1]). $^1$H NMR: (400 MHz, DMSO) δ ppm: 1.68 (s, 3H), 3.94 (s, 2H), 3.76 (s, 1H), 3.81 (s, 2H), 3.98 (s, 3H), 5.08-5.10 (d, J=7.6, 1H), 6.01-6.03 (d, J=8, 1H), 6.37-6.41 (t, 1H), 6.58-6.75 (m, 2H), 6.86 (s, 2H), 7.20-7.29 (m, 6H), 7.45-7.49 (m, 1H).

Synthesis of 1-benzyl-7-((3,4-dihydroquinolin-1 (2H)-yl)methyl)-5-oxo-8-(3-(trifluoromethyl)phenyl)-1,2,3,5-tetrahydroimidazo[1,2-a]pyridine-3-carboxylic acid (Compound 228)

Compound 228

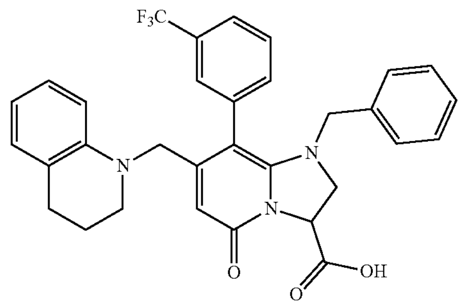

Prepared by a procedure similar to that reported for 1-benzyl-6-chloro-7-((3,4-dihydroquinolin-1 (2H)-yl) methyl)-5-oxo-8-(3-(trifluoromethyl)phenyl)-1,2,3,5-tetrahydroimidazo[1,2-a]pyridine-3-carboxylic acid (Compound 217) omitting the chlorination step, as an off-white solid. The crude product was purified using Prep HPLC Method 1 to give 1-benzyl-7-((3,4-dihydroquinolin-1 (2H)-yl) methyl)-5-oxo-8-(3-(trifluoromethyl)phenyl)-1,2,3,5-tetrahydroimidazo[1,2-a]pyridine-3-carboxylic acid as an off-white solid (Compound 228) (0.08 g, 39.05%). LCMS (Method-J): 100% (RT 5.576, 254.0 nm) (MS: ESI+ve 561 [M+1]). $^1$H NMR: (400 MHz, DMSO) δ ppm: 1.82 (s, 2H), 2.68 (s, 2H), 3.22-3.24 (d, J=6, 2H), 3.67-3.85 (m, 6H), 4.68-4.70 (d, J=8.4, 1H), 5.45 (s, 1H), 6.16-6.18 (d, J=8, 1H), 6.43-6.46 (t, 1H), 6.85-6.92 (m, 4H), 7.20 (s, 3H), 7.46-7.47 (d, J=7.6, 3H), 7.68-7.70 (d, J=7.2, 1H).

Example 244

Synthesis of 1-benzyl-6-chloro-5-oxo-7-(piperidin-1-ylmethyl)-8-(3-(trifluoromethyl)phenyl)-1,2,3,5-tetrahydroimidazo[1,2-a]pyridine-3-carboxylic acid (Compound 218)

Compound 218

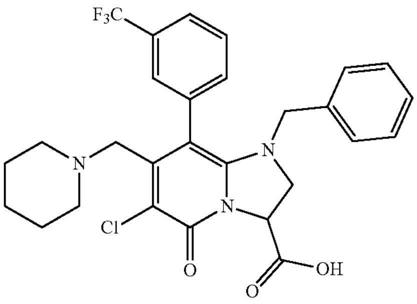

Prepared by a procedure similar to that reported for 1-benzyl-6-chloro-7-((3,4-dihydroquinolin-1 (2H)-yl) methyl)-5-oxo-8-(3-(trifluoromethyl)phenyl)-1,2,3,5-tetrahydroimidazo[1,2-a]pyridine-3-carboxylic acid (Compound 217) as an off-white solid. The crude product was purified using Prep HPLC Method 1 to give 1-benzyl-6-chloro-5-oxo-7-(piperidin-1-ylmethyl)-8-(3-(trifluoromethyl)phenyl)-1,2,3,5-tetrahydroimidazo[1,2-a]pyridine-3-carboxylic acid (Compound 218) as an off-white solid (0.011 g, 5.13%).

LCMS (Method-J): 100% (RT 4.158, 210.0 nm) (MS: ESI+ve 546 [M+1]). $^1$H NMR: (400 MHz, DMSO) δ ppm: 1.93-2.07 (m, 6H), 2.94-3.03 (m, 2H), 3.09 (s, 3H), 3.48 (s, 2H), 3.71-3.80 (m, 2H), 3.93-3.98 (s, 1H), 5.03-5.06 (d, J=10, 1H), 6.88 (s, 2H), 7.20 (s, 3H), 7.41-7.45 (m, 1H), 7.49 (s, 1H), 7.56-7.58 (d, J=5.6, 2H).

Example 245

Synthesis of 1-benzyl-5-oxo-7-(piperidin-1-ylmethyl)-8-(3-(trifluoromethyl) phenyl)-1,2,3,5-tetrahydroimidazo[1,2-a]pyridine-3-carboxylic acid (Compound 229)

Compound 229

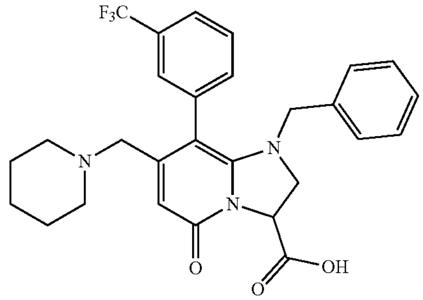

Prepared by a procedure similar to that reported for 1-benzyl-6-chloro-5-oxo-7-(piperidin-1-ylmethyl)-8-(3-(trifluoromethyl)phenyl)-1,2,3,5-tetrahydroimidazo[1,2-a]pyridine-3-carboxylic acid (Compound 218) omitting the chlorination step, as an off-white solid. The crude product was purified using Prep HPLC Method 1 to give 1-benzyl-5-oxo-7-(piperidin-1-ylmethyl)-8-(3-(trifluoromethyl)phenyl)-1,2,3,5 tetrahydroimidazo [1,2-a] pyridine-3-carboxylic acid (Compound 229) as an off-white solid (0.041 g, 20.06%). LCMS (Method-J): 100% (RT 3.567, 202.0 nm) (MS: ESI+ve 512 [M+1]). $^1$H NMR: (400 MHz, DMSO) δ ppm: 1.34 (s, 4H), 2.13 (s, 2H), 2.75 (s, 2H), 3.48 (s, 2H), 3.88-3.97 (m, 4H), 4.97-4.99 (d, J=7.2, 1H), 5.79 (s, 1H), 6.90 (s, 2H), 7.21 (s, 3H), 7.52 (s, 4H).

Example 246

Synthesis of 1-benzyl-6-chloro-5-oxo-7-(((S)-3-phenylpiperidin-1-yl)methyl)-8-(3-(trifluoromethyl) phenyl)-1,2,3,5-tetrahydroimidazo[1,2-a]pyridine-3-carboxylic acid (Compound 230)

Compound 230

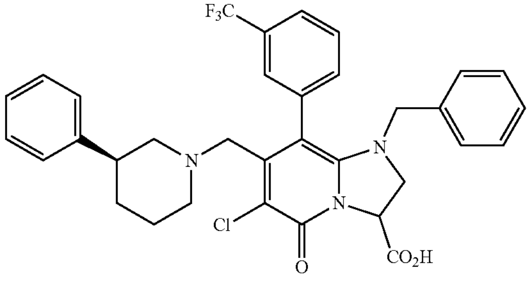

Prepared by a procedure similar to that reported for 1-benzyl-6-chloro-7-((3,4-dihydroquinolin-1 (2H)-yl) methyl)-5-oxo-8-(3-(trifluoromethyl)phenyl)-1,2,3,5-tetrahydroimidazo[1,2-a]pyridine-3-carboxylic acid (Compound 217) as an off-white solid. The crude product was purified using Prep HPLC Method 1 to give 1-benzyl-6-chloro-5-oxo-7-(((S)-3-phenylpiperidin-1-yl)methyl)-8-(3-(trifluoromethyl)phenyl)-1,2,3,5-tetrahydroimidazo[1,2-a] pyridine-3-carboxylic acid (Compound 230) as an off-white solid (0.10 g, 27.7%). LCMS (Method-J): 98.7% (RT 4.429, 220.0 nm) (MS: ESI+ve 623 [M+1]). $^1$H NMR: (400 MHz, DMSO) δ ppm: 1.28 (s, 2H), 1.57 (s, 1H), 1.66 (s, 1H), 1.87-1.93 (t, 2H), 2.06 (s, 1H), 2.33 (s, 2H), 3.00-3.03 (d, J=12, 1H), 3.10-3.19 (m, 1H), 3.50 (s, 1H), 3.76-3.85 (m, 2H), 3.97-4.01 (m, 1H), 5.04-5.06 (d, J=7.2, 1H), 6.89 (s, 2H), 7.03-7.05 (d, J=7.6, 1H), 7.12 (s, 1H), 7.21 (s, 6H), 7.42-7.44 (d, J=7.6, 1H), 7.52 (s, 1H), 7.60 (s, 2H).

Example 247

Synthesis of 1-benzyl-5-oxo-7-(((S)-3-phenylpiperidin-1-yl)methyl)-8-(3-(trifluoromethyl)phenyl)-1,2,3,5-tetrahydroimidazo[1,2-a]pyridine-3-carboxylic acid (Compound 231)

Compound 231

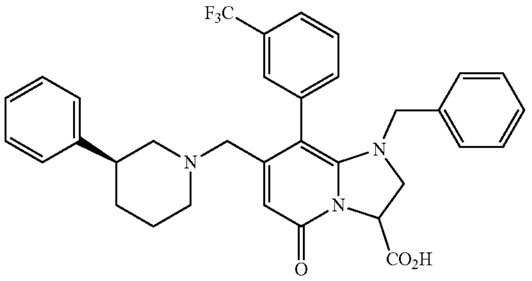

Prepared by a procedure similar to that reported for 1-benzyl-6-chloro-5-oxo-7-(((S)-3-phenylpiperidin-1-yl) methyl)-8-(3-(trifluoromethyl)phenyl)-1,2,3,5-tetrahydroimidazo[1,2-a] pyridine-3-carboxylic acid (Compound 230) omitting the chlorination step, as an off-white solid. The crude product was purified using Prep HPLC Method 1 to give 1-benzyl-5-oxo-7-(((S)-3-phenylpiperidin-1-yl) methyl)-8-(3-(trifluoromethyl)phenyl)-1,2,3,5-tetrahydroimidazo[1,2-a]pyridine-3-carboxylic acid (Compound 231) as an off-white solid (0.051 g, 34.8%). LCMS (Method-J): 100% (RT 3.998, 202.0 nm) (MS: ESI+ve 588 [M+1]). $^1$H NMR: (400 MHz, DMSO) δ ppm: 1.30 (s, 2H), 1.74-1.80 (m, 5H), 2.83-2.85 (d, J=10.4, 2H), 3.47 (s, 1H), 3.82 (s, 3H), 4.97 (s, 1H), 5.80-5.81 (d, J=6.8, 1H), 6.90 (s, 2H), 7.21 (s, 9H), 7.47 (s, 4H).

Example 248

Synthesis of 1-benzyl-6-chloro-5-oxo-7-(((R)-3-phenylpiperidin-1-yl)methyl)-8-(3-(trifluoromethyl) phenyl)-1,2,3,5-tetrahydroimidazo[1,2-a]pyridine-3-carboxylic acid (Compound 237)

Compound 237

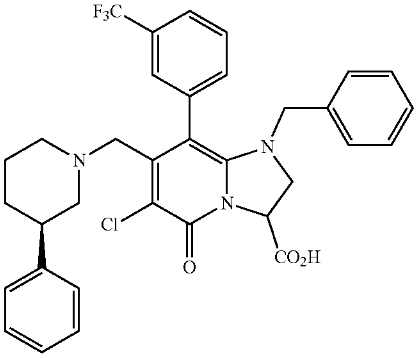

Prepared by a procedure similar to that reported for 1-benzyl-6-chloro-7-((3,4-dihydroquinolin-1 (2H)-yl) methyl)-5-oxo-8-(3-(trifluoromethyl)phenyl)-1,2,3,5-tetrahydroimidazo[1,2-a]pyridine-3-carboxylic acid (Compound 217) as an off-white solid. The crude product was purified using Prep HPLC Method 1 to give 1-benzyl-6-chloro-5-oxo-7-(((R)-3-phenylpiperidin-1-yl)methyl)-8-(3-(trifluoromethyl) phenyl)-1, 2, 3, 5 tetrahydroimidazo [1,2-a]pyridine-3-carboxylic acid (Compound 237) as an off-white solid (0.035 g, 13.7%). LCMS (Method-J): 100% (RT 4.453, 202.0 nm) (MS: ESI+ve 622 [M+1]). $^1$H NMR: (400 MHz, DMSO) δ ppm: 1.29 (s, 3H), 1.52-1.55 (d, J=13.6, 1H), 1.66 (s, 1H), 1.87-1.93 (t, 2H), 2.17-2.23 (m, 1H), 3.06-3.09 (d, J=12, 1H), 3.19-3.22 (d, J=12, 1H), 3.34 (s, 1H), 3.72-3.80 (m, 3H), 4.76 (s, 1H), 6.89 (s, 2H), 7.20 (s, 8H), 7.45 (s, 2H), 7.63 (s, 2H).

Example 249

Synthesis of 1-benzyl-7-(naphthalen-1-ylmethyl)-5-oxo-8-(3-(trifluoromethyl) phenyl)-1,2,3,5-tetrahydroimidazo[1,2-a]pyridine-3-carboxylic acid (Compound 187)

Compound 187

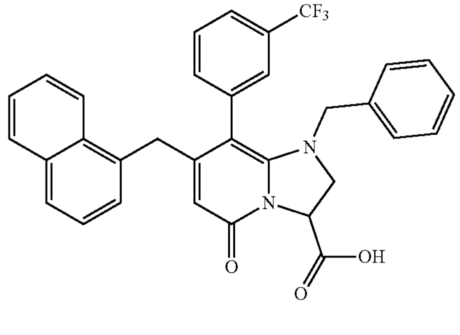

Step-1: Preparation of methyl 1-benzyl-7-(naphthalen-1-ylmethyl)-5-oxo-8-(3-(trifluoromethyl)phenyl)-1,2,3,5-tetrahydroimidazo[1,2-a]pyridine-3-carboxylate

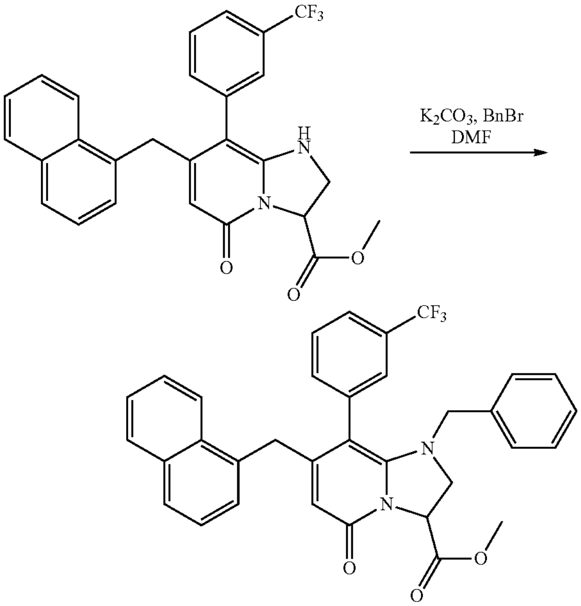

Methyl 7-(naphthalen-1-ylmethyl)-5-oxo-8-(3-(trifluoromethyl)phenyl)-1,2,3,5-tetrahydroimidazo[1,2-a]pyridine-3-carboxylate (3.0 g, 6.270 mmol) was dissolved in DMF (25.0 mL). Potassium carbonate (3.4 g, 25.08 mmol) was added followed by dropwise addition of benzyl bromide (1.28 g, 7.525 mmol). The mixture was stirred for 16 hr then quenched in ice water (500 mL). The mixture was extracted with ethyl acetate (3×300 mL), dried over sodium sulphate and concentrated under reduced pressure. The crude product was purified by column chromatography eluting with 0-5% ethyl acetate/dichloromethane to give methyl 1-benzyl-7-(naphthalen-1-ylmethyl)-5-oxo-8-(3-(trifluoromethyl)phenyl)-1,2,3,5-tetrahydroimidazo[1,2-a]pyridine-3-carboxylate. (0.2 g, 5.61%). LCMS (Method-J): 100% (RT: 18.282, 202.0 nm) (MS: ESI+ve 569.2 [M+1]).

Step-2: Preparation 1-benzyl-7-(naphthalen-1-ylmethyl)-5-oxo-8-(3-(trifluoromethyl)phenyl)-1,2,3,5-tetrahydroimidazo[1,2-a]pyridine-3-carboxylic acid (Compound 187)

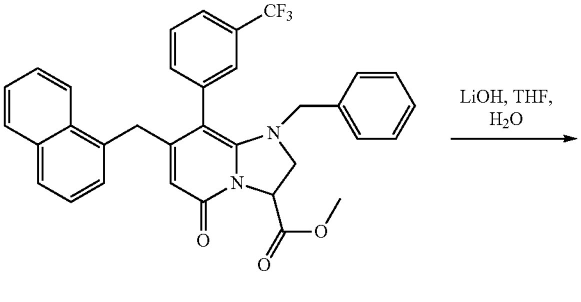

-continued

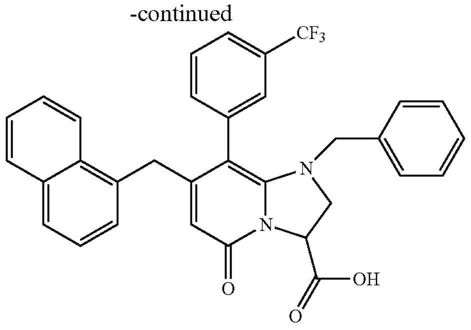

Compound 187

Methyl 1-benzyl-7-(naphthalen-1-ylmethyl)-5-oxo-8-(3-(trifluoromethyl)phenyl)-1,2,3,5-tetrahydroimidazo[1,2-a]pyridine-3-carboxylate (0.06 g, 0.105 mmol) was hydrolyzed using the standard method as for (Compound 004) Step 3, and purified by trituration with ethyl ether to give to give 1-benzyl-7-(naphthalen-1-ylmethyl)-5-oxo-8-(3-(trifluoromethyl)phenyl)-1,2,3,5-tetrahydroimidazo[1,2-a]pyridine-3-carboxylic acid, as a white solid (Compound 187) (0.02 g, 100%). LCMS (Method-J): (RT 2.470, 202.4 nm) (MS: ESI+ve 555.2 [M+1]), $^1$H NMR: (400 MHz, DMSO) δ ppm: 3.48-3.50 (m, 1H), 3.76-3.84 (d, J=32 Hz, 1H), 3.98-4.02 (t, 1H), 4.96 (s, 1H), 5.13-5.17 (d, J=15.6 Hz, 1H), 6.30 (s, 2H), 7.21-7.30 (m, 5H), 7.40-7.47 (m, 5H), 7.54-7.63 (m, 2H), 7.78-7.80 (s, J=8.0 Hz, 1H), 7.88-7.90 (d, J=8 Hz, 1H). 13.29 (s, 1H).

Example 250

Synthesis of 1-benzyl-6-bromo-7-(difluoro(naphthalen-1-yl)methyl)-5-oxo-8-(3-(trifluoromethyl)phenyl)-1,2,3,5-tetrahydroimidazo[1,2-a]pyridine-3-carboxylic acid (Compound 155)

Compound 155

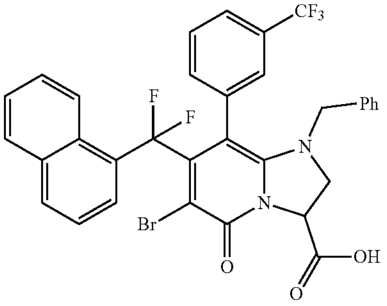

Step 1: Preparation of methyl 6-bromo-7-(difluoro(naphthalen-1-yl)methyl)-5-oxo-8-(3-(trifluoromethyl)phenyl)-1,2,3,5-tetrahydroimidazo[1,2-a]pyridine-3-carboxylate

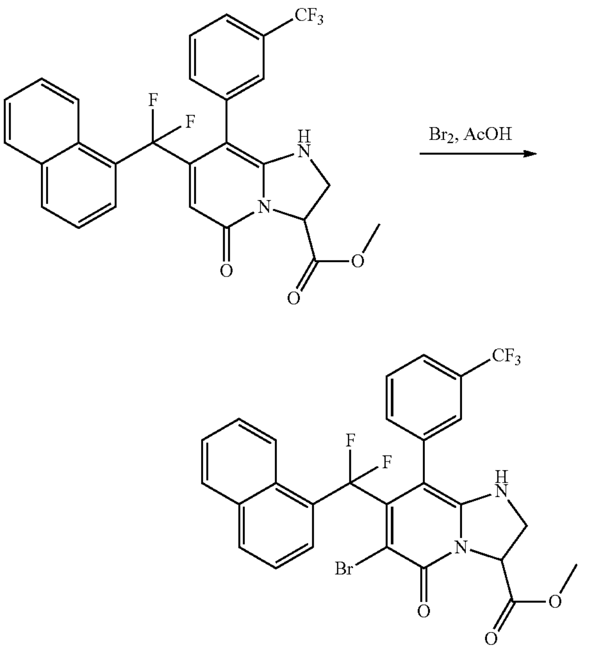

Methyl 7-(difluoro(naphthalen-1-yl)methyl)-5-oxo-8-(3-(trifluoromethyl)phenyl)-1,2,3,5-tetrahydroimidazo[1,2-a]pyridine-3-carboxylate (0.287 g, 0.055 mmol) was dissolved in acetic acid (7 mL), cooled to 0° C. and bromine was added dropwise (0.089 g, 0.557 mmol). The mixture was stirred at room temperature for 3 hr, then quenched into ice-water (10 mL). The resulting precipitate was collected by filtration, dissolved in dichloromethane, dried and concentrated under vacuum. The crude product was purified using column chromatography eluting with 0-2% dichloromethane/Methanol. (0.453 g, 51%). LCMS: (Method-C3)—89.49% (RT: 1.917, 224.0 nm) (MS: ESI+ve 593.3 [M+1]).

Step 2: Preparation of methyl 1-benzyl-6-bromo-7-(difluoro(naphthalen-1-yl)methyl)-5-oxo-8-(3-(trifluoromethyl)phenyl)-1,2,3,5-tetrahydroimidazo[1,2-a]pyridine-3-carboxylate

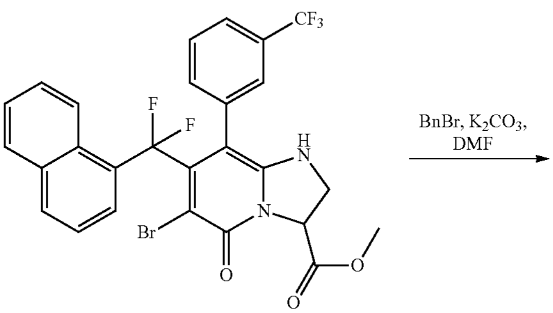

-continued

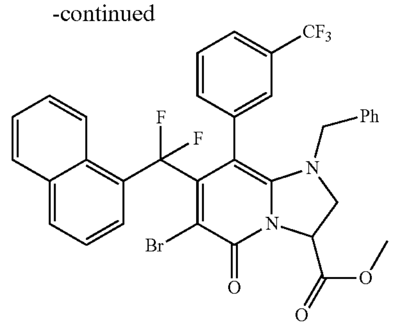

A mixture of methyl 6-bromo-7-(difluoro(naphthalen-1-yl)methyl)-5-oxo-8-(3-(trifluoromethyl)phenyl)-1,2,3,5-tetrahydroimidazo[1,2-a]pyridine-3-carboxylate (0.453 g, 0.763 mmol), N,N-Dimethylformamide (DMF) (7 mL) and potassium carbonate was cooled to 0° C. Benzyl bromide was added dropwise (0.143 g, 0.839 mmol) and the reaction mixture was stirred for 16 hr, followed by quenching with ice water. The resulting precipitate was collected by filtration, dissolved in a mixture of ethyl acetate and methanol, concentrated, and the crude product was then purified by column chromatography eluting with 80% ethyl acetate/hexane to give methyl 1-benzyl-6-bromo-7-(difluoro(naphthalen-1-yl)methyl)-5-oxo-8-(3-(trifluoromethyl)phenyl)-1,2,3,5-tetrahydroimidazo[1,2-a]pyridine-3-carboxylate. (0.040 g, 7.6% yield). LCMS: (Method-C3)—89.57% (RT: 2.131, 222.0 nm) (MS: ESI+ve 685.4 [M+2]).

Step 3: Preparation of 1-benzyl-6-bromo-7-(difluoro(naphthalen-1-yl)methyl)-5-oxo-8-(3-(trifluoromethyl)phenyl)-1,2,3,5-tetrahydroimidazo[1,2-a]pyridine-3-carboxylic acid (Compound 155)

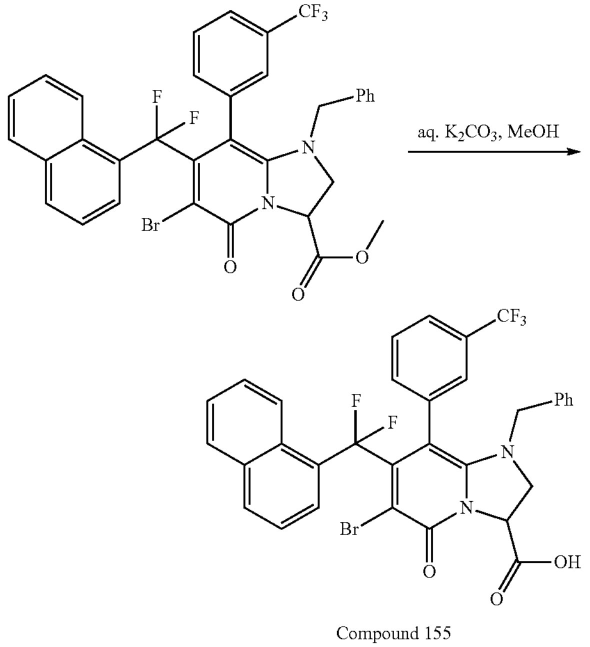

Compound 155

Methyl-1-benzyl-6-bromo-7-(difluoro(naphthalen-1-yl)methyl)-5-oxo-8-(3-(trifluoromethyl) phenyl)-1,2,3,5-tetrahydroimidazo[1,2-a]pyridine-3-carboxylate (0.040 g, 0.058 mmol) was hydrolyzed using the standard method as for (Compound 004) Step 3, and the crude product was purified using Prep HPLC Method 1 to give 1-benzyl-6-bromo-7-(difluoro(naphthalen-1-yl)methyl)-5-oxo-8-(3-(trifluoromethyl)phenyl)-1,2,3,5-tetrahydroimidazo[1,2-a]pyridine-3-carboxylic acid (Compound 155) (0.005 g, 14%).LCMS (Method-C3): 100% (RT: 1.984, 202.0 nm) (MS: ESI+ve 671.4 [M+2]). $^1$H NMR: (400 MHz, DMSO) δ ppm: 3.909 (s, 2H); 4.06-4.12 (d, J=24 Hz, 2H); 4.281 (s, 2H); 6.89-7.06 (m, 3H); 7.20-7.22 (m, 3H); 7.36-7.42 (m, 2H); 7.51-7.53 (m, 3H); 7.704 (s, 1H); 7.98-8.11 (m, 3H); 8.276 (s, 1H).

Example 251

Prep HPLC Method 1

Shimadzu LC-20AP chromatography system with a UV detector. The column used was ymc actus triart c18(250*20) mm, 5 micron, Column flow was 15.0 mL/min. Mobile phase (A) 0.1% formic acid in Water and (B) 100% Acetonitrile.

Prep HPLC Method 2

Shimadzu LC-20AP chromatography system with a UV detector. The column used was X-bridge c8 (250*19) mm, 5 micron, Column flow was 15.0 mL/min. Mobile phase (A) 5 mM ammonium bicarbonate+0.1% ammonia in Water and (B) 100% Acetonitrile.

Prep HPLC Method 3

Shimadzu LC-20AP chromatography system with a UV detector. The column used was X-bridge c18(250*19) mm, 5 micron, Column flow was 12.0 mL/min. Mobile phase (A) 5 mM ammonium bicarbonate+0.1% ammonia in Water and (B) 100% Acetonitrile.

Prep HPLC Method 4

Shimadzu LC-20AP chromatography system with a UV detector. The column used was kromasil eternity xt-5 c18 (250*21.2) mm, 5 micron, Column flow was 15.0 mL/min. Mobile phase were used (A) 0.1% Trifluoro acetic acid in Water and (B) 100% Acetonitrile.

Prep HPLC Method 5

Shimadzu LC-20AP chromatography system with a UV detector. The column used was X-bridge c18(250*19) mm, 5 micron, Column flow was 15.0 mL/min. Mobile phase (A) 0.1% formic acid in Water and (B) 100% Acetonitrile.

Prep HPLC Method 6

Shimadzu LC-20AP chromatography system with a UV detector. The column used was X-bridge c8 (250*19) mm, 5 micron, Column flow was 12.0 mL/min. Mobile phase were used (A) 0.1% formic acid in Water and (B) 100% Acetonitrile. The gradient solvent B was 20-80% over 20 min, 80-80% over 6 min, 100% over 2 min then 100-20% over.

Prep HPLC Method 7

Shimadzu LC-20AP chromatography system with a UV detector. The column used was x-select phenyl hexyl (150*19) mm, 5 micron, Column flow was 13.0 mL/min. Mobile phase (A) 0.1% formic acid in Water and (B) 100% Acetonitrile.

Prep HPLC Method 8

Shimadzu LC-20AP chromatography system with a UV detector. The column used was sunfire c18(250*19) mm, 5 micron, Column flow was 12.0 mL/min. Mobile phase were used (A) 0.1% formic acid in Water and (B) 100% Acetonitrile.

Prep HPLC Method 9

Shimadzu LC-20AP chromatography system with a UV detector. The column used was ymc actus triart c18(250*20) mm, 5 micron. Column flow was 12.0 mL/min. Mobile phase (A) 5 mM ammonium bicarbonate+0.1% ammonia in Water and (B) 100% Acetonitrile.

LCMS Method-C3

Column: BEH C18 (50*2.1 mm) 1.7 um

Mobile phase: (A) 2 mM Ammonium Acetate followed by 0.1% Formic Acid in Water, (B) 0.1% Formic Acid in Acetonitrile Column oven:—Ambient Gradient:

| Time (min) | Flow Rate (mL/min.) | % A | % B |
|---|---|---|---|
| 0.01 | 0.55 | 98 | 2 |
| 0.30 | 0.55 | 98 | 2 |
| 0.60 | 0.55 | 50 | 50 |
| 1.10 | 0.55 | 25 | 75 |
| 2.00 | 0.60 | 0 | 100 |
| 2.70 | 0.60 | 0 | 100 |
| 2.71 | 0.55 | 98 | 2 |
| 3.0 | 0.55 | 98 | 2 |

LCMS Method-F

Column: YMC Triart C18 (150*4.6 mm), 5 μm

Mobile phase: (A) 10 mM ammonium acetate in water, (B) 100% Acetonitrile

Column oven:—Ambient

Gradient:

| Time (min) | Flow Rate (mL/min.) | % A | % B |
|---|---|---|---|
| 0.01 | 1 | 90 | 10 |
| 5.00 | 1 | 10 | 90 |
| 7.00 | 1 | 0 | 100 |
| 11.00 | 1 | 0 | 100 |
| 11.01 | 1 | 90 | 10 |
| 12.00 | 1 | 90 | 10 |

LCMS Method-H

Column: X bridge C18 (50*4.6 mm) 3.5 um

Mobile phase: (A) 5 mM Ammonium Bicarbonate in Water, (B) Acetonitrile

Column oven:—Ambient

Diluent:—water: acetonitrile (1:1)

Gradient:

| Time (min) | Flow Rate (mL/min.) | % A | % B |
|---|---|---|---|
| 0.01 | 1 | 95 | 5 |
| 5.0 | 1 | 10 | 90 |
| 5.8 | 1 | 5 | 95 |
| 7.2 | 1 | 5 | 95 |
| 7.21 | 1 | 95 | 5 |
| 11 | 1 | 95 | 5 |

LCMS Method J

Column: BEH C18 (50*2.1 mm) 1.7 um

Mobile phase: (A) 2 mM Ammonium Acetate followed by 0.1% Formic Acid in Water, (B) 0.1% Formic Acid in Acetonitrile Column oven:—Ambient Gradient:

| Time (min) | Flow Rate (mL/min.) | % A | % B |
|---|---|---|---|
| 0.01 | 0.45 | 98 | 2 |
| 0.50 | 0.45 | 98 | 2 |
| 5.00 | 0.45 | 10 | 90 |
| 6.00 | 0.45 | 5 | 95 |
| 7.00 | 0.45 | 5 | 95 |
| 7.01 | 0.45 | 98 | 2 |
| 8.00 | 0.45 | 98 | 2 |

LCMS Method-D

| | LCMS METHOD | | |
|---|---|---|---|
| Mobile phase | (A) | 10 mM ammonium acetate + 0.1% formic acid in water | |
| | (B) | 0.1% formic acid in Acetonitrile | |
| Instrument: | | Agilent 1290 Infinity RRLC attached with Agilent 6120 Mass detector and Diode array Detector | |
| Column: | | YMC Triart C18 (150*4.6 mm), 5 μm | |
| Flow rate: | | 1.0 mL/min | |
| Column oven temperature: | | Ambient | |
| Run time: | | 14.0 min | |
| Gradient: | | | |
| TIME: | Flow Rate (mL/min) | % A | % B |
| 0 | 1.0 | 90 | 10 |
| 5 | 1.0 | 10 | 90 |
| 6 | 1.0 | 05 | 95 |
| 10 | 1.0 | 05 | 95 |
| 10.01 | 1.0 | 90 | 10 |
| 14 | 1.0 | 90 | 10 |

LIST OF ABBREVIATIONS

ABPR Automated Back Pressure Regulator
ACN Acetonitrile
AcOH Acetic acid
Bn Benzyl
cataCXium A Di(1-adamantyl)-n-butylphosphine
Cbz Carboxybenzyl group (or benzyloxycarbonyl)
CbzCl Benzyl chloroformate
Celite Diatomaceous earth used as a filter agent/aid
DAST Diethylaminosulfur trifluoride
DCC Dicyclohexylcarbodiimide
DCE 1,2-dichloroethane
DCM Dichloromethane
DEA Diethylamine
DIAD Diisopropyl azodicarboxylate
DIPEA Diisopropylethylamine
DMAP 4-Dimethylaminopyridine
DMF Dimethyl formamide
DMSO Dimethylsulfoxide
dppf 1,1'-Ferrocenediyl-bis(diphenylphosphine)
EDC-HCl 3-(Ethyliminomethylideneamino)-N,N-dimethylpropan-1-amine;hydrochloride
EtOH Ethanol
h. or hr Hour
HATU (1-[Bis(dimethylamino)methylene]-1H-1,2,3-triazolo[4,5-b]pyridinium 3-oxide hexafluorophosphate
$^1$H NMR proton ($^1$H) nuclear magnetic resonance spectroscopy/spectrum
HOBT Hydroxybenzotriazole
IPA Isopropyl alcohol (isopropanol)
Lawesson's reagent 2,4-Bis(4-methoxyphenyl)-2,4-dithioxo-1,3,2,4-dithiadiphosphetane
LCMS Liquid chromatography mass spectrum
Oxone Potassium peroxymonosulfate
MCPBA meta-Chloroperoxybenzoic acid
MeOH methanol
MS:ESI Mass Spectrum: electrospray ionization
MTBE Methyl t-butyl ether
NBS N-bromosuccinimide
NCS N-chlorosuccinimide
NMMO N-methyl morpholine N-oxide
nm nanometer
PMB Para-methoxy benzyl or 4-OMe benzyl
PPTs Pyridinium p-toluenesulfonate
Prep HPLC Preparatory high-pressure liquid chromatography
RuPhos 2-Dicyclohexylphosphino-2',6'-diisopropoxybiphenyl
rt room temperature
RT Retention Time (in minutes)
Selectfluor 1-(Chloromethyl)-4-fluoro-1,4-diazoniabicyclo[2.2.2]octane
bis(tetrafluoroborate)
SFC Supercritical Fluid Chromatography
TEA Triethylamine
TFA Trifluoroacetic acid
THF Tetrahydrofuran
TMSCN Trimethylsilyl cyanide
TPP Triphenylphosphine
Xantphos 4,5-Bis(diphenylphosphino)-9,9-dimethylxanthene
+ve Positive ion, or positive ion mode (mass spectrometry)
−ve Negative ion, or negative ion mode (mass spectrometry)

Example 252

The following experiments evaluate the effects of compound 004a in germ-free (GF) Thy1×BDF1 ASO (alpha-synuclein overexpressing) mice mono-colonized with the CsgA-producing *E. coli* MC4100 or its knock-out mutant on GI function, motor symptoms, and CsgA expression levels.

ASO Protocol

Male Germ-free (GF) Thy1×BDF1 ASO mice were generated as previously described (Sampson et al., 2016) at California Institute of Technology ("Caltech"). At 5-8 weeks of age, all experimental ASO animals were inoculated with curli-producing *Escherichia coli* K12 strain MC4100 or with isogenic mutant lacking genes encoding the curli biosynthesis (Δ csgA BAC deletion strain). Animals received ~$10^8$ cfu of the indicated bacterial strains in ~100 μL sodium bicarbonate buffer by oral administration.

Immediately post inoculation, all animals were placed on respective diet treatment (control chow or compound 004a treatment chow available ad libitum) for the duration of the study up to 22-24 weeks of age. Three treatment groups were enrolled: MC4100-control chow N=7-13, MC4100-004a chow N=7-13, and KO CsgA-control chow N=4-11.

Gastrointestinal (GI) Assessment was Performed Over Time

Fecal Output. Multiple fecal pellet collections were performed throughout the course of the experiment. Mice were placed in sterile cups for 15 minutes total with pellets being counted every 5 minutes.

Fecal Water Content. Mice were placed in sterile cups for 15 minutes. Fecal samples were collected counted, pooled, weighed, and dried after 15 minutes.

Motor Symptom Assessment was Performed Over Time

A battery of motor function tests was conducted throughout the experiment. Details of each motor test are described in greater details in Sampson et al., 2016 publication. All motor testing was performed in a random, blinded fashion with respect to which treatment group a given animal belongs.

Pole Descent. A 0.5 m long pole, 1 cm in diameter, wrapped with non-adhesive shelf liner to facilitate the animals grip, was placed into the home-cage. Animals received two days of training to descend from the top of the pole and into the home cage. On day one of training, animals received 3 trials. On the first trial, animals were placed head-down ⅓ the distance above the floor, the second trial from ⅔ the distance, and in the third trial animals were placed at the top. On the second day of training, animals were given 3 trials to descend, head-down, from the top of the pole. On the test day, animals were placed head-down on the top of the pole and timed to descend into the home cage. Timing began when the experimenter released the animal and ended when one hind-limb reached the home cage base.

Wire Hang. The test started with the animal hanging from an elevated wire cage top. The animal was placed on the cage top, which was then inverted and suspended above the home cage; the latency to when the animal falls was recorded.

Adhesive Removal. Round adhesive labels ¼" (Avery, Glendale, CA) were placed on the nasal bridge between the nostrils and forehead. Animals were placed into their home cage (with cage mates removed) and timed to completely remove the sticker. Animals were recorded over three trials Hindlimb Clasping Reflex. Animals were gently lifted upward by the mid-section of the tail and observed over 5-10 s (Zhang et al., 2014). Animals were assigned a score of 0, 1, 2, 3 based on the extent to which the hindlimbs clasped inward. A score of 0, indicated no clasping, was given to animals that freely moved both their limbs and extended them outward. A score of 1 was assigned to animals that clasped one hindlimb inward for the duration of the restraint or if both legs exhibited partial inward clasping. A score of 2 was be given if both legs clasped inward for most of the observation, but still exhibited some flexibility. A score of 3 was assigned if animals displayed complete paralysis of hindlimbs that immediately clasped inward and exhibited no signs of flexibility.

Beam Traversal. A 1 m plexiglass beam (Stark's Plastics, Forest Park, OH) constructed of four segments of 0.25 m in length was used. Each segment was of thinner widths 3.5 cm, 2.5 cm, 1.5 cm, and 0.5 cm, with 1 cm overhangs placed 1 cm below the surface of the beam. The widest segment acted as a loading platform for the animals and the narrowest end placed into home cage. Animals had two days of training to traverse the length of the beam before testing. On the first day of training, animals received 1 trial with the home cage positioned close to the loading platform and were guided forward along the narrowing beam. Animals received two more trials with limited or no assistance to encourage forward movement and stability on the beam. On the second day of training, animals had three trials to traverse the beam and with minimal assistance in forward movement. On the third day, animals were timed over three trials to traverse from the loading platform and to the home cage. Timing began when the animals placed their forelimbs onto the 2.5 cm segment and ended when one forelimb reached the home cage.

Compound Effect on CsgA Expression

Fecal pellets were collected from individual mice, flash-frozen on dry ice within 60 min of defecation and stored at −80° C. RNA was extracted from fecal pellets and CsgA expression quantified by qRT-PCR, relative to housekeeping genes (recA and cysG). RNA was isolated from one to three fecal pellets using Qiagen RNeasy PowerMicrobiome Kit, catalog number 26000-50 following protocol version from August 2018. Detailed procedure described Example 27A in section [000353] where ZymoBIOMICS RNA Miniprep kit was replaced by Qiagen RNeasy PowerMicrobiome Kit.

Example 253

Quantitative RNA Assay for CsgA

Analysis of Human Stool Samples. A stool sample was obtained from a patient using the BioCollective kit. A scoop of stool was placed into a sealable jar with DNA/RNA Shield to promote preservation of the nucleic acid. The sample was placed on dry ice to freeze and promote preservation of the nucleic acid. The sample was stored at <−70° C. The sample was thawed, mixed, and the RNA isolated.

Analysis of Pre-Clinical Rodent Samples. Fecal pellets from mice were collected soon after passage, transferred to tubes, and frozen on dry ice. The samples were stored at <−70° C. and shipped on dry ice. The fecal pellets were homogenized in DNA/RNA Shield, mixed, and the RNA was isolated.

For some samples, the DNA was isolated to measure CsgA DNA levels as a predictor of the relative levels of *E. coli* bacteria in the sample.

To ensure the RNA was not contaminated with DNA, digestion of DNA was performed using the enzyme DNase I. The RNA was then converted to DNA using Reverse Transcriptase.

Quantitative PCR (qPCR) was performed by one of the following methods. The preferred method is to perform qPCR with primers designed to the target gene and housekeeping genes plus Taqman probes. The alternate method for analysis of clinical samples is to preform qPCR with the primers only and detect changes in DNA product levels in each cycle of PRC using SYBR green. The alternate method is preferred for analysis of pre-clinical samples.

DNA Extraction. DNA extraction was carried out using the ZymoBIOMICS™ DNA/RNA Miniprep Kit (Zymo Research, Cat No. R2002), according to the liquid protocol listed in the kit manual and using 250 μL of the primary fecal slurry provided by Axial. DNA concentrations were measured by Quant-iT™ PicoGreen™ dsDNA Assay Kit (Invitrogen).

RNA Extraction. RNA extractions were carried out using the ZymoBIOMICS™RNA Miniprep Kit (Zymo Research, Cat No. R2001), according to the liquid protocol listed in the kit manual and using 250 μL of the stool samples provided by Axial in DNA/RNA Shield. RNA concentrations were measured by using Qubit RNA HS Assay Kit (Cat No. Q32855). RNA quality was assessed via Fragment Analyzer using the High Sensitivity RNA Kit (Cat. No. DNF-472-0500). An additional DNase digestion step was included with the purpose of removing residual genomic DNA contamination. DNase digestion methods included Methods A and B. In Method A (Zymo DNAase I), the DNase I set (Zymo Research, Cat No, E1010) was applied according to kit instructions, followed by addition of 2 μL of 0.5× TE Buffer to each tube and incubation at 75° C. for 10 minutes. In Method B (intermediate method), the DNase I set (Zymo Research, Cat No, E1010) was applied according to kit instructions, followed by addition of 2 μL of 0.5× TE Buffer to each tube and incubation at 37° C. for 10 minutes. Method B is the preferred method.

Reverse Transcription. Subsequent to RNA extraction, first-strand cDNA synthesis reaction was performed by using SuperScript™ II Reverse Transcriptase (RT) kit from Invitrogen (Cat No. 18064-014) or the SuperScript™ IV VILO Reverse Transcriptase (RT) kit from Invitrogen (Cat No. 11766050) with random hexamers. The cDNA concentrations were measured by using Qubit dsDNA HS Assay Kit (Invitrogen Cat No Q32854) for subsequent normalization of PCR template inputs.

Ouantitative PCR. For each assay, primer sets and TaqMan probes were previously designed (Table 5), and were synthesized by Integrated DNA Technologies (Coraville, IA). Primer sets were synthesized by Same Day Oligo 25 nmole production, with purification by standard desalting. Probes were synthesized by Applied Biosystems. After production and receiving the primers and probes, each primer and probe were concentrated to a stock of 100 μM. For qPCR reactions, 500 nM concentration for the primers and 250 nM concertation for the probes were used. Sample analysis was performed in a QuantStudio 7 Flex Real-Time PCR System using MicroAmp Fast Optical 384-well reaction plates (0.1 mL), MicroAmp optical adhesive film, (all Applied Biosystems) and QuantaBio PerfeCTa qPCR ToughMix, Low Rox. Reaction components are listed in Table 6. For template loading, from 2 to 20 ng of template cDNA were loaded onto each reaction. Amplification and optimized thermocycler profile are detailed in Table 7.

TABLE 5

List of custom qPCR primers and probes.

| Name | Position | Sequence | Working Stock for SYBR Assay in µM | Working Stock for Taqman Assay in µM |
|---|---|---|---|---|
| BT-1 (csgA) | Forward | ATGACAGCTCAATCGATCTGA | 10 | 20 |
| | Reverse | TCGCGTTGTTACCAAAGCCAA | 10 | 20 |
| | Probe | TCAGTGGAACGGCAAA | N/A | 10 |
| BT-3 (csgA) | Forward | CACGGTGGTGGCGGTAATAA | 10 | 20 |
| | Reverse1 | GTTACGAGCATCAGCTTGCAG | 10 | 20 |
| | Reverse2 | GTTACGGGCATCAGTTTGCAG | 10 | 20 |
| | Probe | GCAGAGCAAGTGCAGAGTTACC | N/A | 10 |
| cysG-2 | Forward | AACAACGATCAGAAAGCCATT | 10 | 20 |
| | Reverse | TATCGTCAGAAACCAGACGGT | 10 | 20 |
| | Probe | CGCTCGACCATCGC | N/A | 10 |
| hcaT-1 | Forward | TTCTGGCCTGCGTTTGTTTAT | 10 | 20 |
| | Reverse | AGATCAACAGCATATCGCGTG | 10 | 20 |
| | Probe | ATTACGGTTTTAGCGC | N/A | 10 |
| BT-2.2 (csgA) | Forward | TCTGGCAGGTGTTGTTCCTC | 10 | |
| | Reverse | CCGCCGCCATGCTGGGTAAT | 10 | |
| recA | Forward | CTGTTCGTCTCGACATCCGT | 10 | |
| | Reverse | TCGCCGTAGAGGATCTGGAA | 10 | |
| hcaT | Forward | TTCTGGCCTGCGTTTGTTTAT | 10 | |
| | Reverse | AGATCAACAGCATATCGCGTG | 10 | |
| idnT | Forward | ACTCGCTTTGAGAAAGCACCA | 10 | |
| | Reverse | GGTTACCGACAAATTCAAAGA | 10 | |

TABLE 6

List of SYBR and TaqMan reaction components.

| | |
|---|---|
| **SYBR Green** | |
| Master Mix | 5 µL |
| Primer F (10 µM) | 0.5 µL |
| Primer R (10 µM) | 0.5 µL |
| Template | 4 µL |
| Total Volume | 10 µL |
| **Taqman** | |
| Master Mix | 5 µL |
| Primer F (20 µM) | 0.25 µL |
| Primer R (20 µM) | 0.25 µL |
| Probe (10 µM) | 0.25 µL |
| Water | 0.25 µL |
| Template | 4 µL |
| Total Volume | 10 µL |

TABLE 7

Thermocycle profiles for SYBR and TaqMan assays.

| SYBR | Hold | PCR Stage | | Melt | | Hold | PCR Stage | |
|---|---|---|---|---|---|---|---|---|
| Green | Step 1 | Step 1 | Step 2 | Curve | Taqman | Step 1 | Step 1 | Step 2 |
| Time | 10:00 | 00:10 | 00:30 | | Time | 10:00 | 00:15 | 01:00 |
| Temp | 95° | 95° | 60° | | Temp | 95° | 95° | 60° |
| Cycles | 1 | 40 | | 1 | Cycles | 1 | 40 | |

With respect to the use of substantially any plural and/or singular terms herein, those having skill in the art can translate from the plural to the singular and/or from the singular to plural as is appropriate to the context and/or application. The various singular/plural permutations can be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method of using a composition (e.g., a method comprising administering a composition to a subject having an amyloid disorder) is disclosed herein, the corresponding composition for use is also expressly contemplated. For example, for the disclosure of a method of inhibiting, ameliorating, reducing the likelihood, delaying the onset of, treating, or preventing an amyloid disorder administering a composition to a subject, the corresponding composition for use in inhibiting, ameliorating, reducing the likelihood, delaying the onset of, treating, or preventing the amyloid disorder is also expressly contemplated.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A compound of Formula (I):

(I)

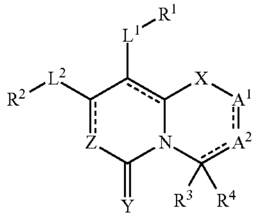

or a pharmaceutically acceptable salt thereof, wherein:

$A^1$ is —$C(R^7)(R^8)$—;

$A^2$ is absent;

$L^1$ is a bond, $(—CH_2—)_m$, —$CF_2$—, or —$C(R^9)(R^{10})$—;

$L^2$ is a bond, $(—CH_2—)_m$, —$CF_2$—, —(C═O)—, or —$C(R^9)(R^{10})$—;

X is —$N(R^{11})$— or —$N(R^{14})$;

Y is O or S;

Z is ═$C(R^{13})$—, ═N—, or —$N(R^{11})$—;

$R^1$ is substituted phenyl or substituted or unsubstituted heterocyclyl;

$R^2$ is substituted or unsubstituted naphthyl, substituted or unsubstituted phenyl, substituted or unsubstituted quinolinyl, substituted or unsubstituted isoquinolinyl, or substituted or unsubstituted heterocyclyl;

$R^3$ and $R^4$ are independently absent, as permitted by valence, or are selected from the group consisting of-H, substituted or unsubstituted $C_1$-$C_{10}$ alkyl, acyl, —$CO_2R^7$, —$CON(R^7)(R^8)$, —P═$O(OH)_2$ and —$SO_2$(OH);

$R^7$ and $R^8$ are independently absent as permitted by valence, or are selected from the group consisting of —H, substituted or unsubstituted $C_1$-$C_{10}$ alkyl, —$(CH_2)_m$-aryl, —$(CH_2)_m$-heteroaryl, —$(CH_2)_m$-substituted or unsubstituted cycloalkyl, and —$R^{14}$; or together form a spiropentanyl ring;

$R^9$ and $R^{10}$ are independently, for each occurrence, —H, —Cl, —Br, —F, —$CF_3$, or $C_1$-$C_{10}$ alkyl;

$R^{11}$ and $R^{12}$ are independently, for each occurrence, —H, acyl, sulfonyl, substituted or unsubstituted $C_1$-$C_{10}$ alkyl, $C_3$-$C_6$ cycloalkyl, $C_{3-6}$ heterocyclyl, substituted or unsubstituted benzyl, —$(CH_2)_o$-(substituted or unsubstituted aryl), or —$(CH_2)_o$-(substituted or unsubstituted heteroaryl);

$R^{13}$ is selected from the group consisting of —H, —OH, —$OR^{11}$, —Cl, —Br, —F, —CN, —$CF_3$, —$CH_2F$, —$CHF_2$, substituted or unsubstituted $C_1$-$C_{10}$ alkyl, $C_1$-$C_{10}$ alkenyl, $C_3$-$C_6$ cycloalkyl, substituted or unsubstituted $C_3$-$C_6$ heterocyclyl, acyl, —$CO_2R^7$, —$(CH_2)_mCO_2N(R^{11})(R^{12})$, —$CON(R^7)(R^8)$, —$(CH_2)_mOH$, —$(CH_2)_mCO_2H$, —$(CH_2)_mNH_2$, —$(CH_2)_mN(R^{11})(R^{12})$, —$N(R^{11})(R^{12})$, —$NR^{11}$(C═O)$(CH_2)_mCH_3$, —$NR^{11}$(C═O)$R^{12}$, and $NR^{12}(SO_2)(CH_2)_mCH_3$;

$R^{14}$ is —H, $C_1$-$C_{10}$ alkyl, $C_1$-$C_{10}$ alkenyl, $C_1$-$C_{10}$ (mono or poly)hydroxylated alkyl, —$(CH_2)_o$—$R^{15}$, —$(CH_2CH_2O)_o$—$R^{15}$, —$(CH_2)_m$—$CO_2H$, —$(CH_2)_m$—$NH_2$, —$(CH_2)_m$—(CO)$NR^{16}R^{17}$, or a protecting group;

$R^{15}$ is —$CON(R^{11})(R^{12})$, —$N(R^{11})(R^{12})$, acyl, —$CO_2R^7$, substituted or unsubstituted aryl, substituted or unsubstituted heteroaryl, substituted or unsubstituted cycloalkyl, or substituted or unsubstituted heterocyclyl;

$R^{16}$ and $R^{17}$ independently are —H or —$CH_3$;

m is, independently for each occurrence, 0-10;

o is independently, for each occurrence, 1-20; and

═ represents a single bond or a double bond.

2. The compound of claim 1, or a pharmaceutically acceptable salt thereof, wherein $L^1$ is a bond.

3. The compound of claim 1, or a pharmaceutically acceptable salt thereof, wherein $L^2$ is —$C(R^9)(R^{10})$—.

4. The compound of claim 1, or a pharmaceutically acceptable salt thereof, wherein Z is ═$C(R^{13})$—.

5. The compound of claim 1, or a pharmaceutically acceptable salt thereof, wherein $R^1$ is trifluoromethylphenyl.

6. The compound of claim 1, or a pharmaceutically acceptable salt thereof, wherein $R^2$ is unsubstituted naphthyl.

7. The compound of claim 1, or a pharmaceutically acceptable salt thereof, wherein $R^3$ is —H and $R^4$ is —$CO_2R^7$.

8. The compound of claim 1, or a pharmaceutically acceptable salt thereof, wherein Y is O.

9. The compound of claim 1, or a pharmaceutically acceptable salt thereof, wherein $R^{13}$ is —Br or —Cl.

10. The compound of claim 1, or a pharmaceutically acceptable salt thereof, having the structure of formula (IX):

(IX)

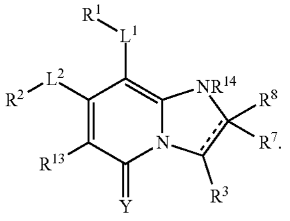

11. The compound of claim 10, or a pharmaceutically acceptable salt thereof, having the structure of Formula (IXa), Formula (IXb), or Formula (IXc):

(IXa)

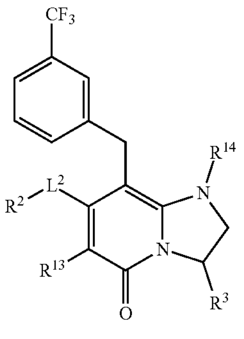

(IXb)

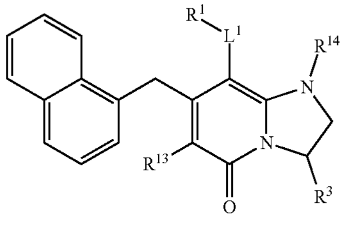

or

-continued (IXc)

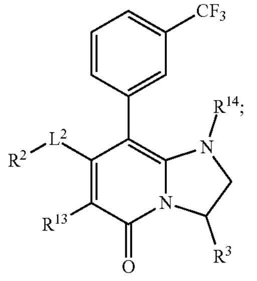

wherein:

$L^1$ is a bond, $(-CH_2-)_m$, or $-CF_2-$;

$L^2$ is a bond, $(-CH_2-)_m$, $-CF_2-$, or $-(C{=}O)-$;

m is, independently for each occurrence, 0-10;

o is, independently for each occurrence, 1-20;

$R^1$ is substituted phenyl, substituted or unsubstituted heterocyclyl;

$R^2$ is substituted or unsubstituted naphthyl, substituted or unsubstituted quinolinyl, substituted or unsubstituted isoquinolinyl, substituted phenyl, or substituted or unsubstituted heterocyclyl;

$R^3$ is $-CO_2H$,

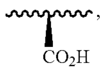

or

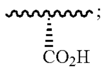

$R^{13}$ is selected from the group consisting of —H, —Cl, —Br, —F, —CN, $-CF_3$, $-CH_2F$, $-CHF_2$, $-(CH_2)$ m-$NMe_2$, $-CONH_2$, $-CO_2H$, and substituted or unsubstituted $C_1$—$C_{10}$ alkyl; and $R^{14}$ is $C_1$-$C_{10}$ alkyl, $-(CH_2)_o$-(unsubstituted cycloalkyl), $-(CH_2)_o$-(substituted or unsubstituted phenyl), $-(CH_2)_o$-naphthyl, or $-(CH_2)_o$-biaryl.

12. The compound of claim 10, selected from the group consisting of:

004

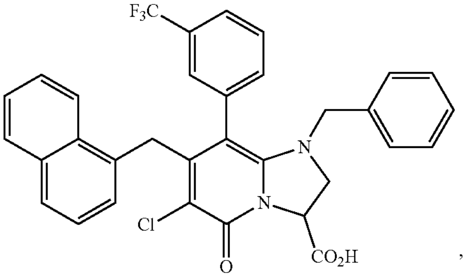

,

004a

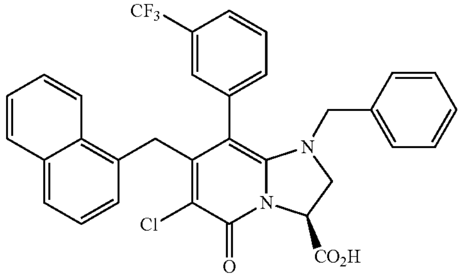

,

-continued

004b

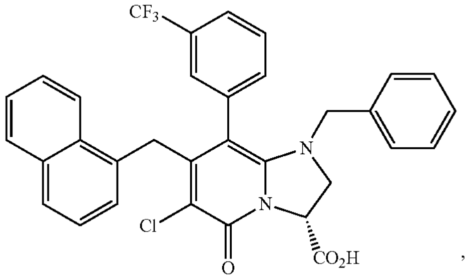

,

080

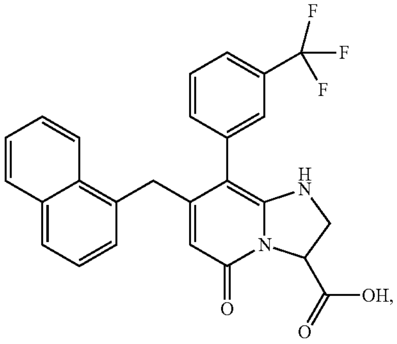

103

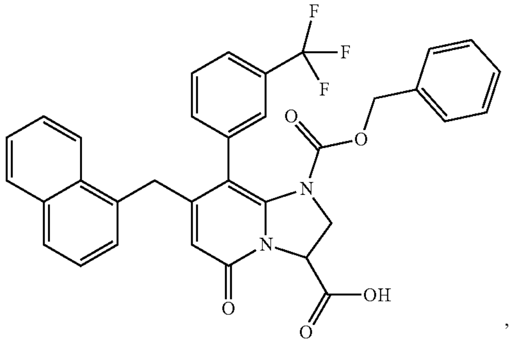

,

104

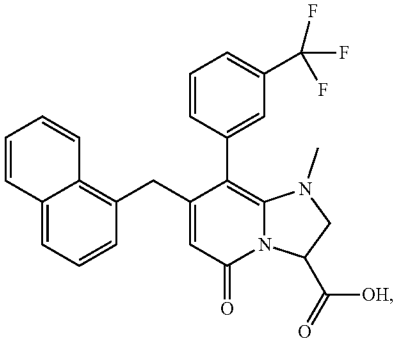

-continued
110
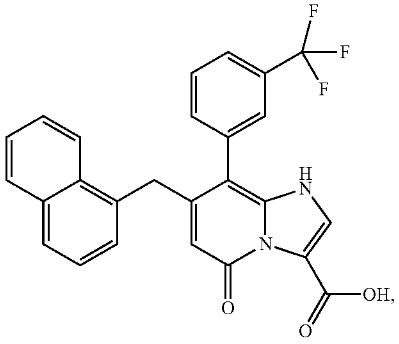
111
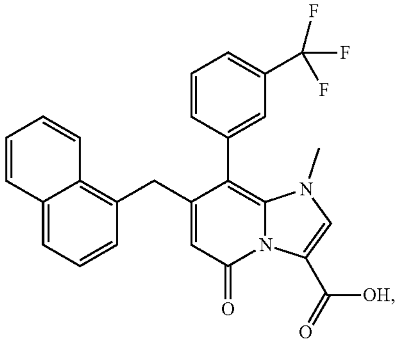
134
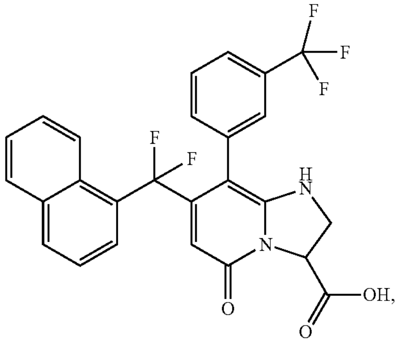
135
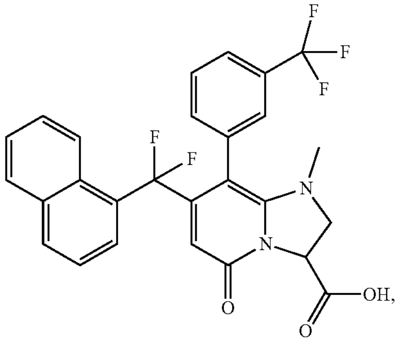
-continued
136
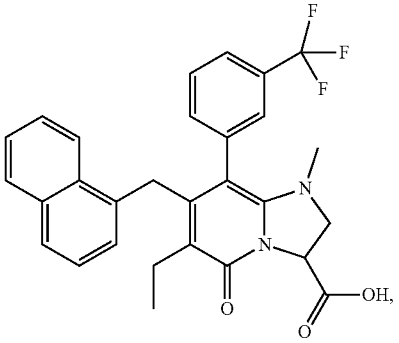
140
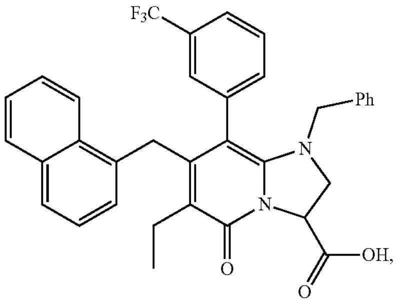
003
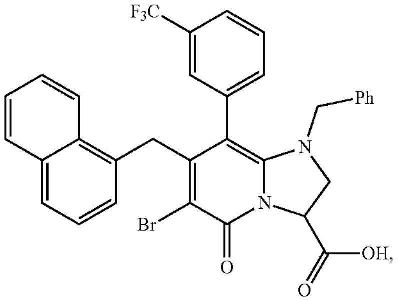
119
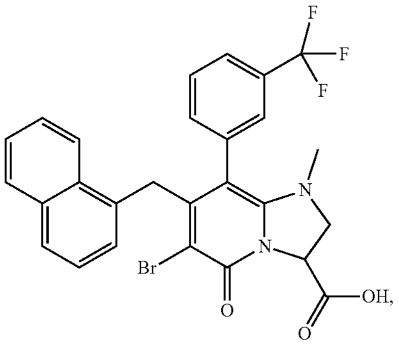

-continued
133
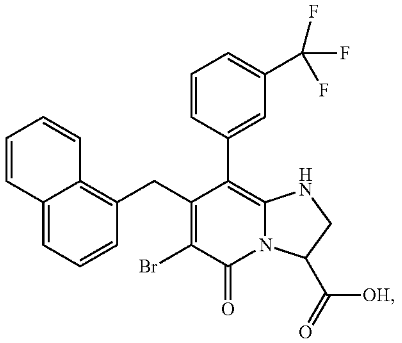
155
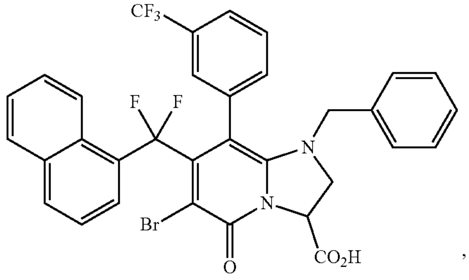
,
162
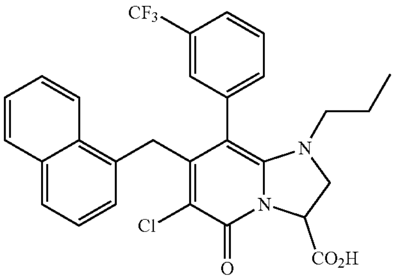
,
163
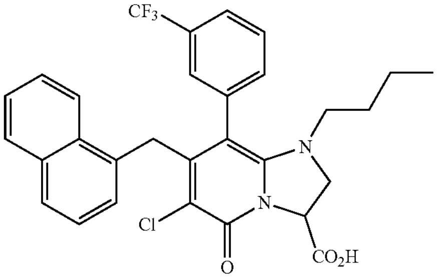
,
164
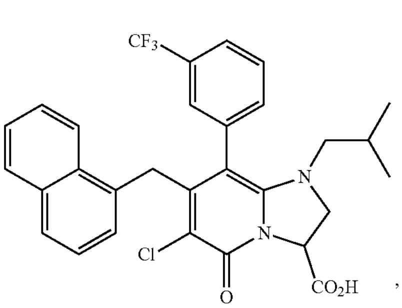
,
-continued
165
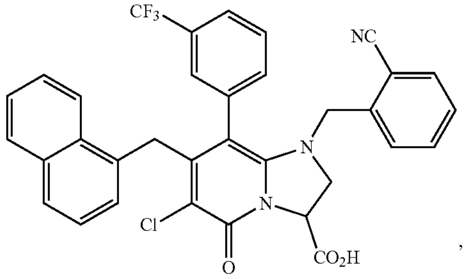
,
166
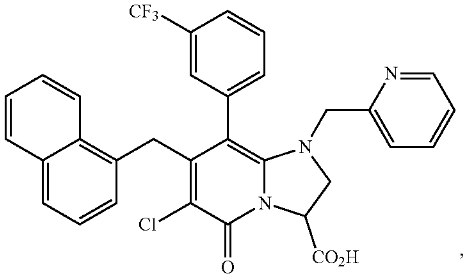
,
167
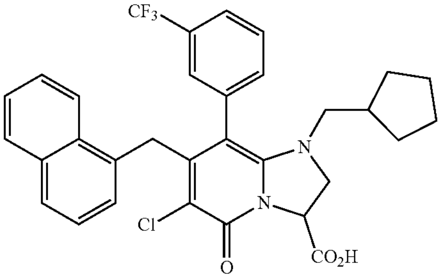
,
168
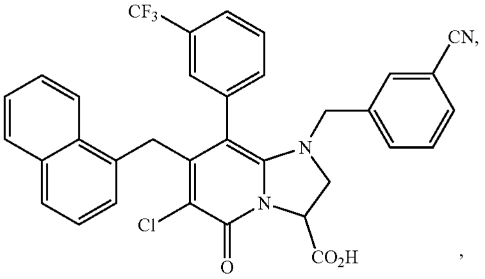
,
169
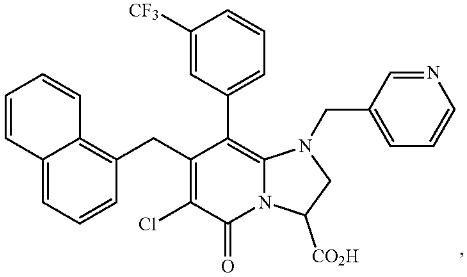
, -continued
170
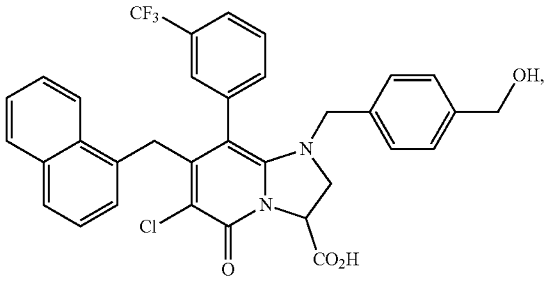
171
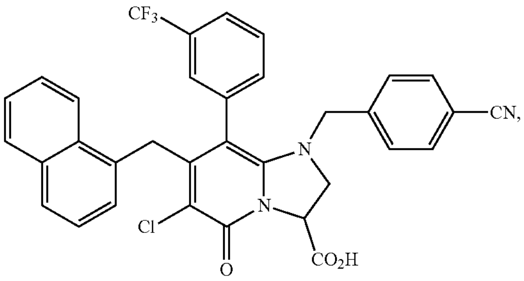
174
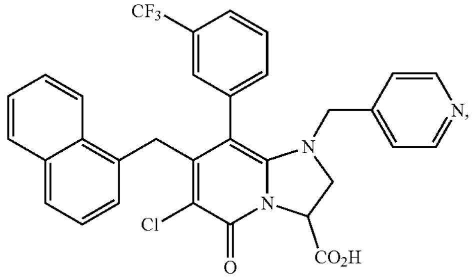
178
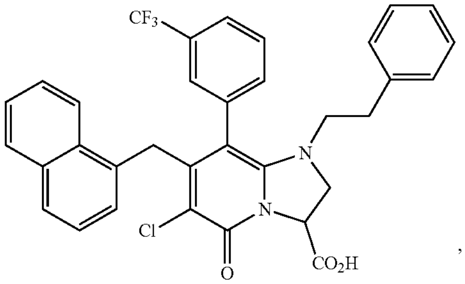
,
179
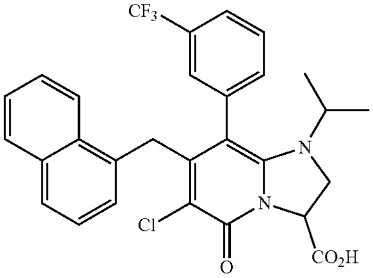
,
-continued
180
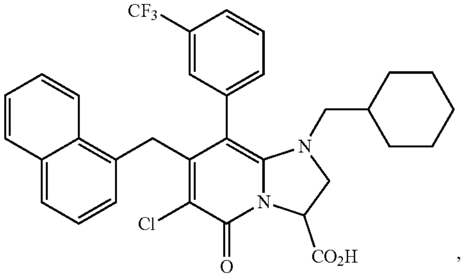
,
181
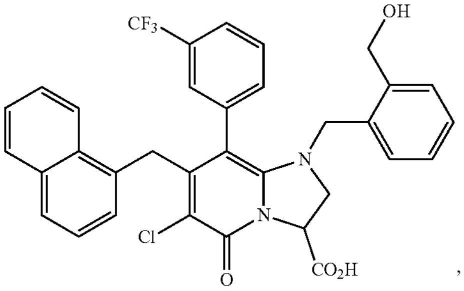
,
182
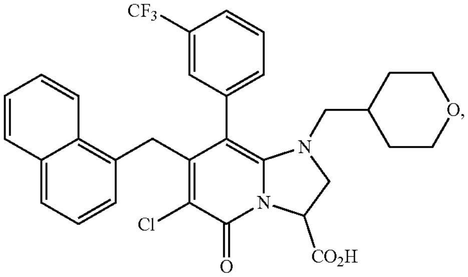
187
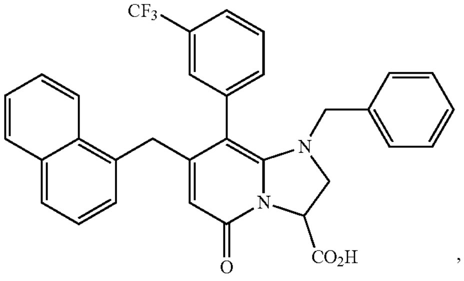
,
189
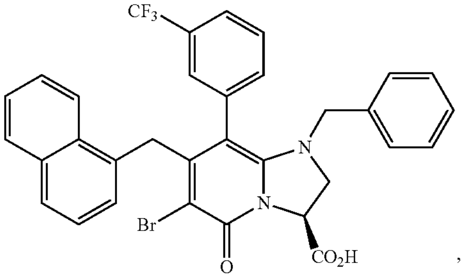
, -continued
190
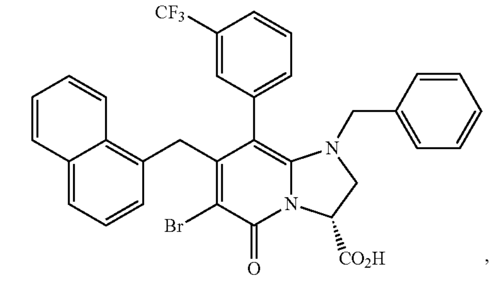
,
191
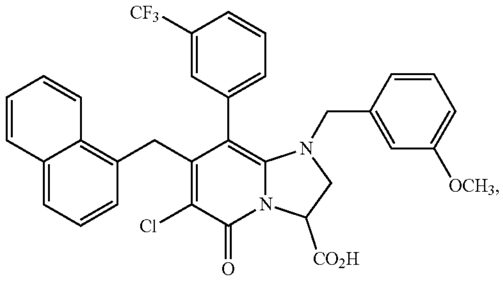
192
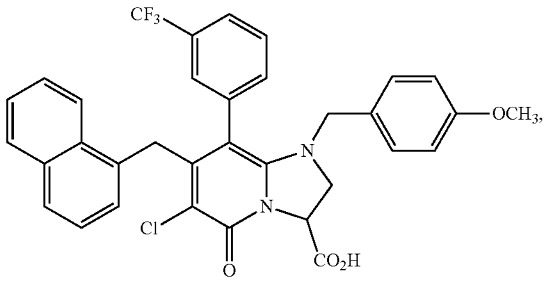
194
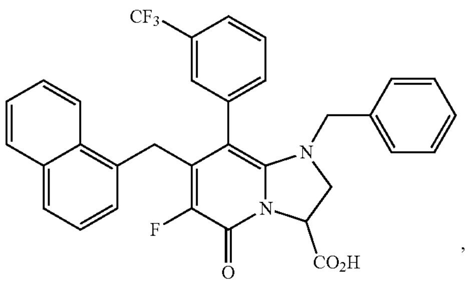
,
195
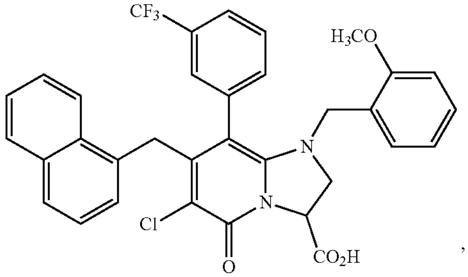
,
-continued
196
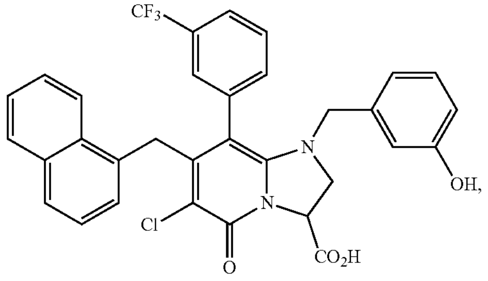
197
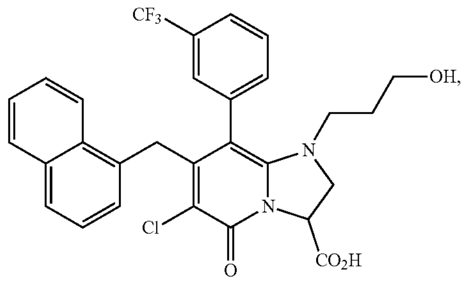
198
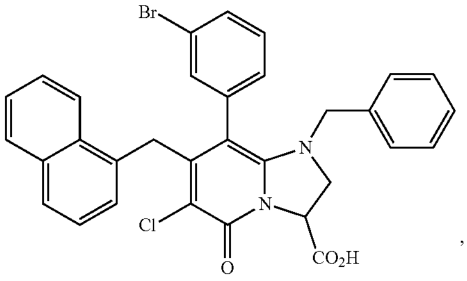
,
199
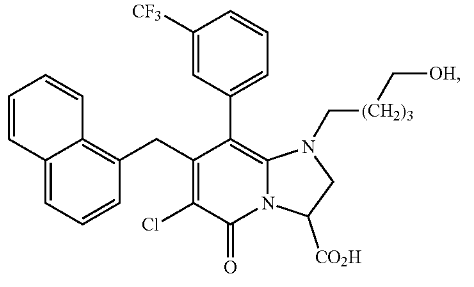
200
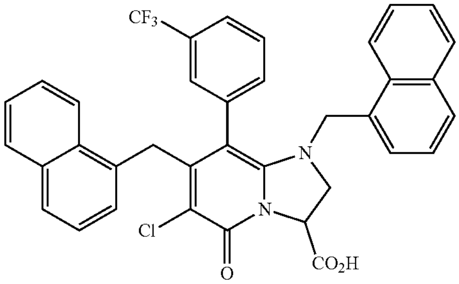
, -continued
201
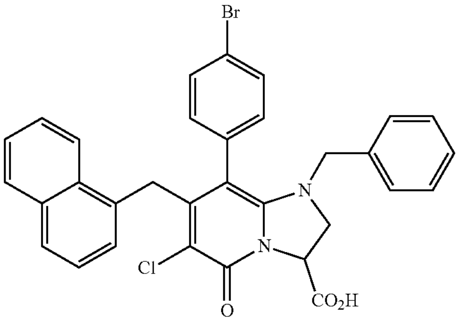
,
202
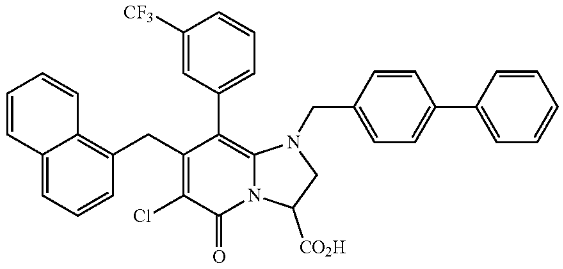
,
203
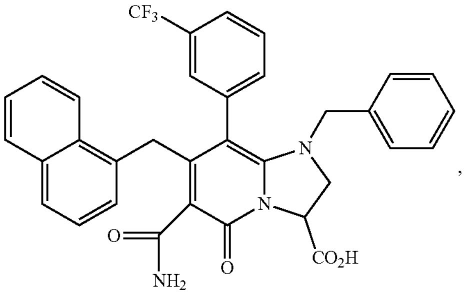
,
204
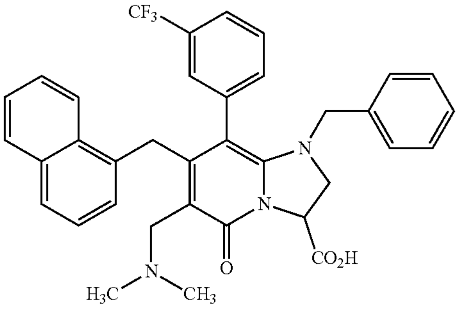
,
205
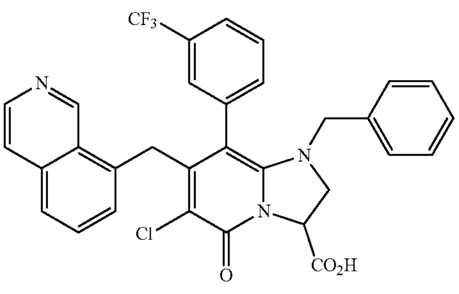
,
-continued
206
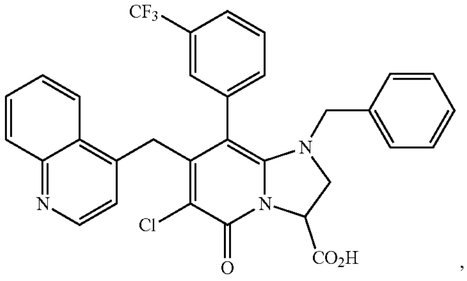
,
207
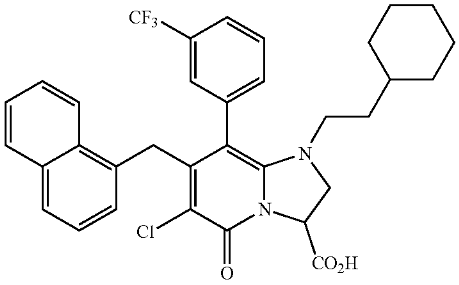
,
208
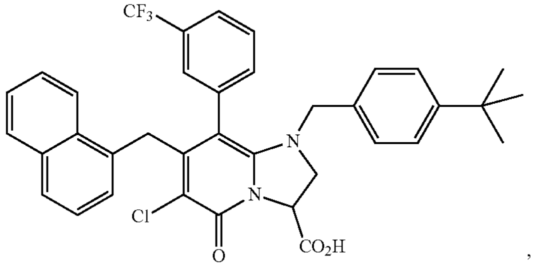
,
209
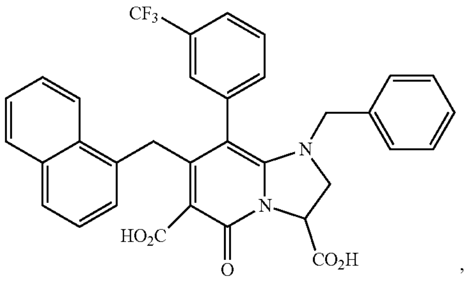
,
210
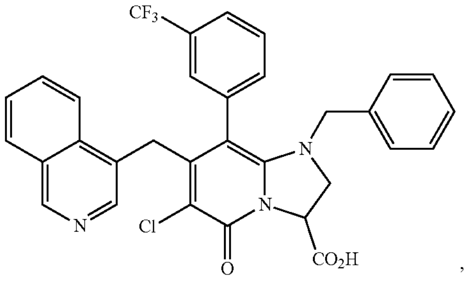
, -continued
211
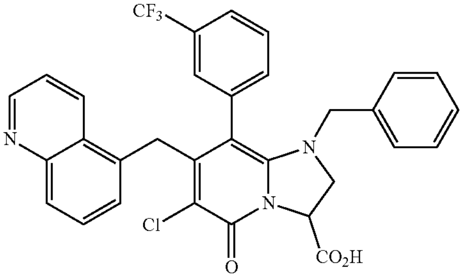
,
212
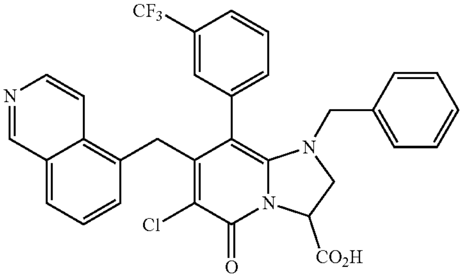
,
213
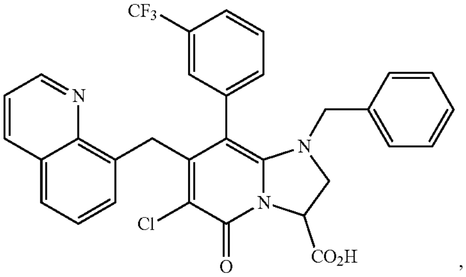
,
214
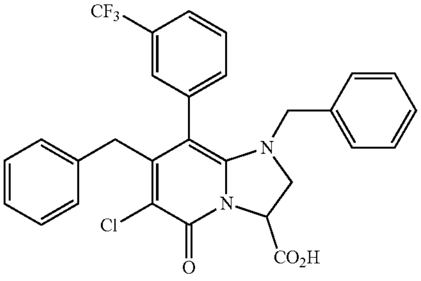
,
215
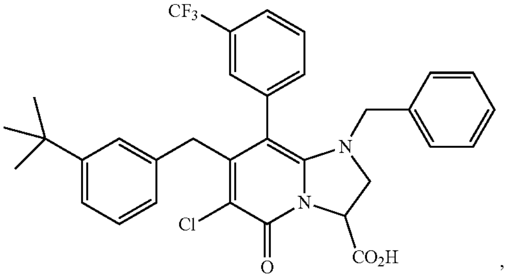
,
-continued
216
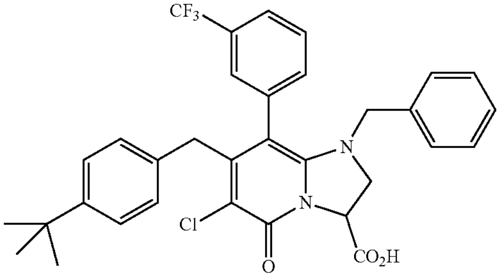
,
217
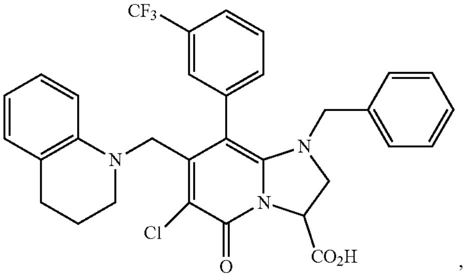
,
218
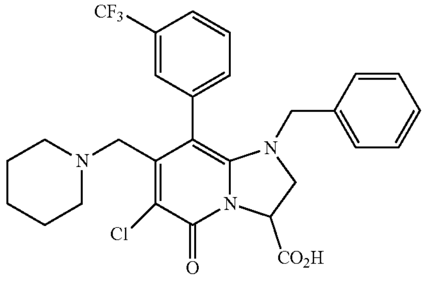
,
219
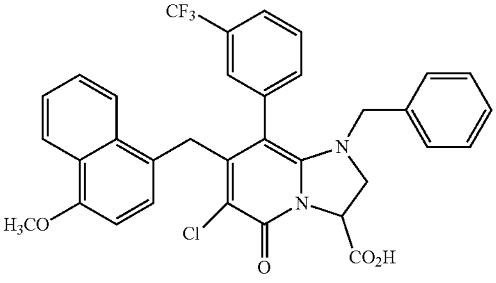
,
220
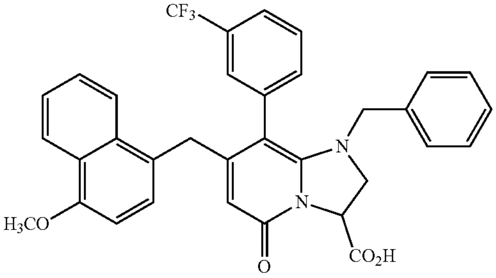
, -continued
221
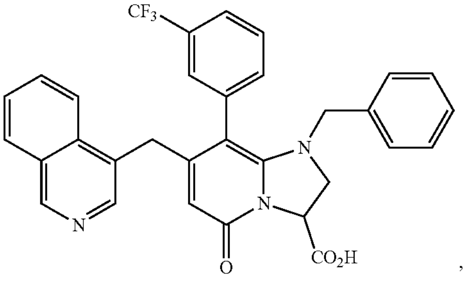
,
222
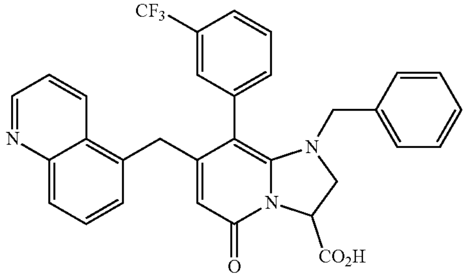
,
223
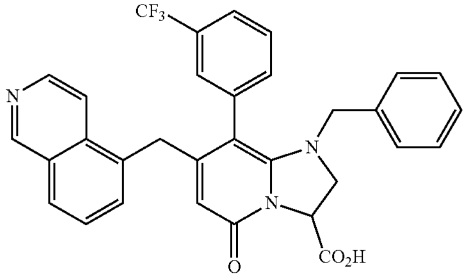
,
224
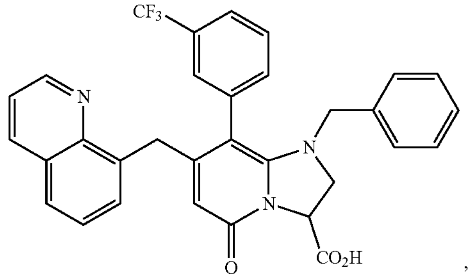
,
225
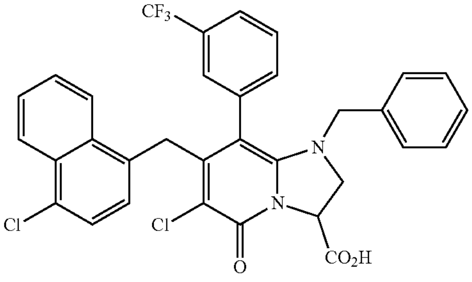
,
-continued
226
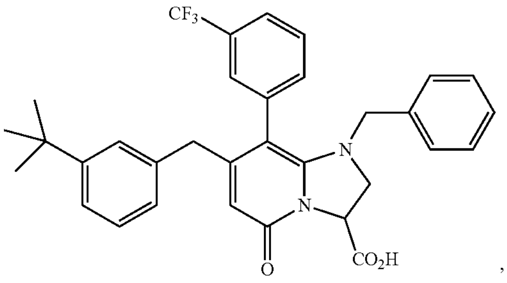
,
227
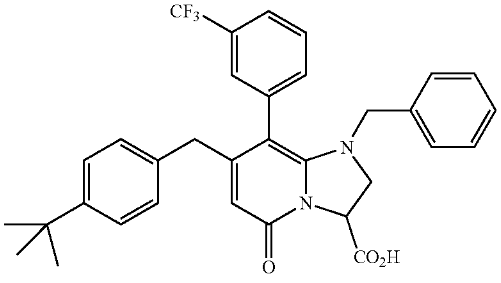
,
228
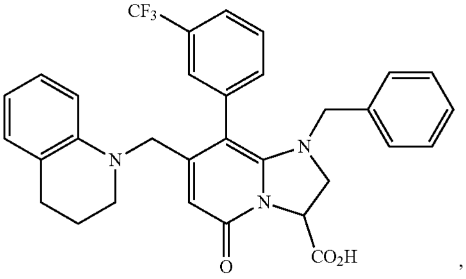
,
229
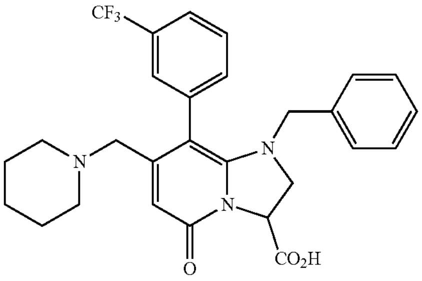
,
230
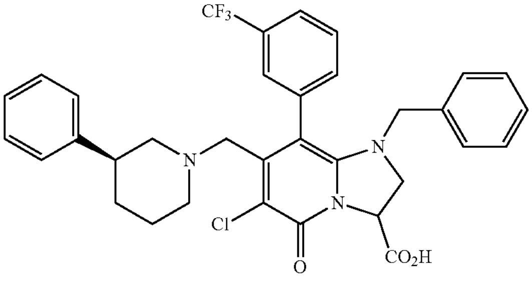
, 231
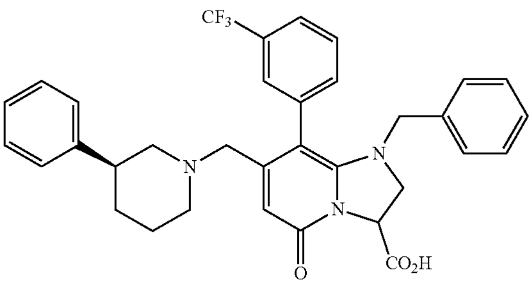
,
232
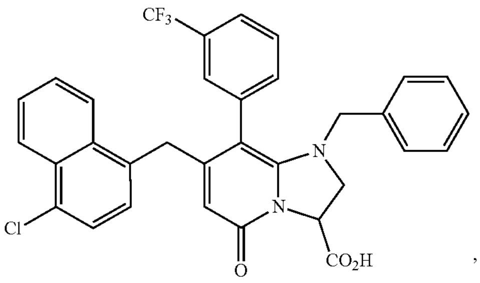
,
233
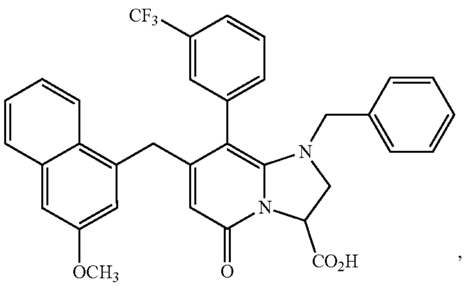
,
234
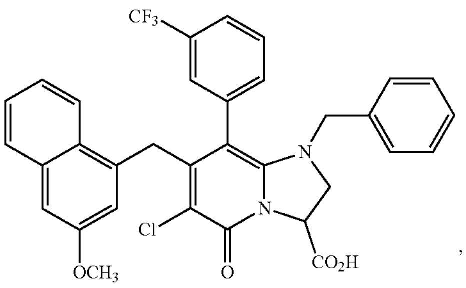
,
235
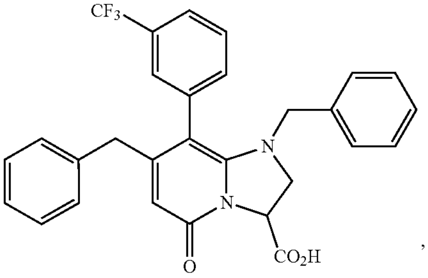
,
236
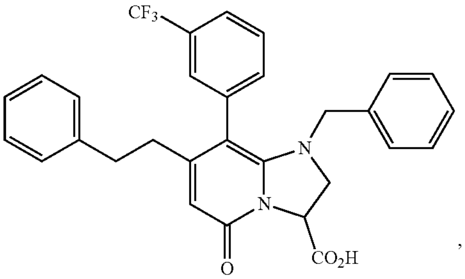
,
237
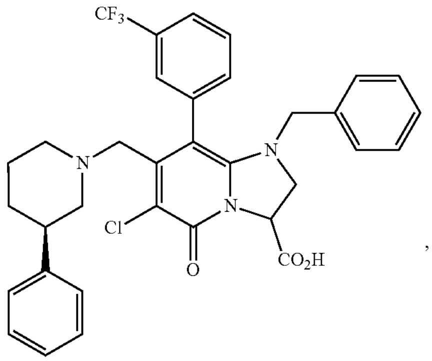
,
238
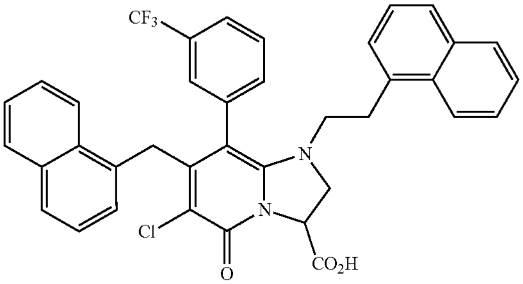
,
239
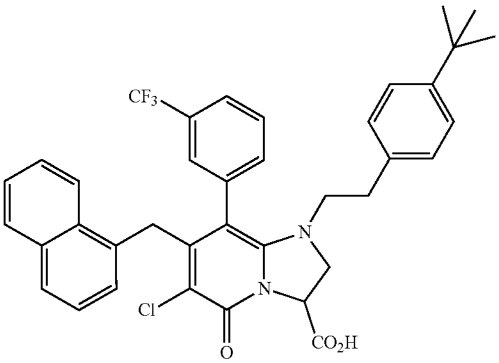
,
240
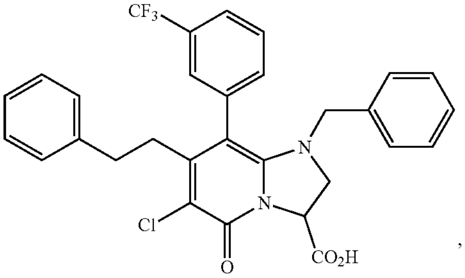
, -continued
161
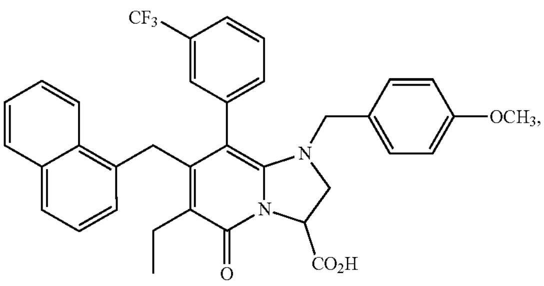
185
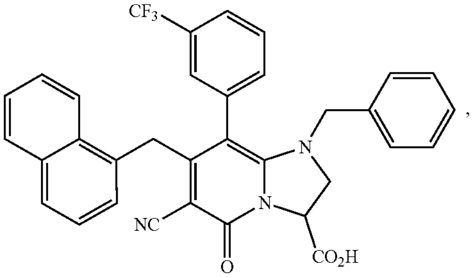
-continued
188
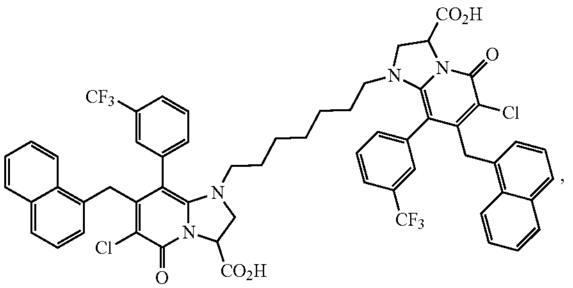
193
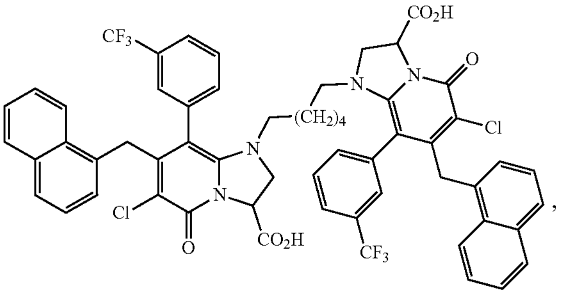
and pharmaceutically acceptable salts thereof.
13. A pharmaceutical composition comprising a compound of claim 1, or a pharmaceutically acceptable salt thereof, and a pharmaceutically acceptable carrier.
14. The pharmaceutical composition of claim 13, wherein the pharmaceutical composition is formulated for enteric delivery.
* * * * *

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1

tctggcaggt gttgttcctc                                                  20


<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2

ccgccgccat gctgggtaat                                                  20
```

-continued

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ctgttcgtct cgacatccgt 20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
tcgccgtaga ggatctggaa 20

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
ttctggcctg cgtttgttta t 21

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
agatcaacag catatcgcgt g 21

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
aacaacgatc agaaagccat t 21

<210> SEQ ID NO 8
<211> LENGTH: 21
<212> TYPE: DNA
<213> ORGANISM: Artificial Sequence
<220> FEATURE:
<223> OTHER INFORMATION: Synthetic

<400> SEQUENCE: 8
tatcgtcaga aaccagacgg t 21

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
actcgctttg agaaagcacc a 21

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
ggttaccgac aaattcaaag a 21

<210> SEQ ID NO 11
<211> LENGTH: 21
<212> TYPE: DNA
<213> ORGANISM: Artificial Sequence
<220> FEATURE:
<223> OTHER INFORMATION: Synthetic

<400> SEQUENCE: 11
atgacagctc aatcgatctg a 21

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
tcgcgttgtt accaaagcca a 21

<210> SEQ ID NO 13
<211> LENGTH: 16
<212> TYPE: DNA
<213> ORGANISM: Artificial Sequence
<220> FEATURE:
<223> OTHER INFORMATION: Synthetic

<400> SEQUENCE: 13
tcagtggaac ggcaaa 16

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
cacggtggtg gcggtaataa 20

<210> SEQ ID NO 15
<211> LENGTH: 21
<212> TYPE: DNA
<213> ORGANISM: Artificial Sequence
<220> FEATURE:
<223> OTHER INFORMATION: Synthetic

<400> SEQUENCE: 15
gttacgagca tcagcttgca g 21

<210> SEQ ID NO 16
<211> LENGTH: 21

<212> TYPE: DNA
<213> ORGANISM: Artificial Sequence
<220> FEATURE:
<223> OTHER INFORMATION: Synthetic

<400> SEQUENCE: 16
gttacgggca tcagtttgca g 21

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
gcagagcaag tgcagagtta cc 22

<210> SEQ ID NO 18
<211> LENGTH: 21
<212> TYPE: DNA
<213> ORGANISM: Artificial Sequence
<220> FEATURE:
<223> OTHER INFORMATION: Synthetic

<400> SEQUENCE: 18
aacaacgatc agaaagccat t 21

<210> SEQ ID NO 19
<211> LENGTH: 21
<212> TYPE: DNA
<213> ORGANISM: Artificial Sequence
<220> FEATURE:
<223> OTHER INFORMATION: Synthetic

<400> SEQUENCE: 19
tatcgtcaga aaccagacgg t 21

<210> SEQ ID NO 20
<211> LENGTH: 14
<212> TYPE: DNA
<213> ORGANISM: Artificial Sequence
<220> FEATURE:
<223> OTHER INFORMATION: Synthetic

<400> SEQUENCE: 20
cgctcgacca tcgc 14

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21
ttctggcctg cgtttgttta t 21

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22
agatcaacag catatcgcgt g 21

<210> SEQ ID NO 23
<211> LENGTH: 16
<212> TYPE: DNA
<213> ORGANISM: Artificial Sequence
<220> FEATURE:
<223> OTHER INFORMATION: Synthetic

<400> SEQUENCE: 23
attacggttt tagcgc 16

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
tctggcaggt gttgttcctc 20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
ccgccgccat gctgggtaat 20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
ctgttcgtct cgacatccgt 20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
tcgccgtaga ggatctggaa 20

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
ttctggcctg cgtttgttta t 21

<210> SEQ ID NO 29
<211> LENGTH: 21
<212> TYPE: DNA
<213> ORGANISM: Artificial Sequence
<220> FEATURE:
<223> OTHER INFORMATION: Synthetic

<400> SEQUENCE: 29
agatcaacag catatcgcgt g 21

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
actcgctttg agaaagcacc a 21

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
ggttaccgac aaattcaaag a 21

<210> SEQ ID NO 32
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: May be modified by an 'N' term
<220> FEATURE:
<221> NAME/KEY: MISC_FEATURE
<222> LOCATION: (6)..(6)
<223> OTHER INFORMATION: May be modified by a 'C' term

<400> SEQUENCE: 32

Gln Tyr Gly Gly Asn Asn
1 5

<210> SEQ ID NO 33
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: May be modified by an 'N' term
<220> FEATURE:
<221> NAME/KEY: MISC_FEATURE
<222> LOCATION: (6)..(6)
<223> OTHER INFORMATION: May be modified by a 'C' term

<400> SEQUENCE: 33

Gln Tyr Gly Gly Asn Ala
1 5